(12) United States Patent
Zheng et al.

(10) Patent No.: US 10,118,948 B2
(45) Date of Patent: Nov. 6, 2018

(54) ANTIMICROBIAL PEPTIDES, PHARMACEUTICAL COMPOSITIONS, AND METHODS OF USE THEREOF

(71) Applicant: The United States of America, as Represented by the Secretary, Department of Health and Human Services, Washington, DC (US)

(72) Inventors: Jie Zheng, Columbia, MD (US); Ann Marie Knolhoff, Silver Spring, MD (US); Eric Wayne Brown, Taneytown, MD (US); Timothy Ray Croley, Severna Park, MD (US)

(73) Assignee: The United States of America, as represented by the Secretary, Department of Health and Human Services, Silver Spring, MD (US)

( * ) Notice: Subject to any disclaimer, the term of this patent is extended or adjusted under 35 U.S.C. 154(b) by 0 days.

(21) Appl. No.: 15/371,683

(22) Filed: Dec. 7, 2016

(65) Prior Publication Data
US 2017/0145057 A1 May 25, 2017

Related U.S. Application Data

(63) Continuation-in-part of application No. PCT/US2015/034859, filed on Jun. 9, 2015.

(60) Provisional application No. 62/009,467, filed on Jun. 9, 2014.

(51) Int. Cl.
| | |
|---|---|
| *A61K 38/10* | (2006.01) |
| *C07K 7/56* | (2006.01) |
| *C07K 19/00* | (2006.01) |
| *C07K 7/08* | (2006.01) |
| *A01N 37/46* | (2006.01) |
| *A61K 47/48* | (2006.01) |
| *A61K 38/00* | (2006.01) |

(52) U.S. Cl.
CPC ............... *C07K 7/56* (2013.01); *A01N 37/46* (2013.01); *A61K 38/10* (2013.01); *A61K 47/48038* (2013.01); *C07K 7/08* (2013.01); *C07K 19/00* (2013.01); *A61K 38/00* (2013.01)

(58) Field of Classification Search
CPC . C07K 7/56; C07K 7/08; C07K 19/00; A01N 37/46; A61K 38/00; A61K 38/10; A61K 47/48038
See application file for complete search history.

(56) References Cited

U.S. PATENT DOCUMENTS

| | | |
|---|---|---|
| 5,762,928 A | 6/1998 | Bolkan |
| 2012/0141423 A1 | 6/2012 | Yousef et al. |
| 2013/0164317 A1 | 6/2013 | Yousef et al. |
| 2017/0145057 A1 | 5/2017 | Zheng et al. |

FOREIGN PATENT DOCUMENTS

| | | |
|---|---|---|
| UA | 15147 U | 6/2006 |
| WO | 2012166392 A1 | 12/2012 |
| WO | 2013086003 A1 | 6/2013 |
| WO | 2015191551 A1 | 12/2015 |

OTHER PUBLICATIONS

Falagas et al, Polymyxins-Infectious Disease and Antimicrobial Agents, from http://www.antimicrobe.org/d05.asp, pp. 1-20, accessed Feb. 4, 2018.*
Zhai et al, Evaluation of the anticryptococcal activity of the antibiotic polymyxin B in vitro and in vivo, International Journal of Antimicrobial Agents, 2013, 41, pp. 250-254.*
Yampolsky et al, The Exchangeability of Amino Acids in Proteins, Genetics, 2005, 170, pp. 1459-1472.*
Rudinger, Peptide Hormones, JA Parsons, Ed., 1976, pp. 1-7.*
SIGMA, 2004, pp. 1-2.*
Berendsen, A Glimpse of the Holy Grail?, Science, 1998, 282, pp. 642-643.*
Voet et al, Biochemistry, John Wiley & Sons Inc., 1995, pp. 235-241.*
Ngo et al, Computational Complexity, Protein Structure Protection, and the Levinthal Paradox, 1994, pp. 491-494.*
Bradley et al., Limits of Cooperativity in a Structurally Modular Protein: Response of the Notch Ankyrin Domain to Analogous Alanine Substitutions in Each Repeat, J. Mol. BloL (2002) 324, 373-386.*
Types of Microorganisms, from https://faculty.weber.edu/coberg/class/2054/Micro2054%20Types%20of%20Microorganisms.htm, pp. 1-5, accessed Feb. 4, 2018.*
List of microorganisms, from https://ecdc.europa.eu/en/healthcare-associated-infections-acute-care-hospitals/database/microorganisms-and-antimicrobial-resistance/list, pp. 1-5, accessed Feb. 4, 2018.*
2018 Official Microbe Mission Microbial Disease List, from www.soinc.org, Aug. 24, 2017, p. 1.*
Alkotaini et al.; "Detection of Secreted Antimicrobial Peptides Isolated From Cell-Free Culture Supernatant of Paenibacillus Alvei AN5"; J Ind Microbial Biotechnol; 40; pp. 571-579; (2013).
Alkotaini et al.; "Isolation and Identification of a New Intracellular Antimicrobial Peptide Produced by Paenibacillus Alvei AN5"; World J Microbial Biotechnol; 30; pp. 1377-1385; (2014).
Anandaraj et al.; "Co-production of Two New Peptide Antibiotics by a Bacterial Isolate Paenibacillus Alvei NP75"; Biochemical and Biophysical Research Communications; 379; pp. 179-185; (2009).
Guo et al.; "Isolation of a *Paenibacillus* sp. Strain and Structural Elucidation of its Broad-Spectrum Lipopeptide Antibiotic"; Appl. Environ. Microbial.; 78(9); pp. 3156-3165; (2012).
International Search Report and Written Opinion; International Application No. PCT/US2015/034859; International Filing Date Jun. 9, 2015; dated Aug. 14, 2015; 12 pages.

(Continued)

*Primary Examiner* — Julie Ha
*Assistant Examiner* — Li N Komatsu
(74) *Attorney, Agent, or Firm* — Klarquist Sparkman, LLP

(57) ABSTRACT

Disclosed herein are novel antimicrobial peptides, pharmaceutical compositions containing the peptides, and methods of use of the peptides to inhibit the growth or proliferation of microbes. The antimicrobial peptides are particularly useful to treat infections of dangerous gram positive organisms such as MRSA and VRSA.

29 Claims, 48 Drawing Sheets

Specification includes a Sequence Listing.

(56) References Cited

OTHER PUBLICATIONS

Anandaraj et al., "Co-production of two new peptide antibiotics by bacterial isolate *Paenibacillus alvei* NP75," *Biochemical and Biophysical Research Communications* 379: 179-185 (available online Dec. 13, 2008).
Antonopoulos et al., "Effect of *Paenibacillus alvei*, strain K165, on the germination *of Verticillium dahlia* miscrosclerota *in planta*," *Biological Control* 46: 166-170 (2008).
Gardener et al., "Ecology of *Bacillus* and *Paenibacillus* spp. in agricultural systems," *Phytopathology* 94: 1252-1258 (2004).
Hoch and DeMoss "Physiological effects of a constitutive tryptophanase in *Bacillus alvei*," *Journal of Bacteriology* 90(3): 604-610 (1965).
International Preliminary Report on Patentability from PCT Application No. PCT/US2012/038584, 5 pages (dated Nov. 20, 2013).
International Search Report from PCT Application No. PCT/US2012/038584, 4 pages (dated Sep. 27, 2012).
Kim et al., "*Paenibacillus elgii* SD17 as a biocontrol agent against soil-borne turf diseases," *Plant Pathology Journal* 21(4): 328-333 (2005).
Liao, "Control of foodborne pathogens and soft-rot bacteria on bell pepper by three strains of bacterial antagonists," *Journal of Food Protection* 72(1): 85-92 (2009).
Written Opinion from PCT Application No. PCT/US2012/038584, 4 pages (dated Sep. 27, 2012).
Cava et al., "Emerging knowledge of regulatory roles of D-amino acids in bacteria," *Cellular and Molecular Life Sciences* 68: 817-831 (e-pub Dec. 14, 2010).
Huang and Yousef, "Paenibacterin, a novel broad-spectrum lipopeptide antibiotic, neutralises endotoxins and promotes survival in a murine model of *Pseudomonas aeruginosa*-induced sepsis," *International Journal of Antimicrobial Agents* 44: 74-77 (2014).
Huang and Yousef, "The lipopeptide antibiotic paenibacterin binds to the bacterial outer membrane and exerts bactericidal activity through cytoplasmic membrane damage," *Applied and Environmental Microbiology* 80(9): 2700-2704 (Feb. 21, 2014).
Huang et al., "Biosynthesis of the new broad-spectrum lipopeptide antibiotic paenibacterin in *Paenibacillus thiaminolyticus* OSY-SE," *Research in Microbiology* 165: 243-251 (e-pub Mar. 5, 2014).
Li et al., "Roles of D-amino acids on the bioactivity of host defense peptides," *International Journal of Molecular Sciences* 17(7): 1023, 27 pages, (Jun. 30, 2016).

\* cited by examiner

SEQ ID NO. 78

Compound of the present invention SEQ ID NO. 4

Compounds Identified in this Work

FA options
$C_{10}H_{19}O^*$   $C_{10}H_{19}O_2^*$
$C_{11}H_{21}O^*$   $C_{11}H_{21}O_2^*$
$C_{12}H_{23}O^*$   $C_{12}H_{23}O_2^*$
$C_{13}H_{25}O^*$   $C_{13}H_{25}O_2^*$
$C_{14}H_{27}O^*$   $C_{14}H_{27}O_2^*$
$C_{15}H_{29}O$     $C_{15}H_{29}O_2^*$ Hydrophobic
Polar, uncharged
Basic, + charged

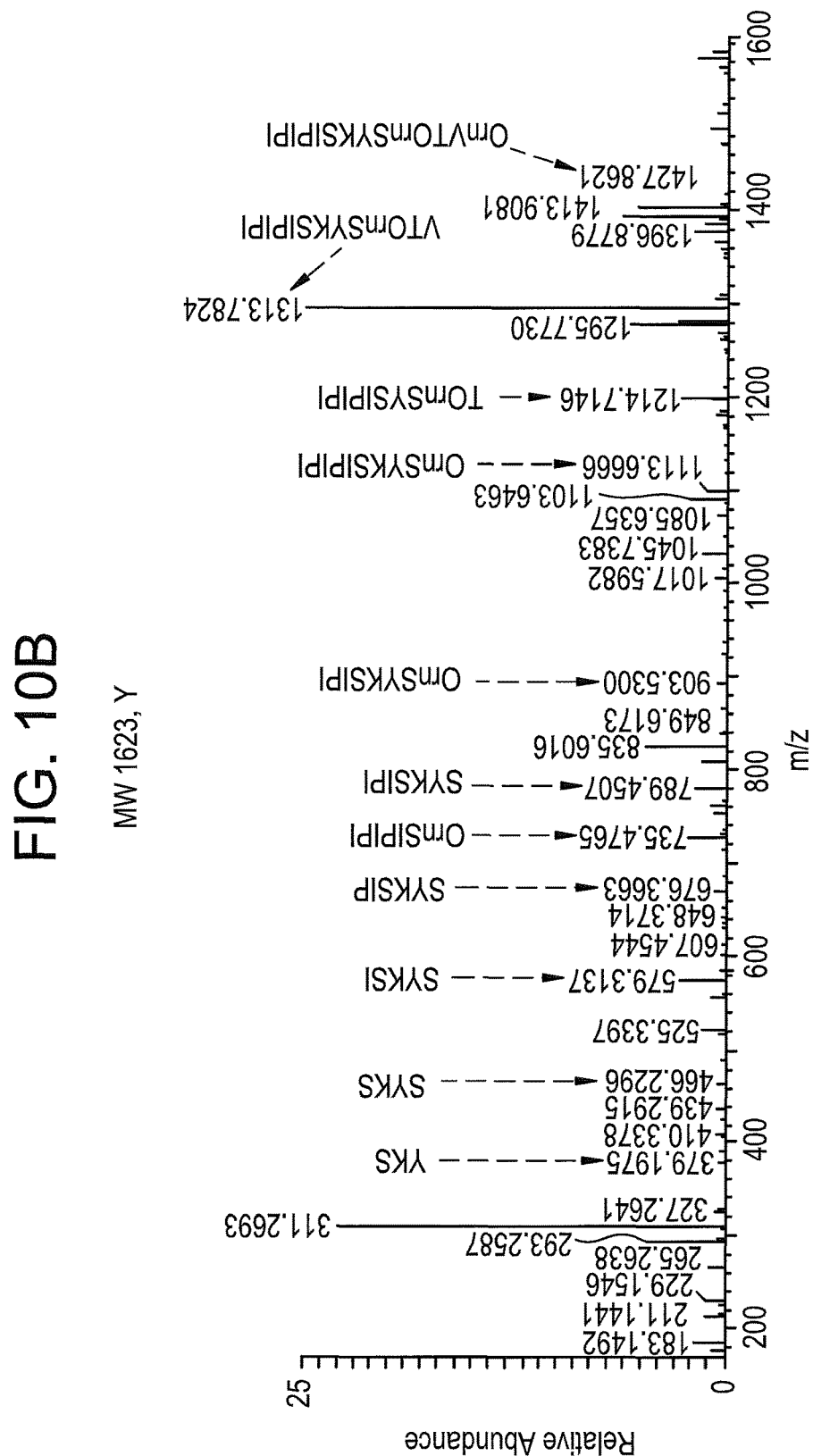

MW 1637

MW 1639 m/z (SEQ ID NO. 77)

FIG. 16A

```
A6_6i_PbtA     1   MNANPNEWYPLTQAQRRIWYTEMMHPNTSVTTVAGTMYIRGKVDVBILKMAIYQVIMQHD
TS_15_PbtA     1   MNANPNEWYPLTQAQRRIWYTEMMHPNTSVTTVAGTMYIRGKVDVBILKMAIYQVIMQHD
OSY_SE_pbtA    1   ------------MEMMHPNTTVSTVAGTLVIRGEVDAAVLKESICQVITQHD A6_6i_PbtA    61   AFRIRIAMTDNQPKQQFAPVEQIVPHVDYLEWDNQIEAESWLQRFNHIPIHMFDPALYHF
TS_15_PbtA    61   AFRIRIAMTDNQPKQQFAPVEQIVPHVDYLEWDNQIEAESWLQRFNHIPIHMFDPALYHF
OSY_SE_pbtA   41   AFRIRIMTQDNQPIQRLEPESALTPEVDYMEWDDHLEAKDWLNRPNRIPISIFDDKLYNF A6_6i_PbtA   121   VVFNVNDEEAWFNLKMNHIATDGVSSHLIAYKIMKNYTAMVSGNADTDEQESTYLDYIPA
TS_15_PbtA   121   VIFNVNDEETWFNLKMNHIATDGVSSHLIAYKIMKNYTAMVSGNADTDEQESTYLDYIPA
OSY_SE_pbtA  101   TVFNVNNQEYVHLKINHIIADGVTSHLIGNKIMQTYMELTSGTFSANDKKNSYLDFTYA A6_6i_PbtA   181   EREYEQSDRYAKDKAYWLDKFSTMPEVIGIKSYPPHSIGTEASRTSITVSGEMYEKLYRF
TS_15_PbtA   181   EREYEQSDRYAKDKAYWLEKFQTMPETTGIKPYPPYSISTEAKRAYVALTGERYEQLKVF
OSY_SE_pbtA  161   EQEYEKSDRYQKDKAYWLEKFQTMPETTGIKPYPPYSISTEAKRAYVALTGERYEQLKVF A6_6i_PbtA   241   SQQHNISLFTLFLGSIYAFLYKTTGNNDIAVGAAYANRTSRQDKDALGMFVSTVAARLTI
TS_15_PbtA   241   SQQHNISLFTLFLGSLYAFLYKTTGNNDIAVGAAYANRTSRQDKDALGMFVSTVAARLTI
OSY_SE_pbtA  221   SEQNNISLFTLFLATVYMFLYKTGNLDIAVGTAYANRTSRKEKEMLGMFVSTVATRLSL A6_6i_PbtA   301   SPDQDVLTFLHNVAKEQKAILRHQKYPYNQLILDLREQNNSVEIQDLYRISIDYMPIRWS
TS_15_PbtA   301   TPDQDVLTFLHNVAKBQKAILLHQKYPYNQLILDLREQNNSVEIQDLYRISIDYMPIRWS
OSY_SE_pbtA  281   DPNQDLISILQRSSFCGHEVDDFAVHVEDMVDDNQIIPNIDYRKQLFEEEVIRIIDQMTI A6_6i_PbtA   361   SHGELAARQRSSFCGHEVDDFAVHVEDMVDDNQIIPNIDYRKQLFEEEVIRIIDQMMTI
TS_15_PbtA   361   SYGELAVRQRSSFCGHEVDDFAVHVEDMVDDNQIIPNIDYRKQLFEEEVIRMIEQMMTI
OSY_SE_pbtA  341   SYGQLSIQQRSSFCGHEVDDLVAHVEDMLDDQQLVINVDYRTQLFEREITRIIEQMLTI A6_6i_PbtA   421   VDQMISNPSQSLQQLSMISDKEAQIILTRFSNGNWSTPQPVGRTIHQLFEEQVERTPDQV
TS_15_PbtA   421   VDQMINNPSQNLQQLSMISDKEAQIILTRFSNGNWSTPQPVGRTIHQLFEBQVERTPDQV
OSY_SE_pbtA  401   VDGILHNPQQTLHELTMLNNEEARKILTQFNDT--AAEFPRDKTVHQLFEEQAARTPNHV A6_6i_PbtA   481   AVVFGDRHLTYKELNEQANCFARTLRAHGVAABQFVGIMADRSIEMVVGILAILKAGGAY
TS_15_PbtA   481   AVVFGDRHLTYKELNEQANCFARTLRAHGVAABQFVGIMADRSIEMVVGILAILKAGGAY
OSY_SE_pbtA  459   AAVEDQLTYRELNERANRLARTIRAEGVQPEQLVGIMADRSLEMVIVGILAILKAGGAY
```

```
A6_6i_PbtA   1619  AYEQAVAIENEAAKEREQGFDIENGDVMRVSVLQTADEVYEVLWISHHIVMDGWCLPLVA
TS_15_PbtA   1619  SYEQAVAIENEAAKERAQGFDIENGNVTRVSVLQTADEVYEVLWISHHIVMDGWCLPLVA
OSY_SE_PbtA  1590  PAKQRAHIENAVNEDKLRGFDLEQDELMKVLMRTAQESYHVLWSHHIMDGWCLPLVA

A6_6i_PbtA   1679  ARVFNTYSALVEDKKPILASVPSYNHYIQWLERQDESAAAAYWNLNYLSGFEETELPHSK
TS_15_PbtA   1679  ARVFSTYSALVEDKKPILASVPSYNQYIQWLERQDESAAAAYWHLHYLSGFEETELPHSK
OSY_SE_PbtA  1650  KEVFDTYSAYVRRHLEKTTVPAYSQYIEWLEQQDEEAASAYWSEYLAGYDQHTALPQGK

A6_6i_PbtA   1739  GRRHSGQYEAGQVQIDLGTSLSLALNQVATQHQVTLNTLLQASWGILLQKYNRTSDIVPG
TS_15_PbtA   1739  GRRHSGQYEAGQVQIDLGTSLSLALNQVATQHQVTLNTLLQASWGILLQKYNRTSDIVPG
OSY_SE_PbtA  1710  DQGRSEAYAAEHIDCELGKDLSVRLNEAAKRNLVTLSTLLQTTWGIMLQKINGTGDVPG

A6_6i_PbtA   1799  SVVSGRPAELVGIEEMIGLFINTIPVRSSQAQERPAEVMTRMQEDALSSAKHDYPLYE
TS_15_PbtA   1799  SVVSGRPAELVGIEEMIGLFINTIPVRSSQAHERFIEVITRMQDDALSSAKHDYPLYE
OSY_SE_PbtA  1770  GVVSGRPADMPGIEEMIGLFINTIPVRTADAGESFADIMCRFQEQALASAKHDYPLYE

A6_6i_PbtA   1859  IQAQCTLKQNITHHMVLENYPMEQQLDQFNSSDGSGLKLTDVTVEQTNYDLNLTIIPG
TS_15_PbtA   1859  IQAQCTLKQDLINHHIMVLENYPMBQQLDQFNSSDGSGLKLTDVTVSEQTNEDLNLIIPG
OSY_SE_PbtA  1830  IQAQSAQKQELINHIMVFENYPMEEQIEQLESTDGKLKLKDVMVTEQTNYDFNLVIMPG

A6_6i_PbtA   1919  DNIVIRFDFNKQALEEADMNVLKQHLLHVLEQVASNPRISIGELQLATDERRAVMMSEFN
TS_15_PbtA   1919  DNIVIRFDFNKQALAETDMNVLKELLLHVLEQVASNPRISIGELQLATDERRAVMMSEFN
OSY_SE_PbtA  1890  DEIVIRLDYNGIVPDRTSMEQLKGHLVNMLEQIAANPQIPVGELELATAAEKAQIVDFN

A6_6i_PbtA   1979  DTFVAYPREKSIERLFEERAEHEPDALAVVFGNEQMTYGALNAAANRMARLRHAGVTNG
TS_15_PbtA   1979  DTFVAYPREKSIHRLFBERAKQEPDALAVVFGNDQMTYGALNAAANRMAWRLRYAGVTSG
OSY_SE_PbtA  1950  NEVWEYPREKTHQLFEEREERIPDAVAVIFEDKREITYAELNAAANRIAHLERDRGVARG

A6_6i_PbtA   2039  ELVGICADRSLDMVVGLLAIMKSGGAYVPIDPAYPQERISAMLEDTSITTMVTQKHLCSL
TS_15_PbtA   2039  ELVGICADRSLEMVVGLLAIMKAGGAYVPIDPAYPQERISAMIEDTSIATMVTQRHLCSL
OSY_SE_PbtA  2010  TLVGICAERSLEMVVGLLGLLKAGGAYVPIDPSYPQERINAMLEDTAISVLTQAHLQTS

A6_6i_PbtA   2099  WPEHFNVILD-VNETDVSNLMEDIESTNISIDGAGDDLAYIIYTSGSTGTPKGVCVTHR
TS_15_PbtA   2099  WPEELNVIALD-DNETDVSNSMEDVES-NIPIDGAGDDLAVIIYTSGSTGTPKGVCVTHR
OSY_SE_PbtA  2070  VPNSIDSVLLDAAAETILEGSWPNLTD----TAATADDVAYIIYTSGSTGIPKGVCVTHR
```

FIG. 16E

```
A6_6i_PbtA    2158  GVVRLVCGATIVEIDSSDVFLQGSTISFDAATFBIWGSLLNGAALAILPSGNVSLTDWSE
TS_15_PbtA    2157  GVVRLVCAATYVEINSSDVFLQGSTISFDAATFBIWGSLLNGAALAILPPGNVSLTDWSE
OSY_SE_pbtA   2126  GVVRLVADANYVDISKDVFLQGSTISFDAATFBIWGSLLNGAALAVLPPGNVSLTEWTR A6_6i_PbtA    2218  AIQRHRVTTLWMTAGLFQVMVEQQIEGFYGVKQLLVGGDVVSPTHVRKVMEKHNGIRVIN
TS_15_PbtA    2217  AIQRHRVTTLWMTAGLFQVMVEQQIEGFYGVKQLLVGGDVVSPTHVRKVMEKHNGIRVIN
OSY_SE_pbtA   2186  AIQQHQVTILWMTAGIFHVMVDNQLQALQGVQQLLVGGDVSKTHATKVLERYNGIRLIN A6_6i_PbtA    2278  GYGPTBNTFFTCCHHTAADLDRGCSIPIGRPISNTRVYLDEAGNALPVGVCGELYAGG
TS_15_PbtA    2277  GYGPTBNTFFTCCHHTAADLDRG-SIPIGRPIGNTRVYLDEAGNV-PVCVCGELYAGG
OSY_SE_pbtA   2246  GYGPTBENTFTCCEHISAADMERP-SIPIGRPIGNTQAYVLDGAGKLLPAGVIGELYTGG A6_6i_PbtA    2338  DGLARGYLNRPELTAEKFVNDPFIPGERLYRTGDLARWLPDGSIEFIGRCDEQVKIRGYR
TS_15_PbtA    2336  DGLARGYLNRPELTAEKFVNDPFIPGERLYRTGDLARWLPDGSIEFIGRCDEQVKIRGYR
OSY_SE_pbtA   2305  DGLAQGYLNRPELTAEKFVDSPIVPATRLYRTGDLARWLPDGTIEFYGRIDDQVKIRGYR A6_6i_PbtA    2398  IEPGEVLAVLIRIDEVGEAAVIAREDSSGQKELCAYFTTEAELSASGLRETLARELPAYM
TS_15_PbtA    2396  IEPGEVLAYLLRIDEVGEAAVIAREDSSGQKELCAYFTAEVELSASGLRETLARELPAYM
OSY_SE_pbtA   2365  IELGEVEAHLLKVEPVQSAAVIARKDESGQNMLCAVYAADKELTASELRSALSQELPGYM A6_6i_PbtA    2458  IPSHPIQIEELPLTPNGKVDRRALPQPGEGMHLNIQ-IQPRTELEAKLALIWKDVLGLEN
TS_15_PbtA    2456  IPSHPIQIEELPLTPNGKVDRRALPEREGLRMNLK-IQPRTELEAKIALIWQDVIGLEN
OSY_SE_pbtA   2425  IPTHFVQVERMPLTPNGKVDRFALPEPRGRIMTGIEHVAPKTPLESKLAHIWQEVIGLEK A6_6i_PbtA    2517  VGVTDSFFBLGGHSLRATTLVSKVHREISVLPLQDVFRYPTIEQMSLAIQGMQKESFAS
TS_15_PbtA    2515  VGVTDSFFELGGHSLRATTLVSKVHREINIALPLQDVFRYPTIEQMSLAIQGMQKESPAS
OSY_SE_pbtA   2485  VSVKDSFFBLGGHSLRATTLVSKLQQELHVSMPIREVFRFPTIEQAQVIGGMEQEYRA A6_6i_PbtA    2577  IPRVEDREWYPVSSAQKRLFVLHQMEGAELSYNMPGVMAIEGKLHRDRLEAAFRSLIARH
TS_15_PbtA    2575  IPRVEDREWYPVSSAQKRLFVLHQMEGAELSYNMPGVMAIEGKLHRDRLEAAFRGLTARE
OSY_SE_pbtA   2545  IPQVGERECYPSSAQKRLVLHQLEGAEQTYNMPGVTLAGPLDRERLETAFRKLISRH A6_6i_PbtA    2637  EVLRTGFEMHNGEPMQRIYSDVEFTVBHWIVGAASEAESVIRSFVRAFQLNKPPLLRVGL
TS_15_PbtA    2635  EVLRTGFEMYNGEPMQRIYSDVEFTVEHGIVGAASEAESVIRSFVRAFQLNKPPLLRVGL
OSY_SE_pbtA   2605  ETLRTGFEMVDGVFVQRMYEEVDFAVEYAQASEEAAGEAV-HAFIRAFDLQKPPLLRIGL
```

```
A6_6i_PbtA    3776  EQVPPLHIQYKDYAAWQQSEAQKEQLKHQKAYWLGQFQGELPILELPTDYARPAMQQYGG
TS_15_PbtA    3774  EEVPPLHIQYKDYAAWQQSEAQKEQLKHQQAYWLDQFQGELPILELPTDYARPAIQQYDG
osy_SE_pbtA   3742  AAIEPLRIQYKDYAAWQLSEAQQDWMKRQEGYWRDVFRGELVMLEMPTDVRPAVQQYAG A6_6i_PbtA    3836  LTLPFRIDKDVADGLNRIAADTGTTLYMVLLAAYTMLHKYTGQEDIVVGTPIAGRTHEE
TS_15_PbtA    3834  LTLPFRIDKDVADGLNRIAADTGTTLYMVLLAAYTIELHKYTGQEDIVVGTPIAGRTHEE
osy_SE_pbtA   3802  STLSFDIDPQMSEGLRRIAAETGTTLYMVLLAAYTIELHKYTGQEDVIVGTPIAGRTHGD A6_6i_PbtA    3896  LQPLIGMFVNTLAIRAYPEGAKAFRSYLDEIRSTMLGAYEHQQYPFEELVEGLQLTRDLS
TS_15_PbtA    3894  LQPLIGMFVNTLAIRAYPEGAKAFRSYLDEIRSTMLGAYEHQQYPFEELVEGLQLTRDIS
osy_SE_pbtA   3862  LQPLIGMFVNTLAIRNYPAGEKTFRSYLAEVKETLGAYEHQNYPFEELVDKLQVARDLS A6_6i_PbtA    3956  RNPLFDTMFALDNTDMKADSLGRLQMKPYPLEYTISKFDVSLDVKADEAGLDCSFEYATS
TS_15_PbtA    3954  RNPLFDTMFALDNTDMMVDSLGETHMKPYPLEYTISKFDVSLDVKADERGLDCSFEYATS
osy_SE_pbtA   3922  RNPLFDTMFALNNTEPETFPLEGLRLTPYPSEYTISKFDLSLDVSEKNDRLECSLEYATA A6_6i_PbtA    4016  LPKSETIHRMABHFSHLLKDIVNHPDAQLGELGMLTVQESDEILQVFNPTHSLKAPNETI
TS_15_PbtA    4014  LPKSETIHRMABHFSQLLKDIVNEPDAQLGELGMIVHESDEILQVFNPTHSLKAPDGTI
osy_SE_pbtA   3982  LVKPDTAERMAQHFQQLLIDSLVDQPEAKLVSLGMLTEEEKAQIQHVFNRAEEAGHSQEKTV A6_6i_PbtA    4076  HRLFEEQAERTPEQPAVVFGNERMTYRELNERANKLARTLRAEGVPEDDLIGVMADRSID
TS_15_PbtA    4074  HRLFEEQAERTPEQPAVVFGNERMTYRELNERANKLARTLRAEGVPEDDLIGVMADRSID
osy_SE_pbtA   4042  PELFEEQVERTFDRIAVVHEDKQLTYRELNERANRLARTLRAEGVPEPEQLVGIMADRSLD A6_6i_PbtA    4136  MVVAVMAVLKSGGAYVPIDPEYPEDRIRYMIEDAKARILLTQGHLQDKVTFEGTWVLLED
TS_15_PbtA    4134  MVAVMAVLKSGGAYVPIDPEYPEDRIRYMIEDAKARILLTQCHLQDKVSFEGTWVLLED
osy_SE_pbtA   4102  MLVGIMAILKSGGAYVPIDPKYPEDRIRYMLDDSHAQVLLAQRMQASVAFAGTWVILDE A6_6i_PbtA    4196  EASYHEDDTNLEPNCEPGHLCYVIYTSGTTGNPKGVMIEHRQLAAMAEAWKAEYELHEPG
TS_15_PbtA    4194  EASYHEDDTNLEPICEPDHLCVIYTSGTTGNPKGVMIEHRQLAAMAEAWKAEYLHEPG
osy_SE_pbtA   4162  EAFYHEDGTNLEPLNEPMELSIYVIYTSGTTGNPKGVMIEHRQIVAIADAWKREYLEEG A6_6i_PbtA    4256  IRWLQWASFSPDVFSGDLARTLLHGGEIMLCPSDTRANPGALAELLRSSGIQMFESTPAL
TS_15_PbtA    4254  IRWLQWASFSPDVFSGDLARTLLHGGEIILCPSDTRANPGALAELLRSSGIQMFESTPAL
osy_SE_pbtA   4222  IRWLQWASFSPDVFSGDMVRTLLYGGELILCPEQARANPAAISEIRKHQIQMFESTPAL
```

FIG. 16I

```
A6_6i_PbtA    4316  VIPLMEHVYEEGLDIDSLRLLIIGSDLCPADEFRKLRDRPSSHMRIINSYGVTEACVDSS
TS_15_PbtA    4314  VIPLMEHVYEERVDIDSLRLLIIGSDLCPADEFRKLLDRFGSHERIINSYGVTEACVDSS
OSY_SE_pbtA   4282  VIPFMDYVYDNLDISLKMLIVGSDHCPTAEFDKLTERCGSHMRIENSYGVTEACVDAC A6_6i_PbtA    4376  YYEPISDSVRSVPIGKPLPYVSMYIIGENLSIQPVGLAGELYIAGAGVGRGYWNRPEMT
TS_15_PbtA    4374  YYEPVLSDPVRSVPIGKPLPYVSMYIIGENLSIQPVGLAGELYIAGAGVGRGYWNRPEMT
OSY_SE_pbtA   4342  YYERTTPDALRTLPIGKPLPAVTMYILDDNRSLQPLGHTGELYIGGAGVGRGYLNRPDLT A6_6i_PbtA    4436  ADKFVRDPFADGQRMYRTGDLAKWLPDGNIELIGRTDHQVKIRGYRIEIGEVESKLQETP
TS_15_PbtA    4434  ADKFVRDPFADGQCMYRTGDLAKWLLDGNIELIGRTDHQVKIRGYRIEIGEVESKLQQTP
OSY_SE_pbtA   4402  VEKFVDNPFMPGARMYRTGDLARWLPDGNIEYAGRIDHQVKIRGYRIBIGEVESQLLAAA A6_6i_PbtA    4496  HIREAAVAKEDSGRKVLCAYTSERELTAGEWRAALAKELPAYMIPSHFMRIERMPLT
TS_15_PbtA    4494  DIREAAVAKEDSGRKVLCAYTTSYRELTAGEWRSALAKEIPAYMIPSHFMRIERMPLT
OSY_SE_pbtA   4462  GVREAAVVAREDSGQKVLCAYFVADSALTVGELRASMAQQLPGYMIPAHFVQLERMPLT A6_6i_PbtA    4556  PNGKLDRKGLPAPEGAAYTGTEYEAPRTDAEIALAAAWQSVLHVERVGTNDHFFELGGDS
TS_15_PbtA    4554  PNGKLDRKGLPAPEGAAYTGTEYEAPRTDAEIALAAAWQSVLHVERVGTNDHFFELGGDS
OSY_SE_pbtA   4522  PNGKVDRKGLPAPEGNAYTGAEHVAPRTAEKTLAAVWQVLGAEQVGLMDHFFELGGDS A6_6i_PbtA    4616  IKSIQVSSRLHQAGYKLEIRDLFKYPTIAQLSPLQPIGRIADQGEVSGEVELTPIQCWT
TS_15_PbtA    4614  IKSIQVSSRLHQAGYKLEIRDLFKYPTIAQLSPLQPIGRIADQGEYHGEVELTPIQRWY
OSY_SE_pbtA   4582  IKSIQVSSRLHQAGYKLEIRDLFKYPTIAELSPHIQPIGRRADQGAVTGEAALTPIQHWF A6_6i_PbtA    4676  FGLDLDDMHHYNQSPMLYRQDGFNEEALRKTLRSIVEHHDALRMVFRKSDAGVTAWNRAI
TS_15_PbtA    4674  FGLDLDDMHHYNQSFLLYRQGGFNEEALRKTLRTIVEHHDALRMVFRKSAAGVTAWNRAI
OSY_SE_pbtA   4642  FGQRFADPHHYNQSIMLYRKEGFDEAARKTIEKIAEHHDALRMVFRKTEGYAAWNRGI A6_6i_PbtA    4736  EEGELFDPLAFDIANSGDAEQVIEAKANDIQASIDLQGGPLVKAGLFRCEQHLLIAIH
TS_15_PbtA    4734  EEGELFDPLAFDIANSGDAEQVIEAKANDIQASIDLQGGPLVKAGLFRCEQHLLIAIH
OSY_SE_pbtA   4702  GEGELYSLNVADFTDDPACYRAIEAKANEIQSGINLQAGPLLRAGLFTCAEGHLLIVIH A6_6i_PbtA    4796  HAVMDGVSWRILLEDIATGYEQACKGDDIRLPSKTDSYAAWSRLVEYAEHTDLGHERSY
TS_15_PbtA    4794  HAVIDGVSWRILLEDISAGYEQACKGDDIRLPSKTDSYAAWSRLVEYASLTDLGHERSY
OSY_SE_pbtA   4762  HAVTDGVSWRILLEDIAAGYEQALKGEAIRLPAKTDSYLTWSKQLSGYAQSPAIEQERSY
```

```
A6_6i_PbtA   5927  GQTYVSVPIGKPIDNTSIYIVNEHNQVQPIGVAGELCIAGVGLARGYWNRPELTAEKFVT
TS_15_PbtA   5928  GQTYVSVPIGKPIDNTSIEIVNEHNQVQPIGVAGELCIAGVGLARGYWNRPELTAEKFVT
OSY_SE_pbtA  5876  GQFYTSVPIGKPIDNTQIYIVNRQDQEQPIGVAGELCIAGVGLARGYLKRPELTAEKFVT A6_6i_PbtA   5987  IPSV-GERMYRTGDLARWLPDGNIEYLGRIDHQVKIRGYRIELGELETALLNVQEIRETV
TS_15_PbtA   5988  IPSV-GERMYRTGDLARWLPDGNIEYLGRIDHQVKIRGYRIELGELESALLNVQEIRETV
OSY_SE_pbtA  5936  IPFMPGARMYRTGDLARWLPDGSIEYLGRIDHQVKIRGYRIELGIEAQLLQVEFIREAV A6_6i_PbtA   6046  VVAREEDGQKSLCAYYVADGDPTVGNLRAALAAELPSYMIPSYFVQLEQMPLAPNGKLD
TS_15_PbtA   6047  VVAREEDGQKSLCAYYVADGDPTACDLRAALAAELPSYMIPSYFVQLEQMPLAPNGKLD
OSY_SE_pbtA  5996  VVAREDESGQKALCAYFAADSELPVSELRSALAVELPGYMIPSYFVQLERIPLSANGKLD A6_6i_PbtA   6106  RKALPAPKDVIQTGTDEAAPRTALEVKLVRIWQEVLGLDQIGVKDDFFELGGHSLRATAL
TS_15_PbtA   6107  RKALPAPKDVIRTGTDRIAPRTALEVKLVRIWQEVLGLDQIGVKDDFFELGGHSLRATAL
OSY_SE_pbtA  6056  RKALPAPGGSMRSGKEHVAPRSLLEVKLVRIWQEVLGLAHVSVKDDFFELGGHSLRATTL A6_6i_PbtA   6166  ASKVSKEMHVALPLRDIFHYSTLEAMAQAIGELEKQBHRAIPIAPMAEHYPLASAQKRLY
TS_15_PbtA   6167  ASKVSKEMHVALPLRDIFHYSTLEAMAQAIGELEKQBHRAIPIAPMAEHYQLASAQKRLY
OSY_SE_pbtA  6116  VSKLHKETNINLPLRDVFRYSILEDMALAIGRTEQREFQTLPQVEASDYPLSSAQKRLY A6_6i_PbtA   6226  ILHQABGAQQSYNMPGAMSVSGHIDRNRLEAALLRLIARHDTLRTSFEMVDGEPVQRVHQ
TS_15_PbtA   6227  ILHQABGAQQSYNMPGAMSVSGHIDRNRLEAALLQIARHDTLRTSFEMVDGEPVQRVHQ
OSY_SE_pbtA  6176  ILQQVEGABQSYNMPGAMSIRGQDRNQFEAAFRGLIAREVFRTSFEMVGGEPMQRVHQ A6_6i_PbtA   6286  HVDFALEYSTAREKDMEQVAKQFVRDFPDLEQPPLLRVGLVQLEQEBQHLILLFDMHHIISD
TS_15_PbtA   6287  HVDFALEYSTAREKDIDQVAEQFVRDFPDLEQPPLLRVGLVQLEQEBQHLILLEDMHHIISD
OSY_SE_pbtA  6236  DTAPAVEYMQANEEAEATAHQFVRTFPDLEQPSLIRVGLIELDR-EEHIMLFDMHHIISD A6_6i_PbtA   6346  GISMDILVDELARLYDGEELPPLEIQYKDYVLWQQAEBASSEQMKEHEEYWLRTLGNELPL
TS_15_PbtA   6347  GISMDILVDELARLIDGEELPPLEIQYKDYVLWQQAEBASSEQMKEHEEYWLRTLGNELPL
OSY_SE_pbtA  6295  GVSMGILVEEFARLYSGEELPPLRIQYKDYAAWQQSEAQSERIKQQEAYWLDALDGELPQ
```

FIG.16M

```
A6_6i_PbtA    6406  LELPTEFARSEQRSYDGDKLHFAIDGQLNEKLQRLASQSGATLYMVLLAAYTLLHKYSG
TS_15_PbtA    6407  LELPTEFARGEQRSYDGDKLHFAIDGQLNEKLQRLASQSGATLYMVLLAAYTLLHKYSG
OSY_SE_pbtA   6355  LELPTDFARPAHQSHEGDTLDFVLDSHMSGGLQRLAEHTGTLLYMVLLAAYTLLHKYSD A6_6i_PbtA    6466  QNDLVVGTPIAGRTHVDVEPLIGMFVNSLAIRNYPNDDKTFRSYLEEVKESTLSAFEHQD
TS_15_PbtA    6467  QNDLVVGTPIAGRTHVDVEPLIGMFVNSLAIRNYPNDDKTFRSYLEEVKESTLSAFEHQD
OSY_SE_pbtA   6415  QEDLIVGTPIAGRTHADVEPLIGMFVNSLALRSYPCGEKSFLSYLEEVKEMTLAAYENQD A6_6i_PbtA    6526  YPFDKLVEQLEDAWVPGRNPVFDTMFVLQNAKARTINLGELAFEPLIPSHTVAKFDLTLE
TS_15_PbtA    6527  YPFDKLVEQLEDAWVPGRNPVFDTMFVLQNAKARTINLRELAFEPLIPSHTVAKFDLTLE
OSY_SE_pbtA   6475  YPFAELVEHVQAVWSPSRNPLFDTMFVLQNTEDRNVRFGELTIEPYTQEHNVAKFDLTLE A6_6i_PbtA    6586  MAIEDGMLSGQFEYCTKLFSANMIANFAEDFLEILSQACEQPDIRLEDIQLSGSAYQEEE
TS_15_PbtA    6587  MAIEDGMLSGQFEYCTKLFSANMIANFAEDFLEILSQACEQPDERLEDIQLSGSANQEEE
OSY_SE_pbtA   6535  IALEDGVMSGHFEYCTRLFTNMVDNFAEDLLSILAQICEQPAIRLGDIHLEGNAEDEE A6_6i_PbtA    6646  --LEEEIDFAF
TS_15_PbtA    6647  --LEEEIDFAF
OSY_SE_pbtA   6595  ASLAEEIDFVP
```

A6 6i PbtA is SEQ ID NO. 11
TS-15 PbtA is SEQ ID NO. 14
OSY SE PbtA is SEQ ID NO. 17

FIG. 17A

```
A6_6i_PbtB    1   --MAFDKEIEFWKAKIDTEDTPTIPYTSTPSSBAARHYSVSVTMPAEISERIIRMSKGS
TS_15_PbtB    1   --MAFDKEIEFWKAKIDTEDTPTLPYTNISSSEAARHYSVSVTMPAEIERIIRMSKGS
OSY_SE_pbtB   1   MNEAFEKETDFWNAQFDAEDSPAILPYSTASISVTARDHSNSISLSADVSQRISHMSRGS A6_6i_PbtB   59   HQAAFMILLGGIQCLLHKYTSENRIVIGMPIVRKAGEKRLPINQVLLKENVNEELTPKS
TS_15_PbtB   59   HQAAFMILLGGIQCLLHKYTSENCIVIGMPIVQKAGEKRLPINQVLLKENVNEELTPKS
OSY_SE_pbtB  61   HLAEYMIHLAGIQCLLFKYTGEESVIVGMPIVRKSKDTRRPINVVTLKNKLGANRTFKS A6_6i_PbtB  119   LLTSLKQSFTEAIRHQEIPFRLITEQMNVQEKNGLPVINTMAALKNIHTVNFIPTVADV
TS_15_PbtB  119   LLTSLKQSFTEAIRHQNIPFRLITEQMNVQEKNGLPVINTMAALKNIHTVNFIPTVADV
OSY_SE_pbtB 121   LTELKTLTAAINHQNIPFRKMTEHLHLEAVNGMPVVNTMVSMKEIHTIEPSQSVVSDI A6_6i_PbtB  179   LFQFEFEAENLLLSVVYNERVIDSVFISQIIEHLQRVLSIVLLEPNTNLGDLRLLSDEET
TS_15_PbtB  179   LFQFEFEAENLLLSVVYNERVIDSVFISQIIEHLQRVLSIVLLEPNTNLGNLRLLSDEET
OSY_SE_pbtB 181   LFQFEWEQDVISLHVTYNENRYDKPFITQIMNHVNSLFADVLYTPERVTQDVNLLSEQET A6_6i_PbtB  239   SLLLHGFNTTAAEYPRDRTIHELFTEQAARRTPDAVAAVGQQQLTYAELNGRANRLARTL
TS_15_PbtB  239   SLLLHGFNATAAEYPRDRTIHELFTEQAARRTPDAVAAVLGQQQLTYAELNGRANRLARTL
OSY_SE_pbtB 241   AQILYEFNDTAADYPRDKTIHQLFEEQEEQTPDAVLFEDKQLTYAELNAANRIAHLL A6_6i_PbtB  299   QNAGVRSDQLVGIMAERSLEMIVGLLAIMKAGGAYVPIDPEYPQERIRYMLEDSGAQTLL
TS_15_PbtB  299   QNAGVRTDQLVGIMAERSLEMIVGLLAIMKAGGAYVPIDPEYPQERIRYMLEDSGAQNLL
OSY_SE_pbtB 301   RERGVARGTLVGICVERSLEMVGLIGIFKAGGAYVPIDPDYPEERTNAMLEDTAISVLL A6_6i_PbtB  359   LQDHLRERV---TYEGTIVDMNSEHNYHDDGTELASVSDSS-NLAYVIYTSGTTGNPKGVM
TS_15_PbtB  359   LQDHLRERV---SYEGTIVDMNSEHNYHDDETELASVSDSS-NLAYVIYTSGTTGNPKGVM
OSY_SE_pbtB 361   TQAELIQTSMPNSIDSVLEDAAAETALEGSWPNITDAAGTADDVAYIIYTSGSTGIPKGVC A6_6i_PbtB  416   IEHRSAVNALLWRIRTYGLSSSDRILQLFSFSPDGFVMSAFCSLLSGAGLFLIKEEDAKD
TS_15_PbtB  416   IEHRSAVNALLWRIRTYGISSSDRLLQLFSFSPDGFVMSAFCSLLSGAGIFLIKEEDAKD
OSY_SE_pbtB 421   VTHRGVVR-LIAAANYVDISKDVFLQGSTISFDAATFEIWGSILNGALAILPP

FIG. 17B

```
                PNVKLIFNEYGPTENSVVATC---AIGLEKDQPITIGTPISNASVLIINTSGELQPLHVPG
A6_6i_PbtB  536 PDVKLIFNEYGPTENSVVATC---AIGLEKDQPITIGTPISNASVLIINTSGELQPLHVPG
TS_15_PbtB  536 QDLRLVNGYGPTBNTTPTCCHEISAADTERLSIPLGRPIANTQVYLDEACKLPVGVVG
OSY_SE_pbtB 538

A6_6i_PbtB  593 ELCIAGEGLARGYLNRPELTEEKPAAHPFVPGERIYHTGDSARWIPNGTIEYLGRIDHQV
TS_15_PbtB  593 ELCIAGEGLARGYLNRPELTEEKPAAHPFVPGERIYHTGDSARWLPNGTIEYLGRIDHQV
OSY_SE_pbtB 598 ELYTGGDGLARGYWNRPELTAEKFVDSPFVPGTRLFYRTGDLARWLPDGTIEYVGRIDDQV A6_6i_PbtB  653 KIRGFRIELGEIESSLKKIAGVREVIVDARPDGNGQHMLCAYMVADAELTVTELRREALSS
TS_15_PbtB  653 KIRGFRIELGEIESSLKNVAGVREVIVDARPDGNGQQMLCAYMVADSVLTVNELRREALSS
OSY_SE_pbtB 658 KISGTRIELGEVBAHLKVESVLDAIVIARQDESGQKTLCAYFTANAELMAGDLRAVLSQ A6_6i_PbtB  713 NLPDYMIPSHFVQMBQLPLTPSGKLIDRKSLPDPQANMAIGTEYIAPRTPLBARLAQIWQE
TS_15_PbtB  713 HPDYMIPSHFVQMEQLPLTPSGKIDRKSIPDPQANIAIGTEYIAPRTPLBARKAQIWQE
OSY_SE_pbtB 718 ELPAYMIPTHP

FIG. 17C

```
A6_6i_PbtB     1073  AADSGTTLYMVLLAAYTVLLHKYTGQEDIVVGTTNAGRMHDDLQPLIGMFVNTLAIRNYP
TS_15_PbtB     1073  AADSGTTLYMVLLAAYTVLLHKYTGQEDIVVGTTNAGRMHDDLQPLIGMFVNTLAIRNYP
OSY_SE_pbtB    1078  AAESGTTLYMVLLAAYTLLQKYTGQEDIIVVGTPNAGRTHGDLQPLIGMFVNTLAIRNYP A6_6i_PbtB     1133  AGESTFRAYLBQVKBQALAAFBHQEYPFBEIVEKLHVTRDMSRNPLFDTMPSLQNMENKD
TS_15_PbtB     1133  AGESTFRAYLBQVKBQALAAFBHQEYPFBEIVEKLRVARDLSRNPLFDTMPSLQNMENKD
OSY_SE_pbtB    1138  AGSKTFLE

FIG. 17D

```
A6_6i_PbtB   1613  LPGVTMYIMDGQRSLLPVGVIGELYIGGPCVGRGYWNRSEMTNEKFVEDPFLQDYRMYRT
TS_15_PbtB   1613  LPGVTMYIMDGQRSLLPVGVIGELYIGGPCVGRGYWNRSEMTSEKFVADPFLQDHRMYRT
OSY_SE_pbtB  1618  LPGVTMYIDDHSLLPVGITGELYIGGPCVGRGYWKRPDLTAEKFVDNPFAPGERMYRI A6_6i_PbtB   1673  GDLARWMPDGNIEYLGIRIDHQAKIRGYRIEIGEVESKLIKVETVRESVIVARQDPNGTKA
TS_15_PbtB   1673  GDLARWMPDGNIEYLGIRIDHQVKIRGYRIEIGEVESKLIKVETVRESVVARQDPNGTKA
OSY_SE_pbtB  1678  GDLARWLPDGNVEYLGIRIDHQVKIRGYRIEIGEVESQLLKTPFIREAVVAREDAGGQKS A6_6i_PbtB   1733  LCAYFVADRNLTVSELRSALADELPAYMIPSYFVQLDRLPLTPNGKVDRKALPAPEAGAH
TS_15_PbtB   1733  LCAYFVADRNLTVSELRSALADELPAYMIPSYFVQLDRIPLTPNGKVDRKALPAPEAGAH
OSY_SE_pbtB  1738  LCAYFVAERELTVSELRGALAAEIPGYMIPSYFVQLKQLPLTPNGKIDRKALPAPEGSAH A6_6i_PbtB   1793  TGIEYVAPRTEEELALANVWQTVLGIERVGVQDHFFELGGDSIKSIQVASRLQQAGYKLE
TS_15_PbtB   1793  TGIEYMAPRTEEELALANVWQTVLGIERVGVEDHFFELGGDSIKSIQVASRLQQAGYKLE
OSY_SE_pbtB  1798  TGTDYVAPRTEAEKTLAAVWQAVLGAERVGLMDHFFELGGDSIKSIQVSRLHQAGYKLE A6_6i_PbtB   1853  IRDLFKYPTIAQLGSHLQRASKVADQGEVSGDVPLTPILGWFFEQQFADAHHYNQSIMLY
TS_15_PbtB   1853  IRDLFKYPTIAQLGSHLQRASKVADQGEVSGDVPLTPILGWFFEQQFADAHHYNQSIMLY
OSY_SE_pbtB  1858  IRDLFKYPTIAELSPHLCPVGRMADQGBVSGTVPLTPIQRWFGQQPADPHHYNQSVMLH A6_6i_PbtB   1913  RREGFDEAAIRNVLQAVTEHHDALRIVFRRNDQGDYTAWNRAIEEGELFHLEVLNLTGSA
TS_15_PbtB   1913  RREGFNEAAIRNVLQAVTEHHDALRIVFRRNDQGDYTAWNRAIEEGELFHLEVLNLTGTI
OSY_SE_pbtB  1918  RKEGFDTAAIRKALQKLVEHHDGLRLVFRKTEEG-YTAWNRGIGEGELYRLYVADFTGVA A6_6i_PbtB   1973  SGDHEQNVRQIIEAKASEIQRSFDLIHDGPLARAGLFRTDEGDHLLIVMHHGVVDGVSWRI
TS_15_PbtB   1973  AGDHEQNVRQIIEAKATEIQRSFDLIHDGPLARAGLFRTDEGDHLLIVIHHAVVDGVSWRI
OSY_SE_pbtB  1977  ACE------RMIEAANEIQSGIDLQAGPLVRAGLFHGADGDHLLIVHHHAVVDGVSWRI A6_6i_PbtB   2033  LLEDIAAGYEQALKGEPVRLIPAKTDSFRTWANHLASYARSEAMIEEQVFWEQAEANATSI
TS_15_PbtB   2033  LLEDIATGYEQALKGEPVRLIPAKTDSFRTWANQLASYARSEAMIEEQIFWEQAEANGTSI
OSY_SE_pbtB  2031  LLEDFAASYEQALKQAERIFKTDSVRTWSDQLVEYARSPVLQRERAYWQRIAQTAK- A6_6i_PbtB   2093  LPLPKDFEABTSLQQDSESVVEWSREETDMLLKHVHRAYNTDMNDILLAALGMAIQQWC
TS_15_PbtB   2093  LSLPKDFEAETSLQQDSESVVEWSREETDMLLKHVHRAYNTDMNDILLAALGMAIQQWC
OSY_SE_pbtB  2090  -PLPRDYEAECSLQQDSESVTVQWSQEATEQLLKHVHRAYNTEMNDILLTALGMAVQKWC
```

```
A6_6i_PbtB    3770  IRYNYLGQFDADLSNNEMSVSPYASGSEISDEQERKYPLDINGVIAEGQLTLGLSYSVKE
TS_15_PbtB    3770  IRYNYLGQFDADLSNNELSVSPYASGSEISDEQERKYPLDINGVIAEGQLTLGLSYSVKE
OSY_SE_pbtB   3763  LRFNYLGQFDQDLQGNELELSYSSGSDMSDEQVRNISLDISGMIVDGLLSLDVSYSGKE A6_6i_PbtB    3830  YRKETMEELGDFLTESLKEIIAHCESQERTQLTPSDVLFKGLSLEWLDRISSQMQHIGEI
TS_15_PbtB    3830  YEKETMEELGDLLTESLKEIIAHCESQERTQLTPSDVLFKGLSLEWLDRISSQMQHIGEI
OSY_SE_pbtB   3823  YRKETIEELAGCLLVSLQEIIDHCAAKERPELTPSDVLQGLSVEELDQIAEQTRRNGEI A6_6i_PbtB    3890  ENVYALTPMQKGMWFHSAMDSLTGAYHEQTMFTLEGSLDVELFSSLNELAKRHAVLRTN
TS_15_PbtB    3890  ENVYALTPMQKGMWFHSAMDSLTGAYHEQTMFTLEGTLDVELFSSLNELAKRHAVLRTN
OSY_SE_pbtB   3883  ENIYTLTPMQKGMWFHSAMDRQSGAYHEQTRFTIEGELTDYFVKSLDALNNEAVLRTN A6_6i_PbtB    3950  FISGPQGEPVQVVFRNKPIGFSFQDVRAINEEBQQSFIKEAVSSDQLLGFDLAQGALMRV
TS_15_PbtB    3950  FISGPQGEPVQVVFRNKPIGFSFQDVRAINEEBQQSFIKEAVSSDQLLGFDLAQGALMRV
OSY_SE_pbtB   3943  FESGWNGEPLQVVFRDKRIGFAYADERELQEADRNRCIEKSAAEDHARGFDLEQDALMRV A6_6i_PbtB    4010  SAIRTGELSCRVLWSSHHILMDGWCLPQLMQELFDTYAALLQKKSPDR-TAVPAYSQYIE
TS_15_PbtB    4010  SAIRTGELSCRVLWSSHHILMDGWCLPQLMQELFDTYAALLQKKSPDR--TVVPAYSQYIE
OSY_SE_pbtB   4003  MVMRTGESSYQVLWSSHHILMDGWCLPQLAKELFDTYSVYLQQHHPEQATSVPAYSQYIE A6_6i_PbtB    4069  WLGQQDBEAAGTYWSAYLDYDQVTEIPQESSAGIDSEPYKAEKWSRELDAGLSASISRT
TS_15_PbtB    4069  WLGQQDBEAAGTYWSAYLADYDQVTEIPQESSAGIDSEPYKAEKWSRELDAGLSASISRA
OSY_SE_pbtB   4063  WLEQQDEAALSAYWSEYLAGYDQQAALPQQTAQG-RGEEYV

FIG. 17I

```
A6_6i_PbtB   4309  ILEQIVDNPRLAVEDIELATEARKSEVVQSFNDTFTNYPRDMMLHRLFEEQAERHPDAVA
TS_15_PbtB   4309  ILEQIVDNPRVAVEDIELATEARKSEVIQSFNDTLTNYPRDMLHRLFEEQAERHPDAVA
OSY_SE_pbtB  4302  VLEQIAANPQVTVGELKLATEAEQAEITSIFNNARTEYPRDKTHRLFEEQAERTPDATA A6_6i_PbtB   4369  ISFRDFQMTYRDLNDRVNRLARTLRAVGVGTDKLVGLMSERSPDMIGIALILKAGGGYV
TS_15_PbtB   4369  ISFRDVQMTYRDLNDRANRLARTLRAVGVGTDKLVGLMSERSPDMIGILAILKAGGGYV
OSY_SE_pbtB  4362  VMYENSQLTYRELNERANRLARTLRADGAGADRLVGLMVERSLDMVGIIAILKSGGAYV A6_6i_PbtB   4429  PIDPEYPGERIRYMLEDSGARIMLAQQHLTGKIPVMDASPLDAIINLDTETSYDSNGSNL
TS_15_PbtB   4429  PIDPEYPEERIRYMLEDSGARIMLAQQHLTGKIPAMDASPLDAIINLDTETSYDSNGSNL
OSY_SE_pbtB  4422  PIDPEYPEBRIRYMLEDSGTQHIYTQRHLQERIPGAGTRVI----LDDEHSYSDSTNL A6_6i_PbtB   4489  RANTDASSENLACVIYTSGTTGKPKGNLTTHERNIVRVRETEYIDITNHDNVLQMSSYAP
TS_15_PbtB   4489  RANTDASSENLAYVIYTSGTTGKPKGNLTTHERNIVRVRETEYIDITNHDNVLQMSSYAP
OSY_SE_pbtB  4477  DLNNGPA--DLAYVIYTSGTTGKPKGNLTMHERNIVRVQGADYIDIG

```
A6_6i_PbtB    6227  SAYQILLSKYCGQDDIIVGTPVAGRNHADLEPLIGMFVNTLAIRNRPQGDKTFQSFLAEV
TS_15_PbtB    6227  SAYQILLSKYCGQDDIIVGTPVAGRNHADLEPLIGMFVNTLAIRNRPQGDKTFQSFLAEV
OSY_SE_pbtB   6215  SAYTVLLSKYSGQEDIIVGTPVAGRAHADLEPLIGMFVNTLAIRNFPAGDKTFLSLLEEV A6_6i_PbtB    6287  KESTLGAFEHQEYPFEELIDLIKLQWETSRNPLFDTVFVLQNTEEREAGIGGLTISPYVT
TS_15_PbtB    6287  KESTLGAFEHQEYPFEELIDLIKLQWETSRNPLFDTVFVLQNTEEREAGIGGLTISPYVT
OSY_SE_pbtB   6275  KETALGAFEHQDYPFEELVERLNVQWDANRNPVFDTMFVMQNTEDHEVRLEALTESPYVL A6_6i_PbtB    6347  DDSVSAKFDLTLSVSEEDDGMKGSPLYASKLFKAAGIHRMRDYLSILSQVCENPRIRIQ
TS_15_PbtB    6347  DDSVSAKFDLTLSVSEEDDGMKGSPLYASKLFKAAGIHRMRDYLSILSQVCENPRIRIQ
OSY_SE_pbtB   6335  DNPIDAKFDLTLFVSEDNDVEKGFQYGTKLFKAAMIEKIMRDFLLVLAQIVEDPHIRLR A6_6i_PbtB    6407  DISISGQQTQEKSKIDTIEFAF
TS_15_PbtB    6407  DISISGQQTQEKSKIDTIEFAF
OSY_SE_pbtB   6395  DIKCNEQSVNNQRSIETIEFAF
```

A6 6i PtbB is SEQ ID NO. 12
TS-15 PtbB is SEQ ID NO. 15
OSY SE PtbB is SEQ ID NO. 18

```
A6_6i_PbtC    1608  TPEVIEVGLPPIGKPIANTSIYINDSFELQPIGVKGELYVSGACVGRGYWGRTDLTEEK
TS_15_PbtC    1608  MPDVIEVGLPPIGKPIANTSIFIVDDSFELQPIGVKGELYVSGASVGRGYWGRTDLTEEK
OSY_SE_pbtC   1607  QASTEGLRTVPIGKPLPGVTMYILDDQHSLLPMGITGELYIGGPCVGRGYWKRPDLTAEK A6_6i_PbtC    1668  FLDNPFAPGERLYKTGDVARWLPDGSIEYVGRSDHQVKIRGFRIELGEVESQLLHVPAVQ
TS_15_PbtC    1668  FLDNPFAPGERLYKTGDVARWLPDGSIEYVGRSDHQVKIRGFRIELGEVESQLLHVPAVQ
OSY_SE_pbtC   1667  FVDNPFAPGERMYRTGDLARWLPDGNVEYLGRIDHQVKIRGVRIELGEVETQLRTPFIR A6_6i_PbtC    1728  EATVALEDHAGQKQLCAYFAERSLTAGELRQALSQELPGYMIPSYFVQLERIPLTPNG
TS_15_PbtC    1728  EATVALEDHAGQKQLCAYFTECSLTAGELRALSQELPGYMIPSYFVQLERIPLTPNG
OSY_SE_pbtC   1727  EAVVAREDVSGQRSLCAYFVAERELTVSELRRALAAELPGYMIPSYFVQMERLPLTPNG A6_6i_PbtC    1788  KIDRRALPKPEGGIETGTEYVAPRTDTEARLARIWQDVLGLPSYGVKDNFFELGGHSLRA
TS_15_PbtC    1788  KIDRRALPKPEGGIETGTEYVAPRTETEARLARIWQDVLGLASYGVKDNFFELGGHSLRA
OSY_SE_pbtC   1787  KIDRKALPAPEGSAHTGAEFVAPRTSLEAQLARIWQEVLGLPDVSVKDNFFDLGGHSLRA A6_6i_PbtC    1848  TTLVSRLYKEMVNFPLRGVFRHPTIEEMAKAITEMHQELYTEIPIAEEKAYYPLSSAQK
TS_15_PbtC    1848  TTLVSRLYKEMVNFPLRGVFRHPTIEEMAKAITEMHQELYTEIPIAEEKAYYPLSSAQK
OSY_SE_pbtC   1847  TTLASKVRKEMHINLPLRDVFYPTIEELAELIAGMKKQEYAVIPLAEERDVPLSSAQK A6_6i_PbtC    1908  RLFIVSQLTGAEVSYNMPGVLIEGELDRAPFERAFQKLIDRHESLRTSFETVRGEPVQR
TS_15_PbtC    1908  RLFIVSQLTGAEVSYNMPGVLIEGELDRARPERAFQKLIDRHESLRTSFETVRGEPVQR
OSY_SE_pbtC   1907  RLIVSQIEGAELSYNMPGVITLEGPLDRTRFDGAFQQLIARHEALRTGFEMVNGEPVQR A6_6i_PbtC    1968  IHSQVEPAIEYHLAAEQDABALITHFVRPFQLKQAPLLRVGLIETGHERHILMPDMHHII
TS_15_PbtC    1968  IHSQVEPAIEYHLAAEKDABALITHFVRPPQLNQAPLLRVGLIETGHERHILMPDMHHII
OSY_SE_pbtC   1967  IERDVRLITVEYVQADEBEAEKLVQRFVRSFDKLRPLLRVGLIAIERERHILMPDMHHI A6_6i_PbtC    2028  SDGVTMGHVVNEFSRIYAGDOLPAIRIQYKDYAVWQQSNEYABKLAHQESYWLKQLDGEL
TS_15_PbtC    2028  SDGVTMGHVVNEFSRIYAGDOLPAIRIQYKDYAWQQSNEYABKLAHQBSYWLKQLDGEL
OSY_SE_pbtC   2027  SDGVTMGIVDEFARLYAGEDLPPLRIQYKDYAVWQQSEDRSVELRRQEAYWIERLQGEL A6_6i_PbtC    2088  PTLELPTDYVRPAVQQFBGDVALFTLTNSQABQLQRLAANYGATLYMVLLAAYTVLLHKY
TS_15_PbtC    2088  PTLELPTDYVRPAVQQFEGDVALFTLTNSQABQLQRLAANYGATLYMVLLAAYTVLLHKY
OSY_SE_pbtC   2087  PVLELPTDYVRPAVQKFDGDVALFTLDPHLSBQLRRIASDTGSTLLYMVLLAAYTLLHKY
```

FIG. 18E

```
A6_6i_PbtC    2148  TGQDDIIVGTPIAGRNHTELEPLVGMFVNTLAIRNYPTGEKSFABLLAEVKDTALAAFEH
TS_15_PbtC    2148  TGQDDIIVGTPIAGRNHTELEPLVGMFVNTLAIRNYPTGEKSFABLLAEVKDTALAAFEN
osy_SE_pbtC   2147  TGQEDIIVGTPIAGRSHSDLEPLIGMFVNTLAVRNYPASEKAFLSYLAEVKETLGAFEH A6_6i_PbtC    2208  QDYPFETLVEKVHKSRDMSRNPVFDTIFSVEHBQQSSFHIDGLRISPYPHSVAKFDLT
TS_15_PbtC    2208  QDYPFETLVEKVHKSRDMSRNPVFDTIFSVEHBQQSSFHIDGLRISPYPHSVAKFDLT
osy_SE_pbtC   2207  QDYPFEDLVEKVRVSRDISRNPLPDTMFSLENAEQGGIEIEGLQLKSYPNEHMTAKPDLT A6_6i_PbtC    2268  FHABQNEBGILCGLGYATALYAKETARRMGEHFVQLIDAIIAEPNAKLMSLNMMSLQERE
TS_15_PbtC    2268  FHABQNEBGILCGLGYATALYAKETAGRMGEHFVQLIDAIIAEPNAKLMSLNMMSLQERE
osy_SE_pbtC   2267  FHABEGBEGILCGLVYATALYKRDTVERMLHFKQLAAIAHDPRAQLSTLNMTAQERE A6_6i_PbtC    2328  QVKLVFNDTIINPREKTIQHLPEEQAEKSPDAVAVQFGGEGLTYREINERSNRLARTLR
TS_15_PbtC    2328  QVKLVFNDTITSYPREKTIQHLPEEQAEKSPDAVAIQFGEERITYREINERSNRLARTLR
osy_SE_pbtC   2327  EIIGVPNDTGKYPREKTIQHLPEEQVERTPDAALIVYGDERMTYRELNGRANRLARTLR A6_6i_PbtC    2388  GKGVKAGRCVGLMTDRSLDMIVAIMATLKAGGAYVPIDPDYPEERIRYMIDDSGTSLLVV
TS_15_PbtC    2388  GKGVKAGRFVGLMTDRSLDMIVAIMATLKAGGAYVPIDPDYPEERIRYMIDDDSGASLLVV
osy_SE_pbtC   2387  TKGVQADRLVGLMAERSLEMIVGILAILKAGGAYVPIDPEYPEERVRYMLEDSGTQILT A6_6i_PbtC    2448  QRHIQANHIPADCMVLVDDEGSYHADGTNLEQHGASDIAVVIYTSGTTGMPKGNLTTH
TS_15_PbtC    2448  QRHFQSNHIAADCLMVIVDDEDSYHADGTNLEQHGASDIAVVIYTSGTTGMPKGNITH
osy_SE_pbtC   2447  QHELQS-RIPVQASFVLEDDEHSYSADDSNLEQNGPADLAVIYTSGTTGKPKGNIATH A6_6i_PbtC    2508  RNIVRVRDAKYIEIDQHDTVLQLSSYAFDGSTFDIFGALLNGAKLVLITREVLDAGRL
TS_15_PbtC    2508  RNIVRVRDAKYIEIDQHDTVLQLSSYAFDGSTFDIFGALMNGAKLVLIPREVLDAGRL
osy_SE_pbtC   2506  RNIVRVQGTSYIDFSERDNVLQLSNYAFDGSTFDMYGALLNGAKLVLIPQETLLEVCKL A6_6i_PbtC    2568  ADTIESKISVMFITTAYFNLLVDLRVDSLREMRAILFGGERASVSHVRKALRHLGPKL
TS_15_PbtC    2568  ADTIEIEKISVMFITTAYFNLLVDLRVDSLREMRAILFGGERASVSHVRKALRHLGPKL
osy_SE_pbtC   2566  AGLIERERISVMFITTAYFNLIDMKADCLREIRTILFGGERVSISHVRKALIQLGPKI
```

FIG. 18F

```
A6_6i_PbtC   3048  GDIDQMIDGVEELKEMLVHHPLLRDQVKNKMRAYWSYATELVNSDIIDANIHALMAEPSE
TS_15_PbtC   3048  GDIDQMIDGVEELKEMLVHHPLLRDQVKNKMRAYWSYATELVNSDIIDANIHALMAEPSE
OSY_SE_pbtC  3046  SDIDQMLEAVGEQEMQLLSNPLIRERVHKMRAYWTYGSQLVNTGAVEANIYALHAEDSD A6_6i_PbtC   3108  VNQAGRGAARDMAGGYSRQVCGVQPTRCARRSASTAPLGSER----------------
TS_15_PbtC   3108  VNQADGEQLATWQEATRGRVVEYNLRGVHEDVLQPPFLEANANVMQAIIRHILEQTMVTH
OSY_SE_pbtC  3106  AVRPDNVTSALWDGATRQAYCEHRLIGVHRLIPGFIEHNVKVIHAVVHQIIEQTRGVH A6_6i_PbtC   3168  -----
TS_15_PbtC   3168  -----
OSY_SE_pbtC  3166  EVLSR A6 6i PbtC is SEQ ID NO. 13
TS-15 PbtC is SEQ ID NO. 16
OSY SE PbtC is SEQ ID NO. 19
```

FIG.18G

ANTIMICROBIAL PEPTIDES, PHARMACEUTICAL COMPOSITIONS, AND METHODS OF USE THEREOF

CROSS-REFERENCE TO RELATED APPLICATIONS

This application is a continuation in part of PCT/US2015/034859, filed on Jun. 9, 2015, which claims priority to U.S. Provisional Application 62/009,467 filed on Jun. 9, 2014, which are incorporated herein by reference in their entirety.

FIELD OF THE DISCLOSURE

The present disclosure is related to antimicrobial peptides, pharmaceutical compositions containing the antimicrobial peptides, and methods of treating microbial infections with the antimicrobial peptides.

BACKGROUND

Antibiotic-resistant pathogenic bacteria such as methicillin resistant *Staphylococcus aureus* (MRSA), fluoroquinolone resistant *Pseudomonas aeruginosa* and *Clostridium difficile*, and multi-drug resistant *Salmonella* spp. are an emerging problem in modern medicine. The loss of efficacy of current antibiotics makes the identification and development of new antibiotics more critical. The environment, for example, is an important source of microbial strains capable of producing potent antimicrobials which can be isolated and purified from their natural sources.

*Paenibacillus*, spore-forming species widely distributed in the environment, are a potential source of new antimicrobials. Strains of *Paenibacillus* can produce diverse antimicrobial agents including lantibiotics, lipopeptides, and macrolides. Lipopeptides, for example, are compounds that are generally not synthesized by ribosomes, and that are active against a wide range of bacteria, fungi, and oomycetes. Lipopeptides can act as antiviral and antitumor agents, immunomodulators or specific toxins and enzyme inhibitors.

There is thus a need to identify and develop antimicrobial agents that are effective against a broad spectrum of microbial pathogens such as Gram-positive and Gram-negative bacteria.

BRIEF SUMMARY

In an aspect, included herein is a peptide of the sequence (SEQ ID NO. 2)
$Xaa_1$-$Xaa_2$-$Xaa_3$-$Xaa_4$-$Xaa_5$-$Xaa_6$-$Xaa_7$-$Xaa_8$-$Xaa_9$-$Pro_{10}$-$Xaa_{11}$-$Pro_{12}$-$Ile_{13}$,, wherein $Xaa_6$ is Tyr, Phe, or Trp; $Xaa_1$, $Xaa_4$ and $Xaa_7$ are each independently Lys or Orn; $Xaa_2$, $Xaa_9$ and $Xaa_{11}$ are each independently Leu, Ile, Val, or Ala; $Xaa_3$, $Xaa_5$, and $Xaa_8$ are each independently Cys, Tyr, Thr, or Ser; wherein the peptide optionally includes a saturated or unsaturated, substituted or unsubstituted, linear or branched $C_4$-$C_{20}$ fatty acid group, or a saturated or unsaturated, linear or branched $C_4$-$C_{20}$ ester covalently linked to $Xaa_1$.

In another aspect, included herein is a peptide of the sequence (SEQ ID NO. 3)
$Xaa_1$-$Val_2$-$Thr_3$-$Xaa_4$-$Ser_5$-$Xaa_6$-$Xaa_7$-$Ser_8$-$Ile_9$-$Pro_{10}$-$Xaa_{11}$-$Pro_{12}$-$Ile_{13}$,, wherein $Xaa_6$ is Tyr, Phe, or Trp; $Xaa_{11}$ is Leu, Ile, Val, or Ala; and $Xaa_1$, $Xaa_4$ and $Xaa_7$ are independently Lys or Orn, wherein the peptide optionally includes a saturated or unsaturated, substituted or unsubstituted, linear or branched $C_4$-$C_{20}$ fatty acid group, or a saturated or unsaturated, linear or branched $C_4$-$C_{20}$ ester covalently linked to $Xaa_1$.

In certain aspects, the peptides are cyclized through a bond between $Thr_3$ and $Ile_{13}$.

Further included herein is a composition comprising the peptides described above and a carrier, vehicle, excipient, or diluent.

In yet another aspect, a process for preparing the peptides described above comprises (a) cultivating a host cell under conditions that allow for production of the peptide; and (b) purifying and isolating the peptide.

In a further aspect, a process for preparing a composition comprising the peptides described above comprises (a) cultivating a host cell under conditions that allow for production of the peptide; (b) purifying and isolating the peptide, and (c) producing a composition comprising the isolated peptide and a carrier, vehicle, excipient, or diluent.

In a still further aspect, a method of inhibiting growth or proliferation of a microbe comprises contacting the microbe or a surface or product which may contain a microbe with the peptide described above.

In a still further aspect, a method of inhibiting growth or proliferation of a microbe in a subject comprises administering to the subject a composition comprising one or more of the peptides described above, wherein the peptide is administered in an amount effective to inhibit growth or proliferation of the microbe.

BRIEF DESCRIPTION OF THE DRAWINGS

FIGS. 10A and 10B show product ion assignments as a result of combined interpretation of multiple $MS^n$ analyses. Representative examples of $MS^2$ spectra are shown for two of the most abundant compounds, containing a Phe (MW 1607) or Tyr (MW 1623) at position 6, respectively. These product ion assignments led to the chemical structure shown in FIG. 8.

FIG. 16A-M is a ptbA alignment for strains A6-6i, TS-15 and OSY SE.

FIG. 17A-M is a ptbB alignment for strains A6-6i, TS-15 and OSY SE.

FIG. 18A-G is a ptbC alignment for strains A6-6i, TS-15 and OSY SE.

Figure 1A:
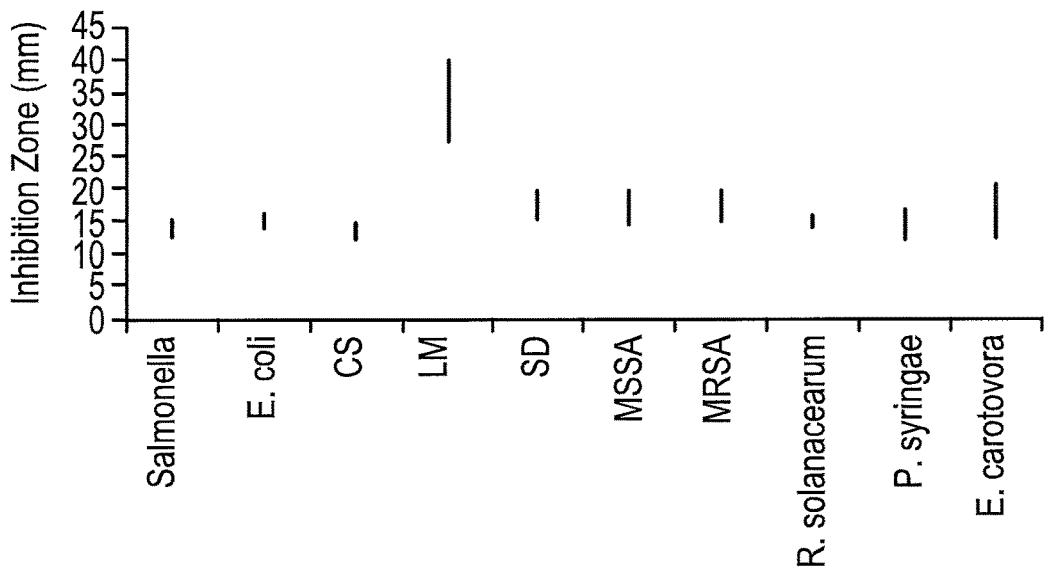
FIGS. 1A and B show in vitro inhibition of foodborne pathogens and tomato bacterial phytopathogens by *Paenibacillus alvei* TS-15 (FIG. 1A; ATCC PTA-121756) and A6-6i (FIG. 1B; ATCC PTA-121885) on tryptic soy agar (TSA). The inhibition zones (mm) were measured against strains from *Salmonella* spp., *Escherichia coli* (*E. coli*), *Cronobacter sakazakii* (CS), *Listeria monocytogenes* (LM), *Shigella dysenteriae* (SD), Methicillin sensitive *Staphylococcus aureus* (MSSA), Methicillin resistant *Staphylococcus aureus* (MRSA), *Ralstonia solanacearum* race 5 (*R. solanacearum*), *Pseudomonas syringae* pv. tomato strain dc3000 (*P. syringae*), and *Erwinia carotovora* subsp. *carotovora* (*E. carotovora*). The plots represents the lowest, highest, and average measurements in each of the species listed above. The experiment was repeated twice.

The above-described and other features will be appreciated and understood by those skilled in the art from the following detailed description, drawings, and appended claims.

DETAILED DESCRIPTION

Described herein are novel peptides, specifically cyclic peptides, that have antimicrobial and broad-spectrum antibacterial activity. Specifically, the peptides are active against dangerous Gram-positive organisms such as MRSA and VRSA.

Recently, tomatoes have been implicated as a primary vehicle in foodborne outbreaks of *Salmonella Newport* and other *Salmonella* serovars. Long-term intervention measures to reduce *Salmonella* prevalence on tomatoes remain elusive for growing and post-harvest environments. A naturally-occurring bacterium identified by 16S rDNA sequencing as *Paenibacillus alvei* was isolated epiphytically from plants native to the Virginia Eastern Shore tomato growing region. After initial antimicrobial activity screening against *Salmonella* and 10 other bacterial pathogens associated with the human food supply, strain TS-15 was further used to challenge an attenuated strain of *S. Newport* on inoculated tomatoes, leaves, and blossoms of tomato plants in an insect-screened high tunnel with a split-plot design. Survival of *Salmonella* after inoculation was measured for groups with and without the antagonist at days 0, 1, 2, 3, and 5 for blossoms and day 6 for tomatoes and leaves, respectively. TS-15 exhibited broad range antimicrobial activity against both major foodborne pathogens and major tomato plant-associated bacterial pathogens. After *P. alvei* strain TS-15 was applied onto the tomatoes, leaves, and blossoms of tomato plants, the concentration of *S. Newport* was significantly lower ($p<0.05$) compared with controls. Surprisingly, more than 90% of the plants had no detectable levels of *Salmonella* by day 5 for blossoms. The naturally occurring antagonist strain TS-15 is highly effective in reducing carriage of *Salmonella Newport* on whole tomato plants. The application of *P. alvei* strain TS-15 is a promising approach for reducing the risk of *Salmonella* contamination during tomato production. In addition, *Paenibacillus* strain A6-6i was found to retain comparable properties. Given to the fact that this activity can be attributed to the bactericidal compounds within, the present inventors have chemically isolated, purified, and identified certain compounds responsible for anti-*Salmonella* and other antibiotic effects including effects on dangerous gram positive organisms such as MRSA and VRSA.

More specifically, antimicrobial compounds were isolated from these *Paenibacillus* strains and a combination of low and high resolution mass spectrometry with multiple-stage tandem mass spectrometry was used for identification. A group of closely related cyclic lipopeptides was identified, differing primarily by fatty acid chain length and one of two possible amino acid substitutions. Variation in the fatty acid length resulted in mass differences of 14 Da and yields groups of related MS$^n$ spectra. Despite the inherent complexity of MS/MS spectra of cyclic compounds, straightforward analysis of these spectra was accomplished by determining differences in complementary product ion series between compounds that differ in molecular weight by 14 Da.

An "antimicrobial compound" is a compound that exhibits antimicrobial activity or a compound that affects microbial activity, meaning a compound that slows or stops growth and/or proliferation, slows or stops the rate of growth and/or proliferation, or stuns, inactivates, or kills a microbe. Antimicrobial compounds include antibiotics, antibacterials (e.g., bactericidal or bacteriostatic agents), antivirals (e.g., virucidal agents), antifungals (e.g., fungicidal or fungistatic agents), mold-inhibiting agents, anthelminthics (e.g., vermifuge or vermicidal agents), antiparasitics, and the like. Antimicrobial activity can be determined using methods described herein as well as methods known in the art.

As used herein, amino acids include alpha-amino acids of the general formula $H_2NCHRCOOH$ when free and HNCHRCO when in a polypeptide, wherein R is an amino acid side chain comprising an organic substituent, as well as uniquely structured amino acids such as, for example, proline Amino acids include, for example, isoleucine, leucine, alanine, asparagine, glutamine, lysine, aspartic acid, glutamic acid, methionine, cysteine, phenylalanine, threonine, tryptophan, glycine, valine, proline, serine, tyrosine, arginine, histidine, norleucine, ornithine, taurine, selenocysteine, selenomethionine, lanthionine, 2-aminoisobutyric acid, dehydroalanine, hypusine, citrulline, 3-aminopropanoic acid, aminobutryic acid (alpha, beta, and gamma) diaminobutyric acid, and the like. The term "amino acid side chain" refers to the various organic substituent groups (e.g., "R" in $H_2NCHRCOOH$) that differentiate one amino acid from another Amino acids include both L-form and D-form amino acids.

In one aspect, an antimicrobial peptide has the sequence:

$$Xaa_1\text{-}Val_2\text{-}Thr_3\text{-}Xaa_4\text{-}Ser_5\text{-}Xaa_6\text{-}Xaa_7\text{-}Ser_8\text{-}Ile_9\text{-}Pro_{10}\text{-}Ile_{11}\text{-}Pro_{12}\text{-}Ile_{13}, \quad \text{(SEQ ID NO. 1)}$$

wherein $Xaa_6$ is Tyr, Phe, or Trp, specifically Tyr or Phe; $Xaa_1$, $Xaa_4$, and $Xaa_7$ are each independently Lys or Orn; or, $$Xaa_1\text{-}Xaa_2\text{-}Xaa_3\text{-}Xaa_4\text{-}Xaa_5\text{-}Xaa_6\text{-}Xaa_7\text{-}Xaa_8\text{-}Xaa_9\text{-}Pro_{10}\text{-}Xaa_{11}\text{-}Pro_{12}\text{-}Ile_{13}, \quad \text{(SEQ ID NO. 2)}$$

wherein $Xaa_6$ is Tyr, Phe, or Trp, specifically Tyr or Phe; $Xaa_1$, $Xaa_4$, and $Xaa_7$ are each independently Lys or Orn; $Xaa_2$, $Xaa_9$ and $Xaa_{11}$ are each independently a hydrophobic amino acid selected from Leu, Ile, Val, and Ala; $Xaa_3$, $Xaa_5$, and $Xaa_8$ are each independently an amino acid selected from amino acids that can form a hydrogen bond, a disulfide bond, a thioether bond, or an ester bond, such as Cys, Tyr, Thr, and Ser.

In a more specific aspect, an antimicrobial peptide has the sequence:

$$Xaa_1\text{-}Val_2\text{-}Thr_3\text{-}Xaa_4\text{-}Ser_5\text{-}Xaa_6\text{-}Xaa_7\text{-}Ser_8\text{-}Ile_9\text{-}Pro_{10}\text{-}Xaa_{11}\text{-}Pro_{12}\text{-}Ile_{13}, \quad \text{(SEQ ID NO. 3)}$$

wherein $Xaa_6$ is Tyr, Phe, or Trp, specifically Tyr or Phe; $Xaa_1$, $Xaa_4$, and $Xaa_7$ are each independently Lys or Orn; $Xaa_{11}$ is a hydrophobic amino acid selected from Leu, Ile, Val, and Ala. In a specific embodiment, $Xaa_1$ and $Xaa_4$ are Orn and $Xaa_{11}$ is Ile; more specifically, $$Orn_1\text{-}Val_2\text{-}Thr_3\text{-}Orn_4\text{-}Ser_5\text{-}Xaa_6\text{-}Xaa_7\text{-}Ser_8\text{-}Ile_9\text{-}Pro_{10}\text{-}Ile_{11}\text{-}Pro_{12}\text{-}Ile_{13}, \quad \text{(SEQ ID NO. 4)}$$

wherein $Xaa_6$ is Tyr or Phe; and $Xaa_7$ is Lys or Orn.

In a specific embodiment, the peptide is $$Orn_1\text{-}Val_2\text{-}Thr_3\text{-}Orn_4\text{-}Ser_5\text{-}Tyr_6\text{-}Lys_7\text{-}Ser_8\text{-}Ile_9\text{-}Pro_{10}\text{-}Ile_{11}\text{-}Pro_{12}\text{-}Ile_{13}. \quad \text{(SEQ ID NO. 77)}$$

In an aspect, the peptide comprises D-Lys at position 7. In another aspect, the peptide comprises L-Lys at position 7

In certain embodiments, the peptides of SEQ ID NOs. 1-4 include a fatty acid group, particularly a saturated or unsaturated, substituted or unsubstituted, linear or branched $C_4$-$C_{20}$ fatty acid group, or a saturated or unsaturated, linear or branched $C_4$-$C_{20}$ ester covalently linked to the amino acid at the 1 position, e.g., $Xaa_1$. The fatty acid chain is diverse in the number of —$CH_2$. For example, the molecular formula of the acyl chain can be $C_{10}H_{19}O$, $C_{11}H_{21}O$, $C_{12}H_{23}O$, $C_{13}H_{25}O$, $C_{14}H_{27}O$, or $C_{15}H_{29}O$. The ester group differs similarly ($C_{10}H_{19}O_2$, $C_{11}H_{21}O_2$, $C_{12}H_{23}O_2$, $C_{13}H_{25}O_2$, $C_{14}H_{27}O_2$, or $C_{15}H_{29}O_2$).

Depending on the functional groups, peptides can be cyclized C-terminus to N-terminus, C-terminus to side-chain, side-chain to N-terminus, or side-chain to side-chain. In one aspect, the peptide is cyclized through a bond between $Thr_3$ and $Ile_{13}$.

In a specific embodiment, when $Xaa_6$ is Tyr, the amino acid at the 1 position is covalently linked to a fatty acid group or an ester group, and when $Xaa_6$ is Phe, the amino acid at the 1 position is covalently linked to a fatty acid group.

It is noted that the presently disclosed compounds are distinct from the cyclic peptides disclosed in US2013/0164317, which requires that $X_{12}$ is an amino acid with a charged side chain. In the present compounds, $X_{12}$ is a Proline, which is expected to impart a unique structure and also antimicrobial properties to the disclosed peptides.

Also included herein are methods of producing an antimicrobial compound, specifically an antimicrobial peptide, by (a) cultivating a host cell under conditions that allow for production of the antimicrobial peptide; and optionally (b) purifying/isolating the antimicrobial peptide.

Host cells are cultivated in a nutrient medium suitable for production of the antimicrobial peptide using techniques known in the art. For example, the cell is cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. A suitable nutrient medium (e.g., a medium comprising carbon and nitrogen sources, inorganic salts, etc.) is used to cultivate the cells. In embodiments wherein the antimicrobial peptide is secreted from the cell into the nutrient medium, the antimicrobial peptide can be recovered directly from the medium. If the antimicrobial peptide is not secreted, it can be recovered from cell lysates or as inclusion bodies. The antimicrobial peptide may be recovered from the nutrient medium or cell lysates by procedures including, but not limited to, centrifugation, filtration, extraction, spray-drying, evaporation, and precipitation.

The antimicrobial peptides disclosed herein may be purified by a variety of procedures including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, and extraction.

Bacterial cultures for the production of the antimicrobial peptides can be grown using suitable methods and media useful for bacterial cell growth, maintenance, and/or protein production.

In some embodiments of this process, the antimicrobial peptide is isolated and/or purified using a suitable technique known in the art, including liquid chromatography, phase separation, using organic solvents and/or aqueous solvent or buffer systems. In some embodiments the antimicrobial peptide is purified to about 75%, 80%, 85%, 90%, 91%, 92%, 93%, 94%, 95%, 96%, 97%, 98%, or 99% or more. Analysis of purity can be made using an analytical method or technique such as, for example, mass spectrometry, gel electrophoresis, fluorescence, colorimetric assays, NMR, UV-Vis, total amino acid hydrolysis, chromatographic separation methods that utilize, for example, liquid chromatographic methods such as HPLC, FPLC, size exclusion, affinity binding, hydrophobic interaction, ionic charge, where purity can be assessed based on peak area.

In other embodiments, the antimicrobial peptides can be generated by standard chemical and/or protein and peptide synthetic techniques as are known in the art. Some embodiments relate to a synthetic strategy that incorporates a combination of chemical, peptide, and enzymatic (e.g., cyclase) synthetic steps. Chemical techniques for cyclizing peptides are well-known in the art.

Aspects of the disclosure relate to compositions and formulations, including pharmaceutical compositions and formulations that comprise an effective amount of at least one antimicrobial peptide. Such compositions and formulations comprise an effective amount of an antimicrobial peptide in combination with a carrier, vehicle, excipient, or diluent, including pharmaceutically and/or agriculturally acceptable carriers, vehicles, excipients, and diluents. An "effective amount" relates to a quantity of an antimicrobial peptide that is high enough to provide a significant positive result (e.g., slow or stop microbial activity) or positive modification of the subject's condition to be treated, and is suitably low enough to avoid serious side effects (at a reasonable benefit/risk ratio). Carriers, vehicles, excipients, and diluents are one or more compatible substances that are suitable for administration to a mammal such as, for example, solid or liquid fillers, diluents, hydrotopes, surface-active agents, and encapsulating substances. "Compatible" means that the components of the composition are capable of being mixed with the active agent, and with each other, in a manner such that there is no interaction which would substantially reduce the efficacy of the composition under ordinary use situations. Carriers, vehicles, excipients, and diluents are suitably of sufficiently high purity and sufficiently low toxicity to render them suitable for administration to the subject being treated, such as a human subject. The carrier, vehicle, excipient, or diluent can be inert, or it can possess pharmaceutical benefits and/or aesthetic benefits, or both. Suitable carriers, vehicles, excipients, and diluents are known in the art.

The antimicrobial compositions are applicable in a variety of products and applications, ranging from, for example, products of low and high pH-values, highly concentrated and diluted products, products usable in the technical field (e.g., in detergents for industrial or house-hold use), in the pharmaceutical field (e.g., for cleaning/disinfection of equipment or in the preparation of pharmaceutical compositions or their packaging, and in surgical supplies and sterilization of tools/hospital operating rooms), in personal care (e.g., in manufacture of cosmetics, shampoos, creams and lotions), in the feed industry (e.g., for cleaning of equipment, in the manufacture, storage, handling and preparation of animal feed and drink products) and in the food and drink industry (post-harvest foods, food processing surfaces and packaging). The antimicrobial peptides are also useful in post-surgical bandage and would dressing prep, external wound healing and cleansing. In addition, the antimicrobial peptides are useful in post-harvest and food preservation applications against spoilage organisms. In embodiments relating to use of the compositions in a product, the antimicrobial composition can be provided as an ingredient in the final product (e.g., cosmetic, detergent, pharmaceutical, food, or drink product). Accordingly, in some embodiments, the compositions are effective against certain yeasts, fungi, and bacteria commonly associated with food-spoilage. Standard methods can be used in the manufacture of such products that comprise one or more of the antimicrobial peptide described herein.

In some embodiments, the antimicrobial composition is present on the surface of the products or inside the products. In some embodiments, the disclosure includes a method for reducing or preventing the presence, growth or activity of a microbe (e.g., gram-positive or gram-negative bacteria) in a product, such as a food or drink product, wherein the method comprises contacting the food or drink product during one or more of the various stages in the food processing process including the stages of the manufacture, the handling, the storage and/or the preparation of the food or drink product with the antibacterial compositions that are disclosed herein. The antimicrobial composition may be applied or introduced by a suitable route or method such as, for example, as a spray, a rinse or a wash solution or as solution wherein the various food products are dipped. Further, the antimicrobial composition may be used to treat containers or packaging film prior to, simultaneously with, or subsequently after packaging the products.

In one aspect, a method of inhibiting growth or proliferation of a microbe comprises contact of the microbe with an antimicrobial peptide as described herein. "Contacting," as used herein as in "contacting a cell," refers to contacting a cell directly or indirectly in vitro, ex vivo, or in vivo (i.e., within a subject, such as a mammal, including humans, mice, rats, rabbits, cats, and dogs). Contacting a cell, which also includes "reacting" a cell, can occur as a result of administration to a subject. Contacting encompasses administration to a cell, tissue, mammal, subject, patient, or human. Further, contacting a cell includes adding an agent to a cell culture. Other suitable methods may include introducing or administering an agent to a cell, tissue, mammal, subject, or patient using appropriate procedures and routes of administration as defined herein.

The antimicrobial compositions described herein may be provided in solid or liquid form. When in liquid form, the composition is typically an aqueous composition, which may be a solution, emulsion, or dispersion.

Accordingly, the methods described herein include administration of one or more pharmaceutical compositions, in which an antimicrobial peptide is admixed together with one or more pharmaceutically acceptable carriers, excipients, buffers, adjuvants, stabilizers, or other materials, as described herein.

"Pharmaceutically acceptable," as used herein, pertains to compounds, materials, compositions, and/or dosage forms which are, within the scope of sound medical judgment, suitable for use in contact with the tissues of a subject (e.g., a human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

The formulations may conveniently be presented in unit dosage form and may be prepared by methods known in the art of pharmacy. Such methods include the step of bringing into association the active compound(s) with the carrier which constitutes one or more accessory ingredients. In general, the formulations are prepared by uniformly and intimately bringing into association the active compound with liquid carriers or finely divided solid carriers or both, and then if necessary shaping the product.

Formulations may be in the form of liquids, solutions, suspensions, emulsions, elixirs, syrups, tablets, lozenges, granules, powders, capsules, cachets, pills, ampoules, suppositories, pessaries, ointments, gels, pastes, creams, sprays, mists, foams, lotions, oils, boluses, electuaries, or aerosols.

Formulations suitable for oral administration (e.g., by ingestion) are typically presented as discrete units such as capsules, cachets or tablets, each containing a predetermined amount of the active compound; as a powder or granules; as a solution or suspension in an aqueous or nonaqueous liquid; or as an oil-in-water liquid emulsion or a water-in-oil liquid emulsion; as a bolus; as an electuary; or as a paste.

A tablet may be made by compression or molding, optionally with one or more accessory ingredients. Compressed tablets are prepared by compressing in a suitable machine the active compound in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); and preservatives (e.g., methyl p-hydroxybenzoate, propyl p-hydroxybenzoate, sorbic acid). Molded tablets are made by molding in a suitable machine a mixture of the powdered compound moistened with an inert liquid diluent. The tablets are optionally coated or scored and may be formulated so as to provide slow or controlled release of the active compound therein using, for example, hydroxypropylmethyl cellulose in varying proportions to provide the desired release profile. Tablets are optionally provided with an enteric coating, to provide release in parts of the gut other than the stomach.

Formulations suitable for parenteral administration (e.g., by injection, including cutaneous, subcutaneous, intramuscular, intravenous and intradermal injection), include aqueous and nonaqueous isotonic, pyrogen-free, sterile injection solutions which may contain anti-oxidants, buffers, preservatives, stabilizers, bacteriostats, and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Examples of isotonic vehicles for use in such formulations include Sodium Chloride Injection, Ringer's Solution, or Lactated Ringer's Injection. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets. Formulations may be in the form of liposomes or other microparticulate systems which are designed to target the active compound to blood components or one or more organs.

Formulations suitable for topical administration (e.g., transdermal, intranasal, ocular, buccal, and sublingual) may be formulated as an ointment, cream, suspension, lotion, powder, solution, past, gel, spray, aerosol, or oil. Alternatively, a formulation may comprise a patch or a dressing such as a bandage or adhesive plaster impregnated with active compounds and optionally one or more excipients or diluents. Formulations suitable for topical administration to the eye also include eye drops wherein the active compound is dissolved or suspended in a suitable carrier, especially an aqueous solvent for the active compound.

Formulations suitable for topical administration via the skin include ointments, creams, and emulsions. When formulated in an ointment, the active compound may optionally be employed with either a paraffinic or a water-miscible ointment base. Alternatively, the active compounds may be formulated in a cream with an oil-in-water cream base. The topical formulations may desirably include a compound which enhances absorption or penetration of the active compound through the skin or other affected areas. Examples of such dermal penetration enhancers include dimethylsulfoxide.

It will be appreciated that appropriate dosages of the active compounds, and compositions comprising the active compounds, can vary from subject to subject. Determining the optimal dosage will generally involve the balancing of the level of therapeutic benefit against any risk or deleterious side effects of the treatments described herein. The selected dosage level will depend on a variety of factors including, but not limited to, the species of the particular subject, the activity of the particular compound, the route of administration, the time of administration, the rate of excretion of the compound, the duration of the treatment, whether other drugs, compounds, and/or materials are used in combination, and the age, sex, weight, condition, general health, and prior medical history of the subject. The amount of compound and route of administration will ultimately be at the discretion of the physician, although generally the dosage will be to achieve local concentrations at the site of action which achieve the desired effect without causing substantial harmful or deleterious side-effects.

Administration in vivo can be effected in one dose, continuously or intermittently (e.g., in divided doses at appropriate intervals) throughout the course of treatment.

Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

In general, a suitable dose of the active compound is in the range of about 100 µg to about 250 mg per kilogram body weight of the subject per day, administered in a single or multiple doses per day.

A method of inhibiting growth or proliferation of a microbe in a subject comprises administering to the subject a composition comprising an antimicrobial peptide, wherein the antimicrobial peptide is administered in an amount effective to inhibit growth or proliferation of the microbe.

In an embodiment, a method of treating a condition or disease associated with the presence of a microbe comprises administering to a subject in need thereof a composition comprising an antimicrobial peptide, wherein the antimicrobial peptide is administered in an amount effective to treat the condition or disease.

In an embodiment, a method of treating a microbial infection comprises administering to a subject in need thereof a composition comprising an antimicrobial peptide, wherein the antimicrobial peptide is administered in an amount effective to treat the microbial infection. Exemplary infections include MRSA, VRSA, and CRE infections.

"Administration" or "administering," as used herein, refers to providing, contacting, and/or delivery of a compound or compounds by an appropriate route to achieve the desired effect. Administration may include, but is not limited to, oral, sublingual, parenteral (e.g., intravenous, subcutaneous, intracutaneous, intramuscular, intraarticular, intraarterial, intrasynovial, intrasternal, intrathecal, intralesional, or intracranial injection), transdermal, topical, buccal, rectal, vaginal, nasal, ophthalmic, via inhalation, and implants.

As used herein, the terms "treatment," "treating," or "treat" refer to both therapeutic treatment and prophylactic or preventative measures. Those subjects in need of treatment include those already showing clinical signs of the particular disease, disorder, or condition as well as those prone to having or developing the disease, disorder, or condition, or those in which the disease, disorder, or condition is to be prevented. Many diseases, disorders, and conditions relate to the presence of microbes and are known to those of skill in the art, including secondary conditions resulting from opportunistic infections arising from other primary diseases and disorders (e.g., immune-suppressing conditions). Thus, a variety of patient classes can benefit from the methods of treatment described herein.

As used herein, the term "subject" is intended to include human and non-human animals. Exemplary human subjects include a human patient having a disorder, e.g., a disorder described herein, or a normal subject. The term "non-human animals" includes all vertebrates, e.g., non-mammals (such as fowl (e.g., ducks, chickens, etc.), amphibians, reptiles) and mammals, such as non-human primates, domesticated and/or agriculturally useful animals (such as horses, goats, sheep, dogs, cats, cows, pigs, etc.), and rodents (such as mice, rats, hamsters, guinea pigs, etc.).

In some embodiments the "effective amount" is an amount sufficient to stop or slow the progression of the disease, disorder, or condition. In some embodiments the effective amount is an amount sufficient to reverse disease, disorder, or condition, or repair the clinical signs of a disease, disorder, or condition. In embodiments the amount is sufficient to stop or slow the progression of an infection that is directly or indirectly related to a microbe. In some embodiments the effective amount is sufficient to stop or slow the proliferation and/or growth of a microbe. In further embodiments, the effective amount is sufficient to kill a microbe.

"Co-administered," as used herein, refers to simultaneous or sequential administration of multiple compounds or agents. A first compound or agent may be administered before, concurrently with, or after administration of a second compound or agent. The first compound or agent and the second compound or agent may be simultaneously or sequentially administered on the same day, or may be sequentially administered within 1 day, 2 days, 3 days, 4 days, 5 days, 6 days, 1 week, 2 weeks, 3 weeks or one month of each other. Suitably, compounds or agents are co-administered during the period in which each of the compounds or agents are exerting at least some physiological effect and/or has remaining efficacy. In some embodiments, the methods described herein can comprise co-administering two or more active agents disclosed herein. In some embodiments, the methods comprising co-administering two or more active agents include at least one antimicrobial agent disclosed herein in combination with a known active agent against a particular indication. In some further embodiments, the known active agent also exhibits antimicrobial activity.

Additional antimicrobial agents can be selected based on the particular method and indication, such that it can provide an additive or a synergistic antimicrobial effect when compared to administration of the antimicrobial agent alone. For example, other antibiotics such as polymyxin B can be concurrently applied to increase its effect against gram-negative bacteria. Furthermore, fungicides can be co-administered for broader protection.

The invention is further illustrated by the following non-limiting examples.

EXAMPLES

Methods

Bacterial Cell Culture: *Paenibacillus alvei* strains A6-6i and TS-15, naturally-occurring bacterium previously isolated from plant and soil native to the Virginia Eastern Shore tomato growing region, were propagated on tryptic soy agar (TSA) at 35° C. The indicator strains (Table 1) included were also propagated on TSA at 35° C. Stock cultures grown overnight at 35° C. on TSA were resuspended in brain heart infusion broth (BHI) with 25% glycerol and stored at −80° C. Three tomato plant-associated bacterial pathogens including *Erwinia carotovora* subsp. *carotovora*, *Pseudomonas syringae* pv. tomato strain dc3000, and *Ralstonia solanacearum* race 5 were grown on TSA at 25° C. (Table 1).

TABLE 1

| Strain | Reference or source |
| --- | --- |
| *Salmonella enterica* subsp. *enterica* serovar Newport #17 | CFSAN laboratory collection |
| *Salmonella enterica* subsp. *enterica* Saintpaul | CFSAN laboratory collection |
| *Salmonella enterica* subsp. *enterica* Montevideo 42N | CFSAN laboratory collection |

TABLE 1-continued

| Strain | Reference or source |
|---|---|
| *Salmonella enterica* subsp. *enterica* Javiana | CFSAN laboratory collection |
| *Salmonella enterica* subsp. *enterica* Typhimurium 368477 | CFSAN laboratory collection |
| *Salmonella enterica* subsp. *enterica* Typhimurium SAR C #1 | SGSC[a] |
| *Salmonella enterica* subsp. *enterica* Typhi SAR C #3 | SGSC |
| *Salmonella enterica* subsp. *arizonae* SAR C #5 | SGSC |
| *Salmonella enterica* subsp. *arizonae* SAR C #7 | SGSC |
| *Salmonella enterica* subsp. *arizonae* SAR C #9 | SGSC |
| *Salmonella bongori* SAR C #11 | SGSC |
| *Salmonella bongori* SAR C #13 | SGSC |
| *Salmonella bongori* SAR C #15 | SGSC |
| *Escherichia coli* O157:H7 IS O57 | CFSAN laboratory collection |
| *Escherichia coli* O157:H7 EDL933 | CFSAN laboratory collection |
| *Escherichia coli* ATCC 51434 | ATCC[b] |
| *Escherichia coli* ATCC BAA-179 | ATCC |
| *Shigella dysenteriae* 2457T | CFSAN laboratory collection |
| *Shigella dysenteriae* BS103 | CFSAN laboratory collection |
| *Cronobacter sakazakii* E932 | CFSAN laboratory collection |
| *Cronobacter sakazakii* E784 | CFSAN laboratory collection |
| *Listeria monocytogenes* N1-225 | CFSAN laboratory collection |
| *Listeria monocytogenes* R2-583 | CFSAN laboratory collection |
| Methicillin-resistant *Staphylococcus aureus* #9 | CFSAN laboratory collection |
| Methicillin-resistant *Staphylococcus aureus* #12 | CFSAN laboratory collection |
| Methicillin-resistant *Staphylococcus aureus* #28 | CFSAN laboratory collection |
| Methicillin-resistant *Staphylococcus aureus* #29 | CFSAN laboratory collection |
| Methicillin-resistant *Staphylococcus aureus* #30 | CFSAN laboratory collection |
| *Staphylococcu aureus* NRS70 | NARSA[c] |
| *Staphylococcu aureus* NRS106 | NARSA |
| *Staphylococcu aureus* NRS107 | NARSA |
| *Staphylococcu aureus* NRS271 | NARSA |
| *Salmonella enterica* Newport #17 ΔtolC::aph | CFSAN laboratory collection |
| *Erwinia carotovora* subsp. *carotovora* | Dr. Dilip Lakshman, ARS[d] |
| *Pseudomonas syringae* pv. tomato strain dc3000 | Dr. Dilip Lakshman, ARS |
| *Ralstonia solanacearum* race 5 | Dr. Dilip Lakshman, ARS |

[a]SGSC, *Salmonella* Genetic Stock Centre, University of Calgary, Canada
[b]ATCC, American Type Culture Collection, Manassas, VA, USA
[c]NARSA, Network on Antimicrobial Resistance in *Staphylococcus aureus*, Chantilly, VA, USA
[d]ARS, Agricultural Research Service, Department of Agriculture, Beltsville, MD, USA Determination of Mode of Action and Spectrum of Antimicrobial Activities To determine mode of action and antimicrobial spectrum of the bacterial antagonists, both agar plug assay (using bacterial culture) and bioscreen assay (using culture supernatant) were performed against a broad spectrum of major foodborne pathogens and bacterial phytopathogens (Table 1). In the agar plug assay, bactericidal effects against pathogenic bacterial strains in the zone of inhibition were confirmed when no viable cells were recovered on TSA plates. In the bioscreen assay, the antagonist supernatant from overnight culture was filter sterilized with a 0.22 μm pore-size cellulose acetate (CA) membrane filter. Each 3 ml TS-15 cell-free culture supernatant (CFCS) was inoculated with 3 μl of $10^8$ cfu/mL bacterial culture (Table 1). Aliquots (200 μl) were then dispensed into sterile Bioscreen C microwell plates (Growth Curves USA, Piscataway, N.J.) and incubated as described for the respective bacterial strains. Bacterial growth was determined in five replicates by measuring O.D.600 at 20-min intervals for 24 hours.

Fraction Collection: The modified method was based on methods known in the art. Cells were removed from Petri dishes using cell scrapers and were deposited into Eppendorf tubes. A final volume of 100 μL of acetonitrile was added for every dish of scraped cells. The samples were shaken for 30 minutes and centrifuged at 7710 g for 15 minutes. The supernatant was removed and evaporated. The sample was reconstituted in water and was filtered with a 0.22 μm Nylon filter. Fraction collection by liquid chromatography (LC) was achieved using a Shimadzu Nexera with a Kinetex C18 column (1.7μ, 100 Å, 150×2.10 mm). The separation was performed with a column temperature of 60° C. and a flow rate of 400 μL/min using water with 0.1% formic acid (v/v) and acetonitrile with 0.1% formic acid (v/v) with the following gradient: 5 min hold at 95% water, 50 min linear gradient from 95% to 5% water, 5 min equilibration at 95% water. Fractions were concentrated and biological activity was tested against MRSA and *E. coli*. Fractions with activity were further examined by multiple mass spectrometry (MS) platforms.

Bioactivity Assay: Ten microliters of the 1-minute fractions from *Paenibacillus alvei* strain A6-6i or TS-15 were spotted directly on plates containing a lawn of $10^6$ cells of *Escherichia coli* O157:H7 strain EDL933 and Methicillin-resistant *Staphylococcus aureus* strain #12, respectively. After incubation at 35±2° C. for 24 hours, the antimicrobial activity exhibited by 1-minute fractions was observed as a clear zone of inhibition (ZI). The fraction that exhibited the ZI was focused henceforth. As a control experiment, 10 μL of serial two-fold polymyxin B (Sigma-Aldrich, St. Louis, Mo.) dilutions starting from 1 mg/mL stock were spotted on a lawn of $10^6$ cells of *Salmonella enterica* serovar Montevideo strain 29N.

Matrix-Assisted Laser Desorption/Ionization Time-of-Flight Mass Spectrometry (MALDI-TOF/MS) Analysis: Fractions that were found to be active were diluted 1:30 in water and 1 μL was placed onto the MALDI target with 1 μL of prepared CHCA matrix (20 mg/mL in 70% acetonitrile with 0.1% formic acid). The MALDI instrument used to analyze the samples was an Applied Biosystems/MDS Sciex 4800 MALDI TOF/TOF Analyzer. The laser power was optimized for each analysis to use the minimum level required for sufficient ionization. Tandem mass spectrometry (MS/MS) was also performed on ions of interest using post-source decay (PSD).

LC/MS Analysis with High-Resolution Mass Spectrometry: The sample extract (prior to fraction collection) and resulting fractions were analyzed using the same LC conditions listed previously coupled to a high-resolution mass spectrometer (Q-EXACTIVE™, Thermo Scientific). The Q-EXACTIVE™ settings used were: 140,000 resolution, 1e6 AGC target, Maximum IT 60 ms, and a mass range of 300-4000 Da was monitored; the settings for the heated electrospray ionization probe (HESI-II) were: 4 kV spray voltage, 50 psi sheath gas, 15 (arbitrary units) auxiliary gas, 380° C. capillary temperature, and 300° C. heater temperature. Active fractions were further analyzed with LC-MS/MS with the following modified conditions: 1 µL injection of the 1:30 diluted fraction, 35,000 resolution for full scan mode, and Maximum IT of 120 ms. MS$^n$ Analysis: Multiple-stage mass spectrometry experiments (MS$^n$) were performed using an Orbitrap ELITE™ (Thermo Scientific). Fractions were diluted 1:30 in 70% methanol with 0.1% formic acid. Infusion for nanospray was accomplished using the Triversa Nanomate (Advion) with 1.5 kV voltage and 0.3 psi gas pressure. A mass range of 225 to 2000 was monitored in full MS mode with 120,000 resolution. Both collision-induced dissociation (CID) and electron-transfer dissociation (ETD) were used for MS/MS and MS$^n$ experiments.

16S rRNA Gene Amplification and Sequencing: Genomic DNA of potential bacterial antagonists was extracted using the WIZARD® genomic DNA purification kit (Promega, Madison, Wis.). A pair of universal primers specific for bacterial 16S rRNA, Eubac27 and R1492, were used to amplify the corresponding gene. PCR amplification of the 16S rRNA was performed with a HOTSTART TAQ® plus DNA polymerase kit (QIAGEN, Valencia, Calif.) under the following conditions: after an initial 5-minute incubation at 95° C., the mixture was subjected to 30 cycles, each including 1 minute at 95° C., 1 minute at 58° C., and 1 minute at 72° C. A final extension was performed at 72° C. for 10 minutes. Both strands of purified PCR products were directly Sanger sequenced using the following primers:27F (5'-AGAGTTTGATCCTGGCTCAG-3'; SEQ ID NO: 72), 1492R (5'-GGTTACCTTGTTACGACTT-3'; SEQ ID NO: 73), 357F (5'-CTCCTACGGGAGGCAGCA-3'; SEQ ID NO: 74), 518R (5'-CGTATTACCGCGGCTGCTGG-3'; SEQ ID NO: 75), and 1100R (5'-AGGGTTGCGCTCGTTG-3'; SEQ ID NO: 76) Sequence fragments were edited and assembled into contigs using Molecular Evolutionary Genetics Analysis software v.5.0(MEGA 5.0). The BLAST algorithm was used for a homology search against GENBANK®. Only results from the highest-score queries were considered for phylotype identification, with 99% minimum similarity.

Whole Genome Sequencing: Genomic DNA was isolated from an overnight culture of each strain using a QIAGEN DNEASY® blood and tissue kit (QIAGEN Inc., Valencia, Calif.). Genome sequencing was performed using 454 Titanium sequencing technology (Roche, Branford, Conn.), achieving >25X average genome coverage. De novo assembly was created for each genome using the 454 Life Sciences Newbler software package, v.2.5.3 (Roche). The genomic DNA of P. alvei strains TS-15 and A6-6i was also sequenced using the Pacific Biosciences (PacBio) RS sequencing platform. A single 10-kb library was sequenced using $C_2$ chemistry on 8 single-molecule real-time (SMRT) cells with a 90-min collection protocol on the PacBio RS. The 10-kb continuous-long-read (CLR) data were de novo assembled using the PacBio hierarchical genome assembly process (HGAP)/Quiver software package, followed by Minimus 2, and they were polished with Quiver. The assembled contigs from both approaches were annotated with the NCBI Prokaryotic Genomes Automatic Annotation Pipeline.

Identification and Characterization of the pbt Gene Cluster: Genomic comparison of pbt gene cluster (NRPS genes involved in the biosynthesis of a non-ribosomal lipopeptide antibiotic) between these two strains and P. thiaminolyticus strain OSY-SE (accession #ALKF00000000) as described in U.S. Publication No. US2013/0164317 was performed. The nonribosomal peptide synthetase (NRPS) machinery is composed of modular multi-domain enzymes which act as an assembly line to incorporate each amino acid monomer by one module. A typical module (C-A-T) in an NRPS contains a carrier Thiolation (T) domain and two catalytic domains, an adenylation (A) domain for amino acid activation and selectivity and a condensation (C) domain catalyzing peptide bond formation. In the termination module (C-A-T-Te), the Te-domain is responsible for releasing the assembled peptide. Additionally, optional epimerase (E) domain may also be present for L- to D-epimerization of amino acids. The NRPS in P. alvei strains A6-6i and TS-15 genomes was analyzed by NRPSpredictor2, a webserver for predicting NRPS adenylation domain. The A domain possesses a conserved binding pocket for amino acid recognition and activation. The substrate specificity of A-domain for amino acid was identified using NRPSpredictor2, based on the fingerprint residues at the substrate-binding site. In addition, epimerization (E) domains and the Te domain were identified (PKS/NRPS analysis webserver).

Example 1: Broad Antimicrobial Spectrum of P. alvei Strains A6-6i and TS-15

Figure 1B:
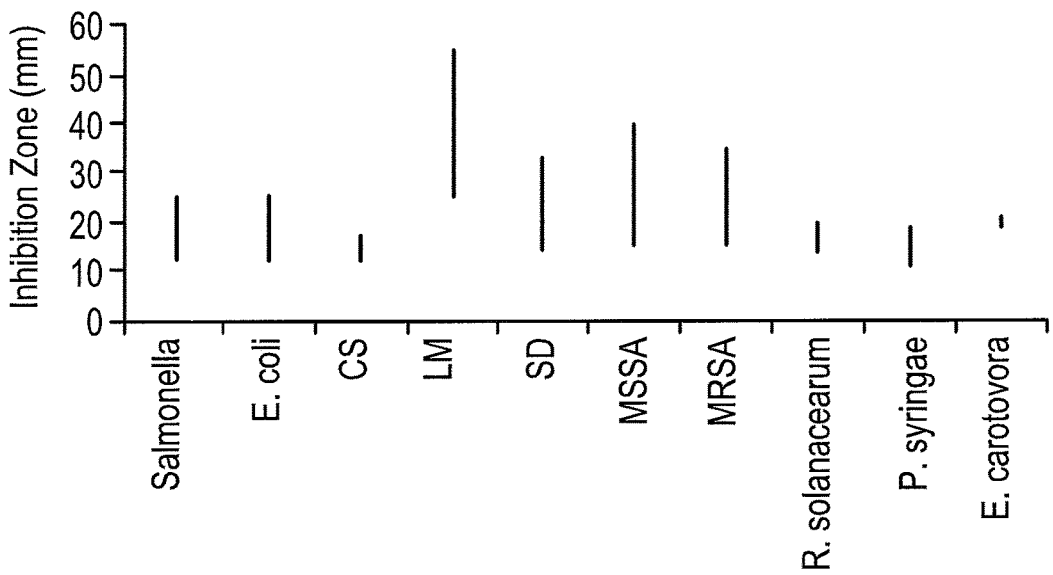

In vitro agar plug assays showed inhibition zones against all the indicator strains including six major foodborne pathogens and three major tomato bacterial phytopathogens when challenged with both P. alvei isolates (FIGS. 1A and 1B). Notably, the antagonist migrated outward from the plug after forming the inhibition zone with SD (S. dysenteriae) or LM (L. monocytogenes), and the antagonistic growth ring expanded with time, especially in the case of Listeria. Both A6-6i and TS-15 had a wide range of inhibition against MRSA strains with zone diameters from 15 to 35 mm, and 15 to 20 mm, respectively. It is also interesting to note that strain A6-6i showed strong inhibitory effects on various MRSA strains tested despite the fact that some strains were resistant to up to 14 different antimicrobial drugs.

Figure 2A:
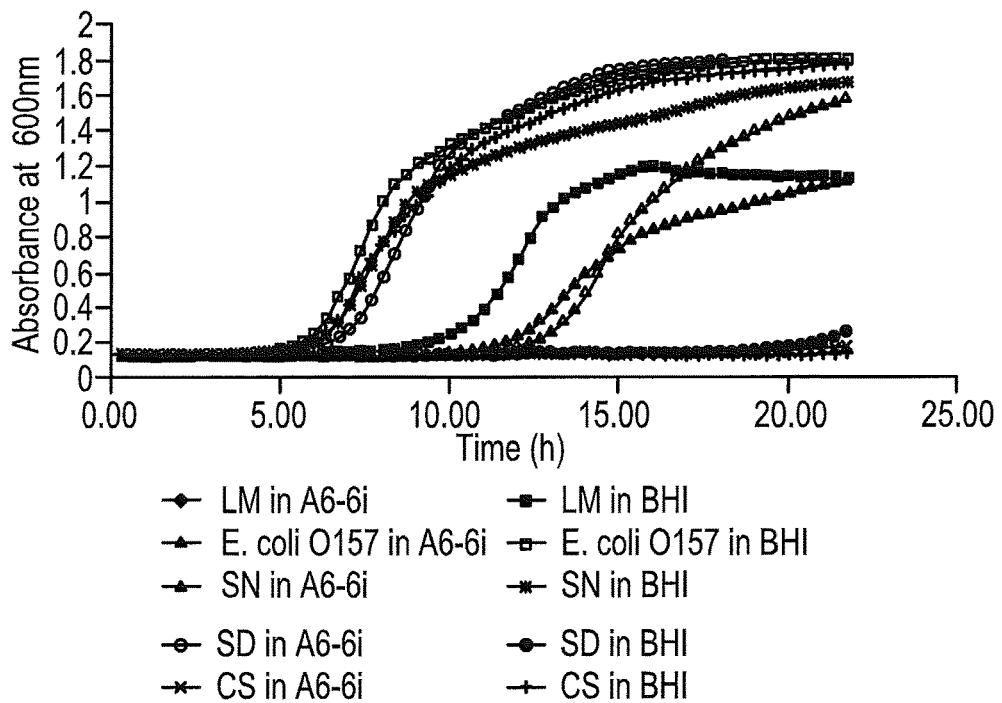
FIGS. 2A and B show growth inhibition of major foodborne pathogens in *P. alvei* A6-6i cell free culture supernatant (CFCS). Brain Heart Infusion (BHI) broth was used as a control. Bacterial growth of A) *L. monocytogenes* (LM), *S. dysenteriae* (SD), *E. coli* O157, *C. sakazakii* (CS), and *S. Newport* strains; and B) Methicillin resistant *S. aureus* (MRSA) strains in *P. alvei* A6-6i CFCS and BHI was determined in five replicates by measuring O.D.$_{600}$ at 20-minute intervals for 24 hours. The experiment was repeated twice.
Figure 2B:
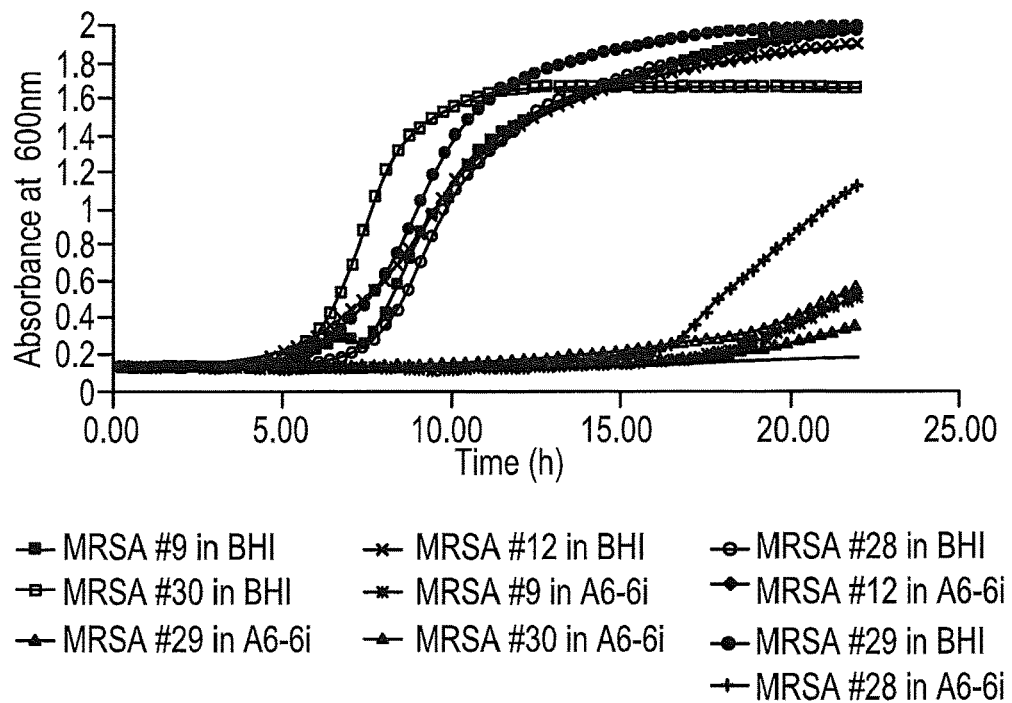

When supernatants were tested against the panel of gram-negative and gram-positive bacteria using the Bioscreen assay, both A6-6i (FIG. 2) and TS-15 (not shown) CFCS exhibited a broad spectrum of antimicrobial activity, in which the lag phase was significantly extended in all the pathogens tested and the cell density was largely reduced at the end of incubation. Furthermore, the lag phase in CS (C. sakazakii), SD (S. dysenteriae), LM (L. monocytogenes), and some MRSA strains were extended to almost 24 hours in both A6-6i and TS-15 CFCS. Compared to A6-6i, CFCS from TS-15 had a much stronger inhibitory effect when tested against SN (S. Newport) (not shown).

Example 2: Bioactivity Results

Figure 3:
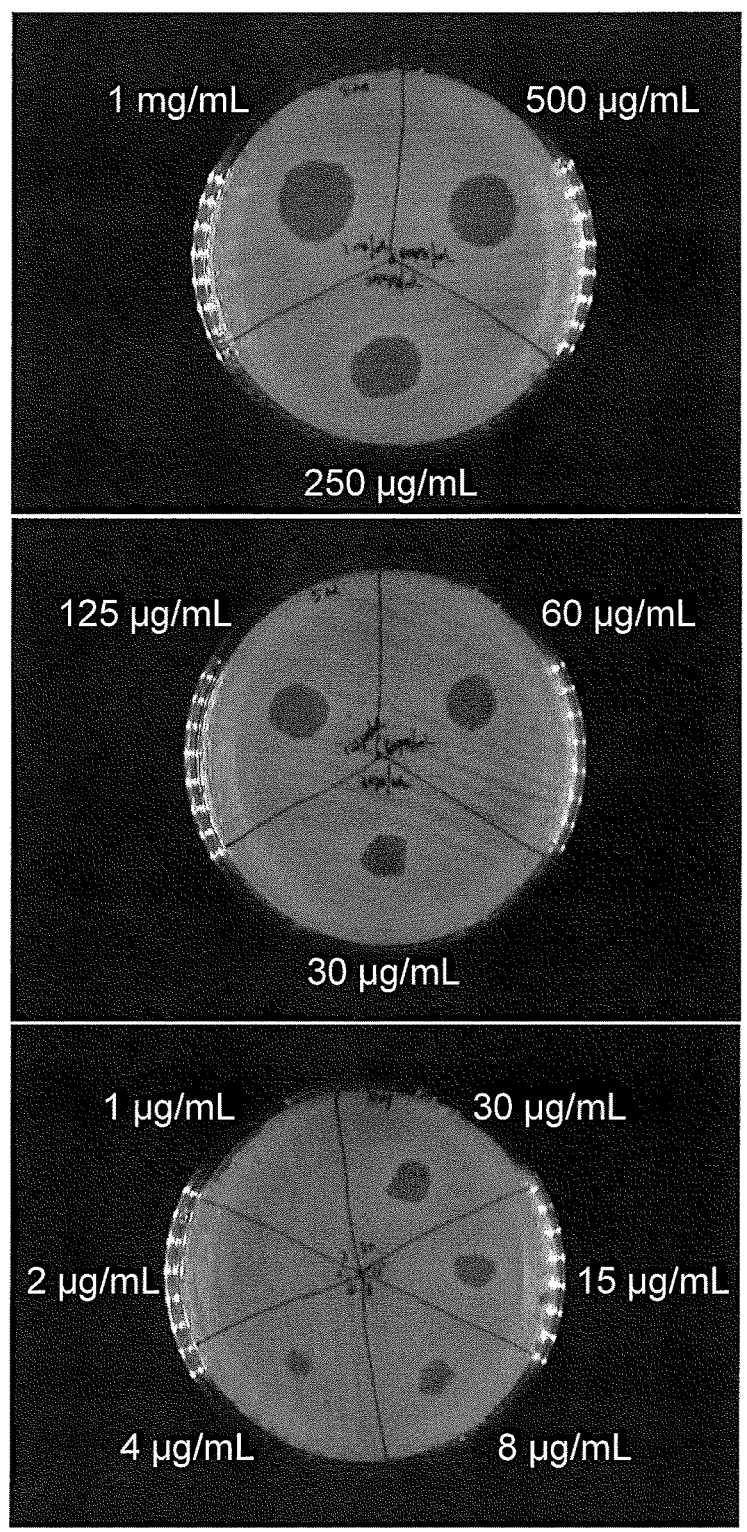
FIG. 3 shows a polymyxin B standard on a *Salmonella* lawn. A 10 µL volume of 2-fold serial polymyxin B dilutions starting from 1 mg/mL to 1 µg/mL was spotted on a lawn of 10⁶ cells of *Salmonella enterica* serovar Montevideo strain 29N. The zone of inhibition (ZI) was observed after 24 hour incubation at 35±2° C.
Figure 4:
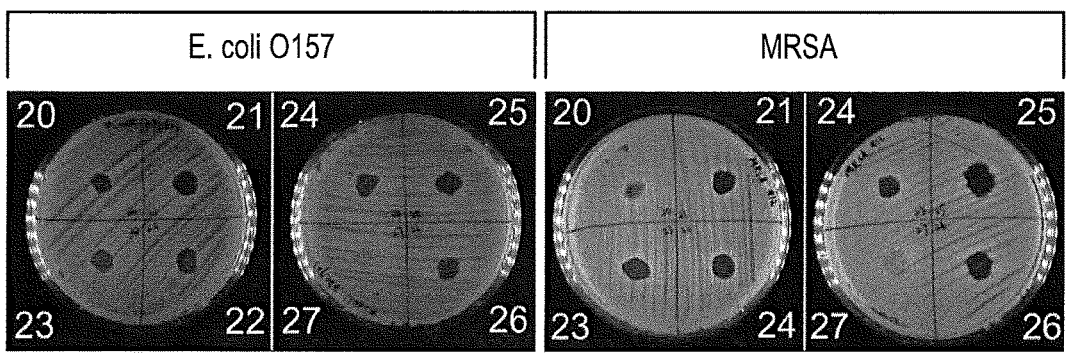
FIG. 4 shows TS-15 1-minute active fractions against pathogens. A 10 μL volume from the 1-minute fractions of *P. alvei* strains TS-15 was spotted on a lawn of 10⁶ cells of A) *Escherichia coli* O157:H7 strain EDL933; B) Methicillin-resistant *Staphylococcus aureus* strain #12. After incubation at 35±2° C. for 24 hours, the antimicrobial activity exhibited by the 1-minute fractions was observed as a clear zone of inhibition (ZI). These experiments were also done for *P. alvei* strain A6-6i (data not shown).

Polymyxin B showed clear antimicrobial dose response against S. Montevideo (control experiment). The minimum inhibitory concentration for polymyxin B to show clear ZI was 4 μg/mL on the lawn of S. Montevideo strain 29N (FIG. 3). Seven of the 1-minute fractions showed antimicrobial activity against both *E. coli* O157:H7 strain EDL933 and Methicillin-resistant *S. aureus* strain #12 (FIG. 4). Similarly, multiple 1-minute fractions from *P. alvei* strain A6-6i exhibited antimicrobial activities against both strains as well (results not shown).

Example 3: Identification of the Primary Peptide Sequence

Figure 5:
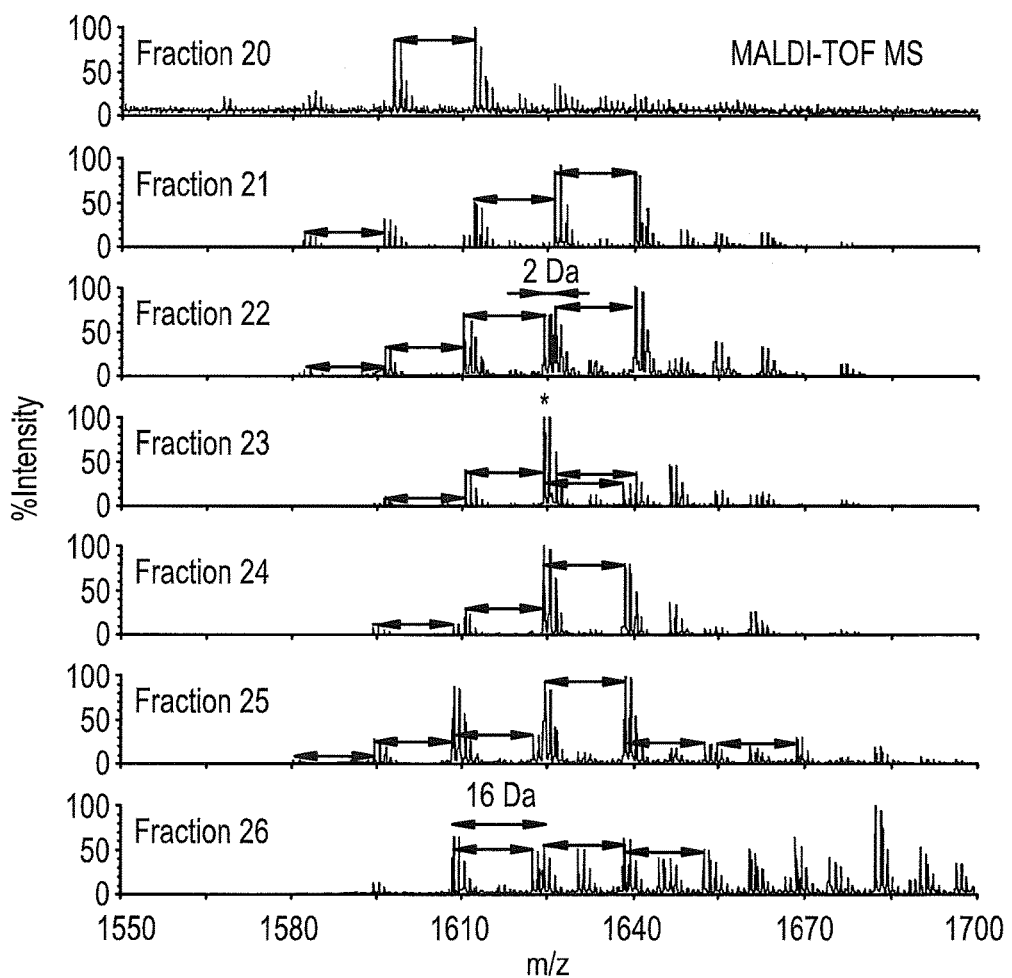
FIG. 5 shows MALDI-TOF MS results for fractions 20-26 from TS-15. The unlabeled arrows indicate a mass difference of 14 Da, which indicates a difference in $CH_2$; an asterisk indicates MW 1623, which is designated as the primary sequence; two examples of a mass difference of 2 and 16 Da are labeled, which correspond to the other molecular variants.

MALDI-TOF MS analysis revealed a number of compounds that were present in each of the seven bioactive fractions, as shown in FIG. 5. The MALDI spectra provided a view of the full complement of compounds from each bioactive fraction within a single spectrum where clusters of these compounds differed by 14 Da, indicated by unlabeled arrows. The compound with a molecular weight of 1623 will be referred to as the primary compound (ion indicated with an asterisk in FIG. 5), although multiple variants of similar abundances are present (FIG. 5).

Figure 6:
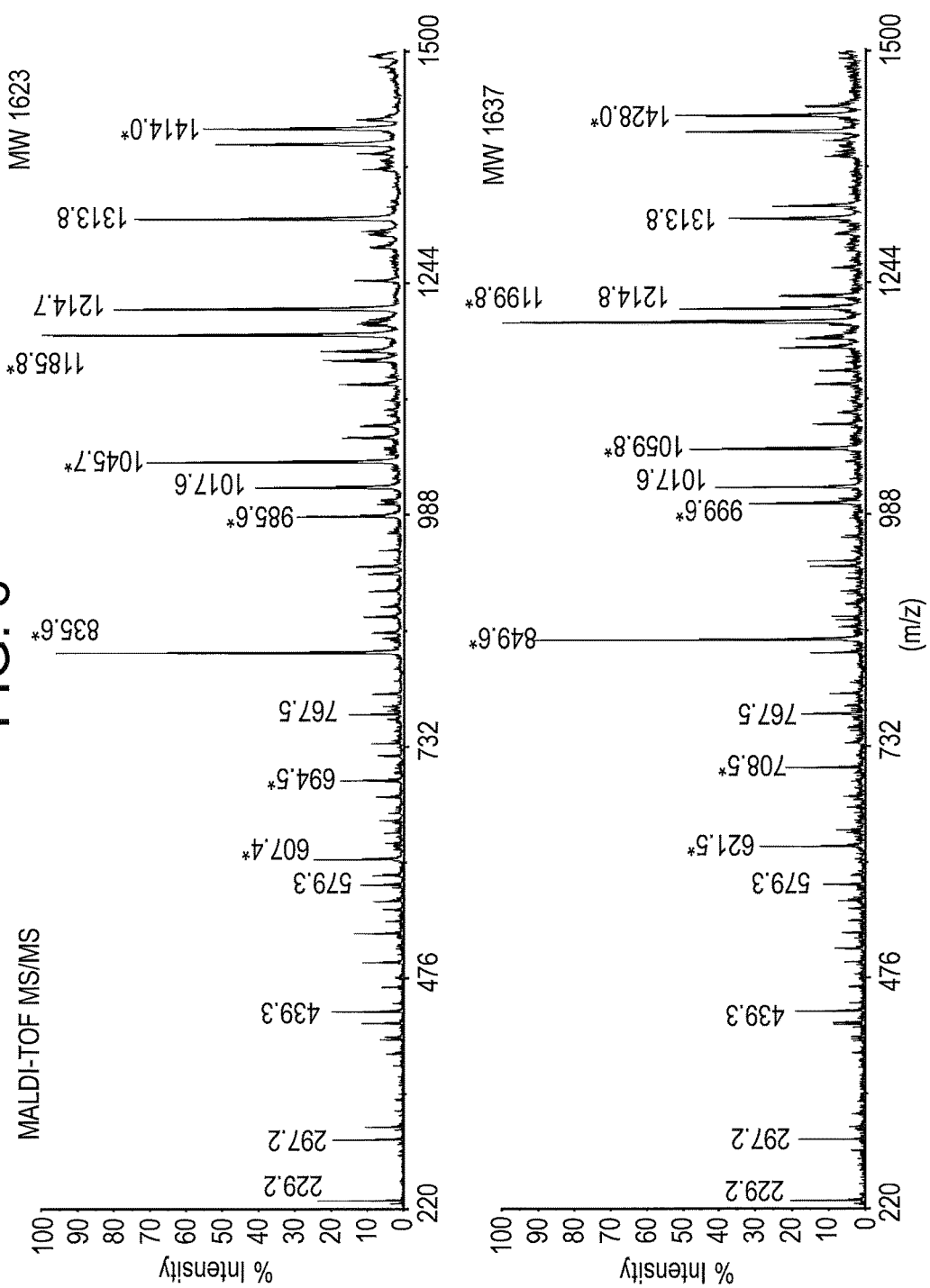
FIG. 6 shows MS/MS similarity. MALDI-TOF MS/MS comparison of two compounds that differ by 14 Da in molecular weight. Mass-to-charge ratios with an asterisk indicate an observed mass difference of 14 Da in the comparison between the two spectra.
Figure 7:
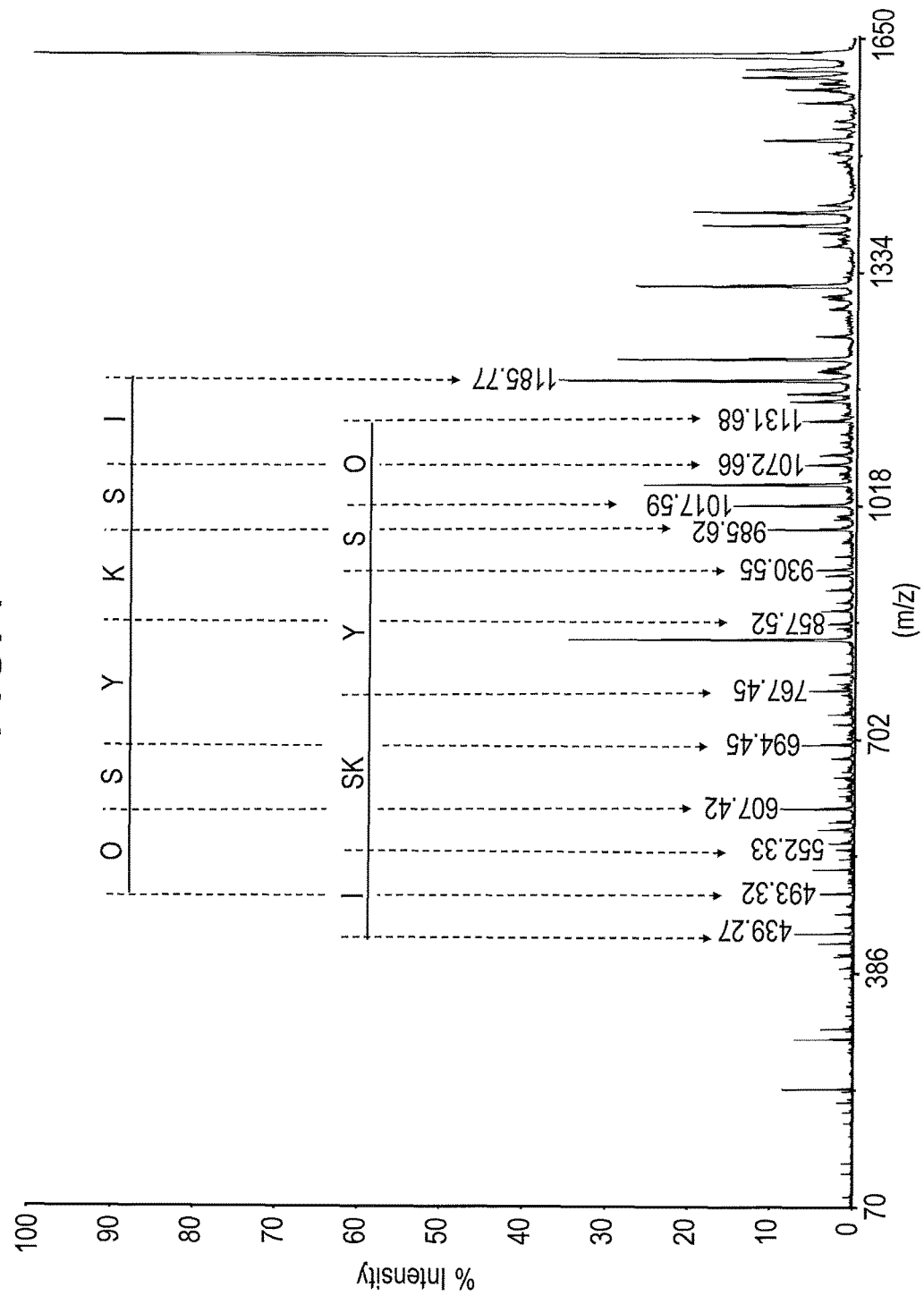
FIG. 7 shows partial sequence information from MALDI-TOF MS/MS spectrum of MW 1623 elucidated by manual de novo sequencing.

The MALDI-TOF MS/MS analyses of these molecular species revealed similar fragmentation patterns, which confirmed that the compounds that differ by 14 Da were related. As illustrated in FIG. 6, comparison of MS/MS spectra of the primary compound, MW 1623, and the compound of MW 1637, which differ in molecular weight by 14 Da, revealed a series of product ions that shared the same mass and a second product ion series that differed by 14 Da, suggesting that the mass discrepancy between compounds was localized to one region of the molecule. This enabled identification of complementary product ion pairs, with one direction corresponding to the product ion series retaining the region of the molecule that contained the 14 Da mass-shift and the other direction corresponding to product ions that were identical between the two peptides (FIG. 7). Manual de novo sequencing resulted in a partial amino acid sequence, yielding a putative sequence assignment.

Figure 8A:
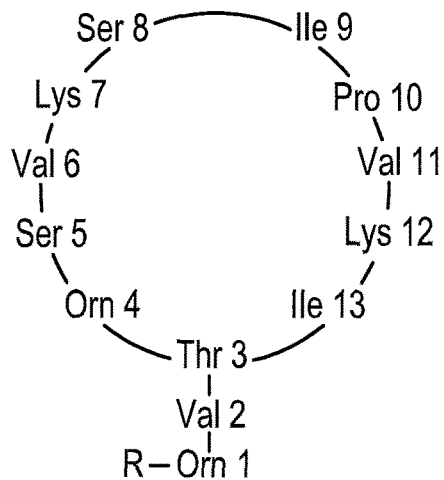
FIGS. 8A and B show schematics of a previously published identified lipopeptide and the peptides discovered in current work. A. Molecule described in U.S. Publication No. US2013/0164317 and referred to as paenibacterin. B. Molecule(s) discovered in current work. The "R" group corresponds to an attached acyl chain in structure A and B; however, the "R" group for the structure in B can also be an ester, for example, when Tyr is at position 6.

A compound of the present invention is shown in FIG. 8 B.

Figure 8B:
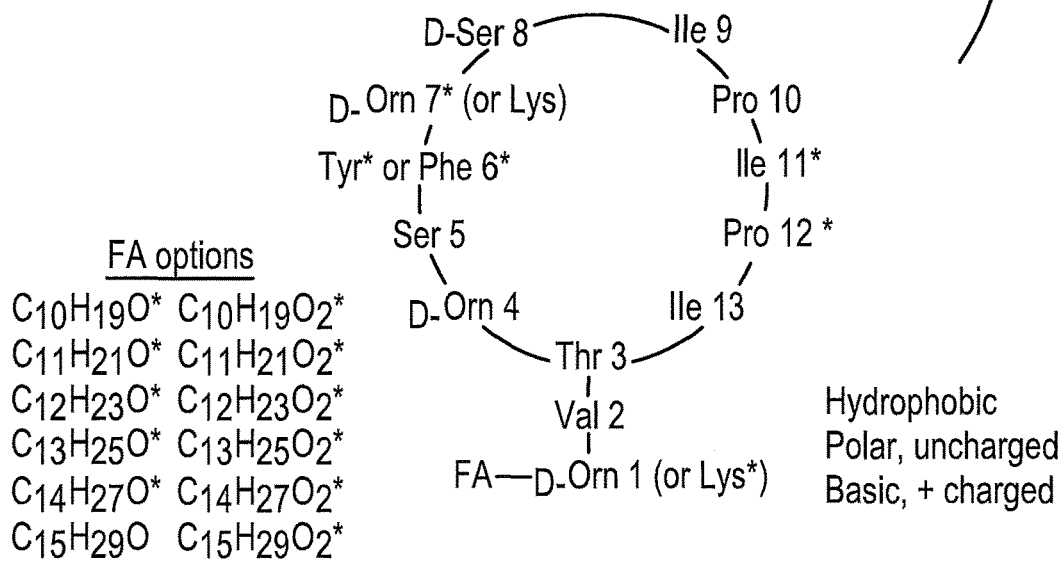

Analysis of MALDI-TOF MS/MS spectra only revealed partial sequence tags. To improve sequence coverage, individual fractions were infused and analyzed with the Orbitrap Elite, allowing for the collection of MS$^n$ data. Again, pairs of MS$^n$ spectra were analyzed and complementary ion pairs were identified based on the presence of 14 Da mass differences. The combined MS$^n$ data allowed a complete amino acid sequence to be determined (FIG. 8B). This amino acid sequence was similar to a previously identified cyclic compound isolated from a different *Paenibacillus* strain which also showed broad-spectrum activity against MRSA and *E. coli*; the structure of that compound, designated as paenibacterin, is shown in FIG. 8 A.

Figure 9:
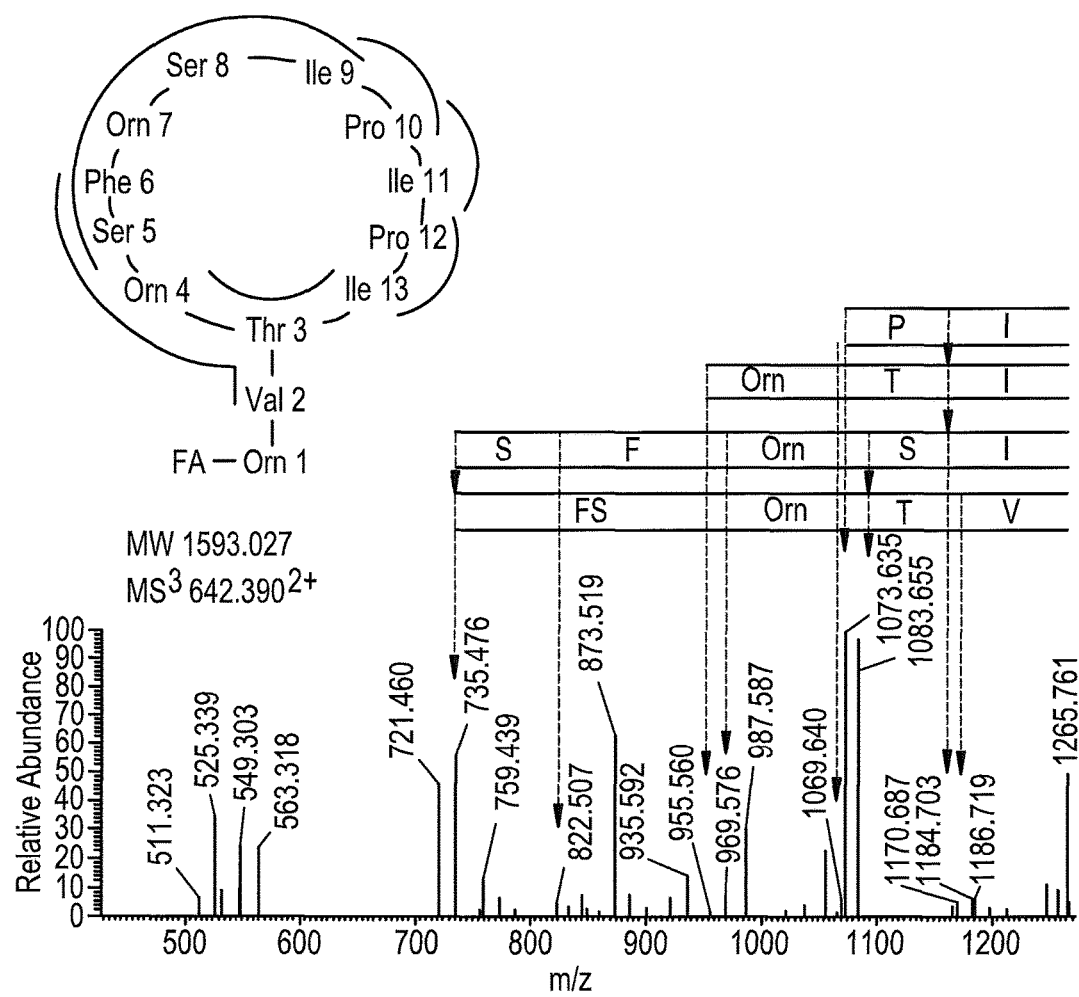
FIG. 9 shows a representative example of different product ion series in an $MS^n$ spectrum ($MS^{3+}642^{2+}$). The corresponding sequences are coded to the amino acids in the inset schematic of the cyclic peptide structure.

By determining which series of product ions did or did not contain the molecular component that results in the 14 Da difference, de novo sequencing by MS$^n$ analysis was more straightforward. This was particularly critical because the compounds were cyclic and resulting MS$^n$ spectra can be difficult to interpret due to multiple ring opening events occurring at a distribution of sites. An example is shown in the MS$^3$ spectrum in FIG. 9 where the ring opens at different amino acid positions, yielding a number of different sequence series within the same spectrum; thus, de novo sequencing of the primary sequence of cyclic peptides can be challenging. However, by using the described approach, the assignment of product ions and the identification of the primary sequence and sequence variants were accomplished without linearizing the molecule. The cumulative ion assignments for the primary amino acid sequence can be found in in FIG. 10A, B.

Subsequent analysis with UPLC coupled to high resolution MS provided accurate mass data which confirmed that there were actually three predominant compound series, with each series containing groups of compounds that differ by 14.02 Da. The most pronounced differences between the three observed series were either a decrease of 15.99 Da or an increase of 1.98 Da in mass compared to the primary compound series; examples are designated with arrows in FIG. 5. A comprehensive list of these compounds and their accurate mass molecular weights can be found in Table 2. These are designated as F, Y, and Y, —CH$_{2+}$O in the table and throughout the figures; F and Y correspond to phenylalanine or tyrosine at position 6 in FIG. 8 B and —CH$_{2+}$O corresponds to a molecular difference in the fatty acid chain.

TABLE 2

| F 649.390$^{2+}$ | | Y 657.394$^{2+}$ | | Y —CH$_2$ + O 657.394$^{2+}$ | |
|---|---|---|---|---|---|
| Nominal Molecular Weight | Complementary Ion Pair | Nominal Molecular Weight | Complementary Ion Pair | Nominal Molecular Weight | Complementary Ion Pair |
| | | 1581 | 269.222$^{1+}$ | | |
| 1579 | 283.238$^{1+}$ | 1595 | 283.238$^{1+}$ | | |
| 1593 | 297.255$^{1+}$ | 1609 | 297.253$^{1+}$ | | |
| 1607 | 311.269$^{1+}$ | 1623 | 311.269$^{1+}$ | 1625 | 313.248$^{1+}$ |
| | | 1637 | 325.285$^{1+}$ | 1639 | 327.264$^{1+}$ |
| | | 1651 | 339.301$^{1+}$ | 1653 | 341.279$^{1+}$ |

Figure 10A:
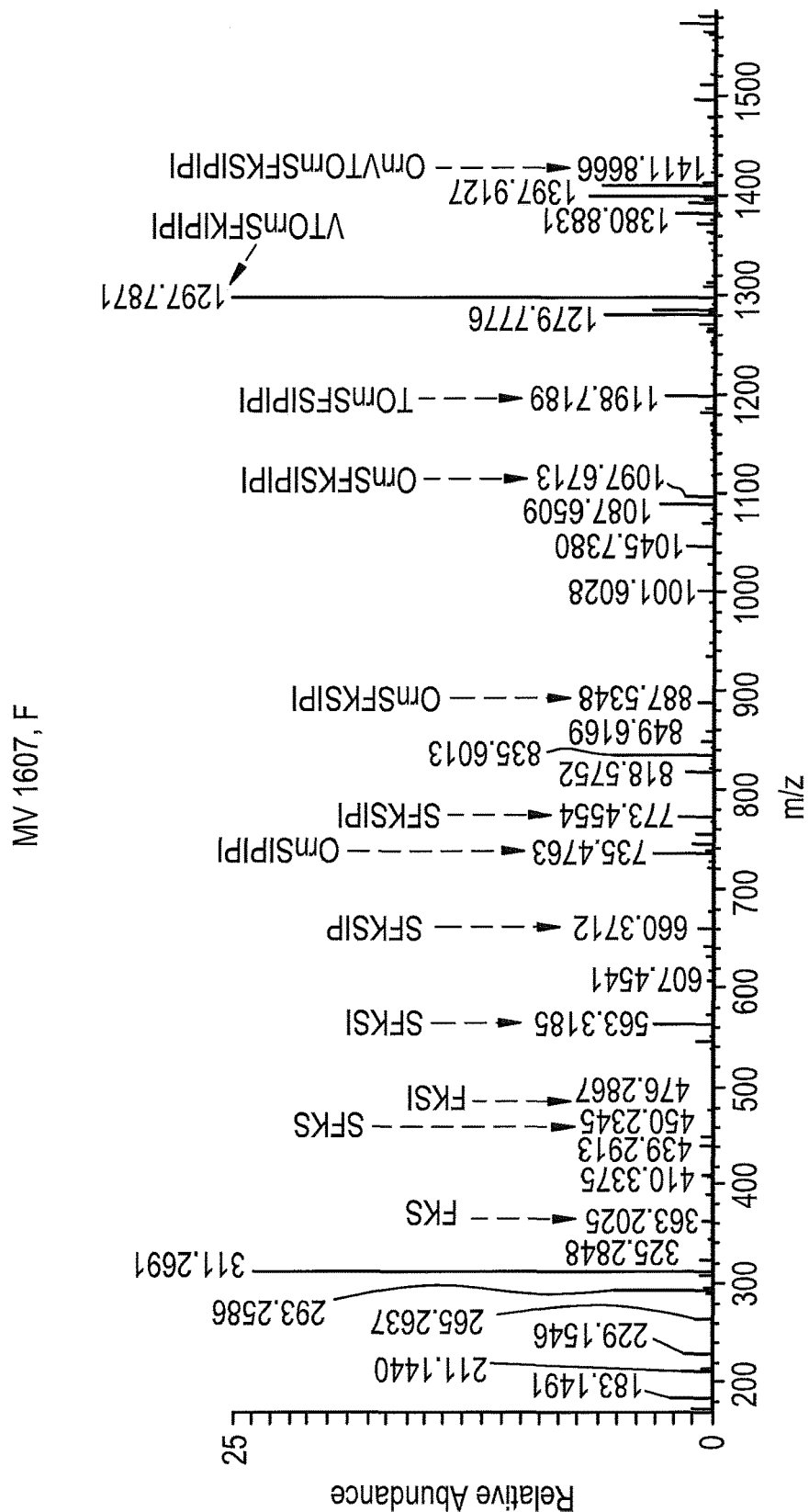
Figure 11:
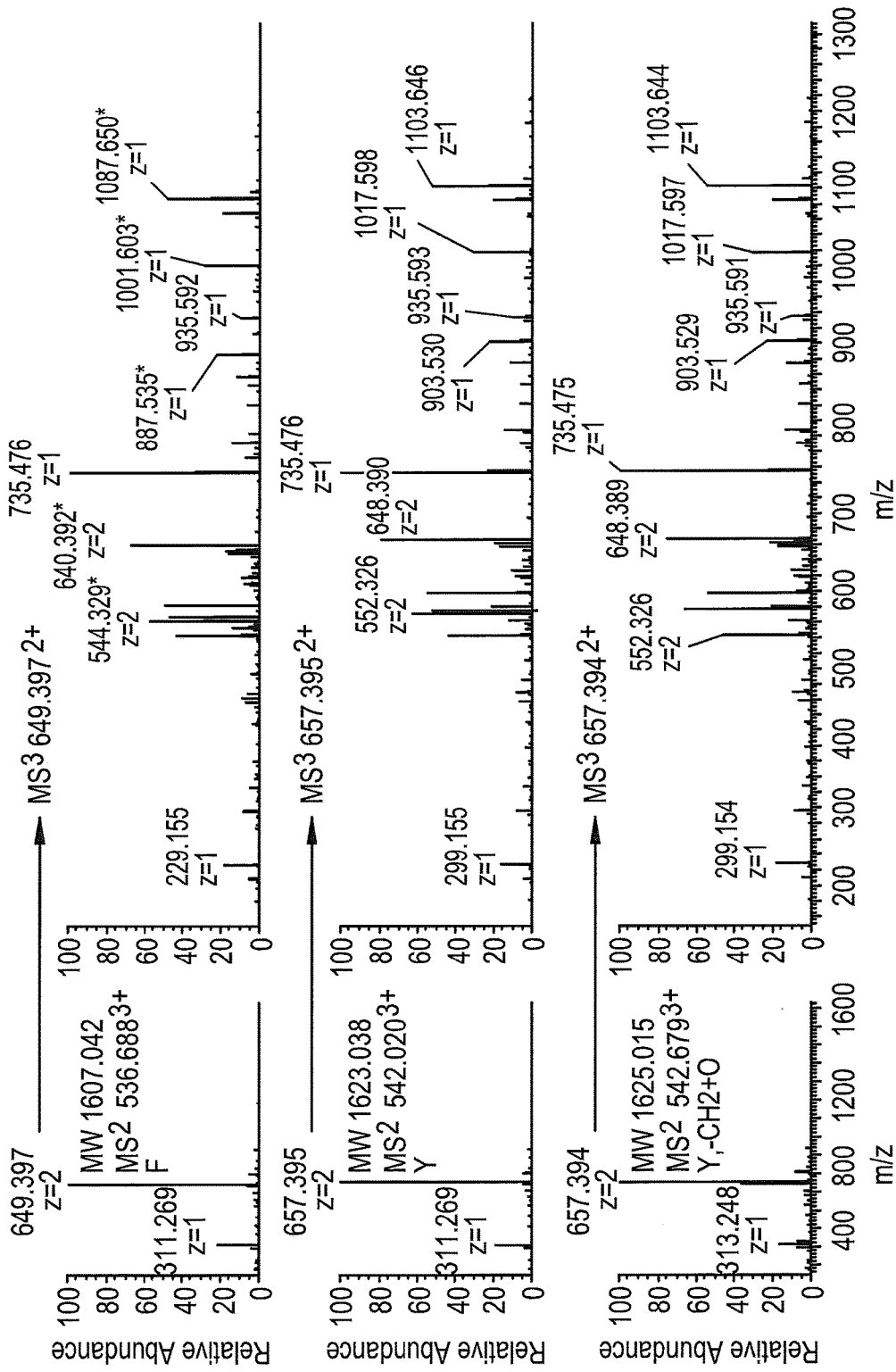
FIG. 11 shows $MS^2$ spectra. Three series of compounds within the class of antibiotics differ by an amino acid or a difference in their attached fatty acid. Compounds that contain a Tyr at position 6 have m/z $657^{2+}$ as a consistent product ion in their resulting MS/MS spectra, while Phe at position 6 results in m/z $649^{2+}$. The m/z values with an asterisk indicate a mass difference of 16 Da between the $MS^3$ spectra, which is the mass difference between Phe and Tyr. The mass difference between MW 1623 and MW 1625 corresponds to one less $CH_2$ group and an additional oxygen in the attached fatty acid ($-CH_2+O$).
Figure 12:
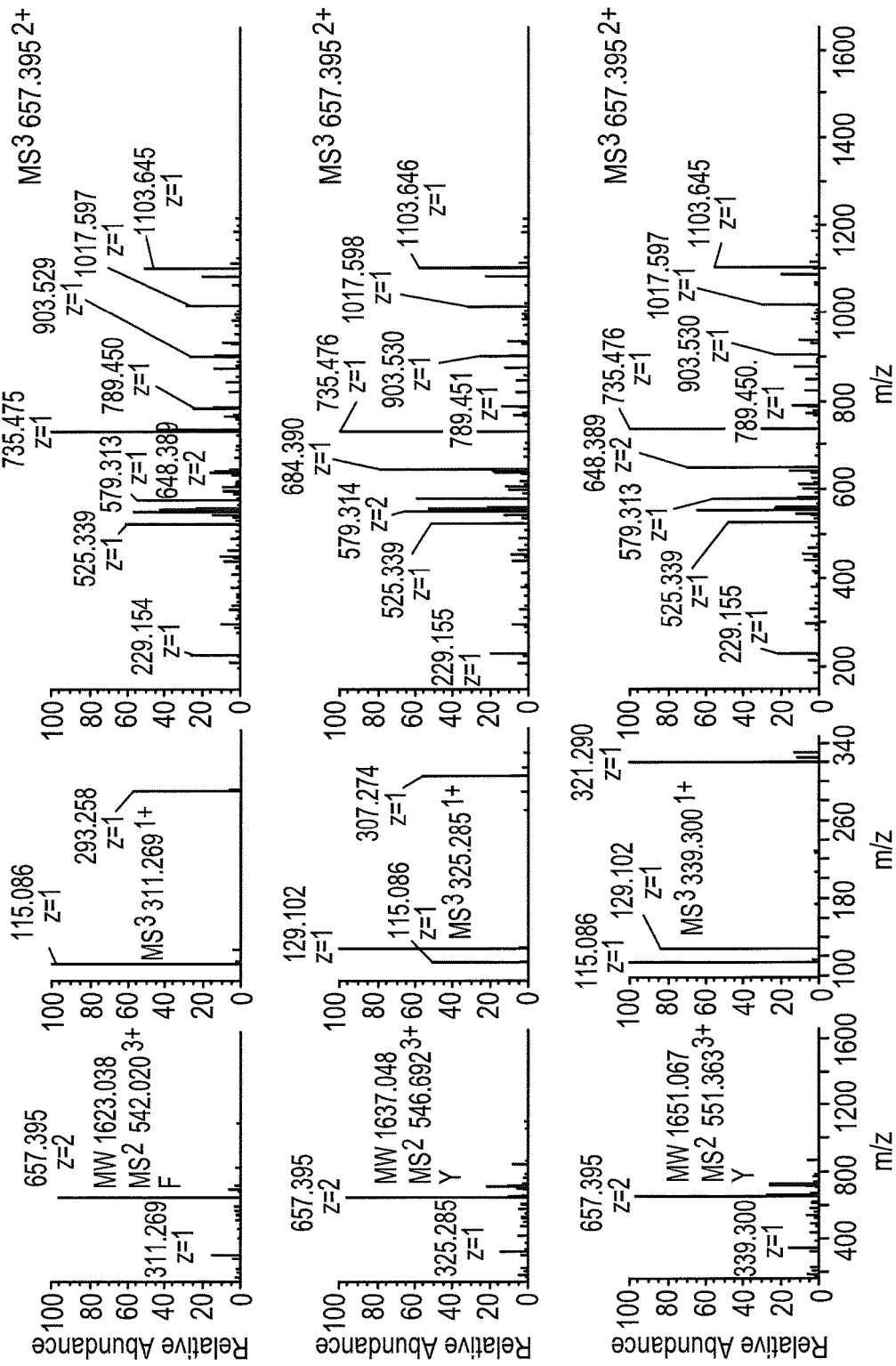
FIG. 12 shows three representative $MS^3$ spectra that demonstrate sequence similarity between compounds of molecular weights that differ by 14 Da and their corresponding complementary ion pair $MS^3$ spectra. $MS^2$ spectra are outlined and $MS^3$ spectra are outlined, with product ions selected for $MS^3$ highlighted.

Two compound series in the bioactive fractions differed from each other by 15.99 Da and exhibited MS$^2$ spectra with all the compounds in one series yielding a product ion at m/z 657$^{2+}$ while the other series generates a product at m/z 649$^{2+}$ (FIG. 11). FIG. 12 illustrates the MS$^n$ spectra of three precursor ions that differed by 14 Da, all of which generated an MS$^2$ product ion at m/z 657$^{2+}$. Because these were conserved product ions within a precursor series that included compounds that differed in molecular weight by 14 Da, we were able to conclude that the region of the compound that yields product ions 657$^{2+}$ or 649$^{2+}$ does not contain the fatty acid. The MS$^3$ spectra of 657$^{2+}$ were consistent with one another confirming that the region of the peptide that generated this sequence was conserved between these compounds (FIG. 12). The MS$^3$ spectra from the ion series that generated an MS$^2$ product ion at 649$^{2+}$ were similar to the 657$^{2+}$MS$^3$ spectra, except for a series of product ions that differed by 16 Da (masses with asterisks in FIG. 12). This enabled the distinction between tyrosine and phenylalanine at position 6 (FIG. 8), designated as Y and F in the tables and figures, respectively; these amino acids differ in molecular weight by 16 Da. Assignments for the MS/MS spectrum for a peptide containing Phe are illustrated in FIG. 10A-B, where a direct comparison can be observed between the peptides containing Phe and Tyr at position 6.

Example 4: Identification of the Attached Fatty Acid

The $MS^2$ spectra of the series of compounds that contain a Tyr at position 6 were dominated by product ion $657^{2+}$ and its complementary ion pair (FIG. 11). While $657^{2+}$ was conserved within the Tyr compound series, its complementary ion contained the same 14 Da mass shift as its precursor (i.e., m/z 311, 325, and 339 in FIG. 12). The same trend was also present for the Phe ion series. A list of the multiple complementary ions for $657^{2+}$ and $649^{2+}$ are listed in Table 3. When these complementary ions were dissociated (examples shown in FIG. 12), a loss of ornithine was observed. Subtracting the cyclized peptide sequence mass from the mass of the entire compound yields the mass attributed to an attached fatty acid; molecular formula generation of these masses yield the molecular formulae of the different fatty acid variants (Table 4 and FIG. 8). These fatty acids are similar to what was observed in Guo, et al., although the lengths of the carbon chains differ and both the TS-15 and A6-6i strains presented in the current work exhibit a greater variability in chain length and composition.

Figure 13:
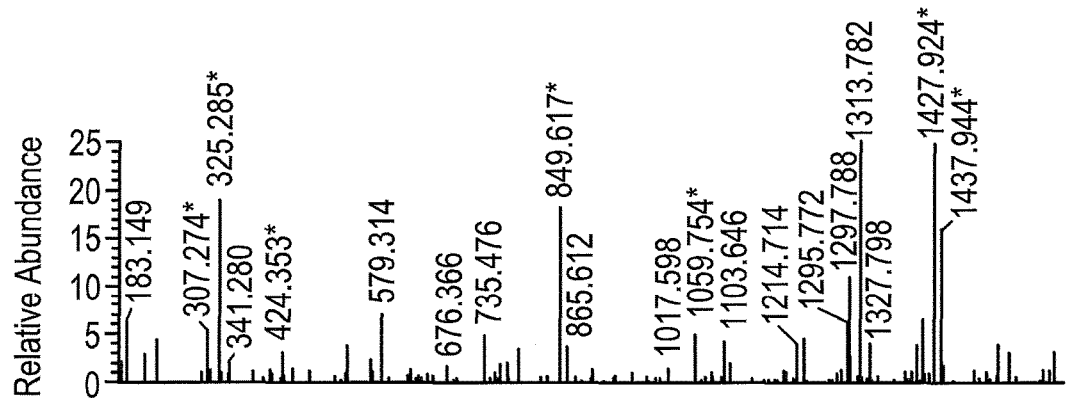
FIG. 13 shows MS/MS comparison of MW 1637 (top) and MW 1639 (bottom). The m/z values with an asterisk indicate a 1.979 Da mass difference between product ions in the two spectra, corresponding to one less $CH_2$ and an additional oxygen in the attached fatty acid compared to the dominant molecular species.
Figure 13:
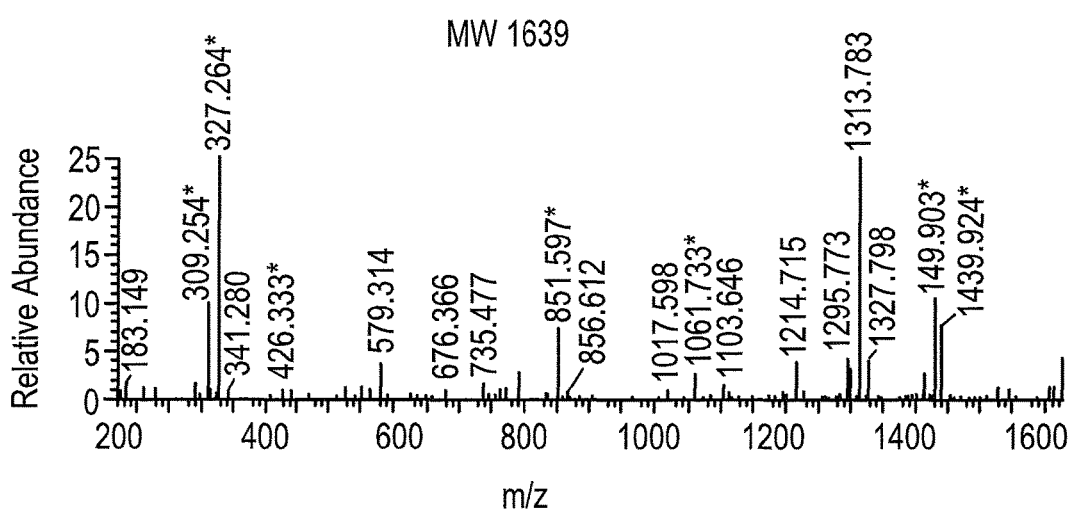

As mentioned previously, three major series of compounds were determined: two series containing a tyrosine at position 6 and one containing phenylalanine. The two compound series containing Tyr differed by a molecular weight of 1.979 Da. Similar to the MS spectral analysis methodology shown in FIG. 2, these compound series also had similar $MS^2$ fragmentation patterns, where some product ion masses are conserved and others differ by 1.979 Da (FIG. 13). This mass difference corresponded to one less $CH_2$ and an additional oxygen (labeled as $—CH_{2+}O$) in the attached fatty acid compared to the tyrosine molecular series.

Example 5: Multiple Compounds with the Same Molecular Weight

Figure 14:
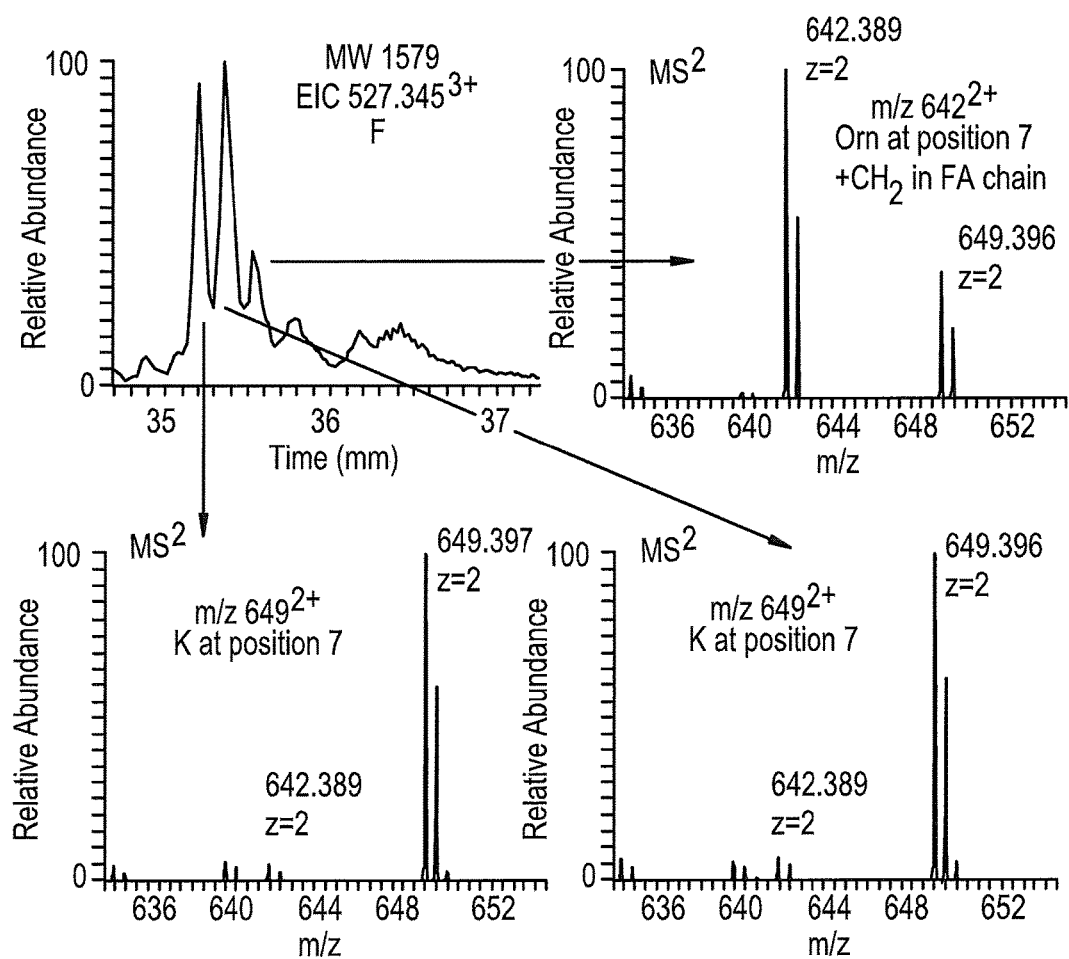
FIG. 14 shows different MS/MS spectra for three compounds of the same molecular weight indicate Lys or Orn at Position 7 in FIG. 8 and potential diversity in the structure of the attached fatty acid due to distinct chromatographic peaks shown in the extracted ion chromatogram (EIC).

It was also observed that more than one of the complementary ion pairs were occasionally present within the same $MS^2$ spectrum in the infusion experiment data. This corresponded to two compounds of the same precursor mass being fragmented within the same isolation window. There were multiple examples in the UPLC and NanoLC/MS data that showed several eluting peaks for entities with the same mass (example shown in FIG. 14). The $MS^2$ spectra of the ions in each of these chromatographic peaks showed small differences in the fragmentation pattern and thus, the primary sequences of these respective peptides. Nearly identical amino acid sequences were confirmed for compounds with an identical molecular weight (1579): a compound with Lys at position 7 and a compound with ornithine at position 7 with an additional $CH_2$ in the attached fatty acid (Lys and ornithine differ by a $CH_2$ in their side chains). Specifically, the product ion at m/z $649^{2+}$ corresponds to Lys at position 7 and m/z $642^{2+}$ corresponds to ornithine at position 7. The two chromatographic peaks with Lys at position 7 may indicate a structural difference in the attached fatty acid resulting in the observed difference in retention time (FIG. 14). A similar substitution was also found at position 1. Some of the subsequent $MS^3$ analyses of the fatty acid containing fragment ions (m/z $325^{1+}$ and $339^{1+}$ in FIG. 5B) indicated that Lys can also be present at position 1 rather than ornithine (m/z $129^{1+}$ in $MS^3$ spectra in FIG. 12). A Lys at position 1 and a decrease of $CH_2$ in the attached fatty acid resulted in identical molecular weights for each compound.

Example 6: Identification and Characterization of the Pbt Gene Cluster

The sequence shown in FIG. 8B was confirmed by genome mining for non-ribosomal peptide synthesis. Many pharmacologically important peptides in bacteria are syn-

TABLE 3

| F $649.390^{2+}$ | | Y $657.394^{2+}$ | | Y $—CH_2 + O$ $657.394^{2+}$ | |
|---|---|---|---|---|---|
| Nominal Molecular Weight | Complementary Ion Pair | Nominal Molecular Weight | Complementary Ion Pair | Nominal Molecular Weight | Complementary Ion Pair |
|  |  | 1581 | $269.222^{1+}$ |  |  |
| 1579 | $283.238^{1+}$ | 1595 | $283.238^{1+}$ |  |  |
| 1593 | $297.255^{1+}$ | 1609 | $297.253^{1+}$ |  |  |
| 1607 | $311.269^{1+}$ | 1623 | $311.269^{1+}$ | 1625 | $313.248^{1+}$ |
|  |  | 1637 | $325.285^{1+}$ | 1639 | $327.264^{1+}$ |
|  |  | 1651 | $339.301^{1+}$ | 1653 | $341.279^{1+}$ |

TABLE 4

| | Y $657.394^{2+}$ | | | | | | |
|---|---|---|---|---|---|---|---|
| $MS^2$ Product Ions$^{1+}$ | 269.222 | 283.238 | 297.253* | 311.269 | 325.285* | 339.301* | |
| $MS^3$ Product Ions$^{1+}$ | 251.212 | 265.227 | 279.243 | 293.258 | 307.274 | 321.290 | Water loss |
|  | 115.086 | 115.086 | 115.086 | 115.086 | 115.086 | 115.086 | Ornithine |
| Molecular Formula of the Fatty Acid | $C_{10}H_{19}O$ | $C_{11}H_{21}O$ | $C_{12}H_{23}O$ | $C_{13}H_{25}O$ | $C_{14}H_{27}O$ | $C_{15}H_{29}O$ | | thesized by nonribosomal peptide synthetases (NRPS). NRPS machinery is composed of modular multi-domain enzymes which act as an assembly line to incorporate each amino acid monomer by one module. A typical module in an NRPS contains an adenylation (A) domain which possesses a conserved binding pocket for the recruitment of amino acid monomers that are to be incorporated into the final peptide product. A single contig of 6536324 bp (G+C content, 46.63%) and a single contig of 6784766 bp (G+C content, 46.69%) representing the complete chromosome for *P. alvei* strains A6-6i and TS-15 was generated, respectively. The draft genome sequences of strain A6-6i and TS-15 are available in DDBJ/EMBL/GENBANK® under GEN-BANK® accession # ATMS00000000 and ATMT00000000, respectively. The DNA sequences of A6-6i ptbA, ptbB, and ptbC are SEQ ID NOs. 5, 6, and 7, respectively. The DNA sequences of TS-15 ptbA, ptbB, and ptbC are SEQ ID NOs. 8, 9, and 10, respectively. The protein sequences for A6-6i ptbA, ptbB, and ptbC are SEQ ID NOs. 11, 12, and 13, respectively. The protein sequences for TS-15 ptbA, ptbB, and ptbC are SEQ ID NOs. 14, 15, and 16, respectively. A local BLASTX analysis against pbt gene cluster in *P. thiaminolyticus* strain OSY-SE (accession #ALKF00000000; U.S. Publication No. US2013/0164317) identified a 49-kb DNA region responsible for the compounds biosynthesis (Table 5). The protein sequences for OSY-SE ptbA, ptbB, and ptbC are SEQ ID NOs. 17, 18, and 19, respectively. Comparative genomic analysis showed 64% to 70% similarities in DNA sequences of the pbt gene cluster between the two *P. alvei* strains and *P. thiaminolyticus* strain OSY-SE; and only 60% to 67% similarities in amino acid sequences (FIGS. 16-18). This DNA region encodes three peptide synthetase units which consist of thirteen modules (Table 5) responsible for incorporating the thirteen amino acids in the compounds. The predicted peptide sequence agreed with the chemical structure of the compounds determined by MS/MS (Table 4). In addition, epimerization (E) domains were found in modules for $Orn_1$, $Orn_4$, $Orn_7$, and $Ser_8$, which indicated that those amino acids might be in the D-form.

The bacterially-produced cyclic peptides are synthesized by a class of enzymes known as the nonribosomal peptide synthetases (NRPSs). NRPSs are found in many organisms and synthesize a number of medically-important peptides such as antibiotics and immunosuppressants. By sequence analysis, 14 NRPS genes have been identified in the *P. alvei* A6-6i and TS-15 genomes. Three NRPS genes which covered 49 kb were found to control the production of the compounds in the current application. NRPSs are large enzymes that are organized into modules made up of functional domains. The entire length of the amino acid sequence showed homology to the Pbt encoded by the pbt gene cluster of *P. thiaminolyticus* strain OSY-SE in the prior art patent (66% similarity to pbtA gene, 66% similarity to pbtB gene, and 59% similarity to pbtC gene). Detailed analysis of the pbtABC gene cluster showed that each gene had domain and module organization as in Table 5B. To predict the substrate specificity-conferring amino acids in the adenylation (A) domain of each module, the structural regions, A3 and A6 motifs in the A domain, were blasted against the NCBI protein database and showed only 36% identity to the ptbB1 module, 38% identity to the ptbC1 module, and 35% identity to the ptbC2 module, indicating structurally unique antibiotics from paenibacterin in the prior art patent.

TABLE 5

A. Amino acid similarities between A6-6i, TS-15, and OSY-SE

|      | A6-6i  | TS-15  |
|------|--------|--------|
| pbtA | 66.95% | 66.73% |
| pbtB | 66.66% | 66.79% |
| pbtC | 59.72% | 59.31% |

B. Modules and domains predicted in the gene cluster

| | |
|---|---|
| pbtA | $CA_{Orn1}TECA_{Val2}TCA_{Thr3}TCA_{Orn4}TECA_{Ser5}T$ |
| pbtB | $CA_{Tyr6}TCA_{Orn7}TECA_{Ser8}TECA_{Ile9}TCA_{Pro10}T$ |
| pbtC | $CA_{Ile11}TCA_{Pro12}TCA_{Ile13}TTe$ |

Table 5 shows the predicted amino acids of the antimicrobial peptides generated by the PKS/NRPS web server. For example, the pbtA gene (encoding a non-ribosomal peptide synthetase) contains 5 modules, each comprised of a C (condensation) domain, an A (adenylation) domain, and a T (thiolation) domain. The A domain is responsible for amino acid activation and selectivity. Because the binding pocket of each A domain is a conserved sequence, the amino acid substrate can be predicted. Additionally, epimerization (E) domains were found in modules for $Orn_1$, $Orn_4$, $Orn_7$, and Serb, which indicate that those amino acids may be in the D-form. Likewise, pbtB gene contains 5 modules and pbtC gene contains 3 modules.

C. Predicted amino acid substrates in the adenylation (A) domain in each module.

```
                               A6-6i

Active site residue with 8 A of    Binding         Predicted
Module    the amino acid substrate           pocket          substrate PbtA1     LAWAFDVFTGDRESVVGSDLNSYGVTEACVDACY  DVGEVGSVDK      D-Orn
          SEQ ID NO. 20                      SEQ ID NO. 21

PbtA2     LGASFDAATFEGWMLVGGDINGYGPTENTTFTCC  DAFWLGGTFK      Val
          SEQ ID NO. 22                      SEQ ID NO. 23

PbtA3     LNSHFDFSVWEGNQIFGGEINMYGITETTVHVTY  DFWNIGMVHK      Thr
          SEQ ID NO. 24                      SEQ ID NO. 25

PbtA4     MAWAFDVFSGDRESIIGSDINSYGVTEACVDSSY  DVGEIGSVDK      D-Orn
          SEQ ID NO. 26                      SEQ ID NO. 27

PbtA5     RWMTFDVSVWEWHFFTSGEINLYGPTEATVDVTY  DVWHFSLVDK      Ser
          SEQ ID NO. 28                      SEQ ID NO. 29

PbtB1     AWRFFDGFVMSCICTLAGEFNEYGPTENSVVATC  DGMITAEVVK      Tyr
          SEQ ID NO. 30                      SEQ ID NO. 31
```

A6-6i

| Module | Active site residue with 8 A of the amino acid substrate | Binding pocket | Predicted substrate |
|---|---|---|---|
| PbtB2 | MAWAFDVFSGDRDCAVGSDINSYGVTETCIDASY SEQ ID NO. 32 | DVGDAGSIDK SEQ ID NO. 33 | D-Orn |
| PbtB3 | RWMTFDVSVWEWHFFTSGEINLYGPTEATVDVTY SEQ ID NO. 34 | DVWHFSLVDK SEQ ID NO. 35 | D-Ser |
| PbtB4 | VETSFDGSTFDGFILFGGEKHVYGPTESTVFATC SEQ ID NO. 36 | DGFFLGVVFK SEQ ID NO. 37 | Ile |
| PbtB5 | LYQAFDVCYQESFIITAGEHNHYGPSETHVVTTY SEQ ID NO. 38 | DVQFIAHVVK SEQ ID NO. 39 | Pro |
| PbtC1 | INTSFDGSAFDGLILFGGEKHAYGPSESTVYATW SEQ ID NO. 40 | DGFLLGAVYK SEQ ID NO. 41 | Ile |
| PbtC2 | LYQAFDVCYQESYIITAGEHNHYGPSETHVVTTY SEQ ID NO. 42 | DVQYIAHVVK SEQ ID NO. 43 | Pro |
| PbtC3 | VDASFDGSTFDGFILFGGEKHVYGPTESTVFATS SEQ ID NO. 44 | DGFFLGVVFK SEQ ID NO. 45 | Ile |

TS-15

| Module | Active site residue with 8 A of the amino acid substrate | Binding pocket | Predicted substrate |
|---|---|---|---|
| PbtA1 | LAWAFDVFTGDRESVVGSDLNSYGVTEACVDACY SEQ ID NO. 46 | DVGEVGSVDK SEQ ID NO. 47 | D-Orn |
| PbtA2 | LAASFDAATFEGWMLVGGDINGYGPTENTTFTCC SEQ ID NO. 48 | DAFWLGGTFK SEQ ID NO. 49 | Val |
| PbtA3 | LNSHFDFSVWEGNQIFGGEINMYGITETTVHVTY SEQ ID NO. 50 | DFWNIGMVHK SEQ ID NO. 51 | Thr |
| PbtA4 | MAWAFDVFSGDRESIIGSDINSYGVTEACVDSSY SEQ ID NO. 52 | DVGEIGSVDK SEQ ID NO. 53 | D-Orn |
| PbtA5 | RWMTFDVSVWEWHFFTSGEINLYGPTEATVDVTY SEQ ID NO. 54 | DVWHFSLVDK SEQ ID NO. 55 | Ser |
| PbtB1 | AWRFFDGFVMSCICTLAGEFNEYGPTENSVVATC SEQ ID NO. 56 | DGMITAEVVK SEQ ID NO. 57 | Tyr |
| PbtB2 | MAWAFDVFSGDRDCAVGSDINSYGVTETCIDASY SEQ ID NO. 58 | DVGDAGSIDK SEQ ID NO. 59 | D-Orn |
| PbtB3 | RWMTFDVSVWEWHFFTSGEINLYGPTEATVDVTY SEQ ID NO. 60 | DVWHFSLVDK SEQ ID NO. 61 | D-Ser |
| PbtB4 | VETSFDGSTFDGFILFGGEKHVYGPTESTVFATC SEQ ID NO. 62 | DGFFLGVVFK SEQ ID NO. 63 | Ile |
| PbtB5 | LYQAFDVCYQESFIITAGEHNHYGPSETHVVTTY SEQ ID NO. 64 | DVQFIAHVVK SEQ ID NO. 65 | Pro |
| PbtC1 | INTSFDGSAFDGLILFGGEKHAYGPSESTVYATW SEQ ID NO. 66 | DGFLLGAVYK SEQ ID NO. 67 | Ile |
| PbtC2 | LYQAFDVCYQESYIITAGEHNHYGPSETHVVTTY SEQ ID NO. 68 | DVQYIAHVVK SEQ ID NO. 69 | Pro |
| PbtC3 | VDASFDGSTFDGFILFGGEKHVYGPTESTVFATS SEQ ID NO. 70 | DGFFLGVVFK SEQ ID NO. 71 | Ile |

Table 5 shows the identification and characterization of the pbt gene cluster. A. DNA sequence similarities and amino acid sequence similarities of the pbt gene cluster between *P. alvei* strains A6-6i and TS-15 and *P. thiaminolyticus* strain OSY-SE. B. Modules and domains identified in the NRPS subunits: C, A, T, E, and Te representing condensation domain, adenylation domain, thiolation domain, epimerization domain, and thioesterase domain, respectively. C. Substrate prediction for each of the 13 modules in the peptide.

It is worth noting that genome mining did not predict the presence of abundant sequence variants. As Lys and ornithine differ by $CH_2$, their binding affinities are likely similar which may be contributing to the observed molecular diversity. Likewise, Tyr and Phe differ by a hydroxyl group. Furthermore, NRPS predictor 2 has lower single amino acid substrate prediction scores for Phe and Lys, which may indicate why these were not additionally predicted in the primary sequence. NRPSpredictor2 also predicted that the epimerization (E) domain was in modules 1, 4, 7, and 8, which indicated that these resulting amino acid substrates may be in the D-form. As expected, NRPS analysis does not offer information about the presence or length of the alkyl chain.

The NRPS analysis confirmed both the presence and order of the amino acids of the peptide assignments made through the combination of MALDI-MS, high-resolution mass spectrometry, and $MS^n$ analysis. NRPS can be used as a screening technique to identify potential nonribosomal peptides which may act as antibiotics; however, it does not yield information regarding any molecular variants that may be produced. Moving forward, NRPS analysis and mass spectrometry can be used to combine rapid prediction of candidate peptides with the molecular specificity of mass spectrometry to enable identification of cyclic antibiotics and their sequence and fatty acid variants despite the presence of molecular diversity and complicated spectra.

Example 6: Design and Characterization of a Synthetic Peptide

Figure 15:
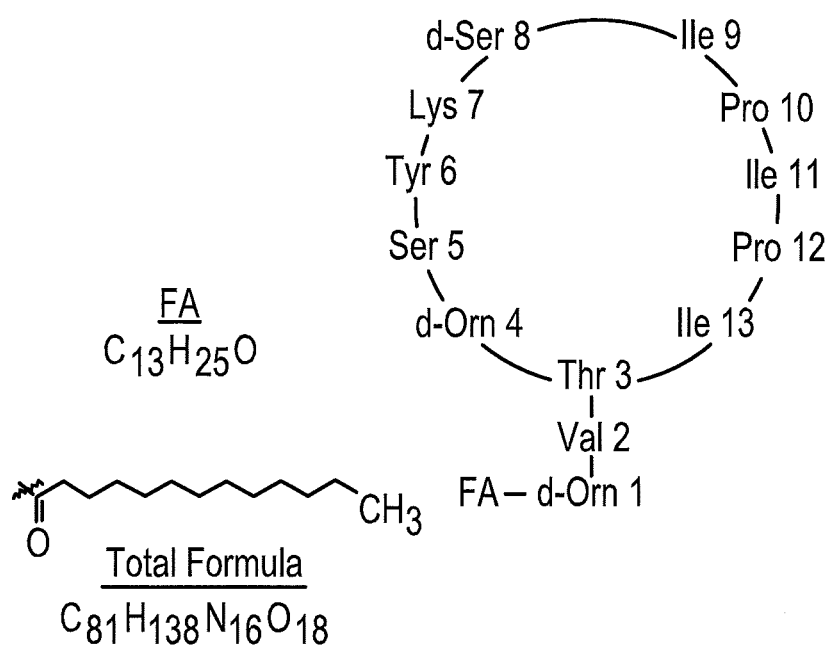
FIG. 15 shows a schematic of a chemically synthesized, fatty acid modified peptide.

Based on the identified sequence in FIG. 8B, a peptide was chemically synthesized in accordance with FIG. 15, referred to herein as synthetic depsipeptide A or Compound A, L-form with L-Lys at position 7.

Minimum inhibitory concentrations (MICs) of synthetic depsipeptide A against selected bacteria, including antibiotic-resistant strains (Table 6), were determined by the broth microdilution method following the procedure of the Clinical and Laboratory Standards Institute (CLSI) as is known in the art. Briefly, synthesized depsipeptide was dissolved in Optima grade water to reach 25.6 mg/ml as the stock concentration. After 100 times dilution in cation-adjusted Mueller-Hinton II broth (CAMHBII) (Becton, Dickinson & Co., Sparks, Md.), the depsipeptide was then further two-fold serially diluted in CAMHBII in clear, sterile, non-treated round bottom 96-well plates (Nunc, Roskilde, Denmark). Bacterial cultures were suspended in demineralized water to achieve a turbidity equivalent to a 0.5 McFarland turbidity standard (Remel, Lenexa, Kans.). An equal volume of culture suspension was added to the diluted depsipeptide to give a final volume of 100 μl/well in the assay plates. Polymyxin B (Sigma, St Louis, Mo.) and vancomycin (Sigma) were used as positive controls in the AST assays. Strains *Escherichia coli* ATCC 25853, *Pseudomonas aeruginosa* ATCC 27853, *Enterococcus faecalis* ATCC 29212, and *Staphylococcus aureus* ATCC 29213 were used as quality control strains in the assays. The MIC end point refers to the lowest concentration of an antimicrobial agent that completely inhibits growth of bacterial cells after incubation at 35C for 20-24 h.

TABLE 6

Table 6. Minimum inhibitory concentrations (MICs) of synthesized depsipeptide and other antibiotics

| Bacterial strain | MIC(μg/ml) | | |
|---|---|---|---|
| | Synthesized depsipeptide | PolymyxinB | Vancomycin |
| *E. coli* ATCC 25853 | 4 | 0.5 | — |
| *Salmonella* Newport #17 | 16 | 1 | — |
| *Enterobacter sakazakii* E784 | 8 | 0.5 | — |
| *E. coli* O157:H7 EDL933 | 4 | 0.5 | — |
| *Serratia marcescens* SBJ-9047 (CRE, clinical isolate) | 32 | >128 | — |
| *Klebsiella pneumoniae* SBJ-9149 (clinical isolate) | 4 | 0.5 | — |
| *Serratia marcescens* SBJ-8283 (CRE, clinical isolate) | 32 | >128 | — |
| *Enterobacter cloacae* SBJ-9395 (CRE, clinical isolate) | 4 | >128 | — |
| *Enterobacter cloacae* SBJ-7612 (clinical isolate) | 4 | 1 | — |
| *Klebsiella pneumoniae* SBJ-9483 (clinical isolate) | 4 | 0.5 | — |
| *Klebsiella pneumoniae* SBJ-9388 (clinical isolate) | 4 | 0.5 | — |
| *Enterobacter cloacae* SBJ-9222 (clinical isolate) | 8 | 1 | — |
| *P. aeruginosa* ATCC-27853 | 8 | 1 | — |
| *P. aeruginosa* SBJ-10884 (PMB-R, clinical isolate) | 4 | | |
| *P. aeruginosa*-03 (PMB-R, clinical isolate) | 8 | | |
| *P. aeruginosa*-02 (PMB-R, clinical isolate) | 8 | | |
| *P. aeruginosa*-01 (PMB-R, clinical isolate) | 8 | | |
| *P. aeruginosa* SBJ-10886 (PMB-R, clinical isolate) | 4 | | |
| *E. faecalis* ATCC 29212 | 4 | — | 2 |
| *Listeria monocytogenes* R2-583 | 2 | — | 1 |
| *S. aureus* ATCC25923 | 2 | — | 1 |
| *S. aureus* 19 (MRSA, MDR clinical isolate) | 4 | — | 1 |
| *S. aureus* 14 (MRSA, MDR clinical isolate) | 4 | — | 1 |
| *S. aureus* 12 (MRSA, MDR clinical isolate) | 4 | — | 1 |
| *S. aureus* ATCC 29213 | 4 | — | 1 |
| *S. aureus* 10 (MRSA, MDR clinical isolate) | 4 | — | 1 |
| *S. aureus* 8 (MRSA, MDR clinical isolate) | 4 | — | 1 |
| *S. aureus* 6 (MRSA, MDR clinical isolate) | 4 | — | 1 |
| *S. aureus* 4 (MRSA, MDR clinical isolate) | 4 | — | 1 |
| *S. aureus* 2 (MRSA, MDR clinical isolate) | 4 | — | 1 |

PMB-R, polymyxin B-resistant; MDR, multidrug-resistant; MRSA, methicillin-resistant *S. aureus*; CRE, carbapenem-resistant.

The synthetic depsipeptide showed a broad antimicrobial spectrum against both Gram-negative and Gram-positive bacteria, including against significant antibiotic-resistant clinical isolates (Table 1). Specifically, the synthesized depsipeptide showed very potent activity against those carbapenem-resistant (CRE) strains and MRSA strains. Additionally, bacteria showed much greater sensitivity to this peptide than to paenibacterin in U.S. Publication No. US2013/0164317.

It is striking that the peptides found in this study are amphiphilic with distinct hydrophilic and hydrophobic regions: hydrophobicity on one side, the other side being predominantly polar and charged amino acids, and a hydrophobic fatty acid chain (FIG. 8B). Major differences between paenibacterin and the compounds discovered in this work are the length of the attached fatty acid, the different combinations of lysine and ornithine at positions 1 and 7, and the amino acids at position 6 and 12. This is particularly interesting because the amino acids at position 6 and 12 have different properties (e.g., hydrophobic, hydrophilic, or positively charged). Furthermore, the presence of D-amino acids influences the structure and properties of the peptide and will also make the compound more resistant to enzymatic degradation and thus inherently more stable.

Aspects of paenibacterin's mode of action have been previously studied. The results suggest that the compound has a high affinity to the negatively-charged outer membrane of gram-negative bacteria. This is likely due to the presence of positively charged amino acids in the molecule, which is similar to the mode of action of polymyxin. Three positively charged amino acids were found in the molecules discovered here compared to four in paenibacterin (FIG. 8), which may result in varying degrees of effectiveness. However, the Lys to Pro substitution at position 12 also increases the hydrophobicity of that portion of the molecule which may result in a better affinity to the hydrophobic core of cellular membranes, a characteristic that may aid in its disruption. Similarly, the presence of Tyr at position 6 contributes to a more polar region of the molecule. The mode of action may also be due to the amphiphilic nature of the compound, acting as a surfactant to disrupt cell membranes. It is notable that polymyxin also has distinct hydrophilic and hydrophobic domains.

It was also determined that paenibacterin resulted in the permeabilization of both gram-positive and -negative cell membranes, which was probably disrupted by the attached fatty acid. The chain length will likely affect observed antimicrobial activity, although it is uncertain if it will be less or more effective with a longer/shorter chain. For polymyxin, it is hypothesized that the fatty acyl chain disrupts the cellular membrane. Studies on the fatty acid chain of polymyxin indicate that antimicrobial activity correlates with the length and bulkiness of this moiety. However, reports are varied and subsequent experiments to design fatty acid analogues for the compounds in this study will yield insight into how this affects antimicrobial activity. It is also interesting that a single strain of bacteria can produce such a large number of molecular variants. This may enable the strain to exert a more concerted antimicrobial effect and may have resulted from extensive selection pressure in the community from which it was isolated.

The major significance of the antimicrobial peptides described herein relates to overcoming the worldwide public health crisis of drug resistance by several major classes of bacterial human pathogens. Several of the most dangerous bacterial pathogens such as MRSA, VRSA, and CRE are resistant to nearly every antibiotic currently in the arsenal of human antimicrobial prophylaxis. CRE, for instance, has no known antibiotic weakness. What is most important is that these antimicrobial peptides may represent entirely new classes of antibiotics, each with the ability to control these deadly bacteria and cure associated pathology. Safety studies in rat with the host organism that produces the antimicrobial peptides was most encouraging, with rats showing no overt pathology from this strain.

Example 7: Antimicrobial Susceptibility of Variant Compounds

The same MIC assay as in Example 6 was used to determine the antimicrobial susceptibility of Compound A, L-form (FIG. 15), and several variants. One variant was Compound A, D-form, with D-Lysine at position 7. Compound B is a variant in the fatty acid chain, with a fatty acid chain composition of $C_{15}H_{29}O$, and having D-Lys at position 7. Compound C is a variant in the fatty acid chain with a fatty acid chain composition of $C_{11}H_{21}O$, and having D-Lys at position 7. Variant D is a sequence variant with Phe at position 6 of the cyclic peptide, and having D-Lys at position 7. All variants were chemically synthesized. The results are given in Table 7.

TABLE 7

Antimicrobial Susceptibility of Variant Compounds

| Bacterial strain | MIC(ug/ml) | | | | | | |
|---|---|---|---|---|---|---|---|
| | A L-form | A D-form | B | C | D | Control 1 | Control 2 |
| Serratia marcescens SBJ-9047 | 32 | 32 | ≥128 | 64 | ≥128 | >128 | |
| Serratia marcescens SBJ-8283 | 32 | 16 | 32 | 32 | 32 | >128 | |
| Enterobacter cloacae SBJ-9395 | 4 | 8 | 16 | 8 | 32 | >128 | |
| Serratia marcescens SAMN 04276915 | ≥128 | 64 | ≥128 | ≥128 | ≥128 | ≥256 | |
| Serratia marcescens SAMN04022954 | ≥128 | 32 | ≥128 | 64 | ≥128 | ≥256 | |
| Serratia marcescens SAMN 04276914 | 64 | 32 | 64 | 64 | 64 | ≥256 | |
| E. faecium ATCC 700221 | 4 | 8 | 4 | 8 | 8 | | ≥256 |
| E. faecium BAA-2318 | 4 | 4 | 4 | 8 | 8 | | ≥256 |
| E. faecium ATCC 2320 | 4 | 8 | 4 | 8 | 8 | | ≥256 |
| E. faecalis ATCC 51575 | 8 | 8 | 8 | 32 | 8 | | ≥256 |
| E. faecalis BAA-2365 | 8 | 8 | 4 | 32 | 8 | | ≥256 |
| S. aureus 19 (MRSA, clinical isolate) | 4 | 8 | 4 | 8 | 8 | | 1 |
| S. aureus 14 (MRSA, clinical isolate) | 4 | 8 | 4 | 8 | 8 | | 1 |
| S. aureus 12 (MRSA, clinical isolate) | 4 | 4 | 4 | 8 | 8 | | 1 |

TABLE 7-continued

Antimicrobial Susceptibility of Variant Compounds

| | MIC(ug/ml) | | | | | | |
|---|---|---|---|---|---|---|---|
| Bacterial strain | A L-form | A D-form | B | C | D | Control 1 | Control 2 |
| *S. aureus* 10 (MRSA, clinical isolate) | 4 | 8 | 4 | 8 | 8 | | 1 |
| *S. aureus* 8 (MRSA, clinical isolate) | 4 | 4 | 4 | 8 | 8 | | 1 |
| *S. aureus* 6 (MRSA, clinical isolate) | 4 | 4 | 8 | 8 | 8 | | 1 |
| *S. aureus* 4 (MRSA, clinical isolate) | 4 | 4 | 4 | 8 | 8 | | 1 |
| *S. aureus* 2 (MRSA, clinical isolate) | 4 | 4 | 4 | 8 | 8 | | 1 |
| *Salmonella* CVM 1290 (cmy2) | 8 | 8 | 16 | 16 | 8 | | |
| *K. pneumoniae* CVM 9246 (shv18, oxa2) | 8 | 8 | 8 | 8 | 8 | | |
| *E. coli* CVM 15100 (mir1) | 8 | 8 | 16 | 8 | 8 | | |
| *E. cloacae* CVM 15101 (P99) | 8 | 8 | 8 | 8 | 8 | | |
| *K. pneumoniae* CVM 15102 (shv5) | 8 | 8 | 8 | 8 | 8 | | |
| *E. coli* CVM 15103 (tem2) | 8 | 8 | 8 | 8 | 8 | | |
| *E. coli* CVM 15104 (shv3) | 8 | 8 | 16 | 8 | 16 | | |
| *K. pneumonia* CVM 15105 (shv5) | 8 | 8 | 16 | 8 | 8 | | |
| *E. coli* CVM 35778 (ctx-m-2) | 8 | 8 | 32 | 16 | 16 | | |
| *S. Newport* CVM 40115 (cmy 2) | 8 | 8 | 16 | 16 | 8 | | |
| *S. Typhimurium* CVM 40117 (ctx-m-5) | 8 | 8 | 16 | 16 | 8 | | |
| *Salmonella* CVM 40118 (oxa-1) | 4 | 4 | 4 | 4 | 8 | | |
| *Salmonella* CVM 40119 (tem 12) | 8 | 16 | 8 | 8 | 8 | | |
| *E. coli* CVM 40126 (oxa-1) | 4 | 8 | 4 | 8 | 8 | | |
| *E. coli* CVM 40127 (oxa-2) | 8 | 8 | 16 | 8 | 8 | | |
| *E. coli* CVM 40128 (oxa-7) | 8 | 8 | 8 | 8 | 8 | | |
| *E. coli* CVM 40129 (oxa-5) | 4 | 8 | 8 | 8 | 8 | | |
| *E. coli* CVM 40130 (oxa-9) | 8 | 8 | 8 | 8 | 8 | | |
| *E. coli* CVM 40131 (ctx-m-2) | 4 | 8 | 8 | 8 | 8 | | |
| *E. coli* CVM 40132 (ctx-m-9) | 8 | 8 | 16 | 8 | 8 | | |
| *E. coli* CVM 40133 (ctx-m-14) | 8 | 16 | 16 | 8 | 8 | | |
| *E. coli* CVM 40134 (ctx-m-15) | 8 | 8 | 8 | 8 | 8 | | |
| *S. Keur massar* CVM 40135 (shv12) | 16 | 16 | 32 | 16 | 16 | | |
| *E. coli* CVM 40136 (tem 52b) | 8 | 16 | 8 | 8 | 16 | | |
| *E. coli* CVM 40137 (DHA-1) | 8 | 8 | 16 | 8 | 8 | | |
| *E. coli* CVM 40138 (LCR-1) | 8 | 8 | 8 | 8 | 8 | | |
| *E. coli* CVM 40139 (fox-1) | 8 | 8 | 16 | 8 | 8 | | |
| *S. Heidelberg* CVM 40140 (cmy-2) | 16 | 16 | 16 | 16 | 16 | | |
| *E. coli* CVM 40141 (imp-1) | 32 | 16 | 16 | 32 | 16 | | |
| *K. pneumonia* CVM 40142 (ges-1) | 8 | 8 | 16 | 8 | 8 | | |
| *E. coli* CVM 40143 (act-1) | 8 | 8 | 16 | 8 | 16 | | |
| *P. aeruginosa* CVM 40144 (PER-1) | 32 | 16 | 32 | 16 | 16 | | |
| *S. Bareilly* CVM40145 (ACC-1) | 16 | 8 | 32 | 16 | 32 | | |
| *E. coli* CVM40146 (vim-1) | 8 | 8 | 8 | 8 | 8 | | |
| *E. coli* CVM 40147 (vim-2) | 16 | 16 | 16 | 16 | 16 | | |
| *E. coli* CVM40148 (veb-1) | 8 | 8 | 8 | 8 | 8 | | |

Control 1 = Polymixin B
Control 2 = Vancomycin

As shown in Table 7, the minimum inhibitory concentrations (MICs) of both D-Lys and L-Lys Compound A were reduced by at least 16 to 64 folds in those polymyxin or vancomycin resistant strains and ESBL producing bacteria as well when comparing to the MICs of resistant antimicrobials that the strains originally developed, although changes in the fatty acid residues showed no comparative improvement. The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

SEQUENCE LISTING

```
<160> NUMBER OF SEQ ID NOS: 78

<210> SEQ ID NO 1
<211> LENGTH: 13
<212> TYPE: PRT
<213> ORGANISM: Paenibacillus strain TS-15
<220> FEATURE:
<221> NAME/KEY: VARIANT
<222> LOCATION: (1)..(1)
<223> OTHER INFORMATION: Lys or Orn
<220> FEATURE:
<221> NAME/KEY: VARIANT
<222> LOCATION: (4)..(4)
<223> OTHER INFORMATION: Lys or Orn
<220> FEATURE:
<221> NAME/KEY: VARIANT
<222> LOCATION: (6)..(6)
<223> OTHER INFORMATION: Tyr, Phe, or Trp
<220> FEATURE:
<221> NAME/KEY: VARIANT
<222> LOCATION: (7)..(7)
<223> OTHER INFORMATION: Lys or Orn

<400> SEQUENCE: 1

Xaa Val Thr Xaa Ser Xaa Xaa Ser Ile Pro Ile Pro Ile
1               5                   10

<210> SEQ ID NO 2
<211> LENGTH: 14
<212> TYPE: PRT
<213> ORGANISM: Paenibacillus strain TS-15
<220> FEATURE:
<221> NAME/KEY: VARIANT
<222> LOCATION: (1)..(1)
<223> OTHER INFORMATION: Lys or Orn
<220> FEATURE:
<221> NAME/KEY: VARIANT
<222> LOCATION: (2)..(2)
<223> OTHER INFORMATION: Leu, Ile, Val, or Ala
<220> FEATURE:
<221> NAME/KEY: VARIANT
<222> LOCATION: (3)..(3)
<223> OTHER INFORMATION: Leu, Ile, Val, or Ala
<220> FEATURE:
```

```
<221> NAME/KEY: VARIANT
<222> LOCATION: (4)..(4)
<223> OTHER INFORMATION: Lys or Orn
<220> FEATURE:
<221> NAME/KEY: VARIANT
<222> LOCATION: (5)..(5)
<223> OTHER INFORMATION: Cys, Tyr, Thr, or Ser
<220> FEATURE:
<221> NAME/KEY: VARIANT
<222> LOCATION: (6)..(6)
<223> OTHER INFORMATION: Tyr, Phe, or Trp
<220> FEATURE:
<221> NAME/KEY: VARIANT
<222> LOCATION: (7)..(7)
<223> OTHER INFORMATION: Lys or Orn
<220> FEATURE:
<221> NAME/KEY: VARIANT
<222> LOCATION: (8)..(8)
<223> OTHER INFORMATION: Cys, Tyr, Thr, or Ser
<220> FEATURE:
<221> NAME/KEY: VARIANT
<222> LOCATION: (9)..(9)
<223> OTHER INFORMATION: Leu, Ile, Val, or Ala
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: VARIANT
<222> LOCATION: (11)..(11)
<223> OTHER INFORMATION: Leu, Ile, Val, or Ala

<400> SEQUENCE: 2

Xaa Xaa Xaa Xaa Xaa Xaa Xaa Xaa Xaa Xaa Pro Ile Pro Ile
1               5                   10

<210> SEQ ID NO 3
<211> LENGTH: 13
<212> TYPE: PRT
<213> ORGANISM: Paenibacillus strain TS-15
<220> FEATURE:
<221> NAME/KEY: VARIANT
<222> LOCATION: (1)..(1)
<223> OTHER INFORMATION: Lys or Orn
<220> FEATURE:
<221> NAME/KEY: VARIANT
<222> LOCATION: (4)..(4)
<223> OTHER INFORMATION: Lys or Orn
<220> FEATURE:
<221> NAME/KEY: VARIANT
<222> LOCATION: (6)..(6)
<223> OTHER INFORMATION: Tyr, Phe, or Trp
<220> FEATURE:
<221> NAME/KEY: VARIANT
<222> LOCATION: (7)..(7)
<223> OTHER INFORMATION: Lys or Orn
<220> FEATURE:
<221> NAME/KEY: VARIANT
<222> LOCATION: (11)..(11)
<223> OTHER INFORMATION: Leu, Ile, Val, or Ala

<400> SEQUENCE: 3

Xaa Val Thr Xaa Ser Xaa Xaa Ser Ile Pro Xaa Pro Ile
1               5                   10

<210> SEQ ID NO 4
<211> LENGTH: 13
<212> TYPE: PRT
<213> ORGANISM: Paenibacillus strain TS-15
<220> FEATURE:
<221> NAME/KEY: VARIANT
<222> LOCATION: (1)..(1)
<223> OTHER INFORMATION: ornithine
<220> FEATURE:
<221> NAME/KEY: VARIANT
```

```
<222> LOCATION: (4)..(4)
<223> OTHER INFORMATION: ornithine
<220> FEATURE:
<221> NAME/KEY: VARIANT
<222> LOCATION: (6)..(6)
<223> OTHER INFORMATION: Tyr or Phe
<220> FEATURE:
<221> NAME/KEY: VARIANT
<222> LOCATION: (7)..(7)
<223> OTHER INFORMATION: Lys or Orn

<400> SEQUENCE: 4

Xaa Val Thr Xaa Ser Xaa Xaa Ser Ile Pro Ile Pro Ile
 1               5                  10

<210> SEQ ID NO 5
<211> LENGTH: 19965
<212> TYPE: DNA
<213> ORGANISM: Paenibacillus strain A6-6i

<400> SEQUENCE: 5
gtgaacgcga atcctaacga atggtatcct ttgacgcaag cgcagcgcag aatctggtac     60
acagaaatga tgcatcctaa tacgtcagtt actaccgttg ctggaacaat gtacatacga    120
ggcaaggtag acgttgagat tttgaaaatg gcgatatatc aagtgattat gcagcatgat    180
gccttccgaa tacgaatcgc aatgacagac aatcagccga agcagcaatt tgctcccgta    240
gagcaaatcg tccctcacgt tgattactta gagtgggata tcagattga agctgagagc    300 tggttacagc gatttaatca tattcctatc catatgttcg acccagcgtt atatcacttt    360
gtcgtattta acgtcaatga tgaggaagca tggttcaatt tgaaaatgaa tcatattgca    420
acggatggcg tctcttctca tcttatcgct tataaaatca tgaagaatta taccgcaatg    480
gtgagtggca acgcggacac ggatgaacaa gagagcactt acctggatta catattcgcg    540
gaacgagagt atgaacaatc tgatcgatac gcgaaagata aggcttattg gctggataag    600
ttcagcacaa tgccagaagt gataggtatc aaatcttacc ctcctcattc aatcggcact    660
gaggccagtc ggacaagcat cacggttagc ggagaaatgt acgagaagct ttaccgattt    720
agccagcagc acaatatcag tctctttact ctatttctag gttctttata cgcatttcta    780
tataagacga cagggaacaa cgatattgct gtcggtgccg cttatgcgaa tcgaacttcc    840
aggcaagaca aggatgcgct gggcatgttc gtaagcacgg tagccgctcg tttgacgatt    900
tccccagacc aagatgtact aaccttccta cataacgttg ccaaagagca aaaagcaatt    960
ttgcggcatc agaagtatcc ttacaaccag cttattcttg atttaagaga gcaaaataat   1020
agtgttgaga ttcaggattt gtaccgtatt tccatcgact atatgccgat acgctggtcc   1080
agtcacggag aactagccgc cgccaacgc agcagctttt gcggtcatga ggtagacgat   1140
tttgcagttc acgtagaaga tatggtggat gataatcaga tcattttcaa tatcgattat   1200
cgcaaacagt tgttcgaaga gcatgaagtc attcgtatca tcgatcaaat gatgaccatc   1260
gttgatcaga tgttgagtaa tccgagccag agcttgcagc agttgtccat gatcagtgat   1320
aaggaagctc agatcatcct gacacgcttc agcaacggga attggtcaac gccgcagcca   1380
gttggacgaa cgattcacca gttgtttgag gaacaggtcg aacgcacgcc tgatcaggtt   1440
gctgtcgtgt tcggagatcg gcacctaacc tacaaggaac tgaacgaaca agccaattgc   1500
ttcgctcgaa cattgcgagc ccatggtgta gcagcagagc aattcgtagg catcatggca   1560
gaccgctcga ttgagatggt cgtcggtata cttgcaatat tgaaggcggg tggagcctac   1620
gttccgatag atcctgaata tccagaagag cgcatttat atatgctgga agactctaat   1680
```

```
gcaagagtac tcgtatcgca aagtcattta cagacacggc tcggttacac aggaacatgg    1740
gtattgcttg atgatgagaa cgactatgaa gcaaaccgcg ataacttgga gtcggtcaac    1800
gaagcacatc atttggctta tgtcatctat acatccggta caactggcaa gccgaagggc    1860
gtcatgattg agcataagca gattacagcc ttgggggatg catggaagca tgcctatcaa    1920
ttagatgaat cgggaattcg gacgctgcaa tgggcaagct tctccttcga cgtatttacg    1980
ggagacatgg tgcgagcgct gctgtacgga ggcgagctta tcatctgccc aagcgaagcg    2040
cgagctaatc ctgaagcgat atgcgagcta atcgcaagac atcgcatcca catattcgaa    2100
tcaaccccag ccctcgttat tccgttgatg aatatgtgc atgaacaaag gaaggatgta     2160
agcagtctgc gcctgctcgt tgtgggctcg gatcattgcc cggctgcgga atatcgcaag    2220
ctgatggaac gattcggctc gcaaatgaga atcctgaaca gctatggcgt gactgaggct    2280
tgcgtcgatg cgtgctatta cgagaaaaat ggtagtgtgg attccatcac catgcttccg    2340
ataggtaaac cactgccttc ggtatccatg tacattctag acgagaacaa ggcgcttcag    2400
ccaattggaa ttgtaggaga gctctacata ggtggagccg tgtcggcag aggttatttg     2460
aaccgtgatg acttgacagc agaaaaattc gttgatgacc cctactcaca aggaaagatg    2520
tatcggacag gtgatttggc aagatggctg ccggacggaa acatcgaata ccttggaagg    2580
ctcgatcatc aagtcaaaat tcggggtaac cggatagaaa taggagaaat tgaaacgcgc    2640
atgctgcaaa catcactcgt gcgggaagcc gttatcgtag cgcgcgagga tgaaaatgga    2700
ctgaaagctc tgtgcgccta ttatgttgcc gacagcgaga tatccgtaca gcaattgcgt    2760
tcaaccctag cagaacaagt accggattat atgattccgt cttatttcat gaagctggaa    2820
cgattgccgc ttacgccgaa cggcaaaatc gatcggaatg gattgcctgc accgtctggt    2880
caggactatt ccggcaagat ttatgtggag cctcgtaacc aagcggaaca aacgctggct    2940
agcatctgga aaatggtgct tggagtcaag cgagtgggta ttttggatca tttcttcgag    3000
ctaggtggag attcgatcaa gtccattcaa gtatcttctc gcatgcagca agctggatat    3060
aagctggata tccgggatct gttcaagtat ccgaccattg aacaaataag tccacatctg    3120
gtggaggttc agcgaaaagc tgagcaggga gaagagagtg tgaggttgg gctcactcct     3180
atattgcgct ggtattttga tcgagatgaa gtgagtctgc atcattacaa tcaatccata    3240
atgctgcacc gcaaggctgg attcgatgaa gcggcacttc gcaatgcatt gcacaagata    3300
acggaacatc atgatgcgct gcgcatggta ttccgccgca cggaacaggg agaatacgcg    3360
gcctggaacc ggagaatcga agaaggcgag ctttaccgtc ttgatgtgtt ggatatcaag    3420
gaacgttccg ctggcgtaga aagcgaagaa tctcttcaca acatgctcat agctgaagcc    3480
aatgtgattc aggcggggtt cgatatagag gcagggccac ttgtaggcgc aggattgttc    3540
cgctgcccag atggagatca cctgcttatc gtcattcatc atgctgttat tgatgccgta    3600
tcttggcgaa ttttgctcga ggatctcgcc actggatacg aacaggcact tcaaggcagc    3660
gagattcgtc tccctgacaa gaccgactcc ttccggttat ggtcaagaga gctttcagca    3720
tatgcacagc agtctaacat gaacgaggag ctgaaatatt ggcaccaagt cgcacagacg    3780
acgattactc cactgccgac ggattatgct ggattgctc ttcaacgaga tagcgaatcg     3840
gtcacggttg aatggagtgc tagtgagacc gaactgctgt tgaagcaggc gcatcgggcc    3900
tataacacgc agatggacga tcttctctta acggcactcg gcattgcatt ccggagatgg    3960
tgtgggcatg agcgcatccg aattaatttg gaaggacatg gtcgggagtc gatcctgcca    4020
```

-continued

```
gatcttgata tcacacgcac ggtaggctgg ttcacgagtg agtatccgca gcttctcgag    4080
gtgggctctg aggaagaact gccgcgaatc atcaagtcgg tcaaagaaga tttgcgcagc    4140
attccgaata aagggattgg ttacggcatt tgtcgatatt tatccaacac gggtatttgt    4200
gaggtttggg gaacagctcc tgaggtcagc ttcaactact tggggcagtt cgaccaagat    4260
ttccagaaca gcgggttttc tccatcgccg tattctaccg gcagcaatat tggggagat     4320 cagctaagac cttatctgct ggacatgaat ggcatggtct cggacggcaa attgcagctc    4380
gacatcagct atggacggac gcaatatcgt gctgagacga ttgagcgatt ggcaagcttg    4440
attcgggaca gcttacttga aatcatcgag cattgtgtgg ccaaggagcg aacagagctc    4500
acgccaagtg acgtgtcatt gcagcgcatt agcattcaag agttggagca gatcgttgaa    4560
cggacaagcg gtatcggtga agtagaggat atctatgcat taacgccgat gcagaaggga    4620
atgtggttcc atacagctat ggacagccag gcggggcct atttcgagct tacacgctta     4680
acgcttgagg gaacgctgaa catcgaagcc ttcgctgcaa gctggaatga actggcggct    4740
cggcatgctg tattccgtac caacttcctc gtcgattcga atggcgaacc actgcaagtt    4800
gtatttcgga gcaagcgcat cagcgtgaag cacgaagatt tgcgttccct gaatgcatat    4860
gagcaggctg tggcgattga gaacgaagcg gccaaggaac gcgaacaagg ctttgacctt    4920
gagaatgggg atgtcatgcg cgtgtccgta ctccagacgg cagacgaagt gtatgaagtt    4980
ctatggatct cccatcacat cgtcatggat ggatggtgtc tcccgctcgt cgctgctgaa    5040
gtattcaaca cgtactccgc gctggtggaa gacaagaagc cgattcttgc ttcggtacct    5100
tcctataatc attacattca atggctggag cggcaggatg aatccgcagc cgcggcctat    5160
tggaacaatt atttgtctgg atttgaagag acgacagaac ttccgcatag caaggggcgc    5220
agacattctg gtcaatatga agcaggtcag gttcagatcg atctaggcac aagcctgagc    5280
cttgctctca atcaagttgc aacgcagcat caagtgacat tgaatacatt gctgcaggca    5340
tcatggggaa ttttgctcca gaaatacaac agaacttcag atattgtatt cggcagcgtt    5400
gtatccggca gaccggcaga actagtcgga atcgaagaga tgattggttt gttcattaac    5460
acgattcccg tgcgtgtgag cagtcaggcg caggagagat ttgcagaagt aatgacgcgt    5520
atgcaagaag atgcattgtc atctgccaag cacgactact atccgttgta tgaaatccaa    5580
gcacagtgca ccctgaagca gaatctcata actcacatca tggttcttga aaactatccg    5640
atggagcagc agctcgatca atttaacagt tcagacggca gtggactgaa gctgacagac    5700
gttaccgtaa cagaacagac gaattatgat ctgaacctca tcatcatacc tggcgacaat    5760
atcgtcattc gcttcgattt taataaacaa gcactcgaag aagcggatat gaatgtgttg    5820
aagcagcatc tgttgcatgt actgaacaa gttgcatcga atccgcggat atccataggta    5880 gagctgcagc tggcgacgga tgaagagcgt gccgtaatga tgagcgaatt taatgatacg    5940
ttcgtggctt atccgcgcga gaagtcgatc catcgattgt tcgaggagcg agctgaacat    6000
gagccagacg cgctagctgt cgtgtttgga aatgaacaga tgacctacgg agcgttgaat    6060
gccgcagcca atcgaatggc tcggagactc cggcatgccg gggtaacgaa cggtgaactg    6120
gttggcatct gcgcggatcg atcgctggat atggtcgtcg gcttactggc aattatgaag    6180
tccggcgggg cttatgtacc gatcgacccg gcttaccctc aagagcggat tagtgcaatg    6240
ctcgaagata catccattac gacgatggtt acacagaagc atctgtgcag cttatggcct    6300
gaacatttta acgtgatcgt gctggatgtt aacgagacag acgtaagcaa cttaatggaa    6360
gatatagaaa gtacaaacct gtctattgat ggggctggag acgatttggc atacatcatc    6420
```

```
tatacgtcag ggtctacggg aacaccgaaa ggggtttgcg taacgcaccg cggggtggtc    6480
aggctcgtat gcggcgcgac gtatgtcgag atcgacagtt cggatgtctt cttgcaaggt    6540
tccacaatct cgttcgatgc agcaacctttt gaaatatggg gaagtctgct gaatggggct    6600
gcgctggcca tcttgccttc tggcaatgtg tcgcttacag attggagcga agcgattcag    6660
cgtcatcggg tgacgacgtt gtggatgaca gctggtttgt tccaggtcat ggttgaacag    6720
caaatcgagg gcttctacgg agtcaagcag ctgcttgtgg gcggagatgt tgtatctcct    6780
acacacgtgc gtaaagtgat ggagaagcat aatggtataa gggtgattaa tggctacggg    6840
ccgacggaaa atacaacctt cacctgctgc cataccatta cggctgctga tttggatcga    6900
ggctgctcga ttccgattgg ccgaccgatt agcaatacgc gagtgtatgt gctggatgaa    6960
gctgggaacg cccttcctgt tggcgtatgt ggagagctgt atgcgggcgg ggatggcttg    7020
gcacgaggat acttgaatcg tccggaattg acagcagaga aattcgtgaa tgatccattt    7080
atcccaggtg aacgcttgta tcggacaggc gatttggcga gatggctgcc agacggttca    7140
atcgaattta tcgggcgctg cgacgaacaa gtgaagattc gcggttaccg gattgaacca    7200
ggtgaggtat tggcctatct tctgcggatc gatgaagtag gcgaggcggc tgtaatcgcg    7260
cgggaggatt cgagtggaca gaaggagcta tgcgcctatt tcacaacgga agctgagcta    7320
tcagctagtg gactaaggga gacactggct cgtgaactgc cagcttacat gatcccgtcg    7380
cattttattc agattgaaga acttcctttg cacctaacg gcaaggtgga tcgcagagct    7440
ctgcctcaac caggggaagg aatgcatttg aatattcaaa tccagccgcg cacggaactg    7500
gaagctaagc tcgcactcat ctggaaggat gtgcttggtc tcgagaacgt aggcgttaca    7560
gattcattct ttgaactggg cggccattcc ttgcgcgcga cgaccctcgt cagcaaggtg    7620
catcgggagt tgagtgttgt gctgccactg caggatgtat tccgctaccc gacgattgaa    7680
caaatgtctc tcgccataca ggggatgcag aaggaaagct ttgcatccat acctcgggtg    7740
gaagaccgag agtggtaccc ggtatcttcc gcgcagaagc ggctgttcgt tcttcatcag    7800
atggagggcg cagaactgtc ctacaatatg ccgggcgtca tggcgattga aggcaagctc    7860
catcgcgatc gcttggaggc ggcattccgc agcttgatag caagacatga agtgctgcgt    7920
accgggttcg aaatgcacaa cggggaaccc atgcagcgaa tttacagcga tgtagaattt    7980
actgtcgagc attggattgt tggagctgca tcggaagcgg agtcagtcat tcgctcgttc    8040
gtacgggcgt tccaattgaa taagccacca ctgcttcggg tcggactgat cgaagtggac    8100
gcaggtcgga acctgttgct gttcgatatg catcatatta tttcggacgg ggcatccatg    8160
ggcattctgc tagatgaatt cgttgcactg tatagcggcg aacaattgcc tgaattgcgt    8220
cttcagtaca aggattatgc ttcgtggcag cattcggaag catacttgtc caagatggaa    8280
gagcagaagg cgtattggct ggagacattg cgaggcgagc ttccagttct gcagctacca    8340
gtggattaca ctcggcctgc attccgcagc tttgcaggaa gcacgttgga attcattgtt    8400
cctgccgaca agacggacca gcttaagcag cttggagcgg gttcggatgc cacgatgtac    8460
atggtgctgc tggcgttgta tacgcccttg cttcacaagt ataccggaca agaagacgtc    8520
atcgtgggga tgccgatagc cggtagaacg catgcagaca tcgagccgct tatcggtatg    8580
ttcgtcaaca cacttccact tcgccattat ccggctggag agaagacgtt ccgctccttc    8640
ctaggggagg ttcggcaatc cacattacaa gcatatgaac accaggaata tccgttcgag    8700
gagcttgttg atcatattca accgacaaga gatgtaagcc gtaatccaat attcgatact    8760
```

-continued

```
gtgctcgtcc tgcaaaatac agaaaaaggc gcatggtcca tcgatgggct tgccgtgacg   8820
ccgaatccga ttgagcatgc cgttgctaag ttcgacctta cacttcatgt cgaagaagat   8880
gtcgatggcc tggcgtgcag tattgaatat gcaaccgcct tgtacaatcg agaaacgatt   8940
gaacggctgg catgccattt caatcaattg ctggaagcag tcataagcaa tcccgatgct   9000
cggttggagc agcttggcat cataacggag acagagaagc agcaattgtt cgaacagttc   9060
aacgatacgt cagcggatta ccgcgtgat aagacgattc accgactgtt cgaggaacag   9120
gtcgaaagaa cgcctgatgc gattgctgta acgggaacag acggattctt gacttaccag   9180
gagctgaatg aacgggctaa cagcttggcg tgggtactgc gtgcagaagg catcggggca   9240
gacaagctgg taggcatcat ggccgagcgt acgactgata tgcttgtggg gctaatcgcc   9300
atactcaagg ccgaggagc ttacgtacca atcgatcccg aatatccaga cgagcgcatc   9360
agttatatgc tgagcgattc cggggcagat attttgctat tgcctcgaca tctgcggaat   9420
caagtcgcct atgagggcac cgtgttgttc cttgatgacg agcagacata cagcggggac   9480
aagtccaacc cgccatcagt caacaaacct tccgatctgg cttatgtcat ctatacatcg   9540
ggaacgactg gcaagccgaa gggtacattg attgaacata agaacgtcgt gcggctgttg   9600
ttcaacagca gaaatctgtt cgacttccgt tcaaccgata catggacgct gttccactcc   9660
ttctgcttcg acttctcggt atgggaaatg tacggcgctt tactatacgg agggaaattg   9720
gtggttgttc cgcagctgac agccaagaac cctgccatgt tcctacagct gctggctgaa   9780
gagcgggtaa cgattttgaa tcagactccg acctatttct atcaattaat aagggaagca   9840
cttacggatg gaagcccaga attgaacatt cgaatggtga tcttcggcgg agaagcgctg   9900
agtccgcagc tgcttaagga ctggagagcg aaatatccgc gcacgcaatt gattaatatg   9960
tacgggatta ctgagacaac ggttcatgtc acgtacaaag agatcacgga agccgagatc   10020
gagcaggcaa gaagcaatat cggattccca atcccgacct tgcgcatcta tattctggat   10080
gcgaatcgac aatgcgtgcc gataggcgtg gctggggaaa tgttcgtcgc aggagaaggg   10140
cttgcacgtg gatatttgaa tcgccctgag ttgaccgcgg acaggttcgt tgacaatcca   10200
ttcgaaccgg gcagcaagat gtacaagaca ggcgacttgg cgaagtggct gcctgacggc   10260
aacattgaat accttggccg gattgatcat caagtaaaaa ttcgcgggta tcgaatcgag   10320
ctaggcgagt agaagcccca agtaacgaag gtagaatcgg ttcgtgaagc cgttgttgtt   10380
gcacgagagg agaatggcga aaagctgttg tgtgcatatt tcgtggcgga tcggcaactg   10440
accgtagggg aaatgagaac cgaattggcg caggagctgc caacttacat gattccatcc   10500
tacttcgtgc agatggagcg gatgccgctt acctccaacg ggaaggttga ccgcaaggcg   10560
ctgcctgcac cggaaggcag catcaacacg ggcaaggaat acgtcgcgcc gcgtacacca   10620
atggaagcta gcttagcccg catgtgggag gaactgcttg gaattgagca ggtcggcgtg   10680
acagacaatt tcttcgagct aggcggacat tccttaagag caactgcgct ggttaacagg   10740
gtgcaccaag agatgaatat ccagttgccg ctgcgcgatg tgttccgctt ctctacgata   10800
gaagaactgg cagctgccat gtccgagatg gcggaggaat cctattcttc gataccagtt   10860
gctgaggttc aggatcatta tccggtatct tccgctcaga gcggctgta catccttcac   10920
cagcttgaag gggcagagca gggctataac atgcctggca tcatgctgct cgaaggcgag   10980
ttggatcgaa gcaggttcga ggctgcattc cgcaaattga ttgcgcatca cgatattttg   11040
cgtaccggct tcgagcttgt gcaggagag gctgtacagc gaatacacga tactgtggat   11100
ttcgcgattg aatatcggaa agtcgaagaa caagaggttc agcagcaagt aaaacagttc   11160
```

```
atccgcacat tcgagcttga taagccgccg ctgcttcgtg tcgggttgat cgagattgcg   11220
gggacgaagg aacagcatgt gcttctgttc gatatgcatc atattatttc cgacggggta   11280
tcgatcggta tcgtgctgca ggaaatcatg cggcactatc acggggaaca ggtaccgccg   11340
cttcatattc aatacaagga ttatgcggca tggcagcaat cagaggccca gaaggaacag   11400
ttgaagcatc agaaagctta ttggcttggc caattccaag gtgaattgcc gatattggag   11460
ctgccaacag actatgctcg tccagccatg cagcaatacg gcggtctgac gctgccattt   11520
agaatcgata aggacgtggc agatggtttg aaccgaattg ccgctgacac cggaacgaca   11580
ttgtacatgg ttctcctagc tgcttatacc gtcatgctgc acaagtatac gggccaagaa   11640
gacatcgtgg tcggaacacc gattgccggc agaacacatg aagaacttca accgttaatt   11700
ggcatgttcg tcaatacgct tgccattcgt gcttatccgg aaggtgctaa ggcattccgt   11760
tcctatctgg atgagattag aagcacaatg ctggggggcct acgagcatca acagtatcca   11820
tttgaggaat tggtggaagg tctgcagttg actaggggatt taagccgcaa tccgctgttt   11880
gacacgatgt tcgccctaga taatacggac atgaaggctg attccctggg cgagcttcaa   11940
atgaagccat atccactgga atacacaata tcgaagttcg atgtgagctt ggatgtgaag   12000
gcggatgagg cggggctgga ttgcagcttc gagtatgcga cttccttgtt caaatcagag   12060
acgatccacc gcatggcaga gcatttcagc catttgttga aggacatcgt caatcacccg   12120
gatgcgcaac tgggcgaact aggaatgctt accgtgcagg agagcgacga gatcttgcag   12180
gtgttcaatc caacccattc attgaaagct cctaacgaaa cgattcatcg attgttcgaa   12240
gaacaggcag aacggacacc agagcaacct gcagtcgtat tcgggaatga gcgcatgact   12300
taccgcgagt tgaacgaacg ggcgaataag cttgcgagaa cattgcgggc agaaggtgtg   12360
gagccagatg acttaattgg cgttatggcc gatcgctcga ttgatatggt cgtggcagtc   12420
atggccgtct tgaagtcagg cggagcctat gtcccgattg atccggaata tccggaggat   12480
cgcattcgct acatgctgga agatgcgaag gcaagaatac ttctgacgca gggtcattta   12540
caagataaag tgaccttcga gggaacgtgg gtgctgctgg aggacgaagc ttcctatcat   12600
gaggacgata cgaacctgga gccgaactgc gagccaggcc atctctgtta tgtcatctat   12660
acatcgggta caaccggcaa tccgaaggga gtcatgatcg agcatcgtca gcttgctgcg   12720
atggcagagg cttggaaggc cgagtatgaa ttgcatgagc cggcattcg ctggctgcaa   12780
tgggcgagct tctcgttcga cgtattctca ggtgatctcg ctcgcacact gctgcatgga   12840
ggagagcttg tactctgccc gagcgataca agagcgaacc caggtgcact agcagagctt   12900
cttcgcagca gcggcattca gatgttcgaa tcgacacctg cgctcgtcat tccgcttatg   12960
gagcatgtgt atgagcatgg cctggacatc gacagcctga gattattaat tattggctcc   13020
gatctgtgtc ctgcagatga attccgcaag ctacgcgatc gcttcagttc acacatgcgc   13080
attattaaca gctatggcgt cacggaagct tgcgttgatt cgagctacta tgagccgatt   13140
tcatcagatt cagtacgctc tgtgccaatc ggtaagccgc ttccttacgt atcgatgtac   13200
attctcggtg agaacttgtc gcttcagcct gttggtctgg ctggagagct gtatatcgca   13260
ggcgccggag tcgacgcgg atactggaat aggccggaaa tgcagcagcaga caaattcgtg   13320
cgcgatccgt tcgctgacgg tcaacgcatg tatcgtacag gggatttggc gaaatggctg   13380
ccggacggca acattgaatt aatcgggcgc accgatcatc aggtgaaaat tcgcggctac   13440
cgcatcgaaa tcggagaggt cgaatcgaag ctgcaggaaa cgccgcatat ccgcgaagca   13500
```

```
gccgtcgtcg cgaaggaaga tggaagcggg cggaaggtac tgtgtgctta ttacacatcc   13560
gagcgtgagc ttacggcagg tgaatggaga gctgcgttag cgaaggaatt gccggcctac   13620
atgataccat cgcacttcat gaggcttgag cgaatgccgc ttacgccgaa cggcaagctg   13680
gatcgcaagg gacttccagc accggaaggc gctgcgtata cggggacgga atatgaagct   13740
ccacgcacgg atgcagagat tgcgttggct gccgcatggc agagtgtctt gcatgtggag   13800 cggggttggaa cgaatgatca tttcttcgaa ctgggtggag attcgatcaa atcgattcaa   13860
gtgtcatcgc gtctgcatca ggctggatac aagttagaaa tacgcgacct gttcaaatac   13920
ccaacgatag cgcaattgag tccgcagctt cagccgatcg gcaggatagc tgatcaaggc   13980
gaggtgtctg gcgaggttga gctgacgcca atccaatgct ggtatttcgg actggatctg   14040
gatgacatgc atcattataa ccagtcgttc atgctgtatc ggcaggacgg atttaatgag   14100
gaggctctgc gcaagacttt acgatccatc gtggagcatc atgatgcgct gcgaatggta   14160
ttccgtaaat cagacgctgg ggttacggct tggaatcggg caatcgaaga gggtgaactg   14220
ttcgacttcc ttgccttcga tatcgcaaac agtggagatg ctgaacaggt tatcgaagcg   14280
aaagcgaacg acatacaggc tagcatcgat ttgcagggcg ggccgcttgt gaaggctgga   14340
ttgttccgct gcgagcaagg ccatcatctg ctcatcgcga tccaccatgc tgtcatggat   14400
ggagtatcat ggcgcatcct gctggaggat atcgcgacag gctacgagca agcgtgcaag   14460
ggtgacgaca ttcgccttgcc ttcgaagacc gattcttatg ctgcgtggtc acggagtttg   14520
gtcgaatatg ctgaacacac ggatttgggt catgagcgca gctattggag acacgtcttg   14580
aacgctggaa cgaatccgct gccgaaggac tttgacacag aatcaagtct gcagcaggac   14640
agtaattccg tcaccgtagc ttggaatcaa caggatacgg agcatttact gaagcgggtg   14700
caccgagcct ataacaccga tatgaatgag atcttgctgg ccgctctcgc gatagccata   14760
cagaaatgga gtgggcacaa tcaaattctc gtcaacctag agggtcatgg acgtgagcca   14820
atcgcaggcg acctagatat ttcacggaca gtcggctggt tcacaagcga atatccggtt   14880
ctgctgaaag cggagcgaga tcgaggtttg gcgtaccaca tcaagagagc gaaggaagaa   14940
ttgcggcaga ttccgaacaa gggaatcggt tacggcatat gccgctactt gtctgagccg   15000
caagatagtt tggaatgggg agctgcccca gagattagct tcaactactt gggacaattc   15060
gatcaagact cgatgggaag cggcatgatg ttgtctccat attcgaaagg ttccgatgga   15120
agcgccttgc atacacgtca atatgtcctc gacatcaatg gcgccataac tgacggcata   15180
ttgaccttgg atatgagcta cagcgagaaa gagtaccgca aggagacgat ggaactgctg   15240
gcaggccatt tccacgagag tctgctcgag atcatcgacc actgtgtctc acgtgagcag   15300
acagaattga cgccgagtga tctgctgctg caaggactga gtatcgaaca gctggagcag   15360
attgctgaag agacgaaaga gcttggcatc atcgaaaata tgtacatgct gacccgatg   15420 cagaagggga tgtggttcca taacgctctc gatggtcaag aaggcgcatc gggtgcttat   15480
ttcgaacaaa cccgatttac tctgcgaggt gagcttgatc ctgccctgtt tgcccagagc   15540
ctgcacgagc tggctgcccg gcattccgtg ctgcggacga acttctgcag cttggacggg   15600
gaaccggtac agatggtgtt ccgggaagga cgaattacat tcacgtacga ggatctgagc   15660
caattgccag ctgatgagca agcagttgtg atggaacgtg ttgtcgcgag cgacaagctg   15720
caagggttcg atctggaacg cgatccgctt gttcgcgtca cattgatgcg tacggaggca   15780
tctagctgcc atgtactgtg gagttctcat catattctga tggatggctg gtgcttgccg   15840
cagttgacgg acgagttgtt ccgcatatac tcagctgtca cgaatcatgc agccggaact   15900
```

```
actgaagcta ctggaacggt cggaattccc ggatctgccg aatccatgcg gaacaaagag    15960
gccaacctgc ctgactatag ccgatatatc gaatggctgg cagagcagga catgagtgcg    16020
gcggcagaat attggaacgg gtacttggcg ggctacgagc agcagacacg attgccaaat    16080
gggaagatca cagtcaagga taagccatat gtgctggaac aagcgtcccg caagctcgga    16140
attgatctta cttcccgtat gattcggatt gccaagcagc atcaagttac gttaaatacg    16200
ctgctgcaag ccgcttgggg gatcgtgctt cagaagtata acgggacgca agatgtcgtg    16260
ttcggcggag tcgtatcggg tcgacctgct gatgttccgg gtgtcgaatc gatgattgga    16320
ctattcatta acacgattcc ggttcgtgta agctgcgaag ccggcgcaag cttctcagac    16380
gtgatggagc agctgcaaaa tgcggcactc gaatctgggc gatatgatta ttatccgctc    16440
tatgagattc aatcgagaac gtcacagaag tcggaactaa tcagccacat catggtgttt    16500
gagaactatc cattggacga gcgaatggag caaaccggag acggtaacga cggagctctc    16560
gctttaaccg atgttcaagc agctgaacag accaattatg atttcaatct aatggtagtg    16620
ccgggtgatg aacttatcat tcgctttgat ttcaactcgg aagtgtatga tcgcggtcat    16680
atggaacggc tgcatcatca tctgatgcat gtactggagc aagtaacagg caatcctgca    16740
atctccattg ctgaagtgca gctctctacc gaagcggaga aggcagaagt ccaatctgca    16800
ttcaatgaca cagttgtcga ctaccctcgc gaacagacga ttcattggat gttcgaagag    16860
caggtgcagc ggacgccgga tgctgcagca gtgctgtatg ggatgacgt cataacctac    16920 cgagagctga cgaacgtgc gaaccggctg caaggacgc tgcgtgcggc aggggttgaa    16980
cccgatcaga ttgtcggtat tatggcagag cgttctctgg agctaatggt tggcattatg    17040
gggattctga aggcaggagg cgcctatgtg cctatcgcac cggattatcc agaggaacgc    17100
attcgatata tgctggacga ttccaaggct caggtgctgc ttgttcaagg aagcgcggga    17160
gaagcggttg acttcgtggg ccgcatcatc aatctggatg atgcagaagc atacgatgag    17220
gacagttcga atcctgagcc agtcaacaag ccgaccgata tagcctacat catctatacg    17280
tcgggaacga ccggacgtcc aaaagggggtt atggtcgagc atacttcggt catcaaccgc    17340
ttgctgtgga tgcagaagcg ctatccgata ggatcggaag atacgattat gcagaagacg    17400
gcgatcacgt ttgacgtatc ggtctgggag ctgttctggt gggcatttgt cggctcgaag    17460
gtgcttatgc tttcagtcgg tggggagaag aacccacatg cgattgtgga tgcgattgag    17520
cgtcaccgga taacgacgat gcacttcgtt ccatccatgc tgcacgcgtt ccttgagcat    17580
gtggagcaaa tgacagatgc agagcgtgag cgcggtctcg caccgctgcg gcaggtgttc    17640
acgagtggcg aggcactgct tgcctcacag gtcgagcggt tccaccgtta tattgcacct    17700
gcaagcggag cgcagcttat taatctatac gggccgactg aggcgacggt ggacgtaacg    17760
tacttcgact gcgagccagg ccagacttat gtaagtgtgc cgattggcaa gccaattgac    17820
aatacgagca tttatatcgt gaatgagcat aatcaagtgc agccgatcgg cgttgctggt    17880
gaactgtgca tcgcgggagt ggggttggcg cgcggttact ggaaccgtcc agagctgaca    17940
gcagagaaat tcgttacaat tccttccgtc ggcgaacgga tgtatcgaac cggagacttg    18000
gcacggtggc tgcctgacgg caatatcgaa tacttgggcc gaatcgacca tcaagtgaaa    18060
atccgcggat atcggattga attgggcgag ctggagactg cactgctgaa tgtccaagaa    18120
attcgggaga cggttgtagt tgcgcgagaa gaggaagacg gacagaaatc actctgcgcc    18180
tattatgtcg cagatggcga tccaacggta ggtaaccttg agcggcgcgct tgctgctgaa    18240
```

```
ctgccaagct acatgattcc atcgtacttc attcagctgg agcagatgcc gctggcgccg   18300
aacggcaagc ttgatcgtaa agcgctccct gctccgaagg acgtgattca gacgggaact   18360
gatcacgccg caccacgaac agcattggaa gtgaagctcg ttcgcatatg gcaggaagta   18420
ctcggtctcg atcaaatcgg agtgaaggac gacttcttcg aattgggcgg gcactccttg   18480
cgcgcaactg cgttggcaag caaggtaagc aaggaaatgc acgttgctct tccgctgcgg   18540
gatattttcc actattcgac gctggaagcg atggcgcagg cgatcggcga gttgagaag    18600 caggagcacc gagcgattcc tatcgcgcca atggccgagc attatccatt ggcttcagcc   18660
cagaagcggt tatacattct tcaccaggct gaaggagcgc agcagagcta acatgccg     18720 ggggcgatgt ccgtaagtgg acacatcgat cgaaatcgac tggaagcggc gctgctgcga   18780
ttgattgcac gccatgacac actgcgcaca agcttcgaaa tggttgatgg tgagcctgta   18840
cagcgcgtac accagcacgt tgatttcgcg ttagagtatt cgactgcgag agagaaggat   18900
atggagcagg ttgccaagca gtttgttcgc gattttgatc tggagcagcc tccactactg   18960
agagtcggac ttgtccaact tgagcaagaa gaacaacatc tattgctgtt cgatatgcat   19020
cacatcatat cggacgggat ctctatggac atattggttg acgagcttgc tcgcttgtac   19080
gacggagagg aacttcctcc acttgaaatc cagtacaaag attatgtgct gtggcagcag   19140
gcagaagcaa gcagcgagca gatgaaggaa catgaagaat actggctgcg gacattgggc   19200
aatgaacttc cgttactgga gctgccgacc gaatttgcaa gaagcgagca gcgcagctat   19260
gacggagata agctgcactt tgcgattgat gggcagttga acgagaagct gcagcgcttg   19320
gcatcccaat cgggagcaac cctatatatg gtgctgctgg cggcttatac gaccttgctt   19380
cataaatatt caggacaaaa tgacctggtt gtgggcaccc caattgcggg cagaacccat   19440
gtagatgtag aaccgctaat cgggatgttc gtcaattcgc ttgcgattcg taattaccca   19500
aatgatgaca agacgttccg cagttattta gaggaagtga aggaatcgac gctgagcgcc   19560
ttcgagcatc aggattatcc gttcgataag ctggtggagc agttagagga tgcttgggtt   19620
ccaggccgta atccggtatt cgacacaatg ttcgtcctgc agaacgcaaa agcgcgcacg   19680
atcaacctgg gagaattggc cttcgagcct ctaattccat cacatacggt tgcgaaattc   19740
gatttaacct tggaaatggc tatcgaagac ggcatgctga gcgggcagtt tgaatattgc   19800
acaaagctgt tttccgccaa catgattgcg aatttcgcag aagacttctt ggaaattcta   19860
tctcaagctt gcgagcagcc tgacatccgc ttggaggata ttcaactgag cggcagtgct   19920
tatcaagagg aagaattgga agaagaaatt gactttgcat tctaa                  19965

<210> SEQ ID NO 6
<211> LENGTH: 19287
<212> TYPE: DNA
<213> ORGANISM: Paenibacillus strain A6-6i

<400> SEQUENCE: 6
atggcttttg ataaagaaat cgaattttgg aaagcgaaac tcgatactga agatacgcct     60
acgactttgc cctacacgag cactccaagc agtgaagcgg cacgacatta ttccgttttct   120 gttacgatgc ctgctgaaat tcggaacga attattcgca tgtctaaggg ctcgcatcaa    180
gcagccttca tgatttttact aggtggcatc caatgcttgc tgcacaaata cacgagcgag   240
aatcgcatcg tcatcggcat gcctattgtg cgaaaagcag gggagaagag acttcccatc   300
aatcaagtcg tcctattgaa ggagaatgtc aatgaagagc tcacgttcaa atccttgctt   360
acttcactga acaatccctt tacagaagcg attcgacatc agcatatccc cttccggctc   420
```

```
ataactgagc agatgaatgt acaagaaaag aatggcttgc ctgtcatcaa tacgatggca      480
gctctgaaga atatacatac cgttaacttt attccaacgg ttgttgcaga tgtattgttc      540
caatttgagt tcgaagctga gaacctcctt ttgagcgttg tatataacga acgtgtctat      600
gactcggtat ttatatcgca aatcattgag catttgcagc gcgtgctgag catcgtattg      660
cttgagccaa atacgaattt gggggatctt cgcttacttt cggatgagga acatcgctg       720 ctcctgcacg gatttaatac aacggctgca gagtatccac gtgaccgaac aattcatgaa      780
ctcttcacgg aacaagcacg tcgcacgccg gatgctgttg cggcagttta tgggcagcaa      840
cagttaacat atgccgagct aaatggaagg gcgaacaggc tggcgcgtac gttacagaac      900
gctggcgttc gatccgatca gctcgttggc atcatggccg aacggtcgct cgaaatgatt      960
gtaggcttgc tagccatcat gaaggctggt ggggcctatg ttccaatcga ccctgaatat     1020
ccgcaggagc gcattcgtta tgctcgagag gattcgggag cgcagacgct actgcttcaa     1080
gaccatcttc gcgagcgtgt cacctatgag ggcacgatcg tggatatgaa tagcgaacat     1140
aattatcatg acgacgggac ggaacttgcc tctgtgtccg attcaagcaa cttggcatat     1200
gtcatctata catcgggcac gacaggcaat ccgaaagggg tcatgattga acatagaagc     1260
gcagtcaatg cgctgttgtg gagaattcgg acatacgggc tttcttcctc cgaccggatt     1320
ctgcaattgt tttcattttc cttttgacggc ttcgtcatga gcgcgttctg ctcattattg     1380
tccggcgcag gtttattttt acttaaggaa gaggacgcga aggatccgct cgccttgcat     1440
ggcgctatca gccaatcagg aatcacgcac ttcatttgcg taccaaatct atacggagcg     1500
ctgctcaatg tgatgcaggc cgagtctgtg tctacgctgc gtacagtgac attggctggc     1560
gagagtgtca gcagtgcatt agtagctaga agcaaggagc agcttcctaa tgtgaagctg     1620
tttaatgaat atggtccaac agagaacagc gtcgtggcga cctgcgcaat tggcctcgag     1680
aaggatcaac ccatcaccat tggtacaccg atctctaatg cgagtgtgct cattttgaat     1740
acttctgggg agttgcagcc gttacatgtg ccgggcgaat tatgcatagc cggtgagggg     1800
ctggcgagag gttacttgaa ccgtcccgaa ttaacggaag agaaatttgc cgctcatcca     1860
tttgtgccag gagaacgcat ttaccatact ggtgattccg ccagatggct gccgaacggc     1920
acaattgaat atttgggacg gattgatcac caagtcaaaa tccgtggatt ccgtatcgag     1980
ctgggcgaaa tcgagtcgag cttgaagaag atagcgggtg tgcgagaggt catcgtggat     2040
gctaggccgg acggtaatgg ccaacatatg ctgtgtgcgt acatggtagc tgacgctgag     2100
cttactgtga cggaattaag ggaggcgttg tcttccaatc tgccggatta catgattcct     2160
tctcactttg tgcaaatgga acagctgcca cttacgccaa gcggcaagct ggatcgcaag     2220
tcattgcccg atccccaagc taacatggct attggcacgg agtatattgc gcctcgtact     2280
ccacttgaag cacgacttgc gcaaatctgg caggagtcgc ttggtgtgga aagggtcggc     2340
atcaaggata atttcttcgc ccttggcgga cactcgctgc gggcagctac attggcaagc     2400
aagcttcaca aggagttgaa cgtcaatgtg ccgcttcggg atttgttccg aaatccgacg     2460
atcgaagaat tggctttgct tatgatggg atggagcagc aggagttcag cgcgattgaa      2520
cgggtgaagg aaagcgagta ttattcggta tcttcagcgc aaaagaggct gtatgtcctg     2580
cagcagctcg aaggtgcgga acagagttac aatatgccgg gtgccatgct gctggaggga     2640
ctgctggata gagaacgcct cgaagcctca ttccgcaagc tgattgcacg acatgagaca     2700
ctgcgtaccg gattcgagct gatggacgga gaaccggtgc agaaggtgta tcaggatgta     2760
```

```
agctttgcca ttgaatatat gcagacaagc gaggcggaag cggcgcagaa agcccgcgaa    2820
tttatccgag cgttcgactt gatgactccg ccgttgatga gggttggctt aattgaaatg    2880
gcaccggatc gacatgtgct cctctatgac atgcaccata tcatttctga cggtgcatct    2940
atgggagtcg tagtagagga gttcgctcgg ttgtacgggg gtgaggagct gccaccgctg    3000
cgtattcaat ataaagactt tgccgcttgg cagcagtcgg aagcacagca gaagcgttcg    3060
aagcagcagg agacctactg gttgcaaaca tttggcggag aactgcctgt acttgagctt    3120
ccaacggatt acgcgcgtcc agccattcag agctacgaag gggagaccta tgaatttacg    3180
gtcgattcgg atataagtac ggcattgcaa cgcctcgcag cggatagcgg aacgacgtta    3240
tacatggttc tgctcgcagc ttacacggtg ctgctgcata agtacacggg tcaggaagat    3300
attgtcgtcg gcacgacgaa cgcagggaga atgcacgacg atttgcagcc gcttattggt    3360
atgttcgtca atacgctcgc aattcgcaat tatccggctg gagaatcgac gtttcgtgct    3420
tatttggaac aagtgaagga gcaggcgtta gctgcatttg aacatcagga gtacccattc    3480
gaagagcttg ttgagaagct tcatgttaca agagacatga gccgcaaccc gctgttcgat    3540
acgatgttct ccctgcaaaa tatggagaac aaggattttg aacttccagg actccaattg    3600
aagccgtatg cttcgaaaca ccaaatatcc aagttcgatc tcagcttgga cgttgcggaa    3660
ggagcggatg ggctcgcttg cagcttggag tatgcttcgt ccttatacag acaagacaca    3720
atcgtaagaa tggcggatca ttatcgacag ctgcttcatt caattgcaca gtcgcctgag    3780
gcgcaaatct ccgtgctcgg gatgttgacg ccgggtgagc aagagcaaat tcgattcaag    3840
ttcaatcatg atccgtcaga aatggagcag aagcacacgg ttcatcaact ctttgaggag    3900
caggccgctc ttacaccgga acgaactgcg gtcgtgcatg agaatgaaca actgtcgtat    3960
cgggagttga acgagagggc gaaccgtctg gcacgtacgc ttcgtcaaca cggcgtgcag    4020
ccggagcagc ttgtcggcat cttggcagac cgttcgctgg acatgatcgt gggcattatg    4080
gcgatcttga aggcaggcgg cgcttacgtt ccaattgatc cgaaatatcc ggaagaacgt    4140
atccgttaca tgctggagga ttccaaggca aacgtattgg tgacgcagag ccatttacag    4200
tctctctcat cgtttgacgg tacatgggtt ctgcttgatg aggagtcatc ctatgctgag    4260
gatgctgcca atcttgtgtc catcactgaa ccacaacact tggcttacgt catttataca    4320
tcgggcacga cggacagcc gaagggtgcc atgatcgagc acagacaact gacagttatg    4380
gcgaaggctt gggagcgtga atatcgtctg cgcgaagaga gtattcgctg gatgcaatgg    4440
gcaagcttct cgttcgacgt attttcaggc gacttgattc gtgcgctgct gcatggcgga    4500
gagctggttc tttgcccaga gcacgcacgt gcgaatccgg ctgaaatcta cgaattgatc    4560
cggaagcatc gtcttcatat gttcgactgc acaccgtcta tcgtcattcc gctcatggaa    4620
tatgtgtatg agaacaagct ggatattagc agcttgaagc ttgtcgccgt tgggtcggac    4680
tattgcccgc cggatgagtt tcagaagatg cttgatcgat ttggttcgca gttccgcatc    4740
attaatagct acggcgtaac ggagacgtgc atcgatgcca gctattatga accaacgact    4800
ccaactgttc caagagcgct gccgattgga aaaccattgc cgggtgtaac gatgtacatt    4860
atggacggac agcgttcctt gctaccggtt ggtgtcatcg gtgagctcta tcggcggt     4920 ccttgcgttg gccgtgggta ttggaatcgc tcggaaatga cgaacgagaa attcgttgaa    4980
gatccattcc ttcaggatta ccggatgtac cgcacagggg atctggctcg ctggatgccg    5040
gatggcaata tcgaatattt aggccgtatc gaccatcaag cgaaaatacg cggttaccgt    5100
attgagatcg gcgaagtcga gtccaagctt ctcaaggtag agacagttcg tgagagtgtc    5160
```

```
atcgtagcgc gtcaggatcc gaacgggaca aaagcattat gcgcttattt cgttgcggat    5220
cgcaatctga cggtgagtga actgagaagc gcattggccg atgaattgcc ggcatatatg    5280
attccatcct attttgttca actggatcgt ctgccgctca caccgaatgg aaaagttgat    5340
cgcaaggcgc tgcctgcccc ggaagcgggt gcgcacacgg ggattgaata cgtggcgcca    5400
cgcacggaag aggagttagc actggcgaat gtatggcaaa ccgtccttgg tattgaacga    5460
gtcggtgtgc aggatcattt cttcgagctt ggaggcgact caattaagtc tatccaagtc    5520
gcttcccgat tgcagcaagc aggctataag cttgaaattc gcgatctgtt caagtaccca    5580
acgattgctc aactgggatc ccacttgcag agggcaagca aggttgcaga tcagggcgaa    5640
gtatcaggtg acgtgccgct acaccgatt cttggatggt ttttcgaaca gcagtttgcc    5700
gacgcgcatc actataacca atcgatcatg ctgtaccgga gagaaggctt tgacgaggcg    5760
gcaatccgca atgtacttca ggcagtaacg gaacatcacg atgcgctgcg catcgtattc    5820
cgacggaacg atcaaggcga ttatacagct tggaaccgcg caatcgaaga aggagaattg    5880
ttccatctgg aagtgctgaa ccttactggc tcagcatcag gtgatcatga gcagaatgta    5940
cggcagatca ttgaagccaa ggctagtgag attcagcgca gcttcgacct gcacgatggg    6000
ccgttggcaa gagccggatt gttccgtacc gatgaggggg atcatcttct gcttgtcatg    6060
caccatggcg ttgttgacgg tgtgtcctgg cgcatcctgc tggaggatat cgctgctgga    6120
tatgaacaag cgttgaaggg agagcctgtt cggctgcctg ccaagacgga cagcttccgc    6180
acatgggcga atcatctcgc gtcatatgcg cgaagcgaag ccatgataga ggaacaagtc    6240
ttctgggaac aggcagaagc gaatgcaacg agtattttgc ctttgccgaa ggatttcgaa    6300
gcggagacat ccttgcagca ggatagcgag tcggtcgtag tggaatggag ccggaggag    6360 acggatatgc tgctgaagca tgttcaccgg gcttataaca cggacatgaa cgacattctg    6420
ctcgcggcgc tcggcatggc tatacagcaa tggtgtggac atgagaaagc cctagttaca    6480
cttgaaggac acggccgcga aaatatcatg ccggagcttg atatttcacg cactgtgggg    6540
tggttcacga gtgaatatcc attcctgctc gagagcgatc cgaacaagag tttgtcctat    6600
cgaatcaaac gaatgaagga aaatttgcga cgtattccga ataaaggcat cggttatggc    6660
attcatcgat atttatcgga ctcaggtatg tctggtacgg aaaatgtatc acgatcagaa    6720
gcatcagctc agccagaaat cagcttcaac tatttgggac aattcgatca ggatttgcag    6780
aacaatgaga tggaagtatc tccatattcg ggcggcgcag agataagcgt tcgtcaggct    6840
cgtaacacca cgcttgattt taacgggatg atatcggctg gggttcttgc attggaagtg    6900
agctacagca gcaagcaata ccgccgcgat acgatcgacc ggctggcagc attgctgaag    6960
ggaagtttgc aggagatcgt tgcccactgc gcatcaaaag ataagccaga attgacacca    7020
agtgacgtat tggttaacgg gcttggtatt gaggatctgg agcgtattgc ggagcagacg    7080
agggatctcg gggacatcga gaacatttat gcactgacgc cgatgcagaa gggaatgtgg    7140
ttccataacg cgatggacgg tcaagcgggg gcttattttg aacagactcg ctttacgatt    7200
caaggagagc ttgacgttca gctattcgca agcagcctag acgtactcgc gacacgacat    7260
gcggtgcttc gcaccaattt cttcagcggc tggaacggag aattgctgca aattgtatac    7320
cggaacaaga atctggaatt tagttacgag gatctaacgg aattgccgga ggatgagaag    7380
caggatcgag ttgaagcgat ggcgcaagct gataagctcc gtggattcga tctggagcac    7440
gatgcgctga tgcgggtgtc cgtgttgcgg acgaacgtga actgcagtca tgtcatttgg    7500
```

```
agctctcatc atattctgat ggacggctgg tgcttgccgc agctcacaca agaatggcta      7560
gagacgtatt ccgattccgt aaatggacgg tctagcagcc gatcgggagc atcgccatac      7620
agcctctata ttgaatggct gtacaagcag gattacacag ctgcatccca gtattggagt      7680
gactatctgg cggattacga tcagcaaacg gttcttccgc agaagaaatc gagcgggcgc      7740
agcgatgtat atattgctga taatctcgta tttgaactgg gcgaggcttt aactgcgaag      7800
atgcatcggt tcgcaaagca gcatcagctg acgctgaaca cgctaatgca ggcggcatgg      7860
ggcattattt tgcaaaagta caacggtacc ggcgacgctg tattcggcgg agtcgtatca      7920
ggtagaccgg cggaaatccc aggcattgaa tccatgattg gactattcat taacaccatt      7980
ccgattcgtg ttgcgtgcga agcggatgac agatttgccg acgttatgaa gcggcttcag      8040
gagaaggcgc tggagtcagg gcggtatgat tattatccgc tgtatgacat acaggcgctt      8100
agcacgcaca agcaggattt gatcaatcat attttggtgt tcgaaaatta cccgatggaa      8160
gagcaaatgg aacaggctgg tgatgagcgg ggacaattga acattaccga tgtgcgggtg      8220
gccgaacaga cgagctatga tttcaatctc gtcgtgatgc caggcgagga catgatgatt      8280
cgcctcgagt acaatgccgt catgtatgat cgagcagata tggagagagt gcggcagcat      8340
ctgattcatg tccttgagca ggtaacagct gatccggcca ttgctgtgaa agatgtccgt      8400
ctggcgaccg acgacgagaa ggcagagctt ctgacggcat tcaatgatac ggaaatcgaa      8460
tatcctcgcg aacagatgat tcatcggatg ttcgaggagc aggttcagcg gacgccggat      8520
gcgacggcgg tgttgtacgg agcagctgcg atgacctacc gggagatgaa tgaacgtgcc      8580
aatcagttgg cgcggacact gcgagcagca ggcgtcgttc cggatcaaat cgtcggtatt      8640
atggcggaac gatcgctaga gctaatggtt ggcatcatgg ggatattgaa agctggcggc      8700
gcctatgtgc cgatcgctcc ggattatccc gaagagcgca tccgatatat gctggacgat      8760
tccgaggctc aagtattgat tgttcaaggc agcgcgggtg aagcgattga ttttgcaggc      8820
cgcgtaatta atctggatga tgctgactcg tacgatcagg acagctcgaa cctagagatg      8880
gtgaacaaac caaccgatat cgcctatatc atctatacat caggtacgac cggacgtccg      8940
aaaggggtta tggtcgagca tacatcagtc atcaaccgct tgttgtggat gcagaagcgg      9000
tacccgattg gcgcggatga cacaattatg cagaagacgg cgatcacgtt cgacgtatcc      9060
gtttgggagc tgttctggtg ggcatttgtc ggctcgaaag tgcttatgct tccagttggc      9120
ggagagaaga atccggcagc aatcgttgag gcgatcgaac aatacgaaat tacgacaatg      9180
cacttcgtac catctatgct gcatgccttc ctcgagcata ttgagcagct gcctgaagcg      9240
gagcgtgagc gcctgtctcc gctgcagcag gtgttcacga gcggagaggc actgttggca      9300
tcgcaggtag agcgattcca tcagtatgtt gtacctgcca gcggagcacg actcatcaat      9360
ctgtacggtc cgacagaggc gacggtggat gtcacgtact tcgactgcga accaggccaa      9420
acttatgtga gcgtgccgat tggcaagccg attgacaata cacgcatcta tattgtgaac      9480
gagcactttc aagtacagcc gatcggcgta gcggcgaac tgtgtatcgc gggcgtcgga      9540
ttggcgcgcg gatactggaa ccgtccagaa ctgacagaag agaaattcgt attggtgcct      9600
tctgtgggtg aacggatgta ccgaacgggc gatctcgcgc ggtggctgcc agacggcaac      9660
atcgaatatt taggacggat tgatcatcag gtgaaaattc gcggttaccg aattgagctt      9720
ggcgagctgg agactgcgct gctgaatatt gacgcggttc gggagacggt tgtcgttgcg      9780
agggaagaca gagcggaca gaagtcactt tgcgcctact atgtagcaga cggagaagca      9840
acaataagtg acctgcgagc cgcacttgcc gccgagctgc cgagctacat gattccatca      9900
```

```
tacttcgtaa ggctggagca gatgccgctg gcgccgaacg gcaagctgga tcgcaaagct   9960
ttgccggctc cagagagaag ccttcaagtt gaatcggaat atgttgcgcc gcgcacggaa  10020
gcggaacaga tgctgacaac cgtatggcaa gccgtacttg gcatcgaacg tgttgggata  10080
accgatcact tcttcgagct tggcggagat tccatcaagt ccattcaagt ggcagcaaga  10140
atgcagcagg cgggcttcaa gcttgaaatt cgcgacttgt tcaaatacccc gacggttaca  10200
cagttggttc catacatgca gccgattaat cgaacggctg atcagggaga agtcgtcggt  10260
gaggtgccga tgacaccgat tctgcattgg ttcgagcatc agcagtttgc gaatccgcat  10320
catttcaatc agtcggtaat gttgtatcgc aaggatggct tgtcgcaga tgcagtgtgc  10380
aaggcgcttc ataagctggt tgaacatcac gatgcgcttc gtattgtaat tcagagaacg  10440
gaacaaggag aatattcgct ctggaaccga tccctagtag aaggcgaact cttcagtatg  10500
gaagagatcg atttaacgga tcagtcggat ttcgctgcag cgattgaagc ggaagcaaac  10560
cacattcaag gcagtattga tctacaggca gggcctctgg tcaaggcagg cttattccac  10620
ggcagtgacg gtgatcactt gctgcttgtt atccaccacg cagtcatcga tggcgtgtct  10680
tggagaatat tgcttgagga tctcgcatca ggctatgaac aggcgctgaa tcaacgccaa  10740
gtacgtctgc cgatgaagac agacagcttc cgtacatggg cggaacagct agtagagtat  10800
gcgaatagtc cagcgatgga taaggaatct gcttattggc tcggcgtcgc gcagacggaa  10860
gtggccgccc tgcctaaaga cagcgagtgc acggtttcct tgcagcgcga cagtgaatcc  10920
gtcgtgctcg agtggaatcg ggaagataca gaacggcttc tgaagcatgt tcaccgtgct  10980
tacaacaccg aaatggatga tattctgctc acagcgcttg gcagggcact catgaagtgg  11040
cgcggcatcg agcgcatact ggttacgctg gaagggcatg gtcgcgagtc cattatacaa  11100
ggcatggata ttacgcggac ggttggctgg tttacgaccg aatatccgtt tgagctcggg  11160
atggaagcga acgacagtct tggatctcag atcaagaagg taaaagagga tttgcgccgc  11220
attccgaaca aggaatcgg gtacggtctg ttccggtatt tatccaattc gggcaaacag  11280
gcttggaatg atgcgccaac gacacaaatt cgttacaact acctgggaca gttcgatgcg  11340
gacttgagca ataacgaaat gagtgtatct ccatatgcaa gcggttcgga gattagcgat  11400
gagcaggagc gcaagtatcc gctcgatatt aacggcgtga tcgcagaagg ccaattgaca  11460
ctgggattaa gttacagcgt caaggagtat cgcaaagaga cgatggagga attgggcgat  11520
ttccttacag aatcactgaa ggaaattatc gcacactgcg aatcacagga acggacgcaa  11580
ttgacgccaa gtgatgtctt gtttaaggga cttagcttgg agtggctgga tcggatatct  11640
tcgcaaatgc agcatatcgg cgagatcgag aatgtatatg cattgacgcc gatgcagaag  11700
ggaatgtggt tccacagcgc gatggacagt ctgacggggg cgtaccatga gcagacgatg  11760
ttcacattgg aaggttcgct tgatgtggaa ctgttctcca gcagtctgaa cgaattggcg  11820
aagcggcacg ctgtgttgcg aacgaacttc attagcggcc ctcaaggcga accgtacaa  11880
gtcgtattcc ggaacaaacc aatcggattc tcgttccagg atgtgcgcgc tttgaatgaa  11940
gaggagcagc aatccttcat taaggaagcg gtcagcagtg accaactgct tggcttcgat  12000
ctcgcacaag gtgccctgat gcgcgtatcg gctatccgta caggggaatt gagctgccgt  12060
gtactgtgga gctctcacca tatcttgatg gacggctggt gcctgccaca gctgatgcaa  12120
gagctgttcg atacgtatgc cgccttgctg cagaagaagt cgccggatag aacagcggtt  12180
ccagcttaca gccaatacat tgaatggcta gggcagcagg acgaggaggc ggccgggact  12240
```

```
tattggtctg catacttgga tgattacgat caggtaacag agatcccgca agaatcatcg    12300
gcgggaatcg atagcgaacc atataaggct gaaaaatgga gtcgtgaatt ggatgctggc    12360
ttgagcgcat ccattagccg gacggcgaga cagcatcagg ttacgcttaa tactttactg    12420
caagcggcat ggggcgttat tttgcaaaaa tacaatggca caaatgatgt tgttttcggc    12480
agcgtcgtat caggcagacc agcagaggtg ccaggcattg agacgatgat cggcttattc    12540
attaatacga ttccgatccg cgtcaagtgc gagggaagca ccagctttgc ggaactgatg    12600
gggctgcttc aagaacaagc gctggagtcc ggcaagtacg attattatcc gctgtatgag    12660
atacaatctc gcagtgcgct gaagcagaat gcgatcagac aaattatggt gttcgagaac    12720
tacccgatgg acgaacagct agagcaggcg ggcggtgacg agcacggtat gccatcctta    12780
actgatgtag cggtggagga acagaccaat tacgacttca acttgatcgt tgtaccggga    12840
gaacaaatct ctattcggtt tgattacaat gctaaccgct tcgtacaagc agacatggaa    12900
cggttgatgg ggcatttgaa caatattttg gagcagatcg tagacaatcc acggattgct    12960
gtagaagatc tggagctcgc gacggaagcc gagaagtcgg aagtagtcca atcattcaac    13020
gatacattta cgaattaccc tcgagacatg atgctgcatc gcttattcga ggaacaagcc    13080
gaacgacatc ctgatgcagt agccatctcc ttccgagatt tccagatgac gtatcgtgat    13140
ttgaacgatc gggtgaaccg attggcacgt acactgcggg cagtcggagt tggaacggat    13200
aagctggtag gcctcatgtc tgaacgttcg ccggatatga ttattggtat tctggcaatc    13260
ttgaaggcag gaggcgggta tgtgccaatc gatccggaat atccgggaga acggattcgg    13320
tacatgcttg aagattccgg tgcgcgaatc atgctggcac agcagcattt aacggggaaa    13380
attccagtca tggacgcatc accacttgat gcaattatca atcttgacac cgaaacatcc    13440
tatgacagca acgttcgaa tcttgaggcg aacacagacg caagcagcga gaacttagcc    13500
tgtgtaatct acacatccgg cacgacgggt aagccgaagg ggaacttgac gacgcaccgc    13560
aatattgtac gtgtggtgag agaaaccgag tatatcgaca tcacaaatca tgacaacgtg    13620
ctgcaaatgt ccagctatgc atttgacggg tcgaccttcg acatctatgg tgcactgctg    13680 aacgggggcca agcttgttct tgtaccacat gagacgcttc tggaagtacg gcaattggct    13740
gagttgatcg tacaagagaa gatttcggtt atgttcatca cgacggcgta cttcaacgta    13800
ctggttgatg tccaggcttc ctgcttgagc aatattcggg ctatcttatt cggtggcgaa    13860
cgggtatctg tcagccacgt tcgcaaggcg ctcaatcatg tcgcgccagg tgcactcaag    13920
catgtatacg gcccgacgga gagtaccgta ttcgcgactt gccacgatgt gcacgaagtc    13980
acggagaatg cggtgacggt accgattgga cgtccgatca gcaatacgtc aatctatatc    14040
gttgatgcga acaataagct gcagccagta ggcgttgccg gcgagttgtg cgtggcaggt    14100
gatggattgg cacgaggata tttgaatcgt ccagacttga cggcagagaa gttcgtcgat    14160
tccccgtacg tccagggaga gcggatgtac cgcacgggag acttggcgaa atggcttcct    14220
gacggttcca ttgaatatgt tggccgaatc gaccaacagg tgaaaattcg cggatatcgg    14280
attgagctag agaaatcga ggcgcagctg ctgaatgtag aggatgtgca ggaagcggtc    14340
gtcgtcgcac gagacactga cacaggcgag aagcagctat gcgcctacta tgtagcgatg    14400
cgtccgcttg aggcgaatca tttgcgcgaa gtgatgggtc aagctatgcc aagttatatg    14460
cttccagcgc actttattca gctggaacag cttccactca caccgaacgg caaggtagac    14520
cgcaaggcgc tgccggctcc ggaagaagga cggagcggag agactttcgt tacgccgcgg    14580
acgccgcttg aagcacagct tgttcaaatt tggcaggatg tgctcggtat tagcagtata    14640
```

```
agcgtgacgg atcatttctt cgagttgggt ggtcattccc tgaaggcgac gctgctcgta   14700
aacagactgc atcaggagct taatatcgag ttgccgttga aagacgtatt tcaatatccg   14760
acgcttgaag tgatggcgaa gcgactcagc aatgcggagg gaagcaggca tgtgagtatc   14820
ccggtggcgg ctccaagcca gcattatccg gtgtcttcgg ctcaaaaacg cttgtatatt   14880
cttcatcagc ttgaagggc ggaactgagt tacaacatgc cgaacatgat gctgcttgag   14940
ggagctgtgg atcttgggcg attggaagaa gccttcaaga gactgattga gcgccatgaa   15000
acgctgcgca ctggatttga gattgtgaac ggcgagcctg tgcaacggat ttacccggaa   15060
gtagacttcg caatcgagca tgtgctcgcc agcgaggaag tgcttcgaa gcttatgcag    15120 cagtttgtgc gttccttcca attggagaaa ccgcctctgc tgcgaatcgg aattatcgaa   15180
ttgtccgaag aacgttccat tctcatgttc gatatgcatc atatcatctc agacggtacg   15240
tcgatgggca ttctcatcaa tgagtttgtc cacttgtaca gtggggcaga gcttacgccg   15300
ctgcggattc aatataagga ttacgccgta tggcagcaat cggatactca gcagaaggca   15360
atgaagctgc aagaaggata ttggctgaag gtgctgggtg gagagcttcc ggtgctggaa   15420
atgccgacgg actccattcg tccgacaacg caaagcttcc gcggagattt gctgcagttc   15480
gatctagatc cagtaagaag tgcggggctg cggagaattg cagcggagaa cggagccaca   15540
atgtacatgt gcttcttgc gctgtacaag acgatgctgc acaagtattc cgctcaagag   15600
gacattatcg taggtacgcc gatcgcaggc cggaaccatg gagacttaca gccgcttctc   15660
ggtatgttcg tcaatacgct ggccattcga agctatccgg ctgccagcaa gactttctta   15720
tcctatttgg atgaaataaa agaaacaacg cttggcgcct cgagaatca gaattatcca     15780 ttcgaagcat tggtcgaaca ggtgcaagtg atgcgcgata tgagccgcaa tccggtattt   15840
gatacgatgt ttatttttgca aaatgcggat caaggtgaaa tgaagatcga tggggtacga   15900
ctccagtcgg tgccgaatga acacaccgta tccaagttcg atttgacctt ccaagcggaa   15960
gaggatgaag cggaaatcgt gtgcagcatt gaatacgcaa cagatttatt caagcgaggc   16020
acgattgagc gaatggcaag acatttcgaa caattagtcg atgcggtgct ggataacccg   16080
caagcaagtc tgtctaactt gagcatggta accaatgagg aaaaggcgct gcttcaggat   16140
aagttcaatg atacggatat ggcgcatcca agcgacaaga cggttcatga actgttcgcg   16200
gaacaggtgg agcggacacc agatgctgtt gctgtcgtct ctggctgcga gcaattaagc   16260
tacggagagc tcaaccggaa ggcgaatcag ctagcgtgga agctgcgtga gtatggggtg   16320
accgcagagc agcctgtcgg gattattgtc gagcgaacgc tggatacagt cgtcgcagtg   16380
atggccgtac tcaaagcatc gggcacattc gtaccgatcg atcccgagta tcctgagacg   16440
cgtattcgct atatgctggc agacagcggg gctaagctgg tgttggcgca atcggagctg   16500
ccggggatca ttcctgatga cgtccgccta attgatgtac gcgatgagtc cctgtaccaa   16560
ggcgacggag ctgacgtacc gaatggcagc aaaccgtcca acctgctcta tatcatctac   16620
acatccggaa cgacgggcaa tccgaaaggg gtcatgctgg agcacggcaa catggtcaac   16680
ctgctgcatt atcagcagaa aggcacgaac attccgatgc cttcgcggat cttgcaatat   16740
gcgtccggca gcttcgatgt atgctatcag gaaatgttct ctgcgctctt gttcggcgga   16800
agcttgtata tggtcgacaa tgagatgcgc aaggatccgg tgcgcttgtt ccaggaaatc   16860
gaaaagcatg aaatcgacgt gttgttcatt ccagtgcgt tcctgaaatt catcttcgcc    16920
gagccagagt gggccgaagc attcccgcgc tgcgttcgcc atatcattac ggcgggcgag   16980
```

```
cagttggtcg tgacaccgca agtgcaggcg tgcttaaagc gactcgatat ctgcctgcac   17040
aaccattacg ggccatcaga gactcatgtc gtgacgacct acacgatgac gccggaaatt   17100
atcgaggttg gtctgccgcc aattggcaag ccaattgcga acacgagcat ttacatcgtg   17160
aacgacagct tcgagctgca gccaatcggc gtgaagggcg agctcttcgt atccggggca   17220
tgtgtcggac gcgggtactg gggaagaacg gacttgacgg aggagaagtt cctagataac   17280
ccgttcgtcc ctggtgagcg gctatacaag acaggtgacg tagcgcgctg gcttccagac   17340
ggcagcatcg attatgtggg ccgaagcgac catcaggtga aaatccgggg cttccgcatt   17400
gagctgggcg aggtggaatc gcagctcttg catgtaccgg cggtacagga ggcgaccgtg   17460
gtggcactgg aagatcatgc gggccagaag cagctgtgcg cgtatttcac agcagagcgc   17520
tcgctcacgg cgggcgagct gcgggcagta ttgtcgcagg agctgccagg ctacatgatt   17580
ccgtcctact tcgtacagtt ggagcggctg ccgctgacgc cgaatgggaa gatcgatcgg   17640
agagcgctgc cgaagccaga aggcggcatt gagactggaa cggagtatgt cgcgccgcgt   17700
acagatacgg aagcaagact tgcacgcatt tggcaggatg tattgggatt accgagcgta   17760
ggcgtgaagg acaacttctt cgagctgggc ggccactcgc tgcgggcaac gacgctggtg   17820
agcaggctgt acaaggaaat gaacgtcaac ttcccgttaa gaggtgtgtt ccgtcatccg   17880
actatcgagg agatgtctca agcaatctcg caaatggaga cctcatggta tacagccatt   17940
ccgattgccg aggagcaaga atactacccg ttatcttcgg ctcagttgcg actctatatc   18000
atgagccagc tggaaggaag cgagctcagc tacaatatgc ctggcatgct ggtgcttgaa   18060
ggacagctga atcgagatca attccagaca gcattttga agctcatcgc tcgtcacgag   18120
actttacgta ctggctttga gatggtagac ggcgagccga tgcagcgcat ccatcgcaat   18180
acggaattcg ctattgacta cagacaggta tccgaggacg aagttccgga gatgattgga   18240 caattatcc gacagttcga cctggagcat ccgccattat tgcgggtcgg gttgttcgaa   18300
gttgggcagg atcggcatat tctcgtctt tgatatgcacc atatcatttc tgacggtgtc   18360
tcaatgagca atttagttga tgaatttact cgattgtatg cgaatgaaga acggcctccg   18420
ctgcgtatcc agtacaaaga ttatgcggta tggcagcagg cgagagagaa tctcgaacgg   18480
aggaagcgcc aagaagacta ttggatgagt gtgctgcaag gcgatcttcc aaacgcagag   18540
ttgccgatgg attatgatag aacgcggtt cgcagcttcg atggggagca gatcgaattc   18600
gaaattaacc cggttgtgac gggacagttg aaccaacttg cttctaatca tgagtgcacg   18660
ctgtacatgt tcttaatgtc cgcctatcag attctgttat ccaaatattg cggtcaggat   18720
gacattattg ttggtactcc tgttgcgggt cgcaatcatg ccgatttgga gccgttgatc   18780
ggtatgttcg tcaatacct cgcgattcgt aaccgtccgc agggcgataa aacgttccaa   18840
tcgttcttgg cagaggtgaa agagtcaaca ttagggggcat tcgaacatca ggagtatcca   18900
ttcgaggaac tgattgacct cttgaagctg cagtgggaga caagccgcaa tccattgttc   18960
gatacggtgt tcgtcctcca gaatacggag gagcgtgaag ccggaatcgg tggattgacg   19020
atatcacctt acgtgacaga tgactcggtc agcgcgaagt tcgatctgac gctatctgta   19080
tcggaagaag acgatgggat gaagggaagc ttcctgtatg cttccaagct gttcaaagca   19140
gctggcatac acagaatgat gagagattac ttgtcaatcc tgtcccaagt atgcgagaac   19200
cctcgcatcc gcattcaaga tatttcgata agtggacagc agacacagga aaagagcaag   19260
atcgacacga ttgagttcgc gttctaa                                      19287
```

<210> SEQ ID NO 7
<211> LENGTH: 9450
<212> TYPE: DNA
<213> ORGANISM: Paenibacillus strain A6-6i

<400> SEQUENCE: 7

| | | | | | |
|---|---|---|---|---|---|
| atgaagtcgg | tatatgagaa | agaagaagcc | tattggaatg | gaatgtttga | ttcggatgac | 60 |
| agcatgagca | tattgccata | ttgcagtaca | cacggaagag | aagcgaacgc | ggatacgaat | 120 |
| gccgccaaag | tgtctatgat | ccgtgcactc | caacagatc | tgtcagacag | aatgaacacc | 180 |
| cttgcgaacg | gttcggatgt | tgccctgtac | atgattggat | tggcaggggt | cacttgcttg | 240 |
| ctccaccatt | atacgaaccg | agaaaatgtg | cttgtaggca | tgccgacaat | agatgaatcg | 300 |
| gaagatgact | catcaccctcg | tgacgtactc | ataatgaaga | cgaatttgac | acgcggaagc | 360 |
| agcttccgtt | ccgtattggg | gtcaatcaag | acagccgtcg | gaggagcatt | ggagcatcgt | 420 |
| catcttccgt | ttcggaagat | ggtacacaac | ctaaacctgg | agatggacac | gaacggactt | 480 |
| ccggtgatga | atacggtagt | gtcttttca | gctatacata | ccgcttctat | cgaccttagc | 540 |
| gtcagctccg | acgtcatatt | ccgattcgat | gcgaaggacg | atggccttca | tttggaggtg | 600 |
| ctttatgatg | aaagccgcta | tgatgcctcc | tatattgcca | ctctattcga | acattttttc | 660 |
| cgactgcttc | attttgtgtt | attccagccg | gatcagccta | tcggcaatac | cgagttattg | 720 |
| tccgctgagg | agaagcatcg | cttgcttcat | gaatttaacg | atgtgtggac | ggatttccct | 780 |
| cgtcaagcaa | cgctatatca | gttcattgag | gaacatgcgg | agcgacagcc | agatgcaatc | 840 |
| gcggtttctt | atgaagatac | caagctgacg | tatcgtgagc | tgaacgcaag | ggcgaatcga | 900 |
| cttgccagaa | cacttagatc | tgaaggtgtg | cagacagaag | cactagttgg | gctcatggct | 960 |
| gaaagatcga | tcgacatgat | tgttgggatg | cttgccgttt | tgaaggcggg | aggcggctac | 1020 |
| gtcgcgattg | atccggagta | tccggaggag | cgcgttcgct | acatgctgga | agattcgggt | 1080 |
| gctcgtgtca | ttctggttca | gcagcatttg | cagaatcgtg | tgccaaatac | ggaatcagca | 1140 |
| gctagactcc | tcacacttga | cgatgagcag | tcttatcatg | aggatgcttc | gaatttggaa | 1200 |
| tcgaggagta | cagctgtaga | tttggcttgc | gtcatctaca | cttcggggac | aacgggtaat | 1260 |
| cccaaaggta | acctgacgac | acaccgcaat | atcgtacgca | tcgtgaagaa | taccaactat | 1320 |
| atcgaaatta | cggagcagga | taaggtactg | caattatcga | gttattcttt | cgatggctcc | 1380 |
| gcattcgata | ttttcggggc | attaacgaat | ggggcccaac | tggttcttgt | tcctcatcat | 1440 |
| acattgcttg | atgcacgcaa | gctggcggag | ctgatcgaaa | cggaacgaat | atcggtcatg | 1500 |
| ctgattacta | ctgcttattt | caatgttctt | gttgacgtaa | acatatcctg | tctgcgtcat | 1560 |
| atccgcgcga | tattgttcgg | aggcgagcgc | tcctctgtcg | cgcatgtgcg | tagagcactt | 1620 |
| gaacagacag | gtccgggaag | actgaagcat | gcctacggcc | cttctgaaag | tacggtatat | 1680 |
| gcgacatggc | atgatgtgac | agagatttcg | gagcgagccg | taagtgtacc | gatcggtcgt | 1740 |
| ccaatcagta | atacagccat | ttatatcgtc | aatgaacgaa | atgatttaca | gccgataggg | 1800 |
| gtatccggtg | agctgtgtgt | agcgggagaa | gggttagttc | gcggatattt | gaaccgtcca | 1860 |
| gaactgactg | agcagaagtt | cgttgataat | ccgttcgtac | cgggagagcg | catgtatcgt | 1920 |
| actggggact | tggcgagatg | gctgccggac | ggaacgattg | aatatgttgg | ccgaatggat | 1980 |
| gatcaggtga | aaatcagagg | ccatcgcatc | gagattgggg | aagtagaggc | gcagctgctc | 2040 |
| aaagtggcgc | cgattcagaa | ggcgacgatt | gtcgtccgag | gccgcgagga | cggagagaag | 2100 |
| cagctgtgcg | catattatgt | agcagatcgt | ctgcttcctg | caggcgagat | tagaacaatg | 2160 |

```
cttgccaaag aactgcctag ttatatgatt ccggcatact tcatccagct tgaacagatg     2220
ccgttgacga ctaacggcaa agtagatcgc aaagccctgc cagaaccgga agagcacgta     2280
caagcagaga cagaatatgt ggcgcctaga agtgaacagg aaattcggct tgcgagagtc     2340
tggcaggaag tgctcggtct aagccgagtc ggtgcaaagg atcatttctt cgagctgggc     2400
ggccattcat tacgagcgac gacactggtc agcaagctgc acaaagaaga gaatatcagc     2460
ctgtctctgc gcgatgtgtt ccgcaatcct actttggaag cgatggccgc gctcatggaa     2520
gatgctcaag gacgcaaatt cgcacccatc ccgacagttg aggagaagga tgtatatccg     2580
gtatcttcgg tgcagaagcg attgttcatt ttgcatcagc tggaaggagc tgagcagagc     2640
tataacatgc caggggcatt actgcttgag ggcgatgttg accggaaccg attggagtat     2700
gcattccgtc agctgatcac acgtcacgaa acgcttcgca ccggctttga aatggtgaat     2760
ggagaacctg tgcagcgcat ttatccgact gttgattttg tagtggaaga gatgtcagcc     2820
ctggaagggt cggaagtcga ggagcaaatc cggcaattca ttcgcgcttt cgatctgtcc     2880
acagcgccac tgttcagggc ggggctgatt aagcttgctc cgcagcgtca cattctcctg     2940
ttcgacatgc accatatcat tcggacggc acgtcaattg gcattatgat cgaggaattc     3000
acaagcttat acagtggcaa tgagcttgag ccgcttcgca ttcagtacaa ggactttgct     3060
gcgtggcagc gttccgagga gcagatcgag cagttgaagc gccaagaaac ttactggttg     3120
cagcaaatgg aaggcgtact tcctgtgctt gagctgccta ctgattatgt acgtcccgct     3180
gtacagagtc atgatggtgc gctgttcgag ttctcgcttg atcgcgagca gagccaagac     3240
ttgaggaaat tagccgccga tacgagaacg accttgtaca tggtgctgct agcggcatac     3300
acgatcatcc ttcacaagta ttcaggccag gaagacattg ttgtaggaac accgattgcg     3360
ggtcgaacgc atgacgatgt gcagccgctt atcggtatgt tcgtcaacac gctggcgatt     3420
cgcaattatc cttcaggatc caagtctgtg cttacctact tggaggaaat caaagaaacg     3480
acgctgggag cgttcgagca tcaggactat ccgtttgagg aactcgtgga gaacgtgcaa     3540
atttcgcgag atatgagtcg tcatccggtc ttcgacacga tgttcgccct tgagaataca     3600
gagcatcgga aattcgatct ggatggactt caggtgaagc catacggtgc tgaatacggc     3660
atggctaagt tcgacttgaa tctgaccgta acagaagatg gcgatggact ctactgcacc     3720
atggagtatg ctacagcatt gtacaatcga tcgaccattg aaaggctttg cggccatttc     3780
ctgcaggtcg ttggaagcat gactcataat ccgcaagcag caatctcatc actgcaaatg     3840
gtaaccagcg aggagaaggc tcaactgcaa catgaattca atggtacggt tatggagtac     3900
tcaagtgaca agacggttca tgaactgttt gcggaacagg tggagcggac accggatgct     3960
gttgctgtcg tctctggcag cgagcaatta agctacggag agctgaaccg taaggcgaat     4020
cagctagcgt ggaagctgcg tgagtatggg gtgaccgcag agcagcctgt cggcattatt     4080
gtcgagcgaa cgctggatac agtcgtcgca gtgatagccg tactcaaagc atcgggcaca     4140
ttcgtaccga tcgatcccga atatccagag acgcgtattc gctacatgtt ggcagacagc     4200
ggggctaagc tggttttggc gcaatcggag ctaccaggga tcatttctga tgacgtccgc     4260
ctaattgatg tacgcgataa gtctctgtac caaggcgacg gagctgacgt accgaatggc     4320
agcaaaccgt ccaacctgct ctatatcatc tacacatccg gcacgacggg caatccgaaa     4380
ggggtcatgc tggagcacgg caacatggtt aacctgctgc attatcagca gaatggcacg     4440
aacattccga tgccttcgcg gatattgcaa tatgcgtctg gcagcttcga tgtatgctat     4500
caggaaatgt tctcagcgct cctgttcggt ggaagcttgt atatggtcga caatgagatg     4560
```

```
cgcaaggatc cggtacgctt gttccaggaa atcgaaaagc atgaaatcga cgtgatgtac    4620
attccagtgg cgttcctgaa attcatcttc gccgagccgg agtgggcaga agcgttcccg    4680
cgctgcgttc gccatatcat tacggcgggc gagcagttgg tcgtgacacc gcaagtgcag    4740
gcgtgcttga agcgactcga tatctgcctg cataaccatt atgggccatc ggagactcat    4800
gtcgtgacga cctatacgat gacgccggaa gttatcgagg ttggtctgcc gccaatcgga    4860
aagccgatcg cgaacacgag catttacatc gtgaacgaca gcttcgagct gcagccgatc    4920
ggcgtgaagg gtgagctcta cgtatctggg gcatgtgtcg gacgcgggta ctggggaaga    4980
acggacttaa cggaggagaa gttcctagat aacccgttcg cccctggtga gcggctgtac    5040
aagacaggtg acgtagcgcg ctggcttcca gacggcagca ttgagtatgt gggccgaagc    5100
gaccatcagg taaaaattcg ggcttccgc attgagctgg gcgaggtgga atcgcagctc    5160
ttgcatgtac cggcggtaca ggaggcgacc gtggtggcac tggaagatca tgcgggccag    5220
aagcagctgt gcgcgtattt cgcggcagag cgctcgctca cggcaggcga gctgcggcaa    5280
gcattgtcgc aggagctgcc aggctacatg attccgtcct acttcgtaca gttggagcgg    5340
ctgccgctga cgccgaatgg gaagatcgat cggagagcgc tgccgaagcc agaaggcggc    5400
attgagactg gaacggagta tgtcgcgccg cgtacagata cggaagcaag acttgcacgc    5460
atttggcagg atgtattggg gttaccaagc gtaggcgtga aggacaactt cttcgagctg    5520
ggtggtcact cgctgcgggc aacgacgctg gtgagcaggc tgtacaagga aatgaacgtc    5580
aacttcccgt taagaggtgt gttccgtcat ccgaccatcg aggagatggc gaaggcgata    5640
accgagatgc atcaagaact ttacacggaa atacctatcg ctgaggaaaa agcctattat    5700
ccgttatctt cagcgcagaa acggctgttc attgtaagcc agctgacagg agccgaggta    5760
agctataaca tgccgggagt gctgattctc gaaggagagc tggatcgtgc gcgattcgaa    5820
cgggctttcc agaagctgat cgaccgacat gaatcgctgc ggacaagctt cgagacggta    5880
cgcggtgagc ctgtgcagcg cattcactcg caggtggagt tcgctatcga atatcacctt    5940
gcagcagaac aagatgcaga ggcgctgatc actcatttcg tacgtccatt ccagcttaaa    6000
caagcaccgc tgctcagagt cggattgatt gaaactggac atgaacgtca tattctgatg    6060
ttcgacatgc accatatcat ttccgatggc gtaacgatgg ggcatgtcgt gaatgaattc    6120
tcccggatat atgcaggcga tcaactgccg gcgctgcgta tccaatataa ggactatgct    6180
gtatggcagc aatccaatga atatgcagag aagcttgcgc atcaggaatc ctattggctg    6240
aagcaattgg acgagaact gccgacgctc gaattgccga ccgattatgt gcgaccggct    6300
gtacagcagt tcgaagggga tgtggccttg ttcaccttaa cgaacagtca ggccgagcag    6360
ttgcaacgat tagcggcaaa ctacggcgca accttataca tggttctgct tgcagcatat    6420
accgtgatcc tgcacaaata tacgggacag gacgatatca ttgtcggtac accgatcgcg    6480
ggccgcaacc atacggaatt ggagccgctc gttgggatgt tcgtcaatac gctcgccatt    6540
cgcaattatc caactggtga gaaatccttc gcagaactgt tggccgaggt gaaggatacg    6600
gccctcgccg cattcgagaa tcaggattat ccgttcgaaa cgttggtaga gaaggttcat    6660
aagtctaggg acatgagccg aaatccagtg ttcgatacga tattcagtgt agagcatgaa    6720
cagcagagtt ccttccatat tgatgggctt cggataagtc catacccgca cagccattct    6780 gtcgcgcaagt tcgacttaac cttccatgcc gaacagaatg aagaagggat actatgtggt    6840
ctagggtatg cgactgcttt atatgcgaaa gagaccgcga ggcggatggg agaacatttc    6900
```

```
gtgcaattaa tagatgccat catcgcagaa ccgaatgcga agctgatgtc tctgaatatg    6960
atgagcctgc aggaaagaga gcaggtcaag ctggtattta atgatacgat aacgaattat    7020
ccgcgggaga agacgattca acatttgttc gaggagcagg cagagaaatc gccggatgcg    7080
gttgccgtcc aattcggagg agaagggctc acataccgcg agttgaatga acggtcgaat    7140
cgcttggcga gaacactgcg aggtaagggt gtaaaagccg gccgctgcgt aggtctaatg    7200
acggatcgtt cgctagacat gattgtagcg attatggcga ccctgaaggc aggcggggca    7260
tatgtgccaa ttgatccgga ctatccagag gaacgcattc gatacatgat cgacgattcg    7320
ggaacatcgc ttctagtcgt tcaacgtcat ttgcaggcga accatattcc tgcggattgc    7380
atggttgtac ttgtagatga tgagggctcc taccacgcag acggcacgaa tctggagcag    7440
cataatgggg cttctgatct cgcctacgtc atttatacgt caggtacaac gggaatgccg    7500
aaggggaatt taacaactca ccgcaacatc gttagagtag tgcgggatgc gaaatatatc    7560
gagatcgatc agcatgacac ggtgctgcaa ttatccagct acgcttttga cggctcgact    7620
ttcgacatat ttggcgcctt gctgaatgga gcgaagcttg tcctgataac gcgcgaggta    7680
gtactcgacg ctggacgatt ggccgacacc atcgagagcg agaagatttc ggtcatgttt    7740
attaccaccg cctatttcaa tctgctcgtc gacctgagag tggacagcct gcgccatatg    7800
cgtgcgatat tgttcggtgg ggagcgcgca tctgtgagcc atgtgcgcaa ggcgctccgg    7860
catttgggtc caggcaagct taagcatgta tatgggccaa cggagagcac cgtatttgcg    7920
actagccaca cgttgatga agtagctgac agcgccgtta ccataccgat cggacgccca    7980
attggcaata cggccgtata tattgttggc gagggagacg ttctgcagcc gattggtgta    8040
gctggtgagt tatgcgtagc gggcgatgga gtagccatag gatatttgaa ccgtccagat    8100
ttgtcaggag ccaagttcgt gaataatccg ttcgttccgg gtgatcgcat gtaccgaacg    8160
ggtgacttgg caagatggct atcagatgga acgatagagt atgtgggacg gaaagacgat    8220
caggtgaaaa tccgtggtta tcgaatcgag cttggtgagg tcgaagctca tctgttagac    8280
cttgaggcga ttcaagaagc tgtggtcatc gtcagggagg aaagtgacgg gcagaagcgc    8340
ctatgcgctt actatgtagc agctcgtctg attacggctg gtgagatgcg gatagctttg    8400
gctcagcagc tcccgggata tatgcttcca tcctacttcg tacagctcga taagcttcca    8460
ctgtcaccga acggcaaggt gaaccggaag gcacttccgg cccctgaatt gcatgtgcag    8520
gcagcctcgg aatacgtggc cccgcgcacg ccgcaagaag tactgcttgc tcacatatgg    8580
agggaggtgc tcgggctagg tcaggtaggc gttaaggata atttcttcga gcttggcggt    8640
cattccttaa gcttaatgag gctagtggag cgcgtctata ccgagactga ggttgaaatc    8700
ccaattcaca gcgtattccg ggagccgaca attgaagcga tggcgtacga aatgttgaaa    8760
tctgaacttg ctggcaaggc aggaaatcac ttcatgaaat tgaacgaaaa cggtcatatc    8820
cctgtcttct gcttccctcc gggacttggc tacggtctca gctacttgga actgccaag    8880 cagctggatc atcactgcat cctgcatggc attgacttta tcgatgatgc tgaaactcgg    8940
gaggaactgc ttgaacgata cgtgaatgcg atccttgctg ttcaaccgca gccgccattt    9000
atattgttag gctattctct aggtggcaat ctgacgttcg aggttgcgaa agcgttggag    9060
tgccgagggt atccggtgtc ggatgtcatc atggttgatt ccttgcggaa gctgaaggtg    9120
catgaagtag acgaattcga cggcgacatc gatcaaatga ttgatggtgt ggaggaactg    9180
aaagaaatgc tggttcacca tcctcttctc cgcgatcaag ttaagaacaa gatgagggc    9240 tactggtcgt acgcgactga actcgttaac tccgacatca ttgatgccaa tattcatgca    9300
```

| | |
|---|---|
| ctgatggcgg agccatccga ggtgaaccag gcaggacggg gagcagctcg cgacatggca | 9360 |
| ggaggctact cgcggcaggt atgcggagta caacctacgc ggtgtgcacg aagaagtgct | 9420 |
| tcaaccgcct ttcttggaag cgaacgctaa | 9450 |

<210> SEQ ID NO 8
<211> LENGTH: 19968
<212> TYPE: DNA
<213> ORGANISM: Paenibacillus strain TS-15

<400> SEQUENCE: 8

| | |
|---|---|
| gtgaacgcga atcctaacga atggtatcct ttgacgcaag cgcagcgcag aatctggtac | 60 |
| acagaaatga tgcatcctaa tacgtcggtt actaccgttg ctggaacaat gtacatacga | 120 |
| ggcaaggtag acgttgagat tttgaaaatg gcgatatatc aagtgatcat gcagcatgat | 180 |
| gccttccgaa tacgaatcgc aatgacagac aatcagccga agcagcaatt tgctcccgta | 240 |
| gagcaaatcg tccctcacgt tgattactta gagtgggata tcagattga agctgagagt | 300 |
| tggttacagc ggtttaatca tattcctatc catatgttcg acccagcgtt ataccacttt | 360 |
| gtcatattta acgtcaatga tgaggaaaca tggttcaatt tgaaaatgaa tcatattgca | 420 |
| acggatggag tctcttctca tcttatcgct tataaaatca tgaagaatta taccgcaatg | 480 |
| gtgagtggca acgcggacac ggacgaacaa gagagcactt acctggacta catattcgcg | 540 |
| gaacgagagt atgaacaatc cgatcgatac gcgaaagata aggcatattg gctggataag | 600 |
| ttcagcacaa tgccagaagt gataggcatc aaatcttacc ctcctcattc aatcggcaca | 660 |
| gaggccagtc ggacaagcac cacggttagc ggagaaatgt acgagaagct ttaccgattt | 720 |
| agccagcagc acaatatcag tctctttact ctatttctag gttctttata cgcatttcta | 780 |
| tataagacga cagggaacaa cgatattgct gtcggtgccg cttatgcgaa tcgaacttcc | 840 |
| aggcaagaca aggatgcgct gggcatgttc gtaagcacgg tagccgctcg tttgacgatt | 900 |
| accccagacc aagacgtact aaccttccta cataacgttg ccaaagagca aaaagcaatt | 960 |
| ttgcggcatc agaagtatcc atacaaccag cttattcttg atttaagaga acaaaataat | 1020 |
| agtgtcgaga ttcaggattt gtaccgtata tccattgact atatgccgat acgctggtcc | 1080 |
| agttacggag aactagctgt ccgccaacgc agcagctttt gcggtcatga ggtggacgat | 1140 |
| tttgcagttc acgtagaaga tatggtggat gataatcaga ttatttttcaa tatcgattat | 1200 |
| cgcaagcagt tgttcgaaga gcatgaggtc attcgtatga tcgaacaaat gatgaccatc | 1260 |
| gttgatcaga tgttgaataa tccgagccag aacttgcagc agttgtccat gatcagtgat | 1320 |
| aaggaagctc agatcatcct gacacgcttc agcaacggga attggtcaac gccgcagcca | 1380 |
| gttgacgaa cgattcacca gttgtttgag gaacaggtcg aacgcacgcc tgatcaggtc | 1440 |
| gctgtcgtgt tcggagatcg gcacctaacc tacaaggaac tgaacgaaca agccaattgc | 1500 |
| ttcgctcgaa cattgcgagc ccatggtgta gcagcagagc aattcgtagg catcatggca | 1560 |
| gaccgctcga ttgagatggt catcggtatt cttgcaatct gaaggcgggg tggagcctac | 1620 |
| gttccgatag atcctgagta cccagaagaa cgcatcctgt atatgctgga agactcaaat | 1680 |
| gcaagagtac tcgtatcgca aagtcatttg cagacgcggg tcggttacac aggaacatgg | 1740 |
| gtattgcttg ataatgagaa cgactacgaa tcaagccgcg ataacttggt gcctgtcaac | 1800 |
| gaagcacatc atttggcgta cgtcatctat acatccggta caactggcaa gccgaagggc | 1860 |
| gtcatgattg agcataagca gattactgcc ttggggatg catggaagca tgcctatcaa | 1920 |

```
ttagatgaac cgggaattcg gacgctgcaa tgggcaagct tctccttcga cgtatttacg   1980
ggagacatgg tgcgagcgct gctgtacgga ggcgagctta tcatctgccc aagcgaagcg   2040
cgagctaacc ctgaagcgat atgtgagcta atcgcaagac atcgcatcca catattcgaa   2100
tcaaccccag cccttgttat tccgttgatg gaatatgtgc atgaacaagg caaggatgta   2160
agcagtctgc gcctgctcgt tgttggctcg gatcattgcc cggccgcgga atatcgcaag   2220
ctgattgaac gattcggctc gcaaatgaga atcctgaaca gctatggcgt gactgaggct   2280
tgcgtcgatg cttgctatta cgagagaaat tgtagtgtgg attccatcac aatgctcccg   2340
ataggtaaac cactgccttc agtatccatg tacattctag acgagaacaa ggcgctccag   2400
ccaatcggaa ttgtaggaga gctctacata ggtggagccg tgtcggcag aggttatctg   2460
aaccgtgatg acttgacagc agaaaaattc gttgatgacc cctactctca aggaaagatg   2520
tatcggacag gtgatttggc aagatggctg ccggacggaa acattgaata ccttggaagg   2580
ctcgatcatc aagtcaaaat tcggggtaat cggatagaaa taggggaaat tgaaacacgc   2640
atgctgcaaa catcacttgt gcgggaagcc gttatcgtag cgcgcgagga tgaaaatgga   2700
ctgaaagctc tgtgcgccta ttatgttgcc gatagcgaga tatccgtaca gcaattgcgt   2760
tcaaccctgg cagaacaagt acctgattat atgattccgt cttatttcat gaagctggaa   2820
cgattgccgc ttacgccgaa cggcaaaatc gatcggaatg gattgcctgc accatctggt   2880
caggactatt ccggcaagat ttatgtggag cctcgtaacc aagcggaaca aacgctggtt   2940
agcatctggc aaatggtgct ggagtcaag cgagttggca ttttggatca tttcttcgag   3000
ctaggtggag attcgatcaa gtccattcaa gtatcatctc gcatgcagca agctggatat   3060
aagctggata tccgggatct gttcaagtat ccgaccattg aacagataag tccacatctg   3120
gtggaggttc agcgaaaagc tgagcaggga aagagaacg tgaggttgg gctcactcct   3180
atattgcgct ggtattttga acgagatgaa gcgagtctgc atcattacaa tcaatccatc   3240
atgctgcacc gcaaggatgg attcgatgag gcggcacttc gcaatgcact gcacaagatt   3300
acggaacatc atgatgcgct cgcatggta ttccgccgta cggaacaggg agaatacgcg   3360
gcctggaacc ggagaatcga agaaggcgag ctttaccgtc ttgatgtgtt ggatatcaag   3420
gaacgttccg ctggcgatga aagcgaagaa tctcttcata acatgctcat ggcagaagct   3480
gatgcgattc agaatgggtt caatttagag gcagggccac tcgtaggtgc aggattgttc   3540
cgctgcccag atggagatca tctgcttatc gtcattcatc atgctgttat cgatgccgta   3600
tcctggcgga ttttgcttga ggatcttgct accggatacg aacaggcact tctaggcagc   3660
gagattcgtc tccctgccaa gagcgattcc ttccggttat ggtcaagaca gctttcagca   3720
tatgcgcagc agtctaacat gaacgaggag ctgaaatatt ggcagcaagt cgcacagacg   3780
acgattactc cactgccgac ggattacgct gggactgctc ttcaacttga tagtgaatcg   3840
gtaacggtcg aatggagtgc taacgagacc gaactgctgt tgaagcaggc gcatcgggcg   3900
tataacacgc agatggacga tcttcttta acggcactcg gcattgcatt ccggagatgg   3960
tgcggacatg agcgtatccg aattaatttg gaaggacatg tcgggagtc gatcctgcca   4020
gatctcgata tcacacgtac ggtaggctgg ttcacgagtg agtatccgca gcttctcgag   4080
gtgggctctg aggaagaact gccgcgaatc atcaagtcag tcaaagaaga tttgcgcagc   4140
attccgaata aagggatcgg ttacggcatt tgtcgatatt tatcagacaa gagtatgcag   4200
gatgattggg gaacagcacc tgaggttagc ttcaactact tggggcagtt cgaccaagat   4260
ttccagaaca gcgggttttc tccatcgccg tattctaccg gcagcaatat tgggggagat   4320
```

```
cagctaagac cttatctgct agacatgaat ggaatggtct cggatggcaa attgcagctc      4380
gacatcagct atggacggac gcaatatcgt gttgagacga ttgagcgatt ggcaagcttg      4440
attcgggaca gcttacttga aatcatcgat cattgtgtgg ccaaagagca aacagagctc      4500
acgccaagtg acgtgtcatt gcagcgcatt agcattcaag agttggagca gatcgttgaa      4560
cggacaagtg gtatcggtga agtagaggat atctatgcat taacgccgat gcagaaggga      4620
atgtggttcc atacagctat ggacagccag gcgggagcct atttcgaact tacgcgctta      4680
acgcttaagg gagcgttgaa catcgaagcc ttcgccgcaa gctggaatga actggccgct      4740
cggcatgctg tattccgtac caacttcctc gtcgattcga acggtgaacc gctgcaagtt      4800
gtatttcgta gcaagcgcat tagcgtgaag cacgaagatt tgcggtccct gaattcatat      4860
gagcaggctg tggcgattga gaacgaagcg gccaaggaac gcgcacaagg ctttgacctt      4920
gagaatggga atgtcatgcg cgtgtccgta ctccagacgg cagacgaagt gtatgaagtg      4980
ctgtggatct cccatcacat cgtcatggat ggttggtgcc tcccgctcgt cgctgctgaa      5040
gtattcagta cgtactccgc actggtggaa gacaagaagc cgattcttgc ttcggtacct      5100
tcctataatc aatacattca atggctggag cggcaggatg aatccgcagc cgcggcctat      5160
tggaaccatt atttgtctgg atttgaagag acgacagaac ttcctcatag caaggggcgc      5220
agacattctg gtcaatatga agcaggtcag gttcagatcg atctaggcac aagcctgagc      5280
ctcgctctca atcaagttgc aacgcagcat caagtgacac tgaatacatt gctgcaggca      5340
tcatggggaa tattgctcca gaaatacaac agaacttcag atattgtatt cggcagtgtt      5400
gtatctggca gaccggcaga actagtcgga atcgaagaga tgattggctt attcattaat      5460
acgattcccg tgcgcgtgag cagtcaggcc catgagagat ttatagaagt aatgacgcga      5520
atgcaagacg atgcattgtc atctgccaag catgactact atccgttgta tgaaattcaa      5580
gcacaatgca cgctgaagca ggatctcatt aatcacatca tggtacttga aaactacccg      5640
atggagcagc agctcgatca gtttaacagt tcggacggca gtggactgaa gctgacagac      5700
gtaaccgtat cagaacaaac gaatttcgat ctgaacctca tcatcattcc tggcgacaat      5760
atcgtcattc gtttcgattt taataaacaa gcactcgcag aaacggatat gaacgtgttg      5820
aaggagcatc tgttgcatgt actgaacaa gttgcatcga atccgcggat atccatagga      5880
gagctgcagc tggcgacgga tgaagagcgt gccgtaatga tgagcgaatt taatgatacg      5940
ttcgtggctt atccgcgcga gaagtcgatc cacagattgt tcgaggagcg agctaaacaa      6000
gagccagacg cgctagccgt cgtgtttgga aatgatcaga tgacctacgg agcgttgaat      6060
gccgcagcca accgaatggc ttggagactc cggtatgctg gagtgacgag cggtgaactg      6120
gttggcatct cgcgggatcg ctcgctgaa atggtcgtcg gcttgctggc aattatgaag      6180
gccggtgggg cttatgtacc gatcgaccca gcttaccctc aagagcggat tagcgcaatg      6240
cttgaagata catccattgc gacgatggtt acgcagaggc atctgtgcag cttatggcct      6300
gaacatctca acgtgattgc gctggatgat aacgagacag acgtaagtaa ttcaatggaa      6360
gatgtagaaa gtaacctgcc tattgatggg gcgggagacg atttggcata catcatctat      6420
acgtcagggt ctacgggaac gccgaaaggg gtctgcgtaa cgcaccgcgg agtcgtcagg      6480
ctcgtatgcg ccgcgacgta tgtcgagatc aacagctcgg atgtcttctt gcaaggttcc      6540
acaatctcgt tcgatgctgc aaccttgaa atatggggca gtctgctgaa tggggctgcg      6600
ctggccatcc tgcctcctgg caatgtgtcg cttacagatt ggagcgaagc gattcagcgt      6660
```

```
catcgggtga cgacgttgtg gatgacagct ggtttgttcc aggtcatggt tgaacagcaa    6720
attgagggct tctacggagt caagcagctc ctggtaggtg gagatgttgt atctcctaca    6780
cacgtgcgca aagtgatgga gaagcataac ggtattaggg tgattaatgg ctacgggccg    6840
acggaaaata caaccttcac ctgctgccat accattacgg ctgctgattt ggatcgaggc    6900
tcaattccga ttggccaacc gattggcaat acgcgagtgt atgtgctgga tgaagctggg    6960
aacgttcttc ccgttggcgt atgcggcgag ctgtatgcgg gcggagatgg tttggcacga    7020
ggatacttga atcgtccgga attgacggca gagaaattcg tgaatgatcc atttatccca    7080
ggcgaacgct tgtatcggac aggtgatttg gcgagatggc tgccggacgg ttcgatcgaa    7140
tttatcgggc gctgcgacga acaagtgaag attcgcggtt accggattga accaggtgag    7200
gttttggcct atcttctgag gatcgatgaa gtaggtgagg cggctgtaat cgcgcgggag    7260
gattcgagtg gacagaagga gctatgtgcc tatttcacag cggaagttga gctatcggct    7320
agtggactaa gggagacact ggctcgtgaa ctgccagctt acatgatccc atcgcatttt    7380
attcagatcg aagaacttcc tttgacacct aacggcaagg tggatcgcag agccctgcct    7440
ctaccagagg aagggctgcg tatgaacttg aagatccaac cgcgtacgga actggaagct    7500
aagcttgcac tcatctggca agatgtgctt ggtctcgaga acgtaggcgt tacagattca    7560
ttctttgaac tgggtggaca ctccttgcgc gcgaccaccc tcgttagcaa ggtacatcgg    7620
gagttgaata tagcgctgcc gctgcaggat gtattccgct acccgacgat tgaacaaatg    7680
tctctcgcca tacaggggat gcagaaggaa agctttgctt ccatacctcg ggtggaagac    7740
cgagaatggt acccggtatc ttccgcgcag aagcggctgt tcgttcttca tcagatggag    7800
ggcgcagaac tgtcctacaa tatgccgggc gtcatggcga ttgaaggcaa gctccatcgc    7860
gatcgcttgg aagcagcatt ccgcggcttg attgcaagac atgaagtgct gcgtaccggg    7920
ttcgaaatgt acaacgggga acctatgcag cgaatttaca gcgatgtaga atttactgtc    7980
gagcatggga tagttggagc tgcatcggaa gcggagtcag tcattcgctc gtttgtacgg    8040
gcgttccaat tgaataagcc cccgctgctt cgggtcggac tgatcgaagt ggacgcggat    8100
cggcacctgt tgctgttcga tatgcatcat atcatttcgg acggggcatc catgggtata    8160
ttgctagatg aattcgttgc actgtatagc ggcgaagaat tgcctgaact gcgtcttcag    8220
tacaaggatt atgcttcgtg gcagcaatcg gaagattact tgtcaaggat ggaagaacag    8280
aaagcgtatt ggctggagac attgcgaggc gagcttccag ttctgcagct tccagtggat    8340
tacactcggc ctgcattccg cagctttgca ggaagcacgc tggaattcat cgttcctgcc    8400
gacaaggcag accagcttaa gcagcttgga gcaggttcgg atgccacaat gtacatggtg    8460
ctgctggcgt tgtatacggc cttgcttcac aaatataccg gacaagaaga cgtcatcgtg    8520
gggatgccga tagccggtag aacgcatgca gacatcgagc cgcttatcgg tatgttcgtc    8580
aacacacttc cacttcgcca ttatccggct ggagagaaga cgttccgctc cttcctaggg    8640
gaggttcggc aatccacatt acaagcatac gaacaccagg aatatccgtt cgaggagctt    8700
gttgatcata ttcaaccgac aagagatgta agccgtaatc caatattcga tactgtgctc    8760
gtcctgcaaa atacagaaaa aggcgcatgg tccatcgatg gacttgccgt gacgccgaat    8820
ccgattgagc atgccgttgc taagttcgac cttacacttc atgtcgaaga aggtatcgat    8880
ggcctggcgt gcagcattga atatgcaaca gctctgtacc accgagaaac gatcgaacgg    8940
ctggcatgcc atttcaatca attgctggag gcagtcataa gcaatccgga agctcggttg    9000
gatcagcttg gcatcataac ggagactgag aagcagcaat tgtttgaaga gttcaacgat    9060
```

```
acgtcagcgg attatccgcg tgataagacg attcaccgac tgttcgagga acaggtcgaa    9120
agaacgcctg atgcgattgc tgtaacggga tcagacggat tcttgactta ccaggagctg    9180
aatgaacggg ctaacagctt ggcatgggta ctgcgtgcag aaggcatcgg ggcagacaag    9240
ctggtaggca tcatggctga gcgtacgacg gatatgcttg tggggctgat cgccatactc    9300
aaggccggag gagcttacgt gccaatcgac ccggaatatc cagaagagcg catcagttac    9360
atgctgagcg attcaggggc agatattttg ctattgcctc gccatctgcg ggagcaagtc    9420
gcctacgaag gcaccgtatt gttccttgat gacgagcaga catacagcgg ggataagtcc    9480
aatccgtcat cggtcaacaa gccttccgat ctggcttatg tcatctatac atcgggaacg    9540
actggcaagc cgaagggtac attgattgaa cataagaacg tcgtgcggct gttgttcaac    9600
agcagaaatc tgttcgactt ccgttcaact gatacatgga cgctgttcca ctccttctgc    9660
ttcgacttct cggtatggga aatgtacggc gccttactat acggaggaag attggtggtt    9720
gtaccacagc ttacagccaa gaaccctgcc atgttcctgc agctgctggc tgaagaacgg    9780
gtaacgattt tgaatcagac accgacctac ttctatcaat taattcggga agcacttgca    9840 gatgaagtc cagaattgaa cattcgaatg gtgatcttcg gcggagaagc gctgagtccg     9900
cagctgctta aggactggag agcgaaatat ccgcgcacgc aattgattaa tatgtacggg    9960
attaccgaga ctacggttca tgtcacgtac aaagagatca cggaaaccga gatcgagcag   10020
gcaagaagca atatcggatt cccaatcccg accttgcgta tctatattct ggatgcgaat   10080
cgaaattgcg tgccgatagg cgtggccggg gaaatgttcg tcgcaggaga agggcttgca   10140
cgcgggtatt tgaatcgccc tgagttgact gaagacagat tcgttgacaa tccattcgaa   10200
ccgggcagca agatgtacaa gacaggcgac ttggcgaagt ggctgcctga cggcaacatt   10260
gaatacctag gccggattga tcatcaagta aaaattcgcg ggtatcggat cgagctaggc   10320
gaggtagaag cccaagtaac gaaggtagaa tcggttcgtg aagccattgt tattgcacgg   10380
gaggagaacg gcgaaaagct gttgtgtgct tacttcgtgg cagatcgaca actgaccgta   10440
ggggaaatga gaaccgaatt ggcgcaggag ctgccagctt acatgattcc atcctacttc   10500
gtgcagttgg agcggatgcc gcttacctcc aacgggaagg ttgaccgcaa ggcgctgcct   10560
gcaccggaag gcagcatcaa cacgggcaag gaatacgtag cgccgcgtac atcaatggaa   10620
gctagcttag ctcgcatgtg ggatgaactg ctcgggattg agcaggtcgg cgtaacagac   10680
aatttcttcg agctaggcgg acattccttg cgcgcaactg cgctggttaa cagggtgcac   10740
caagagatga atattcagtt gccgctgcgc gatgtgttcc ggttctcaac gattgaagaa   10800
ctggcagctg ccatgtccga gatggcagag gaatcctatt cttcgattcc ggttgctgaa   10860
gttcaggaac attatccggt atcttccgct cagaagcggc tgtatatcct tcaccagctt   10920
gaaggggcag agcagggcta acatgcct ggcatcatgc tgattgaagg cgagttggat    10980
cgaagcaggt tcgaggctgc attccgtaaa ttgatcgcgc gtcacgatat attgcgcact   11040
ggcttcgagc tcgtgaaggg agaagctgta cagcggatac acgataccct ggatttcgcg   11100
attgaatatc ggaaagtcga agaacaagag gttcagcagc aagtaaggca gttcattcgt   11160
acattcgagc ttgataagcc gccgctgctt cgtgtcgggt tgatcgagat tgcggaagca   11220
aaggaacagc atgtgcttct gttcgatatg catcatatta tttccgacgg cgtatcgatc   11280
ggtatcgtgc tgcaggaaat catgcggcac tatcacgggg aagaggtacc gccgcttcat   11340
attcaataca aggattatgc ggcatggcag caatcagagg cccagaagga acagttgaag   11400
```

```
catcagcaag catattggct tgaccaattc caaggtgaat tgccgatatt ggagttgcca  11460
acagactatg ctcggccggc cattcagcaa tacgatggcc tcacgctgcc atttagaatc  11520
gataaggacg tggcagatgg cttgaaccga attgccgctg acaccggaac gacattgtac  11580
atggtgctcc tagctgctta taccatcatg cttcacaagt atacgggcca agaagacatc  11640
gtggtcggaa caccgattgc cggcagaaca catgaagagc tgcagccgtt aattggtatg  11700
ttcgtcaata cacttgccat tcgtgcttat ccggaaggtg ctaaggcatt ccgttcctat  11760
ctggatgaga ttagaagcac aatgttgggg gcctacgagc atcaacagta tccatttgag  11820
gaattggtgg aaggtctgca gttgactagg gatttaagtc gcaatccgtt gtttgacacc  11880
atgttcgccc tagacaatac ggacatgatg gttgattcac tcggcgagct tcatatgaag  11940
ccatatccgc tggaatacac aatatcgaag ttcgatgtga gcttggatgt gaaggcagat  12000
gagcgcgggc tggattgcag cttcgagtat gcgacttctt tgttcaaatc agagacgatc  12060
caccgcatgg cagagcattt cagccaattg ttgaaggaca tcgtcaatca cccagatgcg  12120
caactgggcg aactagggat gcttaccgtg cacgagagcg acgagatttt gcaggtgttc  12180
aatccaaccc attcattgaa agctcctgat ggaacgattc atcgattgtt cgaagaacag  12240
gcagaacgga caccggagca acctgcagtc gtgttcggga atgagcgcat gacttaccgc  12300
gagttgaacg aacgggcgaa taagcttgcg agaacattgc gggcagaagg tgtggagcca  12360
gatgacttaa ttggcgttat ggccgatcgc tcgattgata tggtcgtggc agttatggcc  12420
gtcttgaagt caggcggagc ttatgtcccg attgatccgg aatatccaga ggatcgcatt  12480
cgctacatgc tggaagatgc gaaggcaaga atacttctga cgcagtgtca tttacaagat  12540
aaagtgtcct cgagggaac gtgggtgctg ttggaagacg aagcttccta tcatgaggac  12600
gatacgaacc tggagccgat ctgcgaacct gaccatctct gttatgtcat ctatacatca  12660
ggtacaaccg gcaatccgaa gggagtcatg atcgagcatc gtcagctcgc tgcgatggca  12720
gaggcttgga aggccgagta tgaattgcat gagcccggga ttcgctggct gcaatgggcg  12780
agcttctcgt tcgacgtatt ctcaggtgat ctcgctcgca cactgctgca tggaggagag  12840
cttatactct gcccaagcga cacaagagcg aacccgggtg cactagctga gcttcttcgc  12900
agcagcggta ttcagatgtt cgaatcgacg cctgctctcg tcattccgct tatggagcat  12960
gtgtatgagc atcgcgtgga catcgacagc ctgagattat taattattgg ctctgatctg  13020
tgtcctgcag atgaattccg caagctgctc gatcgcttcg gttcacactt gcgcatcatt  13080
aatagctatg cgtcactga agcttgcgtt gactcgagct attatgagcc ggttttatca  13140
gatccagtgc gctctgtgcc aatcggtaag ccgcttcctt atgtatcgat gtacattctc  13200
ggtgagaact tatcgcttca gcctgttggt ctggctggag agctgtatat cgcaggcgct  13260
ggagtcggac gcggatactg gaataggcca gaaatgacag cagacaaatt cgtgcgcgat  13320
ccgtttgctg acgacaatg catgtatcgt acagggatt tggcgaaatg gctgctggac  13380
ggcaacattg aattaatcgg gcgcacagat catcaggtga aaattcgcgg ctaccgcatc  13440
gaaatcggag aggtcgaatc gaagctgcag caaacgccgg atatccgcga agcagccgtc  13500
gtcgcgaagg aagatggaag cgggcggaag gtactgtgtg cttattacac atcctatcgt  13560
gaactgacgg caggtgaatg gagatctgca ttggcgaagg aactgccggc ctacatgata  13620
ccgtcgcact ttatgaggct tgagcggatg ccgcttacgc cgaacggcaa gctggatcgc  13680
aagggacttc cagcaccgga aggcgctgcg tataccggga cggaatatga agctccacgc  13740
acggatgcag agattgcgtt ggctgccgca tggcagagtg tcttgcatgt ggagcgggtt  13800
```

```
ggaacgaatg atcatttctt cgaactgggt ggagactcga tcaaatcgat tcaagtgtca    13860
tcgcgtctgc atcaggctgg atacaagttg gaaatacgag acctattcaa atacccgacg    13920
atagcgcaat tgagtctaca gcttcagccg attggcagga tagctgatca aggcgaggtg    13980
catggcgagg tcgagcttac tccgatccaa cgctggtatt tcggactgga tctggatgac    14040
atgcatcatt ataaccagtc gttcttgctg taccggcagg gcggatttaa tgaagaggct    14100
ctgcgcaaga ctttacgaac catcgtggag catcatgatg cgctgcgaat ggtattccgt    14160
aaatcagccg ctggcgttac ggcttggaac cgggcaatcg aggagggtga gctgttcgac    14220
ttccttgcct tcgatatcgc aaacagtgga gatgcagaac aggttatcga agcgaaagcg    14280
aacgacatac aggctagcat cgatttgcag ggcgggccgc ttgtgaaggc tggattgttc    14340
cgctgcgagc aaggccatca tctgctcatc gcgatccacc atgctgtcat agacggcgtg    14400
tcatggcgca tcctgctgga ggatatatcg gcaggctacg agcaagcgtg caagggtgac    14460
gacatccgct tgccttcgaa gacgattcct tatgctgcgt ggtcacggag tttggtcgaa    14520
tatgcttcac tcacggattt gggtcatgag cgcagctatt ggagacacgt cttgaacgca    14580
ggagcgaatc cgctgccgaa ggactttgac acagaatcaa gtctgcagca ggacagtaat    14640
tccgtcaccg tagcttggaa tcaacaggat acggagcatt tactgaagcg agtgcaccga    14700
gcctataaca ctgatatgaa tgagatcttg ctggccgctc tcgcgatagc catacagaaa    14760
tggagtgggc acaatcaaat tctcatcaac ctcgagggcc atggacgtga gccaatcgct    14820
ggtgacctag atatttcacg gacagtcggc tggttcacga gcgaatatcc ggttctgctg    14880
caagcggagc gagatcgagg attggcgtac cacatcaaga gggcgaagga agaattgcgg    14940
cagattccga acaagggaat cggttacggc atatgccgct acttgtctga gccggatgat    15000
agcttggaat ggggagctgc tccagagatt agcttcaact acttgggaca attcgatcaa    15060
gacacgatgg aaggcggcat tatgttgtct ccatattcga aaggttccga tggaagcgcc    15120
ttgcatacac gtcaatatgt cctcgacatc aattgcgcaa taacgaacgg catgttgacc    15180
ttggatatga gctacagcga gaaagagtac cgcaaggaga cgatggaact gctggcaggc    15240
catttccacg agagtctgct cgagatcatc aaccactgtg tctcacgtga gcagacagaa    15300
ttgacgccga gtgatctgct gctgcatgga ctgagtatcg agcagctgga gcagattgct    15360
gaagagatgc gagagcttgg catcatcgaa aatatgtaca tgttgacccc gatgcagaag    15420
gggatgtggt tccataacgc tctcgatggt caagaaggcg cgacgggtgc atatttcgaa    15480
caaacccgat ttacgctgcg aggtgagctg gatcctgccc tgtttgccca gagcctgcac    15540
gaactggctg cccggcattc cgtgctgagg acgaacttct gcagcttgga cggggaacca    15600
gtacaggtgg ttttccggga aggacggatt acattcacat acgaggatct gagccaattg    15660
ccagctgaag agcaagcagc agtgatagaa cgtattgtcg cgagcgataa gctgcgaggg    15720
ttcgatctgg aacgcgatcc gcttgttcgc gtcacattga tgcgtacgga ggcatccagc    15780
tgccatgtac tatggagttc ccatcatatt ctgatggatg gctggtgctt gccgcagttg    15840
acggacgagt tgttccgcat atactcagcc gtcacgaatc ataatgctgg aactactgaa    15900
gctactggaa ctgtcggaac attaggagcc ttcggagctg ctgaatcttt gcggaacaaa    15960
gaggctggcc tgcctgacta tagccgatat atcgaatggc tggcagagca ggacatgagt    16020
gcggcggcag catattggaa cgggtacttg gcgggatacg agcagcagac acgattgcca    16080
aatgggaaga tcacaggcaa ggataagccg tatgtgctgg aacaagcgtc ccgcaagctc    16140
```

-continued

```
ggaattgagc ttacttcccg tatgattcgg attgccaagc agcatcaagt tacgttaaat    16200
acgctgctgc aggcggcatg ggggatcgtg cttcagaagt ataacggtac gcaagatgtt    16260
gtgttcggcg gagtcgtatc gggtcgacct gctgatgttc cgggtgtcga atcgatgatt    16320
ggactattca ttaacacgat tccggttcgt gtaagcaacg aagccggagc aagcttctca    16380
gacgtgatgg agcagctgca aaatgcggca ctcgaatctg gcgatatga ttattatccg     16440 ctctatgaga ttcaatcgag aacatcacag aagtcggaac taatcagcca catcatggtg    16500
tttgagaact atccattgga cgagcgaatg gagcaaacca gagacggaaa cgacggagct    16560
ctcgctttaa ccgatgttca ggcagctgaa cagacgaatt atgatttcaa tctaatggtc    16620
gtgccgggtg atgaacttat cattcgcttt gatttcaact cggaagtgta tgagcgcggt    16680
catatggaac ggctgcatca tcatctgatg catgtgttgg agcaagtaac gggcaatcct    16740
gcaatctcca tagctgaagt gcagctcgct accgaagctg agaaggccga actccaatct    16800
gcattcaatg acacagctgt cgactaccct cgcgaacaga cgattcatcg gatgttcgaa    16860
gaacaggtgc agcagacgcc ggatgctgca gcagtgctgt atgggatga cagcataacc     16920 taccgagagc tgaacgaacg cgcgaaccag ctggcaagga cgctgcgtgc ggcaggggtt    16980
gaacccgatc agattgtcgg tattatggcc gagcgttccc tggagctaat ggttggcatt    17040
atggggattc tgaaggcggg aggcgcctac gtgcctatcg caccggatta tccagaggat    17100
cgcattcggt atatgctgga cgattccgag gctcaggtgc tgcttgttca aggaagcgcg    17160
ggagaagcag ttgacttcgc gggccgcatc attaatctgg atgatgcaga agcatacgat    17220
ggagacggat cgaatcctga ccagtcaac aagccgaccg atatcgccta catcatctat      17280
acgtctggca cgaccggacg tccgaaaggg gttatggtcg agcatacttc ggtcatcaac    17340
cgcttgctgt ggatgcagaa cgctatccg attggagcgg aagatacgat tatgcagaag     17400
acagcgatca catttgacgt atcggtctgg gagctgttct ggtgggcgtt tgtcggctcg    17460
aaggtgctta tgctttcagt cggtggggag aagagcccac atgcgattgt ggatgcgatt    17520
gagcgtcacc gaataacgac gatgcacttc gtgccatcca tgctgcacgc gttccttgag    17580
catgtggagc aattgacaga tgcagagcgt gagcgcggtc tcgcaccgct gcggcaggtg    17640
ttcacgagtg gcgaggcact gcttgcctcc caggtcgagc ggttccaccg ttatattgca    17700
cctgcaagcg gagcgcagct cattaatctg tatggaccga ctgaggcgac ggtgacgtg     17760 acgtacttcg attgcgagcc aggccagact tatgtaagtg tgccgattgg caagccaatt    17820
gataatacga gcattcatat cgtgaatgag cataatcaag tgcagccgat cggcgttgct    17880
ggtgaactgt gcatcgcggg cgtagggttg gcgcgcggtt actggaaccg tccagagctg    17940
acagcagaga aattcgtcac gattccttcc gtcggcgaac ggatgtatcg aaccggagac    18000
ttagcacggt ggctgcctga cggcaatatc gaatacttgg gtcgaatcga ccatcaggtg    18060
aaaatccgcg gatatcggat tgaattgggc gagctggaaa gtgcactgct gaatgtccaa    18120
gaaattcggg agacggttgt agtcgcgcga gaagaggaag acggacagaa atcgctctgc    18180
gcctattatg tcgcagatgg cgatccaacg gcaggtgacc ttagagcggc gcttgctgct    18240
gaactgccaa gctacatgat tccatcgtac ttcattcggc tggagcagat gccgctggcg    18300
ccgaacggca agcttgatcg taaagcgctc cctgctccga aggacgtgat ccggactgga    18360
actgatcgca tcgcaccacg aacagcattg gaagtgaagc tcgttcgcat atggcaggaa    18420
gtactcggtc tcgatcaaat cggagtgaag gacgacttct tcgaatttggg ggggcactcc   18480 ttacgcgcaa ctgcgttggc aagcaaggta agcaaggaaa tgcacgttgc tcttccgctg    18540
```

```
cgggatattt tccactattc gacgctggaa gcgatggcgc aggcgatcgg cgagttggag    18600
aagcaggagc accgagcgat tcctatcgcg ccaatggccg agcattatca attggcttca    18660
gcccagaagc ggttatacat tctgcaccag gctgaaggag cgcagcagag ctacaatatg    18720 ccggggggcga tgtccgtaag tggacacatc gatcgaaatc gactagaagc ggcgcttctg    18780
caattgattg cacgccatga cacactgcgc acaagcttcg aaatggttga tggtgagcct    18840
gtacagcgcg tacaccagca cgttgatttc gcgttagagt attcgactgc gagagagaag    18900
gatatcgatc aggttgccga gcagtttgtc cgcgattttg atctggagca gcctccgcta    18960
ctgagagtcg gactcgtcca actggagcaa gaagaacaac atctattgct gctcgatatg    19020
catcacatca tttcggacgg gatctctatg gacatattgg ttgacgagct tgctcgcttg    19080
tacgacggag aggaacttcc tccgcttgaa atccagtaca agattatgt gctgtggcag    19140 caggcagaag caagcagcga gcagatgaag gaacatgaag aatactggct gcggacattg    19200
ggcaatgaac ttccgttact ggagctgccg accgaatttg cgagaggcga gcagcgcagc    19260
tatgacggag ataagctgca cttttgcgatt gatgggcagt tgaacgagaa gctgcagcgc    19320
ttggcatccc aatcgggagc aaccctatac atggtgctgc tggcggctta tacgaccttg    19380
cttcataaat attcaggaca aaatgacttg gttgtgggta ccccaattgc gggcagaacc    19440
catgtagatg tagaaccgtt aatcgggatg ttcgtcaatt cgcttgcgat tgcaattac    19500 ccgaatgatg acaagacgtt ccgcagttat ttagaggaag tgaaggaatc gacgctgagc    19560
gccttcgagc atcaggatta tccgttcgat aagctggtgg agcagttaga ggatgcttgg    19620
gttccaggcc gtaatccggt attcgacaca atgttcgtgc tgcagaacgc aaaagcgcgc    19680
acgatcaacc tgagagaatt ggccttcgag cctctaattc catcacatac ggttgcgaaa    19740
ttcgatttaa ccttggaaat ggctattgaa cacggcatgc tgagcgggca gttgaatat    19800 tgcacgaagc tgttttccgc caacatgatt gcgaatttcg cagaagactt cttggagatt    19860
ctatctcaag cttgcgagca gcctgacctc cgcttggagg atattcaact gagcggcagt    19920
gctaatcaag aggaagaatt ggaagaagaa attgactttg cattctaa                 19968
```

<210> SEQ ID NO 9
<211> LENGTH: 19287
<212> TYPE: DNA
<213> ORGANISM: Paenibacillus strain TS-15

<400> SEQUENCE: 9

```
atggcttttg ataagaaaat cgaatttttgg aaagcgaaac tcgatactga agatacgcct      60
actactttgc cctacaccaa catttcaagc agtgaagcgg cacgacatta ttccgtttct     120
gttacgatgc ctgctgaaat tacgaacga ataattcgca tgtctaaagg ctcgcatcaa     180
gcagccttca tgatttttatt aggcggcatc caatgcttgc tgcacaaata cacgagcgag     240
aattgcatcg tcatcggcat gcctatcgtc aaaaagcag gggagaagag acttcccatc     300
aatcaagtcg tcctattgaa ggagaatgtg aatgaagagc tcacgttcaa atccttgcta     360
acctcactga acaatccctt tacagaagcg attcgacatc agaatatccc cttccggctc     420
ataactgagc agatgaatgt gcaagaaaag aatggcttgc tgtcatcaa tacgatggca     480 gctctgaaga atatacatac cgttaacttt attccaacgg ttgttgcaga tgtattgttc     540 caattttgagt tcgaggctga gaacctcctt ttgagcgttg tatataacga acgtgtctat     600
gattcagtgt ttatatcaca aatcattgag catttgcagc gcgtgctgag catcgtattg     660
```

```
cttgagccaa atacgaattt ggggaatctt cgcttgcttt cggatgagga aacatcgctg    720
ctcctgcatg gcttcaatgc gacgcctgca gagtatccgc gtgaccgaac gattcatgaa    780
ctcttcacgg aacaagcacg tcgcacgccg gatgctgttg cagcagtttt ggggcagcaa    840
cagttaacat atgccgagct aaatggaagg gcgaacaggc tggcgcgtac gttacagaac    900
gctggcgttc gaaccgatca gctcgtcggc attatggccg aacggtcgct cgaaatgatt    960
gtaggcttgc tagccatcat gaaggctggt ggggcttatg tgccgatcga ccctgaatat   1020
ccgcaggagc gtattcgtta tgctcgagag gattcgggag cgcagatgct actgcttcaa   1080
gaccatcttc gcgagcgtgt cagctatgag ggcacgatcg tggatatgaa tagcgaacat   1140
aattatcatg acgacgagac ggaacttgcc tctgtgtccg attcaagcaa cttggcatat   1200
gtcatctata cttcgggcac gacaggcaat ccgaaagggg tcatgattga acatagaagc   1260
gcagtcaatg cgctgttgtg gagaattcgg acatacgggc tttcttcctc cgaccgggtt   1320
ctgcaattat tttcattttc ctttgacggc ttcgtcatga gcgcgttctg ctcattattg   1380
tccggcgcag gtttattttt acttaaggaa gaggacgcga aggatccgct cgccttgcat   1440
ggcgctatca gccaatctgg aatcacgcac ttcatttgcg taccaaatct atacggagcg   1500
ctgctcaatg tgatgcaggc cgaatctgtg tctacgctgc gtacagtgac attggctggc   1560
gagagtgtca gcagtgcatt agtagctaga agccaggagc agcttcctga tgtgaagctg   1620
tttaatgaat atgcccgac agagaacagc gtcgtggcga cctgtgcaat cggcctcgag   1680
aaggatcaac ccatcaccat tggtacaccg atctctaatg cgagtgtgct gattttgaat   1740
acttctggag agttgcagcc gttacatgtg ccgggcgaat tatgcatagc cggtgaggga   1800
ctggcgagag gctacttgaa ccgtcccgaa ttaacggaag agaaatttgc cgctcatcca   1860
tttgtgccag gcgaacgtat ttaccatact ggtgattccg ccagatggct gccgaacggc   1920
acaatcgaat atttgggacg aattgatcat caagtcaaaa tccgtggatt ccgaatcgaa   1980
ctgggcgaaa tcgagtcgag cttgaagaat gtagcgggtg tgcgagaggt catcgtggat   2040
gcaaggccgg acggtaatgg ccaacaaatg ctgtgtgcgt acatggtagc agactctgtg   2100
cttactgtga atgaattgag ggaggcgctg tcttcccatc tgccggatta catgattcct   2160
tctcattttg tgcaaatgga acagctgccc cttacgccaa gcggcaagct ggatcgtaag   2220
tcattgcccg atcctcaggc taacattgcg attgggacgg agtatattgc accgcgtact   2280
ccacttgaag cacgtcttgc gcaaatctgg caagagtcgc ttggtgtgga aaggtcggt    2340 atcaaggata atttcttcgc ccttggcgga cattcgctgc gggccgctac attggcaagc   2400
aagcttcaca aggagttgaa cgtcaatgtg ccgcttcgtg atttgttccg taatccgacg   2460
atcgaagaac tggctttgct tatggaaggg atggagcagc aggagtttag cgcgattgaa   2520
cgggtgaagg aacgtgagta ttattcggta tcttcagcgc aaaagaggct gtttgtcctg   2580
cagcagctcg aaggtgcgga acagagttac aatatgccag gtgccatgct gctgagggga   2640
ctgctggata gagaacgcct cgaagcctca ttccgcaagc tgattgcacg acatgagaca   2700
ctgcgtaccg gattcgagct aatggacgga gaaccggtgc agaaggtgta tcagaatgta   2760
agctttgcca ttgaatatat gcaggcaagc gaggaggaag cggcgcagaa agcccgcgaa   2820
tttatccgag cgttcgactt gatgactccg ccgttgctga gggttggctt aattgaaatg   2880
gcaccggatc gacatgtgct cctctatgac atgcaccata tcatttctga cggtgcatct   2940
atgggagtcg tagtagagga gttcgctcgg ttgtacgggg gtgaagagct gccatcgctg   3000
cgcattcaat ataaagactt tgccgcttgg cagcagtcgg aagtacagca gaagcgttcg   3060
```

```
atgcagcagg aggcctattg gttgcaagca tttggcggcg aactgcctgt acttgaactt      3120
ccaacggata acgcgcgtcc agccattcag agctacgaag gggagaccta tgaatttacg      3180
gttgattcgg atataagtac ggcattgcaa cgcctcgcag cggatagcgg aacgacgtta      3240
tacatggttc tgctcgcagc ttacacggtg ctgctgcata agtacacggg tcaggaagat      3300
attgtcgtcg gcacgacgaa cgcagggaga atgcacgacg atttgcagcc gcttattggt      3360
atgttcgtca atacgctcgc aattcgcaat tatccggctg gagaatcgac gttccgtgct      3420
tatttggaac aagtgaaaga gcaggcgtta gctgcatttg aacaccagga gtacccattc      3480
gaagagcttg ttgagaagct tcgagttgca agagacatga gccgcaatcc gctgttcgat      3540
acgatgttct ccctgcaaaa tatggagaat aaggacttcg agcttccagg actccaattg      3600
aagccgtatg gcttcgaaca tcaaatatcc aagttcgatc tcagcttgga cgttgcggaa      3660
ggagcggatg ggctcgcttg cagcttggag tatgcttcgt ccttatacag acaagacaca      3720
atcgtaagaa tggcgaatca ttatcgacag ctgcttcatt caattgcaca gtcgcctgag      3780
gcgcaaatcg ccgtgctcgg gatgttgacg ccgggtgagc aagagcagat tcgattcaag      3840
ttcaatcatg atccgtcaga tatggagcag aagcacacgg ttcatcaact ctttgaggag      3900
caggccgctc ttacaccgga acgaactgcg gtcgtgcatg agaatgaaca actgtcgtat      3960
caggagttga atgagagggc gaaccgtctg gcacgtacgc ttcgtcaaca cggcgtgcag      4020
ccggagcagc tcgtcggcat cttggcagat cgttcgctgg acatgatcgt gggcattatg      4080
gcgatcttga aggcaggcgg cgcttacgtt ccaattgatc cgaaatatcc ggaagaacgt      4140
atccgttaca tgctggagga ttccaaggca aatgtattgg tgacgcagag ccatttacag      4200
tctctctcat cgttcgacgg tacatggggtt ctgcttgatg aggagtcatc ctatgctgag      4260
gatgctgcca atcttgtgtc catcaatgaa ccacaacacc tggcttacgt catttataca      4320
tcgggcacga cggacagcc gaagggtgcc atgatcgagc acagacaact gacagttatg      4380
gcgaaggctt gggaacgtga atatcgtctg cgggaagaga gcattcgctg gatgcaatgg      4440
gcgagcttct cattcgacgt atttcaggc gatttgattc gtgcgctgct gcatggcgga      4500
gagctggttc tttgcccaga gcacgcacgt gcgaatccgg ctgaaatcta cgaattgatc      4560
cggaagcatc gtcttcatat gttcgactgc acaccgtcta tcgtcattcc gctcatggaa      4620
tatgtgtatg agaacaagct ggatatcagc agcttgaagc ttgtcgccgt tgggtcggac      4680
tattgcccgc cggatgagtt tcagaagatg ctggatcgat tcggttcgca gttccgcatc      4740
attaatagct acggcgtgac ggagacatgc atcgatgcca gctattatga accaacgact      4800
ccaactgttc caagagcgct gccgattgga aaaccattgc cgggtgtaac gatgtacatt      4860
atggacggac agcgttcttt gcttccggtt ggtgtcatcg gtgagctcta catcggcggc      4920
ccttgcgtcg gccgtgggta ttggaatcgt tcggaaatga cgagcgagaa attcgtcgca      4980
gatccattcc tccaggatca ccgaatgtac cgcacagggg atctggctcg ctggatgccg      5040
gatggcaaca tcgaatattt aggccgtatc gaccatcagg tgaaaatacg cggttatcgc      5100
atagaaatcg gcgaagtcga gtccaagctt cttaaagtgg agactgttcg ggagagtgtc      5160
gtcgtggcgc gtcaggatcc gaacgggaca aaagcattat gcgcttattt cgttgcggat      5220
cgcaatctga cggtgagtga actgagaagc gcaatggctg atgaattgcc cgcatatatg      5280
attccatcgt atttcgttca attggaccgc ctaccgctta cgccgaatgg aaaagtcgac      5340
cgcaaggcgc tgcctgcccc ggaagcggga gcgcacacgg gcattgaata catggcgcca      5400
```

```
cgcacggaag aggagttagc gctggcgaat gtatggcaaa ctgtccttgg tattgaacga    5460
gtcggtgtgc tggatcattt cttgagctt ggaggcgact ccatcaagtc tatccaagtt    5520
gcttcccgat tgcagcaagc aggctataag cttgaaattc gcgatctgtt caagtatcca    5580
acgattgccc aattggggtc acacttgcag agggcaagca aggtcgcaga tcagggcgaa    5640
gtatcaggtg acgtgccgct tacgccgatt cttggatggt ttttcgaaca gcagtttgcc    5700
gacgcgcatc actataacca gtcgatcatg ctgtaccgga gagaaggctt taacgaagcg    5760
gcaatccgca atgtacttca ggcagtaacg gaacatcacg atgcgctgcg catcgtattc    5820
cgacggaatg atcaaggtga ttatacagct tggaatcggg caatcgaaga aggagaattg    5880
ttccatctgg aagtgctgaa ccttacagga acaacagcag gtgatcatga gcagaatgta    5940
cggcagatca ttgaagccaa ggccacggag attcagcgta gcttcgacct gcacgatggg    6000
ccgttggcaa gagcgggatt gttccgtacc gatgaggggg atcatcttct tcttgtcatg    6060
caccatggcg ttgttgacgg tgtgtcctgc cgcatcctgc tggaggatat cgctactgga    6120
tatgaacaag cgttgaaggg agagcctgtt cggctgcctg ccaagacgga cagcttccgc    6180
acatgggcga atcagctcgc gtcatatgca cgaagcgaag ccatgataga ggaacaaatc    6240
ttctgggaac aggcagaagc gaatggaacg agtattttgt ctttgccgaa ggatttcgaa    6300
gcggagacat ccttgcagca ggatagcgaa tcggtcgtag tggaatggag ccggggaggag    6360 acggatatgc tgctgaagca tgttcaccgg gcttataaca cggacatgaa cgacattctg    6420
ctcgcagcgc tcggcatggc tatacagcaa tggtgtggac atgagaaagc cctagttaca    6480
cttgaaggac acgccgcga gaatatcatg ccggagcttg atatttcgcg cactgtgggg    6540
tggttcacga gtgaatatcc atttctgctc gagagcgatc cgaacaagag tttgtcctat    6600
cgaatcaaac gaatgaagga aaatttgcga cggattccga acaaaggcat cggttatggc    6660
attcatcgat atttatcggg ctcaggtacg tctggtacga aaaatgtatc acgatcagaa    6720
gcatcagctc agccagaaat cagcttcaac tatttgggac aattcgatca ggatttgcag    6780
aacaatgaga tggaagtctc tccatattcg ggcggcgcag agataagcgt tcgtcaggct    6840
cgtaacacca cgcttgattt taacgggatg atatcggctg gggttcttgc attggaagtg    6900
agctacagca gcaagcaata ccgccgcgat acgattgacc ggctggcagg attgctgaag    6960
ggaagtttgc aggagatcgt tgcttactgc gcatcgaaag acaagcctga attgacacct    7020
agtgacgtat tagttaacgg gcttggtatt gaggatctgg agcgtattgc ggagcagacg    7080
agggatctcg gggacatcga gaacatttat gcactgacgc cgatgcagaa gggaatgtgg    7140
ttccataatg cgatggacgg tcaagcgggc gcttattttg aacagactcg ctttacgatt    7200
caaggagagc ttgacgttca gctattcgca agcagcctag atgtactcgc gacgcgccat    7260
gcggtgcttc gcaccaattt cttcagcggc tggaacggag aattgctgca aattgtatac    7320
cggaacaaga atctggaatt tagttacgag gatctatcgg aattgccgga gcatgagaag    7380
caggatcgag ttgaagcgat ggcgcaagct gacaagcagc ggggcttcga tctggagcgc    7440
gatgcgctca tgcgggtgtt cgtgttgcgg acgagcttga actgcagtca tgtcatttgg    7500
agctctcatc atattctgat ggacggctgg tgcttgccgc agctcacgca agaatggctc    7560
gagacgtatt ccgattccgt aaatggacgg tcaagcagcc gatcgggagc atcgccatac    7620
agtctctata ttgaatggct gtacaagcag aattacacag ctgcatccca gtattggagc    7680
gactatctgt cggattacga tcagcaaacg gttcttccgc agaagaaatc gagcgggcgc    7740
agcgatgtat atattgctga caatctcgtt tttgaactgg gcgaggcttt aactgcgaag    7800
```

```
atgcatcggg tagcgaagca gcatcagctg acgctgaaca cgctaatgca ggcggcatgg    7860
ggcattattt tgcagaagta taacaatacc ggggacgctg tattcggcgg agtcgtatca    7920
ggcagaccgg cggaaatccc aggtattgaa tccatgattg gactattcat caacaccatt    7980
ccgattcgag ttgtgtgtga agcggatgac agatttgccg acgtgatgaa gcagcttcag    8040
gagaaggcac tggagtcagg gcggtatgat tattatccgc tgtatgacat ccaggcgctc    8100
agcacgcata agcaggattt gattaatcat attctggtgt tcgagaatta cccgatggaa    8160
gagcaaatgg aacaggctgg tgatgagcgg ggacaattga acattactga tgtgcgagtg    8220
gctgagcaga cgagctatga tttcaatctc gtcgtgatgc caggcgagga tatgatgatt    8280
cgcctcgagt acaatgccgt catgtatgat cgagcagaca tggagagaat acggcagcat    8340
ctgattcacg tcctcaagca ggtaacagca gatccggcca tagctgtgaa agacgtccgt    8400
ctggcgaccg acgacgagaa ggcagagctg ctgacggcat tcaatgatac ggaagtcgaa    8460
tatcctcgcg aacagatgat tcatcggatg ttcgaagagc aggttcagcg gacgccggat    8520
gcgacggcgg tgttgtgtgg agcagctaca atgacctacc gggagatgaa tgaacgtgcc    8580
aatcagttgg cgcggacatt gcgggcagca ggcgtcgtac cggatcagat cgtcggtata    8640
atggcggaac gatcgcttga actaatggtc ggcatcatgg ggatattgaa agctggcggc    8700
gcctatgtgc cgatcgcgcc ggattatccc gaagagcgca tccgatatat gctggacgat    8760
tccgaggctc aagtactgat tgttcaaggc agcgcgggtg aagcaattga ttttgcgggt    8820
cacgttatta atctggacga tgttgactcg tacgatcagg acagttcgaa ccttgagatg    8880
gtcaacaagc cgaccgatat cgcctacatt atctatactt caggtacgac cggacgtccg    8940
aaaggggtta tggtcgagca tacgtcagtc atcaaccgct tgttgtggat gcagaagcgg    9000
tacccgattg atgcggatga caccattatg cagaagacgg cgatcacgtt cgacgtatct    9060
gtttgggagt tgttctggtg ggcatttgtc ggatcgaagg tgctaatgct tccagttggc    9120
ggagagaaga atccggcagc aatcgttgag gcgatcgaac agtacgatat ttctacaatg    9180
cactttgtac catctatgct gcatgccttc ctcgagcata tcgagcagct gcctgaagcc    9240
gaacgtgagc gtctgtctcc actgaagcag gtgttcacca gcggagaggc tctattggca    9300
tcgcaggtcg agcgattcca tcagtatgtt gcacctgcca gcggagcacg actcatcaat    9360
ctgtacggtc cgacagaggc gacggtggat gtcacgtact tcgactgcga accaggccaa    9420
acgtatgtga gcgtgccgat tggcaagccg attgacaaca cacgcattta tattgtgaac    9480
gggaacaatc aagtacagcc gatcggcgta gcgggcgaac tgtgcatcgc gggcgtcgga    9540
ttggcgcgcg atactggaaa tcgccctgaa ctgacagaag agaaattcgt attggtgcct    9600
tccgtgggtg aacggatgta ccgaacgggg gatctcgcgc ggtggctgcc agacggcaac    9660
atcgaatatt tgggacggat tgatcatcag gtgaaaatcc gcggctatcg aatcgagctt    9720
ggcgagcttg agactgcgct gctgaaaatt gacgcggttc gggagacagt cgtcgttgcg    9780
agggaagacg agagcggaca gaagtcactt tgcgcctact atgtagcaga cggagaagca    9840
acagtaagtg acctgcgagc cgcgcttgcc gccgaactgc cgagctacat gattccatca    9900
tacttcgtaa gactggagca gatgccgctg cgccgaacg gcaagctgga tcgcaaagct    9960
ttgccggctc cagagagaag ccttcaagtt gaatcggaat atgttgcgcc gcgcacggaa   10020
gcggaacaga tgctggcaac cgtatggcaa gccgtacttg gcatcgaacg tgtcgggata   10080
accgatcact tcttcgagct tggcggagat tccatcaagt ccattcaagt ggcagcaaga   10140
```

```
atgcagcagg cgggcttcaa gcttgatatt cgcgacttgt tcaaatactc aacggttaca   10200
cagttggttc catacatgca gccgattaat cgaacggctg atcagggaga agtcgtcggt   10260
gaggtgccga tgacaccgat tctgcattgg ttcgagcatc agcagtttgc gaatccgcat   10320
catttcaatc agtcggtaat gctgtatcgc aaggatggct tgtcgcaga tgcagtgcgc    10380
aaggcgcttc ataagttggt tgaacaccac gatgcgcttc gtattgtaat tcagagaacg   10440
gaacaaggag aatattcgct ctggaatcga tccctagtag agggtgagct cttcagtatg   10500
ggagagatcg atttaacgga tcagtcggat ttcgccgcag cgattgaagc ggaagcaaac   10560
cacattcaag gcagtattga tctacaagcg ggacctttgg tcaaggcagg cttattccat   10620
ggcagtgacg gtgatcactt gctgctcgtt atccaccacg cagtcatcga tggcgtgtct   10680
tggagaatat tgcttgagga cctcgcagca ggctatgaac aggcgctgaa tcaacgccag   10740
gtgcgtctgc cgatgaagac agacagcttc cgtacatggg cggaacagct agtagagtat   10800
gcgaatagtc cagcgatgga taaggaatct gcttattggc tcagcgtcgc gcagacggaa   10860
gtggcggccc tgcctaaaga cagcgagtgt acagtttcct tgcagcgcga cagtgaatcc   10920
gttgtgctcg agtggaataa ggaagatacg gaacggcttc tgaagcacgt tcaccgcgct   10980
tacaacaccg aaatgacga tattctgctc acagcgcttg gcagagcact catgaagtgg   11040
cgcggcatcg accgcgtact ggttacgctg aaggacatg gtcgcgagtc cattttacaa    11100
gacatggata ttacgcggac ggttggctgg tttacgaccg aatatccgtt tgagctcggg   11160
atggaagcga acgacagtct tggatctcag atcaagaagg taaaagagga tttgcgccgc   11220
attccgaaca aaggaatcgg gtacggtctg ttccggtatt tatccaattc gggcaaacag   11280
gcttggaatg atgcgccaac gacacaaatt cgttacaact acctgggaca gttcgatgcg   11340
gacttgagca ataacgaact gagcgtatct ccatatgcaa gcggttcgga gattagcgat   11400
gagcaggagc gcaagtatcc gctcgatatt aacggcgtta tcgcagaagg ccaattgacg   11460
ctgggcttaa gttacagtgt caaggagtac cacaaagaga cgatggagga attgggcgat   11520
ctccttacag aatcactgaa ggaaattatc gcacactgcg aatcacagga acggacgcaa   11580
ttgacgccaa gtgatgtctt gtttaaggga cttagcttgg agtggctgga tcggatatct   11640
tcgcaaatgc agcatatcgg agagatcgag aatgtatatg cattgacgcc gatgcagaag   11700
ggaatgtggt tccacagtgc gatggatagt ctgacagggg cgtaccatga gcagacgatg   11760
ttcacattgg aaggtacgct tgatgtggaa ctgttctcca gcagtctgaa cgaattggcg   11820
aagcggcacg ctgtgttgcg aacgaacttc attagcggcc ctcaaggcga accggtacaa   11880
gtcgtattcc ggaacaagcc aatcggattt tcattccagg atgtgcgcgc tctgaatgaa   11940
gaggagcagc aatccttcat taaggaagcg gtcagcagtg accaactgct ggcttcgat    12000
ctcgcacaag gtgccttgat gcgcgtttcg gctatccgta caggggaatt gagctgccgt   12060
gtactgtgga gctctcacca tatcttgatg gacggctggt gcctgcccca gctgatgcaa   12120
gagctgttcg atacgtatgc cgccttgctg cagaagaagt cgccggatag aacagtggtt   12180
ccagcttaca gccaatatat tgaatggcta gggcagcagg acgaggaggc ggccgggact   12240
tattggtctg catacttggc tgattacgat caggtaacag agatcccaca agaatcatcg   12300
gcgggaatcg atagcgaacc atataaggct gaaaaatgga gccgtgaatt ggatgctggc   12360
ttgagcgcat ccatcagccg ggcggcaaga cagcatcagg tcacgctcaa tactttgctg   12420
caagcggcat ggggcgttat tttgcaaaaa tacaatggca caaatgatgt tgtattcggc   12480
agcgtcgtat caggcagacc agcggaggtg ccaggcattg agacgatgat cggcttattc   12540
```

```
attaatacga ttccgatccg cgtcaagtgc gagggaagca ccagctttgc ggaactgatg   12600
gggctgcttc aagagcaagc gctggagtcc ggcaagtacg attattatcc actgtatgag   12660
atacaatctc gcagtgcgct gaagcagaat gcgatcagac aaattatggt gttcgagaac   12720
tacccgatgg acgaacagct agagcaggcg ggcggcgacg agcacggtat gccatcctta   12780
actgatgtag cggtggagga acagaccaat tacgacttca acttgatcgt cgtaccggga   12840
gaacagatct ctattcggtt tgattacaat gctaaccgct tcgtacaagc agacatggaa   12900
cggttgatgg ggcatttgaa caatattttg gagcagatcg tagacaatcc acgggttgct   12960
gtagaagatc tggagctcgc gacggaagcc gagaagtcgg aagtgatcca atcattcaac   13020
gatacactta cgaactaccc gagagacatg atgctgcatc gcttattcga ggaacaagcc   13080
gaacgacatc ctgatgcagt agccatctcc ttccgagatg tccagatgac gtatcgtgat   13140
ttgaacgatc gggcgaaccg attggcacgc acactgcggg cagtcggagt tggaacggat   13200
aagctggtag gtctcatgtc tgaacgttcg ccggatatga ttattggtat tctggcaatc   13260
ttgaaggcag gaggcgggta tgtgccaatc gatccggaat atccggaaga acggattcgg   13320
tacatgcttg aagattccgg tgcgcgaatc atgctggcac agcagcactt aacggggaaa   13380
attccagcaa tggacgcttc accacttgat gcaattatca atcttgacac cgaaacatcc   13440
tatgacagca acggttcgaa tcttgaggcg aacacagatg caagcagcga gaacttagcc   13500
tatgtaatct acacatccgg cacgacgggt aagccgaagg ggaacttgac gacgcaccgc   13560
aatattgtac gtgtggtgag agaaaccgag tacatcgaca tcacgaatca tgacaacgtg   13620
ctgcaaatgt ccagctatgc atttgacggg tcgaccttcg acatctatgg cgcactgctg   13680
aatggggcca agcttgttct tgtaccacac gagacgcttc tggaagtgcg gcaattggct   13740
gagttgatcg tacaagagaa gatttcggtt atgttcatca cgacggcgta cttcaacgta   13800
ctggttgatg tccaggcttc ctgcttgagc aatattcggg ctatcttatt cggtggcgaa   13860
cgggtatctg tcagccacgt ccgcaaggcg cttaatcatg tcgcgccagg tacactcaag   13920
catgtatacg gcccgacgga gagcaccgta ttcgcgactt gccacgatgt atacgaagtc   13980
acggagaatg cggtgacggt accgattgga cgtccgatca gcaatacgtc aatctatatc   14040
gttgatgcga acaataagct gcagccagta ggcgttgccg gcgagttgtg cgtggcaggt   14100
gatggattgg cacgaggata tttgaatcgt ccagacttga cggcagagaa gttcgtcgat   14160
tccccgtacg tccagggaga gcggatgtac cgcacgggag acttggcgaa atggcttcct   14220
gacggttcca ttgaatatgt tggccgaatc gaccaacagg tgaaaattcg cggatatcgg   14280
attgagctag agagatcga ggcgcagctg ctgaatgtag aggatgtgca ggaagcggtc   14340
gtcgtcgcac gagacaatga cacaggcgag aagcagctat gtgcctacta tgtagcgatg   14400
cgtccgcttg aggcgaatca tttgcgcgaa gtgatgggtc aagctatgcc aagttacatg   14460
ctgccagcgc actttgttca gctggaacag cttccactca caccgaacgg caaggtagac   14520
cgcaaggcgc tgccggctcc ggaagaagga cggagcggag agactttcgt tgcaccgcga   14580
acgccgcttg aagcacagct tgttcaaatt tggcaggatg tgctcggtat tagcagtgta   14640
agcgtgacgg ctcatttctt cgagttgggt ggtcattccc tgaaggcgac gctgctcgtg   14700
aacagactgc atcaggagct taatatcgag ttgccgttga aggacgtatt tcaatatccg   14760
acgcttgaag cgatggcgaa gcgacttagc aatgcggaag gaagcaggca tgtgagtatc   14820
ccggtggcgg ctccaagcca gcattatccg gtgtcttcgg ctcaaaaacg cttgtatatt   14880
```

```
cttcatcagc ttgaaggggc ggagctgagt tacaacatgc cgaacatgct gctgcttgag   14940
ggagctgtgg atcttgggcg attggaagaa gccttcaaga gactgattga gcgtcatgaa   15000
acgctgcgca ccggatttga gatcgtgaac ggcgagcctg ttcaacgaat ttacccggaa   15060
gtagacttcg caatcgagca tgtgctcgca agcgaggaag gtgcttcgaa gcttatgcag   15120
cagtttgtgc gttccttcca attggagaag ccgcctctgc tgcgaatcgg agttatcgaa   15180
ttgtccgaag aacgctccat tctcatgttc gatatgcatc atatcatctc agacggttcg   15240
tcgatgggca ttctcatcaa tgaatttgtc cacttgtaca gtggagaaga gcttacgccg   15300
ctgcggattc aatataagga ttacgccgta tggcagcaat cggatactca gcaggaggca   15360
atgaagctgc aagaaggata ttggctgaag gtactggggg gagagcttcc ggtgctggaa   15420
atgccgacgg actccattcg tccgacaacg caaagcttcc gcggagattt gctgcagttc   15480
gatctagatc cagtgagaag tgcggggctg cggagaattg cagcggagaa cggagccacg   15540
atgtatatgg tgctgctcgc gctgtacaag acgatgctgc acaagtactc cggtcaagag   15600
gacattatcg taggtacgcc gatcgcaggc cggaaccatg gagacttaca gccgcttctc   15660
ggcatgttcg tcaatacgct ggccattcga agctatccgg cagccagcaa gactttcttg   15720
tcctatttgg gtgaaataaa agaatcaacg cttggcgcct tcgagaatca gaattatcca   15780
ttcgaggcat tggtcgaaca ggtgcaagtg atgcgcgata tgagccgcaa tccggtattt   15840
gatacgatgt ttattttgca aaatgcggat caaggtgaaa tgaagattga tgggctacga   15900
ctccagtcgg tgccgaatga acacaccgta tccaagttcg atttgacctt ccaagcggaa   15960
gaggatgaag cggaaatcgt gtgcagcatt gaatacgcaa cagatttatt taagcgaggt   16020
acgattgagc gaatggcaag acatttcgaa caattagtcc atacggtgct ggataacccg   16080
caagcaagtc tgtctaactt gagcatggta acaaatgagg aaaaggctct gcttcaggat   16140
aagttcaatg atacggatat ggcgcatcca agcgacaaga cggttcatga actgttcgcg   16200
gaacaggtgg agcggacacc agatgctgtt gctgtcgtct ctggcagcga gcaattaagc   16260
tacggagatc tcaaccggaa agcgaatcag cttgcgtgga agctgcgtga gtatggcgtg   16320
accgcagagc agcctgtcgg cattattgtc gagcgaacgc tggatactgt cgtcgcagtg   16380
ctggctgtac tcaaagcatc gggcactttc gtaccgatcg atcccgaata tccagagacg   16440
cgtattcgct atatgctggc agacagcggg gctaagctgg ttttggcgca atcggagctg   16500
tcagggatca ttcctgatga cgtccgcctg attgatgtac gcgatgagtc cctataccaa   16560
ggcgacggag ctgacgtacc aaatggcagc aaaccgtcca acctgctcta tatcatctac   16620
acatccggaa cgacgggcaa tccgaaaggg gtcatgctgg agcaccgcaa catggtcaac   16680
ctgctgcatt atcagcagaa aggcacgaac attccgatgc cttcgcggat tttgcaatat   16740
gcgtctggca gcttcgatgt atgctatcag gaaatgttct ctgcgctcct gttcggcgga   16800
agcctgtata tggttgacaa tgagatgcgc aaggatccgg tacgcttgtt ccaggaaatc   16860
gaaaagcatg aaatcgacgt gatgtacatt ccagtggcgt tcctaaaatt catcttcgcc   16920
gagccggagt gggcagaagc gttcccgcgc tgcgttcgcc atatcattac ggcgggcgag   16980
cagttggtcg tgacaccgca agtgcaggct tgcttgaagc gactcgatat ctgcctgcac   17040
aaccattacg ggcatcgga gactcatgtt gtgacgacct acacgatgac gccggaagtt   17100
atcgaggttg gtctgccgcc aatcggcaag ccgattgcga acacgagcat ttatatcgtg   17160
aatgacagct ttgagctgca gccgatcggc gtgaagggcg agctctacgt atccggggca   17220
tgtgtcggac gcgggtactg gggaagaacg gacttaactg aggagaagtt ccttgataac   17280
```
ccgttcgccc ctggcgagcg gctgtacaag acaggtgacg tggcgcgctg gcttccagac   17340
ggcagcattg agtatgtggg ccgaagcgac catcaggtga aaattcgggg cttccgcatt   17400
gagctgggcg aggtggaatc gcagttgctg catgtaccgg cggtacagga ggcgaccgtg   17460
gtggcactgg aagatcatgc gggtcagaag cagttgtgcg cgtatttcac agcagaatgc   17520
tcactcacgg ccggcgagct gcgggcagca ttgtcgcagg agctgccagg ctacatgatt   17580
ccgtcctact tcgtacagtt ggagcgactg ccgctgacgc cgaatgggaa gatcgatcgg   17640
agagcgctgc cgaagccaga aggcggcatt gagactggaa cggagtatgt cgcgccgcgt   17700
acagagacgg aagcaaggct tgcacgcatt tggcaggatg tattgggatt agcaagcgta   17760
ggcgtgaagg acaacttctt cgagcttggc ggtcactcgc tgcgggcaac gacgctggtg   17820
agcaggctgt acaaggaaat gaacgtcaac ttcccgttaa ggggtgtgtt ccgtcatccg   17880
actatcgagg agatgtctca agcaatctcg caaatggaga cctcattgta tacagccatt   17940
ccgatcgccg aggagcaaga atactacccg ttatcttcgg ctcagttgcg actctatatc   18000
atgagccagc tggaaggaag cgagctcagc tacaatatgc ctggcatgct ggtgcttgaa   18060
ggacagctga atcgagatca attccagacg gcatttttga agctcatcgc tcgtcacgag   18120
acattgcgta ctggctttga tggtagac ggcgagccga tgcagcgcat ccatcgcaat   18180
acggaattcg ctattgacta cagacaggta tccgaggacg aagttccgga gataattgga   18240
caattcatcc gaccgttcga cctggagcat ccgccattat tgcgggtcgg gttgttcgaa   18300
gttgggcagg atcggcatat tctcgtcttt gatatgcacc acatcatttc tgacggtgcc   18360
tcaatgagca atctagttga tgaatttact cgattgtatg cgaatgaaga acggccgccg   18420
ctgcgtatcc agtacaagga ttatgcagta tggcagcagg cgagtgagaa tcttgagagg   18480
ctgaagcgcc aagaagacta ttggatgagt atgctgcaag gcgatcttcc gaacacagag   18540
ttgccgttgg attatgatag agcggcggtt cgcagcttcg aagggagca gatcgaattc   18600 gaaattaacc cggttgtgac gggccagctg aaccaacttg cttctaatca tgagtgcacg   18660
ctgtacatgg tgttattgtc cgcctatcag attctgttat ccaaatattg cggtcaggat   18720
gacattattg tcggtactcc tgttgcgggt cgcaatcatg ccgatttgga gccattgatc   18780
ggtatgttcg tcaataccct cgcgattcgt aaccgtccgc agggcgataa aacgttccaa   18840
tcgttcttgg cagaggtgaa agagtcaaca ttaggggcat tcgaacatca ggagtatcca   18900
ttcgaggaac tgattgacct cttgaagctg cagtgggaga caagccgcaa tccattgttc   18960
gatacggtgt tcgtcctcca gaatacggag gagcgtgaag ccggaatcgg tggactgacg   19020
atatcgcctt acgtgacaga tgactcggtc agcgcgaagt tcgatctgac gctgtctgta   19080
tcggaagaag acgatggtat gaagggaagc ttcctgtatg cttccaagct gttcaaagca   19140
gctggcatac acagaatgat gagagattac ttgtcaatac tgtcccaagt atgcgagaac   19200
cctcgcatcc gcattcaaga tatttcgata agtggacagc agacacagga aaagagcaag   19260
atcgacacga tcgagttcgc gttctaa                                      19287

<210> SEQ ID NO 10
<211> LENGTH: 9504
<212> TYPE: DNA
<213> ORGANISM: Paenibacillus strain TS-15

<400> SEQUENCE: 10
atgaagtcgg tatatgagaa agaagaagcc tattggaatg ggatgtttga ttcggatgac   60

-continued

| | |
|---|---|
| agcatgagca tcttgccata ttgcagtaca cacggaagag aagcgaacgc ggatacgaat | 120 |
| gccgccaaag tgtctatgat ccgggcactc ccttcagaac tgtcagacag aatgaacacc | 180 |
| cttgcgaacg gttcggatat tgccctgtac atgattggat tggcaggggc cacttgcttg | 240 |
| ctccaccatt atacgaaccg agaaaatgtg cttgtaggca tgccgacgat agatgaatcg | 300 |
| gatgatgact catcacctcg tgacgtactc attatgaaga cgaatttgac acgcggaagc | 360 |
| agcttccgtt ccgtattggg gtcaatcaag acagctgtcg gaggagcagt ggagcatcgt | 420 |
| catcttccgt ttcggaagat ggtacacaac ctaaacctgg agatggacac gaacggactt | 480 |
| ccggtgatga atacggtagt gtcttattca gccatacata ccgcttctat cgaccttagt | 540 |
| gtcagctccg acgtcatgtt ccgattcgat gcgaaggacg atggccttca tttggaggtg | 600 |
| ctttatgatg aaagccgcta tgacgcctcc tatattgcca ctctattcga acattttttc | 660 |
| cgactgcttc attttgtgtt attccagccg gaccagccta tcggcaatgc cgtgttattg | 720 |
| tcggaagatg agaagcatcg cctgcttcat gaatttaacg atgtgtggac ggatttccct | 780 |
| cgtcaagcaa cgctacatca gttcattgag gaacatgcgg aacgacagcc agaggcaatc | 840 |
| gcggtttctt atgaagatac caagctgacg tatcgtgagc tgaatgcccg ggcgaatcgc | 900 |
| cttgcccgaa cacttagatc tgaaggtgtg cagccagaag cgctagttgg tctcatggct | 960 |
| gaaagatcga tcgacatgat tgttgggatg cttgccgttt tgaaggcggg aggcggctac | 1020 |
| gtcgcgattg atccggaata tccggaggag cgcgttcgct acatgctgga agattcgggt | 1080 |
| gctcgtgtca ttctggttca gcagcatttg cagaatcgtg tgccaaatac ggaatcagca | 1140 |
| gctagactcc ttacacttga cgatgagcag tcttatcatg aggatgcttc gaagttggaa | 1200 |
| tcgaagagta cagctgtaga tttggcttgc gtcatctaca cttcggggac aacgggcaat | 1260 |
| cccaaaggta acctgacgac acaccgcaat atcgtacgca tcgtgaagaa taccaactat | 1320 |
| atcgaaatta cggagcagga taaggtactg caattatcga gttattcttt cgatggctcc | 1380 |
| gcattcgata ttttcggggc attaacgaat ggggcccaac tggttcttgt tcctcatcat | 1440 |
| acattgcttg atgcaagcaa gctggcggag ctgatcgaaa cggaacaaat atcggttatg | 1500 |
| ctgattacta ctgcttattt caacgttctt gtagacgtga acgtatcctg cctgcgccat | 1560 |
| atccgcgcga tattgttcgg aggcgagcgc tcttctgtcg cacatgtgcg acaagcactt | 1620 |
| gaacagacag ggccaggaag gctgaagcat gcctacggtc cttctgaaag tacggtatat | 1680 |
| gcgacatggc atgatgtgac agagatttcg gagcaagccg taagtgtacc gatcggtcgt | 1740 |
| cctatcagta atacagccat ctacatcgtc aatgaacgaa atgatttaca gcctataggg | 1800 |
| gtatccggtg agctgtgtgt agcgggagaa ggattagttc gtggatattt gaaccgtcca | 1860 |
| gaactgactg cacagaagtt cgttgataat ccgttcgtac cggagagcg catgtatcgt | 1920 |
| actggggact tggcgagatg gctgccggac ggaacgattg aatatgttgg ccgaatggat | 1980 |
| gatcaggtga aaatcagagg ccatcgcatc gagattgggg aagtagaggc gcagctgctc | 2040 |
| aaagtggcgc tgattcagaa ggcgacgatt gtcgtccgag ccgcgaggga cggagagaag | 2100 |
| cagctgtgcg cgtattatgt agcagatcgt ctgctttctg caggcgagat tagaacaata | 2160 |
| cttgccaaag aactgcctag ttatatgatt ccggcatact tcattcagct tgaacagatg | 2220 |
| ccattgacga ctaacggcaa ggtagatcgt aaagccctgc cagcaccgga agagcacgta | 2280 |
| caagcagaga cggaatatgt ggcgcctaga agtgaacaag aaattcggct tgcgagagtc | 2340 |
| tggcaggaag tgctcggtct aagccgagtt ggtgcaaagg atcatttctt cgagctgggc | 2400 |
| ggtcactcat tacgagcgac gacactagtc agcaagctgc acaaagaaga gaatatcagc | 2460 |

```
ctgtccctcc gcgacgtgtt ccgcaatcct actttggaag cgatggccgc gctcatggaa    2520
gctgctcaag gccgcacatt ctcaccaatc ccgacagttg aagagaagga tgtatatccg    2580
gtatcttcgg tgcagaagcg attgttcatt ttgcatcagc tggaaggagc agagcagagc    2640
tataacatgc caggggcatt actgcttgag ggtgatgttg accggaaccg attggagcat    2700
gcattccgtc agctgatcac acgtcacgaa acgcttcgca ccggctttga tggtgaat     2760 ggagaacctg tgcagcgcat ttatccgact gtagaatttg tagtggaaga gatgtcggcc    2820
gtagaagggg cggaagccga gaagcaaatt cggcaattca ttcgcgcttt cgatctgtcc    2880
acaccgccac tgttcagggc agggctgatt gaacttgctc cgcagcgtca cattctccta    2940
ttcgacatgc accatatcat ttcggacgga acgtcaattg gcattatgat cgaggaattc    3000
acaagcttat acagtgggaa cgagcttgag ccgcttcgca ttcagtacaa ggactttgct    3060
gcgtggcagc gttccgagga gcagatcgag cagttgaaga gccaagaagc ctattggctg    3120
aggcaaatgg aaggcgtact tcctgtgctt gagctgccta ctgattatgt acgtcctgct    3180
gtacagagcc atgatggcgc gttgttcgag ttctcgattg atcgtgagca gagccaagac    3240
ttgaggaatt tagccgccga tacgagaacg accttgtaca tggtgctgct agcggcatac    3300
acgatcatcc tccacaagta ttcaggccag gaagacattg ttgttggaac accgattgcg    3360
ggtcgaacgc acgacgatgt gcagccactt atcggtatgt tcgtcaacac gttggcgatt    3420
cgcaattatc cttctgggtc taagtctgtg cttacctact tggaggaaat caaagaaacg    3480
acgctgggag cgttcgagca tcaagactat ccgttcgagg aactcgtgga aaacgtgcaa    3540
atttcgcgag atatgagccg tcatccggtg ttcgacacga tgttcgccct tgagaataca    3600
gagcatcggg aattcgatct ggatggtctt caggtaaagc cgtacggtgc tgaacacggg    3660
atggctaagt ttgatttgaa tctgaccata acagaagatg gcgatggact ttactgcacc    3720
atggagtatg ctacagcatt gtacaatcgc tcgacgatcg caaggctttg cggccatttc    3780
ctgcaggtcg ttggaagcat gactcataat ccgcaagcgg caatctcatc actgcaaatg    3840
gtaaccatcg aggagaaggc tgagctgcaa gatgaattca atgatacgga tatggtgtac    3900
ccaagtgaca agacggttca tgaactgttc gcggaacagg tggagcggac accagatgct    3960
gttgctgtcg tctctggcag cgagcaatta agctacggag atctcaaccg taaggcgaat    4020
cagcttgcgt ggaagctgcg tgagtatggc gtgaccgcag agcagcctgt cggcattatt    4080
gttgagcgaa cgctggatac agtcgtcgca gtgctggctg tactcaaagc atcgggcaca    4140
ttcgtaccaa ttgatcccga gtatcctgag acgcgtattc gctatgctg gcagacagc    4200 ggggctaagc tggtgttggc gcaatcggat ctgccaggga tcattcctga tgacgtccgc    4260
ctgattgatg tacgcgatga gtccctgtac caaggcgacg gagctgacgt accaaatggc    4320
agcaaaccgt ccaacctact ctatatcatc tacacatccg gaacgacggg caatccgaaa    4380
ggggtcatgt ggagcaccg caacatggtt aacctgctgc attatcagca gaaaggcacg    4440
aacattccga tgccttcgcg gattttgcaa tatgcgtctg gcagcttcga tgtatgctat    4500
caggaaatgt tctctgcgct cctgttcggc ggaagcctgt atatggttga caatgagatg    4560
cgcaaggatc cggtacgctt gttccaggaa atcgaaaagc atgaaatcga cgtgatgtac    4620
attccagtgg cgttcctgaa attcatcttc gccgagccgg agtgggcaga agcgttcccg    4680
cgctgcgttc gccatatcat tacgcgggc gagcagttgg tcgtgacacc gcaagtgcag    4740
gcgtgcttga agcgactcga tatcagcctg cacaaccatt acgggccatc ggagactcat    4800
```

```
gtcgtgacga cctacacgat gatgccagat gttatcgagg ttggtctgcc gccaatcggc    4860
aagccgatcg cgaacacgag cattttatc gtggatgaca gctttgagtt gcagccgatc    4920
ggcgtgaagg gcgagctcta cgtttccggg gcaagtgtcg acgcgggta ctggggaaga    4980 acggacttaa ctgaggagaa gttccttgat aacccgttcg cacctggcga gcggctgtac    5040
aagacaggtg acgtagcgcg ctggcttcca gacggcagca ttgagtatgt gggacgaagt    5100
gaccatcagg tgaaaatccg gggcttccgc attgagctgg gcgaggtgga atcgcagttg    5160
ctgcatgtac cggcggtaca ggaggcgacc atggtggcac tggaagatca tgcgggtcag    5220
aagcagttgt gcgcgtattt cacagcagaa tgctcactca cggccggcga gctgcgggca    5280
gcattgtcgc aggagctgcc aggctacatg attccgtcct acttcgtaca gttggagcga    5340
ctgccgctga cgccgaatgg gaagatcgat cggagagcgc tgccgaagcc agaaggcggc    5400
attgagactg gaacggagta tgtcgcgccg cgtacagaga cggaagcaag gcttgcacgc    5460
atttggcagg atgtattggg attagcaagc gtaggcgtga aggacaactt cttcgagctg    5520
ggcggtcact cgctgcgggc aacgacgctg gtgagcaggc tgtacaagga aatgaacgtc    5580
aacttcccgt taagaggtgt gttccgtcat ccgaccatcg aggagatggc gaaggcgata    5640
accgagatgc atcaagaact ttacacgaaa ataacctatcg ctgaggaaaa agcctattat    5700
ccgttatctt cagcgcagaa aaggctgttc attgtaagcc agctgacagg agccgaggta    5760
agctataaca tgccgggggt gctgattctc gaaggagagc tggatcgtgc gcgattcgaa    5820
cgggctttcc agaagctgat cgaccgacat gaatcgctgc ggacaagctt cgagacggta    5880
cgcggtgagc ctgtacagcg cattcactcg caggtggagt tcgctatcga atatcacctt    5940
gcagcagaaa aagatgcaga ggcgctgatc actcatttcg tacgtccatt ccagcttaat    6000
caagcaccgc tgctcagagt cggattgatt gaaactggac atgaacgcca tattctgatg    6060
ttcgacatgc accatatcat ttccgatggc gtaacgatgg ggcatgtcgt gaatgaattc    6120
tcccggatat atgcaggcga tcaactgccg gcgctgcgta tccaatataa ggactatgct    6180
gcatggcagc aatccaatga atatgcagag aagcttgcgc atcaggaatc ctattggctg    6240
aagcaattgg acggagaact gccgacgctc gaactgccga ctgattatgt gcgaccggct    6300
gtacagcagt tcgaaggtga tgtggccttg ttcaccttaa cgaacagtca ggccgagcag    6360
ctgcaacgat tagcggcaaa ctacggcgca accttatata tggttctgct tgcagcatat    6420
accgtgctcc tgcacaaaata tacgggacag gacgatatca ttgtcggaac accgatcgcg    6480
ggccgcaatc atacggaatt ggagccgctg gttgggatgt tcgtcaatac gctcgccatc    6540
cgcaattatc caacgggtga gaaatccttc gcggaactgt tggcggaggt gaaggatacg    6600
gccctcgccg cattcgagaa tcaggattat ccgttcgaaa cgttggtaga aaggttcat    6660 aagtctcggg atatgagccg aaatccagtg tttgatacga tattcagtgt tgagcatgaa    6720
cagcagagtt ccttccatat cgatgggctt cggataagtc catacccgca cagccattct    6780
gtcgcgaagt tcgatttgac cttccatgcc gaacagaatg aagaagggat actatgtgga    6840
ctaggctatg cgactgcttt atatgcgaaa gagactgcgg ggcggatggg agaacatttc    6900
gtgcaattaa tagatgccat catccgcagaa ccgaatgcga agctaatgtc actgaatatg    6960
atgagcctgc aggaaagaga gcaagtaaag ctggtatttta atgatacgat aacgagttat    7020 ccgcggggaga agacgattca acatttgttc gaagagcagg cagagaaatc gccggatgcg    7080
gttgctatcc aattcggaga agaacggctc acataccgcg agttgaatga acggtcgaat    7140
cgtttggcga gaacactgcg aggtaagggt gtaaaagccg gccgcttcgt aggtctaatg    7200
```

```
acagatcgtt cgctagacat gattgtggcg attatggcga ccctgaaggc aggcggggca    7260
tatgtgccaa ttgatccgga ttatccggaa gaacgcattc gatacatgat cgacgattcg    7320
ggagcatcgc ttctagtcgt gcaacgtcat tttcagtcga accatattgc tgcggattgc    7380
atggttgtac ttgtagatga tgaggactcc tatcacgcag atggcacgaa tctggagcag    7440
cataatgggg cttctgatct cgcctacgtc atttacacgt caggtacaac gggaatgccg    7500 aagggaatt taacaaccca ccgcaacatc gttagagtag tgcgggatgc gaaatatatc    7560
gagatcgatc agcatgacac ggtgctgcaa ttatccagct acgcttttga cggctcaacc    7620
ttcgacatat ttggagcctt gatgaatgga gcgaagcttg tactgattcc gcgcgaggta    7680
gtgctcgacg ctggccgact ggccgacacc atcgagatcg agaagatttc ggtcatgttc    7740
attactactg cctatctcaa tctgctcgtc gacttgagag tggacagtct acgccatatg    7800
cgcgcgatat tgttcggtgg tgaacgcgca tctgtgagcc atgtgcgcaa ggcgctccgg    7860
catttgggcc caggcaagct taagcatgta tacgggccaa cggagagcac cgtatttgcg    7920
actagccaca acgttgatga agtagctgac agcgccgtaa cgataccgat cggacgcccg    7980
attggcaata cggccgtata tatcgttggc gagggagacg ttctgcagcc gattggcgta    8040
gctggtgagt tatgcgtagc gggagatgga gtagccgtag ggtatttgaa ccgcccagaa    8100
ttgtcgggag ccaagttcgt gaataacccg ttcgttccgg gtgatcgcat gtaccgaacg    8160
ggtgatttgg caagatggct ttcagacgga acgatagagt atgtgggacg gatagacgat    8220
caggtgaaaa tacgtggtta tcgaatcgag cttggtgagg tcgaagctca tctgttagac    8280
cttgaggcaa tccaagaagc tgtggtcatc gtcagggagg aaagtgacgg gcagaagcgc    8340
ctatgcgctt actatgtagc aggtcgtccg attacggctg gtgagatgcg atagctttg    8400 gctcaggagc tcccgggata catgcttcca tcctacttcg tacagctcga taagcttcca    8460
ttatcaccga acggcaaggt gaaccggaag gcacttccgg ctcctgaatt gcatgtgcag    8520
gcggcttcgg aatacgtggc tccacgcacg ccacaagaag tactgctcgc tcacatatgg    8580
agggaggtgc tcgggcttgg tcaggtaggc gttaaggata atttcttcga gcttggcgga    8640
cattccttaa gcctgatgaa gcttgtagag cgtgtctata ccgagactga ggttgaaatc    8700
ccaattcaca gcgtattccg ggaaccgaca attgaagcga tggcgtacga gatgttgaaa    8760
tccgaacttg caggcaaggc aggaaatcat tttatgaaat tgaacgaaaa cggtcatatc    8820
cctgtcttct gcttccctcc gggacttggc tacggtctca gctacttgga gctggctaag    8880
caactggatc atcactgcat cctgcatggc atcgacttta tcgatgatgc tgatactcgg    8940
gaggaactgc ttgaacgata cgtggatgct atccttgctg ttcaaccgca gccgccattt    9000
gtattgctcg gttattctct aggcggcaac ctgacgttcg aggttgcgaa agcgctggag    9060
tccagagggt atccggtatc ggatgtcatc atgattgatt ccttgcggaa gctgaaggtg    9120
catgaagtag acgaattcga cggcgacatt gatcagatga ttgatggtgt ggaggagctg    9180
aaagaaatgc tggttcacca tccgcttctc cgcgatcagg tgaagaacaa gatgagggcg    9240
tactggtcgt acgcgactga actcgttaac tccgatatca tcgatgccaa tattcatgca    9300
ctgatggcgg agccatccga ggtgaaccag gcagatgggg agcagctcgc aacatggcag    9360
gaggctactc gcggcaggta tgtggaatac aacctccgcg gtgtgcacga agatgtgctt    9420
caaccgcctt tcttagaagc gaacgctaac gtcatgcaag caatcattcg acatattctc    9480
gagcaaacaa tggttaccca ctag                                           9504
```

<210> SEQ ID NO 11
<211> LENGTH: 6654
<212> TYPE: PRT
<213> ORGANISM: Paenibacillus strain A6-6i

<400> SEQUENCE: 11

```
Met Asn Ala Asn Pro Asn Glu Trp Tyr Pro Leu Thr Gln Ala Gln Arg
1               5                   10                  15

Arg Ile Trp Tyr Thr Glu Met Met His Pro Asn Thr Ser Val Thr Thr
            20                  25                  30

Val Ala Gly Thr Met Tyr Ile Arg Gly Lys Val Asp Val Glu Ile Leu
        35                  40                  45

Lys Met Ala Ile Tyr Gln Val Ile Met Gln His Asp Ala Phe Arg Ile
50                  55                  60

Arg Ile Ala Met Thr Asp Asn Gln Pro Lys Gln Phe Ala Pro Val
65                  70                  75                  80

Glu Gln Ile Val Pro His Val Asp Tyr Leu Glu Trp Asp Asn Gln Ile
                85                  90                  95

Glu Ala Glu Ser Trp Leu Gln Arg Phe Asn His Ile Pro Ile His Met
            100                 105                 110

Phe Asp Pro Ala Leu Tyr His Phe Val Val Phe Asn Val Asn Asp Glu
        115                 120                 125

Glu Ala Trp Phe Asn Leu Lys Met Asn His Ile Ala Thr Asp Gly Val
130                 135                 140

Ser Ser His Leu Ile Ala Tyr Lys Ile Met Lys Asn Tyr Thr Ala Met
145                 150                 155                 160

Val Ser Gly Asn Ala Asp Thr Asp Glu Gln Glu Ser Thr Tyr Leu Asp
                165                 170                 175

Tyr Ile Phe Ala Glu Arg Glu Tyr Glu Gln Ser Asp Arg Tyr Ala Lys
            180                 185                 190

Asp Lys Ala Tyr Trp Leu Asp Lys Phe Ser Thr Met Pro Glu Val Ile
        195                 200                 205

Gly Ile Lys Ser Tyr Pro Pro His Ser Ile Gly Thr Glu Ala Ser Arg
210                 215                 220

Thr Ser Ile Thr Val Ser Gly Glu Met Tyr Glu Lys Leu Tyr Arg Phe
225                 230                 235                 240

Ser Gln Gln His Asn Ile Ser Leu Phe Thr Leu Phe Leu Gly Ser Leu
                245                 250                 255

Tyr Ala Phe Leu Tyr Lys Thr Thr Gly Asn Asn Asp Ile Ala Val Gly
            260                 265                 270

Ala Ala Tyr Ala Asn Arg Thr Ser Arg Gln Asp Lys Asp Ala Leu Gly
        275                 280                 285

Met Phe Val Ser Thr Val Ala Ala Arg Leu Thr Ile Ser Pro Asp Gln
290                 295                 300

Asp Val Leu Thr Phe Leu His Asn Val Ala Lys Glu Gln Lys Ala Ile
305                 310                 315                 320

Leu Arg His Gln Lys Tyr Pro Tyr Asn Gln Leu Ile Leu Asp Leu Arg
                325                 330                 335

Glu Gln Asn Asn Ser Val Glu Ile Gln Asp Leu Tyr Arg Ile Ser Ile
            340                 345                 350

Asp Tyr Met Pro Ile Arg Trp Ser Ser His Gly Glu Leu Ala Ala Arg
        355                 360                 365

Gln Arg Ser Ser Phe Cys Gly His Glu Val Asp Phe Ala Val His
370                 375                 380
```

```
Val Glu Asp Met Val Asp Asp Asn Gln Ile Ile Phe Asn Ile Asp Tyr
385                 390                 395                 400

Arg Lys Gln Leu Phe Glu Glu His Glu Val Ile Arg Ile Ile Asp Gln
                405                 410                 415

Met Met Thr Ile Val Asp Gln Met Leu Ser Asn Pro Ser Gln Ser Leu
            420                 425                 430

Gln Gln Leu Ser Met Ile Ser Asp Lys Glu Ala Gln Ile Ile Leu Thr
        435                 440                 445

Arg Phe Ser Asn Gly Asn Trp Ser Thr Pro Gln Pro Val Gly Arg Thr
    450                 455                 460

Ile His Gln Leu Phe Glu Glu Val Glu Arg Thr Pro Asp Gln Val
465                 470                 475                 480

Ala Val Val Phe Gly Asp Arg His Leu Thr Tyr Lys Glu Leu Asn Glu
                485                 490                 495

Gln Ala Asn Cys Phe Ala Arg Thr Leu Arg Ala His Gly Val Ala Ala
            500                 505                 510

Glu Gln Phe Val Gly Ile Met Ala Asp Arg Ser Ile Glu Met Val Val
        515                 520                 525

Gly Ile Leu Ala Ile Leu Lys Ala Gly Gly Ala Tyr Val Pro Ile Asp
    530                 535                 540

Pro Glu Tyr Pro Glu Glu Arg Ile Leu Tyr Met Leu Glu Asp Ser Asn
545                 550                 555                 560

Ala Arg Val Leu Val Ser Gln Ser His Leu Gln Thr Arg Leu Gly Tyr
                565                 570                 575

Thr Gly Thr Trp Val Leu Leu Asp Asp Glu Asn Asp Tyr Glu Ala Asn
            580                 585                 590

Arg Asp Asn Leu Glu Ser Val Asn Glu Ala His His Leu Ala Tyr Val
        595                 600                 605

Ile Tyr Thr Ser Gly Thr Thr Gly Lys Pro Lys Gly Val Met Ile Glu
    610                 615                 620

His Lys Gln Ile Thr Ala Leu Gly Asp Ala Trp Lys His Ala Tyr Gln
625                 630                 635                 640

Leu Asp Glu Ser Gly Ile Arg Thr Leu Gln Trp Ala Ser Phe Ser Phe
                645                 650                 655

Asp Val Phe Thr Gly Asp Met Val Arg Ala Leu Leu Tyr Gly Gly Glu
            660                 665                 670

Leu Ile Ile Cys Pro Ser Glu Ala Arg Ala Asn Pro Glu Ala Ile Cys
        675                 680                 685

Glu Leu Ile Ala Arg His Arg Ile His Ile Phe Glu Ser Thr Pro Ala
    690                 695                 700

Leu Val Ile Pro Leu Met Glu Tyr Val His Glu Gln Arg Lys Asp Val
705                 710                 715                 720

Ser Ser Leu Arg Leu Leu Val Val Gly Ser Asp His Cys Pro Ala Ala
                725                 730                 735

Glu Tyr Arg Lys Leu Met Glu Arg Phe Gly Ser Gln Met Arg Ile Leu
            740                 745                 750

Asn Ser Tyr Gly Val Thr Glu Ala Cys Val Asp Ala Cys Tyr Tyr Glu
        755                 760                 765

Lys Asn Gly Ser Val Asp Ser Ile Thr Met Leu Pro Ile Gly Lys Pro
    770                 775                 780

Leu Pro Ser Val Ser Met Tyr Ile Leu Asp Glu Asn Lys Ala Leu Gln
785                 790                 795                 800
```

```
Pro Ile Gly Ile Val Gly Glu Leu Tyr Ile Gly Ala Gly Val Gly
                805                 810                 815

Arg Gly Tyr Leu Asn Arg Asp Leu Thr Ala Glu Lys Phe Val Asp
        820                 825                 830

Asp Pro Tyr Ser Gln Gly Lys Met Tyr Arg Thr Gly Asp Leu Ala Arg
            835                 840                 845

Trp Leu Pro Asp Gly Asn Ile Glu Tyr Leu Gly Arg Leu Asp His Gln
850                 855                 860

Val Lys Ile Arg Gly Asn Arg Ile Glu Ile Gly Ile Glu Thr Arg
865                 870                 875                 880

Met Leu Gln Thr Ser Leu Val Arg Glu Ala Val Ile Val Ala Arg Glu
                885                 890                 895

Asp Glu Asn Gly Leu Lys Ala Leu Cys Ala Tyr Val Ala Asp Ser
            900                 905                 910

Glu Ile Ser Val Gln Gln Leu Arg Ser Thr Leu Ala Glu Gln Val Pro
        915                 920                 925

Asp Tyr Met Ile Pro Ser Tyr Phe Met Lys Leu Glu Arg Leu Pro Leu
930                 935                 940

Thr Pro Asn Gly Lys Ile Asp Arg Asn Gly Leu Pro Ala Pro Ser Gly
945                 950                 955                 960

Gln Asp Tyr Ser Gly Lys Ile Tyr Val Glu Pro Arg Asn Gln Ala Glu
            965                 970                 975

Gln Thr Leu Ala Ser Ile Trp Lys Met Val Leu Gly Val Lys Arg Val
        980                 985                 990

Gly Ile Leu Asp His Phe Phe Glu Leu Gly Gly Asp Ser Ile Lys Ser
        995                 1000                1005

Ile Gln Val Ser Ser Arg Met Gln Gln Ala Gly Tyr Lys Leu Asp
        1010                1015                1020

Ile Arg Asp Leu Phe Lys Tyr Pro Thr Ile Glu Gln Ile Ser Pro
        1025                1030                1035

His Leu Val Glu Val Gln Arg Lys Ala Glu Gln Gly Glu Glu Ser
        1040                1045                1050

Gly Glu Val Gly Leu Thr Pro Ile Leu Arg Trp Tyr Phe Asp Arg
        1055                1060                1065

Asp Glu Val Ser Leu His His Tyr Asn Gln Ser Ile Met Leu His
        1070                1075                1080

Arg Lys Ala Gly Phe Asp Glu Ala Ala Leu Arg Asn Ala Leu His
        1085                1090                1095

Lys Ile Thr Glu His His Asp Ala Leu Arg Met Val Phe Arg Arg
        1100                1105                1110

Thr Glu Gln Gly Glu Tyr Ala Ala Trp Asn Arg Arg Ile Glu Glu
        1115                1120                1125

Gly Glu Leu Tyr Arg Leu Asp Val Leu Asp Ile Lys Glu Arg Ser
        1130                1135                1140

Ala Gly Val Glu Ser Glu Glu Ser Leu His Asn Met Leu Ile Ala
        1145                1150                1155

Glu Ala Asn Val Ile Gln Ala Gly Phe Asp Ile Glu Ala Gly Pro
        1160                1165                1170

Leu Val Gly Ala Gly Leu Phe Arg Cys Pro Asp Gly Asp His Leu
        1175                1180                1185

Leu Ile Val Ile His His Ala Val Ile Asp Ala Val Ser Trp Arg
        1190                1195                1200

Ile Leu Leu Glu Asp Leu Ala Thr Gly Tyr Glu Gln Ala Leu Gln
```

-continued

```
        1205                1210                1215
Gly Ser Glu Ile Arg Leu Pro Asp Lys Thr Asp Ser Phe Arg Leu
        1220                1225                1230
Trp Ser Arg Glu Leu Ser Ala Tyr Ala Gln Gln Ser Asn Met Asn
        1235                1240                1245
Glu Glu Leu Lys Tyr Trp His Gln Val Ala Gln Thr Thr Ile Thr
        1250                1255                1260
Pro Leu Pro Thr Asp Tyr Ala Gly Ile Ala Leu Gln Arg Asp Ser
        1265                1270                1275
Glu Ser Val Thr Val Glu Trp Ser Ala Ser Glu Thr Glu Leu Leu
        1280                1285                1290
Leu Lys Gln Ala His Arg Ala Tyr Asn Thr Gln Met Asp Asp Leu
        1295                1300                1305
Leu Leu Thr Ala Leu Gly Ile Ala Phe Arg Arg Trp Cys Gly His
        1310                1315                1320
Glu Arg Ile Arg Ile Asn Leu Glu Gly His Gly Arg Glu Ser Ile
        1325                1330                1335
Leu Pro Asp Leu Asp Ile Thr Arg Thr Val Gly Trp Phe Thr Ser
        1340                1345                1350
Glu Tyr Pro Gln Leu Leu Glu Val Gly Ser Glu Glu Glu Leu Pro
        1355                1360                1365
Arg Ile Ile Lys Ser Val Lys Glu Asp Leu Arg Ser Ile Pro Asn
        1370                1375                1380
Lys Gly Ile Gly Tyr Gly Ile Cys Arg Tyr Leu Ser Asn Thr Gly
        1385                1390                1395
Ile Cys Glu Val Trp Gly Thr Ala Pro Glu Val Ser Phe Asn Tyr
        1400                1405                1410
Leu Gly Gln Phe Asp Gln Asp Phe Gln Asn Ser Gly Phe Ser Pro
        1415                1420                1425
Ser Pro Tyr Ser Thr Gly Ser Asn Ile Gly Gly Asp Gln Leu Arg
        1430                1435                1440
Pro Tyr Leu Leu Asp Met Asn Gly Met Val Ser Asp Gly Lys Leu
        1445                1450                1455
Gln Leu Asp Ile Ser Tyr Gly Arg Thr Gln Tyr Arg Ala Glu Thr
        1460                1465                1470
Ile Glu Arg Leu Ala Ser Leu Ile Arg Asp Ser Leu Leu Glu Ile
        1475                1480                1485
Ile Glu His Cys Val Ala Lys Glu Arg Thr Glu Leu Thr Pro Ser
        1490                1495                1500
Asp Val Ser Leu Gln Arg Ile Ser Ile Gln Glu Leu Glu Gln Ile
        1505                1510                1515
Val Glu Arg Thr Ser Gly Ile Gly Glu Val Glu Asp Ile Tyr Ala
        1520                1525                1530
Leu Thr Pro Met Gln Lys Gly Met Trp Phe His Thr Ala Met Asp
        1535                1540                1545
Ser Gln Ala Gly Ala Tyr Phe Glu Leu Thr Arg Leu Thr Leu Glu
        1550                1555                1560
Gly Thr Leu Asn Ile Glu Ala Phe Ala Ala Ser Trp Asn Glu Leu
        1565                1570                1575
Ala Ala Arg His Ala Val Phe Arg Thr Asn Phe Leu Val Asp Ser
        1580                1585                1590
Asn Gly Glu Pro Leu Gln Val Val Phe Arg Ser Lys Arg Ile Ser
        1595                1600                1605
```

```
Val Lys His Glu Asp Leu Arg Ser Leu Asn Ala Tyr Glu Gln Ala
    1610            1615                1620

Val Ala Ile Glu Asn Glu Ala Ala Lys Glu Arg Glu Gln Gly Phe
    1625            1630                1635

Asp Leu Glu Asn Gly Asp Val Met Arg Val Ser Val Leu Gln Thr
    1640            1645                1650

Ala Asp Glu Val Tyr Glu Val Leu Trp Ile Ser His His Ile Val
    1655            1660                1665

Met Asp Gly Trp Cys Leu Pro Leu Val Ala Ala Glu Val Phe Asn
    1670            1675                1680

Thr Tyr Ser Ala Leu Val Glu Asp Lys Lys Pro Ile Leu Ala Ser
    1685            1690                1695

Val Pro Ser Tyr Asn His Tyr Ile Gln Trp Leu Glu Arg Gln Asp
    1700            1705                1710

Glu Ser Ala Ala Ala Ala Tyr Trp Asn Asn Tyr Leu Ser Gly Phe
    1715            1720                1725

Glu Glu Thr Thr Glu Leu Pro His Ser Lys Gly Arg Arg His Ser
    1730            1735                1740

Gly Gln Tyr Glu Ala Gly Gln Val Gln Ile Asp Leu Gly Thr Ser
    1745            1750                1755

Leu Ser Leu Ala Leu Asn Gln Val Ala Thr Gln His Gln Val Thr
    1760            1765                1770

Leu Asn Thr Leu Leu Gln Ala Ser Trp Gly Ile Leu Leu Gln Lys
    1775            1780                1785

Tyr Asn Arg Thr Ser Asp Ile Val Phe Gly Ser Val Val Ser Gly
    1790            1795                1800

Arg Pro Ala Glu Leu Val Gly Ile Glu Glu Met Ile Gly Leu Phe
    1805            1810                1815

Ile Asn Thr Ile Pro Val Arg Val Ser Ser Gln Ala Gln Glu Arg
    1820            1825                1830

Phe Ala Glu Val Met Thr Arg Met Gln Glu Asp Ala Leu Ser Ser
    1835            1840                1845

Ala Lys His Asp Tyr Tyr Pro Leu Tyr Glu Ile Gln Ala Gln Cys
    1850            1855                1860

Thr Leu Lys Gln Asn Leu Ile Thr His Ile Met Val Leu Glu Asn
    1865            1870                1875

Tyr Pro Met Glu Gln Gln Leu Asp Gln Phe Asn Ser Ser Asp Gly
    1880            1885                1890

Ser Gly Leu Lys Leu Thr Asp Val Thr Val Thr Glu Gln Thr Asn
    1895            1900                1905

Tyr Asp Leu Asn Leu Ile Ile Pro Gly Asp Asn Ile Val Ile
    1910            1915                1920

Arg Phe Asp Phe Asn Lys Gln Ala Leu Glu Glu Ala Asp Met Asn
    1925            1930                1935

Val Leu Lys Gln His Leu Leu His Val Leu Glu Gln Val Ala Ser
    1940            1945                1950

Asn Pro Arg Ile Ser Ile Gly Glu Leu Gln Leu Ala Thr Asp Glu
    1955            1960                1965

Glu Arg Ala Val Met Met Ser Glu Phe Asn Asp Thr Phe Val Ala
    1970            1975                1980

Tyr Pro Arg Glu Lys Ser Ile His Arg Leu Phe Glu Glu Arg Ala
    1985            1990                1995
```

```
Glu His Glu Pro Asp Ala Leu Ala Val Val Phe Gly Asn Glu Gln
2000            2005                2010

Met Thr Tyr Gly Ala Leu Asn Ala Ala Ala Asn Arg Met Ala Arg
2015            2020                2025

Arg Leu Arg His Ala Gly Val Thr Asn Gly Glu Leu Val Gly Ile
2030            2035                2040

Cys Ala Asp Arg Ser Leu Asp Met Val Val Gly Leu Leu Ala Ile
2045            2050                2055

Met Lys Ser Gly Gly Ala Tyr Val Pro Ile Asp Pro Ala Tyr Pro
2060            2065                2070

Gln Glu Arg Ile Ser Ala Met Leu Glu Asp Thr Ser Ile Thr Thr
2075            2080                2085

Met Val Thr Gln Lys His Leu Cys Ser Leu Trp Pro Glu His Phe
2090            2095                2100

Asn Val Ile Val Leu Asp Val Asn Glu Thr Asp Val Ser Asn Leu
2105            2110                2115

Met Glu Asp Ile Glu Ser Thr Asn Leu Ser Ile Asp Gly Ala Gly
2120            2125                2130

Asp Asp Leu Ala Tyr Ile Ile Tyr Thr Ser Gly Ser Thr Gly Thr
2135            2140                2145

Pro Lys Gly Val Cys Val Thr His Arg Gly Val Val Arg Leu Val
2150            2155                2160

Cys Gly Ala Thr Tyr Val Glu Ile Asp Ser Ser Asp Val Phe Leu
2165            2170                2175

Gln Gly Ser Thr Ile Ser Phe Asp Ala Ala Thr Phe Glu Ile Trp
2180            2185                2190

Gly Ser Leu Leu Asn Gly Ala Ala Leu Ala Ile Leu Pro Ser Gly
2195            2200                2205

Asn Val Ser Leu Thr Asp Trp Ser Glu Ala Ile Gln Arg His Arg
2210            2215                2220

Val Thr Thr Leu Trp Met Thr Ala Gly Leu Phe Gln Val Met Val
2225            2230                2235

Glu Gln Gln Ile Glu Gly Phe Tyr Gly Val Lys Gln Leu Leu Val
2240            2245                2250

Gly Gly Asp Val Val Ser Pro Thr His Val Arg Lys Val Met Glu
2255            2260                2265

Lys His Asn Gly Ile Arg Val Ile Asn Gly Tyr Gly Pro Thr Glu
2270            2275                2280

Asn Thr Thr Phe Thr Cys Cys His Thr Ile Thr Ala Ala Asp Leu
2285            2290                2295

Asp Arg Gly Cys Ser Ile Pro Ile Gly Arg Pro Ile Ser Asn Thr
2300            2305                2310

Arg Val Tyr Val Leu Asp Glu Ala Gly Asn Ala Leu Pro Val Gly
2315            2320                2325

Val Cys Gly Glu Leu Tyr Ala Gly Gly Asp Gly Leu Ala Arg Gly
2330            2335                2340

Tyr Leu Asn Arg Pro Glu Leu Thr Ala Glu Lys Phe Val Asn Asp
2345            2350                2355

Pro Phe Ile Pro Gly Glu Arg Leu Tyr Arg Thr Gly Asp Leu Ala
2360            2365                2370

Arg Trp Leu Pro Asp Gly Ser Ile Glu Phe Ile Gly Arg Cys Asp
2375            2380                2385

Glu Gln Val Lys Ile Arg Gly Tyr Arg Ile Glu Pro Gly Glu Val
```

```
                    2390                2395                2400

Leu Ala Tyr Leu Leu Arg Ile Asp Glu Val Gly Glu Ala Ala Val
    2405                2410                2415

Ile Ala Arg Glu Asp Ser Ser Gly Gln Lys Glu Leu Cys Ala Tyr
    2420                2425                2430

Phe Thr Thr Glu Ala Glu Leu Ser Ala Ser Gly Leu Arg Glu Thr
    2435                2440                2445

Leu Ala Arg Glu Leu Pro Ala Tyr Met Ile Pro Ser His Phe Ile
    2450                2455                2460

Gln Ile Glu Glu Leu Pro Leu Thr Pro Asn Gly Lys Val Asp Arg
    2465                2470                2475

Arg Ala Leu Pro Gln Pro Gly Glu Gly Met His Leu Asn Ile Gln
    2480                2485                2490

Ile Gln Pro Arg Thr Glu Leu Glu Ala Lys Leu Ala Leu Ile Trp
    2495                2500                2505

Lys Asp Val Leu Gly Leu Glu Asn Val Gly Val Thr Asp Ser Phe
    2510                2515                2520

Phe Glu Leu Gly Gly His Ser Leu Arg Ala Thr Thr Leu Val Ser
    2525                2530                2535

Lys Val His Arg Glu Leu Ser Val Val Leu Pro Leu Gln Asp Val
    2540                2545                2550

Phe Arg Tyr Pro Thr Ile Glu Gln Met Ser Leu Ala Ile Gln Gly
    2555                2560                2565

Met Gln Lys Glu Ser Phe Ala Ser Ile Pro Arg Val Glu Asp Arg
    2570                2575                2580

Glu Trp Tyr Pro Val Ser Ser Ala Gln Lys Arg Leu Phe Val Leu
    2585                2590                2595

His Gln Met Glu Gly Ala Glu Leu Ser Tyr Asn Met Pro Gly Val
    2600                2605                2610

Met Ala Ile Glu Gly Lys Leu His Arg Asp Arg Leu Glu Ala Ala
    2615                2620                2625

Phe Arg Ser Leu Ile Ala Arg His Glu Val Leu Arg Thr Gly Phe
    2630                2635                2640

Glu Met His Asn Gly Glu Pro Met Gln Arg Ile Tyr Ser Asp Val
    2645                2650                2655

Glu Phe Thr Val Glu His Trp Ile Val Gly Ala Ala Ser Glu Ala
    2660                2665                2670

Glu Ser Val Ile Arg Ser Phe Val Arg Ala Phe Gln Leu Asn Lys
    2675                2680                2685

Pro Pro Leu Leu Arg Val Gly Leu Ile Glu Val Asp Ala Gly Arg
    2690                2695                2700

His Leu Leu Leu Phe Asp Met His His Ile Ile Ser Asp Gly Ala
    2705                2710                2715

Ser Met Gly Ile Leu Leu Asp Glu Phe Val Ala Leu Tyr Ser Gly
    2720                2725                2730

Glu Gln Leu Pro Glu Leu Arg Leu Gln Tyr Lys Asp Tyr Ala Ser
    2735                2740                2745

Trp Gln His Ser Glu Ala Tyr Leu Ser Lys Met Glu Glu Gln Lys
    2750                2755                2760

Ala Tyr Trp Leu Glu Thr Leu Arg Gly Glu Leu Pro Val Leu Gln
    2765                2770                2775

Leu Pro Val Asp Tyr Thr Arg Pro Ala Phe Arg Ser Phe Ala Gly
    2780                2785                2790
```

Ser Thr Leu Glu Phe Ile Val Pro Ala Asp Lys Thr Asp Gln Leu
2795                2800                2805

Lys Gln Leu Gly Ala Gly Ser Asp Ala Thr Met Tyr Met Val Leu
2810                2815                2820

Leu Ala Leu Tyr Thr Ala Leu Leu His Lys Tyr Thr Gly Gln Glu
2825                2830                2835

Asp Val Ile Val Gly Met Pro Ile Ala Gly Arg Thr His Ala Asp
2840                2845                2850

Ile Glu Pro Leu Ile Gly Met Phe Val Asn Thr Leu Pro Leu Arg
2855                2860                2865

His Tyr Pro Ala Gly Glu Lys Thr Phe Arg Ser Phe Leu Gly Glu
2870                2875                2880

Val Arg Gln Ser Thr Leu Gln Ala Tyr Glu His Gln Glu Tyr Pro
2885                2890                2895

Phe Glu Glu Leu Val Asp His Ile Gln Pro Thr Arg Asp Val Ser
2900                2905                2910

Arg Asn Pro Ile Phe Asp Thr Val Leu Val Leu Gln Asn Thr Glu
2915                2920                2925

Lys Gly Ala Trp Ser Ile Asp Gly Leu Ala Val Thr Pro Asn Pro
2930                2935                2940

Ile Glu His Ala Val Ala Lys Phe Asp Leu Thr Leu His Val Glu
2945                2950                2955

Glu Asp Val Asp Gly Leu Ala Cys Ser Ile Glu Tyr Ala Thr Ala
2960                2965                2970

Leu Tyr Asn Arg Glu Thr Ile Glu Arg Leu Ala Cys His Phe Asn
2975                2980                2985

Gln Leu Leu Glu Ala Val Ile Ser Asn Pro Asp Ala Arg Leu Glu
2990                2995                3000

Gln Leu Gly Ile Ile Thr Glu Thr Glu Lys Gln Gln Leu Phe Glu
3005                3010                3015

Gln Phe Asn Asp Thr Ser Ala Asp Tyr Pro Arg Asp Lys Thr Ile
3020                3025                3030

His Arg Leu Phe Glu Glu Gln Val Glu Arg Thr Pro Asp Ala Ile
3035                3040                3045

Ala Val Thr Gly Thr Asp Gly Phe Leu Thr Tyr Gln Glu Leu Asn
3050                3055                3060

Glu Arg Ala Asn Ser Leu Ala Trp Val Leu Arg Ala Glu Gly Ile
3065                3070                3075

Gly Ala Asp Lys Leu Val Gly Ile Met Ala Glu Arg Thr Thr Asp
3080                3085                3090

Met Leu Val Gly Leu Ile Ala Ile Leu Lys Ala Gly Gly Ala Tyr
3095                3100                3105

Val Pro Ile Asp Pro Glu Tyr Pro Asp Glu Arg Ile Ser Tyr Met
3110                3115                3120

Leu Ser Asp Ser Gly Ala Asp Ile Leu Leu Leu Pro Arg His Leu
3125                3130                3135

Arg Asn Gln Val Ala Tyr Glu Gly Thr Val Leu Phe Leu Asp Asp
3140                3145                3150

Glu Gln Thr Tyr Ser Gly Asp Lys Ser Asn Pro Pro Ser Val Asn
3155                3160                3165

Lys Pro Ser Asp Leu Ala Tyr Val Ile Tyr Thr Ser Gly Thr Thr
3170                3175                3180

```
Gly Lys Pro Lys Gly Thr Leu Ile Glu His Lys Asn Val Val Arg
    3185                3190                3195

Leu Leu Phe Asn Ser Arg Asn Leu Phe Asp Phe Arg Ser Thr Asp
    3200                3205                3210

Thr Trp Thr Leu Phe His Ser Phe Cys Phe Asp Phe Ser Val Trp
    3215                3220                3225

Glu Met Tyr Gly Ala Leu Leu Tyr Gly Gly Lys Leu Val Val Val
    3230                3235                3240

Pro Gln Leu Thr Ala Lys Asn Pro Ala Met Phe Leu Gln Leu Leu
    3245                3250                3255

Ala Glu Glu Arg Val Thr Ile Leu Asn Gln Thr Pro Thr Tyr Phe
    3260                3265                3270

Tyr Gln Leu Ile Arg Glu Ala Leu Thr Asp Gly Ser Pro Glu Leu
    3275                3280                3285

Asn Ile Arg Met Val Ile Phe Gly Gly Glu Ala Leu Ser Pro Gln
    3290                3295                3300

Leu Leu Lys Asp Trp Arg Ala Lys Tyr Pro Arg Thr Gln Leu Ile
    3305                3310                3315

Asn Met Tyr Gly Ile Thr Glu Thr Thr Val His Val Thr Tyr Lys
    3320                3325                3330

Glu Ile Thr Glu Ala Glu Ile Glu Gln Ala Arg Ser Asn Ile Gly
    3335                3340                3345

Phe Pro Ile Pro Thr Leu Arg Ile Tyr Ile Leu Asp Ala Asn Arg
    3350                3355                3360

Gln Cys Val Pro Ile Gly Val Ala Gly Glu Met Phe Val Ala Gly
    3365                3370                3375

Glu Gly Leu Ala Arg Gly Tyr Leu Asn Arg Pro Glu Leu Thr Ala
    3380                3385                3390

Asp Arg Phe Val Asp Asn Pro Phe Glu Pro Gly Ser Lys Met Tyr
    3395                3400                3405

Lys Thr Gly Asp Leu Ala Lys Trp Leu Pro Asp Gly Asn Ile Glu
    3410                3415                3420

Tyr Leu Gly Arg Ile Asp His Gln Val Lys Ile Arg Gly Tyr Arg
    3425                3430                3435

Ile Glu Leu Gly Glu Val Glu Ala Gln Val Thr Lys Val Glu Ser
    3440                3445                3450

Val Arg Glu Ala Val Val Val Ala Arg Glu Glu Asn Gly Glu Lys
    3455                3460                3465

Leu Leu Cys Ala Tyr Phe Val Ala Asp Arg Gln Leu Thr Val Gly
    3470                3475                3480

Glu Met Arg Thr Glu Leu Ala Gln Glu Leu Pro Thr Tyr Met Ile
    3485                3490                3495

Pro Ser Tyr Phe Val Gln Met Glu Arg Met Pro Leu Thr Ser Asn
    3500                3505                3510

Gly Lys Val Asp Arg Lys Ala Leu Pro Ala Pro Glu Gly Ser Ile
    3515                3520                3525

Asn Thr Gly Lys Glu Tyr Val Ala Pro Arg Thr Pro Met Glu Ala
    3530                3535                3540

Ser Leu Ala Arg Met Trp Glu Leu Leu Gly Ile Glu Gln Val
    3545                3550                3555

Gly Val Thr Asp Asn Phe Phe Glu Leu Gly Gly His Ser Leu Arg
    3560                3565                3570

Ala Thr Ala Leu Val Asn Arg Val His Gln Glu Met Asn Ile Gln
```

-continued

```
            3575                3580                3585
Leu Pro Leu Arg Asp Val Phe Arg Phe Ser Thr Ile Glu Glu Leu
        3590                3595                3600
Ala Ala Ala Met Ser Glu Met Ala Glu Ser Tyr Ser Ser Ile
    3605                3610                3615
Pro Val Ala Glu Val Gln Asp His Tyr Pro Val Ser Ser Ala Gln
    3620                3625                3630
Lys Arg Leu Tyr Ile Leu His Gln Leu Glu Gly Ala Glu Gln Gly
    3635                3640                3645
Tyr Asn Met Pro Gly Ile Met Leu Leu Glu Gly Glu Leu Asp Arg
    3650                3655                3660
Ser Arg Phe Glu Ala Ala Phe Arg Lys Leu Ile Ala His His Asp
    3665                3670                3675
Ile Leu Arg Thr Gly Phe Glu Leu Val Gln Gly Glu Ala Val Gln
    3680                3685                3690
Arg Ile His Asp Thr Val Asp Phe Ala Ile Glu Tyr Arg Lys Val
    3695                3700                3705
Glu Glu Gln Glu Val Gln Gln Val Lys Gln Phe Ile Arg Thr
    3710                3715                3720
Phe Glu Leu Asp Lys Pro Pro Leu Leu Arg Val Gly Leu Ile Glu
    3725                3730                3735
Ile Ala Gly Thr Lys Glu Gln His Val Leu Leu Phe Asp Met His
    3740                3745                3750
His Ile Ile Ser Asp Gly Val Ser Ile Gly Ile Val Leu Gln Glu
    3755                3760                3765
Ile Met Arg His Tyr His Gly Glu Gln Val Pro Pro Leu His Ile
    3770                3775                3780
Gln Tyr Lys Asp Tyr Ala Ala Trp Gln Gln Ser Glu Ala Gln Lys
    3785                3790                3795
Glu Gln Leu Lys His Gln Lys Ala Tyr Trp Leu Gly Gln Phe Gln
    3800                3805                3810
Gly Glu Leu Pro Ile Leu Glu Leu Pro Thr Asp Tyr Ala Arg Pro
    3815                3820                3825
Ala Met Gln Gln Tyr Gly Gly Leu Thr Leu Pro Phe Arg Ile Asp
    3830                3835                3840
Lys Asp Val Ala Asp Gly Leu Asn Arg Ile Ala Ala Asp Thr Gly
    3845                3850                3855
Thr Thr Leu Tyr Met Val Leu Leu Ala Ala Tyr Thr Val Met Leu
    3860                3865                3870
His Lys Tyr Thr Gly Gln Glu Asp Ile Val Val Gly Thr Pro Ile
    3875                3880                3885
Ala Gly Arg Thr His Glu Glu Leu Gln Pro Leu Ile Gly Met Phe
    3890                3895                3900
Val Asn Thr Leu Ala Ile Arg Ala Tyr Pro Glu Gly Ala Lys Ala
    3905                3910                3915
Phe Arg Ser Tyr Leu Asp Glu Ile Arg Ser Thr Met Leu Gly Ala
    3920                3925                3930
Tyr Glu His Gln Gln Tyr Pro Phe Glu Glu Leu Val Glu Gly Leu
    3935                3940                3945
Gln Leu Thr Arg Asp Leu Ser Arg Asn Pro Leu Phe Asp Thr Met
    3950                3955                3960
Phe Ala Leu Asp Asn Thr Asp Met Lys Ala Asp Ser Leu Gly Glu
    3965                3970                3975
```

```
Leu Gln Met Lys Pro Tyr Pro Leu Glu Tyr Thr Ile Ser Lys Phe
    3980            3985            3990

Asp Val Ser Leu Asp Val Lys Ala Asp Glu Ala Gly Leu Asp Cys
    3995            4000            4005

Ser Phe Glu Tyr Ala Thr Ser Leu Phe Lys Ser Glu Thr Ile His
    4010            4015            4020

Arg Met Ala Glu His Phe Ser His Leu Leu Lys Asp Ile Val Asn
    4025            4030            4035

His Pro Asp Ala Gln Leu Gly Glu Leu Gly Met Leu Thr Val Gln
    4040            4045            4050

Glu Ser Asp Glu Ile Leu Gln Val Phe Asn Pro Thr His Ser Leu
    4055            4060            4065

Lys Ala Pro Asn Glu Thr Ile His Arg Leu Phe Glu Glu Gln Ala
    4070            4075            4080

Glu Arg Thr Pro Glu Gln Pro Ala Val Val Phe Gly Asn Glu Arg
    4085            4090            4095

Met Thr Tyr Arg Glu Leu Asn Glu Arg Ala Asn Lys Leu Ala Arg
    4100            4105            4110

Thr Leu Arg Ala Glu Gly Val Glu Pro Asp Asp Leu Ile Gly Val
    4115            4120            4125

Met Ala Asp Arg Ser Ile Asp Met Val Val Ala Val Met Ala Val
    4130            4135            4140

Leu Lys Ser Gly Gly Ala Tyr Val Pro Ile Asp Pro Glu Tyr Pro
    4145            4150            4155

Glu Asp Arg Ile Arg Tyr Met Leu Glu Asp Ala Lys Ala Arg Ile
    4160            4165            4170

Leu Leu Thr Gln Gly His Leu Gln Asp Lys Val Thr Phe Glu Gly
    4175            4180            4185

Thr Trp Val Leu Leu Glu Asp Glu Ala Ser Tyr His Glu Asp Asp
    4190            4195            4200

Thr Asn Leu Glu Pro Asn Cys Glu Pro Gly His Leu Cys Tyr Val
    4205            4210            4215

Ile Tyr Thr Ser Gly Thr Thr Gly Asn Pro Lys Gly Val Met Ile
    4220            4225            4230

Glu His Arg Gln Leu Ala Ala Met Ala Glu Ala Trp Lys Ala Glu
    4235            4240            4245

Tyr Glu Leu His Glu Pro Gly Ile Arg Trp Leu Gln Trp Ala Ser
    4250            4255            4260

Phe Ser Phe Asp Val Phe Ser Gly Asp Leu Ala Arg Thr Leu Leu
    4265            4270            4275

His Gly Gly Glu Leu Val Leu Cys Pro Ser Asp Thr Arg Ala Asn
    4280            4285            4290

Pro Gly Ala Leu Ala Glu Leu Leu Arg Ser Ser Gly Ile Gln Met
    4295            4300            4305

Phe Glu Ser Thr Pro Ala Leu Val Ile Pro Leu Met Glu His Val
    4310            4315            4320

Tyr Glu His Gly Leu Asp Ile Asp Ser Leu Arg Leu Leu Ile Ile
    4325            4330            4335

Gly Ser Asp Leu Cys Pro Ala Asp Glu Phe Arg Lys Leu Arg Asp
    4340            4345            4350

Arg Phe Ser Ser His Met Arg Ile Ile Asn Ser Tyr Gly Val Thr
    4355            4360            4365
```

```
Glu Ala Cys Val Asp Ser Ser Tyr Tyr Glu Pro Ile Ser Ser Asp
4370                4375                 4380

Ser Val Arg Ser Val Pro Ile Gly Lys Pro Leu Pro Tyr Val Ser
4385                4390                 4395

Met Tyr Ile Leu Gly Glu Asn Leu Ser Leu Gln Pro Val Gly Leu
4400                4405                 4410

Ala Gly Glu Leu Tyr Ile Ala Gly Ala Gly Val Gly Arg Gly Tyr
4415                4420                 4425

Trp Asn Arg Pro Glu Met Thr Ala Asp Lys Phe Val Arg Asp Pro
4430                4435                 4440

Phe Ala Asp Gly Gln Arg Met Tyr Arg Thr Gly Asp Leu Ala Lys
4445                4450                 4455

Trp Leu Pro Asp Gly Asn Ile Glu Leu Ile Gly Arg Thr Asp His
4460                4465                 4470

Gln Val Lys Ile Arg Gly Tyr Arg Ile Glu Ile Gly Glu Val Glu
4475                4480                 4485

Ser Lys Leu Gln Glu Thr Pro His Ile Arg Glu Ala Ala Val Val
4490                4495                 4500

Ala Lys Glu Asp Gly Ser Gly Arg Lys Val Leu Cys Ala Tyr Tyr
4505                4510                 4515

Thr Ser Glu Arg Glu Leu Thr Ala Gly Glu Trp Arg Ala Ala Leu
4520                4525                 4530

Ala Lys Glu Leu Pro Ala Tyr Met Ile Pro Ser His Phe Met Arg
4535                4540                 4545

Leu Glu Arg Met Pro Leu Thr Pro Asn Gly Lys Leu Asp Arg Lys
4550                4555                 4560

Gly Leu Pro Ala Pro Glu Gly Ala Ala Tyr Thr Gly Thr Glu Tyr
4565                4570                 4575

Glu Ala Pro Arg Thr Asp Ala Glu Ile Ala Leu Ala Ala Ala Trp
4580                4585                 4590

Gln Ser Val Leu His Val Glu Arg Val Gly Thr Asn Asp His Phe
4595                4600                 4605

Phe Glu Leu Gly Gly Asp Ser Ile Lys Ser Ile Gln Val Ser Ser
4610                4615                 4620

Arg Leu His Gln Ala Gly Tyr Lys Leu Glu Ile Arg Asp Leu Phe
4625                4630                 4635

Lys Tyr Pro Thr Ile Ala Gln Leu Ser Pro Gln Leu Gln Pro Ile
4640                4645                 4650

Gly Arg Ile Ala Asp Gln Gly Glu Val Ser Gly Glu Val Glu Leu
4655                4660                 4665

Thr Pro Ile Gln Cys Trp Tyr Phe Gly Leu Asp Leu Asp Asp Met
4670                4675                 4680

His His Tyr Asn Gln Ser Phe Met Leu Tyr Arg Gln Asp Gly Phe
4685                4690                 4695

Asn Glu Glu Ala Leu Arg Lys Thr Leu Arg Ser Ile Val Glu His
4700                4705                 4710

His Asp Ala Leu Arg Met Val Phe Arg Lys Ser Asp Ala Gly Val
4715                4720                 4725

Thr Ala Trp Asn Arg Ala Ile Glu Glu Gly Glu Leu Phe Asp Phe
4730                4735                 4740

Leu Ala Phe Asp Ile Ala Asn Ser Gly Asp Ala Glu Gln Val Ile
4745                4750                 4755

Glu Ala Lys Ala Asn Asp Ile Gln Ala Ser Ile Asp Leu Gln Gly
```

```
                4760                4765                4770
Gly Pro Leu Val Lys Ala Gly Leu Phe Arg Cys Glu Gln Gly His
    4775                4780                4785
His Leu Leu Ile Ala Ile His Ala Val Met Asp Gly Val Ser
    4790                4795                4800
Trp Arg Ile Leu Leu Glu Asp Ile Ala Thr Gly Tyr Glu Gln Ala
    4805                4810                4815
Cys Lys Gly Asp Asp Ile Arg Leu Pro Ser Lys Thr Asp Ser Tyr
    4820                4825                4830
Ala Ala Trp Ser Arg Ser Leu Val Glu Tyr Ala Glu His Thr Asp
    4835                4840                4845
Leu Gly His Glu Arg Ser Tyr Trp Arg His Val Leu Asn Ala Gly
    4850                4855                4860
Thr Asn Pro Leu Pro Lys Asp Phe Asp Thr Glu Ser Ser Leu Gln
    4865                4870                4875
Gln Asp Ser Asn Ser Val Thr Val Ala Trp Asn Gln Gln Asp Thr
    4880                4885                4890
Glu His Leu Leu Lys Arg Val His Arg Ala Tyr Asn Thr Asp Met
    4895                4900                4905
Asn Glu Ile Leu Leu Ala Ala Leu Ala Ile Ala Ile Gln Lys Trp
    4910                4915                4920
Ser Gly His Asn Gln Ile Leu Val Asn Leu Glu Gly His Gly Arg
    4925                4930                4935
Glu Pro Ile Ala Gly Asp Leu Asp Ile Ser Arg Thr Val Gly Trp
    4940                4945                4950
Phe Thr Ser Glu Tyr Pro Val Leu Leu Lys Ala Glu Arg Asp Arg
    4955                4960                4965
Gly Leu Ala Tyr His Ile Lys Arg Ala Lys Glu Glu Leu Arg Gln
    4970                4975                4980
Ile Pro Asn Lys Gly Ile Gly Tyr Gly Ile Cys Arg Tyr Leu Ser
    4985                4990                4995
Glu Pro Gln Asp Ser Leu Glu Trp Gly Ala Ala Pro Glu Ile Ser
    5000                5005                5010
Phe Asn Tyr Leu Gly Gln Phe Asp Gln Asp Ser Met Gly Ser Gly
    5015                5020                5025
Met Met Leu Ser Pro Tyr Ser Lys Gly Ser Asp Gly Ser Ala Leu
    5030                5035                5040
His Thr Arg Gln Tyr Val Leu Asp Ile Asn Gly Ala Ile Thr Asp
    5045                5050                5055
Gly Ile Leu Thr Leu Asp Met Ser Tyr Ser Glu Lys Glu Tyr Arg
    5060                5065                5070
Lys Glu Thr Met Glu Leu Leu Ala Gly His Phe His Glu Ser Leu
    5075                5080                5085
Leu Glu Ile Ile Asp His Cys Val Ser Arg Glu Gln Thr Glu Leu
    5090                5095                5100
Thr Pro Ser Asp Leu Leu Leu Gln Gly Leu Ser Ile Glu Gln Leu
    5105                5110                5115
Glu Gln Ile Ala Glu Glu Thr Lys Glu Leu Gly Ile Ile Glu Asn
    5120                5125                5130
Met Tyr Met Leu Thr Pro Met Gln Lys Gly Met Trp Phe His Asn
    5135                5140                5145
Ala Leu Asp Gly Gln Glu Gly Ala Ser Gly Ala Tyr Phe Glu Gln
    5150                5155                5160
```

```
Thr Arg Phe Thr Leu Arg Gly Glu Leu Asp Pro Ala Leu Phe Ala
    5165            5170            5175

Gln Ser Leu His Glu Leu Ala Ala Arg His Ser Val Leu Arg Thr
    5180            5185            5190

Asn Phe Cys Ser Leu Asp Gly Glu Pro Val Gln Met Val Phe Arg
    5195            5200            5205

Glu Gly Arg Ile Thr Phe Thr Tyr Glu Asp Leu Ser Gln Leu Pro
    5210            5215            5220

Ala Asp Glu Gln Ala Val Val Met Glu Arg Val Val Ala Ser Asp
    5225            5230            5235

Lys Leu Gln Gly Phe Asp Leu Glu Arg Asp Pro Leu Val Arg Val
    5240            5245            5250

Thr Leu Met Arg Thr Glu Ala Ser Ser Cys His Val Leu Trp Ser
    5255            5260            5265

Ser His His Ile Leu Met Asp Gly Trp Cys Leu Pro Gln Leu Thr
    5270            5275            5280

Asp Glu Leu Phe Arg Ile Tyr Ser Ala Val Thr Asn His Ala Ala
    5285            5290            5295

Gly Thr Thr Glu Ala Thr Gly Thr Val Gly Ile Pro Gly Ser Ala
    5300            5305            5310

Glu Ser Met Arg Asn Lys Glu Ala Asn Leu Pro Asp Tyr Ser Arg
    5315            5320            5325

Tyr Ile Glu Trp Leu Ala Glu Gln Asp Met Ser Ala Ala Ala Glu
    5330            5335            5340

Tyr Trp Asn Gly Tyr Leu Ala Gly Tyr Glu Gln Gln Thr Arg Leu
    5345            5350            5355

Pro Asn Gly Lys Ile Thr Val Lys Asp Lys Pro Tyr Val Leu Glu
    5360            5365            5370

Gln Ala Ser Arg Lys Leu Gly Ile Asp Leu Thr Ser Arg Met Ile
    5375            5380            5385

Arg Ile Ala Lys Gln His Gln Val Thr Leu Asn Thr Leu Leu Gln
    5390            5395            5400

Ala Ala Trp Gly Ile Val Leu Gln Lys Tyr Asn Gly Thr Gln Asp
    5405            5410            5415

Val Val Phe Gly Gly Val Val Ser Gly Arg Pro Ala Asp Val Pro
    5420            5425            5430

Gly Val Glu Ser Met Ile Gly Leu Phe Ile Asn Thr Ile Pro Val
    5435            5440            5445

Arg Val Ser Cys Glu Ala Gly Ala Ser Phe Ser Asp Val Met Glu
    5450            5455            5460

Gln Leu Gln Asn Ala Ala Leu Glu Ser Gly Arg Tyr Asp Tyr Tyr
    5465            5470            5475

Pro Leu Tyr Glu Ile Gln Ser Arg Thr Ser Gln Lys Ser Glu Leu
    5480            5485            5490

Ile Ser His Ile Met Val Phe Glu Asn Tyr Pro Leu Asp Glu Arg
    5495            5500            5505

Met Glu Gln Thr Gly Asp Gly Asn Asp Gly Ala Leu Ala Leu Thr
    5510            5515            5520

Asp Val Gln Ala Ala Glu Gln Thr Asn Tyr Asp Phe Asn Leu Met
    5525            5530            5535

Val Val Pro Gly Asp Glu Leu Ile Ile Arg Phe Asp Phe Asn Ser
    5540            5545            5550
```

```
Glu Val Tyr Asp Arg Gly His Met Glu Arg Leu His His Leu
    5555                5560                5565

Met His Val Leu Glu Gln Val Thr Gly Asn Pro Ala Ile Ser Ile
    5570                5575                5580

Ala Glu Val Gln Leu Ser Thr Glu Ala Glu Lys Ala Glu Val Gln
    5585                5590                5595

Ser Ala Phe Asn Asp Thr Val Val Asp Tyr Pro Arg Glu Gln Thr
    5600                5605                5610

Ile His Trp Met Phe Glu Glu Gln Val Gln Arg Thr Pro Asp Ala
    5615                5620                5625

Ala Ala Val Leu Tyr Gly Asp Asp Val Ile Thr Tyr Arg Glu Leu
    5630                5635                5640

Asn Glu Arg Ala Asn Arg Leu Ala Arg Thr Leu Arg Ala Ala Gly
    5645                5650                5655

Val Glu Pro Asp Gln Ile Val Gly Ile Met Ala Glu Arg Ser Leu
    5660                5665                5670

Glu Leu Met Val Gly Ile Met Gly Ile Leu Lys Ala Gly Gly Ala
    5675                5680                5685

Tyr Val Pro Ile Ala Pro Asp Tyr Pro Glu Glu Arg Ile Arg Tyr
    5690                5695                5700

Met Leu Asp Asp Ser Lys Ala Gln Val Leu Leu Val Gln Gly Ser
    5705                5710                5715

Ala Gly Glu Ala Val Asp Phe Val Gly Arg Ile Ile Asn Leu Asp
    5720                5725                5730

Asp Ala Glu Ala Tyr Asp Glu Asp Ser Ser Asn Pro Glu Pro Val
    5735                5740                5745

Asn Lys Pro Thr Asp Ile Ala Tyr Ile Ile Tyr Thr Ser Gly Thr
    5750                5755                5760

Thr Gly Arg Pro Lys Gly Val Met Val Glu His Thr Ser Val Ile
    5765                5770                5775

Asn Arg Leu Leu Trp Met Gln Lys Arg Tyr Pro Ile Gly Ser Glu
    5780                5785                5790

Asp Thr Ile Met Gln Lys Thr Ala Ile Thr Phe Asp Val Ser Val
    5795                5800                5805

Trp Glu Leu Phe Trp Trp Ala Phe Val Gly Ser Lys Val Leu Met
    5810                5815                5820

Leu Ser Val Gly Gly Glu Lys Asn Pro His Ala Ile Val Asp Ala
    5825                5830                5835

Ile Glu Arg His Arg Ile Thr Thr Met His Phe Val Pro Ser Met
    5840                5845                5850

Leu His Ala Phe Leu Glu His Val Glu Gln Met Thr Asp Ala Glu
    5855                5860                5865

Arg Glu Arg Gly Leu Ala Pro Leu Arg Gln Val Phe Thr Ser Gly
    5870                5875                5880

Glu Ala Leu Leu Ala Ser Gln Val Glu Arg Phe His Arg Tyr Ile
    5885                5890                5895

Ala Pro Ala Ser Gly Ala Gln Leu Ile Asn Leu Tyr Gly Pro Thr
    5900                5905                5910

Glu Ala Thr Val Asp Val Thr Tyr Phe Asp Cys Glu Pro Gly Gln
    5915                5920                5925

Thr Tyr Val Ser Val Pro Ile Gly Lys Pro Ile Asp Asn Thr Ser
    5930                5935                5940

Ile Tyr Ile Val Asn Glu His Asn Gln Val Gln Pro Ile Gly Val
```

|  |  |  |  |  |  |  |  |  |  |
|---|---|---|---|---|---|---|---|---|---|
| | | 5945 | | | 5950 | | | 5955 | |
| Ala | Gly | Glu | Leu | Cys | Ile | Ala | Gly | Val | Gly | Leu | Ala | Arg | Gly | Tyr |
| | | 5960 | | | | 5965 | | | 5970 | |
| Trp | Asn | Arg | Pro | Glu | Leu | Thr | Ala | Glu | Lys | Phe | Val | Thr | Ile | Pro |
| | | 5975 | | | | 5980 | | | 5985 | |
| Ser | Val | Gly | Glu | Arg | Met | Tyr | Arg | Thr | Gly | Asp | Leu | Ala | Arg | Trp |
| | | 5990 | | | | 5995 | | | 6000 | |
| Leu | Pro | Asp | Gly | Asn | Ile | Glu | Tyr | Leu | Gly | Arg | Ile | Asp | His | Gln |
| | | 6005 | | | | 6010 | | | 6015 | |
| Val | Lys | Ile | Arg | Gly | Tyr | Arg | Ile | Glu | Leu | Gly | Glu | Leu | Glu | Thr |
| | | 6020 | | | | 6025 | | | 6030 | |
| Ala | Leu | Leu | Asn | Val | Gln | Glu | Ile | Arg | Glu | Thr | Val | Val | Val | Ala |
| | | 6035 | | | | 6040 | | | 6045 | |
| Arg | Glu | Glu | Glu | Asp | Gly | Gln | Lys | Ser | Leu | Cys | Ala | Tyr | Tyr | Val |
| | | 6050 | | | | 6055 | | | 6060 | |
| Ala | Asp | Gly | Asp | Pro | Thr | Val | Gly | Asn | Leu | Arg | Ala | Ala | Leu | Ala |
| | | 6065 | | | | 6070 | | | 6075 | |
| Ala | Glu | Leu | Pro | Ser | Tyr | Met | Ile | Pro | Ser | Tyr | Phe | Ile | Gln | Leu |
| | | 6080 | | | | 6085 | | | 6090 | |
| Glu | Gln | Met | Pro | Leu | Ala | Pro | Asn | Gly | Lys | Leu | Asp | Arg | Lys | Ala |
| | | 6095 | | | | 6100 | | | 6105 | |
| Leu | Pro | Ala | Pro | Lys | Asp | Val | Ile | Gln | Thr | Gly | Thr | Asp | His | Ala |
| | | 6110 | | | | 6115 | | | 6120 | |
| Ala | Pro | Arg | Thr | Ala | Leu | Glu | Val | Lys | Leu | Val | Arg | Ile | Trp | Gln |
| | | 6125 | | | | 6130 | | | 6135 | |
| Glu | Val | Leu | Gly | Leu | Asp | Gln | Ile | Gly | Val | Lys | Asp | Asp | Phe | Phe |
| | | 6140 | | | | 6145 | | | 6150 | |
| Glu | Leu | Gly | Gly | His | Ser | Leu | Arg | Ala | Thr | Ala | Leu | Ala | Ser | Lys |
| | | 6155 | | | | 6160 | | | 6165 | |
| Val | Ser | Lys | Glu | Met | His | Val | Ala | Leu | Pro | Leu | Arg | Asp | Ile | Phe |
| | | 6170 | | | | 6175 | | | 6180 | |
| His | Tyr | Ser | Thr | Leu | Glu | Ala | Met | Ala | Gln | Ala | Ile | Gly | Glu | Leu |
| | | 6185 | | | | 6190 | | | 6195 | |
| Glu | Lys | Gln | Glu | His | Arg | Ala | Ile | Pro | Ile | Ala | Pro | Met | Ala | Glu |
| | | 6200 | | | | 6205 | | | 6210 | |
| His | Tyr | Pro | Leu | Ala | Ser | Ala | Gln | Lys | Arg | Leu | Tyr | Ile | Leu | His |
| | | 6215 | | | | 6220 | | | 6225 | |
| Gln | Ala | Glu | Gly | Ala | Gln | Gln | Ser | Tyr | Asn | Met | Pro | Gly | Ala | Met |
| | | 6230 | | | | 6235 | | | 6240 | |
| Ser | Val | Ser | Gly | His | Ile | Asp | Arg | Asn | Arg | Leu | Glu | Ala | Ala | Leu |
| | | 6245 | | | | 6250 | | | 6255 | |
| Leu | Arg | Leu | Ile | Ala | Arg | His | Asp | Thr | Leu | Arg | Thr | Ser | Phe | Glu |
| | | 6260 | | | | 6265 | | | 6270 | |
| Met | Val | Asp | Gly | Glu | Pro | Val | Gln | Arg | Val | His | Gln | His | Val | Asp |
| | | 6275 | | | | 6280 | | | 6285 | |
| Phe | Ala | Leu | Glu | Tyr | Ser | Thr | Ala | Arg | Glu | Lys | Asp | Met | Glu | Gln |
| | | 6290 | | | | 6295 | | | 6300 | |
| Val | Ala | Lys | Gln | Phe | Val | Arg | Asp | Phe | Asp | Leu | Glu | Gln | Pro | Pro |
| | | 6305 | | | | 6310 | | | 6315 | |
| Leu | Leu | Arg | Val | Gly | Leu | Val | Gln | Leu | Glu | Gln | Glu | Glu | Gln | His |
| | | 6320 | | | | 6325 | | | 6330 | |
| Leu | Leu | Leu | Phe | Asp | Met | His | His | Ile | Ile | Ser | Asp | Gly | Ile | Ser |
| | | 6335 | | | | 6340 | | | 6345 | |

```
Met Asp Ile Leu Val Asp Glu Leu Ala Arg Leu Tyr Asp Gly Glu
    6350                6355                6360

Glu Leu Pro Pro Leu Glu Ile Gln Tyr Lys Asp Tyr Val Leu Trp
    6365                6370                6375

Gln Gln Ala Glu Ala Ser Ser Glu Gln Met Lys Glu His Glu Glu
    6380                6385                6390

Tyr Trp Leu Arg Thr Leu Gly Asn Glu Leu Pro Leu Leu Glu Leu
    6395                6400                6405

Pro Thr Glu Phe Ala Arg Ser Glu Gln Arg Ser Tyr Asp Gly Asp
    6410                6415                6420

Lys Leu His Phe Ala Ile Asp Gly Gln Leu Asn Glu Lys Leu Gln
    6425                6430                6435

Arg Leu Ala Ser Gln Ser Gly Ala Thr Leu Tyr Met Val Leu Leu
    6440                6445                6450

Ala Ala Tyr Thr Thr Leu Leu His Lys Tyr Ser Gly Gln Asn Asp
    6455                6460                6465

Leu Val Val Gly Thr Pro Ile Ala Gly Arg Thr His Val Asp Val
    6470                6475                6480

Glu Pro Leu Ile Gly Met Phe Val Asn Ser Leu Ala Ile Arg Asn
    6485                6490                6495

Tyr Pro Asn Asp Asp Lys Thr Phe Arg Ser Tyr Leu Glu Glu Val
    6500                6505                6510

Lys Glu Ser Thr Leu Ser Ala Phe Glu His Gln Asp Tyr Pro Phe
    6515                6520                6525

Asp Lys Leu Val Glu Gln Leu Glu Asp Ala Trp Val Pro Gly Arg
    6530                6535                6540

Asn Pro Val Phe Asp Thr Met Phe Val Leu Gln Asn Ala Lys Ala
    6545                6550                6555

Arg Thr Ile Asn Leu Gly Glu Leu Ala Phe Glu Pro Leu Ile Pro
    6560                6565                6570

Ser His Thr Val Ala Lys Phe Asp Leu Thr Leu Glu Met Ala Ile
    6575                6580                6585

Glu Asp Gly Met Leu Ser Gly Gln Phe Glu Tyr Cys Thr Lys Leu
    6590                6595                6600

Phe Ser Ala Asn Met Ile Ala Asn Phe Ala Glu Asp Phe Leu Glu
    6605                6610                6615

Ile Leu Ser Gln Ala Cys Glu Gln Pro Asp Ile Arg Leu Glu Asp
    6620                6625                6630

Ile Gln Leu Ser Gly Ser Ala Tyr Gln Glu Glu Glu Leu Glu Glu
    6635                6640                6645

Glu Ile Asp Phe Ala Phe
    6650

<210> SEQ ID NO 12
<211> LENGTH: 6428
<212> TYPE: PRT
<213> ORGANISM: Paenibacillus strain A6-6i

<400> SEQUENCE: 12

Met Ala Phe Asp Lys Glu Ile Glu Phe Trp Lys Ala Lys Leu Asp Thr
1               5                   10                  15

Glu Asp Thr Pro Thr Thr Leu Pro Tyr Thr Ser Thr Pro Ser Ser Glu
                20                  25                  30

Ala Ala Arg His Tyr Ser Val Ser Val Thr Met Pro Ala Glu Ile Ser
```

```
                35                  40                  45
Glu Arg Ile Ile Arg Met Ser Lys Gly Ser His Gln Ala Ala Phe Met
 50                  55                  60

Ile Leu Leu Gly Gly Ile Gln Cys Leu Leu His Lys Tyr Thr Ser Glu
 65                  70                  75                  80

Asn Arg Ile Val Ile Gly Met Pro Ile Val Arg Lys Ala Gly Glu Lys
                 85                  90                  95

Arg Leu Pro Ile Asn Gln Val Val Leu Leu Lys Glu Asn Val Asn Glu
                100                 105                 110

Glu Leu Thr Phe Lys Ser Leu Leu Thr Ser Leu Lys Gln Ser Phe Thr
                115                 120                 125

Glu Ala Ile Arg His Gln His Ile Pro Phe Arg Leu Ile Thr Glu Gln
                130                 135                 140

Met Asn Val Gln Glu Lys Asn Gly Leu Pro Val Ile Asn Thr Met Ala
145                 150                 155                 160

Ala Leu Lys Asn Ile His Thr Val Asn Phe Ile Pro Thr Val Val Ala
                165                 170                 175

Asp Val Leu Phe Gln Phe Glu Phe Glu Ala Glu Asn Leu Leu Leu Ser
                180                 185                 190

Val Val Tyr Asn Glu Arg Val Tyr Asp Ser Val Phe Ile Ser Gln Ile
                195                 200                 205

Ile Glu His Leu Gln Arg Val Leu Ser Ile Val Leu Leu Glu Pro Asn
                210                 215                 220

Thr Asn Leu Gly Asp Leu Arg Leu Leu Ser Asp Glu Glu Thr Ser Leu
225                 230                 235                 240

Leu Leu His Gly Phe Asn Thr Thr Ala Ala Glu Tyr Pro Arg Asp Arg
                245                 250                 255

Thr Ile His Glu Leu Phe Thr Glu Gln Ala Arg Arg Thr Pro Asp Ala
                260                 265                 270

Val Ala Ala Val Tyr Gly Gln Gln Gln Leu Thr Tyr Ala Glu Leu Asn
                275                 280                 285

Gly Arg Ala Asn Arg Leu Ala Arg Thr Leu Gln Asn Ala Gly Val Arg
                290                 295                 300

Ser Asp Gln Leu Val Gly Ile Met Ala Glu Arg Ser Leu Glu Met Ile
305                 310                 315                 320

Val Gly Leu Leu Ala Ile Met Lys Ala Gly Gly Ala Tyr Val Pro Ile
                325                 330                 335

Asp Pro Glu Tyr Pro Gln Glu Arg Ile Arg Tyr Met Leu Glu Asp Ser
                340                 345                 350

Gly Ala Gln Thr Leu Leu Leu Gln Asp His Leu Arg Glu Arg Val Thr
                355                 360                 365

Tyr Glu Gly Thr Ile Val Asp Met Asn Ser Glu His Asn Tyr His Asp
                370                 375                 380

Asp Gly Thr Glu Leu Ala Ser Val Ser Asp Ser Ser Asn Leu Ala Tyr
385                 390                 395                 400

Val Ile Tyr Thr Ser Gly Thr Thr Gly Asn Pro Lys Gly Val Met Ile
                405                 410                 415

Glu His Arg Ser Ala Val Asn Ala Leu Leu Trp Arg Ile Arg Thr Tyr
                420                 425                 430

Gly Leu Ser Ser Ser Asp Arg Ile Leu Gln Leu Phe Ser Phe Ser Phe
                435                 440                 445

Asp Gly Phe Val Met Ser Ala Phe Cys Ser Leu Leu Ser Gly Ala Gly
                450                 455                 460
```

-continued

```
Leu Phe Leu Leu Lys Glu Glu Asp Ala Lys Asp Pro Leu Ala Leu His
465                 470                 475                 480

Gly Ala Ile Ser Gln Ser Gly Ile Thr His Phe Ile Cys Val Pro Asn
                485                 490                 495

Leu Tyr Gly Ala Leu Leu Asn Val Met Gln Ala Glu Ser Val Ser Thr
                500                 505                 510

Leu Arg Thr Val Thr Leu Ala Gly Glu Ser Val Ser Ser Ala Leu Val
                515                 520                 525

Ala Arg Ser Lys Glu Gln Leu Pro Asn Val Lys Leu Phe Asn Glu Tyr
                530                 535                 540

Gly Pro Thr Glu Asn Ser Val Val Ala Thr Cys Ala Ile Gly Leu Glu
545                 550                 555                 560

Lys Asp Gln Pro Ile Thr Ile Gly Thr Pro Ile Ser Asn Ala Ser Val
                565                 570                 575

Leu Ile Leu Asn Thr Ser Gly Glu Leu Gln Pro Leu His Val Pro Gly
                580                 585                 590

Glu Leu Cys Ile Ala Gly Glu Gly Leu Ala Arg Gly Tyr Leu Asn Arg
                595                 600                 605

Pro Glu Leu Thr Glu Glu Lys Phe Ala Ala His Pro Phe Val Pro Gly
                610                 615                 620

Glu Arg Ile Tyr His Thr Gly Asp Ser Ala Arg Trp Leu Pro Asn Gly
625                 630                 635                 640

Thr Ile Glu Tyr Leu Gly Arg Ile Asp His Gln Val Lys Ile Arg Gly
                645                 650                 655

Phe Arg Ile Glu Leu Gly Glu Ile Glu Ser Ser Leu Lys Lys Ile Ala
                660                 665                 670

Gly Val Arg Glu Val Ile Val Asp Ala Arg Pro Asp Gly Asn Gly Gln
                675                 680                 685

His Met Leu Cys Ala Tyr Met Val Ala Asp Ala Glu Leu Thr Val Thr
                690                 695                 700

Glu Leu Arg Glu Ala Leu Ser Ser Asn Leu Pro Asp Tyr Met Ile Pro
705                 710                 715                 720

Ser His Phe Val Gln Met Glu Gln Leu Pro Leu Thr Pro Ser Gly Lys
                725                 730                 735

Leu Asp Arg Lys Ser Leu Pro Asp Pro Gln Ala Asn Met Ala Ile Gly
                740                 745                 750

Thr Glu Tyr Ile Ala Pro Arg Thr Pro Leu Glu Ala Arg Leu Ala Gln
                755                 760                 765

Ile Trp Gln Glu Ser Leu Gly Val Glu Arg Val Gly Ile Lys Asp Asn
                770                 775                 780

Phe Phe Ala Leu Gly Gly His Ser Leu Arg Ala Ala Thr Leu Ala Ser
785                 790                 795                 800

Lys Leu His Lys Glu Leu Asn Val Asn Val Pro Leu Arg Asp Leu Phe
                805                 810                 815

Arg Asn Pro Thr Ile Glu Glu Leu Ala Leu Leu Met Asp Gly Met Glu
                820                 825                 830

Gln Gln Glu Phe Ser Ala Ile Glu Arg Val Lys Glu Ser Glu Tyr Tyr
                835                 840                 845

Ser Val Ser Ser Ala Gln Lys Arg Leu Tyr Val Leu Gln Gln Leu Glu
                850                 855                 860

Gly Ala Glu Gln Ser Tyr Asn Met Pro Gly Ala Met Leu Leu Glu Gly
865                 870                 875                 880
```

-continued

Leu Leu Asp Arg Glu Arg Leu Glu Ala Ser Phe Arg Lys Leu Ile Ala
                885                 890                 895

Arg His Glu Thr Leu Arg Thr Gly Phe Glu Leu Met Asp Gly Glu Pro
            900                 905                 910

Val Gln Lys Val Tyr Gln Asp Val Ser Phe Ala Ile Glu Tyr Met Gln
            915                 920                 925

Thr Ser Glu Ala Glu Ala Ala Gln Lys Ala Arg Glu Phe Ile Arg Ala
    930                 935                 940

Phe Asp Leu Met Thr Pro Pro Leu Met Arg Val Gly Leu Ile Glu Met
945                 950                 955                 960

Ala Pro Asp Arg His Val Leu Leu Tyr Asp Met His His Ile Ile Ser
                965                 970                 975

Asp Gly Ala Ser Met Gly Val Val Glu Glu Phe Ala Arg Leu Tyr
            980                 985                 990

Gly Gly Glu Glu Leu Pro Pro Leu Arg Ile Gln Tyr Lys Asp Phe Ala
        995                 1000                1005

Ala Trp Gln Gln Ser Glu Ala Gln Gln Lys Arg Ser Lys Gln Gln
    1010                1015                1020

Glu Thr Tyr Trp Leu Gln Thr Phe Gly Gly Glu Leu Pro Val Leu
    1025                1030                1035

Glu Leu Pro Thr Asp Tyr Ala Arg Pro Ala Ile Gln Ser Tyr Glu
    1040                1045                1050

Gly Glu Thr Tyr Glu Phe Thr Val Asp Ser Asp Ile Ser Thr Ala
    1055                1060                1065

Leu Gln Arg Leu Ala Ala Asp Ser Gly Thr Thr Leu Tyr Met Val
    1070                1075                1080

Leu Leu Ala Ala Tyr Thr Val Leu Leu His Lys Tyr Thr Gly Gln
    1085                1090                1095

Glu Asp Ile Val Val Gly Thr Thr Asn Ala Gly Arg Met His Asp
    1100                1105                1110

Asp Leu Gln Pro Leu Ile Gly Met Phe Val Asn Thr Leu Ala Ile
    1115                1120                1125

Arg Asn Tyr Pro Ala Gly Glu Ser Thr Phe Arg Ala Tyr Leu Glu
    1130                1135                1140

Gln Val Lys Glu Gln Ala Leu Ala Ala Phe Glu His Gln Glu Tyr
    1145                1150                1155

Pro Phe Glu Glu Leu Val Glu Lys Leu His Val Thr Arg Asp Met
    1160                1165                1170

Ser Arg Asn Pro Leu Phe Asp Thr Met Phe Ser Leu Gln Asn Met
    1175                1180                1185

Glu Asn Lys Asp Phe Glu Leu Pro Gly Leu Gln Leu Lys Pro Tyr
    1190                1195                1200

Gly Phe Glu His Gln Ile Ser Lys Phe Asp Leu Ser Leu Asp Val
    1205                1210                1215

Ala Glu Gly Ala Asp Gly Leu Ala Cys Ser Leu Glu Tyr Ala Ser
    1220                1225                1230

Ser Leu Tyr Arg Gln Asp Thr Ile Val Arg Met Ala Asp His Tyr
    1235                1240                1245

Arg Gln Leu Leu His Ser Ile Ala Gln Ser Pro Glu Ala Gln Ile
    1250                1255                1260

Ser Val Leu Gly Met Leu Thr Pro Gly Glu Gln Glu Gln Ile Arg
    1265                1270                1275

Phe Lys Phe Asn His Asp Pro Ser Glu Met Glu Gln Lys His Thr

```
            1280                1285                1290
Val His Gln Leu Phe Glu Glu Gln Ala Ala Leu Thr Pro Glu Arg
    1295                1300                1305
Thr Ala Val Val His Glu Asn Glu Gln Leu Ser Tyr Arg Glu Leu
    1310                1315                1320
Asn Glu Arg Ala Asn Arg Leu Ala Arg Thr Leu Arg Gln His Gly
    1325                1330                1335
Val Gln Pro Glu Gln Leu Val Gly Ile Leu Ala Asp Arg Ser Leu
    1340                1345                1350
Asp Met Ile Val Gly Ile Met Ala Ile Leu Lys Ala Gly Gly Ala
    1355                1360                1365
Tyr Val Pro Ile Asp Pro Lys Tyr Pro Glu Glu Arg Ile Arg Tyr
    1370                1375                1380
Met Leu Glu Asp Ser Lys Ala Asn Val Leu Val Thr Gln Ser His
    1385                1390                1395
Leu Gln Ser Leu Ser Ser Phe Asp Gly Thr Trp Val Leu Leu Asp
    1400                1405                1410
Glu Glu Ser Ser Tyr Ala Glu Asp Ala Ala Asn Leu Val Ser Ile
    1415                1420                1425
Thr Glu Pro Gln His Leu Ala Tyr Val Ile Tyr Thr Ser Gly Thr
    1430                1435                1440
Thr Gly Gln Pro Lys Gly Ala Met Ile Glu His Arg Gln Leu Thr
    1445                1450                1455
Val Met Ala Lys Ala Trp Glu Arg Glu Tyr Arg Leu Arg Glu Glu
    1460                1465                1470
Ser Ile Arg Trp Met Gln Trp Ala Ser Phe Ser Phe Asp Val Phe
    1475                1480                1485
Ser Gly Asp Leu Ile Arg Ala Leu Leu His Gly Gly Glu Leu Val
    1490                1495                1500
Leu Cys Pro Glu His Ala Arg Ala Asn Pro Ala Glu Ile Tyr Glu
    1505                1510                1515
Leu Ile Arg Lys His Arg Leu His Met Phe Asp Cys Thr Pro Ser
    1520                1525                1530
Ile Val Ile Pro Leu Met Glu Tyr Val Tyr Glu Asn Lys Leu Asp
    1535                1540                1545
Ile Ser Ser Leu Lys Leu Val Ala Val Gly Ser Asp Tyr Cys Pro
    1550                1555                1560
Pro Asp Glu Phe Gln Lys Met Leu Asp Arg Phe Gly Ser Gln Phe
    1565                1570                1575
Arg Ile Ile Asn Ser Tyr Gly Val Thr Glu Thr Cys Ile Asp Ala
    1580                1585                1590
Ser Tyr Tyr Glu Pro Thr Thr Pro Thr Val Pro Arg Ala Leu Pro
    1595                1600                1605
Ile Gly Lys Pro Leu Pro Gly Val Thr Met Tyr Ile Met Asp Gly
    1610                1615                1620
Gln Arg Ser Leu Leu Pro Val Gly Val Ile Gly Glu Leu Tyr Ile
    1625                1630                1635
Gly Gly Pro Cys Val Gly Arg Gly Tyr Trp Asn Arg Ser Glu Met
    1640                1645                1650
Thr Asn Glu Lys Phe Val Glu Asp Pro Phe Leu Gln Asp Tyr Arg
    1655                1660                1665
Met Tyr Arg Thr Gly Asp Leu Ala Arg Trp Met Pro Asp Gly Asn
    1670                1675                1680
```

-continued

```
Ile Glu Tyr Leu Gly Arg Ile Asp His Gln Ala Lys Ile Arg Gly
    1685                1690                1695

Tyr Arg Ile Glu Ile Gly Glu Val Glu Ser Lys Leu Leu Lys Val
    1700                1705                1710

Glu Thr Val Arg Glu Ser Val Ile Val Ala Arg Gln Asp Pro Asn
    1715                1720                1725

Gly Thr Lys Ala Leu Cys Ala Tyr Phe Val Ala Asp Arg Asn Leu
    1730                1735                1740

Thr Val Ser Glu Leu Arg Ser Ala Leu Ala Asp Glu Leu Pro Ala
    1745                1750                1755

Tyr Met Ile Pro Ser Tyr Phe Val Gln Leu Asp Arg Leu Pro Leu
    1760                1765                1770

Thr Pro Asn Gly Lys Val Asp Arg Lys Ala Leu Pro Ala Pro Glu
    1775                1780                1785

Ala Gly Ala His Thr Gly Ile Glu Tyr Val Ala Pro Arg Thr Glu
    1790                1795                1800

Glu Glu Leu Ala Leu Ala Asn Val Trp Gln Thr Val Leu Gly Ile
    1805                1810                1815

Glu Arg Val Gly Val Gln Asp His Phe Phe Glu Leu Gly Gly Asp
    1820                1825                1830

Ser Ile Lys Ser Ile Gln Val Ala Ser Arg Leu Gln Gln Ala Gly
    1835                1840                1845

Tyr Lys Leu Glu Ile Arg Asp Leu Phe Lys Tyr Pro Thr Ile Ala
    1850                1855                1860

Gln Leu Gly Ser His Leu Gln Arg Ala Ser Lys Val Ala Asp Gln
    1865                1870                1875

Gly Glu Val Ser Gly Asp Val Pro Leu Thr Pro Ile Leu Gly Trp
    1880                1885                1890

Phe Phe Glu Gln Gln Phe Ala Asp Ala His His Tyr Asn Gln Ser
    1895                1900                1905

Ile Met Leu Tyr Arg Arg Glu Gly Phe Asp Glu Ala Ala Ile Arg
    1910                1915                1920

Asn Val Leu Gln Ala Val Thr Glu His His Asp Ala Leu Arg Ile
    1925                1930                1935

Val Phe Arg Arg Asn Asp Gln Gly Asp Tyr Thr Ala Trp Asn Arg
    1940                1945                1950

Ala Ile Glu Glu Gly Glu Leu Phe His Leu Glu Val Leu Asn Leu
    1955                1960                1965

Thr Gly Ser Ala Ser Gly Asp His Glu Gln Asn Val Arg Gln Ile
    1970                1975                1980

Ile Glu Ala Lys Ala Ser Glu Ile Gln Arg Ser Phe Asp Leu His
    1985                1990                1995

Asp Gly Pro Leu Ala Arg Ala Gly Leu Phe Arg Thr Asp Glu Gly
    2000                2005                2010

Asp His Leu Leu Leu Val Met His His Gly Val Val Asp Gly Val
    2015                2020                2025

Ser Trp Arg Ile Leu Leu Glu Asp Ile Ala Ala Gly Tyr Glu Gln
    2030                2035                2040

Ala Leu Lys Gly Glu Pro Val Arg Leu Pro Ala Lys Thr Asp Ser
    2045                2050                2055

Phe Arg Thr Trp Ala Asn His Leu Ala Ser Tyr Ala Arg Ser Glu
    2060                2065                2070
```

```
Ala Met Ile Glu Glu Gln Val Phe Trp Glu Gln Ala Glu Ala Asn
    2075            2080            2085

Ala Thr Ser Ile Leu Pro Leu Pro Lys Asp Phe Glu Ala Glu Thr
    2090            2095            2100

Ser Leu Gln Gln Asp Ser Glu Ser Val Val Glu Trp Ser Arg
    2105            2110            2115

Glu Glu Thr Asp Met Leu Leu Lys His Val His Arg Ala Tyr Asn
    2120            2125            2130

Thr Asp Met Asn Asp Ile Leu Leu Ala Ala Leu Gly Met Ala Ile
    2135            2140            2145

Gln Gln Trp Cys Gly His Glu Lys Ala Leu Val Thr Leu Glu Gly
    2150            2155            2160

His Gly Arg Glu Asn Ile Met Pro Glu Leu Asp Ile Ser Arg Thr
    2165            2170            2175

Val Gly Trp Phe Thr Ser Glu Tyr Pro Phe Leu Leu Glu Ser Asp
    2180            2185            2190

Pro Asn Lys Ser Leu Ser Tyr Arg Ile Lys Arg Met Lys Glu Asn
    2195            2200            2205

Leu Arg Arg Ile Pro Asn Lys Gly Ile Gly Tyr Gly Ile His Arg
    2210            2215            2220

Tyr Leu Ser Asp Ser Gly Met Ser Gly Thr Glu Asn Val Ser Arg
    2225            2230            2235

Ser Glu Ala Ser Ala Gln Pro Glu Ile Ser Phe Asn Tyr Leu Gly
    2240            2245            2250

Gln Phe Asp Gln Asp Leu Gln Asn Asn Glu Met Glu Val Ser Pro
    2255            2260            2265

Tyr Ser Gly Gly Ala Glu Ile Ser Val Arg Gln Ala Arg Asn Thr
    2270            2275            2280

Thr Leu Asp Phe Asn Gly Met Ile Ser Ala Gly Val Leu Ala Leu
    2285            2290            2295

Glu Val Ser Tyr Ser Ser Lys Gln Tyr Arg Arg Asp Thr Ile Asp
    2300            2305            2310

Arg Leu Ala Ala Leu Leu Lys Gly Ser Leu Gln Glu Ile Val Ala
    2315            2320            2325

His Cys Ala Ser Lys Asp Lys Pro Glu Leu Thr Pro Ser Asp Val
    2330            2335            2340

Leu Val Asn Gly Leu Gly Ile Glu Asp Leu Glu Arg Ile Ala Glu
    2345            2350            2355

Gln Thr Arg Asp Leu Gly Asp Ile Glu Asn Ile Tyr Ala Leu Thr
    2360            2365            2370

Pro Met Gln Lys Gly Met Trp Phe His Asn Ala Met Asp Gly Gln
    2375            2380            2385

Ala Gly Ala Tyr Phe Glu Gln Thr Arg Phe Thr Ile Gln Gly Glu
    2390            2395            2400

Leu Asp Val Gln Leu Phe Ala Ser Ser Leu Asp Val Leu Ala Thr
    2405            2410            2415

Arg His Ala Val Leu Arg Thr Asn Phe Phe Ser Gly Trp Asn Gly
    2420            2425            2430

Glu Leu Leu Gln Ile Val Tyr Arg Asn Lys Asn Leu Glu Phe Ser
    2435            2440            2445

Tyr Glu Asp Leu Thr Glu Leu Pro Glu Asp Glu Lys Gln Asp Arg
    2450            2455            2460

Val Glu Ala Met Ala Gln Ala Asp Lys Leu Arg Gly Phe Asp Leu
```

```
              2465                2470                2475

Glu His Asp Ala Leu Met Arg Val Ser Val Leu Arg Thr Asn Val
    2480                2485                2490

Asn Cys Ser His Val Ile Trp Ser Ser His His Ile Leu Met Asp
    2495                2500                2505

Gly Trp Cys Leu Pro Gln Leu Thr Gln Glu Trp Leu Glu Thr Tyr
    2510                2515                2520

Ser Asp Ser Val Asn Gly Arg Ser Ser Arg Ser Gly Ala Ser
    2525                2530                2535

Pro Tyr Ser Leu Tyr Ile Glu Trp Leu Tyr Lys Gln Asp Tyr Thr
    2540                2545                2550

Ala Ala Ser Gln Tyr Trp Ser Asp Tyr Leu Ala Asp Tyr Asp Gln
    2555                2560                2565

Gln Thr Val Leu Pro Gln Lys Lys Ser Ser Gly Arg Ser Asp Val
    2570                2575                2580

Tyr Ile Ala Asp Asn Leu Val Phe Glu Leu Gly Glu Ala Leu Thr
    2585                2590                2595

Ala Lys Met His Arg Val Ala Lys Gln His Gln Leu Thr Leu Asn
    2600                2605                2610

Thr Leu Met Gln Ala Ala Trp Gly Ile Ile Leu Gln Lys Tyr Asn
    2615                2620                2625

Gly Thr Gly Asp Ala Val Phe Gly Gly Val Val Ser Gly Arg Pro
    2630                2635                2640

Ala Glu Ile Pro Gly Ile Glu Ser Met Ile Gly Leu Phe Ile Asn
    2645                2650                2655

Thr Ile Pro Ile Arg Val Ala Cys Glu Ala Asp Asp Arg Phe Ala
    2660                2665                2670

Asp Val Met Lys Arg Leu Gln Glu Lys Ala Leu Glu Ser Gly Arg
    2675                2680                2685

Tyr Asp Tyr Tyr Pro Leu Tyr Asp Ile Gln Ala Leu Ser Thr His
    2690                2695                2700

Lys Gln Asp Leu Ile Asn His Ile Leu Val Phe Glu Asn Tyr Pro
    2705                2710                2715

Met Glu Glu Gln Met Glu Gln Ala Gly Asp Glu Arg Gly Gln Leu
    2720                2725                2730

Asn Ile Thr Asp Val Arg Val Ala Glu Gln Thr Ser Tyr Asp Phe
    2735                2740                2745

Asn Leu Val Val Met Pro Gly Glu Asp Met Met Ile Arg Leu Glu
    2750                2755                2760

Tyr Asn Ala Val Met Tyr Asp Arg Ala Asp Met Glu Arg Val Arg
    2765                2770                2775

Gln His Leu Ile His Val Leu Glu Gln Val Thr Ala Asp Pro Ala
    2780                2785                2790

Ile Ala Val Lys Asp Val Arg Leu Ala Thr Asp Glu Lys Ala
    2795                2800                2805

Glu Leu Leu Thr Ala Phe Asn Asp Thr Glu Ile Glu Tyr Pro Arg
    2810                2815                2820

Glu Gln Met Ile His Arg Met Phe Glu Glu Gln Val Gln Arg Thr
    2825                2830                2835

Pro Asp Ala Thr Ala Val Leu Tyr Gly Ala Ala Ala Met Thr Tyr
    2840                2845                2850

Arg Glu Met Asn Glu Arg Ala Asn Gln Leu Ala Arg Thr Leu Arg
    2855                2860                2865
```

-continued

```
Ala Ala Gly Val Val Pro Asp Gln Ile Val Gly Ile Met Ala Glu
2870             2875             2880

Arg Ser Leu Glu Leu Met Val Gly Ile Met Gly Ile Leu Lys Ala
2885             2890             2895

Gly Gly Ala Tyr Val Pro Ile Ala Pro Asp Tyr Pro Glu Glu Arg
2900             2905             2910

Ile Arg Tyr Met Leu Asp Asp Ser Glu Ala Gln Val Leu Ile Val
2915             2920             2925

Gln Gly Ser Ala Gly Glu Ala Ile Asp Phe Ala Gly Arg Val Ile
2930             2935             2940

Asn Leu Asp Asp Ala Asp Ser Tyr Asp Gln Asp Ser Ser Asn Leu
2945             2950             2955

Glu Met Val Asn Lys Pro Thr Asp Ile Ala Tyr Ile Ile Tyr Thr
2960             2965             2970

Ser Gly Thr Thr Gly Arg Pro Lys Gly Val Met Val Glu His Thr
2975             2980             2985

Ser Val Ile Asn Arg Leu Leu Trp Met Gln Lys Arg Tyr Pro Ile
2990             2995             3000

Gly Ala Asp Asp Thr Ile Met Gln Lys Thr Ala Ile Thr Phe Asp
3005             3010             3015

Val Ser Val Trp Glu Leu Phe Trp Trp Ala Phe Val Gly Ser Lys
3020             3025             3030

Val Leu Met Leu Pro Val Gly Gly Glu Lys Asn Pro Ala Ala Ile
3035             3040             3045

Val Glu Ala Ile Glu Gln Tyr Glu Ile Thr Thr Met His Phe Val
3050             3055             3060

Pro Ser Met Leu His Ala Phe Leu Glu His Ile Glu Gln Leu Pro
3065             3070             3075

Glu Ala Glu Arg Glu Arg Leu Ser Pro Leu Gln Gln Val Phe Thr
3080             3085             3090

Ser Gly Glu Ala Leu Leu Ala Ser Gln Val Glu Arg Phe His Gln
3095             3100             3105

Tyr Val Val Pro Ala Ser Gly Ala Arg Leu Ile Asn Leu Tyr Gly
3110             3115             3120

Pro Thr Glu Ala Thr Val Asp Val Thr Tyr Phe Asp Cys Glu Pro
3125             3130             3135

Gly Gln Thr Tyr Val Ser Val Pro Ile Gly Lys Pro Ile Asp Asn
3140             3145             3150

Thr Arg Ile Tyr Ile Val Asn Glu His Phe Gln Val Gln Pro Ile
3155             3160             3165

Gly Val Ala Gly Glu Leu Cys Ile Ala Gly Val Gly Leu Ala Arg
3170             3175             3180

Gly Tyr Trp Asn Arg Pro Glu Leu Thr Glu Glu Lys Phe Val Leu
3185             3190             3195

Val Pro Ser Val Gly Glu Arg Met Tyr Arg Thr Gly Asp Leu Ala
3200             3205             3210

Arg Trp Leu Pro Asp Gly Asn Ile Glu Tyr Leu Gly Arg Ile Asp
3215             3220             3225

His Gln Val Lys Ile Arg Gly Tyr Arg Ile Glu Leu Gly Glu Leu
3230             3235             3240

Glu Thr Ala Leu Leu Asn Ile Asp Ala Val Arg Glu Thr Val Val
3245             3250             3255
```

```
Val Ala Arg Glu Asp Glu Ser Gly Gln Lys Ser Leu Cys Ala Tyr
3260                     3265                 3270

Tyr Val Ala Asp Gly Glu Ala Thr Ile Ser Asp Leu Arg Ala Ala
    3275                 3280                 3285

Leu Ala Ala Glu Leu Pro Ser Tyr Met Ile Pro Ser Tyr Phe Val
    3290                 3295                 3300

Arg Leu Glu Gln Met Pro Leu Ala Pro Asn Gly Lys Leu Asp Arg
    3305                 3310                 3315

Lys Ala Leu Pro Ala Pro Glu Arg Ser Leu Gln Val Glu Ser Glu
    3320                 3325                 3330

Tyr Val Ala Pro Arg Thr Glu Ala Glu Gln Met Leu Thr Thr Val
    3335                 3340                 3345

Trp Gln Ala Val Leu Gly Ile Glu Arg Val Gly Ile Thr Asp His
    3350                 3355                 3360

Phe Phe Glu Leu Gly Gly Asp Ser Ile Lys Ser Ile Gln Val Ala
    3365                 3370                 3375

Ala Arg Met Gln Gln Ala Gly Phe Lys Leu Glu Ile Arg Asp Leu
    3380                 3385                 3390

Phe Lys Tyr Pro Thr Val Thr Gln Leu Val Pro Tyr Met Gln Pro
    3395                 3400                 3405

Ile Asn Arg Thr Ala Asp Gln Gly Glu Val Val Gly Glu Val Pro
    3410                 3415                 3420

Met Thr Pro Ile Leu His Trp Phe Glu His Gln Gln Phe Ala Asn
    3425                 3430                 3435

Pro His His Phe Asn Gln Ser Val Met Leu Tyr Arg Lys Asp Gly
    3440                 3445                 3450

Phe Val Ala Asp Ala Val Cys Lys Ala Leu His Lys Leu Val Glu
    3455                 3460                 3465

His His Asp Ala Leu Arg Ile Val Ile Gln Arg Thr Glu Gln Gly
    3470                 3475                 3480

Glu Tyr Ser Leu Trp Asn Arg Ser Leu Val Glu Gly Glu Leu Phe
    3485                 3490                 3495

Ser Met Glu Glu Ile Asp Leu Thr Asp Gln Ser Asp Phe Ala Ala
    3500                 3505                 3510

Ala Ile Glu Ala Glu Ala Asn His Ile Gln Gly Ser Ile Asp Leu
    3515                 3520                 3525

Gln Ala Gly Pro Leu Val Lys Ala Gly Leu Phe His Gly Ser Asp
    3530                 3535                 3540

Gly Asp His Leu Leu Leu Val Ile His His Ala Val Ile Asp Gly
    3545                 3550                 3555

Val Ser Trp Arg Ile Leu Leu Glu Asp Leu Ala Ser Gly Tyr Glu
    3560                 3565                 3570

Gln Ala Leu Asn Gln Arg Gln Val Arg Leu Pro Met Lys Thr Asp
    3575                 3580                 3585

Ser Phe Arg Thr Trp Ala Glu Gln Leu Val Glu Tyr Ala Asn Ser
    3590                 3595                 3600

Pro Ala Met Asp Lys Glu Ser Ala Tyr Trp Leu Gly Val Ala Gln
    3605                 3610                 3615

Thr Glu Val Ala Ala Leu Pro Lys Asp Ser Glu Cys Thr Val Ser
    3620                 3625                 3630

Leu Gln Arg Asp Ser Glu Ser Val Val Leu Glu Trp Asn Arg Glu
    3635                 3640                 3645

Asp Thr Glu Arg Leu Leu Lys His Val His Arg Ala Tyr Asn Thr
```

```
              3650              3655              3660

Glu Met Asp Asp Ile Leu Leu Thr Ala Leu Gly Arg Ala Leu Met
    3665            3670                3675

Lys Trp Arg Gly Ile Glu Arg Ile Leu Val Thr Leu Glu Gly His
    3680            3685                3690

Gly Arg Glu Ser Ile Ile Gln Gly Met Asp Ile Thr Arg Thr Val
    3695            3700                3705

Gly Trp Phe Thr Thr Glu Tyr Pro Phe Glu Leu Gly Met Glu Ala
    3710            3715                3720

Asn Asp Ser Leu Gly Ser Gln Ile Lys Lys Val Lys Glu Asp Leu
    3725            3730                3735

Arg Arg Ile Pro Asn Lys Gly Ile Gly Tyr Gly Leu Phe Arg Tyr
    3740            3745                3750

Leu Ser Asn Ser Gly Lys Gln Ala Trp Asn Asp Ala Pro Thr Thr
    3755            3760                3765

Gln Ile Arg Tyr Asn Tyr Leu Gly Gln Phe Asp Ala Asp Leu Ser
    3770            3775                3780

Asn Asn Glu Met Ser Val Ser Pro Tyr Ala Ser Gly Ser Glu Ile
    3785            3790                3795

Ser Asp Glu Gln Glu Arg Lys Tyr Pro Leu Asp Ile Asn Gly Val
    3800            3805                3810

Ile Ala Glu Gly Gln Leu Thr Leu Gly Leu Ser Tyr Ser Val Lys
    3815            3820                3825

Glu Tyr Arg Lys Glu Thr Met Glu Glu Leu Gly Asp Phe Leu Thr
    3830            3835                3840

Glu Ser Leu Lys Glu Ile Ile Ala His Cys Glu Ser Gln Glu Arg
    3845            3850                3855

Thr Gln Leu Thr Pro Ser Asp Val Leu Phe Lys Gly Leu Ser Leu
    3860            3865                3870

Glu Trp Leu Asp Arg Ile Ser Ser Gln Met Gln His Ile Gly Glu
    3875            3880                3885

Ile Glu Asn Val Tyr Ala Leu Thr Pro Met Gln Lys Gly Met Trp
    3890            3895                3900

Phe His Ser Ala Met Asp Ser Leu Thr Gly Ala Tyr His Glu Gln
    3905            3910                3915

Thr Met Phe Thr Leu Glu Gly Ser Leu Asp Val Glu Leu Phe Ser
    3920            3925                3930

Ser Ser Leu Asn Glu Leu Ala Lys Arg His Ala Val Leu Arg Thr
    3935            3940                3945

Asn Phe Ile Ser Gly Pro Gln Gly Glu Pro Val Gln Val Val Phe
    3950            3955                3960

Arg Asn Lys Pro Ile Gly Phe Ser Phe Gln Asp Val Arg Ala Leu
    3965            3970                3975

Asn Glu Glu Gln Gln Ser Phe Ile Lys Glu Ala Val Ser Ser
    3980            3985                3990

Asp Gln Leu Leu Gly Phe Asp Leu Ala Gln Gly Ala Leu Met Arg
    3995            4000                4005

Val Ser Ala Ile Arg Thr Gly Glu Leu Ser Cys Arg Val Leu Trp
    4010            4015                4020

Ser Ser His His Ile Leu Met Asp Gly Trp Cys Leu Pro Gln Leu
    4025            4030                4035

Met Gln Glu Leu Phe Asp Thr Tyr Ala Ala Leu Leu Gln Lys Lys
    4040            4045                4050
```

-continued

Ser Pro Asp Arg Thr Ala Val Pro Ala Tyr Ser Gln Tyr Ile Glu
4055            4060            4065

Trp Leu Gly Gln Gln Asp Glu Glu Ala Ala Gly Thr Tyr Trp Ser
4070            4075            4080

Ala Tyr Leu Asp Asp Tyr Asp Gln Val Thr Glu Ile Pro Gln Glu
4085            4090            4095

Ser Ser Ala Gly Ile Asp Ser Glu Pro Tyr Lys Ala Glu Lys Trp
4100            4105            4110

Ser Arg Glu Leu Asp Ala Gly Leu Ser Ala Ser Ile Ser Arg Thr
4115            4120            4125

Ala Arg Gln His Gln Val Thr Leu Asn Thr Leu Leu Gln Ala Ala
4130            4135            4140

Trp Gly Val Ile Leu Gln Lys Tyr Asn Gly Thr Asn Asp Val Val
4145            4150            4155

Phe Gly Ser Val Val Ser Gly Arg Pro Ala Glu Val Pro Gly Ile
4160            4165            4170

Glu Thr Met Ile Gly Leu Phe Ile Asn Thr Ile Pro Ile Arg Val
4175            4180            4185

Lys Cys Glu Gly Ser Thr Ser Phe Ala Glu Leu Met Gly Leu Leu
4190            4195            4200

Gln Glu Gln Ala Leu Glu Ser Gly Lys Tyr Asp Tyr Tyr Pro Leu
4205            4210            4215

Tyr Glu Ile Gln Ser Arg Ser Ala Leu Lys Gln Asn Ala Ile Arg
4220            4225            4230

Gln Ile Met Val Phe Glu Asn Tyr Pro Met Asp Glu Gln Leu Glu
4235            4240            4245

Gln Ala Gly Gly Asp Glu His Gly Met Pro Ser Leu Thr Asp Val
4250            4255            4260

Ala Val Glu Glu Gln Thr Asn Tyr Asp Phe Asn Leu Ile Val Val
4265            4270            4275

Pro Gly Glu Gln Ile Ser Ile Arg Phe Asp Tyr Asn Ala Asn Arg
4280            4285            4290

Phe Val Gln Ala Asp Met Glu Arg Leu Met Gly His Leu Asn Asn
4295            4300            4305

Ile Leu Glu Gln Ile Val Asp Asn Pro Arg Ile Ala Val Glu Asp
4310            4315            4320

Leu Glu Leu Ala Thr Glu Ala Glu Lys Ser Glu Val Val Gln Ser
4325            4330            4335

Phe Asn Asp Thr Phe Thr Asn Tyr Pro Arg Asp Met Met Leu His
4340            4345            4350

Arg Leu Phe Glu Glu Gln Ala Glu Arg His Pro Asp Ala Val Ala
4355            4360            4365

Ile Ser Phe Arg Asp Phe Gln Met Thr Tyr Arg Asp Leu Asn Asp
4370            4375            4380

Arg Val Asn Arg Leu Ala Arg Thr Leu Arg Ala Val Gly Val Gly
4385            4390            4395

Thr Asp Lys Leu Val Gly Leu Met Ser Glu Arg Ser Pro Asp Met
4400            4405            4410

Ile Ile Gly Ile Leu Ala Ile Leu Lys Ala Gly Gly Gly Tyr Val
4415            4420            4425

Pro Ile Asp Pro Glu Tyr Pro Gly Glu Arg Ile Arg Tyr Met Leu
4430            4435            4440

```
Glu Asp Ser Gly Ala Arg Ile Met Leu Ala Gln Gln His Leu Thr
4445                4450                4455

Gly Lys Ile Pro Val Met Asp Ala Ser Pro Leu Asp Ala Ile Ile
4460                4465                4470

Asn Leu Asp Thr Glu Thr Ser Tyr Asp Ser Asn Gly Ser Asn Leu
4475                4480                4485

Glu Ala Asn Thr Asp Ala Ser Ser Glu Asn Leu Ala Cys Val Ile
4490                4495                4500

Tyr Thr Ser Gly Thr Thr Gly Lys Pro Lys Gly Asn Leu Thr Thr
4505                4510                4515

His Arg Asn Ile Val Arg Val Arg Glu Thr Glu Tyr Ile Asp
4520                4525                4530

Ile Thr Asn His Asp Asn Val Leu Gln Met Ser Ser Tyr Ala Phe
4535                4540                4545

Asp Gly Ser Thr Phe Asp Ile Tyr Gly Ala Leu Leu Asn Gly Ala
4550                4555                4560

Lys Leu Val Leu Val Pro His Glu Thr Leu Leu Glu Val Arg Gln
4565                4570                4575

Leu Ala Glu Leu Ile Val Gln Glu Lys Ile Ser Val Met Phe Ile
4580                4585                4590

Thr Thr Ala Tyr Phe Asn Val Leu Val Asp Val Gln Ala Ser Cys
4595                4600                4605

Leu Ser Asn Ile Arg Ala Ile Leu Phe Gly Gly Glu Arg Val Ser
4610                4615                4620

Val Ser His Val Arg Lys Ala Leu Asn His Val Ala Pro Gly Ala
4625                4630                4635

Leu Lys His Val Tyr Gly Pro Thr Glu Ser Thr Val Phe Ala Thr
4640                4645                4650

Cys His Asp Val His Glu Val Thr Glu Asn Ala Val Thr Val Pro
4655                4660                4665

Ile Gly Arg Pro Ile Ser Asn Thr Ser Ile Tyr Ile Val Asp Ala
4670                4675                4680

Asn Asn Lys Leu Gln Pro Val Gly Val Ala Gly Glu Leu Cys Val
4685                4690                4695

Ala Gly Asp Gly Leu Ala Arg Gly Tyr Leu Asn Arg Pro Asp Leu
4700                4705                4710

Thr Ala Glu Lys Phe Val Asp Ser Pro Tyr Val Gln Gly Glu Arg
4715                4720                4725

Met Tyr Arg Thr Gly Asp Leu Ala Lys Trp Leu Pro Asp Gly Ser
4730                4735                4740

Ile Glu Tyr Val Gly Arg Ile Asp Gln Gln Val Lys Ile Arg Gly
4745                4750                4755

Tyr Arg Ile Glu Leu Gly Glu Ile Glu Ala Gln Leu Leu Asn Val
4760                4765                4770

Glu Asp Val Gln Glu Ala Val Val Ala Arg Asp Thr Asp Thr
4775                4780                4785

Gly Glu Lys Gln Leu Cys Ala Tyr Tyr Val Ala Met Arg Pro Leu
4790                4795                4800

Glu Ala Asn His Leu Arg Glu Val Met Gly Gln Ala Met Pro Ser
4805                4810                4815

Tyr Met Leu Pro Ala His Phe Ile Gln Leu Glu Gln Leu Pro Leu
4820                4825                4830

Thr Pro Asn Gly Lys Val Asp Arg Lys Ala Leu Pro Ala Pro Glu
```

-continued

```
            4835                4840                4845
Glu Gly Arg Ser Gly Glu Thr Phe Val Thr Pro Arg Thr Pro Leu
    4850                4855                4860
Glu Ala Gln Leu Val Gln Ile Trp Gln Asp Val Leu Gly Ile Ser
    4865                4870                4875
Ser Ile Ser Val Thr Asp His Phe Phe Glu Leu Gly Gly His Ser
    4880                4885                4890
Leu Lys Ala Thr Leu Leu Val Asn Arg Leu His Gln Glu Leu Asn
    4895                4900                4905
Ile Glu Leu Pro Leu Lys Asp Val Phe Gln Tyr Pro Thr Leu Glu
    4910                4915                4920
Val Met Ala Lys Arg Leu Ser Asn Ala Glu Gly Ser Arg His Val
    4925                4930                4935
Ser Ile Pro Val Ala Ala Pro Ser Gln His Tyr Pro Val Ser Ser
    4940                4945                4950
Ala Gln Lys Arg Leu Tyr Ile Leu His Gln Leu Glu Gly Ala Glu
    4955                4960                4965
Leu Ser Tyr Asn Met Pro Asn Met Met Leu Leu Glu Gly Ala Val
    4970                4975                4980
Asp Leu Gly Arg Leu Glu Glu Ala Phe Lys Arg Leu Ile Glu Arg
    4985                4990                4995
His Glu Thr Leu Arg Thr Gly Phe Glu Ile Val Asn Gly Glu Pro
    5000                5005                5010
Val Gln Arg Ile Tyr Pro Glu Val Asp Phe Ala Ile Glu His Val
    5015                5020                5025
Leu Ala Ser Glu Glu Gly Ala Ser Lys Leu Met Gln Gln Phe Val
    5030                5035                5040
Arg Ser Phe Gln Leu Glu Lys Pro Pro Leu Leu Arg Ile Gly Ile
    5045                5050                5055
Ile Glu Leu Ser Glu Glu Arg Ser Ile Leu Met Phe Asp Met His
    5060                5065                5070
His Ile Ile Ser Asp Gly Thr Ser Met Gly Ile Leu Ile Asn Glu
    5075                5080                5085
Phe Val His Leu Tyr Ser Gly Ala Glu Leu Thr Pro Leu Arg Ile
    5090                5095                5100
Gln Tyr Lys Asp Tyr Ala Val Trp Gln Gln Ser Asp Thr Gln Gln
    5105                5110                5115
Lys Ala Met Lys Leu Gln Glu Gly Tyr Trp Leu Lys Val Leu Gly
    5120                5125                5130
Gly Glu Leu Pro Val Leu Glu Met Pro Thr Asp Ser Ile Arg Pro
    5135                5140                5145
Thr Thr Gln Ser Phe Arg Gly Asp Leu Leu Gln Phe Asp Leu Asp
    5150                5155                5160
Pro Val Arg Ser Ala Gly Leu Arg Arg Ile Ala Ala Glu Asn Gly
    5165                5170                5175
Ala Thr Met Tyr Met Val Leu Leu Ala Leu Tyr Lys Thr Met Leu
    5180                5185                5190
His Lys Tyr Ser Ala Gln Glu Asp Ile Ile Val Gly Thr Pro Ile
    5195                5200                5205
Ala Gly Arg Asn His Gly Asp Leu Gln Pro Leu Leu Gly Met Phe
    5210                5215                5220
Val Asn Thr Leu Ala Ile Arg Ser Tyr Pro Ala Ala Ser Lys Thr
    5225                5230                5235
```

Phe Leu Ser Tyr Leu Asp Glu Ile Lys Glu Thr Thr Leu Gly Ala
    5240                5245            5250

Phe Glu Asn Gln Asn Tyr Pro Phe Glu Ala Leu Val Glu Gln Val
    5255                5260            5265

Gln Val Met Arg Asp Met Ser Arg Asn Pro Val Phe Asp Thr Met
    5270                5275            5280

Phe Ile Leu Gln Asn Ala Asp Gln Gly Glu Met Lys Ile Asp Gly
    5285                5290            5295

Val Arg Leu Gln Ser Val Pro Asn Glu His Thr Val Ser Lys Phe
    5300                5305            5310

Asp Leu Thr Phe Gln Ala Glu Asp Glu Ala Glu Ile Val Cys
    5315                5320            5325

Ser Ile Glu Tyr Ala Thr Asp Leu Phe Lys Arg Gly Thr Ile Glu
    5330                5335            5340

Arg Met Ala Arg His Phe Glu Gln Leu Val Asp Ala Val Leu Asp
    5345                5350            5355

Asn Pro Gln Ala Ser Leu Ser Asn Leu Ser Met Val Thr Asn Glu
    5360                5365            5370

Glu Lys Ala Leu Leu Gln Asp Lys Phe Asn Asp Thr Asp Met Ala
    5375                5380            5385

His Pro Ser Asp Lys Thr Val His Glu Leu Phe Ala Glu Gln Val
    5390                5395            5400

Glu Arg Thr Pro Asp Ala Val Ala Val Val Ser Gly Cys Glu Gln
    5405                5410            5415

Leu Ser Tyr Gly Glu Leu Asn Arg Lys Ala Asn Gln Leu Ala Trp
    5420                5425            5430

Lys Leu Arg Glu Tyr Gly Val Thr Ala Glu Gln Pro Val Gly Ile
    5435                5440            5445

Ile Val Glu Arg Thr Leu Asp Thr Val Val Ala Val Met Ala Val
    5450                5455            5460

Leu Lys Ala Ser Gly Thr Phe Val Pro Ile Asp Pro Glu Tyr Pro
    5465                5470            5475

Glu Thr Arg Ile Arg Tyr Met Leu Ala Asp Ser Gly Ala Lys Leu
    5480                5485            5490

Val Leu Ala Gln Ser Glu Leu Pro Gly Ile Ile Pro Asp Asp Val
    5495                5500            5505

Arg Leu Ile Asp Val Arg Asp Glu Ser Leu Tyr Gln Gly Asp Gly
    5510                5515            5520

Ala Asp Val Pro Asn Gly Ser Lys Pro Ser Asn Leu Leu Tyr Ile
    5525                5530            5535

Ile Tyr Thr Ser Gly Thr Thr Gly Asn Pro Lys Gly Val Met Leu
    5540                5545            5550

Glu His Gly Asn Met Val Asn Leu Leu His Tyr Gln Gln Lys Gly
    5555                5560            5565

Thr Asn Ile Pro Met Pro Ser Arg Ile Leu Gln Tyr Ala Ser Gly
    5570                5575            5580

Ser Phe Asp Val Cys Tyr Gln Glu Met Phe Ser Ala Leu Leu Phe
    5585                5590            5595

Gly Gly Ser Leu Tyr Met Val Asp Asn Glu Met Arg Lys Asp Pro
    5600                5605            5610

Val Arg Leu Phe Gln Glu Ile Glu Lys His Glu Ile Asp Val Leu
    5615                5620            5625

```
Phe Ile Pro Val Ala Phe Leu Lys Phe Ile Phe Ala     Glu Pro Glu
5630            5635                5640

Trp Ala Glu Ala Phe Pro Arg Cys Val Arg His Ile     Ile Thr Ala
5645            5650                5655

Gly Glu Gln Leu Val Val Thr Pro Gln Val Gln Ala     Cys Leu Lys
5660            5665                5670

Arg Leu Asp Ile Cys Leu His Asn His Tyr Gly Pro     Ser Glu Thr
5675            5680                5685

His Val Val Thr Thr Tyr Thr Met Thr Pro Glu Ile     Ile Glu Val
5690            5695                5700

Gly Leu Pro Pro Ile Gly Lys Pro Ile Ala Asn Thr     Ser Ile Tyr
5705            5710                5715

Ile Val Asn Asp Ser Phe Glu Leu Gln Pro Ile Gly     Val Lys Gly
5720            5725                5730

Glu Leu Phe Val Ser Gly Ala Cys Val Gly Arg Gly     Tyr Trp Gly
5735            5740                5745

Arg Thr Asp Leu Thr Glu Glu Lys Phe Leu Asp Asn     Pro Phe Val
5750            5755                5760

Pro Gly Glu Arg Leu Tyr Lys Thr Gly Asp Val Ala     Arg Trp Leu
5765            5770                5775

Pro Asp Gly Ser Ile Asp Tyr Val Gly Arg Ser Asp     His Gln Val
5780            5785                5790

Lys Ile Arg Gly Phe Arg Ile Glu Leu Gly Glu Val     Glu Ser Gln
5795            5800                5805

Leu Leu His Val Pro Ala Val Gln Glu Ala Thr Val     Val Ala Leu
5810            5815                5820

Glu Asp His Ala Gly Gln Lys Gln Leu Cys Ala Tyr     Phe Thr Ala
5825            5830                5835

Glu Arg Ser Leu Thr Ala Gly Glu Leu Arg Ala Val     Leu Ser Gln
5840            5845                5850

Glu Leu Pro Gly Tyr Met Ile Pro Ser Tyr Phe Val     Gln Leu Glu
5855            5860                5865

Arg Leu Pro Leu Thr Pro Asn Gly Lys Ile Asp Arg     Arg Ala Leu
5870            5875                5880

Pro Lys Pro Glu Gly Gly Ile Glu Thr Gly Thr Glu     Tyr Val Ala
5885            5890                5895

Pro Arg Thr Asp Thr Glu Ala Arg Leu Ala Arg Ile     Trp Gln Asp
5900            5905                5910

Val Leu Gly Leu Pro Ser Val Gly Val Lys Asp Asn     Phe Phe Glu
5915            5920                5925

Leu Gly Gly His Ser Leu Arg Ala Thr Thr Leu Val     Ser Arg Leu
5930            5935                5940

Tyr Lys Glu Met Asn Val Asn Phe Pro Leu Arg Gly     Val Phe Arg
5945            5950                5955

His Pro Thr Ile Glu Glu Met Ser Gln Ala Ile Ser     Gln Met Glu
5960            5965                5970

Thr Ser Trp Tyr Thr Ala Ile Pro Ile Ala Glu Glu     Gln Glu Tyr
5975            5980                5985

Tyr Pro Leu Ser Ser Ala Gln Leu Arg Leu Tyr Ile     Met Ser Gln
5990            5995                6000

Leu Glu Gly Ser Glu Leu Ser Tyr Asn Met Pro Gly     Met Leu Val
6005            6010                6015

Leu Glu Gly Gln Leu Asn Arg Asp Gln Phe Gln Thr     Ala Phe Leu
```

-continued

```
              6020                6025                6030

Lys Leu Ile Ala Arg His Glu Thr Leu Arg Thr Gly Phe Glu Met
              6035                6040                6045

Val Asp Gly Glu Pro Met Gln Arg Ile His Arg Asn Thr Glu Phe
              6050                6055                6060

Ala Ile Asp Tyr Arg Gln Val Ser Glu Asp Glu Val Pro Glu Met
              6065                6070                6075

Ile Gly Gln Phe Ile Arg Gln Phe Asp Leu Glu His Pro Pro Leu
              6080                6085                6090

Leu Arg Val Gly Leu Phe Glu Val Gly Gln Asp Arg His Ile Leu
              6095                6100                6105

Val Phe Asp Met His His Ile Ile Ser Asp Gly Val Ser Met Ser
              6110                6115                6120

Asn Leu Val Asp Glu Phe Thr Arg Leu Tyr Ala Asn Glu Glu Arg
              6125                6130                6135

Pro Pro Leu Arg Ile Gln Tyr Lys Asp Tyr Ala Val Trp Gln Gln
              6140                6145                6150

Ala Arg Glu Asn Leu Glu Arg Arg Lys Arg Gln Glu Asp Tyr Trp
              6155                6160                6165

Met Ser Val Leu Gln Gly Asp Leu Pro Asn Ala Glu Leu Pro Met
              6170                6175                6180

Asp Tyr Asp Arg Thr Ala Val Arg Ser Phe Asp Gly Glu Gln Ile
              6185                6190                6195

Glu Phe Glu Ile Asn Pro Val Val Thr Gly Gln Leu Asn Gln Leu
              6200                6205                6210

Ala Ser Asn His Glu Cys Thr Leu Tyr Met Val Leu Met Ser Ala
              6215                6220                6225

Tyr Gln Ile Leu Leu Ser Lys Tyr Cys Gly Gln Asp Asp Ile Ile
              6230                6235                6240

Val Gly Thr Pro Val Ala Gly Arg Asn His Ala Asp Leu Glu Pro
              6245                6250                6255

Leu Ile Gly Met Phe Val Asn Thr Leu Ala Ile Arg Asn Arg Pro
              6260                6265                6270

Gln Gly Asp Lys Thr Phe Gln Ser Phe Leu Ala Glu Val Lys Glu
              6275                6280                6285

Ser Thr Leu Gly Ala Phe Glu His Gln Glu Tyr Pro Phe Glu Glu
              6290                6295                6300

Leu Ile Asp Leu Leu Lys Leu Gln Trp Glu Thr Ser Arg Asn Pro
              6305                6310                6315

Leu Phe Asp Thr Val Phe Val Leu Gln Asn Thr Glu Glu Arg Glu
              6320                6325                6330

Ala Gly Ile Gly Gly Leu Thr Ile Ser Pro Tyr Val Thr Asp Asp
              6335                6340                6345

Ser Val Ser Ala Lys Phe Asp Leu Thr Leu Ser Val Ser Glu Glu
              6350                6355                6360

Asp Asp Gly Met Lys Gly Ser Phe Leu Tyr Ala Ser Lys Leu Phe
              6365                6370                6375

Lys Ala Ala Gly Ile His Arg Met Met Arg Asp Tyr Leu Ser Ile
              6380                6385                6390

Leu Ser Gln Val Cys Glu Asn Pro Arg Ile Arg Ile Gln Asp Ile
              6395                6400                6405

Ser Ile Ser Gly Gln Gln Thr Gln Glu Lys Ser Lys Ile Asp Thr
              6410                6415                6420
```

Ile Glu Phe Ala Phe
          6425

<210> SEQ ID NO 13
<211> LENGTH: 3149
<212> TYPE: PRT
<213> ORGANISM: Paenibacillus strain A6-6i

<400> SEQUENCE: 13

Met Lys Ser Val Tyr Glu Lys Glu Ala Tyr Trp Asn Gly Met Phe
1               5                   10                  15

Asp Ser Asp Asp Ser Met Ser Ile Leu Pro Tyr Cys Ser Thr His Gly
            20                  25                  30

Arg Glu Ala Asn Ala Asp Thr Asn Ala Ala Lys Val Ser Met Ile Arg
            35                  40                  45

Ala Leu Pro Thr Asp Leu Ser Asp Arg Met Asn Thr Leu Ala Asn Gly
            50                  55                  60

Ser Asp Val Ala Leu Tyr Met Ile Gly Leu Ala Gly Val Thr Cys Leu
65                  70                  75                  80

Leu His His Tyr Thr Asn Arg Glu Asn Val Leu Val Gly Met Pro Thr
                85                  90                  95

Ile Asp Glu Ser Glu Asp Asp Ser Ser Pro Arg Asp Val Leu Ile Met
            100                 105                 110

Lys Thr Asn Leu Thr Arg Gly Ser Ser Phe Arg Ser Val Leu Gly Ser
            115                 120                 125

Ile Lys Thr Ala Val Gly Gly Ala Leu Glu His Arg His Leu Pro Phe
            130                 135                 140

Arg Lys Met Val His Asn Leu Asn Leu Glu Met Asp Thr Asn Gly Leu
145                 150                 155                 160

Pro Val Met Asn Thr Val Val Ser Phe Ser Ala Ile His Thr Ala Ser
                165                 170                 175

Ile Asp Leu Ser Val Ser Ser Asp Val Ile Phe Arg Phe Asp Ala Lys
            180                 185                 190

Asp Asp Gly Leu His Leu Glu Val Leu Tyr Asp Glu Ser Arg Tyr Asp
            195                 200                 205

Ala Ser Tyr Ile Ala Thr Leu Phe Glu His Phe Phe Arg Leu Leu His
            210                 215                 220

Phe Val Leu Phe Gln Pro Asp Gln Pro Ile Gly Asn Thr Glu Leu Leu
225                 230                 235                 240

Ser Ala Glu Glu Lys His Arg Leu Leu His Glu Phe Asn Asp Val Trp
                245                 250                 255

Thr Asp Phe Pro Arg Gln Ala Thr Leu Tyr Gln Phe Ile Glu Glu His
            260                 265                 270

Ala Glu Arg Gln Pro Asp Ala Ile Ala Val Ser Tyr Glu Asp Thr Lys
            275                 280                 285

Leu Thr Tyr Arg Glu Leu Asn Ala Arg Ala Asn Arg Leu Ala Arg Thr
            290                 295                 300

Leu Arg Ser Glu Gly Val Gln Thr Glu Ala Leu Val Gly Leu Met Ala
305                 310                 315                 320

Glu Arg Ser Ile Asp Met Ile Val Gly Met Leu Ala Val Leu Lys Ala
                325                 330                 335

Gly Gly Gly Tyr Val Ala Ile Asp Pro Glu Tyr Pro Glu Glu Arg Val
            340                 345                 350

Arg Tyr Met Leu Glu Asp Ser Gly Ala Arg Val Ile Leu Val Gln Gln

```
                355                 360                 365
His Leu Gln Asn Arg Val Pro Asn Thr Glu Ser Ala Ala Arg Leu Leu
    370                 375                 380

Thr Leu Asp Asp Glu Gln Ser Tyr His Glu Asp Ala Ser Asn Leu Glu
385                 390                 395                 400

Ser Arg Ser Thr Ala Val Asp Leu Ala Cys Val Ile Tyr Thr Ser Gly
                405                 410                 415

Thr Thr Gly Asn Pro Lys Gly Asn Leu Thr Thr His Arg Asn Ile Val
            420                 425                 430

Arg Ile Val Lys Asn Thr Asn Tyr Ile Glu Ile Thr Glu Gln Asp Lys
            435                 440                 445

Val Leu Gln Leu Ser Ser Tyr Ser Phe Asp Gly Ser Ala Phe Asp Ile
    450                 455                 460

Phe Gly Ala Leu Thr Asn Gly Ala Gln Leu Val Leu Val Pro His His
465                 470                 475                 480

Thr Leu Leu Asp Ala Arg Lys Leu Ala Glu Leu Ile Glu Thr Glu Arg
                485                 490                 495

Ile Ser Val Met Leu Ile Thr Thr Ala Tyr Phe Asn Val Leu Val Asp
            500                 505                 510

Val Asn Ile Ser Cys Leu Arg His Ile Arg Ala Ile Leu Phe Gly Gly
            515                 520                 525

Glu Arg Ser Ser Val Ala His Val Arg Arg Ala Leu Glu Gln Thr Gly
    530                 535                 540

Pro Gly Arg Leu Lys His Ala Tyr Gly Pro Ser Glu Ser Thr Val Tyr
545                 550                 555                 560

Ala Thr Trp His Asp Val Thr Glu Ile Ser Glu Arg Ala Val Ser Val
                565                 570                 575

Pro Ile Gly Arg Pro Ile Ser Asn Thr Ala Ile Tyr Ile Val Asn Glu
            580                 585                 590

Arg Asn Asp Leu Gln Pro Ile Gly Val Ser Gly Glu Leu Cys Val Ala
            595                 600                 605

Gly Glu Gly Leu Val Arg Gly Tyr Leu Asn Arg Pro Glu Leu Thr Glu
    610                 615                 620

Gln Lys Phe Val Asp Asn Pro Phe Val Pro Gly Glu Arg Met Tyr Arg
625                 630                 635                 640

Thr Gly Asp Leu Ala Arg Trp Leu Pro Asp Gly Thr Ile Glu Tyr Val
                645                 650                 655

Gly Arg Met Asp Asp Gln Val Lys Ile Arg Gly His Arg Ile Glu Ile
            660                 665                 670

Gly Glu Val Glu Ala Gln Leu Leu Lys Val Ala Pro Ile Gln Lys Ala
    675                 680                 685

Thr Ile Val Val Arg Gly Arg Glu Asp Gly Glu Lys Gln Leu Cys Ala
    690                 695                 700

Tyr Tyr Val Ala Asp Arg Leu Leu Pro Ala Gly Glu Ile Arg Thr Met
705                 710                 715                 720

Leu Ala Lys Glu Leu Pro Ser Tyr Met Ile Pro Ala Tyr Phe Ile Gln
                725                 730                 735

Leu Glu Gln Met Pro Leu Thr Thr Asn Gly Lys Val Asp Arg Lys Ala
            740                 745                 750

Leu Pro Glu Pro Glu Glu His Val Gln Ala Glu Thr Glu Tyr Val Ala
        755                 760                 765

Pro Arg Ser Glu Gln Glu Ile Arg Leu Ala Arg Val Trp Gln Glu Val
    770                 775                 780
```

```
Leu Gly Leu Ser Arg Val Gly Ala Lys Asp His Phe Phe Glu Leu Gly
785                 790                 795                 800

Gly His Ser Leu Arg Ala Thr Thr Leu Val Ser Lys Leu His Lys Glu
                805                 810                 815

Glu Asn Ile Ser Leu Ser Leu Arg Asp Val Phe Arg Asn Pro Thr Leu
            820                 825                 830

Glu Ala Met Ala Ala Leu Met Glu Asp Ala Gln Gly Arg Lys Phe Ala
            835                 840                 845

Pro Ile Pro Thr Val Glu Glu Lys Asp Val Tyr Pro Val Ser Ser Val
        850                 855                 860

Gln Lys Arg Leu Phe Ile Leu His Gln Leu Gly Ala Glu Gln Ser
865                 870                 875                 880

Tyr Asn Met Pro Gly Ala Leu Leu Glu Gly Asp Val Asp Arg Asn
                885                 890                 895

Arg Leu Glu Tyr Ala Phe Arg Gln Leu Ile Thr Arg His Glu Thr Leu
                900                 905                 910

Arg Thr Gly Phe Glu Met Val Asn Gly Glu Pro Val Gln Arg Ile Tyr
            915                 920                 925

Pro Thr Val Asp Phe Val Val Glu Glu Met Ser Ala Leu Glu Gly Ser
        930                 935                 940

Glu Val Glu Glu Gln Ile Arg Gln Phe Ile Arg Ala Phe Asp Leu Ser
945                 950                 955                 960

Thr Ala Pro Leu Phe Arg Ala Gly Leu Ile Lys Leu Ala Pro Gln Arg
                965                 970                 975

His Ile Leu Leu Phe Asp Met His His Ile Ile Ser Asp Gly Thr Ser
                980                 985                 990

Ile Gly Ile Met Ile Glu Glu Phe Thr Ser Leu Tyr Ser Gly Asn Glu
            995                 1000                1005

Leu Glu Pro Leu Arg Ile Gln Tyr Lys Asp Phe Ala Ala Trp Gln
    1010                1015                1020

Arg Ser Glu Glu Gln Ile Glu Gln Leu Lys Arg Gln Glu Thr Tyr
    1025                1030                1035

Trp Leu Gln Gln Met Glu Gly Val Leu Pro Val Leu Glu Leu Pro
    1040                1045                1050

Thr Asp Tyr Val Arg Pro Ala Val Gln Ser His Asp Gly Ala Leu
    1055                1060                1065

Phe Glu Phe Ser Leu Asp Arg Glu Gln Ser Gln Asp Leu Arg Lys
    1070                1075                1080

Leu Ala Ala Asp Thr Arg Thr Thr Leu Tyr Met Val Leu Leu Ala
    1085                1090                1095

Ala Tyr Thr Ile Ile Leu His Lys Tyr Ser Gly Gln Glu Asp Ile
    1100                1105                1110

Val Val Gly Thr Pro Ile Ala Gly Arg Thr His Asp Asp Val Gln
    1115                1120                1125

Pro Leu Ile Gly Met Phe Val Asn Thr Leu Ala Ile Arg Asn Tyr
    1130                1135                1140

Pro Ser Gly Ser Lys Ser Val Leu Thr Tyr Leu Glu Glu Ile Lys
    1145                1150                1155

Glu Thr Thr Leu Gly Ala Phe Glu His Gln Asp Tyr Pro Phe Glu
    1160                1165                1170

Glu Leu Val Glu Asn Val Gln Ile Ser Arg Asp Met Ser Arg His
    1175                1180                1185
```

```
Pro Val Phe Asp Thr Met Phe Ala Leu Glu Asn Thr Glu His Arg
    1190            1195                1200

Glu Phe Asp Leu Asp Gly Leu Gln Val Lys Pro Tyr Gly Ala Glu
    1205            1210                1215

Tyr Gly Met Ala Lys Phe Asp Leu Asn Leu Thr Val Thr Glu Asp
    1220            1225                1230

Gly Asp Gly Leu Tyr Cys Thr Met Glu Tyr Ala Thr Ala Leu Tyr
    1235            1240                1245

Asn Arg Ser Thr Ile Glu Arg Leu Cys Gly His Phe Leu Gln Val
    1250            1255                1260

Val Gly Ser Met Thr His Asn Pro Gln Ala Ala Ile Ser Ser Leu
    1265            1270                1275

Gln Met Val Thr Ser Glu Glu Lys Ala Gln Leu Gln His Glu Phe
    1280            1285                1290

Asn Gly Thr Val Met Glu Tyr Ser Ser Asp Lys Thr Val His Glu
    1295            1300                1305

Leu Phe Ala Glu Gln Val Glu Arg Thr Pro Asp Ala Val Ala Val
    1310            1315                1320

Val Ser Gly Ser Glu Gln Leu Ser Tyr Gly Glu Leu Asn Arg Lys
    1325            1330                1335

Ala Asn Gln Leu Ala Trp Lys Leu Arg Glu Tyr Gly Val Thr Ala
    1340            1345                1350

Glu Gln Pro Val Gly Ile Ile Val Glu Arg Thr Leu Asp Thr Val
    1355            1360                1365

Val Ala Val Ile Ala Val Leu Lys Ala Ser Gly Thr Phe Val Pro
    1370            1375                1380

Ile Asp Pro Glu Tyr Pro Glu Thr Arg Ile Arg Tyr Met Leu Ala
    1385            1390                1395

Asp Ser Gly Ala Lys Leu Val Leu Ala Gln Ser Glu Leu Pro Gly
    1400            1405                1410

Ile Ile Ser Asp Asp Val Arg Leu Ile Asp Val Arg Asp Lys Ser
    1415            1420                1425

Leu Tyr Gln Gly Asp Gly Ala Asp Val Pro Asn Gly Ser Lys Pro
    1430            1435                1440

Ser Asn Leu Leu Tyr Ile Ile Tyr Thr Ser Gly Thr Thr Gly Asn
    1445            1450                1455

Pro Lys Gly Val Met Leu Glu His Gly Asn Met Val Asn Leu Leu
    1460            1465                1470

His Tyr Gln Gln Asn Gly Thr Asn Ile Pro Met Pro Ser Arg Ile
    1475            1480                1485

Leu Gln Tyr Ala Ser Gly Ser Phe Asp Val Cys Tyr Gln Glu Met
    1490            1495                1500

Phe Ser Ala Leu Leu Phe Gly Gly Ser Leu Tyr Met Val Asp Asn
    1505            1510                1515

Glu Met Arg Lys Asp Pro Val Arg Leu Phe Gln Glu Ile Glu Lys
    1520            1525                1530

His Glu Ile Asp Val Met Tyr Ile Pro Val Ala Phe Leu Lys Phe
    1535            1540                1545

Ile Phe Ala Glu Pro Glu Trp Ala Glu Ala Phe Pro Arg Cys Val
    1550            1555                1560

Arg His Ile Ile Thr Ala Gly Glu Gln Leu Val Val Thr Pro Gln
    1565            1570                1575

Val Gln Ala Cys Leu Lys Arg Leu Asp Ile Cys Leu His Asn His
```

```
              1580                1585                1590
Tyr  Gly  Pro  Ser  Glu  Thr  His  Val  Val  Thr  Thr  Tyr  Thr  Met  Thr
     1595                1600                1605

Pro  Glu  Val  Ile  Glu  Val  Gly  Leu  Pro  Pro  Ile  Gly  Lys  Pro  Ile
     1610                1615                1620

Ala  Asn  Thr  Ser  Ile  Tyr  Ile  Val  Asn  Asp  Ser  Phe  Glu  Leu  Gln
     1625                1630                1635

Pro  Ile  Gly  Val  Lys  Gly  Glu  Leu  Tyr  Val  Ser  Gly  Ala  Cys  Val
     1640                1645                1650

Gly  Arg  Gly  Tyr  Trp  Gly  Arg  Thr  Asp  Leu  Thr  Glu  Glu  Lys  Phe
     1655                1660                1665

Leu  Asp  Asn  Pro  Phe  Ala  Pro  Gly  Glu  Arg  Leu  Tyr  Lys  Thr  Gly
     1670                1675                1680

Asp  Val  Ala  Arg  Trp  Leu  Pro  Asp  Gly  Ser  Ile  Glu  Tyr  Val  Gly
     1685                1690                1695

Arg  Ser  Asp  His  Gln  Val  Lys  Ile  Arg  Gly  Phe  Arg  Ile  Glu  Leu
     1700                1705                1710

Gly  Glu  Val  Glu  Ser  Gln  Leu  Leu  His  Val  Pro  Ala  Val  Gln  Glu
     1715                1720                1725

Ala  Thr  Val  Val  Ala  Leu  Glu  Asp  His  Ala  Gly  Gln  Lys  Gln  Leu
     1730                1735                1740

Cys  Ala  Tyr  Phe  Ala  Ala  Glu  Arg  Ser  Leu  Thr  Ala  Gly  Glu  Leu
     1745                1750                1755

Arg  Gln  Ala  Leu  Ser  Gln  Glu  Leu  Pro  Gly  Tyr  Met  Ile  Pro  Ser
     1760                1765                1770

Tyr  Phe  Val  Gln  Leu  Glu  Arg  Leu  Pro  Leu  Thr  Pro  Asn  Gly  Lys
     1775                1780                1785

Ile  Asp  Arg  Arg  Ala  Leu  Pro  Lys  Pro  Glu  Gly  Gly  Ile  Glu  Thr
     1790                1795                1800

Gly  Thr  Glu  Tyr  Val  Ala  Pro  Arg  Thr  Asp  Thr  Glu  Ala  Arg  Leu
     1805                1810                1815

Ala  Arg  Ile  Trp  Gln  Asp  Val  Leu  Gly  Leu  Pro  Ser  Val  Gly  Val
     1820                1825                1830

Lys  Asp  Asn  Phe  Phe  Glu  Leu  Gly  Gly  His  Ser  Leu  Arg  Ala  Thr
     1835                1840                1845

Thr  Leu  Val  Ser  Arg  Leu  Tyr  Lys  Glu  Met  Asn  Val  Asn  Phe  Pro
     1850                1855                1860

Leu  Arg  Gly  Val  Phe  Arg  His  Pro  Thr  Ile  Glu  Glu  Met  Ala  Lys
     1865                1870                1875

Ala  Ile  Thr  Glu  Met  His  Gln  Glu  Leu  Tyr  Thr  Glu  Ile  Pro  Ile
     1880                1885                1890

Ala  Glu  Glu  Lys  Ala  Tyr  Tyr  Pro  Leu  Ser  Ser  Ala  Gln  Lys  Arg
     1895                1900                1905

Leu  Phe  Ile  Val  Ser  Gln  Leu  Thr  Gly  Ala  Glu  Val  Ser  Tyr  Asn
     1910                1915                1920

Met  Pro  Gly  Val  Leu  Ile  Leu  Glu  Gly  Glu  Leu  Asp  Arg  Ala  Arg
     1925                1930                1935

Phe  Glu  Arg  Ala  Phe  Gln  Lys  Leu  Ile  Asp  Arg  His  Glu  Ser  Leu
     1940                1945                1950

Arg  Thr  Ser  Phe  Glu  Thr  Val  Arg  Gly  Glu  Pro  Val  Gln  Arg  Ile
     1955                1960                1965

His  Ser  Gln  Val  Glu  Phe  Ala  Ile  Glu  Tyr  His  Leu  Ala  Ala  Glu
     1970                1975                1980
```

```
Gln Asp Ala Glu Ala Leu Ile Thr His Phe Val Arg Pro Phe Gln
    1985                1990                1995

Leu Lys Gln Ala Pro Leu Leu Arg Val Gly Leu Ile Glu Thr Gly
    2000                2005                2010

His Glu Arg His Ile Leu Met Phe Asp Met His His Ile Ile Ser
    2015                2020                2025

Asp Gly Val Thr Met Gly His Val Val Asn Glu Phe Ser Arg Ile
    2030                2035                2040

Tyr Ala Gly Asp Gln Leu Pro Ala Leu Arg Ile Gln Tyr Lys Asp
    2045                2050                2055

Tyr Ala Val Trp Gln Gln Ser Asn Glu Tyr Ala Glu Lys Leu Ala
    2060                2065                2070

His Gln Glu Ser Tyr Trp Leu Lys Gln Leu Asp Gly Glu Leu Pro
    2075                2080                2085

Thr Leu Glu Leu Pro Thr Asp Tyr Val Arg Pro Ala Val Gln Gln
    2090                2095                2100

Phe Glu Gly Asp Val Ala Leu Phe Thr Leu Thr Asn Ser Gln Ala
    2105                2110                2115

Glu Gln Leu Gln Arg Leu Ala Ala Asn Tyr Gly Ala Thr Leu Tyr
    2120                2125                2130

Met Val Leu Leu Ala Ala Tyr Thr Val Ile Leu His Lys Tyr Thr
    2135                2140                2145

Gly Gln Asp Asp Ile Ile Val Gly Thr Pro Ile Ala Gly Arg Asn
    2150                2155                2160

His Thr Glu Leu Glu Pro Leu Val Gly Met Phe Val Asn Thr Leu
    2165                2170                2175

Ala Ile Arg Asn Tyr Pro Thr Gly Glu Lys Ser Phe Ala Glu Leu
    2180                2185                2190

Leu Ala Glu Val Lys Asp Thr Ala Leu Ala Ala Phe Glu Asn Gln
    2195                2200                2205

Asp Tyr Pro Phe Glu Thr Leu Val Glu Lys Val His Lys Ser Arg
    2210                2215                2220

Asp Met Ser Arg Asn Pro Val Phe Asp Thr Ile Phe Ser Val Glu
    2225                2230                2235

His Glu Gln Gln Ser Ser Phe His Ile Asp Gly Leu Arg Ile Ser
    2240                2245                2250

Pro Tyr Pro His Ser His Ser Val Ala Lys Phe Asp Leu Thr Phe
    2255                2260                2265

His Ala Glu Gln Asn Glu Glu Gly Ile Leu Cys Gly Leu Gly Tyr
    2270                2275                2280

Ala Thr Ala Leu Tyr Ala Lys Glu Thr Ala Arg Arg Met Gly Glu
    2285                2290                2295

His Phe Val Gln Leu Ile Asp Ala Ile Ile Ala Glu Pro Asn Ala
    2300                2305                2310

Lys Leu Met Ser Leu Asn Met Met Ser Leu Gln Glu Arg Glu Gln
    2315                2320                2325

Val Lys Leu Val Phe Asn Asp Thr Ile Thr Asn Tyr Pro Arg Glu
    2330                2335                2340

Lys Thr Ile Gln His Leu Phe Glu Glu Gln Ala Glu Lys Ser Pro
    2345                2350                2355

Asp Ala Val Ala Val Gln Phe Gly Gly Glu Gly Leu Thr Tyr Arg
    2360                2365                2370
```

```
Glu Leu Asn Glu Arg Ser Asn Arg Leu Ala Arg Thr Leu Arg Gly
    2375                2380                2385

Lys Gly Val Lys Ala Gly Arg Cys Val Gly Leu Met Thr Asp Arg
    2390                2395                2400

Ser Leu Asp Met Ile Val Ala Ile Met Ala Thr Leu Lys Ala Gly
    2405                2410                2415

Gly Ala Tyr Val Pro Ile Asp Pro Asp Tyr Pro Glu Glu Arg Ile
    2420                2425                2430

Arg Tyr Met Ile Asp Asp Ser Gly Thr Ser Leu Leu Val Val Gln
    2435                2440                2445

Arg His Leu Gln Ala Asn His Ile Pro Ala Asp Cys Met Val Val
    2450                2455                2460

Leu Val Asp Asp Glu Gly Ser Tyr His Ala Asp Gly Thr Asn Leu
    2465                2470                2475

Glu Gln His Asn Gly Ala Ser Asp Leu Ala Tyr Val Ile Tyr Thr
    2480                2485                2490

Ser Gly Thr Thr Gly Met Pro Lys Gly Asn Leu Thr Thr His Arg
    2495                2500                2505

Asn Ile Val Arg Val Val Arg Asp Ala Lys Tyr Ile Glu Ile Asp
    2510                2515                2520

Gln His Asp Thr Val Leu Gln Leu Ser Ser Tyr Ala Phe Asp Gly
    2525                2530                2535

Ser Thr Phe Asp Ile Phe Gly Ala Leu Leu Asn Gly Ala Lys Leu
    2540                2545                2550

Val Leu Ile Thr Arg Glu Val Val Leu Asp Ala Gly Arg Leu Ala
    2555                2560                2565

Asp Thr Ile Glu Ser Glu Lys Ile Ser Val Met Phe Ile Thr Thr
    2570                2575                2580

Ala Tyr Phe Asn Leu Leu Val Asp Leu Arg Val Asp Ser Leu Arg
    2585                2590                2595

His Met Arg Ala Ile Leu Phe Gly Gly Glu Arg Ala Ser Val Ser
    2600                2605                2610

His Val Arg Lys Ala Leu Arg His Leu Gly Pro Gly Lys Leu Lys
    2615                2620                2625

His Val Tyr Gly Pro Thr Glu Ser Thr Val Phe Ala Thr Ser His
    2630                2635                2640

Asn Val Asp Glu Val Ala Asp Ser Ala Val Thr Ile Pro Ile Gly
    2645                2650                2655

Arg Pro Ile Gly Asn Thr Ala Val Tyr Ile Val Gly Glu Gly Asp
    2660                2665                2670

Val Leu Gln Pro Ile Gly Val Ala Gly Glu Leu Cys Val Ala Gly
    2675                2680                2685

Asp Gly Val Ala Ile Gly Tyr Leu Asn Arg Pro Asp Leu Ser Gly
    2690                2695                2700

Ala Lys Phe Val Asn Asn Pro Phe Val Pro Gly Asp Arg Met Tyr
    2705                2710                2715

Arg Thr Gly Asp Leu Ala Arg Trp Leu Ser Asp Gly Thr Ile Glu
    2720                2725                2730

Tyr Val Gly Arg Lys Asp Asp Gln Val Lys Ile Arg Gly Tyr Arg
    2735                2740                2745

Ile Glu Leu Gly Glu Val Glu Ala His Leu Leu Asp Leu Glu Ala
    2750                2755                2760

Ile Gln Glu Ala Val Val Ile Val Arg Glu Glu Ser Asp Gly Gln
```

```
            2765                2770                2775
Lys Arg Leu Cys Ala Tyr Tyr Val Ala Ala Arg Leu Ile Thr Ala
        2780                2785                2790
Gly Glu Met Arg Ile Ala Leu Ala Gln Gln Leu Pro Gly Tyr Met
        2795                2800                2805
Leu Pro Ser Tyr Phe Val Gln Leu Asp Lys Leu Pro Leu Ser Pro
        2810                2815                2820
Asn Gly Lys Val Asn Arg Lys Ala Leu Pro Ala Pro Glu Leu His
        2825                2830                2835
Val Gln Ala Ala Ser Glu Tyr Val Ala Pro Arg Thr Pro Gln Glu
        2840                2845                2850
Val Leu Leu Ala His Ile Trp Arg Glu Val Leu Gly Leu Gly Gln
        2855                2860                2865
Val Gly Val Lys Asp Asn Phe Phe Glu Leu Gly Gly His Ser Leu
        2870                2875                2880
Ser Leu Met Arg Leu Val Glu Arg Val Tyr Thr Glu Thr Glu Val
        2885                2890                2895
Glu Ile Pro Ile His Ser Val Phe Arg Glu Pro Thr Ile Glu Ala
        2900                2905                2910
Met Ala Tyr Glu Met Leu Lys Ser Glu Leu Ala Gly Lys Ala Gly
        2915                2920                2925
Asn His Phe Met Lys Leu Asn Glu Asn Gly His Ile Pro Val Phe
        2930                2935                2940
Cys Phe Pro Pro Gly Leu Gly Tyr Gly Leu Ser Tyr Leu Glu Leu
        2945                2950                2955
Ala Lys Gln Leu Asp His His Cys Ile Leu His Gly Ile Asp Phe
        2960                2965                2970
Ile Asp Asp Ala Glu Thr Arg Glu Glu Leu Leu Glu Arg Tyr Val
        2975                2980                2985
Asn Ala Ile Leu Ala Val Gln Pro Gln Pro Phe Ile Leu Leu
        2990                2995                3000
Gly Tyr Ser Leu Gly Gly Asn Leu Thr Phe Glu Val Ala Lys Ala
        3005                3010                3015
Leu Glu Cys Arg Gly Tyr Pro Val Ser Asp Val Ile Met Val Asp
        3020                3025                3030
Ser Leu Arg Lys Leu Lys Val His Glu Val Asp Glu Phe Asp Gly
        3035                3040                3045
Asp Ile Asp Gln Met Ile Asp Gly Val Glu Glu Leu Lys Glu Met
        3050                3055                3060
Leu Val His His Pro Leu Leu Arg Asp Gln Val Lys Asn Lys Met
        3065                3070                3075
Arg Ala Tyr Trp Ser Tyr Ala Thr Glu Leu Val Asn Ser Asp Ile
        3080                3085                3090
Ile Asp Ala Asn Ile His Ala Leu Met Ala Glu Pro Ser Glu Val
        3095                3100                3105
Asn Gln Ala Gly Arg Gly Ala Ala Arg Asp Met Ala Gly Gly Tyr
        3110                3115                3120
Ser Arg Gln Val Cys Gly Val Gln Pro Thr Arg Cys Ala Arg Arg
        3125                3130                3135
Ser Ala Ser Thr Ala Phe Leu Gly Ser Glu Arg
        3140                3145

<210> SEQ ID NO 14
```

```
<211> LENGTH: 6655
<212> TYPE: PRT
<213> ORGANISM: Paenibacillus strain TS-15

<400> SEQUENCE: 14

Met Asn Ala Asn Pro Asn Glu Trp Tyr Pro Leu Thr Gln Ala Gln Arg
1               5                   10                  15

Arg Ile Trp Tyr Thr Glu Met Met His Pro Asn Thr Ser Val Thr Thr
            20                  25                  30

Val Ala Gly Thr Met Tyr Ile Arg Gly Lys Val Asp Val Glu Ile Leu
        35                  40                  45

Lys Met Ala Ile Tyr Gln Val Ile Met Gln His Asp Ala Phe Arg Ile
50                  55                  60

Arg Ile Ala Met Thr Asp Asn Gln Pro Lys Gln Gln Phe Ala Pro Val
65                  70                  75                  80

Glu Gln Ile Val Pro His Val Asp Tyr Leu Glu Trp Asp Asn Gln Ile
                85                  90                  95

Glu Ala Glu Ser Trp Leu Gln Arg Phe Asn His Ile Pro Ile His Met
            100                 105                 110

Phe Asp Pro Ala Leu Tyr His Phe Val Ile Phe Asn Val Asn Asp Glu
        115                 120                 125

Glu Thr Trp Phe Asn Leu Lys Met Asn His Ile Ala Thr Asp Gly Val
    130                 135                 140

Ser Ser His Leu Ile Ala Tyr Lys Ile Met Lys Asn Tyr Thr Ala Met
145                 150                 155                 160

Val Ser Gly Asn Ala Asp Thr Asp Glu Gln Glu Ser Thr Tyr Leu Asp
                165                 170                 175

Tyr Ile Phe Ala Glu Arg Glu Tyr Glu Gln Ser Asp Arg Tyr Ala Lys
            180                 185                 190

Asp Lys Ala Tyr Trp Leu Asp Lys Phe Ser Thr Met Pro Glu Val Ile
        195                 200                 205

Gly Ile Lys Ser Tyr Pro Pro His Ser Ile Gly Thr Glu Ala Ser Arg
    210                 215                 220

Thr Ser Thr Thr Val Ser Gly Glu Met Tyr Glu Lys Leu Tyr Arg Phe
225                 230                 235                 240

Ser Gln Gln His Asn Ile Ser Leu Phe Thr Leu Phe Leu Gly Ser Leu
                245                 250                 255

Tyr Ala Phe Leu Tyr Lys Thr Thr Gly Asn Asn Asp Ile Ala Val Gly
            260                 265                 270

Ala Ala Tyr Ala Asn Arg Thr Ser Arg Gln Asp Lys Asp Ala Leu Gly
        275                 280                 285

Met Phe Val Ser Thr Val Ala Ala Arg Leu Thr Ile Thr Pro Asp Gln
    290                 295                 300

Asp Val Leu Thr Phe Leu His Asn Val Ala Lys Glu Gln Lys Ala Ile
305                 310                 315                 320

Leu Arg His Gln Lys Tyr Pro Tyr Asn Gln Leu Ile Leu Asp Leu Arg
                325                 330                 335

Glu Gln Asn Asn Ser Val Glu Ile Gln Asp Leu Tyr Arg Ile Ser Ile
            340                 345                 350

Asp Tyr Met Pro Ile Arg Trp Ser Tyr Gly Glu Leu Ala Val Arg
        355                 360                 365

Gln Arg Ser Ser Phe Cys Gly His Glu Val Asp Asp Phe Ala Val His
    370                 375                 380

Val Glu Asp Met Val Asp Asp Asn Gln Ile Ile Phe Asn Ile Asp Tyr
```

-continued

```
            385                 390                 395                 400

Arg Lys Gln Leu Phe Glu Glu His Glu Val Ile Arg Met Ile Glu Gln
                        405                 410                 415

Met Met Thr Ile Val Asp Gln Met Leu Asn Asn Pro Ser Gln Asn Leu
                        420                 425                 430

Gln Gln Leu Ser Met Ile Ser Asp Lys Glu Ala Gln Ile Ile Leu Thr
                        435                 440                 445

Arg Phe Ser Asn Gly Asn Trp Ser Thr Pro Gln Pro Val Gly Arg Thr
                        450                 455                 460

Ile His Gln Leu Phe Glu Glu Val Glu Arg Thr Pro Asp Gln Val
    465                 470                 475                 480

Ala Val Val Phe Gly Asp Arg His Leu Thr Tyr Lys Glu Leu Asn Glu
                        485                 490                 495

Gln Ala Asn Cys Phe Ala Arg Thr Leu Arg Ala His Gly Val Ala Ala
                        500                 505                 510

Glu Gln Phe Val Gly Ile Met Ala Asp Arg Ser Ile Glu Met Val Ile
                        515                 520                 525

Gly Ile Leu Ala Ile Leu Lys Ala Gly Gly Ala Tyr Val Pro Ile Asp
    530                 535                 540

Pro Glu Tyr Pro Glu Glu Arg Ile Leu Tyr Met Leu Glu Asp Ser Asn
    545                 550                 555                 560

Ala Arg Val Leu Val Ser Gln Ser His Leu Gln Thr Arg Val Gly Tyr
                        565                 570                 575

Thr Gly Thr Trp Val Leu Leu Asp Asn Glu Asn Asp Tyr Glu Ser Ser
                        580                 585                 590

Arg Asp Asn Leu Val Pro Val Asn Glu Ala His His Leu Ala Tyr Val
                        595                 600                 605

Ile Tyr Thr Ser Gly Thr Thr Gly Lys Pro Lys Gly Val Met Ile Glu
                        610                 615                 620

His Lys Gln Ile Thr Ala Leu Gly Asp Ala Trp Lys His Ala Tyr Gln
    625                 630                 635                 640

Leu Asp Glu Pro Gly Ile Arg Thr Leu Gln Trp Ala Ser Phe Ser Phe
                        645                 650                 655

Asp Val Phe Thr Gly Asp Met Val Arg Ala Leu Leu Tyr Gly Gly Glu
                        660                 665                 670

Leu Ile Ile Cys Pro Ser Glu Ala Arg Ala Asn Pro Glu Ala Ile Cys
                        675                 680                 685

Glu Leu Ile Ala Arg His Arg Ile His Ile Phe Glu Ser Thr Pro Ala
                        690                 695                 700

Leu Val Ile Pro Leu Met Glu Tyr Val His Glu Gln Gly Lys Asp Val
    705                 710                 715                 720

Ser Ser Leu Arg Leu Val Val Gly Ser Asp His Cys Pro Ala Ala
                        725                 730                 735

Glu Tyr Arg Lys Leu Ile Glu Arg Phe Gly Ser Gln Met Arg Ile Leu
                        740                 745                 750

Asn Ser Tyr Gly Val Thr Glu Ala Cys Val Asp Ala Cys Tyr Tyr Glu
                        755                 760                 765

Arg Asn Cys Ser Val Asp Ser Ile Thr Met Leu Pro Ile Gly Lys Pro
                        770                 775                 780

Leu Pro Ser Val Ser Met Tyr Ile Leu Asp Glu Asn Lys Ala Leu Gln
    785                 790                 795                 800

Pro Ile Gly Ile Val Gly Glu Leu Tyr Ile Gly Gly Ala Gly Val Gly
                        805                 810                 815
```

```
Arg Gly Tyr Leu Asn Arg Asp Asp Leu Thr Ala Glu Lys Phe Val Asp
            820                 825                 830

Asp Pro Tyr Ser Gln Gly Lys Met Tyr Arg Thr Gly Asp Leu Ala Arg
            835                 840                 845

Trp Leu Pro Asp Gly Asn Ile Glu Tyr Leu Gly Arg Leu Asp His Gln
    850                 855                 860

Val Lys Ile Arg Gly Asn Arg Ile Glu Ile Gly Glu Ile Glu Thr Arg
865                 870                 875                 880

Met Leu Gln Thr Ser Leu Val Arg Glu Ala Val Ile Val Ala Arg Glu
                885                 890                 895

Asp Glu Asn Gly Leu Lys Ala Leu Cys Ala Tyr Tyr Val Ala Asp Ser
            900                 905                 910

Glu Ile Ser Val Gln Gln Leu Arg Ser Thr Leu Ala Glu Gln Val Pro
            915                 920                 925

Asp Tyr Met Ile Pro Ser Tyr Phe Met Lys Leu Glu Arg Leu Pro Leu
    930                 935                 940

Thr Pro Asn Gly Lys Ile Asp Arg Asn Gly Leu Pro Ala Pro Ser Gly
945                 950                 955                 960

Gln Asp Tyr Ser Gly Lys Ile Tyr Val Glu Pro Arg Asn Gln Ala Glu
                965                 970                 975

Gln Thr Leu Val Ser Ile Trp Gln Met Val Leu Gly Val Lys Arg Val
            980                 985                 990

Gly Ile Leu Asp His Phe Phe Glu Leu Gly Gly Asp Ser Ile Lys Ser
        995                1000                1005

Ile Gln Val Ser Ser Arg Met Gln Gln Ala Gly Tyr Lys Leu Asp
    1010                1015                1020

Ile Arg Asp Leu Phe Lys Tyr Pro Thr Ile Glu Gln Ile Ser Pro
    1025                1030                1035

His Leu Val Glu Val Gln Arg Lys Ala Glu Gln Gly Glu Glu Asn
    1040                1045                1050

Gly Glu Val Gly Leu Thr Pro Ile Leu Arg Trp Tyr Phe Glu Arg
    1055                1060                1065

Asp Glu Ala Ser Leu His His Tyr Asn Gln Ser Ile Met Leu His
    1070                1075                1080

Arg Lys Asp Gly Phe Asp Glu Ala Ala Leu Arg Asn Ala Leu His
    1085                1090                1095

Lys Ile Thr Glu His His Asp Ala Leu Arg Met Val Phe Arg Arg
    1100                1105                1110

Thr Glu Gln Gly Glu Tyr Ala Ala Trp Asn Arg Arg Ile Glu Glu
    1115                1120                1125

Gly Glu Leu Tyr Arg Leu Asp Val Leu Asp Ile Lys Glu Arg Ser
    1130                1135                1140

Ala Gly Asp Glu Ser Glu Glu Ser Leu His Asn Met Leu Met Ala
    1145                1150                1155

Glu Ala Asp Ala Ile Gln Asn Gly Phe Asn Leu Glu Ala Gly Pro
    1160                1165                1170

Leu Val Gly Ala Gly Leu Phe Arg Cys Pro Asp Gly Asp His Leu
    1175                1180                1185

Leu Ile Val Ile His His Ala Val Ile Asp Ala Val Ser Trp Arg
    1190                1195                1200

Ile Leu Leu Glu Asp Leu Ala Thr Gly Tyr Glu Gln Ala Leu Leu
    1205                1210                1215
```

```
Gly Ser Glu Ile Arg Leu Pro Ala Lys Ser Asp Ser Phe Arg Leu
1220                1225                1230

Trp Ser Arg Gln Leu Ser Ala Tyr Ala Gln Gln Ser Asn Met Asn
1235                1240                1245

Glu Glu Leu Lys Tyr Trp Gln Val Ala Gln Thr Thr Ile Thr
1250                1255                1260

Pro Leu Pro Thr Asp Tyr Ala Gly Thr Ala Leu Gln Leu Asp Ser
1265                1270                1275

Glu Ser Val Thr Val Glu Trp Ser Ala Asn Glu Thr Glu Leu Leu
1280                1285                1290

Leu Lys Gln Ala His Arg Ala Tyr Asn Thr Gln Met Asp Asp Leu
1295                1300                1305

Leu Leu Thr Ala Leu Gly Ile Ala Phe Arg Arg Trp Cys Gly His
1310                1315                1320

Glu Arg Ile Arg Ile Asn Leu Glu Gly His Gly Arg Glu Ser Ile
1325                1330                1335

Leu Pro Asp Leu Asp Ile Thr Arg Thr Val Gly Trp Phe Thr Ser
1340                1345                1350

Glu Tyr Pro Gln Leu Leu Glu Val Gly Ser Glu Glu Leu Pro
1355                1360                1365

Arg Ile Ile Lys Ser Val Lys Glu Asp Leu Arg Ser Ile Pro Asn
1370                1375                1380

Lys Gly Ile Gly Tyr Gly Ile Cys Arg Tyr Leu Ser Asp Lys Ser
1385                1390                1395

Met Gln Asp Asp Trp Gly Thr Ala Pro Glu Val Ser Phe Asn Tyr
1400                1405                1410

Leu Gly Gln Phe Asp Gln Asp Phe Gln Asn Ser Gly Phe Ser Pro
1415                1420                1425

Ser Pro Tyr Ser Thr Gly Ser Asn Ile Gly Gly Asp Gln Leu Arg
1430                1435                1440

Pro Tyr Leu Leu Asp Met Asn Gly Met Val Ser Asp Gly Lys Leu
1445                1450                1455

Gln Leu Asp Ile Ser Tyr Gly Arg Thr Gln Tyr Arg Val Glu Thr
1460                1465                1470

Ile Glu Arg Leu Ala Ser Leu Ile Arg Asp Ser Leu Leu Glu Ile
1475                1480                1485

Ile Asp His Cys Val Ala Lys Glu Gln Thr Glu Leu Thr Pro Ser
1490                1495                1500

Asp Val Ser Leu Gln Arg Ile Ser Ile Gln Glu Leu Glu Gln Ile
1505                1510                1515

Val Glu Arg Thr Ser Gly Ile Gly Glu Val Glu Asp Ile Tyr Ala
1520                1525                1530

Leu Thr Pro Met Gln Lys Gly Met Trp Phe His Thr Ala Met Asp
1535                1540                1545

Ser Gln Ala Gly Ala Tyr Phe Glu Leu Thr Arg Leu Thr Leu Lys
1550                1555                1560

Gly Ala Leu Asn Ile Glu Ala Phe Ala Ala Ser Trp Asn Glu Leu
1565                1570                1575

Ala Ala Arg His Ala Val Phe Arg Thr Asn Phe Leu Val Asp Ser
1580                1585                1590

Asn Gly Glu Pro Leu Gln Val Val Phe Arg Ser Lys Arg Ile Ser
1595                1600                1605

Val Lys His Glu Asp Leu Arg Ser Leu Asn Ser Tyr Glu Gln Ala
```

-continued

```
            1610                1615                1620

Val Ala Ile Glu Asn Glu Ala Lys Glu Arg Ala Gln Gly Phe
    1625                1630                1635

Asp Leu Glu Asn Gly Asn Val Met Arg Val Ser Val Leu Gln Thr
    1640                1645                1650

Ala Asp Glu Val Tyr Glu Val Leu Trp Ile Ser His His Ile Val
    1655                1660                1665

Met Asp Gly Trp Cys Leu Pro Leu Val Ala Ala Glu Val Phe Ser
    1670                1675                1680

Thr Tyr Ser Ala Leu Val Glu Asp Lys Lys Pro Ile Leu Ala Ser
    1685                1690                1695

Val Pro Ser Tyr Asn Gln Tyr Ile Gln Trp Leu Glu Arg Gln Asp
    1700                1705                1710

Glu Ser Ala Ala Ala Ala Tyr Trp Asn His Tyr Leu Ser Gly Phe
    1715                1720                1725

Glu Glu Thr Thr Glu Leu Pro His Ser Lys Gly Arg Arg His Ser
    1730                1735                1740

Gly Gln Tyr Glu Ala Gly Gln Val Gln Ile Asp Leu Gly Thr Ser
    1745                1750                1755

Leu Ser Leu Ala Leu Asn Gln Val Ala Thr Gln His Gln Val Thr
    1760                1765                1770

Leu Asn Thr Leu Leu Gln Ala Ser Trp Gly Ile Leu Leu Gln Lys
    1775                1780                1785

Tyr Asn Arg Thr Ser Asp Ile Val Phe Gly Ser Val Val Ser Gly
    1790                1795                1800

Arg Pro Ala Glu Leu Val Gly Ile Glu Glu Met Ile Gly Leu Phe
    1805                1810                1815

Ile Asn Thr Ile Pro Val Arg Val Ser Ser Gln Ala His Glu Arg
    1820                1825                1830

Phe Ile Glu Val Met Thr Arg Met Gln Asp Asp Ala Leu Ser Ser
    1835                1840                1845

Ala Lys His Asp Tyr Tyr Pro Leu Tyr Glu Ile Gln Ala Gln Cys
    1850                1855                1860

Thr Leu Lys Gln Asp Leu Ile Asn His Ile Met Val Leu Glu Asn
    1865                1870                1875

Tyr Pro Met Glu Gln Gln Leu Asp Gln Phe Asn Ser Ser Asp Gly
    1880                1885                1890

Ser Gly Leu Lys Leu Thr Asp Val Thr Val Ser Glu Gln Thr Asn
    1895                1900                1905

Phe Asp Leu Asn Leu Ile Ile Ile Pro Gly Asp Asn Ile Val Ile
    1910                1915                1920

Arg Phe Asp Phe Asn Lys Gln Ala Leu Ala Glu Thr Asp Met Asn
    1925                1930                1935

Val Leu Lys Glu His Leu Leu His Val Leu Glu Gln Val Ala Ser
    1940                1945                1950

Asn Pro Arg Ile Ser Ile Gly Glu Leu Gln Leu Ala Thr Asp Glu
    1955                1960                1965

Glu Arg Ala Val Met Met Ser Glu Phe Asn Asp Thr Phe Val Ala
    1970                1975                1980

Tyr Pro Arg Glu Lys Ser Ile His Arg Leu Phe Glu Glu Arg Ala
    1985                1990                1995

Lys Gln Glu Pro Asp Ala Leu Ala Val Val Phe Gly Asn Asp Gln
    2000                2005                2010
```

-continued

Met Thr Tyr Gly Ala Leu Asn Ala Ala Asn Arg Met Ala Trp
2015              2020             2025

Arg Leu Arg Tyr Ala Gly Val Thr Ser Gly Glu Leu Val Gly Ile
2030              2035             2040

Cys Ala Asp Arg Ser Leu Glu Met Val Val Gly Leu Leu Ala Ile
2045              2050             2055

Met Lys Ala Gly Gly Ala Tyr Val Pro Ile Asp Pro Ala Tyr Pro
2060              2065             2070

Gln Glu Arg Ile Ser Ala Met Leu Glu Asp Thr Ser Ile Ala Thr
2075              2080             2085

Met Val Thr Gln Arg His Leu Cys Ser Leu Trp Pro Glu His Leu
2090              2095             2100

Asn Val Ile Ala Leu Asp Asp Asn Glu Thr Asp Val Ser Asn Ser
2105              2110             2115

Met Glu Asp Val Glu Ser Asn Leu Pro Ile Asp Gly Ala Gly Asp
2120              2125             2130

Asp Leu Ala Tyr Ile Ile Tyr Thr Ser Gly Ser Thr Gly Thr Pro
2135              2140             2145

Lys Gly Val Cys Val Thr His Arg Gly Val Val Arg Leu Val Cys
2150              2155             2160

Ala Ala Thr Tyr Val Glu Ile Asn Ser Ser Asp Val Phe Leu Gln
2165              2170             2175

Gly Ser Thr Ile Ser Phe Asp Ala Ala Thr Phe Glu Ile Trp Gly
2180              2185             2190

Ser Leu Leu Asn Gly Ala Ala Leu Ala Ile Leu Pro Pro Gly Asn
2195              2200             2205

Val Ser Leu Thr Asp Trp Ser Glu Ala Ile Gln Arg His Arg Val
2210              2215             2220

Thr Thr Leu Trp Met Thr Ala Gly Leu Phe Gln Val Met Val Glu
2225              2230             2235

Gln Gln Ile Glu Gly Phe Tyr Gly Val Lys Gln Leu Leu Val Gly
2240              2245             2250

Gly Asp Val Val Ser Pro Thr His Val Arg Lys Val Met Glu Lys
2255              2260             2265

His Asn Gly Ile Arg Val Ile Asn Gly Tyr Gly Pro Thr Glu Asn
2270              2275             2280

Thr Thr Phe Thr Cys Cys His Thr Ile Thr Ala Ala Asp Leu Asp
2285              2290             2295

Arg Gly Ser Ile Pro Ile Gly Gln Pro Ile Gly Asn Thr Arg Val
2300              2305             2310

Tyr Val Leu Asp Glu Ala Gly Asn Val Leu Pro Val Gly Val Cys
2315              2320             2325

Gly Glu Leu Tyr Ala Gly Gly Asp Gly Leu Ala Arg Gly Tyr Leu
2330              2335             2340

Asn Arg Pro Glu Leu Thr Ala Glu Lys Phe Val Asn Asp Pro Phe
2345              2350             2355

Ile Pro Gly Glu Arg Leu Tyr Arg Thr Gly Asp Leu Ala Arg Trp
2360              2365             2370

Leu Pro Asp Gly Ser Ile Glu Phe Ile Gly Arg Cys Asp Glu Gln
2375              2380             2385

Val Lys Ile Arg Gly Tyr Arg Ile Glu Pro Gly Glu Val Leu Ala
2390              2395             2400

```
Tyr Leu Leu Arg Ile Asp Glu Val Gly Glu Ala Ala Val Ile Ala
    2405                2410                2415

Arg Glu Asp Ser Ser Gly Gln Lys Glu Leu Cys Ala Tyr Phe Thr
    2420                2425                2430

Ala Glu Val Glu Leu Ser Ala Ser Gly Leu Arg Glu Thr Leu Ala
    2435                2440                2445

Arg Glu Leu Pro Ala Tyr Met Ile Pro Ser His Phe Ile Gln Ile
    2450                2455                2460

Glu Glu Leu Pro Leu Thr Pro Asn Gly Lys Val Asp Arg Arg Ala
    2465                2470                2475

Leu Pro Leu Pro Glu Glu Gly Leu Arg Met Asn Leu Lys Ile Gln
    2480                2485                2490

Pro Arg Thr Glu Leu Glu Ala Lys Leu Ala Leu Ile Trp Gln Asp
    2495                2500                2505

Val Leu Gly Leu Glu Asn Val Gly Val Thr Asp Ser Phe Phe Glu
    2510                2515                2520

Leu Gly Gly His Ser Leu Arg Ala Thr Thr Leu Val Ser Lys Val
    2525                2530                2535

His Arg Glu Leu Asn Ile Ala Leu Pro Leu Gln Asp Val Phe Arg
    2540                2545                2550

Tyr Pro Thr Ile Glu Gln Met Ser Leu Ala Ile Gln Gly Met Gln
    2555                2560                2565

Lys Glu Ser Phe Ala Ser Ile Pro Arg Val Glu Asp Arg Glu Trp
    2570                2575                2580

Tyr Pro Val Ser Ser Ala Gln Lys Arg Leu Phe Val Leu His Gln
    2585                2590                2595

Met Glu Gly Ala Glu Leu Ser Tyr Asn Met Pro Gly Val Met Ala
    2600                2605                2610

Ile Glu Gly Lys Leu His Arg Asp Arg Leu Glu Ala Ala Phe Arg
    2615                2620                2625

Gly Leu Ile Ala Arg His Glu Val Leu Arg Thr Gly Phe Glu Met
    2630                2635                2640

Tyr Asn Gly Glu Pro Met Gln Arg Ile Tyr Ser Asp Val Glu Phe
    2645                2650                2655

Thr Val Glu His Gly Ile Val Gly Ala Ala Ser Glu Ala Glu Ser
    2660                2665                2670

Val Ile Arg Ser Phe Val Arg Ala Phe Gln Leu Asn Lys Pro Pro
    2675                2680                2685

Leu Leu Arg Val Gly Leu Ile Glu Val Asp Ala Asp Arg His Leu
    2690                2695                2700

Leu Leu Phe Asp Met His His Ile Ile Ser Asp Gly Ala Ser Met
    2705                2710                2715

Gly Ile Leu Leu Asp Glu Phe Val Ala Leu Tyr Ser Gly Glu Glu
    2720                2725                2730

Leu Pro Glu Leu Arg Leu Gln Tyr Lys Asp Tyr Ala Ser Trp Gln
    2735                2740                2745

Gln Ser Glu Asp Tyr Leu Ser Arg Met Glu Glu Gln Lys Ala Tyr
    2750                2755                2760

Trp Leu Glu Thr Leu Arg Gly Glu Leu Pro Val Leu Gln Leu Pro
    2765                2770                2775

Val Asp Tyr Thr Arg Pro Ala Phe Arg Ser Phe Ala Gly Ser Thr
    2780                2785                2790

Leu Glu Phe Ile Val Pro Ala Asp Lys Ala Asp Gln Leu Lys Gln
```

```
                    2795                 2800                 2805
Leu Gly Ala Gly Ser Asp Ala Thr Met Tyr Met Val Leu Leu Ala
    2810                 2815                 2820
Leu Tyr Thr Ala Leu Leu His Lys Tyr Thr Gly Gln Glu Asp Val
    2825                 2830                 2835
Ile Val Gly Met Pro Ile Ala Gly Arg Thr His Ala Asp Ile Glu
    2840                 2845                 2850
Pro Leu Ile Gly Met Phe Val Asn Thr Leu Pro Leu Arg His Tyr
    2855                 2860                 2865
Pro Ala Gly Glu Lys Thr Phe Arg Ser Phe Leu Gly Glu Val Arg
    2870                 2875                 2880
Gln Ser Thr Leu Gln Ala Tyr Glu His Gln Glu Tyr Pro Phe Glu
    2885                 2890                 2895
Glu Leu Val Asp His Ile Gln Pro Thr Arg Asp Val Ser Arg Asn
    2900                 2905                 2910
Pro Ile Phe Asp Thr Val Leu Val Leu Gln Asn Thr Glu Lys Gly
    2915                 2920                 2925
Ala Trp Ser Ile Asp Gly Leu Ala Val Thr Pro Asn Pro Ile Glu
    2930                 2935                 2940
His Ala Val Ala Lys Phe Asp Leu Thr Leu His Val Glu Glu Gly
    2945                 2950                 2955
Ile Asp Gly Leu Ala Cys Ser Ile Glu Tyr Ala Thr Ala Leu Tyr
    2960                 2965                 2970
His Arg Glu Thr Ile Glu Arg Leu Ala Cys His Phe Asn Gln Leu
    2975                 2980                 2985
Leu Glu Ala Val Ile Ser Asn Pro Glu Ala Arg Leu Asp Gln Leu
    2990                 2995                 3000
Gly Ile Ile Thr Glu Thr Glu Lys Gln Gln Leu Phe Glu Glu Phe
    3005                 3010                 3015
Asn Asp Thr Ser Ala Asp Tyr Pro Arg Asp Lys Thr Ile His Arg
    3020                 3025                 3030
Leu Phe Glu Glu Gln Val Glu Arg Thr Pro Asp Ala Ile Ala Val
    3035                 3040                 3045
Thr Gly Ser Asp Gly Phe Leu Thr Tyr Gln Glu Leu Asn Glu Arg
    3050                 3055                 3060
Ala Asn Ser Leu Ala Trp Val Leu Arg Ala Glu Gly Ile Gly Ala
    3065                 3070                 3075
Asp Lys Leu Val Gly Ile Met Ala Glu Arg Thr Thr Asp Met Leu
    3080                 3085                 3090
Val Gly Leu Ile Ala Ile Leu Lys Ala Gly Gly Ala Tyr Val Pro
    3095                 3100                 3105
Ile Asp Pro Glu Tyr Pro Glu Glu Arg Ile Ser Tyr Met Leu Ser
    3110                 3115                 3120
Asp Ser Gly Ala Asp Ile Leu Leu Leu Pro Arg His Leu Arg Glu
    3125                 3130                 3135
Gln Val Ala Tyr Glu Gly Thr Val Leu Phe Leu Asp Asp Glu Gln
    3140                 3145                 3150
Thr Tyr Ser Gly Asp Lys Ser Asn Pro Ser Ser Val Asn Lys Pro
    3155                 3160                 3165
Ser Asp Leu Ala Tyr Val Ile Tyr Thr Ser Gly Thr Thr Gly Lys
    3170                 3175                 3180
Pro Lys Gly Thr Leu Ile Glu His Lys Asn Val Val Arg Leu Leu
    3185                 3190                 3195
```

```
Phe Asn Ser Arg Asn Leu Phe Asp Phe Arg Ser Thr Asp Thr Trp
    3200                3205                3210

Thr Leu Phe His Ser Phe Cys Phe Asp Phe Ser Val Trp Glu Met
    3215                3220                3225

Tyr Gly Ala Leu Leu Tyr Gly Gly Arg Leu Val Val Val Pro Gln
    3230                3235                3240

Leu Thr Ala Lys Asn Pro Ala Met Phe Leu Gln Leu Leu Ala Glu
    3245                3250                3255

Glu Arg Val Thr Ile Leu Asn Gln Thr Pro Thr Tyr Phe Tyr Gln
    3260                3265                3270

Leu Ile Arg Glu Ala Leu Ala Asp Gly Ser Pro Glu Leu Asn Ile
    3275                3280                3285

Arg Met Val Ile Phe Gly Gly Glu Ala Leu Ser Pro Gln Leu Leu
    3290                3295                3300

Lys Asp Trp Arg Ala Lys Tyr Pro Arg Thr Gln Leu Ile Asn Met
    3305                3310                3315

Tyr Gly Ile Thr Glu Thr Thr Val His Val Thr Tyr Lys Glu Ile
    3320                3325                3330

Thr Glu Thr Glu Ile Glu Gln Ala Arg Ser Asn Ile Gly Phe Pro
    3335                3340                3345

Ile Pro Thr Leu Arg Ile Tyr Ile Leu Asp Ala Asn Arg Asn Cys
    3350                3355                3360

Val Pro Ile Gly Val Ala Gly Glu Met Phe Val Ala Gly Glu Gly
    3365                3370                3375

Leu Ala Arg Gly Tyr Leu Asn Arg Pro Glu Leu Thr Glu Asp Arg
    3380                3385                3390

Phe Val Asp Asn Pro Phe Glu Pro Gly Ser Lys Met Tyr Lys Thr
    3395                3400                3405

Gly Asp Leu Ala Lys Trp Leu Pro Asp Gly Asn Ile Glu Tyr Leu
    3410                3415                3420

Gly Arg Ile Asp His Gln Val Lys Ile Arg Gly Tyr Arg Ile Glu
    3425                3430                3435

Leu Gly Glu Val Glu Ala Gln Val Thr Lys Val Glu Ser Val Arg
    3440                3445                3450

Glu Ala Ile Val Ile Ala Arg Glu Glu Asn Gly Glu Lys Leu Leu
    3455                3460                3465

Cys Ala Tyr Phe Val Ala Asp Arg Gln Leu Thr Val Gly Glu Met
    3470                3475                3480

Arg Thr Glu Leu Ala Gln Glu Leu Pro Ala Tyr Met Ile Pro Ser
    3485                3490                3495

Tyr Phe Val Gln Leu Glu Arg Met Pro Leu Thr Ser Asn Gly Lys
    3500                3505                3510

Val Asp Arg Lys Ala Leu Pro Ala Pro Glu Gly Ser Ile Asn Thr
    3515                3520                3525

Gly Lys Glu Tyr Val Ala Pro Arg Thr Ser Met Glu Ala Ser Leu
    3530                3535                3540

Ala Arg Met Trp Asp Glu Leu Leu Gly Ile Glu Gln Val Gly Val
    3545                3550                3555

Thr Asp Asn Phe Phe Glu Leu Gly Gly His Ser Leu Arg Ala Thr
    3560                3565                3570

Ala Leu Val Asn Arg Val His Gln Glu Met Asn Ile Gln Leu Pro
    3575                3580                3585
```

```
Leu Arg Asp Val Phe Arg Phe Ser Thr Ile Glu Glu Leu Ala Ala
3590                3595                3600

Ala Met Ser Glu Met Ala Glu Glu Ser Tyr Ser Ser Ile Pro Val
3605                3610                3615

Ala Glu Val Gln Glu His Tyr Pro Val Ser Ser Ala Gln Lys Arg
3620                3625                3630

Leu Tyr Ile Leu His Gln Leu Glu Gly Ala Glu Gln Gly Tyr Asn
3635                3640                3645

Met Pro Gly Ile Met Leu Ile Glu Gly Glu Leu Asp Arg Ser Arg
3650                3655                3660

Phe Glu Ala Ala Phe Arg Lys Leu Ile Ala Arg His Asp Ile Leu
3665                3670                3675

Arg Thr Gly Phe Glu Leu Val Lys Gly Glu Ala Val Gln Arg Ile
3680                3685                3690

His Asp Thr Leu Asp Phe Ala Ile Glu Tyr Arg Lys Val Glu Glu
3695                3700                3705

Gln Glu Val Gln Gln Val Arg Gln Phe Ile Arg Thr Phe Glu
3710                3715                3720

Leu Asp Lys Pro Pro Leu Leu Arg Val Gly Leu Ile Glu Ile Ala
3725                3730                3735

Glu Ala Lys Glu Gln His Val Leu Leu Phe Asp Met His His Ile
3740                3745                3750

Ile Ser Asp Gly Val Ser Ile Gly Ile Val Leu Gln Glu Ile Met
3755                3760                3765

Arg His Tyr His Gly Glu Glu Val Pro Pro Leu His Ile Gln Tyr
3770                3775                3780

Lys Asp Tyr Ala Ala Trp Gln Gln Ser Glu Ala Gln Lys Glu Gln
3785                3790                3795

Leu Lys His Gln Gln Ala Tyr Trp Leu Asp Gln Phe Gln Gly Glu
3800                3805                3810

Leu Pro Ile Leu Glu Leu Pro Thr Asp Tyr Ala Arg Pro Ala Ile
3815                3820                3825

Gln Gln Tyr Asp Gly Leu Thr Leu Pro Phe Arg Ile Asp Lys Asp
3830                3835                3840

Val Ala Asp Gly Leu Asn Arg Ile Ala Ala Asp Thr Gly Thr Thr
3845                3850                3855

Leu Tyr Met Val Leu Leu Ala Ala Tyr Thr Ile Met Leu His Lys
3860                3865                3870

Tyr Thr Gly Gln Glu Asp Ile Val Val Gly Thr Pro Ile Ala Gly
3875                3880                3885

Arg Thr His Glu Glu Leu Gln Pro Leu Ile Gly Met Phe Val Asn
3890                3895                3900

Thr Leu Ala Ile Arg Ala Tyr Pro Glu Gly Ala Lys Ala Phe Arg
3905                3910                3915

Ser Tyr Leu Asp Glu Ile Arg Ser Thr Met Leu Gly Ala Tyr Glu
3920                3925                3930

His Gln Gln Tyr Pro Phe Glu Glu Leu Val Glu Gly Leu Gln Leu
3935                3940                3945

Thr Arg Asp Leu Ser Arg Asn Pro Leu Phe Asp Thr Met Phe Ala
3950                3955                3960

Leu Asp Asn Thr Asp Met Met Val Asp Ser Leu Gly Glu Leu His
3965                3970                3975

Met Lys Pro Tyr Pro Leu Glu Tyr Thr Ile Ser Lys Phe Asp Val
```

```
            3980              3985              3990
Ser Leu Asp Val Lys Ala Asp Glu Arg Gly Leu Asp Cys Ser Phe
    3995              4000              4005
Glu Tyr Ala Thr Ser Leu Phe Lys Ser Glu Thr Ile His Arg Met
    4010              4015              4020
Ala Glu His Phe Ser Gln Leu Leu Lys Asp Ile Val Asn His Pro
    4025              4030              4035
Asp Ala Gln Leu Gly Glu Leu Gly Met Leu Thr Val His Glu Ser
    4040              4045              4050
Asp Glu Ile Leu Gln Val Phe Asn Pro Thr His Ser Leu Lys Ala
    4055              4060              4065
Pro Asp Gly Thr Ile His Arg Leu Phe Glu Glu Gln Ala Glu Arg
    4070              4075              4080
Thr Pro Glu Gln Pro Ala Val Val Phe Gly Asn Glu Arg Met Thr
    4085              4090              4095
Tyr Arg Glu Leu Asn Glu Arg Ala Asn Lys Leu Ala Arg Thr Leu
    4100              4105              4110
Arg Ala Glu Gly Val Glu Pro Asp Asp Leu Ile Gly Val Met Ala
    4115              4120              4125
Asp Arg Ser Ile Asp Met Val Val Ala Val Met Ala Val Leu Lys
    4130              4135              4140
Ser Gly Gly Ala Tyr Val Pro Ile Asp Pro Glu Tyr Pro Glu Asp
    4145              4150              4155
Arg Ile Arg Tyr Met Leu Glu Asp Ala Lys Ala Arg Ile Leu Leu
    4160              4165              4170
Thr Gln Cys His Leu Gln Asp Lys Val Ser Phe Glu Gly Thr Trp
    4175              4180              4185
Val Leu Leu Glu Asp Glu Ala Ser Tyr His Glu Asp Asp Thr Asn
    4190              4195              4200
Leu Glu Pro Ile Cys Glu Pro Asp His Leu Cys Tyr Val Ile Tyr
    4205              4210              4215
Thr Ser Gly Thr Thr Gly Asn Pro Lys Gly Val Met Ile Glu His
    4220              4225              4230
Arg Gln Leu Ala Ala Met Ala Glu Ala Trp Lys Ala Glu Tyr Glu
    4235              4240              4245
Leu His Glu Pro Gly Ile Arg Trp Leu Gln Trp Ala Ser Phe Ser
    4250              4255              4260
Phe Asp Val Phe Ser Gly Asp Leu Ala Arg Thr Leu Leu His Gly
    4265              4270              4275
Gly Glu Leu Ile Leu Cys Pro Ser Asp Thr Arg Ala Asn Pro Gly
    4280              4285              4290
Ala Leu Ala Glu Leu Leu Arg Ser Ser Gly Ile Gln Met Phe Glu
    4295              4300              4305
Ser Thr Pro Ala Leu Val Ile Pro Leu Met Glu His Val Tyr Glu
    4310              4315              4320
His Arg Val Asp Ile Asp Ser Leu Arg Leu Leu Ile Ile Gly Ser
    4325              4330              4335
Asp Leu Cys Pro Ala Asp Glu Phe Arg Lys Leu Leu Asp Arg Phe
    4340              4345              4350
Gly Ser His Leu Arg Ile Ile Asn Ser Tyr Gly Val Thr Glu Ala
    4355              4360              4365
Cys Val Asp Ser Ser Tyr Tyr Glu Pro Val Leu Ser Asp Pro Val
    4370              4375              4380
```

```
Arg Ser Val Pro Ile Gly Lys Pro Leu Pro Tyr Val Ser Met Tyr
    4385             4390             4395

Ile Leu Gly Glu Asn Leu Ser Leu Gln Pro Val Gly Leu Ala Gly
    4400             4405             4410

Glu Leu Tyr Ile Ala Gly Ala Gly Val Gly Arg Gly Tyr Trp Asn
    4415             4420             4425

Arg Pro Glu Met Thr Ala Asp Lys Phe Val Arg Asp Pro Phe Ala
    4430             4435             4440

Asp Gly Gln Cys Met Tyr Arg Thr Gly Asp Leu Ala Lys Trp Leu
    4445             4450             4455

Leu Asp Gly Asn Ile Glu Leu Ile Gly Arg Thr Asp His Gln Val
    4460             4465             4470

Lys Ile Arg Gly Tyr Arg Ile Glu Ile Gly Glu Val Glu Ser Lys
    4475             4480             4485

Leu Gln Gln Thr Pro Asp Ile Arg Glu Ala Ala Val Val Ala Lys
    4490             4495             4500

Glu Asp Gly Ser Gly Arg Lys Val Leu Cys Ala Tyr Tyr Thr Ser
    4505             4510             4515

Tyr Arg Glu Leu Thr Ala Gly Glu Trp Arg Ser Ala Leu Ala Lys
    4520             4525             4530

Glu Leu Pro Ala Tyr Met Ile Pro Ser His Phe Met Arg Leu Glu
    4535             4540             4545

Arg Met Pro Leu Thr Pro Asn Gly Lys Leu Asp Arg Lys Gly Leu
    4550             4555             4560

Pro Ala Pro Glu Gly Ala Ala Tyr Thr Gly Thr Glu Tyr Glu Ala
    4565             4570             4575

Pro Arg Thr Asp Ala Glu Ile Ala Leu Ala Ala Ala Trp Gln Ser
    4580             4585             4590

Val Leu His Val Glu Arg Val Gly Thr Asn Asp His Phe Phe Glu
    4595             4600             4605

Leu Gly Gly Asp Ser Ile Lys Ser Ile Gln Val Ser Ser Arg Leu
    4610             4615             4620

His Gln Ala Gly Tyr Lys Leu Glu Ile Arg Asp Leu Phe Lys Tyr
    4625             4630             4635

Pro Thr Ile Ala Gln Leu Ser Leu Gln Leu Gln Pro Ile Gly Arg
    4640             4645             4650

Ile Ala Asp Gln Gly Glu Val His Gly Glu Val Glu Leu Thr Pro
    4655             4660             4665

Ile Gln Arg Trp Tyr Phe Gly Leu Asp Leu Asp Asp Met His His
    4670             4675             4680

Tyr Asn Gln Ser Phe Leu Leu Tyr Arg Gln Gly Gly Phe Asn Glu
    4685             4690             4695

Glu Ala Leu Arg Lys Thr Leu Arg Thr Ile Val Glu His His Asp
    4700             4705             4710

Ala Leu Arg Met Val Phe Arg Lys Ser Ala Ala Gly Val Thr Ala
    4715             4720             4725

Trp Asn Arg Ala Ile Glu Glu Gly Glu Leu Phe Asp Phe Leu Ala
    4730             4735             4740

Phe Asp Ile Ala Asn Ser Gly Asp Ala Glu Gln Val Ile Glu Ala
    4745             4750             4755

Lys Ala Asn Asp Ile Gln Ala Ser Ile Asp Leu Gln Gly Gly Pro
    4760             4765             4770
```

```
Leu Val Lys Ala Gly Leu Phe Arg Cys Glu Gln Gly His His Leu
4775                 4780                 4785

Leu Ile Ala Ile His His Ala Val Ile Asp Gly Val Ser Trp Arg
4790                 4795                 4800

Ile Leu Leu Glu Asp Ile Ser Ala Gly Tyr Glu Gln Ala Cys Lys
4805                 4810                 4815

Gly Asp Asp Ile Arg Leu Pro Ser Lys Thr Asp Ser Tyr Ala Ala
4820                 4825                 4830

Trp Ser Arg Ser Leu Val Glu Tyr Ala Ser Leu Thr Asp Leu Gly
4835                 4840                 4845

His Glu Arg Ser Tyr Trp Arg His Val Leu Asn Ala Gly Ala Asn
4850                 4855                 4860

Pro Leu Pro Lys Asp Phe Asp Thr Glu Ser Ser Leu Gln Gln Asp
4865                 4870                 4875

Ser Asn Ser Val Thr Val Ala Trp Asn Gln Gln Asp Thr Glu His
4880                 4885                 4890

Leu Leu Lys Arg Val His Arg Ala Tyr Asn Thr Asp Met Asn Glu
4895                 4900                 4905

Ile Leu Leu Ala Ala Leu Ala Ile Ala Ile Gln Lys Trp Ser Gly
4910                 4915                 4920

His Asn Gln Ile Leu Ile Asn Leu Glu Gly His Gly Arg Glu Pro
4925                 4930                 4935

Ile Ala Gly Asp Leu Asp Ile Ser Arg Thr Val Gly Trp Phe Thr
4940                 4945                 4950

Ser Glu Tyr Pro Val Leu Leu Gln Ala Glu Arg Asp Arg Gly Leu
4955                 4960                 4965

Ala Tyr His Ile Lys Arg Ala Lys Glu Glu Leu Arg Gln Ile Pro
4970                 4975                 4980

Asn Lys Gly Ile Gly Tyr Gly Ile Cys Arg Tyr Leu Ser Glu Pro
4985                 4990                 4995

Asp Asp Ser Leu Glu Trp Gly Ala Ala Pro Glu Ile Ser Phe Asn
5000                 5005                 5010

Tyr Leu Gly Gln Phe Asp Gln Asp Thr Met Glu Gly Gly Ile Met
5015                 5020                 5025

Leu Ser Pro Tyr Ser Lys Gly Ser Asp Gly Ser Ala Leu His Thr
5030                 5035                 5040

Arg Gln Tyr Val Leu Asp Ile Asn Cys Ala Ile Thr Asn Gly Met
5045                 5050                 5055

Leu Thr Leu Asp Met Ser Tyr Ser Glu Lys Glu Tyr Arg Lys Glu
5060                 5065                 5070

Thr Met Glu Leu Leu Ala Gly His Phe His Glu Ser Leu Leu Glu
5075                 5080                 5085

Ile Ile Asn His Cys Val Ser Arg Glu Gln Thr Glu Leu Thr Pro
5090                 5095                 5100

Ser Asp Leu Leu Leu His Gly Leu Ser Ile Glu Gln Leu Glu Gln
5105                 5110                 5115

Ile Ala Glu Glu Met Arg Glu Leu Gly Ile Ile Glu Asn Met Tyr
5120                 5125                 5130

Met Leu Thr Pro Met Gln Lys Gly Met Trp Phe His Asn Ala Leu
5135                 5140                 5145

Asp Gly Gln Glu Gly Ala Thr Gly Ala Tyr Phe Glu Gln Thr Arg
5150                 5155                 5160

Phe Thr Leu Arg Gly Glu Leu Asp Pro Ala Leu Phe Ala Gln Ser
```

```
            5165                5170                5175

Leu His Glu Leu Ala Ala Arg His Ser Val Leu Arg Thr Asn Phe
            5180                5185                5190

Cys Ser Leu Asp Gly Glu Pro Val Gln Val Val Phe Arg Glu Gly
            5195                5200                5205

Arg Ile Thr Phe Thr Tyr Glu Asp Leu Ser Gln Leu Pro Ala Glu
            5210                5215                5220

Glu Gln Ala Ala Val Ile Glu Arg Ile Val Ala Ser Asp Lys Leu
            5225                5230                5235

Arg Gly Phe Asp Leu Glu Arg Asp Pro Leu Val Arg Val Thr Leu
            5240                5245                5250

Met Arg Thr Glu Ala Ser Ser Cys His Val Leu Trp Ser Ser His
            5255                5260                5265

His Ile Leu Met Asp Gly Trp Cys Leu Pro Gln Leu Thr Asp Glu
            5270                5275                5280

Leu Phe Arg Ile Tyr Ser Ala Val Thr Asn His Asn Ala Gly Thr
            5285                5290                5295

Thr Glu Ala Thr Gly Thr Val Gly Thr Leu Gly Ala Phe Gly Ala
            5300                5305                5310

Ala Glu Ser Leu Arg Asn Lys Glu Ala Gly Leu Pro Asp Tyr Ser
            5315                5320                5325

Arg Tyr Ile Glu Trp Leu Ala Glu Gln Asp Met Ser Ala Ala Ala
            5330                5335                5340

Ala Tyr Trp Asn Gly Tyr Leu Ala Gly Tyr Glu Gln Gln Thr Arg
            5345                5350                5355

Leu Pro Asn Gly Lys Ile Thr Gly Lys Asp Lys Pro Tyr Val Leu
            5360                5365                5370

Glu Gln Ala Ser Arg Lys Leu Gly Ile Glu Leu Thr Ser Arg Met
            5375                5380                5385

Ile Arg Ile Ala Lys Gln His Gln Val Thr Leu Asn Thr Leu Leu
            5390                5395                5400

Gln Ala Ala Trp Gly Ile Val Leu Gln Lys Tyr Asn Gly Thr Gln
            5405                5410                5415

Asp Val Val Phe Gly Gly Val Val Ser Gly Arg Pro Ala Asp Val
            5420                5425                5430

Pro Gly Val Glu Ser Met Ile Gly Leu Phe Ile Asn Thr Ile Pro
            5435                5440                5445

Val Arg Val Ser Asn Glu Ala Gly Ala Ser Phe Ser Asp Val Met
            5450                5455                5460

Glu Gln Leu Gln Asn Ala Ala Leu Glu Ser Gly Arg Tyr Asp Tyr
            5465                5470                5475

Tyr Pro Leu Tyr Glu Ile Gln Ser Arg Thr Ser Gln Lys Ser Glu
            5480                5485                5490

Leu Ile Ser His Ile Met Val Phe Glu Asn Tyr Pro Leu Asp Glu
            5495                5500                5505

Arg Met Glu Gln Thr Arg Asp Gly Asn Asp Gly Ala Leu Ala Leu
            5510                5515                5520

Thr Asp Val Gln Ala Ala Glu Gln Thr Asn Tyr Asp Phe Asn Leu
            5525                5530                5535

Met Val Val Pro Gly Asp Glu Leu Ile Ile Arg Phe Asp Phe Asn
            5540                5545                5550

Ser Glu Val Tyr Glu Arg Gly His Met Glu Arg Leu His His His
            5555                5560                5565
```

```
Leu Met His Val Leu Glu Gln Val Thr Gly Asn Pro Ala Ile Ser
    5570            5575            5580

Ile Ala Glu Val Gln Leu Ala Thr Glu Ala Glu Lys Ala Glu Leu
    5585            5590            5595

Gln Ser Ala Phe Asn Asp Thr Ala Val Asp Tyr Pro Arg Glu Gln
    5600            5605            5610

Thr Ile His Arg Met Phe Glu Glu Val Gln Gln Thr Pro Asp
    5615            5620            5625

Ala Ala Ala Val Leu Tyr Gly Asp Asp Ser Ile Thr Tyr Arg Glu
    5630            5635            5640

Leu Asn Glu Arg Ala Asn Gln Leu Ala Arg Thr Leu Arg Ala Ala
    5645            5650            5655

Gly Val Glu Pro Asp Gln Ile Val Gly Ile Met Ala Glu Arg Ser
    5660            5665            5670

Leu Glu Leu Met Val Gly Ile Met Gly Ile Leu Lys Ala Gly Gly
    5675            5680            5685

Ala Tyr Val Pro Ile Ala Pro Asp Tyr Pro Glu Asp Arg Ile Arg
    5690            5695            5700

Tyr Met Leu Asp Asp Ser Glu Ala Gln Val Leu Val Gln Gly
    5705            5710            5715

Ser Ala Gly Glu Ala Val Asp Phe Ala Gly Arg Ile Ile Asn Leu
    5720            5725            5730

Asp Asp Ala Glu Ala Tyr Asp Gly Asp Gly Ser Asn Pro Glu Pro
    5735            5740            5745

Val Asn Lys Pro Thr Asp Ile Ala Tyr Ile Ile Tyr Thr Ser Gly
    5750            5755            5760

Thr Thr Gly Arg Pro Lys Gly Val Met Val Glu His Thr Ser Val
    5765            5770            5775

Ile Asn Arg Leu Leu Trp Met Gln Lys Arg Tyr Pro Ile Gly Ala
    5780            5785            5790

Glu Asp Thr Ile Met Gln Lys Thr Ala Ile Thr Phe Asp Val Ser
    5795            5800            5805

Val Trp Glu Leu Phe Trp Trp Ala Phe Val Gly Ser Lys Val Leu
    5810            5815            5820

Met Leu Ser Val Gly Gly Glu Lys Ser Pro His Ala Ile Val Asp
    5825            5830            5835

Ala Ile Glu Arg His Arg Ile Thr Thr Met His Phe Val Pro Ser
    5840            5845            5850

Met Leu His Ala Phe Leu Glu His Val Glu Gln Leu Thr Asp Ala
    5855            5860            5865

Glu Arg Glu Arg Gly Leu Ala Pro Leu Arg Gln Val Phe Thr Ser
    5870            5875            5880

Gly Glu Ala Leu Leu Ala Ser Gln Val Glu Arg Phe His Arg Tyr
    5885            5890            5895

Ile Ala Pro Ala Ser Gly Ala Gln Leu Ile Asn Leu Tyr Gly Pro
    5900            5905            5910

Thr Glu Ala Thr Val Asp Val Thr Tyr Phe Asp Cys Glu Pro Gly
    5915            5920            5925

Gln Thr Tyr Val Ser Val Pro Ile Gly Lys Pro Ile Asp Asn Thr
    5930            5935            5940

Ser Ile His Ile Val Asn Glu His Asn Gln Val Gln Pro Ile Gly
    5945            5950            5955
```

```
Val Ala Gly Glu Leu Cys Ile Ala Gly Val Gly Leu Ala Arg Gly
5960                5965                5970

Tyr Trp Asn Arg Pro Glu Leu Thr Ala Glu Lys Phe Val Thr Ile
5975                5980                5985

Pro Ser Val Gly Glu Arg Met Tyr Arg Thr Gly Asp Leu Ala Arg
5990                5995                6000

Trp Leu Pro Asp Gly Asn Ile Glu Tyr Leu Gly Arg Ile Asp His
6005                6010                6015

Gln Val Lys Ile Arg Gly Tyr Arg Ile Glu Leu Gly Glu Leu Glu
6020                6025                6030

Ser Ala Leu Leu Asn Val Gln Glu Ile Arg Glu Thr Val Val Val
6035                6040                6045

Ala Arg Glu Glu Glu Asp Gly Gln Lys Ser Leu Cys Ala Tyr Tyr
6050                6055                6060

Val Ala Asp Gly Asp Pro Thr Ala Gly Asp Leu Arg Ala Ala Leu
6065                6070                6075

Ala Ala Glu Leu Pro Ser Tyr Met Ile Pro Ser Tyr Phe Ile Arg
6080                6085                6090

Leu Glu Gln Met Pro Leu Ala Pro Asn Gly Lys Leu Asp Arg Lys
6095                6100                6105

Ala Leu Pro Ala Pro Lys Asp Val Ile Arg Thr Gly Thr Asp Arg
6110                6115                6120

Ile Ala Pro Arg Thr Ala Leu Glu Val Lys Leu Val Arg Ile Trp
6125                6130                6135

Gln Glu Val Leu Gly Leu Asp Gln Ile Gly Val Lys Asp Asp Phe
6140                6145                6150

Phe Glu Leu Gly Gly His Ser Leu Arg Ala Thr Ala Leu Ala Ser
6155                6160                6165

Lys Val Ser Lys Glu Met His Val Ala Leu Pro Leu Arg Asp Ile
6170                6175                6180

Phe His Tyr Ser Thr Leu Glu Ala Met Ala Gln Ala Ile Gly Glu
6185                6190                6195

Leu Glu Lys Gln Glu His Arg Ala Ile Pro Ile Ala Pro Met Ala
6200                6205                6210

Glu His Tyr Gln Leu Ala Ser Ala Gln Lys Arg Leu Tyr Ile Leu
6215                6220                6225

His Gln Ala Glu Gly Ala Gln Gln Ser Tyr Asn Met Pro Gly Ala
6230                6235                6240

Met Ser Val Ser Gly His Ile Asp Arg Asn Arg Leu Glu Ala Ala
6245                6250                6255

Leu Leu Gln Leu Ile Ala Arg His Asp Thr Leu Arg Thr Ser Phe
6260                6265                6270

Glu Met Val Asp Gly Glu Pro Val Gln Arg Val His Gln His Val
6275                6280                6285

Asp Phe Ala Leu Glu Tyr Ser Thr Ala Arg Glu Lys Asp Ile Asp
6290                6295                6300

Gln Val Ala Glu Gln Phe Val Arg Asp Phe Asp Leu Glu Gln Pro
6305                6310                6315

Pro Leu Leu Arg Val Gly Leu Val Gln Leu Glu Gln Glu Glu Gln
6320                6325                6330

His Leu Leu Leu Leu Asp Met His His Ile Ile Ser Asp Gly Ile
6335                6340                6345

Ser Met Asp Ile Leu Val Asp Glu Leu Ala Arg Leu Tyr Asp Gly
```

```
6350 6355 6360

Glu Glu Leu Pro Pro Leu Glu Ile Gln Tyr Lys Asp Tyr Val Leu
6365 6370 6375

Trp Gln Gln Ala Glu Ala Ser Ser Glu Gln Met Lys Glu His Glu
6380 6385 6390

Glu Tyr Trp Leu Arg Thr Leu Gly Asn Glu Leu Pro Leu Leu Glu
6395 6400 6405

Leu Pro Thr Glu Phe Ala Arg Gly Glu Gln Arg Ser Tyr Asp Gly
6410 6415 6420

Asp Lys Leu His Phe Ala Ile Asp Gly Gln Leu Asn Glu Lys Leu
6425 6430 6435

Gln Arg Leu Ala Ser Gln Ser Gly Ala Thr Leu Tyr Met Val Leu
6440 6445 6450

Leu Ala Ala Tyr Thr Thr Leu Leu His Lys Tyr Ser Gly Gln Asn
6455 6460 6465

Asp Leu Val Val Gly Thr Pro Ile Ala Gly Arg Thr His Val Asp
6470 6475 6480

Val Glu Pro Leu Ile Gly Met Phe Val Asn Ser Leu Ala Ile Arg
6485 6490 6495

Asn Tyr Pro Asn Asp Asp Lys Thr Phe Arg Ser Tyr Leu Glu Glu
6500 6505 6510

Val Lys Glu Ser Thr Leu Ser Ala Phe Glu His Gln Asp Tyr Pro
6515 6520 6525

Phe Asp Lys Leu Val Glu Gln Leu Glu Asp Ala Trp Val Pro Gly
6530 6535 6540

Arg Asn Pro Val Phe Asp Thr Met Phe Val Leu Gln Asn Ala Lys
6545 6550 6555

Ala Arg Thr Ile Asn Leu Arg Glu Leu Ala Phe Glu Pro Leu Ile
6560 6565 6570

Pro Ser His Thr Val Ala Lys Phe Asp Leu Thr Leu Glu Met Ala
6575 6580 6585

Ile Glu Asp Gly Met Leu Ser Gly Gln Phe Glu Tyr Cys Thr Lys
6590 6595 6600

Leu Phe Ser Ala Asn Met Ile Ala Asn Phe Ala Glu Asp Phe Leu
6605 6610 6615

Glu Ile Leu Ser Gln Ala Cys Glu Gln Pro Asp Leu Arg Leu Glu
6620 6625 6630

Asp Ile Gln Leu Ser Gly Ser Ala Asn Gln Glu Glu Glu Leu Glu
6635 6640 6645

Glu Glu Ile Asp Phe Ala Phe
6650 6655

<210> SEQ ID NO 15
<211> LENGTH: 6428
<212> TYPE: PRT
<213> ORGANISM: Paenibacillus strain TS-15

<400> SEQUENCE: 15

Met Ala Phe Asp Lys Glu Ile Glu Phe Trp Lys Ala Lys Leu Asp Thr
1 5 10 15

Glu Asp Thr Pro Thr Thr Leu Pro Tyr Thr Asn Ile Ser Ser Ser Glu
20 25 30

Ala Ala Arg His Tyr Ser Val Ser Val Thr Met Pro Ala Glu Ile Thr
35 40 45

-continued

Glu Arg Ile Ile Arg Met Ser Lys Gly Ser His Gln Ala Ala Phe Met
            50                  55                  60

Ile Leu Leu Gly Gly Ile Gln Cys Leu His Lys Tyr Thr Ser Glu
 65                  70                  75                  80

Asn Cys Ile Val Ile Gly Met Pro Ile Val Gln Lys Ala Gly Glu Lys
                    85                  90                  95

Arg Leu Pro Ile Asn Gln Val Val Leu Leu Lys Glu Asn Val Asn Glu
                100                 105                 110

Glu Leu Thr Phe Lys Ser Leu Thr Ser Leu Lys Gln Ser Phe Thr
                115                 120                 125

Glu Ala Ile Arg His Gln Asn Ile Pro Phe Arg Leu Ile Thr Glu Gln
            130                 135                 140

Met Asn Val Gln Glu Lys Asn Gly Leu Pro Val Ile Asn Thr Met Ala
145                 150                 155                 160

Ala Leu Lys Asn Ile His Thr Val Asn Phe Ile Pro Thr Val Ala
                165                 170                 175

Asp Val Leu Phe Gln Phe Glu Phe Glu Ala Glu Asn Leu Leu Leu Ser
                180                 185                 190

Val Val Tyr Asn Glu Arg Val Tyr Asp Ser Val Phe Ile Ser Gln Ile
                195                 200                 205

Ile Glu His Leu Gln Arg Val Leu Ser Ile Val Leu Leu Glu Pro Asn
            210                 215                 220

Thr Asn Leu Gly Asn Leu Arg Leu Leu Ser Asp Glu Glu Thr Ser Leu
225                 230                 235                 240

Leu Leu His Gly Phe Asn Ala Thr Ala Ala Glu Tyr Pro Arg Asp Arg
                245                 250                 255

Thr Ile His Glu Leu Phe Thr Glu Gln Ala Arg Arg Thr Pro Asp Ala
                260                 265                 270

Val Ala Ala Val Leu Gly Gln Gln Gln Leu Thr Tyr Ala Glu Leu Asn
                275                 280                 285

Gly Arg Ala Asn Arg Leu Ala Arg Thr Leu Gln Asn Ala Gly Val Arg
            290                 295                 300

Thr Asp Gln Leu Val Gly Ile Met Ala Glu Arg Ser Leu Glu Met Ile
305                 310                 315                 320

Val Gly Leu Leu Ala Ile Met Lys Ala Gly Gly Ala Tyr Val Pro Ile
                325                 330                 335

Asp Pro Glu Tyr Pro Gln Glu Arg Ile Arg Tyr Met Leu Glu Asp Ser
                340                 345                 350

Gly Ala Gln Met Leu Leu Leu Gln Asp His Leu Arg Glu Arg Val Ser
            355                 360                 365

Tyr Glu Gly Thr Ile Val Asp Met Asn Ser Glu His Asn Tyr His Asp
370                 375                 380

Asp Glu Thr Glu Leu Ala Ser Val Ser Asp Ser Ser Asn Leu Ala Tyr
385                 390                 395                 400

Val Ile Tyr Thr Ser Gly Thr Thr Gly Asn Pro Lys Gly Val Met Ile
                405                 410                 415

Glu His Arg Ser Ala Val Asn Ala Leu Leu Trp Arg Ile Arg Thr Tyr
            420                 425                 430

Gly Leu Ser Ser Ser Asp Arg Val Leu Gln Leu Phe Ser Phe Ser Phe
            435                 440                 445

Asp Gly Phe Val Met Ser Ala Phe Cys Ser Leu Leu Ser Gly Ala Gly
            450                 455                 460

Leu Phe Leu Leu Lys Glu Glu Asp Ala Lys Asp Pro Leu Ala Leu His

```
            465                 470                 475                 480
Gly Ala Ile Ser Gln Ser Gly Ile Thr His Phe Ile Cys Val Pro Asn
                    485                 490                 495
Leu Tyr Gly Ala Leu Leu Asn Val Met Gln Ala Glu Ser Val Ser Thr
                500                 505                 510
Leu Arg Thr Val Thr Leu Ala Gly Glu Ser Val Ser Ser Ala Leu Val
                515                 520                 525
Ala Arg Ser Gln Glu Gln Leu Pro Asp Val Lys Leu Phe Asn Glu Tyr
                530                 535                 540
Gly Pro Thr Glu Asn Ser Val Val Ala Thr Cys Ala Ile Gly Leu Glu
545                 550                 555                 560
Lys Asp Gln Pro Ile Thr Ile Gly Thr Pro Ile Ser Asn Ala Ser Val
                565                 570                 575
Leu Ile Leu Asn Thr Ser Gly Glu Leu Gln Pro Leu His Val Pro Gly
                580                 585                 590
Glu Leu Cys Ile Ala Gly Glu Gly Leu Ala Arg Gly Tyr Leu Asn Arg
                595                 600                 605
Pro Glu Leu Thr Glu Glu Lys Phe Ala Ala His Pro Phe Val Pro Gly
610                 615                 620
Glu Arg Ile Tyr His Thr Gly Asp Ser Ala Arg Trp Leu Pro Asn Gly
625                 630                 635                 640
Thr Ile Glu Tyr Leu Gly Arg Ile Asp His Gln Val Lys Ile Arg Gly
                645                 650                 655
Phe Arg Ile Glu Leu Gly Glu Ile Glu Ser Ser Leu Lys Asn Val Ala
                660                 665                 670
Gly Val Arg Glu Val Ile Val Asp Ala Arg Pro Asp Gly Asn Gly Gln
                675                 680                 685
Gln Met Leu Cys Ala Tyr Met Val Ala Asp Ser Val Leu Thr Val Asn
                690                 695                 700
Glu Leu Arg Glu Ala Leu Ser Ser His Leu Pro Asp Tyr Met Ile Pro
705                 710                 715                 720
Ser His Phe Val Gln Met Glu Gln Leu Pro Leu Thr Pro Ser Gly Lys
                725                 730                 735
Leu Asp Arg Lys Ser Leu Pro Asp Pro Gln Ala Asn Ile Ala Ile Gly
                740                 745                 750
Thr Glu Tyr Ile Ala Pro Arg Thr Pro Leu Glu Ala Arg Leu Ala Gln
                755                 760                 765
Ile Trp Gln Glu Ser Leu Gly Val Glu Lys Val Gly Ile Lys Asp Asn
770                 775                 780
Phe Phe Ala Leu Gly Gly His Ser Leu Arg Ala Ala Thr Leu Ala Ser
785                 790                 795                 800
Lys Leu His Lys Glu Leu Asn Val Asn Val Pro Leu Arg Asp Leu Phe
                805                 810                 815
Arg Asn Pro Thr Ile Glu Glu Leu Ala Leu Leu Met Glu Gly Met Glu
                820                 825                 830
Gln Gln Glu Phe Ser Ala Ile Glu Arg Val Lys Glu Arg Glu Tyr Tyr
                835                 840                 845
Ser Val Ser Ser Ala Gln Lys Arg Leu Phe Val Leu Gln Gln Leu Glu
                850                 855                 860
Gly Ala Glu Gln Ser Tyr Asn Met Pro Gly Ala Met Leu Leu Glu Gly
865                 870                 875                 880
Leu Leu Asp Arg Glu Arg Leu Glu Ala Ser Phe Arg Lys Leu Ile Ala
                885                 890                 895
```

-continued

Arg His Glu Thr Leu Arg Thr Gly Phe Glu Leu Met Asp Gly Glu Pro
              900                 905                 910

Val Gln Lys Val Tyr Gln Asn Val Ser Phe Ala Ile Glu Tyr Met Gln
              915                 920                 925

Ala Ser Glu Glu Glu Ala Ala Gln Lys Ala Arg Glu Phe Ile Arg Ala
              930                 935                 940

Phe Asp Leu Met Thr Pro Pro Leu Leu Arg Val Gly Leu Ile Glu Met
945                 950                 955                 960

Ala Pro Asp Arg His Val Leu Leu Tyr Asp Met His His Ile Ile Ser
              965                 970                 975

Asp Gly Ala Ser Met Gly Val Val Glu Glu Phe Ala Arg Leu Tyr
              980                 985                 990

Gly Gly Glu Glu Leu Pro Ser Leu Arg Ile Gln Tyr Lys Asp Phe Ala
              995                 1000                1005

Ala Trp Gln Gln Ser Glu Val Gln Gln Lys Arg Ser Met Gln Gln
       1010                1015                1020

Glu Ala Tyr Trp Leu Gln Ala Phe Gly Gly Glu Leu Pro Val Leu
       1025                1030                1035

Glu Leu Pro Thr Asp Asn Ala Arg Pro Ala Ile Gln Ser Tyr Glu
       1040                1045                1050

Gly Glu Thr Tyr Glu Phe Thr Val Asp Ser Asp Ile Ser Thr Ala
       1055                1060                1065

Leu Gln Arg Leu Ala Ala Asp Ser Gly Thr Thr Leu Tyr Met Val
       1070                1075                1080

Leu Leu Ala Ala Tyr Thr Val Leu Leu His Lys Tyr Thr Gly Gln
       1085                1090                1095

Glu Asp Ile Val Val Gly Thr Thr Asn Ala Gly Arg Met His Asp
       1100                1105                1110

Asp Leu Gln Pro Leu Ile Gly Met Phe Val Asn Thr Leu Ala Ile
       1115                1120                1125

Arg Asn Tyr Pro Ala Gly Glu Ser Thr Phe Arg Ala Tyr Leu Glu
       1130                1135                1140

Gln Val Lys Glu Gln Ala Leu Ala Ala Phe Glu His Gln Glu Tyr
       1145                1150                1155

Pro Phe Glu Glu Leu Val Glu Lys Leu Arg Val Ala Arg Asp Met
       1160                1165                1170

Ser Arg Asn Pro Leu Phe Asp Thr Met Phe Ser Leu Gln Asn Met
       1175                1180                1185

Glu Asn Lys Asp Phe Glu Leu Pro Gly Leu Gln Leu Lys Pro Tyr
       1190                1195                1200

Gly Phe Glu His Gln Ile Ser Lys Phe Asp Leu Ser Leu Asp Val
       1205                1210                1215

Ala Glu Gly Ala Asp Gly Leu Ala Cys Ser Leu Glu Tyr Ala Ser
       1220                1225                1230

Ser Leu Tyr Arg Gln Asp Thr Ile Val Arg Met Ala Asn His Tyr
       1235                1240                1245

Arg Gln Leu Leu His Ser Ile Ala Gln Ser Pro Glu Ala Gln Ile
       1250                1255                1260

Ala Val Leu Gly Met Leu Thr Pro Gly Glu Gln Glu Gln Ile Arg
       1265                1270                1275

Phe Lys Phe Asn His Asp Pro Ser Asp Met Glu Gln Lys His Thr
       1280                1285                1290

-continued

Val His Gln Leu Phe Glu Glu Gln Ala Ala Leu Thr Pro Glu Arg
1295            1300                1305

Thr Ala Val Val His Glu Asn Glu Gln Leu Ser Tyr Gln Glu Leu
1310            1315                1320

Asn Glu Arg Ala Asn Arg Leu Ala Arg Thr Leu Arg Gln His Gly
1325            1330                1335

Val Gln Pro Glu Gln Leu Val Gly Ile Leu Ala Asp Arg Ser Leu
1340            1345                1350

Asp Met Ile Val Gly Ile Met Ala Ile Leu Lys Ala Gly Gly Ala
1355            1360                1365

Tyr Val Pro Ile Asp Pro Lys Tyr Pro Glu Glu Arg Ile Arg Tyr
1370            1375                1380

Met Leu Glu Asp Ser Lys Ala Asn Val Leu Val Thr Gln Ser His
1385            1390                1395

Leu Gln Ser Leu Ser Ser Phe Asp Gly Thr Trp Val Leu Leu Asp
1400            1405                1410

Glu Glu Ser Ser Tyr Ala Glu Asp Ala Ala Asn Leu Val Ser Ile
1415            1420                1425

Asn Glu Pro Gln His Leu Ala Tyr Val Ile Tyr Thr Ser Gly Thr
1430            1435                1440

Thr Gly Gln Pro Lys Gly Ala Met Ile Glu His Arg Gln Leu Thr
1445            1450                1455

Val Met Ala Lys Ala Trp Glu Arg Glu Tyr Arg Leu Arg Glu Glu
1460            1465                1470

Ser Ile Arg Trp Met Gln Trp Ala Ser Phe Ser Phe Asp Val Phe
1475            1480                1485

Ser Gly Asp Leu Ile Arg Ala Leu Leu His Gly Gly Glu Leu Val
1490            1495                1500

Leu Cys Pro Glu His Ala Arg Ala Asn Pro Ala Glu Ile Tyr Glu
1505            1510                1515

Leu Ile Arg Lys His Arg Leu His Met Phe Asp Cys Thr Pro Ser
1520            1525                1530

Ile Val Ile Pro Leu Met Glu Tyr Val Tyr Glu Asn Lys Leu Asp
1535            1540                1545

Ile Ser Ser Leu Lys Leu Val Ala Val Gly Ser Asp Tyr Cys Pro
1550            1555                1560

Pro Asp Glu Phe Gln Lys Met Leu Asp Arg Phe Gly Ser Gln Phe
1565            1570                1575

Arg Ile Ile Asn Ser Tyr Gly Val Thr Glu Thr Cys Ile Asp Ala
1580            1585                1590

Ser Tyr Tyr Glu Pro Thr Thr Pro Thr Val Pro Arg Ala Leu Pro
1595            1600                1605

Ile Gly Lys Pro Leu Pro Gly Val Thr Met Tyr Ile Met Asp Gly
1610            1615                1620

Gln Arg Ser Leu Leu Pro Val Gly Val Ile Gly Glu Leu Tyr Ile
1625            1630                1635

Gly Gly Pro Cys Val Gly Arg Gly Tyr Trp Asn Arg Ser Glu Met
1640            1645                1650

Thr Ser Glu Lys Phe Val Ala Asp Pro Phe Leu Gln Asp His Arg
1655            1660                1665

Met Tyr Arg Thr Gly Asp Leu Ala Arg Trp Met Pro Asp Gly Asn
1670            1675                1680

Ile Glu Tyr Leu Gly Arg Ile Asp His Gln Val Lys Ile Arg Gly

-continued

```
            1685                1690                1695
Tyr Arg Ile Glu Ile Gly Glu Val Glu Ser Lys Leu Leu Lys Val
        1700                1705                1710
Glu Thr Val Arg Glu Ser Val Val Ala Arg Gln Asp Pro Asn
        1715                1720                1725
Gly Thr Lys Ala Leu Cys Ala Tyr Phe Val Ala Asp Arg Asn Leu
        1730                1735                1740
Thr Val Ser Glu Leu Arg Ser Ala Met Ala Asp Glu Leu Pro Ala
        1745                1750                1755
Tyr Met Ile Pro Ser Tyr Phe Val Gln Leu Asp Arg Leu Pro Leu
        1760                1765                1770
Thr Pro Asn Gly Lys Val Asp Arg Lys Ala Leu Pro Ala Pro Glu
        1775                1780                1785
Ala Gly Ala His Thr Gly Ile Glu Tyr Met Ala Pro Arg Thr Glu
        1790                1795                1800
Glu Glu Leu Ala Leu Ala Asn Val Trp Gln Thr Val Leu Gly Ile
        1805                1810                1815
Glu Arg Val Gly Val Leu Asp His Phe Glu Leu Gly Gly Asp
        1820                1825                1830
Ser Ile Lys Ser Ile Gln Val Ala Ser Arg Leu Gln Gln Ala Gly
        1835                1840                1845
Tyr Lys Leu Glu Ile Arg Asp Leu Phe Lys Tyr Pro Thr Ile Ala
        1850                1855                1860
Gln Leu Gly Ser His Leu Gln Arg Ala Ser Lys Val Ala Asp Gln
        1865                1870                1875
Gly Glu Val Ser Gly Asp Val Pro Leu Thr Pro Ile Leu Gly Trp
        1880                1885                1890
Phe Phe Glu Gln Gln Phe Ala Asp Ala His His Tyr Asn Gln Ser
        1895                1900                1905
Ile Met Leu Tyr Arg Arg Glu Gly Phe Asn Glu Ala Ala Ile Arg
        1910                1915                1920
Asn Val Leu Gln Ala Val Thr Glu His His Asp Ala Leu Arg Ile
        1925                1930                1935
Val Phe Arg Arg Asn Asp Gln Gly Asp Tyr Thr Ala Trp Asn Arg
        1940                1945                1950
Ala Ile Glu Glu Gly Glu Leu Phe His Leu Glu Val Leu Asn Leu
        1955                1960                1965
Thr Gly Thr Thr Ala Gly Asp His Glu Gln Asn Val Arg Gln Ile
        1970                1975                1980
Ile Glu Ala Lys Ala Thr Glu Ile Gln Arg Ser Phe Asp Leu His
        1985                1990                1995
Asp Gly Pro Leu Ala Arg Ala Gly Leu Phe Arg Thr Asp Glu Gly
        2000                2005                2010
Asp His Leu Leu Leu Val Met His His Gly Val Val Asp Gly Val
        2015                2020                2025
Ser Trp Arg Ile Leu Leu Glu Asp Ile Ala Thr Gly Tyr Glu Gln
        2030                2035                2040
Ala Leu Lys Gly Glu Pro Val Arg Leu Pro Ala Lys Thr Asp Ser
        2045                2050                2055
Phe Arg Thr Trp Ala Asn Gln Leu Ala Ser Tyr Ala Arg Ser Glu
        2060                2065                2070
Ala Met Ile Glu Glu Gln Ile Phe Trp Glu Gln Ala Glu Ala Asn
        2075                2080                2085
```

```
Gly Thr Ser Ile Leu Ser Leu Pro Lys Asp Phe Glu Ala Glu Thr
    2090                2095                2100

Ser Leu Gln Gln Asp Ser Glu Ser Val Val Val Glu Trp Ser Arg
    2105                2110                2115

Glu Glu Thr Asp Met Leu Leu Lys His Val His Arg Ala Tyr Asn
    2120                2125                2130

Thr Asp Met Asn Asp Ile Leu Leu Ala Ala Leu Gly Met Ala Ile
    2135                2140                2145

Gln Gln Trp Cys Gly His Glu Lys Ala Leu Val Thr Leu Glu Gly
    2150                2155                2160

His Gly Arg Glu Asn Ile Met Pro Glu Leu Asp Ile Ser Arg Thr
    2165                2170                2175

Val Gly Trp Phe Thr Ser Glu Tyr Pro Phe Leu Leu Glu Ser Asp
    2180                2185                2190

Pro Asn Lys Ser Leu Ser Tyr Arg Ile Lys Arg Met Lys Glu Asn
    2195                2200                2205

Leu Arg Arg Ile Pro Asn Lys Gly Ile Gly Tyr Gly Ile His Arg
    2210                2215                2220

Tyr Leu Ser Gly Ser Gly Thr Ser Gly Thr Lys Asn Val Ser Arg
    2225                2230                2235

Ser Glu Ala Ser Ala Gln Pro Glu Ile Ser Phe Asn Tyr Leu Gly
    2240                2245                2250

Gln Phe Asp Gln Asp Leu Gln Asn Asn Glu Met Glu Val Ser Pro
    2255                2260                2265

Tyr Ser Gly Gly Ala Glu Ile Ser Val Arg Gln Ala Arg Asn Thr
    2270                2275                2280

Thr Leu Asp Phe Asn Gly Met Ile Ser Ala Gly Val Leu Ala Leu
    2285                2290                2295

Glu Val Ser Tyr Ser Ser Lys Gln Tyr Arg Arg Asp Thr Ile Asp
    2300                2305                2310

Arg Leu Ala Gly Leu Leu Lys Gly Ser Leu Gln Glu Ile Val Ala
    2315                2320                2325

Tyr Cys Ala Ser Lys Asp Lys Pro Glu Leu Thr Pro Ser Asp Val
    2330                2335                2340

Leu Val Asn Gly Leu Gly Ile Glu Asp Leu Glu Arg Ile Ala Glu
    2345                2350                2355

Gln Thr Arg Asp Leu Gly Asp Ile Glu Asn Ile Tyr Ala Leu Thr
    2360                2365                2370

Pro Met Gln Lys Gly Met Trp Phe His Asn Ala Met Asp Gly Gln
    2375                2380                2385

Ala Gly Ala Tyr Phe Glu Gln Thr Arg Phe Thr Ile Gln Gly Glu
    2390                2395                2400

Leu Asp Val Gln Leu Phe Ala Ser Ser Leu Asp Val Leu Ala Thr
    2405                2410                2415

Arg His Ala Val Leu Arg Thr Asn Phe Phe Ser Gly Trp Asn Gly
    2420                2425                2430

Glu Leu Leu Gln Ile Val Tyr Arg Asn Lys Asn Leu Glu Phe Ser
    2435                2440                2445

Tyr Glu Asp Leu Ser Glu Leu Pro Glu His Glu Lys Gln Asp Arg
    2450                2455                2460

Val Glu Ala Met Ala Gln Ala Asp Lys Gln Arg Gly Phe Asp Leu
    2465                2470                2475
```

-continued

Glu Arg Asp Ala Leu Met Arg Val Phe Val Leu Arg Thr Ser Leu
2480                    2485                2490

Asn Cys Ser His Val Ile Trp Ser Ser His His Ile Leu Met Asp
2495                    2500                2505

Gly Trp Cys Leu Pro Gln Leu Thr Gln Glu Trp Leu Glu Thr Tyr
2510                    2515                2520

Ser Asp Ser Val Asn Gly Arg Ser Ser Ser Arg Ser Gly Ala Ser
2525                    2530                2535

Pro Tyr Ser Leu Tyr Ile Glu Trp Leu Tyr Lys Gln Asn Tyr Thr
2540                    2545                2550

Ala Ala Ser Gln Tyr Trp Ser Asp Tyr Leu Ser Asp Tyr Asp Gln
2555                    2560                2565

Gln Thr Val Leu Pro Gln Lys Lys Ser Ser Gly Arg Ser Asp Val
2570                    2575                2580

Tyr Ile Ala Asp Asn Leu Val Phe Glu Leu Gly Glu Ala Leu Thr
2585                    2590                2595

Ala Lys Met His Arg Val Ala Lys Gln His Gln Leu Thr Leu Asn
2600                    2605                2610

Thr Leu Met Gln Ala Ala Trp Gly Ile Ile Leu Gln Lys Tyr Asn
2615                    2620                2625

Asn Thr Gly Asp Ala Val Phe Gly Gly Val Val Ser Gly Arg Pro
2630                    2635                2640

Ala Glu Ile Pro Gly Ile Glu Ser Met Ile Gly Leu Phe Ile Asn
2645                    2650                2655

Thr Ile Pro Ile Arg Val Val Cys Glu Ala Asp Asp Arg Phe Ala
2660                    2665                2670

Asp Val Met Lys Gln Leu Gln Glu Lys Ala Leu Glu Ser Gly Arg
2675                    2680                2685

Tyr Asp Tyr Tyr Pro Leu Tyr Asp Ile Gln Ala Leu Ser Thr His
2690                    2695                2700

Lys Gln Asp Leu Ile Asn His Ile Leu Val Phe Glu Asn Tyr Pro
2705                    2710                2715

Met Glu Glu Gln Met Glu Gln Ala Gly Asp Glu Arg Gly Gln Leu
2720                    2725                2730

Asn Ile Thr Asp Val Arg Val Ala Glu Gln Thr Ser Tyr Asp Phe
2735                    2740                2745

Asn Leu Val Val Met Pro Gly Glu Asp Met Met Ile Arg Leu Glu
2750                    2755                2760

Tyr Asn Ala Val Met Tyr Asp Arg Ala Asp Met Glu Arg Ile Arg
2765                    2770                2775

Gln His Leu Ile His Val Leu Lys Gln Val Thr Ala Asp Pro Ala
2780                    2785                2790

Ile Ala Val Lys Asp Val Arg Leu Ala Thr Asp Asp Glu Lys Ala
2795                    2800                2805

Glu Leu Leu Thr Ala Phe Asn Asp Thr Glu Val Glu Tyr Pro Arg
2810                    2815                2820

Glu Gln Met Ile His Arg Met Phe Glu Glu Gln Val Gln Arg Thr
2825                    2830                2835

Pro Asp Ala Thr Ala Val Leu Cys Gly Ala Ala Thr Met Thr Tyr
2840                    2845                2850

Arg Glu Met Asn Glu Arg Ala Asn Gln Leu Ala Arg Thr Leu Arg
2855                    2860                2865

Ala Ala Gly Val Val Pro Asp Gln Ile Val Gly Ile Met Ala Glu

```
            2870                2875                2880
Arg Ser Leu Glu Leu Met Val Gly Ile Met Gly Ile Leu Lys Ala
        2885                2890                2895
Gly Gly Ala Tyr Val Pro Ile Ala Pro Asp Tyr Pro Glu Glu Arg
        2900                2905                2910
Ile Arg Tyr Met Leu Asp Asp Ser Glu Ala Gln Val Leu Ile Val
        2915                2920                2925
Gln Gly Ser Ala Gly Glu Ala Ile Asp Phe Ala Gly His Val Ile
        2930                2935                2940
Asn Leu Asp Asp Val Asp Ser Tyr Asp Gln Asp Ser Ser Asn Leu
        2945                2950                2955
Glu Met Val Asn Lys Pro Thr Asp Ile Ala Tyr Ile Ile Tyr Thr
        2960                2965                2970
Ser Gly Thr Thr Gly Arg Pro Lys Gly Val Met Val Glu His Thr
        2975                2980                2985
Ser Val Ile Asn Arg Leu Leu Trp Met Gln Lys Arg Tyr Pro Ile
        2990                2995                3000
Asp Ala Asp Asp Thr Ile Met Gln Lys Thr Ala Ile Thr Phe Asp
        3005                3010                3015
Val Ser Val Trp Glu Leu Phe Trp Trp Ala Phe Val Gly Ser Lys
        3020                3025                3030
Val Leu Met Leu Pro Val Gly Gly Glu Lys Asn Pro Ala Ala Ile
        3035                3040                3045
Val Glu Ala Ile Glu Gln Tyr Asp Ile Ser Thr Met His Phe Val
        3050                3055                3060
Pro Ser Met Leu His Ala Phe Leu Glu His Ile Glu Gln Leu Pro
        3065                3070                3075
Glu Ala Glu Arg Glu Arg Leu Ser Pro Leu Lys Gln Val Phe Thr
        3080                3085                3090
Ser Gly Glu Ala Leu Leu Ala Ser Gln Val Glu Arg Phe His Gln
        3095                3100                3105
Tyr Val Ala Pro Ala Ser Gly Ala Arg Leu Ile Asn Leu Tyr Gly
        3110                3115                3120
Pro Thr Glu Ala Thr Val Asp Val Thr Tyr Phe Asp Cys Glu Pro
        3125                3130                3135
Gly Gln Thr Tyr Val Ser Val Pro Ile Gly Lys Pro Ile Asp Asn
        3140                3145                3150
Thr Arg Ile Tyr Ile Val Asn Gly Asn Asn Gln Val Gln Pro Ile
        3155                3160                3165
Gly Val Ala Gly Glu Leu Cys Ile Ala Gly Val Gly Leu Ala Arg
        3170                3175                3180
Gly Tyr Trp Asn Arg Pro Glu Leu Thr Glu Glu Lys Phe Val Leu
        3185                3190                3195
Val Pro Ser Val Gly Glu Arg Met Tyr Arg Thr Gly Asp Leu Ala
        3200                3205                3210
Arg Trp Leu Pro Asp Gly Asn Ile Glu Tyr Leu Gly Arg Ile Asp
        3215                3220                3225
His Gln Val Lys Ile Arg Gly Tyr Arg Ile Glu Leu Gly Glu Leu
        3230                3235                3240
Glu Thr Ala Leu Leu Lys Ile Asp Ala Val Arg Glu Thr Val Val
        3245                3250                3255
Val Ala Arg Glu Asp Glu Ser Gly Gln Lys Ser Leu Cys Ala Tyr
        3260                3265                3270
```

```
Tyr Val Ala Asp Gly Glu Ala Thr Val Ser Asp Leu Arg Ala Ala
3275                3280                3285

Leu Ala Ala Glu Leu Pro Ser Tyr Met Ile Pro Ser Tyr Phe Val
3290                3295                3300

Arg Leu Glu Gln Met Pro Leu Ala Pro Asn Gly Lys Leu Asp Arg
3305                3310                3315

Lys Ala Leu Pro Ala Pro Glu Arg Ser Leu Gln Val Glu Ser Glu
3320                3325                3330

Tyr Val Ala Pro Arg Thr Glu Ala Glu Gln Met Leu Ala Thr Val
3335                3340                3345

Trp Gln Ala Val Leu Gly Ile Glu Arg Val Gly Ile Thr Asp His
3350                3355                3360

Phe Phe Glu Leu Gly Gly Asp Ser Ile Lys Ser Ile Gln Val Ala
3365                3370                3375

Ala Arg Met Gln Gln Ala Gly Phe Lys Leu Asp Ile Arg Asp Leu
3380                3385                3390

Phe Lys Tyr Ser Thr Val Thr Gln Leu Val Pro Tyr Met Gln Pro
3395                3400                3405

Ile Asn Arg Thr Ala Asp Gln Gly Glu Val Val Gly Glu Val Pro
3410                3415                3420

Met Thr Pro Ile Leu His Trp Phe Glu His Gln Phe Ala Asn
3425                3430                3435

Pro His His Phe Asn Gln Ser Val Met Leu Tyr Arg Lys Asp Gly
3440                3445                3450

Phe Val Ala Asp Ala Val Arg Lys Ala Leu His Lys Leu Val Glu
3455                3460                3465

His His Asp Ala Leu Arg Ile Val Ile Gln Arg Thr Glu Gln Gly
3470                3475                3480

Glu Tyr Ser Leu Trp Asn Arg Ser Leu Val Glu Gly Glu Leu Phe
3485                3490                3495

Ser Met Gly Glu Ile Asp Leu Thr Asp Gln Ser Asp Phe Ala Ala
3500                3505                3510

Ala Ile Glu Ala Glu Ala Asn His Ile Gln Gly Ser Ile Asp Leu
3515                3520                3525

Gln Ala Gly Pro Leu Val Lys Ala Gly Leu Phe His Gly Ser Asp
3530                3535                3540

Gly Asp His Leu Leu Leu Val Ile His His Ala Val Ile Asp Gly
3545                3550                3555

Val Ser Trp Arg Ile Leu Leu Glu Asp Leu Ala Ala Gly Tyr Glu
3560                3565                3570

Gln Ala Leu Asn Gln Arg Gln Val Arg Leu Pro Met Lys Thr Asp
3575                3580                3585

Ser Phe Arg Thr Trp Ala Glu Gln Leu Val Glu Tyr Ala Asn Ser
3590                3595                3600

Pro Ala Met Asp Lys Glu Ser Ala Tyr Trp Leu Ser Val Ala Gln
3605                3610                3615

Thr Glu Val Ala Ala Leu Pro Lys Asp Ser Glu Cys Thr Val Ser
3620                3625                3630

Leu Gln Arg Asp Ser Glu Ser Val Val Leu Glu Trp Asn Lys Glu
3635                3640                3645

Asp Thr Glu Arg Leu Leu Lys His Val His Arg Ala Tyr Asn Thr
3650                3655                3660
```

-continued

| | | | | | | | | | | | | | |
|---|---|---|---|---|---|---|---|---|---|---|---|---|---|
| Glu | Met | Asp | Asp | Ile | Leu | Leu | Thr | Ala | Leu | Gly | Arg | Ala | Leu | Met |
| | 3665 | | | | 3670 | | | | | 3675 | | | | |
| Lys | Trp | Arg | Gly | Ile | Asp | Arg | Val | Leu | Val | Thr | Leu | Glu | Gly | His |
| | 3680 | | | | 3685 | | | | | 3690 | | | | |
| Gly | Arg | Glu | Ser | Ile | Leu | Gln | Asp | Met | Asp | Ile | Thr | Arg | Thr | Val |
| | 3695 | | | | 3700 | | | | | 3705 | | | | |
| Gly | Trp | Phe | Thr | Thr | Glu | Tyr | Pro | Phe | Glu | Leu | Gly | Met | Glu | Ala |
| | 3710 | | | | 3715 | | | | | 3720 | | | | |
| Asn | Asp | Ser | Leu | Gly | Ser | Gln | Ile | Lys | Lys | Val | Lys | Glu | Asp | Leu |
| | 3725 | | | | 3730 | | | | | 3735 | | | | |
| Arg | Arg | Ile | Pro | Asn | Lys | Gly | Ile | Gly | Tyr | Gly | Leu | Phe | Arg | Tyr |
| | 3740 | | | | 3745 | | | | | 3750 | | | | |
| Leu | Ser | Asn | Ser | Gly | Lys | Gln | Ala | Trp | Asn | Asp | Ala | Pro | Thr | Thr |
| | 3755 | | | | 3760 | | | | | 3765 | | | | |
| Gln | Ile | Arg | Tyr | Asn | Tyr | Leu | Gly | Gln | Phe | Asp | Ala | Asp | Leu | Ser |
| | 3770 | | | | 3775 | | | | | 3780 | | | | |
| Asn | Asn | Glu | Leu | Ser | Val | Ser | Pro | Tyr | Ala | Ser | Gly | Ser | Glu | Ile |
| | 3785 | | | | 3790 | | | | | 3795 | | | | |
| Ser | Asp | Glu | Gln | Glu | Arg | Lys | Tyr | Pro | Leu | Asp | Ile | Asn | Gly | Val |
| | 3800 | | | | 3805 | | | | | 3810 | | | | |
| Ile | Ala | Glu | Gly | Gln | Leu | Thr | Leu | Gly | Leu | Ser | Tyr | Ser | Val | Lys |
| | 3815 | | | | 3820 | | | | | 3825 | | | | |
| Glu | Tyr | His | Lys | Glu | Thr | Met | Glu | Glu | Leu | Gly | Asp | Leu | Leu | Thr |
| | 3830 | | | | 3835 | | | | | 3840 | | | | |
| Glu | Ser | Leu | Lys | Glu | Ile | Ile | Ala | His | Cys | Glu | Ser | Gln | Glu | Arg |
| | 3845 | | | | 3850 | | | | | 3855 | | | | |
| Thr | Gln | Leu | Thr | Pro | Ser | Asp | Val | Leu | Phe | Lys | Gly | Leu | Ser | Leu |
| | 3860 | | | | 3865 | | | | | 3870 | | | | |
| Glu | Trp | Leu | Asp | Arg | Ile | Ser | Ser | Gln | Met | Gln | His | Ile | Gly | Glu |
| | 3875 | | | | 3880 | | | | | 3885 | | | | |
| Ile | Glu | Asn | Val | Tyr | Ala | Leu | Thr | Pro | Met | Gln | Lys | Gly | Met | Trp |
| | 3890 | | | | 3895 | | | | | 3900 | | | | |
| Phe | His | Ser | Ala | Met | Asp | Ser | Leu | Thr | Gly | Ala | Tyr | His | Glu | Gln |
| | 3905 | | | | 3910 | | | | | 3915 | | | | |
| Thr | Met | Phe | Thr | Leu | Glu | Gly | Thr | Leu | Asp | Val | Glu | Leu | Phe | Ser |
| | 3920 | | | | 3925 | | | | | 3930 | | | | |
| Ser | Ser | Leu | Asn | Glu | Leu | Ala | Lys | Arg | His | Ala | Val | Leu | Arg | Thr |
| | 3935 | | | | 3940 | | | | | 3945 | | | | |
| Asn | Phe | Ile | Ser | Gly | Pro | Gln | Gly | Glu | Pro | Val | Gln | Val | Val | Phe |
| | 3950 | | | | 3955 | | | | | 3960 | | | | |
| Arg | Asn | Lys | Pro | Ile | Gly | Phe | Ser | Phe | Gln | Asp | Val | Arg | Ala | Leu |
| | 3965 | | | | 3970 | | | | | 3975 | | | | |
| Asn | Glu | Glu | Glu | Gln | Gln | Ser | Phe | Ile | Lys | Glu | Ala | Val | Ser | Ser |
| | 3980 | | | | 3985 | | | | | 3990 | | | | |
| Asp | Gln | Leu | Leu | Gly | Phe | Asp | Leu | Ala | Gln | Gly | Ala | Leu | Met | Arg |
| | 3995 | | | | 4000 | | | | | 4005 | | | | |
| Val | Ser | Ala | Ile | Arg | Thr | Gly | Glu | Leu | Ser | Cys | Arg | Val | Leu | Trp |
| | 4010 | | | | 4015 | | | | | 4020 | | | | |
| Ser | Ser | His | His | Ile | Leu | Met | Asp | Gly | Trp | Cys | Leu | Pro | Gln | Leu |
| | 4025 | | | | 4030 | | | | | 4035 | | | | |
| Met | Gln | Glu | Leu | Phe | Asp | Thr | Tyr | Ala | Ala | Leu | Leu | Gln | Lys | Lys |
| | 4040 | | | | 4045 | | | | | 4050 | | | | |
| Ser | Pro | Asp | Arg | Thr | Val | Val | Pro | Ala | Tyr | Ser | Gln | Tyr | Ile | Glu |

-continued

```
                4055                4060                4065
Trp Leu Gly Gln Gln Asp Glu Glu Ala Ala Gly Thr Tyr Trp Ser
        4070                4075                4080
Ala Tyr Leu Ala Asp Tyr Asp Gln Val Thr Glu Ile Pro Gln Glu
        4085                4090                4095
Ser Ser Ala Gly Ile Asp Ser Glu Pro Tyr Lys Ala Glu Lys Trp
        4100                4105                4110
Ser Arg Glu Leu Asp Ala Gly Leu Ser Ala Ser Ile Ser Arg Ala
        4115                4120                4125
Ala Arg Gln His Gln Val Thr Leu Asn Thr Leu Gln Ala Ala
        4130                4135                4140
Trp Gly Val Ile Leu Gln Lys Tyr Asn Gly Thr Asn Asp Val Val
        4145                4150                4155
Phe Gly Ser Val Val Ser Gly Arg Pro Ala Glu Val Pro Gly Ile
        4160                4165                4170
Glu Thr Met Ile Gly Leu Phe Ile Asn Thr Ile Pro Ile Arg Val
        4175                4180                4185
Lys Cys Glu Gly Ser Thr Ser Phe Ala Glu Leu Met Gly Leu Leu
        4190                4195                4200
Gln Glu Gln Ala Leu Glu Ser Gly Lys Tyr Asp Tyr Tyr Pro Leu
        4205                4210                4215
Tyr Glu Ile Gln Ser Arg Ser Ala Leu Lys Gln Asn Ala Ile Arg
        4220                4225                4230
Gln Ile Met Val Phe Glu Asn Tyr Pro Met Asp Glu Gln Leu Glu
        4235                4240                4245
Gln Ala Gly Gly Asp Glu His Gly Met Pro Ser Leu Thr Asp Val
        4250                4255                4260
Ala Val Glu Glu Gln Thr Asn Tyr Asp Phe Asn Leu Ile Val Val
        4265                4270                4275
Pro Gly Glu Gln Ile Ser Ile Arg Phe Asp Tyr Asn Ala Asn Arg
        4280                4285                4290
Phe Val Gln Ala Asp Met Glu Arg Leu Met Gly His Leu Asn Asn
        4295                4300                4305
Ile Leu Glu Gln Ile Val Asp Asn Pro Arg Val Ala Val Glu Asp
        4310                4315                4320
Leu Glu Leu Ala Thr Glu Ala Glu Lys Ser Glu Val Ile Gln Ser
        4325                4330                4335
Phe Asn Asp Thr Leu Thr Asn Tyr Pro Arg Asp Met Met Leu His
        4340                4345                4350
Arg Leu Phe Glu Glu Gln Ala Glu Arg His Pro Asp Ala Val Ala
        4355                4360                4365
Ile Ser Phe Arg Asp Val Gln Met Thr Tyr Arg Asp Leu Asn Asp
        4370                4375                4380
Arg Ala Asn Arg Leu Ala Arg Thr Leu Arg Ala Val Gly Val Gly
        4385                4390                4395
Thr Asp Lys Leu Val Gly Leu Met Ser Glu Arg Ser Pro Asp Met
        4400                4405                4410
Ile Ile Gly Ile Leu Ala Ile Leu Lys Ala Gly Gly Gly Tyr Val
        4415                4420                4425
Pro Ile Asp Pro Glu Tyr Pro Glu Glu Arg Ile Arg Tyr Met Leu
        4430                4435                4440
Glu Asp Ser Gly Ala Arg Ile Met Leu Ala Gln Gln His Leu Thr
        4445                4450                4455
```

```
Gly Lys Ile Pro Ala Met Asp Ala Ser Pro Leu Asp Ala Ile Ile
    4460            4465            4470

Asn Leu Asp Thr Glu Thr Ser Tyr Asp Ser Asn Gly Ser Asn Leu
    4475            4480            4485

Glu Ala Asn Thr Asp Ala Ser Ser Glu Asn Leu Ala Tyr Val Ile
    4490            4495            4500

Tyr Thr Ser Gly Thr Thr Gly Lys Pro Lys Gly Asn Leu Thr Thr
    4505            4510            4515

His Arg Asn Ile Val Arg Val Arg Glu Thr Glu Tyr Ile Asp
    4520            4525            4530

Ile Thr Asn His Asp Asn Val Leu Gln Met Ser Ser Tyr Ala Phe
    4535            4540            4545

Asp Gly Ser Thr Phe Asp Ile Tyr Gly Ala Leu Leu Asn Gly Ala
    4550            4555            4560

Lys Leu Val Leu Val Pro His Glu Thr Leu Leu Glu Val Arg Gln
    4565            4570            4575

Leu Ala Glu Leu Ile Val Gln Glu Lys Ile Ser Val Met Phe Ile
    4580            4585            4590

Thr Thr Ala Tyr Phe Asn Val Leu Val Asp Val Gln Ala Ser Cys
    4595            4600            4605

Leu Ser Asn Ile Arg Ala Ile Leu Phe Gly Gly Glu Arg Val Ser
    4610            4615            4620

Val Ser His Val Arg Lys Ala Leu Asn His Val Ala Pro Gly Thr
    4625            4630            4635

Leu Lys His Val Tyr Gly Pro Thr Glu Ser Thr Val Phe Ala Thr
    4640            4645            4650

Cys His Asp Val Tyr Glu Val Thr Glu Asn Ala Val Thr Val Pro
    4655            4660            4665

Ile Gly Arg Pro Ile Ser Asn Thr Ser Ile Tyr Ile Val Asp Ala
    4670            4675            4680

Asn Asn Lys Leu Gln Pro Val Gly Val Ala Gly Glu Leu Cys Val
    4685            4690            4695

Ala Gly Asp Gly Leu Ala Arg Gly Tyr Leu Asn Arg Pro Asp Leu
    4700            4705            4710

Thr Ala Glu Lys Phe Val Asp Ser Pro Tyr Val Gln Gly Glu Arg
    4715            4720            4725

Met Tyr Arg Thr Gly Asp Leu Ala Lys Trp Leu Pro Asp Gly Ser
    4730            4735            4740

Ile Glu Tyr Val Gly Arg Ile Asp Gln Gln Val Lys Ile Arg Gly
    4745            4750            4755

Tyr Arg Ile Glu Leu Gly Glu Ile Glu Ala Gln Leu Leu Asn Val
    4760            4765            4770

Glu Asp Val Gln Glu Ala Val Val Val Ala Arg Asp Asn Asp Thr
    4775            4780            4785

Gly Glu Lys Gln Leu Cys Ala Tyr Tyr Val Ala Met Arg Pro Leu
    4790            4795            4800

Glu Ala Asn His Leu Arg Glu Val Met Gly Gln Ala Met Pro Ser
    4805            4810            4815

Tyr Met Leu Pro Ala His Phe Val Gln Leu Glu Gln Leu Pro Leu
    4820            4825            4830

Thr Pro Asn Gly Lys Val Asp Arg Lys Ala Leu Pro Ala Pro Glu
    4835            4840            4845
```

| | | | | | | | | | | | |
|---|---|---|---|---|---|---|---|---|---|---|---|
| Glu | Gly | Arg | Ser | Gly | Glu | Thr | Phe | Val | Ala | Pro | Arg | Thr | Pro | Leu |

Glu Gly Arg Ser Gly Glu Thr Phe Val Ala Pro Arg Thr Pro Leu
    4850                4855                4860

Glu Ala Gln Leu Val Gln Ile Trp Gln Asp Val Leu Gly Ile Ser
    4865                4870                4875

Ser Val Ser Val Thr Ala His Phe Phe Glu Leu Gly Gly His Ser
    4880                4885                4890

Leu Lys Ala Thr Leu Leu Val Asn Arg Leu His Gln Glu Leu Asn
    4895                4900                4905

Ile Glu Leu Pro Leu Lys Asp Val Phe Gln Tyr Pro Thr Leu Glu
    4910                4915                4920

Ala Met Ala Lys Arg Leu Ser Asn Ala Glu Gly Ser Arg His Val
    4925                4930                4935

Ser Ile Pro Val Ala Ala Pro Ser Gln His Tyr Pro Val Ser Ser
    4940                4945                4950

Ala Gln Lys Arg Leu Tyr Ile Leu His Gln Leu Glu Gly Ala Glu
    4955                4960                4965

Leu Ser Tyr Asn Met Pro Asn Met Leu Leu Glu Gly Ala Val
    4970                4975                4980

Asp Leu Gly Arg Leu Glu Glu Ala Phe Lys Arg Leu Ile Glu Arg
    4985                4990                4995

His Glu Thr Leu Arg Thr Gly Phe Glu Ile Val Asn Gly Glu Pro
    5000                5005                5010

Val Gln Arg Ile Tyr Pro Glu Val Asp Phe Ala Ile Glu His Val
    5015                5020                5025

Leu Ala Ser Glu Glu Gly Ala Ser Lys Leu Met Gln Gln Phe Val
    5030                5035                5040

Arg Ser Phe Gln Leu Glu Lys Pro Pro Leu Leu Arg Ile Gly Val
    5045                5050                5055

Ile Glu Leu Ser Glu Glu Arg Ser Ile Leu Met Phe Asp Met His
    5060                5065                5070

His Ile Ile Ser Asp Gly Ser Ser Met Gly Ile Leu Ile Asn Glu
    5075                5080                5085

Phe Val His Leu Tyr Ser Gly Glu Glu Leu Thr Pro Leu Arg Ile
    5090                5095                5100

Gln Tyr Lys Asp Tyr Ala Val Trp Gln Gln Ser Asp Thr Gln Gln
    5105                5110                5115

Glu Ala Met Lys Leu Gln Glu Gly Tyr Trp Leu Lys Val Leu Gly
    5120                5125                5130

Gly Glu Leu Pro Val Leu Glu Met Pro Thr Asp Ser Ile Arg Pro
    5135                5140                5145

Thr Thr Gln Ser Phe Arg Gly Asp Leu Leu Gln Phe Asp Leu Asp
    5150                5155                5160

Pro Val Arg Ser Ala Gly Leu Arg Arg Ile Ala Ala Glu Asn Gly
    5165                5170                5175

Ala Thr Met Tyr Met Val Leu Leu Ala Leu Tyr Lys Thr Met Leu
    5180                5185                5190

His Lys Tyr Ser Gly Gln Glu Asp Ile Ile Val Gly Thr Pro Ile
    5195                5200                5205

Ala Gly Arg Asn His Gly Asp Leu Gln Pro Leu Leu Gly Met Phe
    5210                5215                5220

Val Asn Thr Leu Ala Ile Arg Ser Tyr Pro Ala Ala Ser Lys Thr
    5225                5230                5235

Phe Leu Ser Tyr Leu Gly Glu Ile Lys Glu Ser Thr Leu Gly Ala

```
                    5240                  5245                        5250

Phe Glu Asn Gln Asn Tyr Pro Phe Glu Ala Leu Val Glu Gln Val
            5255                  5260                        5265

Gln Val Met Arg Asp Met Ser Arg Asn Pro Val Phe Asp Thr Met
            5270                  5275                        5280

Phe Ile Leu Gln Asn Ala Asp Gln Gly Glu Met Lys Ile Asp Gly
            5285                  5290                        5295

Leu Arg Leu Gln Ser Val Pro Asn Glu His Thr Val Ser Lys Phe
            5300                  5305                        5310

Asp Leu Thr Phe Gln Ala Glu Glu Asp Glu Ala Glu Ile Val Cys
            5315                  5320                        5325

Ser Ile Glu Tyr Ala Thr Asp Leu Phe Lys Arg Gly Thr Ile Glu
            5330                  5335                        5340

Arg Met Ala Arg His Phe Glu Gln Leu Val His Thr Val Leu Asp
            5345                  5350                        5355

Asn Pro Gln Ala Ser Leu Ser Asn Leu Ser Met Val Thr Asn Glu
            5360                  5365                        5370

Glu Lys Ala Leu Leu Gln Asp Lys Phe Asn Asp Thr Asp Met Ala
            5375                  5380                        5385

His Pro Ser Asp Lys Thr Val His Glu Leu Phe Ala Glu Gln Val
            5390                  5395                        5400

Glu Arg Thr Pro Asp Ala Val Ala Val Val Ser Gly Ser Glu Gln
            5405                  5410                        5415

Leu Ser Tyr Gly Asp Leu Asn Arg Lys Ala Asn Gln Leu Ala Trp
            5420                  5425                        5430

Lys Leu Arg Glu Tyr Gly Val Thr Ala Glu Gln Pro Val Gly Ile
            5435                  5440                        5445

Ile Val Glu Arg Thr Leu Asp Thr Val Val Ala Val Leu Ala Val
            5450                  5455                        5460

Leu Lys Ala Ser Gly Thr Phe Val Pro Ile Asp Pro Glu Tyr Pro
            5465                  5470                        5475

Glu Thr Arg Ile Arg Tyr Met Leu Ala Asp Ser Gly Ala Lys Leu
            5480                  5485                        5490

Val Leu Ala Gln Ser Glu Leu Ser Gly Ile Ile Pro Asp Asp Val
            5495                  5500                        5505

Arg Leu Ile Asp Val Arg Asp Glu Ser Leu Tyr Gln Gly Asp Gly
            5510                  5515                        5520

Ala Asp Val Pro Asn Gly Ser Lys Pro Ser Asn Leu Leu Tyr Ile
            5525                  5530                        5535

Ile Tyr Thr Ser Gly Thr Thr Gly Asn Pro Lys Gly Val Met Leu
            5540                  5545                        5550

Glu His Arg Asn Met Val Asn Leu Leu His Tyr Gln Gln Lys Gly
            5555                  5560                        5565

Thr Asn Ile Pro Met Pro Ser Arg Ile Leu Gln Tyr Ala Ser Gly
            5570                  5575                        5580

Ser Phe Asp Val Cys Tyr Gln Glu Met Phe Ser Ala Leu Leu Phe
            5585                  5590                        5595

Gly Gly Ser Leu Tyr Met Val Asp Asn Glu Met Arg Lys Asp Pro
            5600                  5605                        5610

Val Arg Leu Phe Gln Glu Ile Glu Lys His Glu Ile Asp Val Met
            5615                  5620                        5625

Tyr Ile Pro Val Ala Phe Leu Lys Phe Ile Phe Ala Glu Pro Glu
            5630                  5635                        5640
```

```
Trp Ala Glu Ala Phe Pro Arg Cys Val Arg His Ile Ile Thr Ala
5645                5650                5655

Gly Glu Gln Leu Val Val Thr Pro Gln Val Gln Ala Cys Leu Lys
5660                5665                5670

Arg Leu Asp Ile Cys Leu His Asn His Tyr Gly Pro Ser Glu Thr
5675                5680                5685

His Val Val Thr Thr Tyr Thr Met Thr Pro Glu Val Ile Glu Val
5690                5695                5700

Gly Leu Pro Pro Ile Gly Lys Pro Ile Ala Asn Thr Ser Ile Tyr
5705                5710                5715

Ile Val Asn Asp Ser Phe Glu Leu Gln Pro Ile Gly Val Lys Gly
5720                5725                5730

Glu Leu Tyr Val Ser Gly Ala Cys Val Gly Arg Gly Tyr Trp Gly
5735                5740                5745

Arg Thr Asp Leu Thr Glu Glu Lys Phe Leu Asp Asn Pro Phe Ala
5750                5755                5760

Pro Gly Glu Arg Leu Tyr Lys Thr Gly Asp Val Ala Arg Trp Leu
5765                5770                5775

Pro Asp Gly Ser Ile Glu Tyr Val Gly Arg Ser Asp His Gln Val
5780                5785                5790

Lys Ile Arg Gly Phe Arg Ile Glu Leu Gly Glu Val Glu Ser Gln
5795                5800                5805

Leu Leu His Val Pro Ala Val Gln Glu Ala Thr Val Val Ala Leu
5810                5815                5820

Glu Asp His Ala Gly Gln Lys Gln Leu Cys Ala Tyr Phe Thr Ala
5825                5830                5835

Glu Cys Ser Leu Thr Ala Gly Glu Leu Arg Ala Ala Leu Ser Gln
5840                5845                5850

Glu Leu Pro Gly Tyr Met Ile Pro Ser Tyr Phe Val Gln Leu Glu
5855                5860                5865

Arg Leu Pro Leu Thr Pro Asn Gly Lys Ile Asp Arg Arg Ala Leu
5870                5875                5880

Pro Lys Pro Glu Gly Gly Ile Glu Thr Gly Thr Glu Tyr Val Ala
5885                5890                5895

Pro Arg Thr Glu Thr Glu Ala Arg Leu Ala Arg Ile Trp Gln Asp
5900                5905                5910

Val Leu Gly Leu Ala Ser Val Gly Val Lys Asp Asn Phe Phe Glu
5915                5920                5925

Leu Gly Gly His Ser Leu Arg Ala Thr Thr Leu Val Ser Arg Leu
5930                5935                5940

Tyr Lys Glu Met Asn Val Asn Phe Pro Leu Arg Gly Val Phe Arg
5945                5950                5955

His Pro Thr Ile Glu Glu Met Ser Gln Ala Ile Ser Gln Met Glu
5960                5965                5970

Thr Ser Leu Tyr Thr Ala Ile Pro Ile Ala Glu Glu Gln Glu Tyr
5975                5980                5985

Tyr Pro Leu Ser Ser Ala Gln Leu Arg Leu Tyr Ile Met Ser Gln
5990                5995                6000

Leu Glu Gly Ser Glu Leu Ser Tyr Asn Met Pro Gly Met Leu Val
6005                6010                6015

Leu Glu Gly Gln Leu Asn Arg Asp Gln Phe Gln Thr Ala Phe Leu
6020                6025                6030
```

```
Lys Leu Ile Ala Arg His Glu Thr Leu Arg Thr Gly Phe Glu Met
6035                6040                6045

Val Asp Gly Glu Pro Met Gln Arg Ile His Arg Asn Thr Glu Phe
6050                6055                6060

Ala Ile Asp Tyr Arg Gln Val Ser Glu Asp Val Pro Glu Ile
6065                6070                6075

Ile Gly Gln Phe Ile Arg Pro Phe Asp Leu Glu His Pro Pro Leu
6080                6085                6090

Leu Arg Val Gly Leu Phe Glu Val Gly Gln Asp Arg His Ile Leu
6095                6100                6105

Val Phe Asp Met His His Ile Ile Ser Asp Gly Ala Ser Met Ser
6110                6115                6120

Asn Leu Val Asp Glu Phe Thr Arg Leu Tyr Ala Asn Glu Glu Arg
6125                6130                6135

Pro Pro Leu Arg Ile Gln Tyr Lys Asp Tyr Ala Val Trp Gln Gln
6140                6145                6150

Ala Ser Glu Asn Leu Glu Arg Leu Lys Arg Gln Glu Asp Tyr Trp
6155                6160                6165

Met Ser Met Leu Gln Gly Asp Leu Pro Asn Thr Glu Leu Pro Leu
6170                6175                6180

Asp Tyr Asp Arg Ala Ala Val Arg Ser Phe Glu Gly Glu Gln Ile
6185                6190                6195

Glu Phe Glu Ile Asn Pro Val Val Thr Gly Gln Leu Asn Gln Leu
6200                6205                6210

Ala Ser Asn His Glu Cys Thr Leu Tyr Met Val Leu Leu Ser Ala
6215                6220                6225

Tyr Gln Ile Leu Leu Ser Lys Tyr Cys Gly Gln Asp Asp Ile Ile
6230                6235                6240

Val Gly Thr Pro Val Ala Gly Arg Asn His Ala Asp Leu Glu Pro
6245                6250                6255

Leu Ile Gly Met Phe Val Asn Thr Leu Ala Ile Arg Asn Arg Pro
6260                6265                6270

Gln Gly Asp Lys Thr Phe Gln Ser Phe Leu Ala Glu Val Lys Glu
6275                6280                6285

Ser Thr Leu Gly Ala Phe Glu His Gln Glu Tyr Pro Phe Glu Glu
6290                6295                6300

Leu Ile Asp Leu Leu Lys Leu Gln Trp Glu Thr Ser Arg Asn Pro
6305                6310                6315

Leu Phe Asp Thr Val Phe Val Leu Gln Asn Thr Glu Glu Arg Glu
6320                6325                6330

Ala Gly Ile Gly Gly Leu Thr Ile Ser Pro Tyr Val Thr Asp Asp
6335                6340                6345

Ser Val Ser Ala Lys Phe Asp Leu Thr Leu Ser Val Ser Glu Glu
6350                6355                6360

Asp Asp Gly Met Lys Gly Ser Phe Leu Tyr Ala Ser Lys Leu Phe
6365                6370                6375

Lys Ala Ala Gly Ile His Arg Met Met Arg Asp Tyr Leu Ser Ile
6380                6385                6390

Leu Ser Gln Val Cys Glu Asn Pro Arg Ile Arg Ile Gln Asp Ile
6395                6400                6405

Ser Ile Ser Gly Gln Gln Thr Gln Glu Lys Ser Lys Ile Asp Thr
6410                6415                6420

Ile Glu Phe Ala Phe
```

6425

<210> SEQ ID NO 16
<211> LENGTH: 3167
<212> TYPE: PRT
<213> ORGANISM: Paenibacillus strain TS-15

<400> SEQUENCE: 16

| | | | | | | | | | | | | | | |
|---|---|---|---|---|---|---|---|---|---|---|---|---|---|---|
| Met | Lys | Ser | Val | Tyr | Glu | Lys | Glu | Ala | Tyr | Trp | Asn | Gly | Met | Phe |
| 1 | | | | 5 | | | | | 10 | | | | | 15 |
| Asp | Ser | Asp | Asp | Ser | Met | Ser | Ile | Leu | Pro | Tyr | Cys | Ser | Thr | His | Gly |
| | | | 20 | | | | | 25 | | | | | 30 | | |
| Arg | Glu | Ala | Asn | Ala | Asp | Thr | Asn | Ala | Ala | Lys | Val | Ser | Met | Ile | Arg |
| | | 35 | | | | | 40 | | | | | 45 | | | |
| Ala | Leu | Pro | Ser | Glu | Leu | Ser | Asp | Arg | Met | Asn | Thr | Leu | Ala | Asn | Gly |
| | 50 | | | | | 55 | | | | | 60 | | | | |
| Ser | Asp | Ile | Ala | Leu | Tyr | Met | Ile | Gly | Leu | Ala | Gly | Ala | Thr | Cys | Leu |
| 65 | | | | | 70 | | | | | 75 | | | | | 80 |
| Leu | His | His | Tyr | Thr | Asn | Arg | Glu | Asn | Val | Leu | Val | Gly | Met | Pro | Thr |
| | | | | 85 | | | | | 90 | | | | | 95 | |
| Ile | Asp | Glu | Ser | Asp | Asp | Ser | Ser | Pro | Arg | Asp | Val | Leu | Ile | Met |
| | | | 100 | | | | | 105 | | | | | 110 | | |
| Lys | Thr | Asn | Leu | Thr | Arg | Gly | Ser | Ser | Phe | Arg | Ser | Val | Leu | Gly | Ser |
| | | 115 | | | | | 120 | | | | | 125 | | | |
| Ile | Lys | Thr | Ala | Val | Gly | Gly | Ala | Val | Glu | His | Arg | His | Leu | Pro | Phe |
| | 130 | | | | | 135 | | | | | 140 | | | | |
| Arg | Lys | Met | Val | His | Asn | Leu | Asn | Leu | Glu | Met | Asp | Thr | Asn | Gly | Leu |
| 145 | | | | | 150 | | | | | 155 | | | | | 160 |
| Pro | Val | Met | Asn | Thr | Val | Val | Ser | Tyr | Ser | Ala | Ile | His | Thr | Ala | Ser |
| | | | | 165 | | | | | 170 | | | | | 175 | |
| Ile | Asp | Leu | Ser | Val | Ser | Ser | Asp | Val | Met | Phe | Arg | Phe | Asp | Ala | Lys |
| | | | 180 | | | | | 185 | | | | | 190 | | |
| Asp | Asp | Gly | Leu | His | Leu | Glu | Val | Leu | Tyr | Asp | Glu | Ser | Arg | Tyr | Asp |
| | | 195 | | | | | 200 | | | | | 205 | | | |
| Ala | Ser | Tyr | Ile | Ala | Thr | Leu | Phe | Glu | His | Phe | Arg | Leu | Leu | His |
| | 210 | | | | | 215 | | | | | 220 | | | | |
| Phe | Val | Leu | Phe | Gln | Pro | Asp | Gln | Pro | Ile | Gly | Asn | Ala | Val | Leu | Leu |
| 225 | | | | | 230 | | | | | 235 | | | | | 240 |
| Ser | Glu | Asp | Glu | Lys | His | Arg | Leu | Leu | His | Glu | Phe | Asn | Asp | Val | Trp |
| | | | | 245 | | | | | 250 | | | | | 255 | |
| Thr | Asp | Phe | Pro | Arg | Gln | Ala | Thr | Leu | His | Gln | Phe | Ile | Glu | His |
| | | | 260 | | | | | 265 | | | | | 270 | | |
| Ala | Glu | Arg | Gln | Pro | Glu | Ala | Ile | Ala | Val | Ser | Tyr | Glu | Asp | Thr | Lys |
| | | 275 | | | | | 280 | | | | | 285 | | | |
| Leu | Thr | Tyr | Arg | Glu | Leu | Asn | Ala | Arg | Ala | Asn | Arg | Leu | Ala | Arg | Thr |
| | 290 | | | | | 295 | | | | | 300 | | | | |
| Leu | Arg | Ser | Glu | Gly | Val | Gln | Pro | Glu | Ala | Leu | Val | Gly | Leu | Met | Ala |
| 305 | | | | | 310 | | | | | 315 | | | | | 320 |
| Glu | Arg | Ser | Ile | Asp | Met | Ile | Val | Gly | Met | Leu | Ala | Val | Leu | Lys | Ala |
| | | | | 325 | | | | | 330 | | | | | 335 | |
| Gly | Gly | Gly | Tyr | Val | Ala | Ile | Asp | Pro | Glu | Tyr | Pro | Glu | Glu | Arg | Val |
| | | | 340 | | | | | 345 | | | | | 350 | | |
| Arg | Tyr | Met | Leu | Glu | Asp | Ser | Gly | Ala | Arg | Val | Ile | Leu | Val | Gln | Gln |
| | | 355 | | | | | 360 | | | | | 365 | | | |

```
His Leu Gln Asn Arg Val Pro Asn Thr Glu Ser Ala Ala Arg Leu Leu
    370                 375                 380

Thr Leu Asp Asp Glu Gln Ser Tyr His Glu Asp Ala Ser Lys Leu Glu
385                 390                 395                 400

Ser Lys Ser Thr Ala Val Asp Leu Ala Cys Val Ile Tyr Thr Ser Gly
                405                 410                 415

Thr Thr Gly Asn Pro Lys Gly Asn Leu Thr Thr His Arg Asn Ile Val
            420                 425                 430

Arg Ile Val Lys Asn Thr Asn Tyr Ile Glu Ile Thr Glu Gln Asp Lys
                435                 440                 445

Val Leu Gln Leu Ser Ser Tyr Ser Phe Asp Gly Ser Ala Phe Asp Ile
    450                 455                 460

Phe Gly Ala Leu Thr Asn Gly Ala Gln Leu Val Leu Val Pro His His
465                 470                 475                 480

Thr Leu Leu Asp Ala Ser Lys Leu Ala Glu Leu Ile Glu Thr Glu Gln
                485                 490                 495

Ile Ser Val Met Leu Ile Thr Thr Ala Tyr Phe Asn Val Leu Val Asp
                500                 505                 510

Val Asn Val Ser Cys Leu Arg His Ile Arg Ala Ile Leu Phe Gly Gly
    515                 520                 525

Glu Arg Ser Ser Val Ala His Val Arg Gln Ala Leu Glu Gln Thr Gly
    530                 535                 540

Pro Gly Arg Leu Lys His Ala Tyr Gly Pro Ser Glu Ser Thr Val Tyr
545                 550                 555                 560

Ala Thr Trp His Asp Val Thr Glu Ile Ser Glu Gln Ala Val Ser Val
                565                 570                 575

Pro Ile Gly Arg Pro Ile Ser Asn Thr Ala Ile Tyr Ile Val Asn Glu
                580                 585                 590

Arg Asn Asp Leu Gln Pro Ile Gly Val Ser Gly Glu Leu Cys Val Ala
    595                 600                 605

Gly Glu Gly Leu Val Arg Gly Tyr Leu Asn Arg Pro Glu Leu Thr Ala
    610                 615                 620

Gln Lys Phe Val Asp Asn Pro Phe Val Pro Gly Glu Arg Met Tyr Arg
625                 630                 635                 640

Thr Gly Asp Leu Ala Arg Trp Leu Pro Asp Gly Thr Ile Glu Tyr Val
                645                 650                 655

Gly Arg Met Asp Asp Gln Val Lys Ile Arg Gly His Arg Ile Glu Ile
                660                 665                 670

Gly Glu Val Glu Ala Gln Leu Leu Lys Val Ala Leu Ile Gln Lys Ala
                675                 680                 685

Thr Ile Val Val Arg Gly Arg Glu Asp Gly Glu Lys Gln Leu Cys Ala
    690                 695                 700

Tyr Tyr Val Ala Asp Arg Leu Leu Ser Ala Gly Glu Ile Arg Thr Ile
705                 710                 715                 720

Leu Ala Lys Glu Leu Pro Ser Tyr Met Ile Pro Ala Tyr Phe Ile Gln
                725                 730                 735

Leu Glu Gln Met Pro Leu Thr Thr Asn Gly Lys Val Asp Arg Lys Ala
                740                 745                 750

Leu Pro Ala Pro Glu Glu His Val Gln Ala Glu Thr Glu Tyr Val Ala
                755                 760                 765

Pro Arg Ser Glu Gln Glu Ile Arg Leu Ala Arg Val Trp Gln Glu Val
    770                 775                 780

Leu Gly Leu Ser Arg Val Gly Ala Lys Asp His Phe Phe Glu Leu Gly
```

```
               785                 790                 795                 800
         Gly His Ser Leu Arg Ala Thr Thr Leu Val Ser Lys Leu His Lys Glu
                         805                 810                 815
         Glu Asn Ile Ser Leu Ser Leu Arg Asp Val Phe Arg Asn Pro Thr Leu
                         820                 825                 830
         Glu Ala Met Ala Ala Leu Met Glu Ala Ala Gln Gly Arg Thr Phe Ser
                         835                 840                 845
         Pro Ile Pro Thr Val Glu Glu Lys Asp Val Tyr Pro Val Ser Ser Val
                 850                 855                 860
         Gln Lys Arg Leu Phe Ile Leu His Gln Leu Glu Gly Ala Glu Gln Ser
         865                 870                 875                 880
         Tyr Asn Met Pro Gly Ala Leu Leu Glu Gly Asp Val Asp Arg Asn
                         885                 890                 895
         Arg Leu Glu His Ala Phe Arg Gln Leu Ile Thr Arg His Glu Thr Leu
                         900                 905                 910
         Arg Thr Gly Phe Glu Met Val Asn Gly Glu Pro Val Gln Arg Ile Tyr
                         915                 920                 925
         Pro Thr Val Glu Phe Val Val Glu Met Ser Ala Val Glu Gly Ala
                 930                 935                 940
         Glu Ala Glu Lys Gln Ile Arg Gln Phe Ile Arg Ala Phe Asp Leu Ser
         945                 950                 955                 960
         Thr Pro Pro Leu Phe Arg Ala Gly Leu Ile Glu Leu Ala Pro Gln Arg
                         965                 970                 975
         His Ile Leu Leu Phe Asp Met His His Ile Ile Ser Asp Gly Thr Ser
                         980                 985                 990
         Ile Gly Ile Met Ile Glu Glu Phe Thr Ser Leu Tyr Ser Gly Asn Glu
                         995                 1000                1005
         Leu Glu Pro Leu Arg Ile Gln Tyr Lys Asp Phe Ala Ala Trp Gln
                 1010                1015                1020
         Arg Ser Glu Glu Gln Ile Glu Gln Leu Lys Ser Gln Glu Ala Tyr
                 1025                1030                1035
         Trp Leu Arg Gln Met Glu Gly Val Leu Pro Val Leu Glu Leu Pro
                 1040                1045                1050
         Thr Asp Tyr Val Arg Pro Ala Val Gln Ser His Asp Gly Ala Leu
                 1055                1060                1065
         Phe Glu Phe Ser Ile Asp Arg Glu Gln Ser Gln Asp Leu Arg Asn
                 1070                1075                1080
         Leu Ala Ala Asp Thr Arg Thr Thr Leu Tyr Met Val Leu Leu Ala
                 1085                1090                1095
         Ala Tyr Thr Ile Ile Leu His Lys Tyr Ser Gly Gln Glu Asp Ile
                 1100                1105                1110
         Val Val Gly Thr Pro Ile Ala Gly Arg Thr His Asp Asp Val Gln
                 1115                1120                1125
         Pro Leu Ile Gly Met Phe Val Asn Thr Leu Ala Ile Arg Asn Tyr
                 1130                1135                1140
         Pro Ser Gly Ser Lys Ser Val Leu Thr Tyr Leu Glu Glu Ile Lys
                 1145                1150                1155
         Glu Thr Thr Leu Gly Ala Phe Glu His Gln Asp Tyr Pro Phe Glu
                 1160                1165                1170
         Glu Leu Val Glu Asn Val Gln Ile Ser Arg Asp Met Ser Arg His
                 1175                1180                1185
         Pro Val Phe Asp Thr Met Phe Ala Leu Glu Asn Thr Glu His Arg
                 1190                1195                1200
```

-continued

Glu Phe Asp Leu Asp Gly Leu Gln Val Lys Pro Tyr Gly Ala Glu
1205                1210                1215

His Gly Met Ala Lys Phe Asp Leu Asn Leu Thr Ile Thr Glu Asp
1220                1225                1230

Gly Asp Gly Leu Tyr Cys Thr Met Glu Tyr Ala Thr Ala Leu Tyr
1235                1240                1245

Asn Arg Ser Thr Ile Ala Arg Leu Cys Gly His Phe Leu Gln Val
1250                1255                1260

Val Gly Ser Met Thr His Asn Pro Gln Ala Ala Ile Ser Ser Leu
1265                1270                1275

Gln Met Val Thr Ile Glu Glu Lys Ala Glu Leu Gln Asp Glu Phe
1280                1285                1290

Asn Asp Thr Asp Met Val Tyr Pro Ser Asp Lys Thr Val His Glu
1295                1300                1305

Leu Phe Ala Glu Gln Val Glu Arg Thr Pro Asp Ala Val Ala Val
1310                1315                1320

Val Ser Gly Ser Glu Gln Leu Ser Tyr Gly Asp Leu Asn Arg Lys
1325                1330                1335

Ala Asn Gln Leu Ala Trp Lys Leu Arg Glu Tyr Gly Val Thr Ala
1340                1345                1350

Glu Gln Pro Val Gly Ile Ile Val Glu Arg Thr Leu Asp Thr Val
1355                1360                1365

Val Ala Val Leu Ala Val Leu Lys Ala Ser Gly Thr Phe Val Pro
1370                1375                1380

Ile Asp Pro Glu Tyr Pro Glu Thr Arg Ile Arg Tyr Met Leu Ala
1385                1390                1395

Asp Ser Gly Ala Lys Leu Val Leu Ala Gln Ser Asp Leu Pro Gly
1400                1405                1410

Ile Ile Pro Asp Asp Val Arg Leu Ile Asp Val Arg Asp Glu Ser
1415                1420                1425

Leu Tyr Gln Gly Asp Gly Ala Asp Val Pro Asn Gly Ser Lys Pro
1430                1435                1440

Ser Asn Leu Leu Tyr Ile Ile Tyr Thr Ser Gly Thr Thr Gly Asn
1445                1450                1455

Pro Lys Gly Val Met Leu Glu His Arg Asn Met Val Asn Leu Leu
1460                1465                1470

His Tyr Gln Gln Lys Gly Thr Asn Ile Pro Met Pro Ser Arg Ile
1475                1480                1485

Leu Gln Tyr Ala Ser Gly Ser Phe Asp Val Cys Tyr Gln Glu Met
1490                1495                1500

Phe Ser Ala Leu Leu Phe Gly Gly Ser Leu Tyr Met Val Asp Asn
1505                1510                1515

Glu Met Arg Lys Asp Pro Val Arg Leu Phe Gln Glu Ile Glu Lys
1520                1525                1530

His Glu Ile Asp Val Met Tyr Ile Pro Val Ala Phe Leu Lys Phe
1535                1540                1545

Ile Phe Ala Glu Pro Glu Trp Ala Glu Ala Phe Pro Arg Cys Val
1550                1555                1560

Arg His Ile Ile Thr Ala Gly Glu Gln Leu Val Val Thr Pro Gln
1565                1570                1575

Val Gln Ala Cys Leu Lys Arg Leu Asp Ile Ser Leu His Asn His
1580                1585                1590

```
Tyr Gly Pro Ser Glu Thr His Val Val Thr Tyr Thr Met Met
1595                1600                1605

Pro Asp Val Ile Glu Val Gly Leu Pro Pro Ile Gly Lys Pro Ile
1610                1615                1620

Ala Asn Thr Ser Ile Phe Ile Val Asp Asp Ser Phe Glu Leu Gln
1625                1630                1635

Pro Ile Gly Val Lys Gly Glu Leu Tyr Val Ser Gly Ala Ser Val
1640                1645                1650

Gly Arg Gly Tyr Trp Gly Arg Thr Asp Leu Thr Glu Glu Lys Phe
1655                1660                1665

Leu Asp Asn Pro Phe Ala Pro Gly Glu Arg Leu Tyr Lys Thr Gly
1670                1675                1680

Asp Val Ala Arg Trp Leu Pro Asp Gly Ser Ile Glu Tyr Val Gly
1685                1690                1695

Arg Ser Asp His Gln Val Lys Ile Arg Gly Phe Arg Ile Glu Leu
1700                1705                1710

Gly Glu Val Glu Ser Gln Leu Leu His Val Pro Ala Val Gln Glu
1715                1720                1725

Ala Thr Met Val Ala Leu Glu Asp His Ala Gly Gln Lys Gln Leu
1730                1735                1740

Cys Ala Tyr Phe Thr Ala Glu Cys Ser Leu Thr Ala Gly Glu Leu
1745                1750                1755

Arg Ala Ala Leu Ser Gln Glu Leu Pro Gly Tyr Met Ile Pro Ser
1760                1765                1770

Tyr Phe Val Gln Leu Glu Arg Leu Pro Leu Thr Pro Asn Gly Lys
1775                1780                1785

Ile Asp Arg Arg Ala Leu Pro Lys Pro Glu Gly Gly Ile Glu Thr
1790                1795                1800

Gly Thr Glu Tyr Val Ala Pro Arg Thr Glu Thr Glu Ala Arg Leu
1805                1810                1815

Ala Arg Ile Trp Gln Asp Val Leu Gly Leu Ala Ser Val Gly Val
1820                1825                1830

Lys Asp Asn Phe Phe Glu Leu Gly Gly His Ser Leu Arg Ala Thr
1835                1840                1845

Thr Leu Val Ser Arg Leu Tyr Lys Glu Met Asn Val Asn Phe Pro
1850                1855                1860

Leu Arg Gly Val Phe Arg His Pro Thr Ile Glu Glu Met Ala Lys
1865                1870                1875

Ala Ile Thr Glu Met His Gln Glu Leu Tyr Thr Glu Ile Pro Ile
1880                1885                1890

Ala Glu Glu Lys Ala Tyr Tyr Pro Leu Ser Ser Ala Gln Lys Arg
1895                1900                1905

Leu Phe Ile Val Ser Gln Leu Thr Gly Ala Glu Val Ser Tyr Asn
1910                1915                1920

Met Pro Gly Val Leu Ile Leu Glu Gly Glu Leu Asp Arg Ala Arg
1925                1930                1935

Phe Glu Arg Ala Phe Gln Lys Leu Ile Asp Arg His Glu Ser Leu
1940                1945                1950

Arg Thr Ser Phe Glu Thr Val Arg Gly Glu Pro Val Gln Arg Ile
1955                1960                1965

His Ser Gln Val Glu Phe Ala Ile Glu Tyr His Leu Ala Ala Glu
1970                1975                1980

Lys Asp Ala Glu Ala Leu Ile Thr His Phe Val Arg Pro Phe Gln
```

```
              1985                1990                1995
Leu Asn Gln Ala Pro Leu Leu Arg Val Gly Leu Ile Glu Thr Gly
              2000                2005                2010

His Glu Arg His Ile Leu Met Phe Asp Met His His Ile Ile Ser
              2015                2020                2025

Asp Gly Val Thr Met Gly His Val Val Asn Glu Phe Ser Arg Ile
              2030                2035                2040

Tyr Ala Gly Asp Gln Leu Pro Ala Leu Arg Ile Gln Tyr Lys Asp
              2045                2050                2055

Tyr Ala Ala Trp Gln Gln Ser Asn Glu Tyr Ala Glu Lys Leu Ala
              2060                2065                2070

His Gln Glu Ser Tyr Trp Leu Lys Gln Leu Asp Gly Glu Leu Pro
              2075                2080                2085

Thr Leu Glu Leu Pro Thr Asp Tyr Val Arg Pro Ala Val Gln Gln
              2090                2095                2100

Phe Glu Gly Asp Val Ala Leu Phe Thr Leu Thr Asn Ser Gln Ala
              2105                2110                2115

Glu Gln Leu Gln Arg Leu Ala Ala Asn Tyr Gly Ala Thr Leu Tyr
              2120                2125                2130

Met Val Leu Leu Ala Ala Tyr Thr Val Leu Leu His Lys Tyr Thr
              2135                2140                2145

Gly Gln Asp Asp Ile Ile Val Gly Thr Pro Ile Ala Gly Arg Asn
              2150                2155                2160

His Thr Glu Leu Glu Pro Leu Val Gly Met Phe Val Asn Thr Leu
              2165                2170                2175

Ala Ile Arg Asn Tyr Pro Thr Gly Glu Lys Ser Phe Ala Glu Leu
              2180                2185                2190

Leu Ala Glu Val Lys Asp Thr Ala Leu Ala Ala Phe Glu Asn Gln
              2195                2200                2205

Asp Tyr Pro Phe Glu Thr Leu Val Glu Lys Val His Lys Ser Arg
              2210                2215                2220

Asp Met Ser Arg Asn Pro Val Phe Asp Thr Ile Phe Ser Val Glu
              2225                2230                2235

His Glu Gln Gln Ser Ser Phe His Ile Asp Gly Leu Arg Ile Ser
              2240                2245                2250

Pro Tyr Pro His Ser His Ser Val Ala Lys Phe Asp Leu Thr Phe
              2255                2260                2265

His Ala Glu Gln Asn Glu Glu Gly Ile Leu Cys Gly Leu Gly Tyr
              2270                2275                2280

Ala Thr Ala Leu Tyr Ala Lys Glu Thr Ala Gly Arg Met Gly Glu
              2285                2290                2295

His Phe Val Gln Leu Ile Asp Ala Ile Ala Glu Pro Asn Ala
              2300                2305                2310

Lys Leu Met Ser Leu Asn Met Met Ser Leu Gln Glu Arg Glu Gln
              2315                2320                2325

Val Lys Leu Val Phe Asn Asp Thr Ile Thr Ser Tyr Pro Arg Glu
              2330                2335                2340

Lys Thr Ile Gln His Leu Phe Glu Glu Gln Ala Glu Lys Ser Pro
              2345                2350                2355

Asp Ala Val Ala Ile Gln Phe Gly Glu Glu Arg Leu Thr Tyr Arg
              2360                2365                2370

Glu Leu Asn Glu Arg Ser Asn Arg Leu Ala Arg Thr Leu Arg Gly
              2375                2380                2385
```

Lys Gly Val Lys Ala Gly Arg Phe Val Gly Leu Met Thr Asp Arg
2390                 2395                 2400

Ser Leu Asp Met Ile Val Ala Ile Met Ala Thr Leu Lys Ala Gly
2405                 2410                 2415

Gly Ala Tyr Val Pro Ile Asp Pro Asp Tyr Pro Glu Glu Arg Ile
2420                 2425                 2430

Arg Tyr Met Ile Asp Asp Ser Gly Ala Ser Leu Leu Val Val Gln
2435                 2440                 2445

Arg His Phe Gln Ser Asn His Ile Ala Ala Asp Cys Met Val Val
2450                 2455                 2460

Leu Val Asp Asp Glu Asp Ser Tyr His Ala Asp Gly Thr Asn Leu
2465                 2470                 2475

Glu Gln His Asn Gly Ala Ser Asp Leu Ala Tyr Val Ile Tyr Thr
2480                 2485                 2490

Ser Gly Thr Thr Gly Met Pro Lys Gly Asn Leu Thr Thr His Arg
2495                 2500                 2505

Asn Ile Val Arg Val Val Arg Asp Ala Lys Tyr Ile Glu Ile Asp
2510                 2515                 2520

Gln His Asp Thr Val Leu Gln Leu Ser Ser Tyr Ala Phe Asp Gly
2525                 2530                 2535

Ser Thr Phe Asp Ile Phe Gly Ala Leu Met Asn Gly Ala Lys Leu
2540                 2545                 2550

Val Leu Ile Pro Arg Glu Val Val Leu Asp Ala Gly Arg Leu Ala
2555                 2560                 2565

Asp Thr Ile Glu Ile Glu Lys Ile Ser Val Met Phe Ile Thr Thr
2570                 2575                 2580

Ala Tyr Leu Asn Leu Leu Val Asp Leu Arg Val Asp Ser Leu Arg
2585                 2590                 2595

His Met Arg Ala Ile Leu Phe Gly Gly Glu Arg Ala Ser Val Ser
2600                 2605                 2610

His Val Arg Lys Ala Leu Arg His Leu Gly Pro Gly Lys Leu Lys
2615                 2620                 2625

His Val Tyr Gly Pro Thr Glu Ser Thr Val Phe Ala Thr Ser His
2630                 2635                 2640

Asn Val Asp Glu Val Ala Asp Ser Ala Val Thr Ile Pro Ile Gly
2645                 2650                 2655

Arg Pro Ile Gly Asn Thr Ala Val Tyr Ile Val Gly Glu Gly Asp
2660                 2665                 2670

Val Leu Gln Pro Ile Gly Val Ala Gly Glu Leu Cys Val Ala Gly
2675                 2680                 2685

Asp Gly Val Ala Val Gly Tyr Leu Asn Arg Pro Glu Leu Ser Gly
2690                 2695                 2700

Ala Lys Phe Val Asn Asn Pro Phe Val Pro Gly Asp Arg Met Tyr
2705                 2710                 2715

Arg Thr Gly Asp Leu Ala Arg Trp Leu Ser Asp Gly Thr Ile Glu
2720                 2725                 2730

Tyr Val Gly Arg Ile Asp Asp Gln Val Lys Ile Arg Gly Tyr Arg
2735                 2740                 2745

Ile Glu Leu Gly Glu Val Glu Ala His Leu Leu Asp Leu Glu Ala
2750                 2755                 2760

Ile Gln Glu Ala Val Val Ile Val Arg Glu Glu Ser Asp Gly Gln
2765                 2770                 2775

```
Lys Arg Leu Cys Ala Tyr Tyr Val Ala Gly Arg Pro Ile Thr Ala
2780                2785                2790

Gly Glu Met Arg Ile Ala Leu Ala Gln Glu Leu Pro Gly Tyr Met
2795                2800                2805

Leu Pro Ser Tyr Phe Val Gln Leu Asp Lys Leu Pro Leu Ser Pro
2810                2815                2820

Asn Gly Lys Val Asn Arg Lys Ala Leu Pro Ala Pro Glu Leu His
2825                2830                2835

Val Gln Ala Ala Ser Glu Tyr Val Ala Pro Arg Thr Pro Gln Glu
2840                2845                2850

Val Leu Leu Ala His Ile Trp Arg Glu Val Leu Gly Leu Gly Gln
2855                2860                2865

Val Gly Val Lys Asp Asn Phe Phe Glu Leu Gly Gly His Ser Leu
2870                2875                2880

Ser Leu Met Lys Leu Val Glu Arg Val Tyr Thr Glu Thr Glu Val
2885                2890                2895

Glu Ile Pro Ile His Ser Val Phe Arg Glu Pro Thr Ile Glu Ala
2900                2905                2910

Met Ala Tyr Glu Met Leu Lys Ser Glu Leu Ala Gly Lys Ala Gly
2915                2920                2925

Asn His Phe Met Lys Leu Asn Glu Asn Gly His Ile Pro Val Phe
2930                2935                2940

Cys Phe Pro Pro Gly Leu Gly Tyr Gly Leu Ser Tyr Leu Glu Leu
2945                2950                2955

Ala Lys Gln Leu Asp His His Cys Ile Leu His Gly Ile Asp Phe
2960                2965                2970

Ile Asp Asp Ala Asp Thr Arg Glu Glu Leu Leu Glu Arg Tyr Val
2975                2980                2985

Asp Ala Ile Leu Ala Val Gln Pro Gln Pro Pro Phe Val Leu Leu
2990                2995                3000

Gly Tyr Ser Leu Gly Gly Asn Leu Thr Phe Glu Val Ala Lys Ala
3005                3010                3015

Leu Glu Ser Arg Gly Tyr Pro Val Ser Asp Val Ile Met Ile Asp
3020                3025                3030

Ser Leu Arg Lys Leu Lys Val His Glu Val Asp Glu Phe Asp Gly
3035                3040                3045

Asp Ile Asp Gln Met Ile Asp Gly Val Glu Glu Leu Lys Glu Met
3050                3055                3060

Leu Val His His Pro Leu Leu Arg Asp Gln Val Lys Asn Lys Met
3065                3070                3075

Arg Ala Tyr Trp Ser Tyr Ala Thr Glu Leu Val Asn Ser Asp Ile
3080                3085                3090

Ile Asp Ala Asn Ile His Ala Leu Met Ala Glu Pro Ser Glu Val
3095                3100                3105

Asn Gln Ala Asp Gly Glu Gln Leu Ala Thr Trp Gln Glu Ala Thr
3110                3115                3120

Arg Gly Arg Tyr Val Glu Tyr Asn Leu Arg Gly Val His Glu Asp
3125                3130                3135

Val Leu Gln Pro Pro Phe Leu Glu Ala Asn Ala Asn Val Met Gln
3140                3145                3150

Ala Ile Ile Arg His Ile Leu Glu Gln Thr Met Val Thr His
3155                3160                3165
```

```
<210> SEQ ID NO 17
<211> LENGTH: 6605
<212> TYPE: PRT
<213> ORGANISM: Paenibacillus strain OSY SE

<400> SEQUENCE: 17

Met Glu Met Met His Pro Asn Thr Thr Val Ser Thr Val Ala Gly Thr
1               5                   10                  15

Leu Val Ile Arg Gly Glu Val Asp Ala Ala Val Leu Lys Glu Ser Ile
            20                  25                  30

Cys Gln Val Ile Thr Gln His Asp Ala Phe Arg Ile Arg Ile Met Thr
        35                  40                  45

Gln Asp Asn Gln Pro Ile Gln Arg Leu Glu Pro Glu Ser Ala Ile Thr
    50                  55                  60

Pro Glu Val Asp Tyr Met Glu Trp Asp His Leu Glu Ala Lys Asp
65                  70                  75                  80

Trp Leu Asn Arg Phe Asn Arg Ile Pro Ile Ser Ile Phe Asp Asp Lys
                85                  90                  95

Leu Tyr Asn Phe Thr Val Phe Asn Val Asn Asn Gln Glu Tyr Trp Ile
            100                 105                 110

His Leu Lys Ile Asn His Ile Ile Ala Asp Gly Val Thr Ser His Leu
        115                 120                 125

Ile Gly Asn Lys Ile Met Gln Thr Tyr Met Glu Leu Thr Ser Gly Thr
    130                 135                 140

Phe Ser Ala Asn Asp Lys Lys Asn Ser Tyr Leu Asp Tyr Thr Tyr Ala
145                 150                 155                 160

Glu Gln Glu Tyr Glu Lys Ser Asp Arg Tyr Gln Lys Asp Lys Ala Tyr
                165                 170                 175

Trp Leu Glu Lys Phe Gln Thr Met Pro Glu Thr Thr Gly Ile Lys Pro
            180                 185                 190

Tyr Pro Pro Tyr Ser Ile Ser Thr Glu Ala Lys Arg Ala Tyr Val Ala
        195                 200                 205

Leu Thr Gly Glu Arg Tyr Glu Gln Leu Lys Val Phe Ser Glu Gln Asn
    210                 215                 220

Asn Ile Ser Leu Phe Thr Leu Phe Leu Ala Thr Val Tyr Met Phe Leu
225                 230                 235                 240

Tyr Lys Thr Thr Gly Asn Leu Asp Ile Ala Val Gly Thr Ala Tyr Ala
                245                 250                 255

Asn Arg Thr Ser Arg Lys Glu Lys Glu Met Leu Gly Met Phe Val Ser
            260                 265                 270

Thr Val Ala Thr Arg Leu Ser Leu Asp Pro Asn Gln Asp Leu Ile Ser
        275                 280                 285

Ile Leu His Asn Val Ser Lys Glu Gln Lys Thr Asn Leu Arg His Gln
    290                 295                 300

Lys Tyr Pro Tyr Asn Gln Leu Ile Leu Asp Leu Arg Lys Glu His Lys
305                 310                 315                 320

His Ser Asp Ile Gln Asp Leu Tyr Gly Val Ser Val Asp Tyr Met Pro
                325                 330                 335

Ile Asn Trp Ser Ser Tyr Gly Gln Leu Ser Ile Gln Gln Arg Ser Ser
            340                 345                 350

Phe Cys Gly His Glu Val Asp Leu Ala Val His Val Glu Asp Met
        355                 360                 365

Leu Asp Asp Gln Gln Leu Val Ile Asn Val Asp Tyr Arg Ile Gln Leu
    370                 375                 380
```

```
Phe Glu Glu Arg Glu Ile Thr Arg Ile Ile Glu Gln Met Leu Thr Ile
385                 390                 395                 400

Val Asp Gly Ile Leu His Asn Pro Gln Gln Thr Leu His Glu Leu Thr
            405                 410                 415

Met Leu Asn Asn Glu Glu Ala Arg Lys Ile Leu Thr Gln Phe Asn Asp
        420                 425                 430

Thr Ala Ala Glu Phe Pro Arg Asp Lys Thr Val His Gln Leu Phe Glu
    435                 440                 445

Glu Gln Ala Ala Arg Thr Pro Asn His Val Ala Val Tyr Glu Asp
450                 455                 460

Glu Gln Leu Thr Tyr Arg Glu Leu Asn Glu Arg Ala Asn Arg Leu Ala
465                 470                 475                 480

Arg Thr Leu Arg Ala Glu Gly Val Gln Pro Glu Gln Leu Val Gly Ile
            485                 490                 495

Met Ala Asp Arg Ser Leu Glu Met Ile Val Gly Ile Leu Ala Ile Leu
        500                 505                 510

Lys Ala Gly Gly Ala Tyr Val Pro Ile Asp Pro Glu Tyr Pro Glu Glu
    515                 520                 525

Arg Ile Arg Tyr Met Leu Asp Asp Ser Asn Ala Arg Val Leu Leu Ala
530                 535                 540

Gln Arg His Leu Gln Ala Arg Ile Ala Phe Thr Gly Thr Trp Val Ile
545                 550                 555                 560

Leu Asp Glu Asn Ala Phe Tyr Asp Glu Asp Gly Thr Asn Leu Glu Ser
            565                 570                 575

Asn Asn Asp Pro Ser Asn Leu Ser Tyr Val Ile Tyr Thr Ser Gly Thr
        580                 585                 590

Thr Gly Lys Pro Lys Gly Val Met Ile Glu His Arg Gln Leu Val Ala
    595                 600                 605

Met Ala His Ala Trp Lys Ser Arg Tyr His Leu His Glu Ala Gly Ile
610                 615                 620

Arg Trp Leu Gln Trp Ala Ser Phe Ser Phe Asp Val Phe Ser Gly Asp
625                 630                 635                 640

Met Val Arg Thr Leu Leu Asn Gly Gly Glu Leu Ile Leu Cys Pro Gly
            645                 650                 655

His Ala Arg Ala Asn Pro Glu Ala Ile Cys Glu Leu Ile Arg Lys His
        660                 665                 670

Arg Ile Gln Met Phe Glu Ser Thr Pro Ala Leu Val Val Pro Leu Met
    675                 680                 685

Glu Tyr Ile Tyr Asp Asn Lys Met Asp Ile His Ser Leu Gln Leu Leu
690                 695                 700

Ile Ile Gly Ser Asp Tyr Cys Pro Ala Glu Glu Phe Gln Lys Leu Met
705                 710                 715                 720

Glu Arg Phe Gly Ser Gln Met Arg Ile Leu Asn Ser Tyr Gly Val Thr
            725                 730                 735

Glu Ala Cys Val Asp Ala Ser Tyr Phe Glu Gln Thr Ser Asp Ala
        740                 745                 750

Leu Arg Thr Leu Pro Ile Gly Lys Pro Leu Ala Val Ser Met Met
    755                 760                 765

Val Leu Asp Asp Asn Arg Ser Leu Gln Pro Ile Gly Ile Thr Gly Glu
770                 775                 780

Leu Tyr Ile Gly Gly Ala Cys Val Gly Arg Gly Tyr Leu Asn Arg Pro
785                 790                 795                 800

Asp Leu Thr Ala Glu Lys Phe Val Asp Asn Pro Tyr Ala Pro Ser Glu
```

```
                  805                 810                 815
Met Met Tyr Arg Thr Gly Asp Leu Ala Arg Trp Leu Pro Asp Gly Asn
              820                 825                 830

Ile Glu Tyr Leu Gly Arg Ile Asp His Gln Val Lys Ile Arg Gly Tyr
              835                 840                 845

Arg Ile Glu Ile Gly Glu Ile Glu Ser Gln Leu Leu Lys Ala Glu Ser
850                 855                 860

Val Arg Glu Ser Val Val Ala Arg Glu Asp Gly Ser Gly Gln Lys
865                 870                 875                 880

Val Leu Cys Ala Tyr Tyr Val Ala Asp Arg Glu Leu Thr Val Asn Glu
              885                 890                 895

Leu Arg Gly Lys Met Ala Glu Glu Leu Pro Gly Tyr Met Ile Pro Ser
              900                 905                 910

Tyr Phe Met Gln Leu Gln Met Pro Leu Thr Pro Asn Gly Lys Val
              915                 920                 925

Asp Arg Lys Gly Leu Pro Ala Pro Glu Gly Ser Ala His Thr Gly Thr
              930                 935                 940

Glu Tyr Val Glu Pro Ser Ser Ala Ala Glu Lys Met Leu Ala Ala Val
945                 950                 955                 960

Trp Gln Ala Val Leu Gly Ile Glu Arg Val Gly Ala Ser Glu His Phe
              965                 970                 975

Phe Glu Leu Gly Gly Asp Ser Ile Lys Ser Ile Gln Val Ser Ser Arg
              980                 985                 990

Leu Arg Gln Ala Gly Tyr Lys Met Glu Ile Arg Asp Leu Phe Lys Tyr
              995                 1000                1005

Pro Thr Ile Ala Glu Leu Ser Leu His Ile Gln Pro Ala Gly Arg
              1010                1015                1020

Met Ala Asp Gln Ser Glu Val Val Gly Lys Ala Glu Leu Thr Pro
              1025                1030                1035

Ile Gln Arg Trp Phe Phe Ala Gln Arg Phe Ala Asp Pro His His
              1040                1045                1050

Tyr Asn Gln Ser Ile Met Leu Tyr Arg Lys Glu Gly Phe Asp Glu
              1055                1060                1065

Ala Ala Ile Arg Lys Thr Leu Glu Lys Ile Ala Glu His His Asp
              1070                1075                1080

Ala Leu Arg Met Val Phe Arg Lys Thr Glu Ser Gly Tyr Ala Ala
              1085                1090                1095

Trp Asn Arg Gly Ile Gly Glu Gly Glu Leu Tyr Arg Leu Asn Val
              1100                1105                1110

Ala Asp Phe Arg Asn Glu Ser Ala Cys Gly Pro Leu Ile Ala Ala
              1115                1120                1125

Gln Ala Asn Glu Ile Gln Gly Gly Ile Asp Ile Glu Thr Gly Pro
              1130                1135                1140

Leu Val Arg Ala Gly Leu Phe Gln Cys Ala Asp Gly Asp His Leu
              1145                1150                1155

Leu Leu Val Ile His His Thr Val Ile Asp Gly Val Ser Trp Arg
              1160                1165                1170

Ile Leu Leu Glu Asp Ile Ala Val Gly Tyr Glu Gln Ala Leu Lys
              1175                1180                1185

Gly Glu Glu Val Arg Leu Pro Ser Lys Thr Asp Ala Tyr Arg Thr
              1190                1195                1200

Trp Ser Glu Arg Leu Ala Ser Tyr Ala Asp Ser Gln Thr Val Ile
              1205                1210                1215
```

```
Asn Glu Arg Ala Tyr Trp Gln Arg Ile Thr Gln Thr Glu Met Asn
    1220            1225            1230

Pro Leu Pro Lys Asp Tyr Glu Ala Asp Cys Ser Leu Gln Lys Asp
    1235            1240            1245

Ser Glu Ser Val Ile Val Gln Trp Ser Pro Glu Asp Thr Glu Gln
    1250            1255            1260

Leu Leu Lys His Val His Lys Ala Tyr Asn Thr Glu Met Asn Asp
    1265            1270            1275

Ile Leu Leu Thr Ala Leu Gly Thr Ala Val Gln Arg Trp Ser Gly
    1280            1285            1290

Arg Asp Arg Val Leu Val Asn Leu Glu Gly His Gly Arg Glu Ala
    1295            1300            1305

Ile Ile Ala Asp Ile Asp Ile Ser Arg Thr Val Gly Trp Phe Thr
    1310            1315            1320

Ser Glu Tyr Pro Val Leu Leu Glu Met Glu Gln Ala Lys Gly Leu
    1325            1330            1335

Ser Tyr Arg Ile Lys Lys Val Lys Glu Asp Leu Arg Gln Ile Pro
    1340            1345            1350

Asn Lys Gly Ile Gly Tyr Gly Ile Cys Arg Tyr Met Ser Asp Leu
    1355            1360            1365

Pro Tyr Glu Ala Ser Trp Gly Ala Asn Pro Glu Ile Ser Phe Asn
    1370            1375            1380

Tyr Leu Gly Gln Phe Asp Gln Asp Leu Gln Ser Asn Gly Met Leu
    1385            1390            1395

Met Ser Pro Leu Ser Ser Gly Ser Asn Thr Ser Gly Asn Gln Ala
    1400            1405            1410

Arg Gln Tyr Ala Leu Asp Ile Asn Gly Met Ile Met Asp Gly Ser
    1415            1420            1425

Leu Val Phe Asp Leu Ser Tyr Gly Ser Lys Glu Tyr Arg Arg Glu
    1430            1435            1440

Thr Ile Glu Asp Leu Ala Gly Met Leu Gln Glu Ile Leu Arg Glu
    1445            1450            1455

Ile Ile Ala His Cys Thr Ala Lys Glu Arg Pro Glu Leu Thr Pro
    1460            1465            1470

Ser Asp Val Leu Leu Gln Gly Leu Ser Val Glu Glu Leu Glu Gln
    1475            1480            1485

Ile Val Glu Gln Thr Gln His Ile Gly Asp Ile Glu Asn Met Tyr
    1490            1495            1500

Lys Leu Thr Pro Met Gln Lys Gly Met Trp Phe His Ser Ala Met
    1505            1510            1515

Asp Arg Gln Ala Gly Ala Tyr Phe Glu Gln Thr Arg Phe Thr Leu
    1520            1525            1530

Gln Gly Asp Leu Asp Val Asp Ala Phe Ala Lys Ser Trp Thr Ala
    1535            1540            1545

Leu Ala Ala Arg His Thr Val Leu Arg Thr Asn Phe His Asn Gly
    1550            1555            1560

Trp Lys Gly Glu Pro Leu Gln Ile Val Tyr Arg Asp Lys Arg Ile
    1565            1570            1575

Gly Phe Ala Tyr Glu Asp Val Ser Ala Leu Lys Pro Ala Lys Gln
    1580            1585            1590

Arg Ala His Ile Glu Asn Ala Val Asn Glu Asp Lys Leu Arg Gly
    1595            1600            1605
```

```
Phe Asp Leu Glu Gln Asp Glu Leu Met Arg Val Leu Val Met Arg
1610                1615                1620

Thr Ala Gln Glu Ser Tyr His Val Leu Trp Ser Ser His His Ile
1625                1630                1635

Leu Met Asp Gly Trp Cys Leu Pro Leu Val Ala Lys Glu Val Phe
1640                1645                1650

Asp Thr Tyr Ser Ala Tyr Val Arg His Arg His Leu Glu Lys Thr
1655                1660                1665

Thr Val Pro Ala Tyr Ser Gln Tyr Ile Glu Trp Leu Glu Gln Gln
1670                1675                1680

Asp Glu Glu Ala Ala Ser Ala Tyr Trp Ser Glu Tyr Leu Ala Gly
1685                1690                1695

Tyr Asp Gln His Thr Ala Leu Pro Gln Gly Lys Asp Gln Gly Arg
1700                1705                1710

Ser Glu Ala Tyr Ala Ala Glu His Ile Asp Cys Glu Leu Gly Lys
1715                1720                1725

Asp Leu Ser Val Arg Leu Asn Glu Ala Ala Lys Arg Asn Leu Val
1730                1735                1740

Thr Leu Ser Thr Leu Leu Gln Thr Thr Trp Gly Ile Met Leu Gln
1745                1750                1755

Lys Tyr Asn Gly Thr Gly Asp Val Val Phe Gly Val Val Ser
1760                1765                1770

Gly Arg Pro Ala Asp Met Pro Gly Ile Glu Glu Met Ile Gly Leu
1775                1780                1785

Phe Ile Asn Thr Ile Pro Val Arg Val Thr Ala Asp Ala Gly Glu
1790                1795                1800

Ser Phe Ala Asp Ile Met Cys Arg Leu Gln Glu Gln Ala Leu Ala
1805                1810                1815

Ser Ala Lys His Asp His Tyr Pro Leu Tyr Glu Ile Gln Ala Gln
1820                1825                1830

Ser Ala Gln Lys Gln Glu Leu Ile Asn His Ile Met Val Phe Glu
1835                1840                1845

Asn Tyr Pro Met Glu Glu Gln Ile Glu Gln Leu Glu Ser Leu Asp
1850                1855                1860

Gly Lys Gly Leu Lys Leu Lys Asp Val Met Val Thr Glu Gln Thr
1865                1870                1875

Asn Tyr Asp Phe Asn Leu Val Ile Met Pro Gly Asp Glu Ile Val
1880                1885                1890

Ile Arg Leu Asp Tyr Asn Gly Ile Val Phe Asp Arg Thr Ser Met
1895                1900                1905

Glu Gln Leu Lys Gly His Leu Val Asn Met Leu Glu Gln Ile Ala
1910                1915                1920

Ala Asn Pro Gln Ile Pro Val Gly Glu Leu Glu Leu Ala Thr Ala
1925                1930                1935

Ala Glu Lys Ala Gln Ile Val Asp Val Phe Asn Thr Val Val
1940                1945                1950

Glu Tyr Pro Arg Glu Lys Thr Ile His Gln Leu Phe Glu Glu Arg
1955                1960                1965

Glu Glu Arg Ile Pro Asp Ala Val Ala Val Ile Phe Glu Asp Lys
1970                1975                1980

Arg Leu Thr Tyr Ala Glu Leu Asn Ala Ala Ala Asn Arg Ile Ala
1985                1990                1995

His Leu Leu Arg Asp Arg Gly Val Ala Arg Gly Thr Leu Val Gly
```

-continued

```
              2000                2005                2010
Ile Cys Ala Glu Arg Ser Leu Glu Met Val Val Gly Leu Leu Gly
     2015                2020                2025
Ile Leu Lys Ala Gly Gly Ala Tyr Val Pro Ile Asp Pro Ser Tyr
     2030                2035                2040
Pro Gln Glu Arg Ile Asn Ala Met Leu Glu Asp Thr Ala Ile Ser
     2045                2050                2055
Val Met Leu Thr Gln Ala His Leu Gln Thr Ser Val Pro Asn Ser
     2060                2065                2070
Ile Asp Ser Val Leu Leu Asp Ala Ala Ala Glu Thr Ile Leu Glu
     2075                2080                2085
Gly Ser Trp Pro Asn Leu Thr Asp Thr Ala Ala Thr Ala Asp Asp
     2090                2095                2100
Val Ala Tyr Ile Ile Tyr Thr Ser Gly Ser Thr Gly Ile Pro Lys
     2105                2110                2115
Gly Val Cys Val Thr His Arg Gly Val Val Arg Leu Val Ala Asp
     2120                2125                2130
Ala Asn Tyr Val Asp Ile Ser Ser Lys Asp Val Phe Leu Gln Gly
     2135                2140                2145
Ser Thr Ile Ser Phe Asp Ala Ala Thr Phe Glu Ile Trp Gly Ser
     2150                2155                2160
Leu Leu Asn Gly Ala Ala Leu Ala Val Leu Pro Pro Gly Asn Val
     2165                2170                2175
Ser Leu Thr Glu Trp Thr Arg Ala Ile Gln Gln His Gln Val Thr
     2180                2185                2190
Ile Leu Trp Leu Thr Ala Gly Leu Phe His Val Met Val Asp Asn
     2195                2200                2205
Gln Leu Gln Ala Leu Gln Gly Val Gln Gln Leu Leu Val Gly Gly
     2210                2215                2220
Asp Val Val Ser Lys Thr His Ala Thr Lys Val Leu Glu Arg Tyr
     2225                2230                2235
Asn Gly Ile Arg Leu Ile Asn Gly Tyr Gly Pro Thr Glu Asn Thr
     2240                2245                2250
Thr Phe Thr Cys Cys His Glu Ile Ser Ala Ala Asp Met Glu Arg
     2255                2260                2265
Pro Ser Ile Pro Ile Gly Arg Pro Ile Gly Asn Thr Gln Ala Tyr
     2270                2275                2280
Val Leu Asp Gly Ala Gly Lys Leu Leu Pro Ala Gly Val Ile Gly
     2285                2290                2295
Glu Leu Tyr Thr Gly Gly Asp Gly Leu Ala Gln Gly Tyr Leu Asn
     2300                2305                2310
Arg Pro Glu Leu Thr Ala Glu Lys Phe Val Asp Ser Pro Ile Val
     2315                2320                2325
Pro Ala Thr Arg Leu Tyr Arg Thr Gly Asp Leu Ala Arg Trp Leu
     2330                2335                2340
Pro Asp Gly Thr Ile Glu Tyr Val Gly Arg Ile Asp Asp Gln Val
     2345                2350                2355
Lys Ile Arg Gly Tyr Arg Ile Glu Leu Gly Glu Val Glu Ala His
     2360                2365                2370
Leu Leu Lys Val Glu Pro Val Gln Ser Ala Ala Val Ile Ala Arg
     2375                2380                2385
Lys Asp Glu Ser Gly Gln Asn Met Leu Cys Ala Tyr Tyr Ala Ala
     2390                2395                2400
```

```
Asp Lys Glu Leu Thr Ala Ser Glu Leu Arg Ser Ala Leu Ser Gln
2405                2410                2415

Glu Leu Pro Gly Tyr Met Ile Pro Thr His Phe Val Gln Val Glu
2420                2425                2430

Arg Met Pro Leu Thr Pro Asn Gly Lys Val Asp Arg Lys Ala Leu
2435                2440                2445

Pro Glu Pro Glu Gly Arg Ile Met Thr Gly Ile Glu His Val Ala
2450                2455                2460

Pro Arg Thr Pro Leu Glu Ser Lys Leu Ala His Ile Trp Gln Glu
2465                2470                2475

Val Leu Gly Leu Glu Lys Val Ser Val Lys Asp Ser Phe Phe Glu
2480                2485                2490

Leu Gly Gly His Ser Leu Arg Ala Thr Thr Leu Val Ser Lys Leu
2495                2500                2505

Gln Gln Glu Leu His Val Ser Met Pro Leu Arg Glu Val Phe Arg
2510                2515                2520

Phe Pro Thr Ile Glu Glu Gln Ala Gln Val Ile Gly Gly Met Glu
2525                2530                2535

Gln Glu Glu Tyr Arg Ala Ile Pro Gln Val Gly Glu Arg Glu Cys
2540                2545                2550

Tyr Pro Val Ser Ser Ala Gln Lys Arg Leu Tyr Ile Leu His Gln
2555                2560                2565

Leu Glu Gly Ala Glu Gln Thr Tyr Asn Met Pro Gly Val Met Thr
2570                2575                2580

Leu Ala Gly Pro Leu Asp Arg Glu Arg Leu Glu Thr Ala Phe Arg
2585                2590                2595

Lys Leu Ile Ser Arg His Glu Thr Leu Arg Thr Gly Phe Glu Met
2600                2605                2610

Val Asp Gly Val Pro Val Gln Arg Val Tyr Glu Glu Val Asp Phe
2615                2620                2625

Ala Val Glu Tyr Ala Gln Ala Ser Glu Glu Ala Ala Gly Glu Ala
2630                2635                2640

Val His Ala Phe Ile Arg Ala Phe Asp Leu Gln Lys Pro Pro Leu
2645                2650                2655

Leu Arg Ile Gly Leu Ile Glu Leu Ala Lys Glu Arg His Leu Leu
2660                2665                2670

Met Phe Asp Met His His Ile Ile Ser Asp Gly Ala Ser Ile Gly
2675                2680                2685

Ile Leu Ile Glu Glu Phe Val Arg Leu Tyr Arg Gly Glu Glu Ile
2690                2695                2700

Ser Pro Leu Arg Ile Gln Tyr Lys Asp Tyr Ala Ala Trp Leu Gln
2705                2710                2715

Ser Glu Ala Gln Gln Asp Trp Ser Lys Gln Gln Glu Ala Tyr Trp
2720                2725                2730

Leu Asp Ala Leu Arg Gly Glu Leu Pro Val Leu Glu Leu Pro Thr
2735                2740                2745

Asp Tyr Ala Arg Pro Leu Phe Arg Ser Tyr Glu Gly Ser Thr Phe
2750                2755                2760

Glu Phe Thr Ile Gln Arg Arg Glu Ala Glu Arg Leu Arg Gln Leu
2765                2770                2775

Ala Ala Glu Ser Gly Ala Thr Leu Tyr Met Val Leu Leu Ala Leu
2780                2785                2790
```

Tyr Thr Thr Met Leu His Lys Tyr Thr Gly Gln Glu Asp Ile Ile
2795                  2800                 2805

Val Gly Met Pro Ile Ala Gly Arg Thr His Gly Asp Leu Gln Pro
2810                  2815                 2820

Leu Ile Gly Met Phe Val Asn Thr Leu Ala Ile Arg Ser Tyr Pro
2825                  2830                 2835

Ala Gly Glu Lys Thr Phe Leu Ser Phe Leu Glu Glu Val Lys Asp
2840                  2845                 2850

Thr Thr Met Arg Ala Tyr Glu His Gln Asp Tyr Pro Phe Glu Glu
2855                  2860                 2865

Leu Val Glu Asn Val Arg Val Pro Arg Asp Ala Ser Arg Asn Pro
2870                  2875                 2880

Leu Phe Asp Thr Val Phe Val Leu Gln Asn Thr Glu Gln Gly Thr
2885                  2890                 2895

Phe Asp Ile Asp Gly Leu Gln Leu Leu Pro His Pro Ala Glu His
2900                  2905                 2910

Pro Val Ala Lys Phe Asp Leu Thr Phe His Ile Glu Glu Glu Glu
2915                  2920                 2925

Glu Gly Leu Ala Cys Ser Ile Glu Tyr Ala Thr Ala Leu Phe Gln
2930                  2935                 2940

Arg Glu Thr Val Ala Arg Met Ala Gln His Phe Arg Gln Leu Val
2945                  2950                 2955

Glu Ala Val Thr Gly Glu Pro Val Asp Arg Leu Asp Arg Leu Glu
2960                  2965                 2970

Met Leu Thr Ala Glu Glu Lys Val Gln Leu Val Asp Arg Phe Asn
2975                  2980                 2985

Asp Thr Gly Ala Asp Tyr Pro Arg Glu Lys Thr Ile His Leu Leu
2990                  2995                 3000

Phe Glu Glu Gln Ala Glu Arg Thr Pro Ala Ala Val Ala Val Ile
3005                  3010                 3015

Phe Glu Asn Ala Gln Leu Thr Tyr Arg Glu Leu Asn Glu Arg Ala
3020                  3025                 3030

Asn Arg Leu Ala His Thr Leu Arg Ala Lys Asp Val Gln Thr Asp
3035                  3040                 3045

Ser Leu Val Gly Ile Met Ala Glu Arg Ser Pro Glu Met Ile Val
3050                  3055                 3060

Gly Ile Leu Ala Ile Leu Lys Ala Gly Gly Ala Tyr Val Pro Ile
3065                  3070                 3075

Asp Pro Glu Tyr Pro Glu Glu Arg Ile Arg Tyr Met Leu Asp Asp
3080                  3085                 3090

Ser Gly Ala Gln Val Leu Leu Pro His Asp Leu Arg Asp Lys
3095                  3100                 3105

Val Gly Phe Asp Gly Thr Val Val Met Leu Asp Asp Glu Gln Ser
3110                  3115                 3120

Tyr Val Glu Asp Ser Ser Asn Pro Ala Thr Ala Ser Lys Pro Ser
3125                  3130                 3135

Asp Leu Ala Tyr Val Ile Tyr Thr Ser Gly Thr Thr Gly Lys Pro
3140                  3145                 3150

Lys Gly Thr Leu Ile Glu His Lys Asn Val Val Arg Leu Leu Phe
3155                  3160                 3165

Asn Ser Lys Asn Leu Phe Asp Phe Asn Ser Ala Asp Thr Trp Thr
3170                  3175                 3180

Leu Phe His Ser Phe Cys Phe Asp Phe Ser Val Trp Glu Met Tyr

```
            3185                3190                3195

Gly Ala Leu Leu Tyr Gly Gly Arg Leu Val Val Pro Gln Leu
        3200                3205                3210

Thr Ala Lys Asn Pro Ala Gln Phe Leu Glu Leu Leu His Glu Gln
    3215                3220                3225

Gln Val Thr Ile Leu Asn Gln Thr Pro Thr Tyr Phe Tyr Gln Leu
    3230                3235                3240

Leu Arg Glu Ala Leu Ala Glu Pro Gly Gln Glu Leu Lys Val Arg
    3245                3250                3255

Lys Val Ile Phe Gly Gly Glu Ala Leu Asn Pro Gln Leu Leu Lys
    3260                3265                3270

Asp Trp Lys Thr Lys Tyr Pro His Thr Gln Leu Ile Asn Met Tyr
    3275                3280                3285

Gly Ile Thr Glu Thr Thr Val His Val Thr Tyr Lys Glu Ile Thr
    3290                3295                3300

Gln Val Glu Ile Glu Gln Ala Lys Ser Asn Ile Gly Arg Pro Ile
    3305                3310                3315

Pro Thr Leu Lys Val Tyr Val Leu Asp Ala Asn Arg Gln Cys Val
    3320                3325                3330

Pro Val Gly Val Ala Gly Glu Met Tyr Val Ala Gly Asp Gly Leu
    3335                3340                3345

Ala Arg Gly Tyr Leu His Arg Pro Glu Leu Thr Ala Asp Lys Phe
    3350                3355                3360

Val Asp Ser Pro Phe Glu Ser Gly Gly Arg Met Tyr Arg Thr Gly
    3365                3370                3375

Asp Leu Ala Arg Trp Leu Pro Asp Gly Asn Ile Glu Tyr Leu Gly
    3380                3385                3390

Arg Ile Asp His Gln Val Lys Ile Arg Gly Tyr Arg Ile Glu Leu
    3395                3400                3405

Gly Glu Val Glu Ala Gln Leu Thr Lys Val Asp Pro Val Arg Glu
    3410                3415                3420

Ala Ile Val Ile Ala Arg Glu Asp Gly His Gly Glu Lys Gln Leu
    3425                3430                3435

Cys Ala Tyr Phe Val Ala Ala Arg Glu Leu Thr Val Gly Glu Leu
    3440                3445                3450

Arg Gln Glu Leu Ser His Ala Leu Pro Ala Tyr Met Ile Pro Ala
    3455                3460                3465

Tyr Phe Val Gln Leu Glu Arg Met Pro Leu Thr Pro Asn Gly Lys
    3470                3475                3480

Ile Asp Arg Lys Ala Leu Pro Ala Pro Glu Asp Ser Val Asn Thr
    3485                3490                3495

Gly Thr Glu Tyr Ile Ala Pro Arg Thr Leu Leu Glu Ser Asp Leu
    3500                3505                3510

Thr Arg Ile Trp Gln Asp Val Leu Gly Leu Glu Ser Ile Gly Val
    3515                3520                3525

Lys Asp Asn Phe Phe Glu Leu Gly Gly His Ser Leu Arg Ala Thr
    3530                3535                3540

Thr Leu Val Asn Lys Val His Gln Glu Met Asn Val Asn Leu Pro
    3545                3550                3555

Leu Arg Asp Val Phe Arg Phe Ser Thr Ile Glu Glu Met Ala Cys
    3560                3565                3570

Ala Ile Ala Glu Met Glu Gln Arg Thr Tyr Met Ser Ile Pro Ala
    3575                3580                3585
```

```
Ile Glu Thr Arg Asp Tyr Tyr Pro Val Ser Ser Ala Gln Lys Arg
3590                3595                3600

Leu Tyr Ile Leu His Gln Ile Glu Gly Ala Glu Gln Gly Tyr Asn
3605                3610                3615

Met Pro Gly Val Leu Leu Leu Glu Gly Met Leu Asp Gln Glu Lys
3620                3625                3630

Phe Glu Glu Ala Phe His Gly Ile Val Ala Arg His Glu Thr Leu
3635                3640                3645

Arg Thr Gly Phe Glu Met Val Asn Gly Glu Pro Val Gln Arg Val
3650                3655                3660

Tyr Glu Lys Val Asp Phe Ala Val Glu Tyr Arg Gln Ala Asp Glu
3665                3670                3675

Glu Glu Val Glu Ala Val Arg Asp Phe Val Arg Thr Phe Asp
3680                3685                3690

Leu Glu Lys Pro Pro Leu Leu Arg Ile Gly Leu Leu Glu Leu Ala
3695                3700                3705

Lys Glu Arg His Val Leu Leu Tyr Asp Met His His Ile Ile Ser
3710                3715                3720

Asp Gly Val Ser Met Gly Ile Val Val Glu Glu Phe Val Arg Leu
3725                3730                3735

Tyr Ala Gly Ala Ala Leu Glu Pro Leu Arg Ile Gln Tyr Lys Asp
3740                3745                3750

Tyr Ala Ala Trp Gln Leu Ser Glu Ala Gln Gln Asp Trp Met Lys
3755                3760                3765

Arg Gln Glu Gly Tyr Trp Arg Asp Val Phe Arg Gly Glu Leu Pro
3770                3775                3780

Val Leu Glu Met Pro Thr Asp Tyr Val Arg Pro Ala Val Gln Gln
3785                3790                3795

Tyr Ala Gly Ser Thr Leu Ser Phe Asp Ile Asp Pro Gln Met Ser
3800                3805                3810

Glu Gly Leu Arg Arg Ile Ala Ala Glu Thr Gly Thr Thr Leu Tyr
3815                3820                3825

Met Val Leu Leu Ala Ala Tyr Thr Ile Leu Leu His Lys Tyr Thr
3830                3835                3840

Gly Gln Glu Asp Val Ile Val Gly Thr Pro Ile Ala Gly Arg Thr
3845                3850                3855

His Gly Asp Leu Gln Pro Leu Ile Gly Met Phe Val Asn Thr Leu
3860                3865                3870

Ala Ile Arg Asn Tyr Pro Ala Gly Glu Lys Thr Phe Arg Ser Tyr
3875                3880                3885

Leu Ala Glu Val Lys Glu Thr Thr Leu Gly Ala Tyr Glu His Gln
3890                3895                3900

Asn Tyr Pro Phe Glu Glu Leu Val Asp Lys Leu Gln Val Ala Arg
3905                3910                3915

Asp Leu Ser Arg Asn Pro Leu Phe Asp Thr Met Phe Ala Leu Asn
3920                3925                3930

Asn Thr Glu Pro Glu Thr Phe Pro Leu Glu Gly Leu Arg Leu Thr
3935                3940                3945

Pro Tyr Pro Ser Glu Tyr Thr Ile Ser Lys Phe Asp Leu Ser Leu
3950                3955                3960

Asp Val Ser Glu Lys Asn Asp Arg Leu Glu Cys Ser Leu Glu Tyr
3965                3970                3975
```

```
Ala Thr Ala Leu Tyr Lys Pro Asp Thr Ala Glu Arg Met Ala Gln
3980            3985            3990

His Phe Gln Gln Leu Ile Asp Ser Ile Val Asp Gln Pro Glu Ala
3995            4000            4005

Lys Leu Val Ser Leu Gly Met Leu Thr Glu Glu Glu Lys Ala Gln
4010            4015            4020

Ile Gln His Val Phe Asn Arg Ala Glu Ala Gly His Ser Gln Glu
4025            4030            4035

Lys Thr Val Pro Glu Leu Phe Glu Glu Gln Val Glu Arg Thr Pro
4040            4045            4050

Asp Arg Ile Ala Val Val His Glu Asp Lys Gln Leu Thr Tyr Arg
4055            4060            4065

Glu Leu Asn Glu Arg Ala Asn Arg Leu Ala Arg Thr Leu Arg Ala
4070            4075            4080

Glu Gly Val Glu Pro Glu Gln Leu Val Gly Ile Met Ala Asp Arg
4085            4090            4095

Ser Leu Asp Met Ile Val Gly Ile Met Ala Ile Leu Lys Ser Gly
4100            4105            4110

Gly Ala Tyr Val Pro Ile Asp Pro Lys Tyr Pro Glu Asp Arg Ile
4115            4120            4125

Arg Tyr Met Leu Asp Asp Ser His Ala Gln Val Leu Leu Ala Gln
4130            4135            4140

Arg His Met Gln Ala Ser Val Ala Phe Ala Gly Thr Trp Val Ile
4145            4150            4155

Leu Asp Glu Glu Ala Phe Tyr His Glu Asp Gly Thr Asn Leu Glu
4160            4165            4170

Pro Leu Asn Glu Pro Met His Leu Ser Tyr Val Ile Tyr Thr Ser
4175            4180            4185

Gly Thr Thr Gly Asn Pro Lys Gly Val Met Ile Glu His Arg Gln
4190            4195            4200

Leu Val Ala Ile Ala Asp Ala Trp Lys Arg Glu Tyr Arg Leu Glu
4205            4210            4215

Glu Glu Gly Ile Arg Trp Leu Gln Trp Ala Ser Phe Ser Phe Asp
4220            4225            4230

Val Phe Ser Gly Asp Met Val Arg Thr Leu Leu Tyr Gly Gly Glu
4235            4240            4245

Leu Ile Leu Cys Pro Glu Gln Ala Arg Ala Asn Pro Ala Ala Ile
4250            4255            4260

Ser Glu Leu Ile Arg Lys His Gln Ile Gln Met Phe Glu Ser Thr
4265            4270            4275

Pro Ala Leu Val Ile Pro Phe Met Asp Tyr Val Tyr Asp Asn Asn
4280            4285            4290

Leu Asp Ile Ser Ser Leu Lys Met Leu Ile Val Gly Ser Asp His
4295            4300            4305

Cys Pro Thr Ala Glu Phe Asp Lys Leu Thr Glu Arg Cys Gly Ser
4310            4315            4320

His Met Arg Ile Leu Asn Ser Tyr Gly Val Thr Glu Ala Cys Val
4325            4330            4335

Asp Ala Cys Tyr Tyr Glu Arg Thr Thr Pro Asp Ala Leu Arg Thr
4340            4345            4350

Leu Pro Ile Gly Lys Pro Leu Pro Ala Val Thr Met Tyr Ile Leu
4355            4360            4365

Asp Asp Asn Arg Ser Leu Gln Pro Ile Gly His Thr Gly Glu Leu
```

-continued

|  |  |  |  |  |  |  |  |  |  |
|---|---|---|---|---|---|---|---|---|---|
|  |  | 4370 |  |  | 4375 |  |  | 4380 |  |
| Tyr | Ile 4385 | Gly | Gly | Ala | Gly 4390 | Val | Gly | Arg 4395 | Gly | Tyr | Leu | Asn | Arg | Pro |

Tyr Ile Gly Gly Ala Gly Val Gly Arg Gly Tyr Leu Asn Arg Pro
    4385                4390                4395

Asp Leu Thr Val Glu Lys Phe Val Asp Asn Pro Phe Met Pro Gly
    4400                4405                4410

Ala Arg Met Tyr Arg Thr Gly Asp Leu Ala Arg Trp Leu Pro Asp
    4415                4420                4425

Gly Asn Ile Glu Tyr Ala Gly Arg Ile Asp His Gln Val Lys Ile
    4430                4435                4440

Arg Gly Tyr Arg Ile Glu Ile Gly Glu Val Glu Ser Gln Leu Leu
    4445                4450                4455

Ala Ala Ala Gly Val Arg Glu Ala Ala Val Val Ala Arg Glu Asp
    4460                4465                4470

Gly Ser Gly Gln Lys Val Leu Cys Ala Tyr Phe Val Ala Asp Ser
    4475                4480                4485

Ala Leu Thr Val Gly Glu Leu Arg Ala Ser Met Ala Gln Gln Leu
    4490                4495                4500

Pro Gly Tyr Met Ile Pro Ala His Phe Val Gln Leu Glu Arg Met
    4505                4510                4515

Pro Leu Thr Pro Asn Gly Lys Val Asp Arg Lys Gly Leu Pro Ala
    4520                4525                4530

Pro Glu Gly Asn Ala Tyr Thr Gly Ala Glu His Val Ala Pro Arg
    4535                4540                4545

Thr Glu Ala Glu Lys Thr Leu Ala Ala Val Trp Gln Val Val Leu
    4550                4555                4560

Gly Ala Glu Gln Val Gly Leu Met Asp His Phe Phe Glu Leu Gly
    4565                4570                4575

Gly Asp Ser Ile Lys Ser Ile Gln Val Ser Ser Arg Leu His Gln
    4580                4585                4590

Ala Gly Tyr Lys Leu Glu Ile Arg Asp Leu Phe Lys Tyr Pro Thr
    4595                4600                4605

Ile Ala Glu Leu Ser Pro His Ile Gln Pro Ile Gly Arg Lys Ala
    4610                4615                4620

Asp Gln Gly Ala Val Thr Gly Glu Ala Ala Leu Thr Pro Ile Gln
    4625                4630                4635

His Trp Phe Phe Gly Gln Arg Phe Ala Asp Pro His His Tyr Asn
    4640                4645                4650

Gln Ser Ile Met Leu Tyr Arg Lys Glu Gly Phe Asp Glu Ala Ala
    4655                4660                4665

Ile Arg Lys Thr Leu Glu Lys Ile Ala Glu His His Asp Ala Leu
    4670                4675                4680

Arg Met Val Phe Arg Lys Thr Glu His Gly Tyr Ala Ala Trp Asn
    4685                4690                4695

Arg Gly Ile Gly Glu Gly Glu Leu Tyr Ser Leu Asn Val Ala Asp
    4700                4705                4710

Phe Thr Asp Asp Pro Ala Cys Tyr Arg Ala Ile Glu Ala Lys Ala
    4715                4720                4725

Asn Glu Ile Gln Ser Gly Ile Asn Leu Gln Ala Gly Pro Leu Leu
    4730                4735                4740

Arg Ala Gly Leu Phe Thr Cys Ala His Gly His His Leu Leu Ile
    4745                4750                4755

Val Ile His His Ala Val Thr Asp Gly Val Ser Trp Arg Ile Leu
    4760                4765                4770

-continued

```
Leu Glu Asp Ile Ala Ala Gly Tyr Glu Gln Ala Leu Lys Gly Glu
    4775                4780                4785

Ala Ile Arg Leu Pro Ala Lys Thr Asp Ser Tyr Leu Thr Trp Ser
    4790                4795                4800

Lys Gln Leu Ser Gly Tyr Ala Gln Ser Pro Ala Ile Glu Gln Glu
    4805                4810                4815

Arg Ser Tyr Trp Gln Arg Ile Ala Gln Ser Asn Thr Lys Pro Leu
    4820                4825                4830

Pro Lys Asp Arg Thr Val Asn Val Ser Leu Gln Arg Asp Ser Glu
    4835                4840                4845

Ser Val Ser Val Gln Trp Ser Arg Glu Asp Thr Glu Gln Leu Leu
    4850                4855                4860

Lys His Val His Arg Ala Tyr Asn Thr Asp Met Asn Asp Ile Leu
    4865                4870                4875

Leu Thr Ala Leu Gly Met Ala Ile Gln Gln Trp Ser Gly Arg Asp
    4880                4885                4890

Arg Met Leu Val Asn Leu Glu Gly His Gly Arg Glu Ser Ile Met
    4895                4900                4905

Ala Asp Val Asp Ile Ser Arg Thr Val Gly Trp Phe Thr Ser Glu
    4910                4915                4920

Tyr Pro Val Leu Leu Glu Met Glu Pro Asp Lys Ser Leu Ser His
    4925                4930                4935

Cys Ile Lys Lys Val Lys Glu Asp Leu Arg Gln Ile Pro His Lys
    4940                4945                4950

Gly Ile Gly Tyr Gly Ile Cys Arg Tyr Leu Ser Gly Thr Met Glu
    4955                4960                4965

Asp Ala Ala Trp Gly Thr Ala Pro Glu Ile Ser Phe Asn Tyr Leu
    4970                4975                4980

Gly Gln Phe Asp Gln Asp Leu Asn Ser Asn Gly Met Glu Met Ser
    4985                4990                4995

Pro Tyr Ser Ser Gly Thr Asp Ala Ser Gly Lys Gln Val Arg Gln
    5000                5005                5010

Tyr Ala Leu Asp Ile Asn Gly Gly Ile Thr Asp Gly Ser Leu Ser
    5015                5020                5025

Phe Asp Leu Ser Tyr Ser Arg Lys Glu Tyr Arg Arg Glu Thr Met
    5030                5035                5040

Glu Asp Leu Ala Gly Arg Leu Arg Glu Ser Leu Gln Glu Ile Ile
    5045                5050                5055

Ala His Cys Ala Ala Lys Glu Arg Thr Glu Leu Thr Pro Ser Asp
    5060                5065                5070

Val Leu Leu Gln Gly Leu Ser Val Glu Glu Leu Glu Leu Ile Val
    5075                5080                5085

Glu Gln Thr Arg His Val Gly Glu Ile Glu Asn Ile Tyr Ala Leu
    5090                5095                5100

Thr Pro Met Gln Lys Gly Met Trp Phe His Asn Ala Ile Asp Gln
    5105                5110                5115

Gln Ala Gly Ala Tyr Phe Glu Gln Thr Arg Phe Thr Ile Gln Gly
    5120                5125                5130

Val Leu Asp Val Asp Val Phe Ala Met Ser Leu Asn Val Leu Ala
    5135                5140                5145

Lys Arg His Ala Val Leu Arg Thr Asn Phe Tyr Ser Gly Trp Asn
    5150                5155                5160
```

```
Gly Glu Pro Leu Gln Ile Val Tyr Arg Asp Lys Arg Ile Ala Phe
5165                5170                5175

Val Tyr Glu Asp Leu Arg His Leu Pro Ala Ala Glu Gln Thr Ala
5180                5185                5190

His Ile Glu His Ala Ala Arg Glu Asp Lys Leu Lys Gly Phe Asp
5195                5200                5205

Leu Glu Gln Asp Ala Leu Val Arg Val Ala Leu Met Arg Thr Gly
5210                5215                5220

Ala Ala Ser Cys Arg Val Leu Trp Ser Ser His His Ile Leu Met
5225                5230                5235

Asp Gly Trp Cys Leu Pro Gln Leu Thr Gln Glu Leu Phe Asp Thr
5240                5245                5250

Tyr Ser Ser Tyr Met Lys Gln His His Asp Glu Gln Ala Leu Pro
5255                5260                5265

Ala Tyr Ser Gln Ser Ser Tyr Ser Gln Tyr Ile Glu Trp Leu Glu
5270                5275                5280

Gln Gln Asp Glu Glu Ala Ala Ala Gly Tyr Trp Ser Glu Tyr Leu
5285                5290                5295

Ala Gly Tyr Asp Gln Gln Thr Leu Leu Pro Gln Gly Lys Thr Gln
5300                5305                5310

Gly Arg Asp Glu Ala Tyr Val Leu Glu His Val Val Cys Glu Leu
5315                5320                5325

Gly Lys Thr Leu Thr Gly Arg Met Ser Gln Leu Ala Lys Gln His
5330                5335                5340

Ser Val Thr Leu Asn Thr Leu Leu Gln Ala Ala Trp Gly Ile Ile
5345                5350                5355

Leu Gln Lys Tyr Asn Gly Thr Asp Asp Val Val Phe Gly Gly Val
5360                5365                5370

Val Ser Gly Arg Pro Ala Ala Ile Pro Gly Ile Glu Thr Met Ile
5375                5380                5385

Gly Leu Phe Ile Asn Thr Ile Pro Val Arg Val Ala Cys Ala Ala
5390                5395                5400

Glu Thr Ser Phe Thr Gln Val Met Arg Arg Leu Gln Glu Gln Ala
5405                5410                5415

Leu Asp Ser Gly Arg Tyr Asp Tyr Tyr Pro Leu Tyr Glu Ile Gln
5420                5425                5430

Ala Gln Cys Ala Gln Lys Gln Glu Leu Ile Ser His Ile Met Val
5435                5440                5445

Phe Glu Asn Tyr Pro Val Asp Glu Gln Met Glu Gln Thr Gly Ser
5450                5455                5460

Lys Asp Ser Gly Thr Leu Ser Ile Thr Asp Val Glu Val Ala Glu
5465                5470                5475

Gln Thr Asn Tyr Asp Phe Asn Leu Met Val Val Pro Gly Glu Glu
5480                5485                5490

Leu Val Val Arg Phe Asp Phe Asn Gly Ser Val Phe Asp Arg Thr
5495                5500                5505

Ser Ile Glu Arg Leu Thr Gly His Leu Val His Val Leu Glu Gln
5510                5515                5520

Ile Thr Ala Asn Pro Gln Ile Ser Val Gly Asp Leu Glu Leu Ala
5525                5530                5535

Thr Ala Ala Glu Lys Val Glu Ile Val Asp Val Phe Asn Asp Thr
5540                5545                5550

Ala Ala Asp Tyr Pro Arg Glu Lys Thr Ile His Gln Met Phe Glu
```

|      |      |      |      |      |      |      |      |      |      |      |
|------|------|------|------|------|------|------|------|------|------|------|
|      |      |      | 5555 |      |      | 5560 |      |      | 5565 |      |
| Glu  | Gln  | Val  | Glu  | Arg  | Thr  | Pro  | Asp  | Ala  | Val  | Ala  | Val  | Met  | Phe  | Glu  |
| 5570 |      |      |      |      | 5575 |      |      |      | 5580 |      |
| Gln  | Glu  | Arg  | Leu  | Thr  | Tyr  | Arg  | Glu  | Leu  | Asn  | Cys  | Val  | Asn  | Arg  |
| 5585 |      |      |      |      | 5590 |      |      |      | 5595 |      |
| Leu  | Ala  | Arg  | Thr  | Leu  | Arg  | Thr  | Gln  | Gly  | Val  | Gln  | Pro  | Asp  | Gln  | Arg  |
| 5600 |      |      |      |      | 5605 |      |      |      | 5610 |      |
| Val  | Gly  | Ile  | Met  | Val  | Glu  | Arg  | Ser  | Leu  | Glu  | Met  | Met  | Val  | Gly  | Ile  |
| 5615 |      |      |      |      | 5620 |      |      |      | 5625 |      |
| Met  | Ala  | Ile  | Leu  | Lys  | Ala  | Gly  | Gly  | Ala  | Tyr  | Val  | Pro  | Ile  | Ala  | Pro  |
| 5630 |      |      |      |      | 5635 |      |      |      | 5640 |      |
| Asp  | Tyr  | Pro  | Glu  | Glu  | Arg  | Ile  | His  | Tyr  | Met  | Leu  | Glu  | Asp  | Ser  | Gly  |
| 5645 |      |      |      |      | 5650 |      |      |      | 5655 |      |
| Ala  | Gln  | Val  | Leu  | Leu  | Leu  | Gln  | Gly  | Arg  | Ser  | Gly  | Glu  | Ser  | Val  | Ser  |
| 5660 |      |      |      |      | 5665 |      |      |      | 5670 |      |
| Phe  | Ala  | Gly  | Arg  | Ile  | Val  | Asn  | Leu  | Asp  | Asp  | Glu  | Ser  | Ser  | Tyr  | Ala  |
| 5675 |      |      |      |      | 5680 |      |      |      | 5685 |      |
| Glu  | Asp  | Gly  | Ser  | Asn  | Leu  | Glu  | Trp  | Val  | Asn  | Gln  | Ala  | Ser  | Asp  | Ala  |
| 5690 |      |      |      |      | 5695 |      |      |      | 5700 |      |
| Ala  | Tyr  | Val  | Ile  | Tyr  | Thr  | Ser  | Gly  | Thr  | Thr  | Gly  | Lys  | Pro  | Lys  | Gly  |
| 5705 |      |      |      |      | 5710 |      |      |      | 5715 |      |
| Val  | Leu  | Val  | Glu  | His  | Gly  | Ser  | Val  | Ile  | Asn  | Arg  | Leu  | Leu  | Trp  | Met  |
| 5720 |      |      |      |      | 5725 |      |      |      | 5730 |      |
| Gln  | Lys  | Gln  | Tyr  | Pro  | Ile  | Asn  | Ala  | Asn  | Asp  | Thr  | Ile  | Met  | Gln  | Lys  |
| 5735 |      |      |      |      | 5740 |      |      |      | 5745 |      |
| Thr  | Ala  | Ile  | Thr  | Phe  | Asp  | Val  | Ser  | Val  | Trp  | Glu  | Leu  | Phe  | Trp  | Trp  |
| 5750 |      |      |      |      | 5755 |      |      |      | 5760 |      |
| Ala  | Phe  | Val  | Gly  | Ser  | Lys  | Val  | Cys  | Leu  | Leu  | Pro  | Val  | Gly  | Gly  | Glu  |
| 5765 |      |      |      |      | 5770 |      |      |      | 5775 |      |
| Lys  | Asn  | Pro  | Ala  | Val  | Ile  | Leu  | Asp  | Thr  | Ile  | Ala  | Gln  | Gln  | His  | Ile  |
| 5780 |      |      |      |      | 5785 |      |      |      | 5790 |      |
| Ser  | Thr  | Met  | His  | Phe  | Val  | Pro  | Ser  | Met  | Leu  | His  | Ala  | Phe  | Leu  | Glu  |
| 5795 |      |      |      |      | 5800 |      |      |      | 5805 |      |
| Tyr  | Val  | Glu  | Glu  | Gln  | Pro  | Ile  | Ala  | Glu  | Arg  | Glu  | Arg  | Ser  | Leu  | Ala  |
| 5810 |      |      |      |      | 5815 |      |      |      | 5820 |      |
| Ala  | Leu  | Ser  | Arg  | Val  | Phe  | Ala  | Ser  | Gly  | Glu  | Ala  | Leu  | Thr  | Leu  | Ser  |
| 5825 |      |      |      |      | 5830 |      |      |      | 5835 |      |
| Gln  | Val  | Glu  | Arg  | Phe  | Glu  | Arg  | Cys  | Ile  | Ala  | Pro  | Ala  | Ser  | Gly  | Ala  |
| 5840 |      |      |      |      | 5845 |      |      |      | 5850 |      |
| Arg  | Leu  | Ile  | Asn  | Leu  | Tyr  | Gly  | Pro  | Thr  | Glu  | Ala  | Thr  | Val  | Asp  | Val  |
| 5855 |      |      |      |      | 5860 |      |      |      | 5865 |      |
| Thr  | Tyr  | Tyr  | Asp  | Cys  | Glu  | Ala  | Gly  | Gln  | Pro  | Tyr  | Thr  | Ser  | Val  | Pro  |
| 5870 |      |      |      |      | 5875 |      |      |      | 5880 |      |
| Ile  | Gly  | Lys  | Pro  | Ile  | Asp  | Asn  | Thr  | Gln  | Ile  | Tyr  | Ile  | Val  | Asn  | Arg  |
| 5885 |      |      |      |      | 5890 |      |      |      | 5895 |      |
| Gln  | Asp  | Gln  | Leu  | Gln  | Pro  | Ile  | Gly  | Val  | Ala  | Gly  | Glu  | Leu  | Cys  | Ile  |
| 5900 |      |      |      |      | 5905 |      |      |      | 5910 |      |
| Ala  | Gly  | Val  | Gly  | Leu  | Ala  | Arg  | Gly  | Tyr  | Leu  | Lys  | Arg  | Pro  | Glu  | Leu  |
| 5915 |      |      |      |      | 5920 |      |      |      | 5925 |      |
| Thr  | Ala  | Glu  | Lys  | Phe  | Val  | Thr  | Ile  | Pro  | Phe  | Met  | Pro  | Gly  | Ala  | Arg  |
| 5930 |      |      |      |      | 5935 |      |      |      | 5940 |      |
| Met  | Tyr  | Arg  | Thr  | Gly  | Asp  | Leu  | Ala  | Arg  | Trp  | Leu  | Pro  | Asp  | Gly  | Ser  |
| 5945 |      |      |      |      | 5950 |      |      |      | 5955 |      |

-continued

```
Ile Glu Tyr Leu Gly Arg Ile Asp His Gln Val Lys Ile Arg Gly
5960                5965                5970

Tyr Arg Ile Glu Leu Gly Glu Ile Glu Ala Gln Leu Leu Gln Val
    5975                5980                5985

Glu Phe Ile Arg Glu Ala Val Val Val Ala Arg Glu Asp Glu Ser
    5990                5995                6000

Gly Gln Lys Ala Leu Cys Ala Tyr Phe Ala Ala Asp Ser Glu Leu
    6005                6010                6015

Pro Val Ser Glu Leu Arg Ser Ala Leu Ala Val Glu Leu Pro Gly
    6020                6025                6030

Tyr Met Ile Pro Ser Tyr Phe Val Gln Leu Glu Arg Leu Pro Leu
    6035                6040                6045

Ser Ala Asn Gly Lys Leu Asp Arg Lys Ala Leu Pro Ala Pro Gly
    6050                6055                6060

Gly Ser Met Arg Ser Gly Lys Glu His Val Ala Pro Arg Ser Leu
    6065                6070                6075

Leu Glu Val Lys Leu Val Arg Ile Trp Gln Glu Val Leu Gly Leu
    6080                6085                6090

Ala His Val Ser Val Lys Asp Asp Phe Phe Glu Leu Gly Gly His
    6095                6100                6105

Ser Leu Arg Ala Thr Thr Leu Val Ser Lys Leu His Lys Glu Leu
    6110                6115                6120

Asn Ile Asn Leu Pro Leu Arg Asp Val Phe Arg Tyr Ser Ile Leu
    6125                6130                6135

Glu Asp Met Ala Leu Ala Ile Gly Arg Thr Glu Gln Arg Glu Phe
    6140                6145                6150

Gln Thr Ile Pro Gln Val Glu Ala Ser Asp Tyr Tyr Pro Leu Ser
    6155                6160                6165

Ser Ala Gln Lys Arg Leu Tyr Ile Val Gln Gln Val Glu Gly Ala
    6170                6175                6180

Glu Gln Ser Tyr Asn Met Pro Gly Ala Met Ser Ile Arg Gly Gln
    6185                6190                6195

Leu Asp Arg Asn Gln Phe Glu Ala Ala Phe Arg Gly Leu Ile Ala
    6200                6205                6210

Arg His Glu Val Phe Arg Thr Ser Phe Glu Met Val Gly Gly Glu
    6215                6220                6225

Pro Met Gln Arg Val His Gln Asp Thr Ala Phe Ala Val Glu Tyr
    6230                6235                6240

Met Gln Ala Asn Glu Glu Glu Ala Glu Ala Ile Ala His Gln Phe
    6245                6250                6255

Val Arg Thr Phe Asp Leu Glu Gln Pro Ser Leu Leu Arg Val Gly
    6260                6265                6270

Leu Ile Glu Leu Asp Arg Glu His His Ile Met Leu Phe Asp Met
    6275                6280                6285

His His Ile Ile Ser Asp Gly Val Ser Met Gly Ile Leu Val Glu
    6290                6295                6300

Glu Phe Ala Arg Leu Tyr Ser Gly Glu Glu Leu Pro Pro Leu Arg
    6305                6310                6315

Ile Gln Tyr Lys Asp Tyr Ala Ala Trp Gln Gln Ser Glu Ala Gln
    6320                6325                6330

Ser Glu Arg Ile Lys Gln Gln Glu Ala Tyr Trp Leu Asp Ala Leu
    6335                6340                6345
```

-continued

Asp Gly Glu Leu Pro Gln Leu Glu Leu Pro Thr Asp Phe Ala Arg
6350                6355                6360

Pro Ala His Gln Ser His Glu Gly Asp Thr Leu Asp Phe Val Ile
6365                6370                6375

Asp Ser His Met Ser Gly Gly Leu Gln Arg Leu Ala Glu His Thr
6380                6385                6390

Gly Thr Thr Leu Tyr Met Val Leu Leu Ala Ala Tyr Thr Ile Leu
6395                6400                6405

Leu His Lys Tyr Ser Asp Gln Glu Asp Ile Ile Val Gly Thr Pro
6410                6415                6420

Ile Ala Gly Arg Thr His Ala Asp Val Glu Pro Leu Ile Gly Met
6425                6430                6435

Phe Val Asn Ser Leu Ala Leu Arg Ser Tyr Pro Cys Gly Glu Lys
6440                6445                6450

Ser Phe Leu Ser Tyr Leu Glu Glu Val Lys Glu Met Thr Leu Ala
6455                6460                6465

Ala Tyr Glu Asn Gln Asp Tyr Pro Phe Ala Glu Leu Val Glu His
6470                6475                6480

Val Gln Ala Val Trp Ser Pro Ser Arg Asn Pro Leu Phe Asp Thr
6485                6490                6495

Met Phe Val Leu Gln Asn Thr Glu Asp Arg Asn Val Arg Phe Gly
6500                6505                6510

Glu Leu Thr Ile Glu Pro Tyr Thr Gln His His Asn Val Ala Lys
6515                6520                6525

Phe Asp Leu Thr Leu Glu Ile Ala Leu Glu Asp Gly Val Met Ser
6530                6535                6540

Gly His Phe Glu Tyr Cys Thr Arg Leu Phe Thr Thr Asn Met Val
6545                6550                6555

Asp Asn Phe Ala Glu Asp Leu Leu Ser Ile Leu Ala Gln Ile Cys
6560                6565                6570

Glu Gln Pro Ala Ile Arg Leu Gly Asp Ile His Leu His Gly Asn
6575                6580                6585

Ala Glu Glu Asp Glu Glu Ala Ser Leu Ala Glu Glu Ile Asp Phe
6590                6595                6600

Val Phe
6605

<210> SEQ ID NO 18
<211> LENGTH: 6416
<212> TYPE: PRT
<213> ORGANISM: Paenibacillus strain OSY SE

<400> SEQUENCE: 18

Met Asn Leu Ala Phe Glu Lys Glu Thr Asp Phe Trp Asn Ala Gln Phe
1               5                   10                  15

Asp Ala Glu Asp Ser Pro Ala Ile Leu Pro Tyr Ser Thr Ala Ser Ile
            20                  25                  30

Ser Val Thr Ala Arg Asp His Ser Asn Ser Ile Ser Leu Ser Ala Asp
        35                  40                  45

Val Ser Gln Arg Ile Ser His Met Ser Arg Gly Ser His Leu Ala Glu
50 55 60

Tyr Met Ile Leu Leu Ala Gly Ile Gln Cys Leu Leu Tyr Lys Tyr Thr
65 70 75 80

Gly Glu Glu Ser Val Ile Val Gly Met Pro Ile Val Arg Lys Ser Lys
85 90 95

Asp Thr Arg Arg Pro Ile Asn Asn Val Val Ile Leu Lys Asn Lys Leu
            100                 105                 110

Gly Ala Asn Arg Thr Phe Lys Ser Leu Leu Thr Glu Leu Lys Thr Thr
            115                 120                 125

Leu Thr Ala Ala Ile Asn His Gln Asn Ile Pro Phe Arg Lys Met Thr
130                 135                 140

Glu His Leu His Leu Glu Ala Val Asn Gly Val Pro Val Val Asn Thr
145                 150                 155                 160

Met Val Ser Met Lys Glu Ile His Thr Ile Glu Phe Ser Gln Ser Val
                165                 170                 175

Val Ser Asp Ile Leu Phe Gln Phe Glu Trp Glu Gln Asp Val Ile Ser
            180                 185                 190

Leu His Val Thr Tyr Asn Glu Asn Arg Tyr Asp Lys Pro Phe Ile Thr
        195                 200                 205

Gln Ile Met Asn His Val Asn Ser Leu Phe Ala Asp Val Leu Tyr Thr
    210                 215                 220

Pro Glu Arg Val Leu Gln Asp Val Asn Leu Leu Ser Glu Gln Glu Thr
225                 230                 235                 240

Ala Gln Leu Leu Tyr Glu Phe Asn Asp Thr Ala Ala Asp Tyr Pro Arg
                245                 250                 255

Asp Lys Thr Ile His Gln Leu Phe Glu Glu Gln Glu Gln Thr Pro
            260                 265                 270

Asp Ala Val Ala Val Leu Phe Glu Asp Lys Gln Leu Thr Tyr Ala Glu
            275                 280                 285

Leu Asn Ala Ala Ala Asn Arg Ile Ala His Leu Leu Arg Glu Arg Gly
        290                 295                 300

Val Ala Arg Gly Thr Leu Val Gly Ile Cys Val Glu Arg Ser Leu Glu
305                 310                 315                 320

Met Val Ile Gly Leu Leu Gly Ile Leu Lys Ala Gly Ala Tyr Val
                325                 330                 335

Pro Ile Asp Pro Asp Tyr Pro Glu Glu Arg Thr Asn Ala Met Leu Glu
            340                 345                 350

Asp Thr Ala Ile Ser Val Leu Leu Thr Gln Ala His Leu Gln Thr Ser
            355                 360                 365

Met Pro Asn Ser Ile Asp Ser Val Leu Leu Asp Ala Ala Ala Glu Thr
        370                 375                 380

Ala Leu Glu Gly Ser Trp Pro Asn Leu Thr Asp Ala Ala Gly Thr Ala
385                 390                 395                 400

Asp Asp Val Ala Tyr Ile Ile Tyr Thr Ser Gly Ser Thr Gly Ile Pro
                405                 410                 415

Lys Gly Val Cys Val Thr His Arg Gly Val Val Arg Leu Ile Ala Ala
            420                 425                 430

Ala Asn Tyr Val Asp Ile Ser Ser Lys Asp Val Phe Leu Gln Gly Ser
        435                 440                 445

Thr Ile Ser Phe Asp Ala Ala Thr Phe Glu Ile Trp Gly Ser Leu Leu
    450                 455                 460

Asn Gly Ala Ala Leu Ala Ile Leu Pro Pro Gly Asn Val Ser Leu Thr
465                 470                 475                 480

Glu Trp Thr Glu Ala Ile Gln Gln His Gln Val Thr Ile Leu Trp Leu
                485                 490                 495

Thr Ala Gly Leu Phe His Val Met Val Glu Asn Gln Leu Gln Ala Leu
            500                 505                 510

```
Gln Gly Val Gln Gln Leu Leu Val Gly Gly Asp Val Ser Lys Thr
            515                 520                 525
His Ala Lys Lys Val Leu Glu Arg Tyr Gln Asp Ile Arg Leu Val Asn
530                 535                 540
Gly Tyr Gly Pro Thr Glu Asn Thr Thr Phe Thr Cys Cys His Glu Ile
545                 550                 555                 560
Ser Ala Ala Asp Thr Glu Arg Leu Ser Ile Pro Ile Gly Arg Pro Ile
                565                 570                 575
Ala Asn Thr Gln Val Tyr Val Leu Asp Glu Ala Gly Lys Leu Leu Pro
            580                 585                 590
Val Gly Val Val Gly Glu Leu Tyr Thr Gly Gly Asp Gly Leu Ala Arg
            595                 600                 605
Gly Tyr Trp Asn Arg Pro Glu Leu Thr Ala Glu Lys Phe Val Asp Ser
            610                 615                 620
Pro Phe Val Pro Gly Thr Arg Leu Tyr Arg Thr Gly Asp Leu Ala Arg
625                 630                 635                 640
Trp Leu Pro Asp Gly Thr Ile Glu Tyr Val Gly Arg Ile Asp Asp Gln
                645                 650                 655
Val Lys Ile Ser Gly Tyr Arg Ile Glu Leu Gly Glu Val Glu Ala His
            660                 665                 670
Leu Leu Lys Val Glu Ser Val Leu Asp Ala Ile Val Ile Ala Arg Gln
            675                 680                 685
Asp Glu Ser Gly Gln Lys Thr Leu Cys Ala Tyr Phe Thr Ala Asn Ala
    690                 695                 700
Glu Leu Met Ala Gly Asp Leu Arg Ala Val Leu Ser Gln Glu Leu Pro
705                 710                 715                 720
Ala Tyr Met Ile Pro Thr His Phe Val Gln Val Asp Arg Met Pro Leu
                725                 730                 735
Thr Pro Asn Gly Lys Val Asp Arg Arg Ala Leu Pro Glu Pro Glu Gly
            740                 745                 750
Leu Ile Met Thr Gly Lys Glu His Val Ala Pro Arg Thr Pro Leu Glu
            755                 760                 765
Ser Asn Leu Ala His Leu Trp Gln Glu Val Leu Gly Leu Glu Lys Val
770                 775                 780
Ser Val Lys Asp Ser Phe Phe Glu Ile Gly Gly His Ser Leu Arg Ala
785                 790                 795                 800
Thr Thr Leu Ala Ser Lys Leu His Lys Glu Leu His Val Ser Leu Pro
                805                 810                 815
Leu Arg Asp Ile Phe Arg His Pro Thr Ile Glu Glu Leu Ala Cys Leu
            820                 825                 830
Ile Asp Gly Met Glu Arg Gln Glu Tyr Arg Gln Ile Pro Leu Leu Asp
            835                 840                 845
Glu Arg Asp Trp Tyr Pro Val Ser Ser Ala Gln Lys Arg Leu Tyr Ile
850                 855                 860
Leu His Gln Leu Glu Gly Ala Glu Gln Ser Tyr Asn Met Pro Gly Val
865                 870                 875                 880
Met Leu Leu Glu Gly Gln Leu Asp Arg Asn Arg Phe Glu Glu Ala Phe
                885                 890                 895
Arg Ser Leu Ile Gly Arg His Glu Thr Leu Arg Thr Gly Phe Glu Met
            900                 905                 910
Val Asn Gly Glu Pro Val Gln Arg Ile Cys Arg Glu Val Asn Phe Ser
            915                 920                 925
Val Glu Met Met Gln Ala Ser Glu Gly Glu Ala Asp Ala Ala Ile Arg
```

```
                930            935            940
Ser Phe Ile Arg Pro Phe Asp Leu Glu Lys Pro Pro Leu Arg Val
945                 950            955            960
Gly Leu Ile Glu Leu Ser Gln Asp Arg His Ile Leu Met Tyr Asp Met
            965            970            975
His His Ile Ile Ser Asp Gly Val Ser Met Glu Ile Val Glu Glu
        980            985            990
Phe Val Arg Leu Tyr Gly Gly Glu Lys Leu Pro Pro Leu Arg Ile Gln
        995            1000           1005
Tyr Lys Asp Tyr Ala Ala Trp Gln Gln Ser Glu Pro Gln Gln Glu
    1010            1015           1020
Leu Met Lys Gln Gln Glu Ser Tyr Trp Leu Gln Ala Phe Gly Gly
    1025            1030           1035
Glu Leu Pro Val Leu Glu Met Pro Ala Asp Tyr Ala Arg Pro Ser
    1040            1045           1050
Val Gln Ser Tyr Glu Gly Asp Thr Phe Glu Phe Ala Ile Asp Pro
    1055            1060           1065
Gly Leu Ser Glu Ala Leu Arg Arg Ile Ala Ala Glu Ser Gly Thr
    1070            1075           1080
Thr Leu Tyr Met Val Leu Leu Ala Ala Tyr Thr Ile Leu Leu Gln
    1085            1090           1095
Lys Tyr Thr Gly Gln Glu Asp Ile Ile Val Gly Thr Pro Asn Ala
    1100            1105           1110
Gly Arg Thr His Gly Asp Leu Gln Pro Leu Ile Gly Met Phe Val
    1115            1120           1125
Asn Thr Leu Ala Ile Arg Asn Tyr Pro Ala Gly Ser Lys Thr Phe
    1130            1135           1140
Leu Glu Tyr Leu Glu Gln Val Lys Glu Thr Ser Leu Gly Ala Phe
    1145            1150           1155
Glu Asn Gln Asp Tyr Pro Phe Glu Glu Leu Val Glu Lys Leu Gln
    1160            1165           1170
Val Ala Arg Asp Leu Ser Arg Asn Pro Leu Phe Asp Thr Met Phe
    1175            1180           1185
Ser Leu His Asn Met Asp Ser Lys Asp Leu Glu Leu Ala Glu Leu
    1190            1195           1200
Arg Leu Lys Pro Tyr Pro Ala Glu Tyr Lys Val Ala Lys Phe Asp
    1205            1210           1215
Leu Ser Leu Asp Val Ala Glu Gly Ala Glu Gly Met Ala Cys Ser
    1220            1225           1230
Leu Glu Tyr Ala Thr Ala Leu Tyr Arg Arg Glu Ser Ile Glu Arg
    1235            1240           1245
Met Ala Lys His Phe Gly Gln Leu Leu Glu Ala Ile Thr Gln Glu
    1250            1255           1260
Pro Glu Ala Arg Leu Ser Ser Leu Gly Met Leu Thr Glu Glu Glu
    1265            1270           1275
Lys Ala Gln Ile Gln His Val Phe Asn Asp Ala Glu Ala Gly Arg
    1280            1285           1290
Ser Gln Gln Lys Thr Val Pro Glu Leu Phe Glu Glu Gln Val Glu
    1295            1300           1305
Arg Thr Pro Asp Arg Ile Ala Val Val His Glu Asp Lys Gln Leu
    1310            1315           1320
Thr Tyr Arg Glu Leu Asn Glu Arg Ala Asn Arg Leu Ala Arg Thr
    1325            1330           1335
```

```
Leu Arg Ala Glu Asp Val Lys Pro Gln Leu Val Gly Ile Met
    1340            1345                1350

Ala Asp Arg Ser Leu Asp Met Ile Val Gly Ile Met Ala Ile Leu
    1355                1360                1365

Lys Ser Gly Gly Ala Tyr Val Pro Ile Asp Pro Lys Tyr Pro Glu
    1370                1375                1380

Asp Arg Ile His Tyr Met Leu Asp Asp Ser Asn Ala Gln Val Leu
    1385                1390                1395

Leu Ala Gln Arg His Leu Gln Ala Arg Ala Ala Phe Ser Gly Arg
    1400                1405                1410

Arg Ile Thr Leu Asp Glu Glu Ala Phe Tyr Asp Glu Asp Gly Ser
    1415                1420                1425

Asn Leu Glu Arg Val Asn Gln Pro Glu His Leu Ser Tyr Val Ile
    1430                1435                1440

Tyr Thr Ser Gly Thr Thr Gly Lys Pro Lys Gly Val Met Ile Glu
    1445                1450                1455

His Arg Gln Met Ala Val Leu Ser Ala Ala Trp Glu Ser Glu Tyr
    1460                1465                1470

Gly Leu Arg Glu Glu Ser Met Arg Trp Met Gln Trp Ala Ser Phe
    1475                1480                1485

Ser Phe Asp Val Phe Ser Gly Asp Leu Ile Arg Ala Leu Leu His
    1490                1495                1500

Gly Gly Glu Leu Ile Leu Cys Pro Glu Glu Ser Arg Ala Asn Pro
    1505                1510                1515

Ala Glu Ile Tyr Glu Leu Ile Arg Lys His Arg Ile Gln Met Phe
    1520                1525                1530

Asp Val Thr Pro Ser Leu Ala Ile Pro Leu Met Glu Tyr Val Tyr
    1535                1540                1545

Glu Asn Lys Leu Asp Ile Ser Ser Met Lys Leu Ala Val Val Gly
    1550                1555                1560

Ala Asp His Cys Pro Lys Glu Glu Phe Gln Lys Leu Leu Glu Arg
    1565                1570                1575

Phe Gly Ser Gln Met Arg Ile Val Asn Ser Tyr Gly Val Thr Glu
    1580                1585                1590

Thr Thr Ile Asp Ser Cys Tyr Phe Glu Gln Ala Ser Thr Glu Gly
    1595                1600                1605

Leu Arg Thr Val Pro Ile Gly Lys Pro Leu Pro Gly Val Thr Met
    1610                1615                1620

Tyr Ile Leu Asp Asp His His Ser Leu Leu Pro Val Gly Ile Thr
    1625                1630                1635

Gly Glu Leu Tyr Ile Gly Gly Pro Cys Val Gly Arg Gly Tyr Trp
    1640                1645                1650

Lys Arg Pro Asp Leu Thr Ala Glu Lys Phe Val Asp Asn Pro Phe
    1655                1660                1665

Ala Pro Gly Glu Arg Met Tyr Arg Thr Gly Asp Leu Ala Arg Trp
    1670                1675                1680

Leu Pro Asp Gly Asn Val Glu Tyr Leu Gly Arg Ile Asp His Gln
    1685                1690                1695

Val Lys Ile Arg Gly Tyr Arg Ile Glu Ile Gly Glu Val Glu Ser
    1700                1705                1710

Gln Leu Leu Lys Thr Pro Phe Ile Arg Glu Ala Val Val Val Ala
    1715                1720                1725
```

Arg Glu Asp Ala Gly Gly Gln Lys Ser Leu Cys Ala Tyr Phe Val
1730                1735                1740

Ala Glu Arg Glu Leu Thr Val Ser Glu Leu Arg Gly Ala Leu Ala
1745                1750                1755

Ala Glu Leu Pro Gly Tyr Met Ile Pro Ser Tyr Phe Val Gln Leu
1760                1765                1770

Lys Gln Leu Pro Leu Thr Pro Asn Gly Lys Ile Asp Arg Lys Ala
1775                1780                1785

Leu Pro Ala Pro Glu Gly Ser Ala His Thr Gly Thr Asp Tyr Val
1790                1795                1800

Ala Pro Arg Thr Glu Ala Glu Lys Thr Leu Ala Ala Val Trp Gln
1805                1810                1815

Ala Val Leu Gly Ala Glu Arg Val Gly Leu Met Asp His Phe Phe
1820                1825                1830

Glu Leu Gly Gly Asp Ser Ile Lys Ser Ile Gln Val Ser Ser Arg
1835                1840                1845

Leu His Gln Ala Gly Tyr Lys Leu Glu Ile Arg Asp Leu Phe Lys
1850                1855                1860

Tyr Pro Thr Ile Ala Glu Leu Ser Pro His Ile Gln Pro Val Gly
1865                1870                1875

Arg Met Ala Asp Gln Gly Glu Val Ser Gly Thr Val Pro Leu Thr
1880                1885                1890

Pro Ile Gln Arg Trp Tyr Phe Gly Gln Gln Phe Ala Asp Pro His
1895                1900                1905

His Tyr Asn Gln Ser Val Met Leu His Arg Lys Glu Gly Phe Asp
1910                1915                1920

Thr Ala Ala Ile Arg Lys Ala Leu Gln Lys Leu Val Glu His His
1925                1930                1935

Asp Gly Leu Arg Met Val Phe Arg Lys Thr Glu Glu Gly Tyr Thr
1940                1945                1950

Ala Trp Asn Arg Gly Ile Gly Glu Gly Glu Leu Tyr Arg Leu Tyr
1955                1960                1965

Val Ala Asp Phe Thr Gly Val Ala Ala Cys Glu Arg Met Ile Glu
1970                1975                1980

Ala Ala Ala Asn Glu Ile Gln Ser Gly Ile Asp Leu Gln Ala Gly
1985                1990                1995

Pro Leu Val Arg Ala Gly Leu Phe His Gly Ala Asp Gly Asp His
2000                2005                2010

Leu Leu Ile Val Ile His His Ala Val Val Asp Gly Val Ser Trp
2015                2020                2025

Arg Ile Leu Leu Glu Asp Phe Ala Ala Ser Tyr Glu Gln Ala Leu
2030                2035                2040

Lys Gly Gln Ala Leu Arg Leu Pro Phe Lys Thr Asp Ser Tyr Arg
2045                2050                2055

Thr Trp Ser Asp Gln Leu Val Glu Tyr Ala Arg Ser Pro Val Met
2060                2065                2070

Gln Arg Glu Arg Ala Tyr Trp Gln Arg Ile Ala Gln Thr Ala Ala
2075                2080                2085

Lys Pro Leu Pro Arg Asp Tyr Glu Ala Glu Cys Ser Leu Gln Gln
2090                2095                2100

Asp Ser Glu Ser Val Thr Val Gln Trp Ser Gln Glu Ala Thr Glu
2105                2110                2115

Gln Leu Leu Lys His Val His Arg Ala Tyr Asn Thr Glu Met Asn

```
                2120                2125                2130

Asp Ile Leu Leu Thr Ala Leu Gly Met Ala Val Gln Lys Trp Cys
    2135                2140                2145

Gly Arg Asp Arg Val Leu Val Thr Leu Glu Gly His Gly Arg Glu
    2150                2155                2160

Ser Ile Met Thr Asp Ile Asp Ile Thr Arg Thr Val Gly Trp Phe
    2165                2170                2175

Thr Ser Glu Tyr Pro Val Leu Leu Glu Met Glu Pro Asp Lys Ser
    2180                2185                2190

Leu Ser Ser Arg Ile Lys Lys Met Lys Glu Asp Leu Arg Gln Ile
    2195                2200                2205

Pro Asn Lys Gly Ile Gly Tyr Gly Ile Gly Arg Tyr Met Ser Glu
    2210                2215                2220

Leu His Asp Glu Ala Val Trp Gly Gly Ala Glu Pro Asp Ile Ser
    2225                2230                2235

Phe Asn Tyr Leu Gly Gln Phe Asp Gln Asp Met Lys Asn Asn Glu
    2240                2245                2250

Met Glu Val Ser Pro Tyr Ser Ser Gly Met Glu Val Ser Arg Gln
    2255                2260                2265

Gln Ala Arg Thr His Ala Leu Asp Ile Asn Gly Met Val Ala Asp
    2270                2275                2280

Gly Ser Leu Ala Leu Glu Leu Ser Tyr Ser Arg Lys Glu Tyr Arg
    2285                2290                2295

Lys Glu Thr Ile Glu Ala Leu Ser Ile Tyr Leu Gln Glu Ser Leu
    2300                2305                2310

Gln Glu Ile Ile Leu His Cys Thr Ala Lys Glu Arg Pro Glu Val
    2315                2320                2325

Thr Pro Ser Asp Ile Leu Leu Gln Gly Leu Ser Val Glu Glu Leu
    2330                2335                2340

Glu Gln Ile Ala Lys Gln Thr Gln Arg Ile Gly Asp Ile Glu Asn
    2345                2350                2355

Met Tyr Thr Leu Thr Pro Met Gln Lys Gly Met Trp Phe His Ser
    2360                2365                2370

Ala Met Asp Gln His Ala Gly Ala Tyr Phe Glu Gln Thr Arg Phe
    2375                2380                2385

Thr Leu Gln Gly Ala Leu Asp Val Glu Val Phe Ala Lys Ser Leu
    2390                2395                2400

Asp Ala Leu Ala Lys Gln His Ala Val Leu Arg Thr Asn Phe Tyr
    2405                2410                2415

Asn Gly Trp Asn Gly Glu Leu Leu Gln Ile Val Phe Arg Asp Lys
    2420                2425                2430

Arg Leu Gly Phe Ala Tyr Glu Asp Leu Cys Ala Leu Pro Glu Ala
    2435                2440                2445

Glu Arg Glu Thr His Val Glu Thr Leu Thr Gln Glu Asp Arg Met
    2450                2455                2460

Arg Gly Phe Asp Leu Glu Gln Asp Ala Leu Met Arg Val Ser Val
    2465                2470                2475

Val Arg Met Ala Glu Glu Ser Tyr Gln Val Leu Trp Ser Ser His
    2480                2485                2490

His Ile Leu Met Asp Gly Trp Cys Leu Pro Gln Leu Thr Gln Glu
    2495                2500                2505

Trp Phe Asp Thr Tyr Ser Ala Tyr Val Gln His Gln His Leu Glu
    2510                2515                2520
```

```
Arg Thr Thr Ala Pro Ala Tyr Ser Gln Tyr Ile Glu Trp Leu Glu
2525                2530                2535

Gln Gln Asp Asp Gln Ala Ala Ser Ala Tyr Trp Ala Asn Tyr Leu
2540                2545                2550

Ala Gly Tyr Asp Gln Gln Thr Val Leu Pro Gln Ala Lys Gly Gln
2555                2560                2565

Gly Arg Ser Asp Glu Tyr Ala Ala Glu Arg Ile Leu Cys Glu Leu
2570                2575                2580

Gly Lys Ala Leu Thr Gly Arg Met Ser His Val Ala Lys Gln His
2585                2590                2595

Gln Val Thr Leu Asn Thr Leu Met Gln Ala Ala Trp Ala Ile Leu
2600                2605                2610

Leu Gln Lys Tyr Asn Gly Thr Asp Asp Val Val Phe Gly Gly Val
2615                2620                2625

Val Ser Gly Arg Pro Ala Glu Ile Pro Gly Ile Glu Ala Met Ile
2630                2635                2640

Gly Leu Phe Ile Asn Thr Ile Pro Val Arg Val Thr Cys Glu Ala
2645                2650                2655

Glu Thr Ser Phe Ala Glu Leu Met Gly Arg Leu Gln Glu Gln Ala
2660                2665                2670

Leu Glu Ser Gly Arg Tyr Asp Tyr Tyr Pro Leu Tyr Glu Ile Gln
2675                2680                2685

Ala Gln Cys Glu Gln Lys Gln Asp Leu Ile Ser His Leu Met Val
2690                2695                2700

Phe Glu Asn Tyr Pro Met Glu Glu Gln Met Glu Gln Ala Gly Ser
2705                2710                2715

Asp Asp Arg Gly Lys Leu Thr Ile Thr Asp Val Glu Val Ala Glu
2720                2725                2730

Gln Thr Asn Tyr Asp Phe Asn Leu Val Val Val Pro Gly Asp Glu
2735                2740                2745

Ile Val Ile Arg Leu Glu Tyr Asn Ala Asn Val Phe Asp Arg Glu
2750                2755                2760

Ser Ile Glu Gln Leu Gln Gly His Leu Val His Val Leu Glu Gln
2765                2770                2775

Ile Thr Ala Asn Pro His Met Ala Val Gly Glu Leu Glu Leu Ala
2780                2785                2790

Thr Ala Gly Glu Lys Thr Gln Leu Met Leu Ala Phe Asn Asp Thr
2795                2800                2805

Ala Ala Glu Tyr Pro Arg Glu Lys Thr Ile His Gln Met Phe Glu
2810                2815                2820

Glu Gln Ala Glu Arg Thr Pro Asp Ala Ala Ala Val Leu Phe Glu
2825                2830                2835

Gln Glu Gln Leu Thr Tyr Arg Glu Leu Asn Glu Arg Ala Asn Arg
2840                2845                2850

Leu Ala Arg Thr Leu Arg Ala Leu Gly Val Gln Pro Asp Gln Leu
2855                2860                2865

Val Gly Ile Met Ala Glu Arg Ser Leu Glu Met Met Val Gly Ile
2870                2875                2880

Met Ala Ile Leu Lys Ala Gly Gly Ala Tyr Val Pro Ile Ala Ala
2885                2890                2895

Asp Ser Pro Glu Glu Arg Ile Arg Tyr Leu Leu Glu Asp Ser Gly
2900                2905                2910
```

-continued

| | | | | | | | | | | | |
|---|---|---|---|---|---|---|---|---|---|---|---|
| Ala | Gln | Val | Leu | Leu | Gln | Gly | Arg | Ala | Gly | Glu | Val | Ser |
| 2915 | | | | | 2920 | | | | 2925 | | | |
| Phe | Ala | Gly | Arg | Ile | Val | Asn | Leu | Asp | Asp | Ala | Asn | Ser | Tyr | Ala |
| 2930 | | | | | 2935 | | | | 2940 | | | |
| Gly | Asp | Gly | Ser | Asn | Pro | Glu | Arg | Val | Asn | Gln | Ala | Ser | Asp | Ala |
| 2945 | | | | | 2950 | | | | 2955 | | | |
| Ala | Tyr | Val | Ile | Tyr | Thr | Ser | Gly | Thr | Thr | Gly | Arg | Pro | Lys | Gly |
| 2960 | | | | | 2965 | | | | 2970 | | | |
| Val | Leu | Val | Glu | His | Gly | Ser | Val | Ile | Asn | Arg | Leu | Leu | Trp | Met |
| 2975 | | | | | 2980 | | | | 2985 | | | |
| Gln | Lys | Arg | Tyr | Pro | Ile | Gly | Pro | Ser | Asp | Thr | Ile | Met | Gln | Lys |
| 2990 | | | | | 2995 | | | | 3000 | | | |
| Thr | Ala | Ile | Thr | Phe | Asp | Val | Ser | Val | Trp | Glu | Leu | Phe | Trp | Trp |
| 3005 | | | | | 3010 | | | | 3015 | | | |
| Ala | Phe | Val | Gly | Ser | Lys | Val | Cys | Leu | Leu | Pro | Val | Gly | Gly | Glu |
| 3020 | | | | | 3025 | | | | 3030 | | | |
| Lys | Asn | Pro | Ala | Val | Ile | Leu | Asp | Thr | Ile | Glu | Arg | Gln | His | Ile |
| 3035 | | | | | 3040 | | | | 3045 | | | |
| Ser | Thr | Met | His | Phe | Val | Pro | Ser | Met | Leu | His | Ala | Phe | Leu | Glu |
| 3050 | | | | | 3055 | | | | 3060 | | | |
| Tyr | Val | Glu | Glu | Gln | Pro | Val | Ala | Glu | Arg | Glu | Arg | Ser | Leu | Ala |
| 3065 | | | | | 3070 | | | | 3075 | | | |
| Ser | Leu | Arg | Arg | Val | Phe | Ala | Ser | Gly | Glu | Ala | Leu | Thr | Ala | Ser |
| 3080 | | | | | 3085 | | | | 3090 | | | |
| Gln | Ala | Glu | Arg | Phe | Glu | Arg | Cys | Ile | Ala | Pro | Val | Asn | Gly | Ala |
| 3095 | | | | | 3100 | | | | 3105 | | | |
| Arg | Leu | Ile | Asn | Leu | Tyr | Gly | Pro | Thr | Glu | Ala | Thr | Val | Asp | Val |
| 3110 | | | | | 3115 | | | | 3120 | | | |
| Thr | Tyr | Phe | Asp | Cys | Gln | Ala | Gly | Gln | Pro | Tyr | Thr | Ser | Val | Pro |
| 3125 | | | | | 3130 | | | | 3135 | | | |
| Ile | Gly | Arg | Pro | Ile | Asp | Asn | Thr | Gln | Ile | Tyr | Ile | Val | Asn | Arg |
| 3140 | | | | | 3145 | | | | 3150 | | | |
| Gln | Asn | Gln | Leu | Gln | Pro | Ile | Gly | Val | Ala | Gly | Glu | Leu | Cys | Ile |
| 3155 | | | | | 3160 | | | | 3165 | | | |
| Ala | Gly | Ala | Gly | Leu | Ala | Arg | Gly | Tyr | Trp | Glu | Arg | Pro | Glu | Leu |
| 3170 | | | | | 3175 | | | | 3180 | | | |
| Thr | Ala | Glu | Lys | Phe | Val | Glu | Ile | Pro | Phe | Lys | Pro | Ser | Glu | Arg |
| 3185 | | | | | 3190 | | | | 3195 | | | |
| Met | Tyr | Arg | Thr | Gly | Asp | Leu | Ala | Arg | Trp | Leu | Pro | Asp | Gly | Asn |
| 3200 | | | | | 3205 | | | | 3210 | | | |
| Ile | Glu | Tyr | Leu | Gly | Arg | Leu | Asp | His | Gln | Val | Lys | Ile | Arg | Gly |
| 3215 | | | | | 3220 | | | | 3225 | | | |
| Tyr | Arg | Ile | Glu | Leu | Gly | Glu | Ile | Glu | Ala | Gln | Leu | Leu | Gln | Ala |
| 3230 | | | | | 3235 | | | | 3240 | | | |
| Ala | Ala | Ile | Arg | Glu | Thr | Val | Val | Val | Ala | Arg | Glu | Asp | Glu | Ser |
| 3245 | | | | | 3250 | | | | 3255 | | | |
| Gly | Gln | Lys | Ala | Leu | Cys | Ala | Tyr | Phe | Ala | Ala | Asp | Ser | Glu | Leu |
| 3260 | | | | | 3265 | | | | 3270 | | | |
| Thr | Val | Ser | Glu | Leu | Arg | Ser | Ala | Leu | Ala | Ala | Gln | Leu | Pro | Asp |
| 3275 | | | | | 3280 | | | | 3285 | | | |
| Tyr | Met | Ile | Pro | Ser | Tyr | Phe | Val | Gln | Leu | Glu | Arg | Leu | Pro | Leu |
| 3290 | | | | | 3295 | | | | 3300 | | | |
| Ser | Ala | Asn | Gly | Lys | Ile | Asp | Arg | Lys | Ala | Leu | Pro | Ser | Pro | Glu |

-continued

```
            3305                3310                3315
Gly Ser Leu Tyr Thr Gly Thr Glu Tyr Val Ala Pro Arg Thr Glu
            3320                3325                3330
Ala Glu Lys Thr Ile Ala Val Val Trp Gln Ala Val Leu Gly Ile
            3335                3340                3345
Glu Arg Val Gly Val Thr Asp His Phe Phe Glu Leu Gly Gly Asp
            3350                3355                3360
Ser Ile Lys Ser Ile Gln Val Ala Ser Arg Leu Gln Gln Ala Gly
            3365                3370                3375
Tyr Lys Leu Glu Ile Arg Glu Leu Phe Lys Tyr Pro Thr Ile Ala
            3380                3385                3390
Gln Leu Ser Leu Gln Val Arg Pro Val Ala Arg Met Ala Asp Gln
            3395                3400                3405
Gly Glu Val Ala Gly Glu Met Pro Leu Thr Pro Ile Leu Ser Trp
            3410                3415                3420
Phe Met Glu Gln Glu Phe Ala Asn Pro His His Phe Asn Gln Ser
            3425                3430                3435
Ile Met Leu His Arg Gln Glu Gly Phe Asp Glu Val Ala Ile Arg
            3440                3445                3450
Lys Thr Leu His Asn Ile Val Glu His Asp Ala Leu Arg Met
            3455                3460                3465
Val Phe Arg Lys Thr Glu His Gly Gly Tyr Lys Ala Trp Asn Arg
            3470                3475                3480
Gly Ile Ser Glu Gly Asp Leu Tyr Ser Leu Asp Val Ala Asp Phe
            3485                3490                3495
Lys Glu Asp Pro Glu Cys Gly Arg Ser Ile Glu Ala Lys Ala Asn
            3500                3505                3510
Glu Ile Gln Ser Gly Ile Asp Leu Gln Thr Gly Pro Leu Val Lys
            3515                3520                3525
Ala Gly Leu Phe His Cys Ala Asp Gly Asp His Leu Leu Ile Val
            3530                3535                3540
Ile His His Thr Val Ile Asp Gly Ile Ser Trp Arg Ile Leu Leu
            3545                3550                3555
Glu Asp Ile Ala Asp Gly Tyr Glu Gln Ala Leu Lys Gly Gln Glu
            3560                3565                3570
Ile Arg Leu Pro Val Lys Thr Asp Ser Tyr Arg Ile Trp Ser Glu
            3575                3580                3585
Gln Leu Ala Thr Tyr Ala His Ser Ser Asp Leu Glu Asn Glu Arg
            3590                3595                3600
Ala Tyr Trp Gln Arg Ile Ala Gln Thr Asp Thr Glu Pro Leu Pro
            3605                3610                3615
Lys Asp Trp Glu Ala Ala Cys Ser Leu Gln Arg Glu Ser Glu Ser
            3620                3625                3630
Val Asn Val Gln Trp Ser Arg Glu Asp Thr Glu Arg Leu Leu Lys
            3635                3640                3645
His Val His Arg Ala Tyr Asn Thr Glu Met Asn Asp Ile Leu Leu
            3650                3655                3660
Ala Ala Leu Gly Met Ala Val His Lys Trp Cys Gly Arg Asp Arg
            3665                3670                3675
Val Leu Val Thr Leu Glu Gly His Gly Arg Glu Ser Ile Leu Thr
            3680                3685                3690
Asp Ile Asp Ile Thr Arg Thr Val Gly Trp Phe Thr Ser Glu Tyr
            3695                3700                3705
```

-continued

```
Pro Val Leu Ile Glu Ala Glu Pro Asp Lys Thr Leu Ser Tyr Arg
    3710                3715                3720

Ile Lys Gln Val Lys Glu Asn Leu Arg Arg Ile Pro Asn Lys Gly
    3725                3730                3735

Ile Gly Tyr Gly Ile Cys Arg Tyr Leu Ser Ser Ala Gln Glu Pro
    3740                3745                3750

Ala Trp Thr Glu Ala Phe Thr Pro Glu Leu Arg Phe Asn Tyr Leu
    3755                3760                3765

Gly Gln Phe Asp Gln Asp Leu Gln Gly Asn Glu Leu Glu Leu Ser
    3770                3775                3780

Ser Tyr Ser Ser Gly Ser Asp Met Ser Asp Glu Gln Val Arg Asn
    3785                3790                3795

Tyr Ser Leu Asp Ile Ser Gly Met Ile Val Asp Gly Leu Leu Ser
    3800                3805                3810

Leu Asp Val Ser Tyr Ser Gly Lys Glu Tyr Arg Lys Glu Thr Ile
    3815                3820                3825

Glu Glu Leu Ala Gly Cys Leu Leu Val Ser Leu Gln Glu Ile Ile
    3830                3835                3840

Asp His Cys Ala Ala Lys Glu Arg Pro Glu Leu Thr Pro Ser Asp
    3845                3850                3855

Val Leu Leu Gln Gly Leu Ser Val Glu Glu Leu Asp Gln Ile Ala
    3860                3865                3870

Glu Gln Thr Arg Arg Asn Gly Glu Ile Glu Asn Ile Tyr Thr Leu
    3875                3880                3885

Thr Pro Met Gln Lys Gly Met Trp Phe His Ser Ala Met Asp Arg
    3890                3895                3900

Gln Ser Gly Ala Tyr His Glu Gln Thr Arg Phe Thr Ile Glu Gly
    3905                3910                3915

Glu Leu Asp Thr Asp Val Phe Val Lys Ser Leu Asp Ala Leu Ala
    3920                3925                3930

Asn Asn His Ala Val Leu Arg Thr Asn Phe Leu Ser Gly Trp Asn
    3935                3940                3945

Gly Glu Pro Leu Gln Val Val Phe Arg Asp Lys Arg Ile Gly Phe
    3950                3955                3960

Ala Tyr Ala Asp Leu Arg Glu Leu Gln Glu Ala Asp Arg Asn Arg
    3965                3970                3975

Cys Ile Glu Lys Ser Ala Ala Glu Asp His Ala Arg Gly Phe Asp
    3980                3985                3990

Leu Glu Gln Asp Ala Leu Met Arg Val Met Val Met Arg Thr Gly
    3995                4000                4005

Glu Ser Ser Tyr Gln Val Ile Trp Ser Ser His His Ile Leu Met
    4010                4015                4020

Asp Gly Trp Cys Leu Pro Gln Leu Ala Lys Glu Leu Phe Asp Thr
    4025                4030                4035

Tyr Ser Val Tyr Leu Gln Gln His His Pro Glu Gln Ala Thr Ser
    4040                4045                4050

Val Pro Ala Tyr Ser Gln Tyr Ile Glu Trp Leu Glu Gln Gln Asp
    4055                4060                4065

Glu Ala Ala Ala Ser Ala Tyr Trp Ser Glu Tyr Leu Ala Gly Tyr
    4070                4075                4080

Asp Gln Gln Ala Ala Leu Pro Gln Gln Thr Ala Gln Gly Arg Gly
    4085                4090                4095
```

-continued

```
Glu Glu Tyr Val Ala Glu Lys Leu Thr Cys Glu Leu Gly Lys Thr
    4100              4105              4110

Leu Ser Gly Arg Met Ser Arg Val Ala Arg Gln His Gln Val Thr
    4115              4120              4125

Leu Asn Thr Leu Leu Gln Ala Ala Trp Gly Ile Ile Leu Gln Lys
    4130              4135              4140

Tyr Asn Gly Thr Arg Asp Thr Val Phe Gly Ser Val Val Ser Gly
    4145              4150              4155

Arg Pro Ala Glu Ile Pro Gly Ile Glu Ala Met Ile Gly Leu Phe
    4160              4165              4170

Ile Asn Thr Ile Pro Val Arg Val Ser Cys Glu Ala Lys Thr Ser
    4175              4180              4185

Phe Ala Glu Val Met Gly Arg Leu Gln Glu Gln Ala Leu Glu Ser
    4190              4195              4200

Gly Lys Tyr Asp Tyr Tyr Pro Leu Tyr Glu Ile Gln Ala Arg Cys
    4205              4210              4215

Ser Gln Lys Gln Asp Leu Ile Ser Gln Ile Met Val Phe Glu Asn
    4220              4225              4230

Tyr Pro Met Asp Glu Gln Met Glu Gln Ala Gly Asn Asp Asp Gln
    4235              4240              4245

Gly Met Leu Ala Ile Thr Asn Val Glu Val Ala Glu Gln Thr Asn
    4250              4255              4260

Tyr Asp Phe Asn Phe Ile Val Val Pro Gly Glu Glu Ile Val Ile
    4265              4270              4275

Asn Phe Asp Tyr Asn Ala Arg Val Phe Asp Arg Thr Ser Met Glu
    4280              4285              4290

Arg Leu Gln Gly His Leu Val Asn Val Leu Glu Gln Ile Ala Ala
    4295              4300              4305

Asn Pro Gln Val Thr Val Gly Glu Leu Lys Leu Ala Thr Glu Ala
    4310              4315              4320

Glu Gln Ala Glu Ile Thr Ser Ile Phe Asn Asn Ala Arg Thr Glu
    4325              4330              4335

Tyr Pro Arg Asp Lys Thr Ile His Arg Leu Phe Glu Glu Gln Ala
    4340              4345              4350

Glu Arg Thr Pro Asp Ala Ile Ala Val Met Tyr Glu Asn Ser Gln
    4355              4360              4365

Leu Thr Tyr Arg Glu Leu Asn Glu Arg Ala Asn Arg Leu Ala Arg
    4370              4375              4380

Thr Leu Arg Ala Asp Gly Ala Gly Ala Asp Arg Leu Val Gly Leu
    4385              4390              4395

Met Val Glu Arg Ser Leu Asp Met Met Val Gly Ile Ile Ala Ile
    4400              4405              4410

Leu Lys Ser Gly Gly Ala Tyr Val Pro Ile Asp Pro Glu Tyr Pro
    4415              4420              4425

Glu Glu Arg Ile Arg Tyr Met Leu Glu Asp Ser Gly Thr Gln Ile
    4430              4435              4440

Ile Val Thr Gln Arg His Leu Gln Glu Arg Ile Pro Gly Ala Gly
    4445              4450              4455

Thr Arg Val Ile Leu Asp Asp Glu His Ser Tyr Ser Ser Asp Ser
    4460              4465              4470

Thr Asn Leu Asp Leu Asn Asn Gly Pro Ala Asp Leu Ala Tyr Val
    4475              4480              4485

Ile Tyr Thr Ser Gly Thr Thr Gly Lys Pro Lys Gly Asn Leu Thr
```

```
               4490                4495                4500
Met His  Arg  Asn  Ile  Val  Arg  Val  Val  Gln  Gly  Ala  Asp  Tyr  Ile
     4505                4510                4515

Asp Ile  Gly  Glu  Gln  Asp  Asn  Val  Leu  Gln  Leu  Ser  Ser  Tyr  Ala
     4520                4525                4530

Phe Asp  Gly  Ser  Thr  Phe  Asp  Met  Tyr  Gly  Ala  Leu  Leu  Asn  Gly
     4535                4540                4545

Ala Arg  Leu  Val  Leu  Ile  Pro  Gln  Glu  Thr  Leu  Leu  Asp  Val  Glu
     4550                4555                4560

Arg Leu  Ala  Glu  Leu  Ile  Glu  Arg  Glu  Arg  Ile  Ser  Val  Met  Phe
     4565                4570                4575

Ile Thr  Thr  Ala  Phe  Phe  Asn  Val  Leu  Val  Asp  Val  Lys  Ala  Asp
     4580                4585                4590

Cys Leu  Arg  His  Ile  Arg  Ala  Ile  Leu  Phe  Gly  Gly  Glu  Arg  Val
     4595                4600                4605

Ser Val  Ser  His  Val  Arg  Lys  Ala  Leu  Arg  His  Leu  Gly  Pro  Gly
     4610                4615                4620

Lys Ile  Lys  His  Val  Tyr  Gly  Pro  Thr  Glu  Ser  Thr  Val  Phe  Ala
     4625                4630                4635

Thr Cys  His  Asp  Val  Asn  Glu  Val  Ala  Ala  Asp  Ala  Leu  Asn  Val
     4640                4645                4650

Pro Ile  Gly  Arg  Pro  Ile  Ser  Asn  Thr  Thr  Ile  Tyr  Ile  Val  Asn
     4655                4660                4665

Glu Glu  Asn  Gly  Leu  Gln  Pro  Ile  Gly  Val  Ala  Gly  Glu  Leu  Cys
     4670                4675                4680

Val Ala  Gly  Asp  Gly  Leu  Ala  Arg  Gly  Tyr  Leu  Asn  Arg  Pro  Glu
     4685                4690                4695

Leu Thr  Ala  Glu  Lys  Phe  Val  Asp  Asn  Pro  Phe  Val  Pro  Gly  Glu
     4700                4705                4710

Arg Met  Tyr  Arg  Thr  Gly  Asp  Leu  Ala  Arg  Trp  Leu  Pro  Asp  Gly
     4715                4720                4725

Ser Ile  Glu  Tyr  Val  Gly  Arg  Ile  Asp  His  Gln  Val  Lys  Ile  Arg
     4730                4735                4740

Gly Tyr  Arg  Ile  Glu  Leu  Gly  Glu  Val  Glu  Ala  His  Leu  Leu  Lys
     4745                4750                4755

Val Gln  Pro  Val  Gln  Glu  Gly  Thr  Val  Val  Ala  Arg  Glu  Thr  Gly
     4760                4765                4770

Ser Gly  Glu  Lys  Gln  Leu  Cys  Ala  Tyr  Phe  Val  Ala  Glu  Ser  Thr
     4775                4780                4785

Leu Ser  Ala  Ser  Glu  Leu  Arg  Gly  Ala  Met  Ala  Gln  Gln  Leu  Pro
     4790                4795                4800

Gly Tyr  Met  Ile  Pro  Ser  Tyr  Phe  Val  Gln  Leu  Glu  Arg  Met  Pro
     4805                4810                4815

Leu Thr  Pro  Asn  Gly  Lys  Val  Asp  Gln  Lys  Ala  Leu  Pro  Ala  Pro
     4820                4825                4830

Glu Glu  His  Val  Gln  Thr  Gly  Thr  Glu  Tyr  Ile  Ala  Pro  Arg  Thr
     4835                4840                4845

Pro Gln  Glu  Glu  Gln  Leu  Ala  Arg  Ile  Trp  Gln  Glu  Val  Leu  Gly
     4850                4855                4860

Leu Glu  Lys  Val  Gly  Val  Asn  Asp  Asn  Phe  Phe  Glu  Leu  Gly  Gly
     4865                4870                4875

His Ser  Leu  Arg  Ala  Thr  Thr  Met  Ala  Ser  Lys  Leu  His  Lys  Glu
     4880                4885                4890
```

-continued

```
Leu Ser Ile Glu Leu Pro Leu Arg Asp Val Phe Lys His Pro Thr
    4895                4900                4905

Leu Glu Ala Met Ala Glu Arg Ile Ala Gly Leu Gly Gln Gln Met
    4910                4915                4920

Tyr Thr Ser Ile Pro Leu Val Glu Glu Gln Ala His Tyr Pro Leu
    4925                4930                4935

Ser Ser Ala Gln Lys Arg Leu Tyr Ile Leu His Gln Leu Glu Gly
    4940                4945                4950

Ala Glu Leu Ser Tyr Asn Met Pro Asn Met Leu Leu Leu Glu Gly
    4955                4960                4965

Ala Leu Asp Arg Glu Arg Phe Glu Ala Ala Phe Arg Lys Leu Ile
    4970                4975                4980

Ala Arg His Glu Ser Phe Arg Thr Gly Phe Glu Met Ile Asn Gly
    4985                4990                4995

Glu Pro Met Gln Arg Ile Tyr Glu Asn Val Asp Phe Ala Val Glu
    5000                5005                5010

Tyr Met Gln Ala Ser Asp Lys Glu Ala Glu Ala Arg Leu Arg Gln
    5015                5020                5025

Phe Val Arg Ala Phe Lys Leu Glu Glu Pro Pro Leu Leu Arg Val
    5030                5035                5040

Gly Leu Ile Glu Leu Ala Gln Glu Arg His Ile Leu Met Phe Asp
    5045                5050                5055

Met His His Ile Val Ser Asp Gly Thr Ser Met Gly Ile Leu Ile
    5060                5065                5070

Asn Glu Phe Val Arg Leu Tyr Gly Gly Glu Glu Leu Gln Pro Leu
    5075                5080                5085

Arg Ile Gln Tyr Lys Asp Phe Ala Ala Trp Gln Gln Ser Asp Ala
    5090                5095                5100

Arg Gln Glu Gln Met Lys Gln Gln Glu Ala Tyr Trp Leu Gln Ala
    5105                5110                5115

Leu Gly Gly Glu Leu Pro Val Leu Glu Met Pro Thr Asp His Val
    5120                5125                5130

Arg Pro Ala Val Gln Ser Phe Arg Gly Asp Ile Leu Gln Phe Val
    5135                5140                5145

Ile Gly Arg Asp Gln Cys Ala Ala Leu Arg His Ile Gly Ser Glu
    5150                5155                5160

Asn Gly Ala Thr Leu Tyr Met Val Leu Leu Ala Ala Tyr Thr Ala
    5165                5170                5175

Leu Leu His Lys Tyr Thr Gly Gln Glu Asp Ile Ile Val Gly Thr
    5180                5185                5190

Pro Ile Ala Gly Arg Asn His Gly Asp Val Gln Pro Leu Ile Gly
    5195                5200                5205

Met Phe Val Asn Thr Leu Ala Ile Arg Asn Tyr Pro Met Gly Glu
    5210                5215                5220

Lys Thr Phe His Ser Tyr Leu Glu Glu Val Lys Asp Thr Thr Leu
    5225                5230                5235

Gly Ala Tyr Glu Asn Gln Asn Tyr Pro Phe Glu Asp Leu Val Glu
    5240                5245                5250

Asn Val Gln Val Ala Arg Asp Met Ser Arg Asn Pro Ile Phe Asp
    5255                5260                5265

Thr Met Phe Ile Leu Gln Asn Ala Glu Gln Gly Glu Met Asn Ile
    5270                5275                5280
```

-continued

| | | | | | | | | | | | |
|---|---|---|---|---|---|---|---|---|---|---|---|
| Asn | Gly | Leu | His | Ile | Ala | Asn | Tyr | Gln | Ser | Glu | His | Thr | Val | Ser |
| | 5285 | | | | 5290 | | | | | 5295 | | | | |

Lys Phe Asp Leu Thr Phe Gln Ala Glu Glu Ala Glu Glu Glu Ile
    5300                5305                5310

Val Cys Ser Ile Glu Tyr Ala Thr Glu Leu Tyr Glu Leu Glu Thr
    5315                5320                5325

Val Glu Arg Met Ala Gly His Phe Thr Gln Leu Ile Asp Ala Val
    5330                5335                5340

Val Gly Asn Pro His Ala Arg Leu Ala Ser Leu Gln Met Val Thr
    5345                5350                5355

Ala Glu Glu Gln Asp Gln Ile Gln Asn Ile Phe Asn Ala Thr Asp
    5360                5365                5370

Met Gly Tyr Pro Arg Glu Lys Thr Ile His Gln Met Phe Glu Glu
    5375                5380                5385

Gln Ala Glu Arg Thr Pro Asp Ala Pro Ala Val Ser Phe Gly Asp
    5390                5395                5400

Glu Met Leu Thr Tyr Arg Glu Leu Asn Arg Lys Ala Asn Gln Leu
    5405                5410                5415

Ala Trp Val Leu Arg Asp Arg Gly Val Ala Ser Glu Arg Pro Val
    5420                5425                5430

Gly Ile Met Val Glu Arg Ser Ile Ala Met Val Val Gly Val Leu
    5435                5440                5445

Ala Val Leu Lys Ala Gly Gly Thr Phe Val Pro Ile Asp Pro Glu
    5450                5455                5460

Tyr Pro Glu Thr Arg Ile Arg Tyr Met Leu Glu Asp Ser Gly Ala
    5465                5470                5475

Lys Leu Ala Leu Thr Glu Leu Ala Trp Phe Glu Val Ile Pro Pro
    5480                5485                5490

Glu Val Glu Lys Val Asp Ile His Asp Ala Ser Leu Tyr Gln Gly
    5495                5500                5505

His Asp Glu Asn Val Pro Asn Glu Ser Glu Pro Ser Asn Leu Leu
    5510                5515                5520

Tyr Ile Ile Tyr Thr Ser Gly Thr Thr Gly Asn Pro Lys Gly Val
    5525                5530                5535

Met Leu Glu Gln Arg Asn Leu Ile Asn Leu Leu His Tyr Glu Gln
    5540                5545                5550

Val Gly Thr Ser Ile Pro Leu Pro Ser Arg Ile Leu Gln Tyr Ala
    5555                5560                5565

Ser Asn Ser Phe Asp Val Cys Tyr Gln Glu Met Phe Ser Ala Leu
    5570                5575                5580

Leu Phe Gly Gly Cys Leu Phe Leu Ile Pro Asn Glu Ala Arg Lys
    5585                5590                5595

Asp Pro Ala Gln Leu Phe Thr Trp Ile Gln Asp Asn Gly Ile Glu
    5600                5605                5610

Val Leu Tyr Leu Pro Val Ala Phe Leu Lys Phe Ile Phe Ala Glu
    5615                5620                5625

Pro Glu Trp Ala Glu Arg Phe Pro Asp Cys Val Thr His Ile Ile
    5630                5635                5640

Thr Ala Gly Glu Gln Leu Val Val Thr Pro Gln Ile Gln Ala Cys
    5645                5650                5655

Leu Gln Arg Leu Arg Ile Ser Leu His Asn His Tyr Gly Pro Ser
    5660                5665                5670

Glu Thr His Val Val Thr Ala Tyr Thr Met Glu Pro Asp Asp Ile

```
            5675                5680                5685

Ala Val Gly Leu Pro Pro Ile Gly Ala Pro Ile Ala Asn Thr Ala
        5690                5695                5700

Ile Tyr Ile Leu Asn Asp Arg Leu Glu Leu Gln Pro Ile Gly Ile
        5705                5710                5715

Ala Gly Glu Leu Tyr Val Ser Gly Asp Cys Val Gly Arg Gly Tyr
        5720                5725                5730

Trp Gly Arg Gln Glu Leu Thr Asp Glu Lys Phe Ile Ala Asn Pro
        5735                5740                5745

Phe Ala Pro Gly Asp Leu Met Tyr Lys Thr Gly Asp Val Ala Arg
        5750                5755                5760

Trp Leu Pro Asp Gly Thr Ile Glu Tyr Val Gly Arg Ser Asp His
        5765                5770                5775

Gln Val Lys Ile Arg Gly Phe Arg Ile Glu Leu Gly Glu Val Glu
        5780                5785                5790

Ser Gln Leu Leu Ser Val Glu Phe Val Gln Glu Ala Thr Val Met
        5795                5800                5805

Ala Arg Glu Asp Asp Gly Gly Gln Lys Gln Leu Cys Ala Tyr Phe
        5810                5815                5820

Val Ala Glu Arg Pro Leu Ser Ala Ala Glu Leu Arg Gly Gly Leu
        5825                5830                5835

Ser Gln Asp Leu Pro Gly Tyr Met Ile Pro Ser Tyr Phe Val Gln
        5840                5845                5850

Leu Asp Arg Leu Pro Leu Thr Pro Asn Gly Lys Ile Asp Arg Arg
        5855                5860                5865

Ala Leu Pro Glu Pro Glu Gly Ser Leu His Thr Gly Ala Glu Phe
        5870                5875                5880

Val Ala Pro Arg Thr Pro Leu Glu Ala Gln Leu Ala Arg Ile Trp
        5885                5890                5895

Gln Asp Val Leu Gly Leu Pro Asp Val Ser Val Lys Asp Asn Phe
        5900                5905                5910

Phe Asp Leu Gly Gly His Ser Leu Arg Ala Thr Thr Leu Ala Ser
        5915                5920                5925

Lys Val Phe Lys Glu Met His Val Asn Leu Pro Leu Arg Asp Val
        5930                5935                5940

Phe Arg Cys Pro Thr Ile Glu Glu Met Ala Gly Met Ile Ala Gly
        5945                5950                5955

Met Glu Lys Gln Glu Tyr Ala Ala Ile Pro Leu Ala Glu Glu Ser
        5960                5965                5970

Asp Val Tyr Pro Leu Ser Ser Ala Gln Lys Arg Leu Tyr Ile Val
        5975                5980                5985

Ser Gln Leu Glu Gly Ala Asp Leu Ser Tyr Asn Met Pro Gly Val
        5990                5995                6000

Val Ser Leu Glu Gly Thr Leu Asp Arg Glu Arg Phe Glu Leu Ala
        6005                6010                6015

Phe Leu Lys Leu Ile Ser Arg His Glu Thr Leu Arg Thr Gly Phe
        6020                6025                6030

Asp Met Val Asp Gly Glu Pro Ile Gln Arg Val His Arg Ser Val
        6035                6040                6045

Lys Phe Val Val Glu His Arg Lys Ala Ala Thr Val Gln Asp Ala
        6050                6055                6060

Glu Gln Leu Ile Arg Arg Phe Ile Arg Thr Phe Asp Leu Arg Lys
        6065                6070                6075
```

Pro Pro Leu Leu Arg Val Gly Leu Val Glu Leu Glu Arg Glu Arg
        6080                6085                6090

His Ile Leu Met Phe Asp Met His His Ile Ile Ser Asp Gly Ala
        6095                6100                6105

Ser Leu Gly Asn Leu Val Ser Glu Phe Ala Gln Leu Tyr Ala Gly
        6110                6115                6120

Glu Glu Arg Ala Pro Leu Arg Ile Gln Tyr Lys Asp Tyr Ala Val
        6125                6130                6135

Trp Gln Gln Ser Gly Val His Ser Glu His Met Lys Arg Gln Glu
        6140                6145                6150

Ala Tyr Trp Leu Glu Lys Leu Ala Gly Glu Leu Pro Val Val Glu
        6155                6160                6165

Leu Pro Thr Asp Tyr Asp Arg Pro Ala Val Arg Ser Phe Glu Gly
        6170                6175                6180

Ala Gln Ile Glu Phe Glu Val Asp Ala Ala Leu Thr Gln Arg Leu
        6185                6190                6195

Ser Gln Leu Ala Ser Asn Arg Glu Ser Thr Leu Tyr Met Val Leu
        6200                6205                6210

Leu Ser Ala Tyr Thr Val Leu Leu Ser Lys Tyr Ser Gly Gln Glu
        6215                6220                6225

Asp Ile Ile Val Gly Thr Pro Val Ala Gly Arg Ala His Ala Asp
        6230                6235                6240

Leu Glu Pro Leu Ile Gly Met Phe Val Asn Thr Leu Ala Ile Arg
        6245                6250                6255

Asn His Pro Ala Gly Asp Lys Thr Phe Leu Ser Leu Leu Glu Glu
        6260                6265                6270

Val Lys Glu Thr Ala Leu Gly Ala Phe Glu His Gln Asp Tyr Pro
        6275                6280                6285

Phe Glu Glu Leu Val Glu Arg Leu Asn Val Gln Trp Asp Ala Asn
        6290                6295                6300

Arg Asn Pro Val Phe Asp Thr Met Phe Val Met Gln Asn Thr Glu
        6305                6310                6315

Asp His Glu Val Arg Leu Glu Ala Leu Thr Leu Ser Pro Tyr Val
        6320                6325                6330

Leu Asp Asn Pro Ile Asp Ala Lys Phe Asp Leu Thr Leu Phe Val
        6335                6340                6345

Ser Glu Asp Asn Asp Val Ile Lys Gly Gly Phe Gln Tyr Gly Thr
        6350                6355                6360

Lys Leu Phe Lys Ala Ala Met Ile His Lys Ile Met Arg Asp Phe
        6365                6370                6375

Leu Leu Val Leu Ala Gln Ile Val Glu Asp Pro His Ile Arg Leu
        6380                6385                6390

Arg Asp Ile Lys Cys Asn Glu Gln Ser Val Asn Asn Gln Arg Ser
        6395                6400                6405

Ile Glu Thr Ile Glu Phe Ala Phe
        6410                6415

<210> SEQ ID NO 19
<211> LENGTH: 3170
<212> TYPE: PRT
<213> ORGANISM: Paenibacillus strain OSY SE

<400> SEQUENCE: 19

Met Lys Ser Val Phe Asp Lys Glu Glu Ala Tyr Trp Asn Glu Lys Phe

-continued

```
1               5                   10                  15
Asp Ser Glu Asp Ser Ile Ser Val Leu Pro Tyr Ser Asn Ser Ser Asn
            20                  25                  30

Asn Asn Met Gly Arg Val Asn Thr Met Gly Val Ile Asn Arg Thr Leu
            35                  40                  45

Pro Pro Glu Leu Ser Gln Arg Ile Ile Thr Leu Ala Asn Gly Ser Asp
            50                  55                  60

Met Ala Val Tyr Met Ile Val Leu Ala Gly Val Thr Ser Leu Leu Tyr
65                  70                  75                  80

Lys Tyr Thr Asn Arg Glu Asn Val Leu Val Gly Met Pro Ala Tyr Thr
                85                  90                  95

Ala Leu His Gly Glu His Pro Pro Ile His Asp Phe Leu Val Ile Lys
                100                 105                 110

Asn Asn Val Asn Ser Lys Ser Thr Phe Lys Ser Leu Leu Gly Gln Ile
                115                 120                 125

Lys Ala Ser Val Ser Glu Ala Leu Glu His Gln His Leu Pro Phe Arg
                130                 135                 140

Lys Met Phe Arg Gln Leu Asn Leu Gln Val Asp Pro Gln Gly Leu Pro
145                 150                 155                 160

Ile Val Asn Thr Leu Val Ser Tyr Thr Asn Ile His Thr Ala Ser Leu
                165                 170                 175

Glu Gln Ser Ala Ala Glu Ala Ala Phe Gln Phe Glu Phe Val Asn
                180                 185                 190

Asp Arg Ile Gln Leu Arg Met Ser Phe Asp Asp Asn Arg Tyr Arg Ser
                195                 200                 205

Asp Tyr Val Glu Ser Met Leu Ala His Phe Phe Arg Leu Leu Ser Val
        210                 215                 220

Val Leu Phe Gln Pro Glu Leu Glu Ile Gly Lys Val Glu Leu Leu Ser
225                 230                 235                 240

Glu His Glu Gln His His Leu Leu Ala Ile Leu Asn Asp Thr Arg Thr
                245                 250                 255

Glu Tyr Pro Arg Gln Lys Thr Leu His Gln Leu Phe Glu Glu Gln Ala
                260                 265                 270

Glu Arg Met Pro Asp Ala Leu Ala Ala Leu Phe Glu Asp Lys Arg Leu
        275                 280                 285

Thr Tyr Ala Glu Leu Asn Ala Ala Ala Asn Arg Ile Ala Arg Leu Leu
        290                 295                 300

Arg Asp Arg Gly Val Val Arg Gly Thr Leu Val Gly Ile Cys Ala Glu
305                 310                 315                 320

Arg Ser Leu Glu Met Val Ile Gly Leu Leu Gly Ile Leu Lys Ala Gly
                325                 330                 335

Gly Ala Tyr Val Pro Ile Asp Pro Ser Tyr Pro Gln Glu Arg Ile Asn
                340                 345                 350

Ala Met Leu Glu Asp Thr Ala Ile Ser Val Met Leu Thr Gln Ala His
                355                 360                 365

Leu Gln Thr Ser Val Pro Asn Ser Leu Asp Ser Val Leu Leu Asp Thr
                370                 375                 380

Ala Ala Glu Met Thr Leu Glu Gly Ser Trp Pro Asn Leu Thr Asp Thr
385                 390                 395                 400

Ala Ala Thr Ala Asp Asp Val Ala Tyr Ile Ile Tyr Thr Ser Gly Ser
                405                 410                 415

Thr Gly Ile Pro Lys Gly Val Cys Val Thr His Arg Gly Val Val Arg
                420                 425                 430
```

```
Leu Val Val Ala Ala Asn Tyr Val Asp Ile Ser Ser Lys Asp Val Phe
            435                 440                 445

Leu Gln Gly Ser Thr Ile Ser Phe Asp Ala Ala Thr Phe Glu Ile Trp
            450                 455                 460

Gly Ser Leu Leu Asn Gly Ala Ala Leu Ala Ile Leu Pro Pro Gly Asn
465             470                 475                 480

Leu Ser Leu Thr Glu Trp Thr Gln Ala Ile Gln Gln His Gln Val Thr
            485                 490                 495

Ile Leu Trp Leu Thr Ala Gly Leu Phe His Val Met Val Glu Asn Gln
            500                 505                 510

Leu Gln Ala Leu Gln Gly Val Gln Gln Leu Leu Val Gly Gly Asp Val
            515                 520                 525

Val Ser Gln Thr His Ala Lys Lys Val Leu Glu Arg Tyr Lys Asp Ile
            530                 535                 540

Arg Leu Val Asn Gly Tyr Gly Pro Thr Glu Asn Thr Thr Phe Thr Cys
545             550                 555                 560

Cys His Glu Ile Ser Ala Ala Asp Met Glu Arg Leu Ser Ile Pro Ile
                565                 570                 575

Gly Arg Pro Ile Ala Asn Thr Gln Val Tyr Val Leu Asp Glu Ala Gly
            580                 585                 590

Lys Leu Leu Pro Val Gly Val Val Gly Glu Leu Tyr Thr Gly Gly Asp
            595                 600                 605

Gly Leu Ala Gln Gly Tyr Trp Asn Arg Pro Glu Leu Thr Ala Glu Lys
            610                 615                 620

Phe Val Asp Asn Pro Phe Val Pro Gly Thr Arg Leu Tyr Arg Thr Gly
625             630                 635                 640

Asp Leu Ala Arg Trp Leu Pro Asp Gly Thr Leu Glu Tyr Val Gly Arg
            645                 650                 655

Ile Asp Asp Gln Val Lys Ile Arg Gly Tyr Arg Ile Glu Leu Gly Glu
            660                 665                 670

Val Glu Ala His Leu Leu Lys Val Glu Ser Val Leu Asp Ala Ile Val
            675                 680                 685

Ile Ala Arg Gln Asp Glu Ser Gly Gln Lys Thr Leu Cys Ala Tyr Phe
            690                 695                 700

Thr Ala His Ala Glu Leu Met Ala Gly Asp Leu Arg Ala Ala Leu Ser
705             710                 715                 720

Gln Glu Leu Pro Val Tyr Met Ile Pro Thr His Leu Val Gln Val Asp
            725                 730                 735

Gln Met Pro Leu Thr Pro Asn Gly Lys Val Asp Arg Arg Ala Leu Pro
            740                 745                 750

Glu Pro Glu Gly Leu Ile Met Thr Gly Ile Glu His Val Ala Pro Arg
            755                 760                 765

Ser Pro Leu Glu Ser Lys Leu Ala His Ile Trp Gln Glu Val Leu Gly
            770                 775                 780

Leu Glu Lys Val Ser Val Lys Asp Ser Phe Phe Glu Ile Gly Gly His
785             790                 795                 800

Ser Leu Arg Ala Thr Thr Leu Ala Ser Lys Leu His Lys Glu Leu His
                805                 810                 815

Val Ser Leu Leu Leu Arg Asp Ile Phe Arg His Pro Thr Ile Glu Glu
            820                 825                 830

Leu Ala Arg Leu Ile Asp Gly Met Glu Arg Gln Ala Tyr Arg Gln Ile
            835                 840                 845
```

```
Pro Leu Leu Asp Glu Arg Asp Trp Tyr Pro Val Ser Ser Ala Gln Lys
    850                 855                 860
Arg Leu Tyr Ile Leu His Gln Leu Glu Gly Ala Glu Gln Ser Tyr Asn
865                 870                 875                 880
Met Pro Gly Val Met Leu Leu Glu Gly Gln Leu Asp Arg Asn Arg Phe
                885                 890                 895
Glu Glu Ala Phe Gly Ser Leu Ile Gly Arg His Glu Thr Leu Arg Thr
            900                 905                 910
Gly Phe Glu Met Val Asn Gly Glu Pro Val Gln Arg Val Cys Arg Glu
        915                 920                 925
Val Asn Phe Ser Val Glu Met Met Gln Ala Ser Glu Glu Ala Glu
930                 935                 940
Ala Val Val Arg Ser Phe Ile Arg Pro Phe Asp Leu Glu Lys Pro Pro
945                 950                 955                 960
Leu Leu Arg Val Gly Leu Ile Glu Leu Asp Gln Asp Arg His Ile Leu
                965                 970                 975
Met Tyr Asp Met His His Ile Ile Ser Asp Gly Val Ser Met Gly Ile
            980                 985                 990
Val Val Glu Glu Phe Val Arg Leu Tyr Gly Gly Glu Glu Leu Pro Pro
        995                 1000                1005
Pro Arg Ile Gln Tyr Lys Asp Tyr Ala Ala Trp Gln Gln Ser Glu
    1010                1015                1020
Pro Gln Gln Glu Leu Met Lys Gln Glu Ser Tyr Trp Leu Gln
    1025                1030                1035
Ser Leu Gly Gly Glu Leu Pro Val Leu Glu Leu Pro Ala Asp Tyr
    1040                1045                1050
Ala Arg Pro Ser Val Gln Ser Tyr Glu Gly Asp Thr Phe Glu Phe
    1055                1060                1065
Ala Ile Asp Pro Arg Leu Ser Glu Ala Leu His Gly Val Ala Ala
    1070                1075                1080
Glu Ser Gly Thr Thr Leu Tyr Met Val Leu Leu Ala Ala Tyr Thr
    1085                1090                1095
Ile Leu Leu His Lys Tyr Thr Gly Gln Glu Asp Ile Ile Val Gly
    1100                1105                1110
Thr Pro Asn Ala Gly Arg Thr His Gly Asp Leu Gln Pro Leu Ile
    1115                1120                1125
Gly Met Phe Val Asn Thr Leu Ala Ile Arg Asn Tyr Pro Ala Gly
    1130                1135                1140
Ser Lys Thr Phe Leu Glu Tyr Leu Glu Glu Val Lys Glu Thr Ser
    1145                1150                1155
Leu Gly Ala Phe Glu Asn Gln Asp Tyr Pro Phe Glu Glu Leu Val
    1160                1165                1170
Glu Lys Leu Gln Val Ala Arg Asp Leu Ser Arg Asn Pro Leu Phe
    1175                1180                1185
Asp Thr Met Phe Ala Leu Gln Asn Met Asp Asp Lys Asp Leu Glu
    1190                1195                1200
Leu Ala Gly Leu Arg Leu Lys Pro Tyr Pro Ala Glu Tyr Lys Val
    1205                1210                1215
Ala Lys Phe Asp Leu Ser Leu Asp Val Ala Glu Gly Val Glu Gly
    1220                1225                1230
Met Ala Cys Ser Leu Glu Tyr Ala Thr Ala Leu Tyr Arg Pro Glu
    1235                1240                1245
Ser Ile Glu Arg Met Ala Lys His Phe Gly Arg Leu Leu Glu Ala
```

```
                1250                1255                1260

Val Ala His Glu Pro Glu Ala Arg Leu Ala Ser Leu Gly Met Leu
            1265                1270                1275

Thr Glu Glu Glu Glu Gln Ile Arg His Val Phe Asn Asp Thr
        1280                1285                1290

Glu Ala Gly Arg Ser Gln Gln Asn Thr Val Pro Glu Leu Phe Glu
            1295                1300                1305

Glu Gln Val Glu Arg Thr Pro Asp Arg Ile Ala Val Val His Glu
            1310                1315                1320

Asp Lys Gln Leu Thr Tyr Arg Glu Leu Asn Glu Arg Ala Asn Arg
            1325                1330                1335

Leu Ala Arg Thr Leu Arg Ala Glu Gly Val Lys Pro Glu Gln Leu
            1340                1345                1350

Val Gly Ile Met Ala Asp Arg Ser Leu Glu Met Ile Val Gly Ile
            1355                1360                1365

Met Ala Ile Leu Lys Ser Gly Gly Ala Tyr Val Pro Ile Asp Pro
            1370                1375                1380

Gln Tyr Pro Glu Asp Arg Ile His Tyr Met Leu Asp Asn Ser Asn
            1385                1390                1395

Ala Gln Val Leu Leu Ala Gln Arg His Leu Gln Ala Arg Ala Ala
            1400                1405                1410

Phe Ser Gly Arg Arg Ile Met Leu Asp Glu Glu Ala Phe Tyr Gly
            1415                1420                1425

Ala Asp Gly Ser Asn Leu Glu Arg Val Asn Gln Pro Glu His Leu
            1430                1435                1440

Ser Tyr Val Ile Tyr Thr Ser Gly Thr Thr Gly Lys Pro Lys Gly
            1445                1450                1455

Val Met Ile Glu His Arg Gln Met Ala Val Leu Ser Ala Ala Trp
            1460                1465                1470

Glu Arg Glu Tyr Gly Leu Gln Glu Glu Ser Met Arg Trp Met Gln
            1475                1480                1485

Trp Ala Ser Phe Ser Phe Asp Val Phe Ser Gly Asp Leu Ile Arg
            1490                1495                1500

Ala Leu Leu His Gly Gly Glu Leu Ile Leu Cys Pro Glu Asp Ala
            1505                1510                1515

Arg Ala Asn Pro Ala Glu Ile Tyr Glu Leu Ile Arg Lys His Arg
            1520                1525                1530

Ile Gln Met Phe Asp Val Thr Pro Ser Leu Val Ile Pro Leu Met
            1535                1540                1545

Glu Tyr Val Tyr Glu Asn Lys Leu Asp Ile Ser Ser Met Lys Leu
            1550                1555                1560

Ala Val Val Gly Ala Asp His Cys Pro Lys Glu Glu Phe Gln Lys
            1565                1570                1575

Leu Leu Glu Arg Phe Gly Ser Gln Met Arg Ile Val Asn Ser Tyr
            1580                1585                1590

Gly Val Thr Glu Thr Thr Ile Asp Ser Cys Tyr Phe Glu Gln Ala
            1595                1600                1605

Ser Thr Glu Gly Leu Arg Thr Val Pro Ile Gly Lys Pro Leu Pro
            1610                1615                1620

Gly Val Thr Met Tyr Ile Leu Asp Asp Gln His Ser Leu Leu Pro
            1625                1630                1635

Val Gly Ile Thr Gly Glu Leu Tyr Ile Gly Gly Pro Cys Val Gly
            1640                1645                1650
```

-continued

Arg Gly Tyr Trp Lys Arg Pro Asp Leu Thr Ala Glu Lys Phe Val
1655                1660                1665

Asp Asn Pro Phe Ala Pro Gly Glu Arg Met Tyr Arg Thr Gly Asp
1670                1675                1680

Leu Ala Arg Trp Leu Pro Asp Gly Asn Val Glu Tyr Leu Gly Arg
1685                1690                1695

Ile Asp His Gln Val Lys Ile Arg Gly Tyr Arg Ile Glu Ile Gly
1700                1705                1710

Glu Val Glu Thr Gln Leu Leu Arg Thr Pro Phe Ile Arg Glu Ala
1715                1720                1725

Val Val Val Ala Arg Glu Asp Val Ser Gly Gln Lys Ser Leu Cys
1730                1735                1740

Ala Tyr Phe Val Ala Glu Arg Glu Leu Thr Val Ser Glu Leu Arg
1745                1750                1755

Arg Ala Leu Ala Ala Glu Leu Pro Gly Tyr Met Ile Pro Ser Tyr
1760                1765                1770

Phe Val Gln Met Glu Arg Leu Pro Leu Thr Pro Asn Gly Lys Ile
1775                1780                1785

Asp Arg Lys Ala Leu Pro Ala Pro Glu Gly Ser Ala His Thr Gly
1790                1795                1800

Ala Glu Phe Val Ala Pro Arg Thr Ser Leu Glu Ala Gln Leu Ala
1805                1810                1815

Arg Ile Trp Gln Glu Val Leu Gly Leu Pro Asp Val Ser Val Lys
1820                1825                1830

Asp Asn Phe Phe Asp Leu Gly Gly His Ser Leu Arg Ala Thr Thr
1835                1840                1845

Leu Ala Ser Lys Val Phe Lys Glu Met His Ile Asn Leu Pro Leu
1850                1855                1860

Arg Asp Val Phe Arg Tyr Pro Thr Ile Glu Glu Leu Ala Glu Leu
1865                1870                1875

Ile Ala Gly Met Lys Lys Gln Glu Tyr Ala Val Ile Pro Leu Ala
1880                1885                1890

Glu Glu Arg Asp Val Tyr Pro Leu Ser Ser Ala Gln Lys Arg Leu
1895                1900                1905

Tyr Ile Val Ser Gln Leu Glu Gly Ala Glu Leu Ser Tyr Asn Met
1910                1915                1920

Pro Gly Val Ile Thr Leu Glu Gly Pro Leu Asp Arg Thr Arg Phe
1925                1930                1935

Asp Gly Ala Phe Gln Gln Leu Ile Ala Arg His Glu Ala Leu Arg
1940                1945                1950

Thr Gly Phe Glu Met Val Asn Gly Glu Pro Val Gln Arg Ile His
1955                1960                1965

Arg Asp Val Arg Leu Thr Val Glu Tyr Val Gln Ala Asp Glu Glu
1970                1975                1980

Glu Ala Glu Lys Leu Val Gln Arg Phe Val Arg Ser Phe Asp Leu
1985                1990                1995

Lys Leu Arg Pro Leu Leu Arg Val Gly Leu Ile Ala Ile Glu Arg
2000                2005                2010

Glu Arg His Ile Leu Met Phe Asp Met His His Ile Ile Ser Asp
2015                2020                2025

Gly Val Thr Met Gly Ile Leu Val Asp Glu Phe Ala Arg Leu Tyr
2030                2035                2040

```
Ala Gly Glu Asp Leu Pro Pro Leu Arg Ile Gln Tyr Lys Asp Tyr
    2045                2050                2055

Ala Val Trp Gln Gln Ser Glu Asp Arg Ser Val Glu Leu Arg Arg
    2060                2065                2070

Gln Glu Ala Tyr Trp Leu Glu Arg Leu Gln Gly Glu Leu Pro Val
    2075                2080                2085

Leu Glu Leu Pro Thr Asp Tyr Val Arg Pro Ala Val Gln Lys Phe
    2090                2095                2100

Asp Gly Asp Val Ala Leu Phe Thr Ile Asp Pro His Leu Ser Glu
    2105                2110                2115

Gln Leu Arg Arg Leu Ala Ser Asp Thr Gly Ser Thr Leu Tyr Met
    2120                2125                2130

Val Leu Leu Ala Ala Tyr Thr Thr Leu Leu His Lys Tyr Thr Gly
    2135                2140                2145

Gln Glu Asp Ile Ile Val Gly Thr Pro Ile Ala Gly Arg Ser His
    2150                2155                2160

Ser Asp Leu Glu Pro Leu Ile Gly Met Phe Val Asn Thr Leu Ala
    2165                2170                2175

Val Arg Asn Tyr Pro Ala Ser Glu Lys Ala Phe Leu Ser Tyr Leu
    2180                2185                2190

Ala Glu Val Lys Glu Thr Thr Leu Gly Ala Phe Glu His Gln Asp
    2195                2200                2205

Tyr Pro Phe Glu Asp Leu Val Glu Lys Val Arg Val Ser Arg Asp
    2210                2215                2220

Leu Ser Arg Asn Pro Leu Phe Asp Thr Met Phe Ser Leu Glu Asn
    2225                2230                2235

Ala Glu Gln Gly Gly Ile Glu Ile Glu Gly Leu Gln Leu Lys Ser
    2240                2245                2250

Tyr Pro Asn Glu His Met Thr Ala Lys Phe Asp Leu Thr Phe His
    2255                2260                2265

Ala Glu Glu Gly Glu Glu Gly Ile Leu Cys Gly Leu Val Tyr Ala
    2270                2275                2280

Thr Ala Leu Tyr Lys Arg Asp Thr Val Glu Arg Met Met Leu His
    2285                2290                2295

Phe Lys Gln Leu Leu Ala Ala Ile Ala His Asp Pro Arg Ala Gln
    2300                2305                2310

Leu Ser Thr Leu Asn Met Met Thr Ala Gln Glu Arg Glu Glu Ile
    2315                2320                2325

Ile Gly Val Phe Asn Asp Thr Gly Thr Lys Tyr Pro Arg Glu Lys
    2330                2335                2340

Thr Ile Gln His Leu Phe Glu Glu Gln Val Glu Arg Thr Pro Asp
    2345                2350                2355

Ala Ala Ala Ile Val Tyr Gly Asp Glu Arg Met Thr Tyr Arg Glu
    2360                2365                2370

Leu Asn Gly Arg Ala Asn Arg Leu Ala Arg Thr Leu Arg Thr Lys
    2375                2380                2385

Gly Val Gln Ala Asp Arg Leu Val Gly Leu Met Ala Glu Arg Ser
    2390                2395                2400

Leu Glu Met Ile Val Gly Ile Leu Ala Ile Leu Lys Ala Gly Gly
    2405                2410                2415

Ala Tyr Val Pro Ile Asp Pro Glu Tyr Pro Glu Glu Arg Val Arg
    2420                2425                2430

Tyr Met Leu Glu Asp Ser Gly Thr Gln Ile Ile Leu Thr Gln His
```

```
                2435                    2440                    2445
Glu Leu Gln Ser Arg Ile Pro Val Gln Ala Ser Phe Val Leu Leu
    2450                    2455                    2460
Asp Asp Glu His Ser Tyr Ser Ala Asp Ser Asn Leu Glu Gln
    2465                    2470                    2475
Asn Asn Gly Pro Ala Asp Leu Ala Tyr Val Ile Tyr Thr Ser Gly
    2480                    2485                    2490
Thr Thr Gly Lys Pro Lys Gly Asn Leu Ala Thr His Arg Asn Ile
    2495                    2500                    2505
Val Arg Val Val Gln Gly Thr Ser Tyr Ile Asp Phe Ser Glu Arg
    2510                    2515                    2520
Asp Asn Val Leu Gln Leu Ser Asn Tyr Ala Phe Asp Gly Ser Thr
    2525                    2530                    2535
Phe Asp Met Tyr Gly Ala Leu Leu Asn Gly Ala Lys Leu Val Leu
    2540                    2545                    2550
Ile Pro Gln Glu Thr Leu Leu Glu Val Gly Lys Leu Ala Gly Leu
    2555                    2560                    2565
Ile Glu Arg Glu Arg Ile Ser Val Met Phe Ile Thr Thr Ala Tyr
    2570                    2575                    2580
Phe Asn Ile Leu Ile Asp Met Lys Ala Asp Cys Leu Arg His Ile
    2585                    2590                    2595
Arg Thr Ile Leu Phe Gly Gly Glu Arg Val Ser Ile Ser His Val
    2600                    2605                    2610
Arg Lys Ala Leu Tyr Gln Leu Gly Pro Gly Lys Ile Lys His Val
    2615                    2620                    2625
Tyr Gly Pro Thr Glu Ser Thr Val Phe Ala Thr Cys His Asp Val
    2630                    2635                    2640
Asn Glu Val Ala Glu Asp Ala Val Thr Val Pro Ile Gly Arg Pro
    2645                    2650                    2655
Ile Ser Asn Thr Thr Ile Tyr Ile Val Asn Ala Gln Asn Asp Leu
    2660                    2665                    2670
Gln Pro Ile Gly Val Ala Gly Glu Leu Cys Ile Ala Gly Asp Gly
    2675                    2680                    2685
Leu Ala Arg Gly Tyr Leu Asn Arg Pro Glu Leu Thr Ala Ala Lys
    2690                    2695                    2700
Phe Val Asp Asn Pro Phe Ala Pro Arg Glu Arg Met Tyr Arg Thr
    2705                    2710                    2715
Gly Asp Leu Ala Arg Trp Leu Pro Asp Gly Thr Ile Glu Tyr Val
    2720                    2725                    2730
Gly Arg Ile Asp Asp Gln Val Lys Ile Arg Gly Tyr Arg Ile Glu
    2735                    2740                    2745
Leu Gly Glu Val Glu Thr His Leu Leu Arg Val Glu Pro Ile Gln
    2750                    2755                    2760
Glu Ala Thr Val Ile Ala Arg Glu Ser Asp Ser Gly Glu Lys Arg
    2765                    2770                    2775
Leu Cys Ala Tyr Tyr Val Ala Asp Arg Pro Leu Pro Ala Asn Glu
    2780                    2785                    2790
Leu Arg Gly Ile Leu Ala Gln Asp Leu Pro Gly Tyr Met Ile Pro
    2795                    2800                    2805
Leu His Phe Val Gln Leu Asp Arg Met Pro Leu Thr Pro Asn Gly
    2810                    2815                    2820
Lys Val Asp Arg Lys Ala Leu Pro Ala Pro Glu Asp His Leu Met
    2825                    2830                    2835
```

Thr Gly Thr Glu Tyr Val Ala Pro Arg Thr Thr Gln Glu Ala Gln
    2840                2845                2850

Leu Ala Gln Ile Trp Gln Glu Val Leu Gly Ile Glu Lys Ile Gly
    2855                2860                2865

Val Gln Asp Asn Phe Phe Glu Leu Gly Gly His Ser Ile Ser Leu
    2870                2875                2880

Met Gln Leu Ile His Arg Ile Tyr Ile Glu Leu Gly Ala Glu Ile
    2885                2890                2895

Ala Leu His Ser Val Phe Gln Arg Pro Thr Val Glu Ala Met Ala
    2900                2905                2910

Tyr Glu Ile Val Lys Val Glu Tyr Glu Glu Lys Ser Ser Ser Gln
    2915                2920                2925

Phe Thr Lys Leu Asn Glu Asn Gly Leu Val Asn Val Phe Cys Leu
    2930                2935                2940

Pro Pro Gly Phe Gly Tyr Gly Leu Ser Tyr Leu Glu Leu Ala Lys
    2945                2950                2955

Gln Met Glu Asn Ser Cys Ile Leu Tyr Gly Ile Asp Phe Ile Asp
    2960                2965                2970

Asp Ala Glu Ser Tyr Glu Asp Met Leu Asp Arg Tyr Val Asp Ala
    2975                2980                2985

Val Val Ala Ile Gln Ser Gln Ser Pro Tyr Val Leu Leu Gly Tyr
    2990                2995                3000

Ser Leu Gly Gly Asn Leu Thr Phe Glu Ile Ala Lys Ala Met Glu
    3005                3010                3015

Lys Arg Gly Tyr Arg Val Ser Asp Ile Ile Met Leu Asp Ser Thr
    3020                3025                3030

Arg Lys Leu Ala Ala Gln Thr Val Asp Glu Phe Glu Ser Asp Ile
    3035                3040                3045

Asp Gln Met Leu Glu Ala Val Gly Glu Gln Glu Met Gln Leu Leu
    3050                3055                3060

Ser Asn Pro Leu Ile Arg Glu Arg Val Lys His Lys Met Arg Ala
    3065                3070                3075

Tyr Trp Thr Tyr Gly Ser Gln Leu Val Asn Thr Gly Ala Val Glu
    3080                3085                3090

Ala Asn Ile Tyr Ala Leu Ile Ala Glu Asp Ser Asp Ala Val Arg
    3095                3100                3105

Pro Asp Asn Val Thr Ser Ala Leu Trp Asp Gly Ala Thr Arg Gln
    3110                3115                3120

Ala Tyr Cys Glu His Arg Leu Ile Gly Val His Glu Asp Val Leu
    3125                3130                3135

Leu Pro Gly Phe Ile Glu His Asn Val Lys Val Ile His Ala Val
    3140                3145                3150

Val His Gln Ile Ile Glu Gln Thr Arg Gly Val His Glu Val Leu
    3155                3160                3165

Ser Arg
    3170

<210> SEQ ID NO 20
<211> LENGTH: 34
<212> TYPE: PRT
<213> ORGANISM: Paenibacillus strain A6-6i

<400> SEQUENCE: 20

Leu Ala Trp Ala Phe Asp Val Phe Thr Gly Asp Arg Glu Ser Val Val

```
                1               5                  10                  15
Gly Ser Asp Leu Asn Ser Tyr Gly Val Thr Glu Ala Cys Val Asp Ala
                20                  25                  30

Cys Tyr

<210> SEQ ID NO 21
<211> LENGTH: 10
<212> TYPE: PRT
<213> ORGANISM: Paenibacillus strain A6-6i

<400> SEQUENCE: 21

Asp Val Gly Glu Val Gly Ser Val Asp Lys
1               5                   10

<210> SEQ ID NO 22
<211> LENGTH: 34
<212> TYPE: PRT
<213> ORGANISM: Paenibacillus strain A6-6i

<400> SEQUENCE: 22

Leu Gly Ala Ser Phe Asp Ala Ala Thr Phe Glu Gly Trp Met Leu Val
1               5                   10                  15

Gly Gly Asp Ile Asn Gly Tyr Gly Pro Thr Glu Asn Thr Thr Phe Thr
                20                  25                  30

Cys Cys

<210> SEQ ID NO 23
<211> LENGTH: 10
<212> TYPE: PRT
<213> ORGANISM: Paenibacillus strain A6-6i

<400> SEQUENCE: 23

Asp Ala Phe Trp Leu Gly Gly Thr Phe Lys
1               5                   10

<210> SEQ ID NO 24
<211> LENGTH: 34
<212> TYPE: PRT
<213> ORGANISM: Paenibacillus strain A6-6i

<400> SEQUENCE: 24

Leu Asn Ser His Phe Asp Phe Ser Val Trp Glu Gly Asn Gln Ile Phe
1               5                   10                  15

Gly Gly Glu Ile Asn Met Tyr Gly Ile Thr Glu Thr Thr Val His Val
                20                  25                  30

Thr Tyr

<210> SEQ ID NO 25
<211> LENGTH: 10
<212> TYPE: PRT
<213> ORGANISM: Paenibacillus strain A6-6i

<400> SEQUENCE: 25

Asp Phe Trp Asn Ile Gly Met Val His Lys
1               5                   10

<210> SEQ ID NO 26
<211> LENGTH: 34
<212> TYPE: PRT
<213> ORGANISM: Paenibacillus strain A6-6i

<400> SEQUENCE: 26
```

```
Met Ala Trp Ala Phe Asp Val Phe Ser Gly Asp Arg Glu Ser Ile Ile
1               5                   10                  15

Gly Ser Asp Ile Asn Ser Tyr Gly Val Thr Glu Ala Cys Val Asp Ser
            20                  25                  30

Ser Tyr

<210> SEQ ID NO 27
<211> LENGTH: 10
<212> TYPE: PRT
<213> ORGANISM: Paenibacillus strain A6-6i

<400> SEQUENCE: 27

Asp Val Gly Glu Ile Gly Ser Val Asp Lys
1               5                   10

<210> SEQ ID NO 28
<211> LENGTH: 34
<212> TYPE: PRT
<213> ORGANISM: Paenibacillus strain A6-6i

<400> SEQUENCE: 28

Arg Trp Met Thr Phe Asp Val Ser Val Trp Glu Trp His Phe Phe Thr
1               5                   10                  15

Ser Gly Glu Ile Asn Leu Tyr Gly Pro Thr Glu Ala Thr Val Asp Val
            20                  25                  30

Thr Tyr

<210> SEQ ID NO 29
<211> LENGTH: 10
<212> TYPE: PRT
<213> ORGANISM: Paenibacillus strain A6-6i

<400> SEQUENCE: 29

Asp Val Trp His Phe Ser Leu Val Asp Lys
1               5                   10

<210> SEQ ID NO 30
<211> LENGTH: 34
<212> TYPE: PRT
<213> ORGANISM: Paenibacillus strain A6-6i

<400> SEQUENCE: 30

Ala Trp Arg Phe Phe Asp Gly Phe Val Met Ser Cys Ile Cys Thr Leu
1               5                   10                  15

Ala Gly Glu Phe Asn Glu Tyr Gly Pro Thr Glu Asn Ser Val Val Ala
            20                  25                  30

Thr Cys

<210> SEQ ID NO 31
<211> LENGTH: 10
<212> TYPE: PRT
<213> ORGANISM: Paenibacillus strain A6-6i

<400> SEQUENCE: 31

Asp Gly Met Ile Thr Ala Glu Val Val Lys
1               5                   10

<210> SEQ ID NO 32
<211> LENGTH: 34
<212> TYPE: PRT
<213> ORGANISM: Paenibacillus strain A6-6i
```

<400> SEQUENCE: 32

Met Ala Trp Ala Phe Asp Val Phe Ser Gly Asp Arg Asp Cys Ala Val
1               5                   10                  15

Gly Ser Asp Ile Asn Ser Tyr Gly Val Thr Glu Thr Cys Ile Asp Ala
            20                  25                  30

Ser Tyr

<210> SEQ ID NO 33
<211> LENGTH: 10
<212> TYPE: PRT
<213> ORGANISM: Paenibacillus strain A6-6i

<400> SEQUENCE: 33

Asp Val Gly Asp Ala Gly Ser Ile Asp Lys
1               5                   10

<210> SEQ ID NO 34
<211> LENGTH: 34
<212> TYPE: PRT
<213> ORGANISM: Paenibacillus strain A6-6i

<400> SEQUENCE: 34

Arg Trp Met Thr Phe Asp Val Ser Val Trp Glu Trp His Phe Phe Thr
1               5                   10                  15

Ser Gly Glu Ile Asn Leu Tyr Gly Pro Thr Glu Ala Thr Val Asp Val
            20                  25                  30

Thr Tyr

<210> SEQ ID NO 35
<211> LENGTH: 10
<212> TYPE: PRT
<213> ORGANISM: Paenibacillus strain A6-6i

<400> SEQUENCE: 35

Asp Val Trp His Phe Ser Leu Val Asp Lys
1               5                   10

<210> SEQ ID NO 36
<211> LENGTH: 34
<212> TYPE: PRT
<213> ORGANISM: Paenibacillus strain A6-6i

<400> SEQUENCE: 36

Val Glu Thr Ser Phe Asp Gly Ser Thr Phe Asp Gly Phe Ile Leu Phe
1               5                   10                  15

Gly Gly Glu Lys His Val Tyr Gly Pro Thr Glu Ser Thr Val Phe Ala
            20                  25                  30

Thr Cys

<210> SEQ ID NO 37
<211> LENGTH: 10
<212> TYPE: PRT
<213> ORGANISM: Paenibacillus strain A6-6i

<400> SEQUENCE: 37

Asp Gly Phe Phe Leu Gly Val Val Phe Lys
1               5                   10

<210> SEQ ID NO 38
<211> LENGTH: 34

```
<212> TYPE: PRT
<213> ORGANISM: Paenibacillus strain A6-6i

<400> SEQUENCE: 38

Leu Tyr Gln Ala Phe Asp Val Cys Tyr Gln Glu Ser Phe Ile Ile Thr
1               5                   10                  15

Ala Gly Glu His Asn His Tyr Gly Pro Ser Glu Thr His Val Val Thr
            20                  25                  30

Thr Tyr

<210> SEQ ID NO 39
<211> LENGTH: 10
<212> TYPE: PRT
<213> ORGANISM: Paenibacillus strain A6-6i

<400> SEQUENCE: 39

Asp Val Gln Phe Ile Ala His Val Val Lys
1               5                   10

<210> SEQ ID NO 40
<211> LENGTH: 34
<212> TYPE: PRT
<213> ORGANISM: Paenibacillus strain A6-6i

<400> SEQUENCE: 40

Ile Asn Thr Ser Phe Asp Gly Ser Ala Phe Asp Gly Leu Ile Leu Phe
1               5                   10                  15

Gly Gly Glu Lys His Ala Tyr Gly Pro Ser Glu Ser Thr Val Tyr Ala
            20                  25                  30

Thr Trp

<210> SEQ ID NO 41
<211> LENGTH: 10
<212> TYPE: PRT
<213> ORGANISM: Paenibacillus strain A6-6i

<400> SEQUENCE: 41

Asp Gly Phe Leu Leu Gly Ala Val Tyr Lys
1               5                   10

<210> SEQ ID NO 42
<211> LENGTH: 34
<212> TYPE: PRT
<213> ORGANISM: Paenibacillus strain A6-6i

<400> SEQUENCE: 42

Leu Tyr Gln Ala Phe Asp Val Cys Tyr Gln Glu Ser Tyr Ile Ile Thr
1               5                   10                  15

Ala Gly Glu His Asn His Tyr Gly Pro Ser Glu Thr His Val Val Thr
            20                  25                  30

Thr Tyr

<210> SEQ ID NO 43
<211> LENGTH: 10
<212> TYPE: PRT
<213> ORGANISM: Paenibacillus strain A6-6i

<400> SEQUENCE: 43

Asp Val Gln Tyr Ile Ala His Val Val Lys
1               5                   10
```

```
<210> SEQ ID NO 44
<211> LENGTH: 34
<212> TYPE: PRT
<213> ORGANISM: Paenibacillus strain A6-6i

<400> SEQUENCE: 44

Val Asp Ala Ser Phe Asp Gly Ser Thr Phe Asp Gly Phe Ile Leu Phe
1               5                   10                  15

Gly Gly Glu Lys His Val Tyr Gly Pro Thr Glu Ser Thr Val Phe Ala
            20                  25                  30

Thr Ser

<210> SEQ ID NO 45
<211> LENGTH: 10
<212> TYPE: PRT
<213> ORGANISM: Paenibacillus strain A6-6i

<400> SEQUENCE: 45

Asp Gly Phe Phe Leu Gly Val Val Phe Lys
1               5                   10

<210> SEQ ID NO 46
<211> LENGTH: 34
<212> TYPE: PRT
<213> ORGANISM: Paenibacillus strain TS-15

<400> SEQUENCE: 46

Leu Ala Trp Ala Phe Asp Val Phe Thr Gly Asp Arg Glu Ser Val Val
1               5                   10                  15

Gly Ser Asp Leu Asn Ser Tyr Gly Val Thr Glu Ala Cys Val Asp Ala
            20                  25                  30

Cys Tyr

<210> SEQ ID NO 47
<211> LENGTH: 10
<212> TYPE: PRT
<213> ORGANISM: Paenibacillus strain TS-15

<400> SEQUENCE: 47

Asp Val Gly Glu Val Gly Ser Val Asp Lys
1               5                   10

<210> SEQ ID NO 48
<211> LENGTH: 34
<212> TYPE: PRT
<213> ORGANISM: Paenibacillus strain TS-15

<400> SEQUENCE: 48

Leu Ala Ala Ser Phe Asp Ala Ala Thr Phe Glu Gly Trp Met Leu Val
1               5                   10                  15

Gly Gly Asp Ile Asn Gly Tyr Gly Pro Thr Glu Asn Thr Thr Phe Thr
            20                  25                  30

Cys Cys

<210> SEQ ID NO 49
<211> LENGTH: 10
<212> TYPE: PRT
<213> ORGANISM: Paenibacillus strain TS-15

<400> SEQUENCE: 49

Asp Ala Phe Trp Leu Gly Gly Thr Phe Lys
1               5                   10
```

<210> SEQ ID NO 50
<211> LENGTH: 34
<212> TYPE: PRT
<213> ORGANISM: Paenibacillus strain TS-15

<400> SEQUENCE: 50

Leu Asn Ser His Phe Asp Phe Ser Val Trp Glu Gly Asn Gln Ile Phe
1               5                   10                  15

Gly Gly Glu Ile Asn Met Tyr Gly Ile Thr Glu Thr Thr Val His Val
            20                  25                  30

Thr Tyr

<210> SEQ ID NO 51
<211> LENGTH: 10
<212> TYPE: PRT
<213> ORGANISM: Paenibacillus strain TS-15

<400> SEQUENCE: 51

Asp Phe Trp Asn Ile Gly Met Val His Lys
1               5                   10

<210> SEQ ID NO 52
<211> LENGTH: 34
<212> TYPE: PRT
<213> ORGANISM: Paenibacillus strain TS-15

<400> SEQUENCE: 52

Met Ala Trp Ala Phe Asp Val Phe Ser Gly Asp Arg Glu Ser Ile Ile
1               5                   10                  15

Gly Ser Asp Ile Asn Ser Tyr Gly Val Thr Glu Ala Cys Val Asp Ser
            20                  25                  30

Ser Tyr

<210> SEQ ID NO 53
<211> LENGTH: 10
<212> TYPE: PRT
<213> ORGANISM: Paenibacillus strain TS-15

<400> SEQUENCE: 53

Asp Val Gly Glu Ile Gly Ser Val Asp Lys
1               5                   10

<210> SEQ ID NO 54
<211> LENGTH: 34
<212> TYPE: PRT
<213> ORGANISM: Paenibacillus strain TS-15

<400> SEQUENCE: 54

Arg Trp Met Thr Phe Asp Val Ser Val Trp Glu Trp His Phe Phe Thr
1               5                   10                  15

Ser Gly Glu Ile Asn Leu Tyr Gly Pro Thr Glu Ala Thr Val Asp Val
            20                  25                  30

Thr Tyr

<210> SEQ ID NO 55
<211> LENGTH: 10
<212> TYPE: PRT
<213> ORGANISM: Paenibacillus strain TS-15

<400> SEQUENCE: 55

Asp Val Trp His Phe Ser Leu Val Asp Lys
1               5                   10

<210> SEQ ID NO 56
<211> LENGTH: 34
<212> TYPE: PRT
<213> ORGANISM: Paenibacillus strain TS-15

<400> SEQUENCE: 56

Ala Trp Arg Phe Phe Asp Gly Phe Val Met Ser Cys Ile Cys Thr Leu
1               5                   10                  15

Ala Gly Glu Phe Asn Glu Tyr Gly Pro Thr Glu Asn Ser Val Val Ala
            20                  25                  30

Thr Cys

<210> SEQ ID NO 57
<211> LENGTH: 10
<212> TYPE: PRT
<213> ORGANISM: Paenibacillus strain TS-15

<400> SEQUENCE: 57

Asp Gly Met Ile Thr Ala Glu Val Val Lys
1               5                   10

<210> SEQ ID NO 58
<211> LENGTH: 34
<212> TYPE: PRT
<213> ORGANISM: Paenibacillus strain TS-15

<400> SEQUENCE: 58

Met Ala Trp Ala Phe Asp Val Phe Ser Gly Asp Arg Asp Cys Ala Val
1               5                   10                  15

Gly Ser Asp Ile Asn Ser Tyr Gly Val Thr Glu Thr Cys Ile Asp Ala
            20                  25                  30

Ser Tyr

<210> SEQ ID NO 59
<211> LENGTH: 10
<212> TYPE: PRT
<213> ORGANISM: Paenibacillus strain TS-15

<400> SEQUENCE: 59

Asp Val Gly Asp Ala Gly Ser Ile Asp Lys
1               5                   10

<210> SEQ ID NO 60
<211> LENGTH: 34
<212> TYPE: PRT
<213> ORGANISM: Paenibacillus strain TS-15

<400> SEQUENCE: 60

Arg Trp Met Thr Phe Asp Val Ser Val Trp Glu Trp His Phe Phe Thr
1               5                   10                  15

Ser Gly Glu Ile Asn Leu Tyr Gly Pro Thr Glu Ala Thr Val Asp Val
            20                  25                  30

Thr Tyr

<210> SEQ ID NO 61
<211> LENGTH: 10
<212> TYPE: PRT
<213> ORGANISM: Paenibacillus strain TS-15

```
<400> SEQUENCE: 61

Asp Val Trp His Phe Ser Leu Val Asp Lys
1               5                   10

<210> SEQ ID NO 62
<211> LENGTH: 34
<212> TYPE: PRT
<213> ORGANISM: Paenibacillus strain TS-15

<400> SEQUENCE: 62

Val Glu Thr Ser Phe Asp Gly Ser Thr Phe Asp Gly Phe Ile Leu Phe
1               5                   10                  15

Gly Gly Glu Lys His Val Tyr Gly Pro Thr Glu Ser Thr Val Phe Ala
            20                  25                  30

Thr Cys

<210> SEQ ID NO 63
<211> LENGTH: 10
<212> TYPE: PRT
<213> ORGANISM: Paenibacillus strain TS-15

<400> SEQUENCE: 63

Asp Gly Phe Phe Leu Gly Val Val Phe Lys
1               5                   10

<210> SEQ ID NO 64
<211> LENGTH: 34
<212> TYPE: PRT
<213> ORGANISM: Paenibacillus strain TS-15

<400> SEQUENCE: 64

Leu Tyr Gln Ala Phe Asp Val Cys Tyr Gln Glu Ser Phe Ile Ile Thr
1               5                   10                  15

Ala Gly Glu His Asn His Tyr Gly Pro Ser Glu Thr His Val Val Thr
            20                  25                  30

Thr Tyr

<210> SEQ ID NO 65
<211> LENGTH: 10
<212> TYPE: PRT
<213> ORGANISM: Paenibacillus strain TS-15

<400> SEQUENCE: 65

Asp Val Gln Phe Ile Ala His Val Val Lys
1               5                   10

<210> SEQ ID NO 66
<211> LENGTH: 34
<212> TYPE: PRT
<213> ORGANISM: Paenibacillus strain TS-15

<400> SEQUENCE: 66

Ile Asn Thr Ser Phe Asp Gly Ser Ala Phe Asp Gly Leu Ile Leu Phe
1               5                   10                  15

Gly Gly Glu Lys His Ala Tyr Gly Pro Ser Glu Ser Thr Val Tyr Ala
            20                  25                  30

Thr Trp

<210> SEQ ID NO 67
<211> LENGTH: 10
<212> TYPE: PRT
```

<213> ORGANISM: Paenibacillus strain TS-15

<400> SEQUENCE: 67

Asp Gly Phe Leu Leu Gly Ala Val Tyr Lys
1               5                   10

<210> SEQ ID NO 68
<211> LENGTH: 34
<212> TYPE: PRT
<213> ORGANISM: Paenibacillus strain TS-15

<400> SEQUENCE: 68

Leu Tyr Gln Ala Phe Asp Val Cys Tyr Gln Glu Ser Tyr Ile Ile Thr
1               5                   10                  15

Ala Gly Glu His Asn His Tyr Gly Pro Ser Glu Thr His Val Val Thr
            20                  25                  30

Thr Tyr

<210> SEQ ID NO 69
<211> LENGTH: 10
<212> TYPE: PRT
<213> ORGANISM: Paenibacillus strain TS-15

<400> SEQUENCE: 69

Asp Val Gln Tyr Ile Ala His Val Val Lys
1               5                   10

<210> SEQ ID NO 70
<211> LENGTH: 34
<212> TYPE: PRT
<213> ORGANISM: Paenibacillus strain TS-15

<400> SEQUENCE: 70

Val Asp Ala Ser Phe Asp Gly Ser Thr Phe Asp Gly Phe Ile Leu Phe
1               5                   10                  15

Gly Gly Glu Lys His Val Tyr Gly Pro Thr Glu Ser Thr Val Phe Ala
            20                  25                  30

Thr Ser

<210> SEQ ID NO 71
<211> LENGTH: 10
<212> TYPE: PRT
<213> ORGANISM: Paenibacillus strain TS-15

<400> SEQUENCE: 71

Asp Gly Phe Phe Leu Gly Val Val Phe Lys
1               5                   10

<210> SEQ ID NO 72
<211> LENGTH: 20
<212> TYPE: DNA
<213> ORGANISM: Artificial Sequence
<220> FEATURE:
<223> OTHER INFORMATION: Primer

<400> SEQUENCE: 72
agagtttgat cctggctcag                                        20

<210> SEQ ID NO 73
<211> LENGTH: 19
<212> TYPE: DNA
<213> ORGANISM: Artificial Sequence
<220> FEATURE:

```
<223> OTHER INFORMATION: primer

<400> SEQUENCE: 73
ggttaccttg ttacgactt                                                    19

<210> SEQ ID NO 74
<211> LENGTH: 18
<212> TYPE: DNA
<213> ORGANISM: Artificial Sequence
<220> FEATURE:
<223> OTHER INFORMATION: primer

<400> SEQUENCE: 74
ctcctacggg aggcagca                                                     18

<210> SEQ ID NO 75
<211> LENGTH: 20
<212> TYPE: DNA
<213> ORGANISM: Artificial Sequence
<220> FEATURE:
<223> OTHER INFORMATION: primer

<400> SEQUENCE: 75
cgtattaccg cggctgctgg                                                   20

<210> SEQ ID NO 76
<211> LENGTH: 16
<212> TYPE: DNA
<213> ORGANISM: Artificial Sequence
<220> FEATURE:
<223> OTHER INFORMATION: primer

<400> SEQUENCE: 76
agggttgcgc tcgttg                                                       16

<210> SEQ ID NO 77
<211> LENGTH: 13
<212> TYPE: PRT
<213> ORGANISM: Paenibacillus strain TS-15
<220> FEATURE:
<221> NAME/KEY: VARIANT
<222> LOCATION: (1)..(1)
<223> OTHER INFORMATION: Ornithine
<220> FEATURE:
<221> NAME/KEY: VARIANT
<222> LOCATION: (4)..(4)
<223> OTHER INFORMATION: Ornithine

<400> SEQUENCE: 77

Xaa Val Thr Xaa Ser Thr Leu Ser Ile Pro Ile Pro Ile
1               5                   10

<210> SEQ ID NO 78
<211> LENGTH: 13
<212> TYPE: PRT
<213> ORGANISM: Paenibacillus strain OSY SE
<220> FEATURE:
<221> NAME/KEY: VARIANT
<222> LOCATION: (1)..(1)
<223> OTHER INFORMATION: Ornithine
<220> FEATURE:
<221> NAME/KEY: VARIANT
<222> LOCATION: (4)..(4)
<223> OTHER INFORMATION: Ornithine
```

```
<400> SEQUENCE: 78

Xaa Val Thr Xaa Ser Val Leu Ser Ile Pro Val Leu Ile
1               5                   10
```

The invention claimed is:

1. A method of inhibiting growth or proliferation of a bacterium, comprising contacting the bacterium with an effective amount of a peptide comprising the amino acid sequence:

$Xaa_1$-$Val_2$-$Thr_3$-D-$Orn_4$-$Ser_5$-$Xaa_6$-$Xaa_7$-D-$Ser_8$-$Ile_9$-$Pro_{10}$-$Ile_{11}$-$Pro_{12}$-$Ile_{13}$, wherein $Xaa_6$ is Tyr or Phe, wherein $Xaa_1$ and $Xaa_7$ are each independently L-Lys D-Lys or D-Orn, and wherein the peptide optionally comprises a saturated or unsaturated, substituted or unsubstituted, linear or branched, $C_4$-$C_{20}$ fatty acid group, or a saturated or unsaturated, linear or branched $C_4$-$C_{20}$ ester covalently linked to $Xaa_1$, thereby inhibiting the growth or proliferation of the bacterium.

2. The method of claim 1, wherein the bacterium is a Gram positive bacterium.

3. The method of claim 1, wherein the infection bacterium is *Enterococcus (E.) faecalis*, methicillin resistant *Staphylococcus aureus* (MRSA), vancomycin resistant *Staphylococcus aureus* (VRSA), or carbapenem resistant *Enterobacteriaceae* (CRE).

4. The method of claim 1, wherein the peptide comprises the saturated or unsaturated, substituted or unsubstituted, linear or branched $C_4$-$C_{20}$ fatty acid group covalently linked to $Xaa_1$.

5. The method of claim 1, wherein the fatty acid group has the formula $C_{10}H_{19}O$, $C_{11}H_{21}O$, $C_{12}H_{23}O$, $C_{13}H_{25}O$, $C_{14}H_{27}O$, or $C_{15}H_{29}O$.

6. The method of claim 5, wherein the peptide comprises the sequence: D-$Orn_1$-$Val_2$-$Thr_3$-D-$Orn_4$-$Ser_5$-$Tyr_6$-$Lys_7$-D-$Ser_8$-$Ile_9$-$Pro_{10}$-$Ile_{11}$-$Pro_{12}$-$Ile_{13}$.

7. The method of claim 1, wherein $Xaa_1$ is D-Orn and $Xaa_7$ is L-Lys or D-Lys.

8. The method of claim 1, wherein the bacterium is a Gram negative bacterium.

9. A method of inhibiting growth or proliferation of a bacterium in a subject in need thereof, the method comprising administering to the subject a composition comprising a peptide and a pharmaceutically acceptable carrier, wherein the peptide comprises the amino acid sequence:

$Xaa_1$-$Val_2$-$Thr_3$-D-$Orn_4$-$Ser_5$-$Xaa_6$-$Xaa_7$-D-$Ser_8$-$Ile_9$-$Pro_{10}$-$Ile_{11}$-$Pro_{12}$-$Ile_{13}$, wherein $Xaa_6$ is Tyr or Phe, wherein $Xaa_1$ and $Xaa_7$ are each independently L-Lys, D-Lys or D-Orn, wherein the peptide optionally comprises a saturated or unsaturated, substituted or unsubstituted, linear or branched, $C_4$-$C_{20}$ fatty acid group, or a saturated or unsaturated, linear or branched $C_4$-$C_{20}$ ester covalently linked to $Xaa_1$, and wherein the composition is administered in an amount effective to inhibit growth or proliferation of the bacterium.

10. The method of claim 9, wherein the bacterium is a Gram positive bacterium.

11. The method of claim 9, wherein the subject is a mammal.

12. The method of claim 11, wherein the subject is a human subject.

13. The method of claim 9, wherein the peptide comprises the saturated or unsaturated, substituted or unsubstituted, linear or branched $C_4$-$C_{20}$ fatty acid group, or the saturated or unsaturated, linear or branched $C_4$-$C_{20}$ ester covalently linked to $Xaa_1$.

14. The method of claim 13, wherein $Xaa_1$ is D-Orn.

15. The method of claim 14, wherein the peptide comprises the saturated or unsaturated, substituted or unsubstituted, linear or branched $C_4$-$C_{20}$ fatty acid group covalently linked to $Xaa_1$.

16. The method of claim 15, wherein the fatty acid group has the formula $C_{10}H_{19}O$, $C_{11}H_{21}O$, $C_{12}H_{23}O$, $C_{13}H_{25}O$, $C_{14}H_{27}O$, or $C_{15}H_{29}O$.

17. The method of claim 16, wherein $Xaa_6$ of the peptide is Phe.

18. The method of claim 9, wherein $Xaa_6$ of the peptide is Tyr and the peptide comprises the saturated or unsaturated, linear or branched $C_4$-$C_{20}$ ester covalently linked to $Xaa_1$.

19. The method of claim 18, wherein the ester has the formula $C_{10}H_{19}O_2$, $C_{11}H_{21}O_2$, $C_{12}H_{23}O_2$, $C_{13}H_{25}O_2$, $C_{14}H_{27}O_2$, or $C_{15}H_{29}O_2$.

20. The method of claim 9, wherein the peptide is cyclized through a bond between $Thr_3$ and $Ile_{13}$.

21. The method of claim 9, wherein $Xaa_7$ of the peptide is D-Lys or L-Lys.

22. The method of claim 9, wherein $Xaa_1$ is D-Orn and $Xaa_7$ is L-Lys or D-Lys.

23. The method of claim 22, wherein the composition further comprises a second peptide, and wherein the second peptide comprises the sequence: D-$Orn_1$-$Val_2$-$Thr_3$-D-$Orn_4$-$Ser_5$-$Tyr_6$-D-$Lys_7$-D-$Ser_8$-$Ile_9$-$Pro_{10}$-$Ile_{11}$-$Pro_{12}$-$Ile_{13}$.

24. The method of claim 22, wherein the bacterium is a Gram positive bacterium.

25. The method of claim 9, wherein the peptide is covalently bound to $C_{13}H_{25}O$.

26. The method of claim 9, wherein the bacterium is vancomycin resistant *enterococci* (VRE).

27. A method of inhibiting growth or proliferation of a Gram positive bacterium in a subject in need thereof, the method comprising contacting the bacterium with an effective amount of a peptide comprising the amino acid sequence D-$Orn_1$-$Val_2$-$Thr_3$-D-$Orn_4$-$Ser_5$-$Tyr_6$-$Lys_7$-D-$Ser_8$-$Ile_9$-$Pro_{10}$-$Ile_{11}$-$Pro_{12}$-$Ile_{13}$, wherein the peptide is covalently linked to $C_{13}H_{25}O$, thereby inhibiting the growth or proliferation of the bacterium.

28. The method of claim 27, wherein the bacterium is *Enterococcus (E.) faecalis*.

29. The method of claim 27, further comprising contacting the Gram positive bacterium with an effective amount of a second peptide, wherein the second peptide comprises the sequence: D-$Orn_1$-$Val_2$-$Thr_3$-D-$Orn_4$-$Ser_5$-$Tyr_6$-D-$Lys_7$-D-$Ser_8$-$Ile_9$-$Pro_{10}$-$Ile_{11}$-$Pro_{12}$-$Ile_{13}$.

* * * * *